US007998701B2

(12) United States Patent
Chua et al.

(10) Patent No.: US 7,998,701 B2
(45) Date of Patent: Aug. 16, 2011

(54) MOLECULE

(75) Inventors: Kaw Yan Chua, Singapore (SG); See Voon Seow, Singapore (SG); Prasanna Ratnakar Kolatkar, Singapore (SG)

(73) Assignees: National University of Singapore, Singapore (SG); **Agency for Science, Technology and Research (A*STAR)**, Singapore (SG)

( * ) Notice: Subject to any disclaimer, the term of this patent is extended or adjusted under 35 U.S.C. 154(b) by 894 days.

(21) Appl. No.: 10/553,674

(22) PCT Filed: Apr. 16, 2004

(86) PCT No.: PCT/SG2004/000098

§ 371 (c)(1),
(2), (4) Date: Oct. 17, 2005

(87) PCT Pub. No.: WO2004/092210

PCT Pub. Date: Oct. 28, 2004

(65) Prior Publication Data

US 2006/0275312 A1 Dec. 7, 2006

(30) Foreign Application Priority Data

Apr. 17, 2003 (GB) ................................. 0308988.5

(51) Int. Cl.
*C12P 21/06* (2006.01)
*C12P 21/04* (2006.01)

(52) U.S. Cl. ..................................... 435/69.1; 435/69.7

(58) Field of Classification Search ........................ None
See application file for complete search history.

(56) References Cited

U.S. PATENT DOCUMENTS

| | | | | |
|---|---|---|---|---|
| 5,917,026 | A | 6/1999 | Lowenadler et al. | |
| 2004/0071718 | A1* | 4/2004 | Tsai | 424/185.1 |

FOREIGN PATENT DOCUMENTS

| | | | |
|---|---|---|---|
| WO | WO 98/32866 | | 7/1998 |
| WO | WO 99/06544 | | 2/1999 |
| WO | WO 02/22680 | A2 | 3/2002 |

OTHER PUBLICATIONS

Blumenthal et al. 'Definition of an allergen.' Allergens and Allergen Immunotherapy. Ed. R. Lockey, S. Bukantzand j. Bousquet. New York: Marcel Decker, 2004. pp. 37-50.*

Colman et al. 'Effects of amino acid sequence changes on antibody-antigen interactions.' Research in Immunology 145(1):33-36, 1994.*

Skolnick et al. 'From genes to protein structure and function: novel applications of computational approaches in the genomic era.' Trends in Biotech. 18:34-39, 2000.*

Attwood et al. 'The Babel of Bioinformatics.' Science 290(5491):471-473, 2000.*

Tarzi et al. 'Peptide immunotherapy for allergic disease.' Expert Opin. Biol. Therap. 3(4):617-626, 2003.*

Hsu, Hoa-Chi, et al., "Fip-vvo, a new fungal immunomodulatory protein isolated from *Volvariella volvacea,* " *Biochem Journal,* vol. 323, No. 2, pp. 557-565 (1997).

Ko, Jiunn-Liang, et al., "Molecular cloning and expression of a fungal immunomodulary protein, FIP-fve, from *Flammulina velutipes,* " *Journal of the Formosan Medical Association,* vol. 96, No. 7, pp. 517-524 (1997).

Ko, Jiunn-Liang, et al., "A new fungal immunodulatory protein, FIP-fve isolated from the edible mushroom, *Flammulina velutipes* and its complete amino acid," *European Journal of Biochemistry,* vol. 228, No. 2 pp. 244-249 (1995).

Murasugi, Akira, et al., "Molecular cloning of a cDNA and a gene encoding an immunomodulary protein, ling Zhi-8, from a fungus, gandoderma-lucidum," Journal of Biological Chemistry, vol. 266, No. 4, pp. 2486-2493 (1991).

Paaventhan, Palasingam, et al., "A 1.7 Å structure of Fve, a member of the new fungal immunomodulatory protein family," Journal of Molecular Biology, vol. 332, No. 2, pp. 461-470 (2003).

* cited by examiner

*Primary Examiner* — Nora Rooney
(74) *Attorney, Agent, or Firm* — Mark J. FitzGerald; Nixon Peabody LLP

(57) ABSTRACT

We describe an Fve polypeptide being a fragment, homologue, variant or derivative of Fve protein, which comprises at least one biological activity of Fve protein. Uses of such a polypeptide, etc, and nucleic acids encoding these, in the treatment and prevention of allergy and cancer are also disclosed.

2 Claims, 57 Drawing Sheets

(A)

(B)

*IFN-γ production at day 3*

TNF-α production at day 3

Mice received subcutaneous injection of a mixture of 10 ug of major mite allergen Der p 1 and 10 ug of Fve at days 0 and 14. Results showed that Der p1+ Fve induced higher Der p 1-specific IgG2a (pink) than Der p 1 alone (Blue).

(A)

(B)

| Blo t 5 | Fve | Bt5-Fve

| Blo t 5 | FveR27A | Bt5-FveR27A

| Blo t 5 | FveT29A | Bt5-FveT29A

| Der p 2 | FveR27A | Dp2-FveR27A

| Der p 2 | FveT29A | Dp2-FveT29A

| Blo t 5 | Der p 2 | FveR27A | Bt5-Dp2-FveR27A

| Blo t 5 | Der p 2 | FveT29A | Bt5-Dp2-FveT29A (1a)

Control: Non-stimulated (10x10 magnification)

(1b)

Control : Non-stimulated (40x10 magnification)

(2a)

20ug of GST 10x10

(2b)

20ug of GST 40x10

(3a)

20ug of Blo t 5 10x10

(3b)

20ug of Blo t 5 40x10

(4a)

20ug of native FIP-Fve 10x10

(4b)

20ug of native FIP-Fve 40x10

(5a)

20ug of Bt5-Fve 10x10

(5b)

20ug of Bt5-Fve 40x10

(6a)

40ug of Bt5-Fve 10x10

(6b)

40ug of Bt5-Fve 40x10

(7a)

40ug of Bt5-FveR27A 10x10

(7b)

40ug of Bt5-FveR27A 40x10

(8a)

20ug of Der p 2 10x10

(8b)

20ug of Der p 2 40x10

(9a)

40ug of GST-Dp2-FveR27A 10x10

(9b)

40ug of GST-Dp2-FveR27A 40x10

(A)

(B)

(A)

(B)

MOLECULE

CLAIM OF PRIORITY

This application claims priority under 35 USC 371 to International Application No. PCT/SG2004/000098, filed on Apr. 16, 2004, which claims priority to Great Britain Patent Application No. 0308988.5, filed on Apr. 17, 2003, the entire contents of which are hereby incorporated by reference.

FIELD

The present invention relates to the fields of microbiology. It also relates to the fields of medicine, especially therapy and diagnosis.

BACKGROUND

Some microorganisms are capable of acting as immunomodulating agents, such as *Mycobacterium smegmatis* is used in Freund's complete adjuvant and OK432 from *Streptococcus pygens* as the anti-tumor potentiator. Many polysaccharide immunomodulating agents have also been detected and isolated from Basidiomycetes class of fungi, such as lentinan, schizophyllan, TML and SF AI. A novel family of fungal immunomodulatory proteins has been isolated from the edible mushrooms, such as Vvo from *Volvariella volvacea* (grass mushroom), LZ-S from *Ganoderma lucidum* (Ling-Zhi), Gts from *Ganoderma tsugae* (songshan lingzhi), and Fve from *Flammulina velutipes* (golden needle mushroom).

Although the therapeutic value of a number of mushrooms has been documented, the active components that confer such therapeutic effects are not well understood.

Ko et al (Eur. J. Biochem., 228, 244-2419) describes the isolation and purification of a protein known as FIP-fve from Golden Needle Mushroom extracts. The authors describe a method of extracting this protein, as well as some biochemical properties of FIP-fve. The amino acid sequence of FIP-fve is presented. FIP-fve is shown to cause proliferation of human peripheral blood lymphocytes, and mice sensitised to BSA are protected against anaphylactic shock by periodic injections of FIP-fve. A hind-paw edema test shows that FIP-fve inhibits antibody production against antigen 48/80. Finally, the authors show that FIP-fve induces expression of IL-2 and IFN-γ in spleen cells from mouse.

An amino acid sequence of FIP-fve is found as GenBank accession numbers:S69147 immunomodulatory protein FIP-fve—golden needle mushroom gi|7438667|pir||S69147 [7438667] and P80412 IMMUNOMODULATORY PROTEIN FIP-FVE gi|729544|sp|P80412|FVE_FLAVE [729544].

SUMMARY

According to a first aspect of the present invention, we provide an Fve polypeptide comprising at least one biological activity of native Fve protein, and being a fragment, homologue, variant or derivative thereof.

Preferably, the Fve polypeptide comprises an immunomodulatory activity. Preferably, the biological activity is selected from the group consisting of: up-regulation of expression of Th1/Tc1 cytokines, preferably IFN-γ and TNF-α, down-regulation of expression of Th2/Tc2 cytokines, preferably IL-4 and IL-13, up-regulation of expression of T regulatory (Tr) cytokines IL-10 and TGF-β, hemagglutination activity, cell aggregation activity, lymphocyte aggregation activity, lymphoproliferation activity, up-regulation of expression of IL-2, IFN-γ, TNF-α, but not IL-4 in $CD3^+$ T cells, interaction with T and NK cells, adjuvant activity, stimulation of $CD3^+$ $CD16^+$ $CD56^+$ natural killer (NK) T cells and $CD3^+$ $CD8^+$ $CD18^{+bright}$ T cells, and up-regulation of allergen specific Th1 immune responses.

Preferably, the polypeptide comprises between 2 to 20 residues of amino acid sequence flanking the glycine residue corresponding to position 28 of Fve.

Preferably, the polypeptide comprises the sequence RGT or the sequence RGD.

Preferably, the polypeptide has a sequence as set out in Appendix A or Appendix B.

There is provided, according to a second aspect of the present invention, a Fve polypeptide comprising an sequence selected from the group consisting of: Fve R27A, Fve T29A, GST-Fve (wild type), GST-Fve R27A, and GST-Fve T29A, and fragments, homologues, variants and derivatives thereof.

We provide, according to a third aspect of the present invention, a polypeptide comprising a first portion comprising at least a portion of Fve and a second portion comprising at least a portion of an allergen.

Preferably, the allergen comprises an allergen from a mite, preferably from Family Glycyphagidae or Family Pyroglyphidae, preferably a group 1 allergen (Der p 1, Der f 1, Blo t 1, Eur m1, Lep d 1), a group 2 allergen (Der p 2, Der f2, Blo t 2, Eur m 2, Lep d 2), a group 5 allergen (Blo t 5, Der p 5, Der f 5, Eur m 5, Lep d 5) a group 15 allergen (Der p 15, Der f 15, Blot 15, Eur m 15, Lep d 15).

Preferably, the Fve polypeptide or a polypeptide is selected from the group consisting of: Blo t 5-Fve, Blo t 5-FveR27A, Blo t 5-FveT29A, GST-Der p 2-FveR27A, GST-Der p 2-FveT29A, Blo t 5-Der p 2-FveR27A, and Blo t 5-Der p 2-FveT29A. More preferably, it comprises Blo t 5-FveT29A, Der p 2-FveT29A, or Blo t 5-Der p 2-FveT29A.

Preferably, the allergen is selected from the group consisting of: tree pollen allergen, Bet v 1 and Bet v 2 from birch tree; grass pollen allergen, Phl p 1 and Phl p 2 from timothy grass; weed pollen allergen, antigen E from ragweed; major feline antigen, Fel d; major fungal allergen, Asp f1, Asp f2, and Asp f3 from *Aspergillus fumigatus*.

As a fourth aspect of the present invention, there is provided a polypeptide comprising a first portion comprising at least a portion of Fve and a second portion comprising at least a portion of a viral antigen selected from the group consisting of: E6 and E7 from HPV; core Ag and E2 from HCV; core and surface antigens from HBV; LMP-1, LMP-2, EBNA-2, EBNA-3 from EBV; and Tax from HTLV-1.

Preferably, it comprises HCV Core23-FveT29A, or HPV E7-FveT29A.

We also provide a polypeptide comprising a first portion comprising at least a portion of Fve and a second portion comprising at least a portion of a viral antigen selected from the group consisting of antigens from Adenovirus, Parainfluenza 3 virus, Human Immunodeficiency Virus (HIV), Herpes simplex virus, HSV, Respiratory syncytial virus, RSV, and Influenza A, Flu A.

We provide, according to a fifth aspect of the present invention, a polypeptide comprising a first portion comprising at least a portion of Fve and a second portion comprising at least a portion of a tumour-associated antigen selected from the group consisting of: MAGE-1, MAGE-2, MAGE-3, BAGE, GAGE, PRAME, SSX-2, Tyrosinase, MART-1, NY-ESO-1, gp100, TRP-1, TRP-2, A2 melanotope, BCR/ABL, Proteinase-3/Myeloblastin, HER2/neu, CEA, P1A, HK2, PAPA, PSA, PSCA, PSMA, pg75, MUM-1, MUC-1, BTA, GnT-V, β-catenin, CDK4, and P15.

Preferably, it comprises MAGE3-FveT29A, MART1-FveT29A or CEA-FveT29A.

The present invention, in a sixth aspect, provides a nucleic acid encoding a Fve polypeptide or a polypeptide according to any preceding statement of invention.

Preferably, the nucleic acid comprises CGT GGT ACC, or a sequence which differs from the above by virtue of the degeneracy of the genetic code and which encodes a sequence RGT.

In a seventh aspect of the present invention, there is provided a nucleic acid comprising a sequence encoding at least a portion of Fve and a sequence encoding at least a portion of an allergen.

Preferably, it comprises Blo t 5-FveT29A, Der p 2-FveT29A, or Blo t 5-Der p 2-FveT29A.

According to an eighth aspect of the present invention, we provide a nucleic acid comprising a sequence encoding at least a portion of Fve and a sequence encoding at least a portion of a viral antigen selected from the group consisting of: E6 and E7 from HPV; core Ag and E2 from HCV; core and surface antigens from HBV; LMP-1, LMP-2, EBNA-2, EBNA-3 from EBV; and Tax from HTLV-1.

Preferably, it comprises HCV Core23-FveT29A, or HPV E7-FveT29A.

We also provide a nucleic acid comprising a sequence encoding at least a portion of Fve and a sequence encoding at least a portion of a viral antigen selected from the group consisting of antigens from Adenovirus, Parainfluenza 3 virus, Human Immunodeficiency Virus (HIV), Herpes simplex virus, HSV, Respiratory syncytial virus, RSV, and Influenza A, Flu A.

We provide, according to a ninth aspect of the invention, a nucleic acid comprising a sequence encoding at least a portion of Fve and a sequence encoding at least a portion of a tumour associated antigen selected from the group consisting of: MAGE-1, MAGE-2, MAGE-3, BAGE, GAGE, PRAME, SSX-2, Tyrosinase, MART-1, NY-ESO-1, gp100, TRP-1, TRP-2, A2 melanotope, BCR/ABL, Proteinase-3/Myeloblastin, HER2/neu, CEA, P1A, HK2, PAPA, PSA, PSCA, PSMA, pg75, MUM-1, MUC-1, BTA, GnT-V, β-catenin, CDK4, and P15.

Preferably, it comprises MAGE3-FveT29A, MART1-FveT29A or CEA-FveT29A.

There is provided, in accordance with a tenth aspect of the present invention, a nucleic acid selected from the group consisting of: Fve R27A, Fve T29A, GST-Fve (wild type), GST-Fve R27A, GST-Fve T29A, Blo t 5-Fve, Blo t 5-FveR27A, Blo t 5-FveT29A, GST-Der p 2-FveR27A, GST-Der p 2-FveT29A, Blo t 5-Der p 2-FveR27A, Blo t 5-Der p 2-FveT29A, and fragments, homologues, variants and derivatives thereof.

As an eleventh aspect of the invention, we provide a vector, preferably an expression vector, comprising a nucleic acid sequence as set out above.

We provide, according to a twelfth aspect of the invention, there is provided DNA vaccine comprising a nucleic acid encoding Fve, a nucleic acid, or a vector as set out above.

According to a thirteenth aspect of the present invention, we provide host cell comprising a nucleic acid encoding Fve, a nucleic acid, or a vector as set out above.

There is provided, according to a fourteenth aspect of the present invention, transgenic non-human organism comprising a nucleic acid encoding Fve, a nucleic acid, or a vector as set out above.

Preferably, the transgenic non-human organism is a bacterium, a yeast, a fungus, a plant or an animal, preferably a mouse.

According to a sixteenth aspect of the present invention, we provide a pharmaceutical composition comprising a polypeptide, a nucleic acid, a vector, a DNA vaccine, or a host cell as set out above, together with a pharmaceutically acceptable carrier or diluent.

According to a seventeenth aspect of the present invention, we provide the use of a native Fve polypeptide, or an Fve polypeptide, nucleic acid, vector, DNA vaccine, host cell, transgenic organism, or a pharmaceutical composition as set out above as an immumodulator.

According to an eighteenth aspect of the present invention, we provide the use of a native Fve polypeptide, or an Fve polypeptide, nucleic acid, vector, DNA vaccine, host cell, transgenic organism, or a pharmaceutical composition as set out above to enhance an immune response in a mammal.

According to a nineteenth aspect of the present invention, we provide the use of a native Fve polypeptide, or an Fve polypeptide, nucleic acid, vector, DNA vaccine, host cell, transgenic organism, or a pharmaceutical composition as set out above to stimulate proliferation of $CD3^+$ $CD8^+$ $CD18^{+bright}$ T cells.

According to a twentieth aspect of the present invention, we provide the use of a native Fve polypeptide, or an Fve polypeptide, nucleic acid, vector, DNA vaccine, host cell, transgenic organism, or a pharmaceutical composition as set out above to stimulate proliferation of $CD3^+$ $CD16^+$ $CD56^+$ natural killer (NK) T cells.

According to a twenty first aspect of the present invention, we provide the use of a native Fve polypeptide, or an Fve polypeptide, nucleic acid, vector, DNA vaccine, host cell, transgenic organism, or a pharmaceutical composition as set out above to stimulate production of IL-2, IL-10, TGF-β, IFN-γ or TNF-α in $CD3^+$ cells.

Preferably, production of IL-4 is not stimulated in the $CD3^+$ cells.

According to a twenty second aspect of the present invention, we provide the use of a native Fve polypeptide, or an Fve polypeptide, nucleic acid, vector, DNA vaccine, host cell, transgenic organism, or a pharmaceutical composition as set out above as an adjuvant for a vaccine.

According to a twenty third aspect of the present invention, we provide the use of a native Fve polypeptide, or an Fve polypeptide, nucleic acid, vector, DNA vaccine, host cell, transgenic organism, or a pharmaceutical composition as set out above in a method of treatment or prophylaxis of a disease.

According to a twenty fourth aspect of the present invention, we provide the use of a native Fve polypeptide, or an Fve polypeptide, nucleic acid, vector or host cell as set out above for the preparation of a pharmaceutical composition for the treatment of a disease.

According to a twenty fifth aspect of the present invention, we provide a method of treating an individual suffering from a disease or preventing the occurrence of a disease in an individual, the method comprising administering to the individual a therapeutically or prophylactically effective amount of a native Fve polypeptide, or an Fve polypeptide, nucleic acid, vector, DNA vaccine, host cell, transgenic organism, or a pharmaceutical composition as set out above.

Preferably, the use or method is such that disease comprises an atopic disease or allergy.

Preferably, the allergy is selected from the group consisting of: allergic asthma, a seasonal respiratory allergy, a perennial respiratory allergy, allergic rhinitis, hayfever, nonallergic rhinitis, vasomotor rhinitis, irritant rhinitis, an allergy against grass pollen, weed pollen, tree pollen or animal danders, an allergy associated with allergic asthma and a food allergy.

Preferably, the allergy is to a house dust mite from Family Glyphagidae, preferably *Blomia tropicalis* or from Family Pyroglyphidae, preferably *Dermatophagoides pteronyssinus* or *Dermatophagoides farinae*, or to fungi or fungal spores, preferably *Aspergillus fumigatus*.

In an alternative embodiment, the disease comprises a cancer.

According to a twenty seventh aspect of the present invention, we provide the use of a DNA vaccine as described, in a method of treatment or prevention of a cancer, or in a method of suppressing tumour progression.

Preferably, the cancer comprises a T cell lymphoma, melanoma, lung cancer, colon cancer, breast cancer or prostate cancer.

According to a twenty eighth aspect of the present invention, we provide a method of identifying a molecule capable of binding to Fve, the method comprising exposing a native Fve polypeptide, or an Fve polypeptide or nucleic acid, vector, host cell or transgenic organism according as set out above to a candidate molecule and detecting whether the candidate molecule binds to the native Fve polypeptide, or an Fve polypeptide or nucleic acid, vector, host cell or transgenic organism.

According to a twenty ninth aspect of the present invention, we provide a method of identifying an agonist or antagonist of an Fve polypeptide, the method comprising: (a) providing a cell or organism; (b) exposing the cell or organism to a native Fve polypeptide, or an Fve polypeptide or nucleic acid, vector, host cell or transgenic organism as set out above; (c) exposing the cell to a candidate molecule; and (d) detecting an Fve mediated effect.

Preferably, the Fve mediated effect is selected from the biological activities set out above.

Preferably, the method further comprises isolating or synthesising a selected or identified molecule.

According to a thirtieth aspect of the present invention, we provide a molecule identified or selected using such a method.

According to a thirty first aspect of the present invention, we provide a native Fve polypeptide, or an Fve polypeptide in crystalline form.

Preferably, the crystal has the structural coordinates shown in Appendix C.

According to a thirty second aspect of the present invention, we provide a model for at least part of Fve made using such a crystal.

According to a thirty third aspect of the present invention, we provide a method of screening for a receptor capable of binding to Fve, or designing a ligand capable of modulating the interaction between Fve and an Fve receptor, comprising the use of such a model.

According to a thirty fourth aspect of the present invention, we provide a computer readable medium having stored thereon the structure of such a crystal or such a model.

According to a thirty fifth aspect of the present invention, we provide a ligand identified by the method set out above.

According to a thirty sixth aspect of the present invention, we provide a use of such a molecule or such a ligand for the treatment or prevention of a disease in an individual.

According to a thirty seventh aspect of the present invention, we provide a pharmaceutical composition comprising such a molecule or such a ligand and optionally a pharmaceutically acceptable carrier, diluent, excipient or adjuvant or any combination thereof.

According to a thirty eighth aspect of the present invention, we provide a method of treating and/or preventing a disease comprising administering such a molecule or such a ligand and/or such a pharmaceutical composition to a mammalian patient.

According to a thirty ninth aspect of the present invention, we provide a method of amplifying a sub-population of cells, the method comprising: (a) obtaining a population of cells from an individual; (b) amplifying $CD3^+$ $CD8^+$ and $CD18^{+bright}$ T cells by exposing the population of cells to a native Fve polypeptide, or an Fve polypeptide or nucleic acid, vector, host cell or transgenic organism as set out above.

Preferably, the method further comprises the step of: (c) isolating the $CD3^+$ $CD8^+$ and $CD18^{+bright}$ T cells.

According to a fortieth aspect of the present invention, we provide a method of treating an individual suffering from a disease or preventing the occurrence of a disease in an individual, the method comprising amplifying a $CD3^+$ $CD8^+$ and $CD18^{+bright}$ T cell by such a method, and administering the amplified $CD3^+$ $CD8^+$ and $CD18^{+bright}$ T cell to an individual.

According to a forty first aspect of the present invention, we provide a combination comprising a first component comprising an immunomodulator and a second component comprising at least a portion of an allergen, a viral antigen or a tumour associated antigen.

Preferably, the first component is separate from the second component. Alternatively, or in addition, the first component may be associated with the second component. Preferably, the combination comprises a fusion protein.

The first component may comprise a native Fve polypeptide, or a polypeptide as set out above. The second component may comprise an allergen selected from the group consisting of: a mite allergen, an mite allergen from Family Glycyphagidae or Family Pyroglyphidae, a group 1 allergen (Der p 1, Der f 1, Blo t 1, Eur m1, Lep d 1), a group 2 allergen (Der p 2, Der f 2, Blo t 2, Eur m 2, Lep d 2), a group 5 allergen (Blo t 5, Der p 5, Der f 5, Eur m 5, Lep d 5), a group 15 allergen (Der p 15, Der f 15, Blot 15, Eur m 15, Lep d 15), a tree pollen allergen, Bet v 1 and Bet v 2 from birch tree; grass pollen allergen, Phl p 1 and Phl p 2 from timothy grass; weed pollen allergen, antigen E from ragweed; major feline antigen, Fel d; major fungal allergen, Asp f1, Asp f2, and Asp f3 from *Aspergillus fumigatus*.

In preferred embodiments, the second component comprises a viral antigen selected from the group consisting of: E6 and E7 from HPV; core Ag and E2 from HCV; core and surface antigens from HBV; LMP-1, LMP-2, EBNA-2, EBNA-3 from EBV; and Tax from HTLV-1. Alternatively, or in addition, the second component may comprise a tumour-associated antigen selected from the group consisting of: MAGE-1, MAGE-2, MAGE-3, BAGE, GAGE, PRAME, SSX-2, Tyrosinase, MART-1, NY-ESO-1, gp100, TRP-1, TRP-2, A2 melanotope, BCR/ABL, Proteinase-3/Myeloblastin, HER2/neu, CEA, P1A, HK2, PAPA, PSA, PSCA, PSMA, pg75, MUM-1, MUC-1, BTA, GnT-V, β-catenin, CDK4, and P15.

We further disclose an immunomodulator-antigen conjugate, preferably an immunomodulator-allergen conjugate, an immunomodulator-tumour associated antigen conjugate or a immunomodulator-viral antigen conjugate, in which the immunomodulator preferably comprises an Fve polypeptide.

Splenocytes are stained with anti-Pan NK PE and anti-BrdU FITC monoclonal antibodies and then analyzed with flow cytometry.

Figure 29:
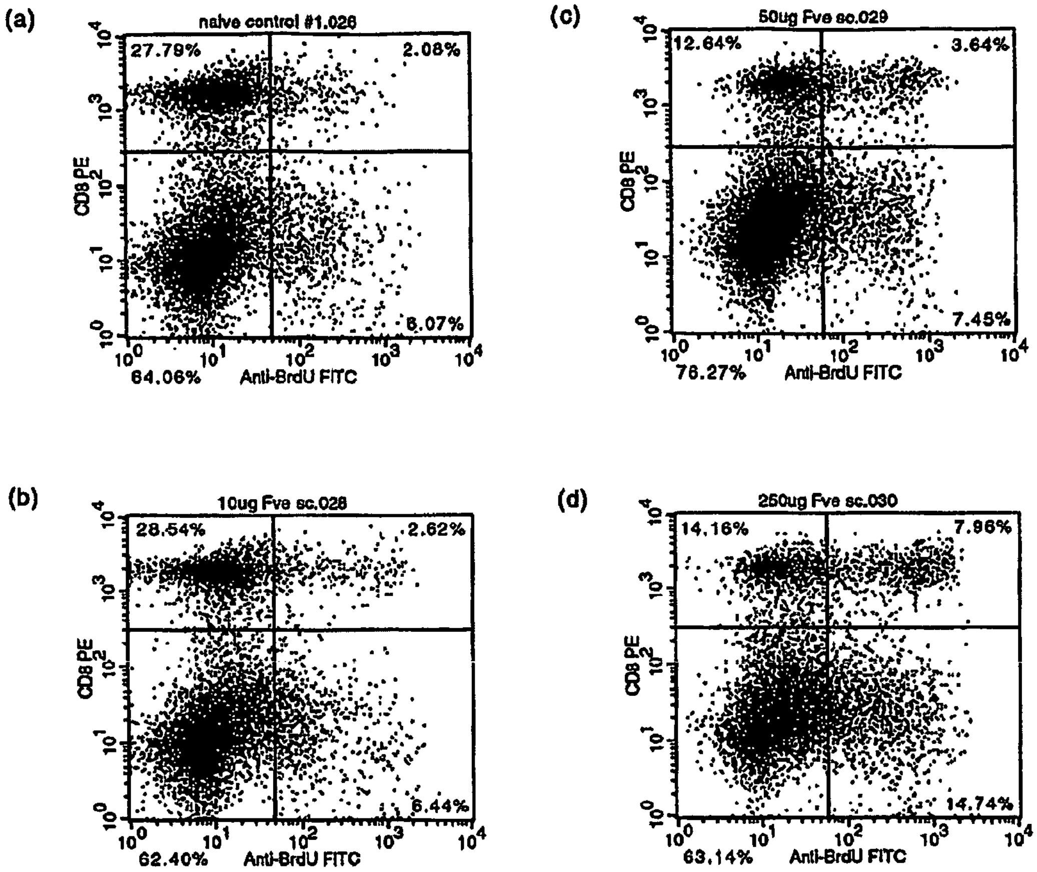

FIG. 29. Proportion of in vivo BrdU incorporated $CD8^+$ T cells from spleen of C57BL/6J naïve mice (a), or mouse received three consecutive subcutaneous injections with 10 μg of Fve (b), 50 μg of Fve (c), 250 μg of Fve (d). Splenocytes are stained with anti-CD8 PE and anti-BrdU FITC monoclonal antibodies and then analyzed with flow cytometry.

Figure 30:
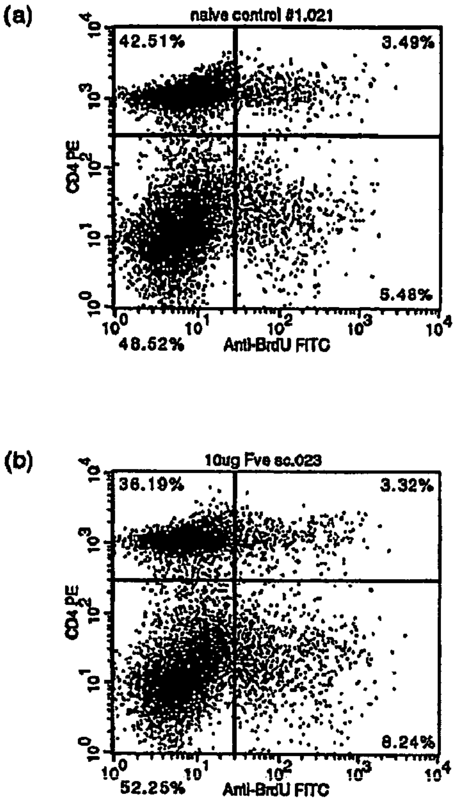

FIG. 30. Proportion of in vivo BrdU incorporated $CD4^+$ T cells from spleen of C57BL/6J naïve mice (a), or mouse received three consecutive subcutaneous injections with 10 μg of Fve (b), 50 μg of Fve (c), 250 μg of Fve (d). Splenocytes are stained with anti-CD4 PE and anti-BrdU FITC monoclonal antibodies and then analyzed with flow cytometry.

Figure 31:
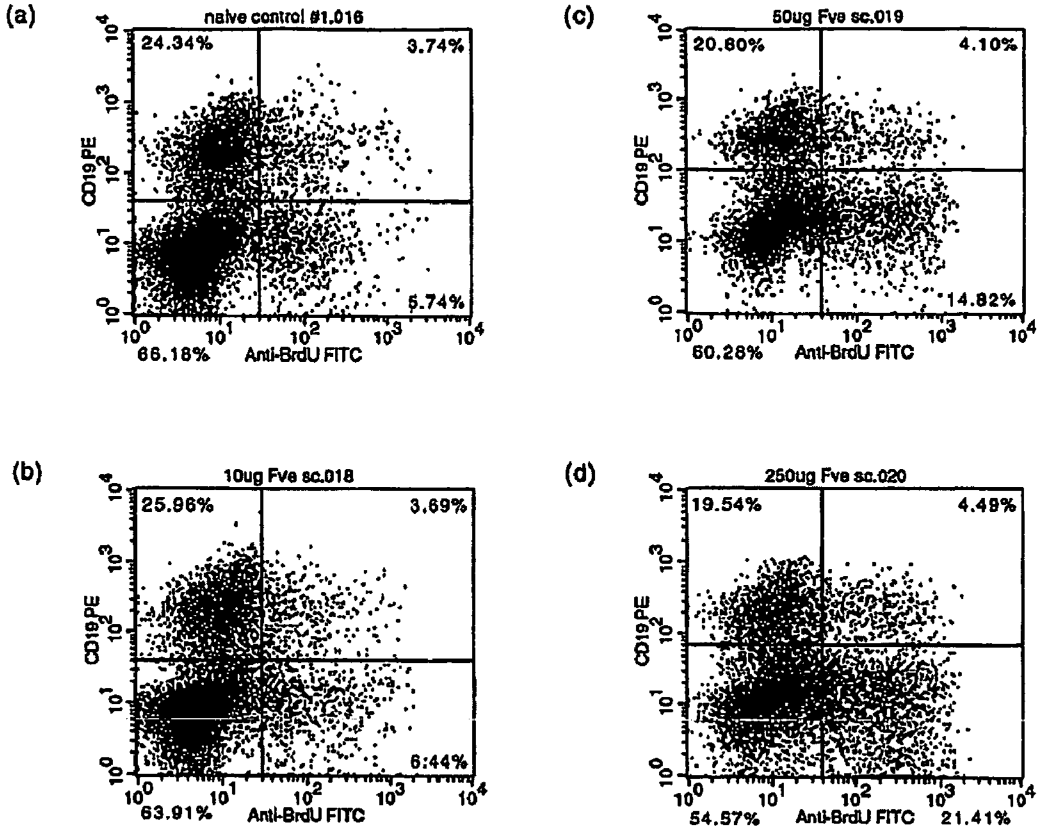

FIG. 31. Proportion of in vivo BrdU incorporated $CD19^+$ B cells from spleen of C57BL/6J naïve mice (a), or mouse received three consecutive subcutaneous injections with 10 μg of Fve (b), 50 μg of Fve (c), 250 μg of Fve (d). Splenocytes are stained with anti-CD19 PE and anti-BrdU FITC monoclonal antibodies and then analyzed with flow cytometry.

Figure 32:
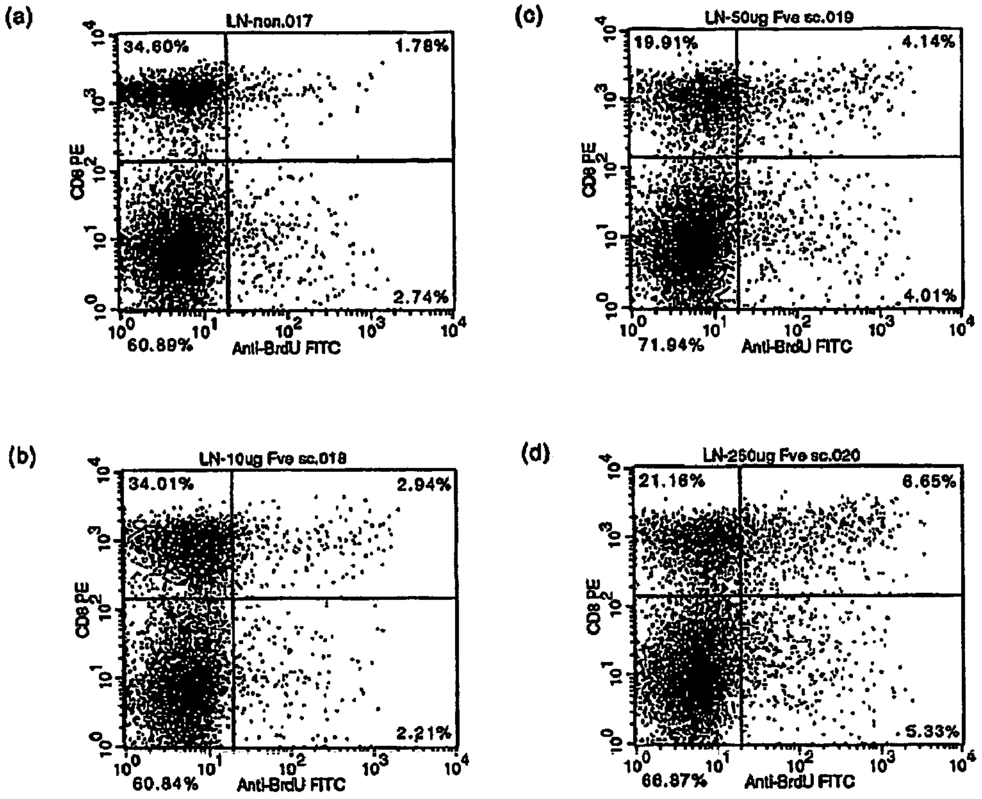

FIG. 32. Proportion of in vivo BrdU incorporated $CD8^+$ T cells from lymph nodes of C57BL/6J naïve mice (a), or mouse received three consecutive subcutaneous injections with 10 μg of Fve (b), 50 μg of Fve (c), 250 μg of Fve (d). Lymph nodes are stained with anti-CD8 PE and anti-BrdU FITC monoclonal antibodies and then analyzed with flow cytometry.

Figure 33:
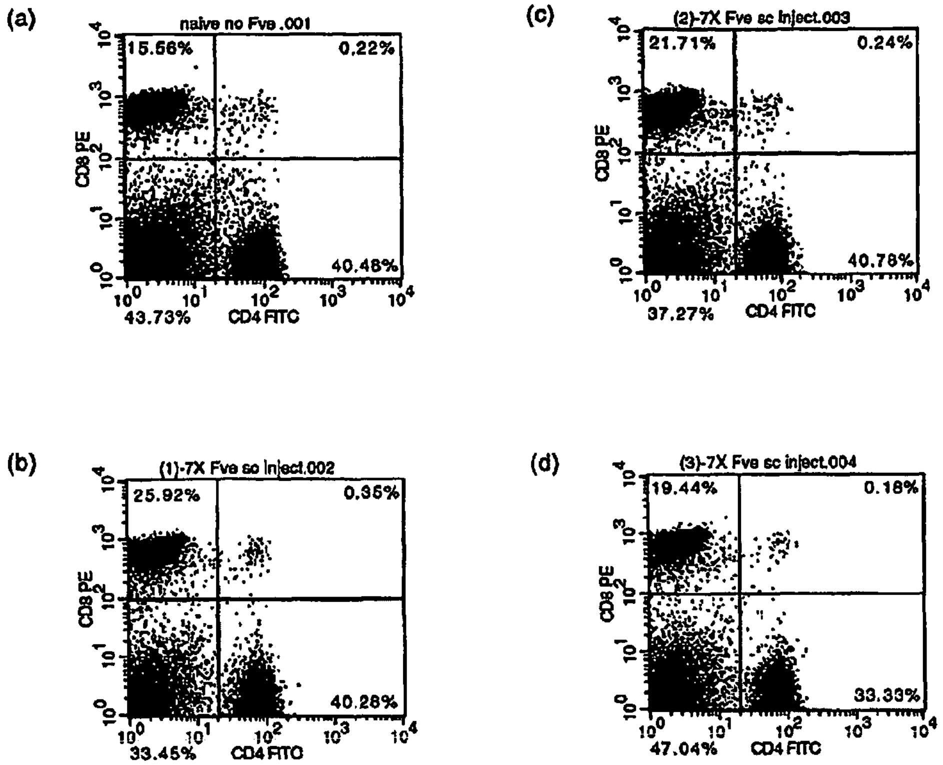

FIG. 33. Proportion of $CD4^+$ and $CD8^+$ T cell subsets from mouse peripheral blood mononuclear cells of Balb/cJ naïve mouse (a), or mouse received seven consecutive subcutaneous injections with 125 μg of Fve. Panels (b), (c), (d) represent results for three respective individual mouse. Mouse peripheral blood mononuclear cells are collected in a tube with anti-coagulant. Cells are stained with anti-CD8 PE and anti-CD4 FITC monoclonal antibodies and then analyzed by flow cytometry.

Figure 34:
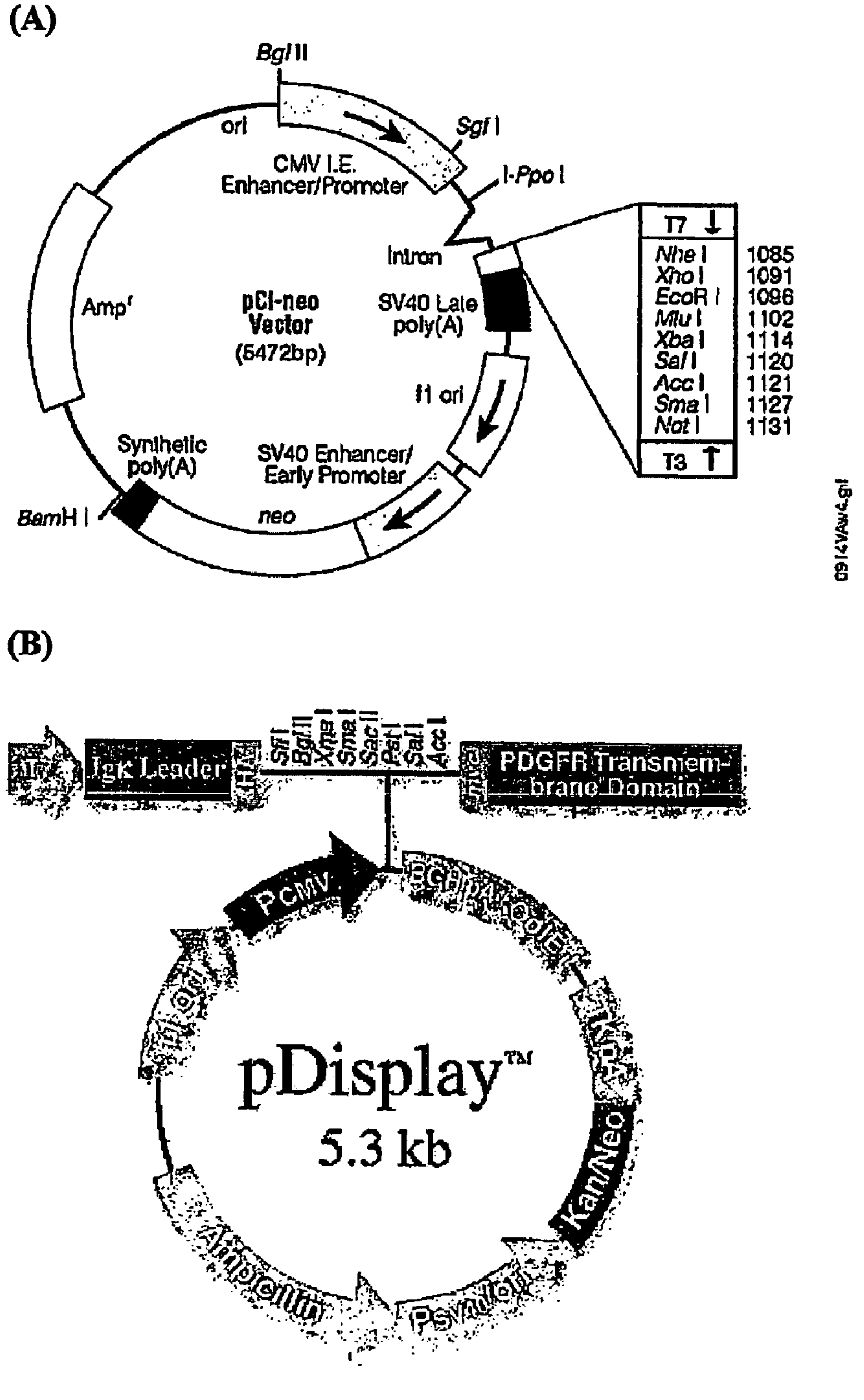

FIG. 34. Schematic representative of two mammalian eukaryotic expression vectors. (A) pCI-neo can constitutively express high level of recombinant protein in mammalian cells (Picture adopted from Promega, USA). (B) pDisplay can display recombinant protein to the surface of mammalian cells (Picture adopted from Invitrogen life technologies, USA).

Figure 35:
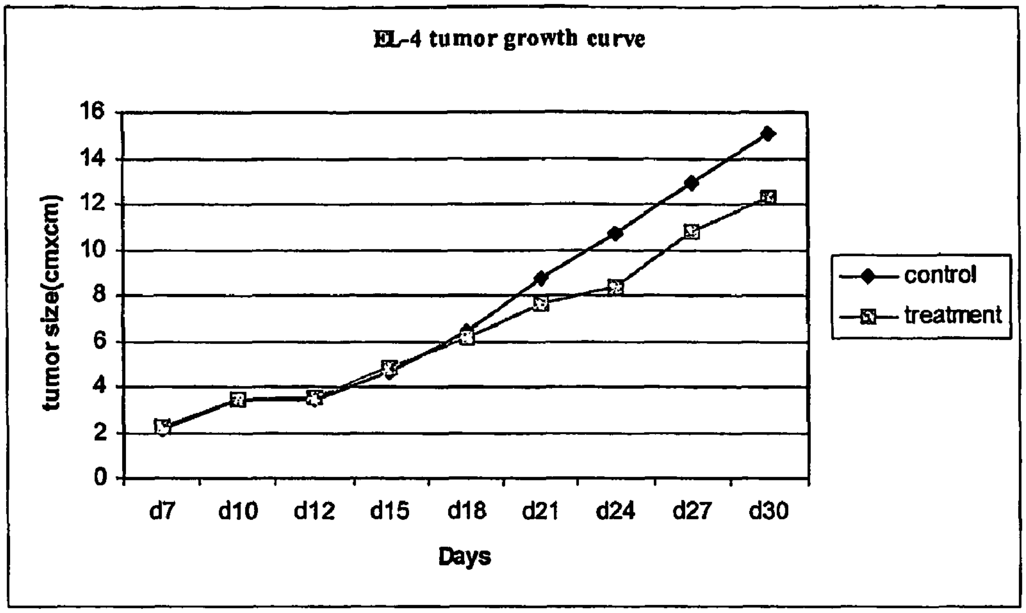

FIG. 35. Growth suppression of EL4 solid tumor. C57BL mice are inoculated with $8\times10^6$ EL4 cells have reduced tumor growing rate in the group treated with pCIneo-fve plasmid DNA and Fve protein (Square curve). The control group received pCIneo DNA vector alone and 1×PBS (Diamond curve). EL4 tumor formation is observed at day 3. 100 μg of pCIneo-fve DNA is intramuscularly injected into the tibialis muscle at days 0 and 7.20 μg of Fve protein is given by subcutaneous injection at days 5, 7, 9, 11, 13, 15, and 18, respectively.

Figure 36:
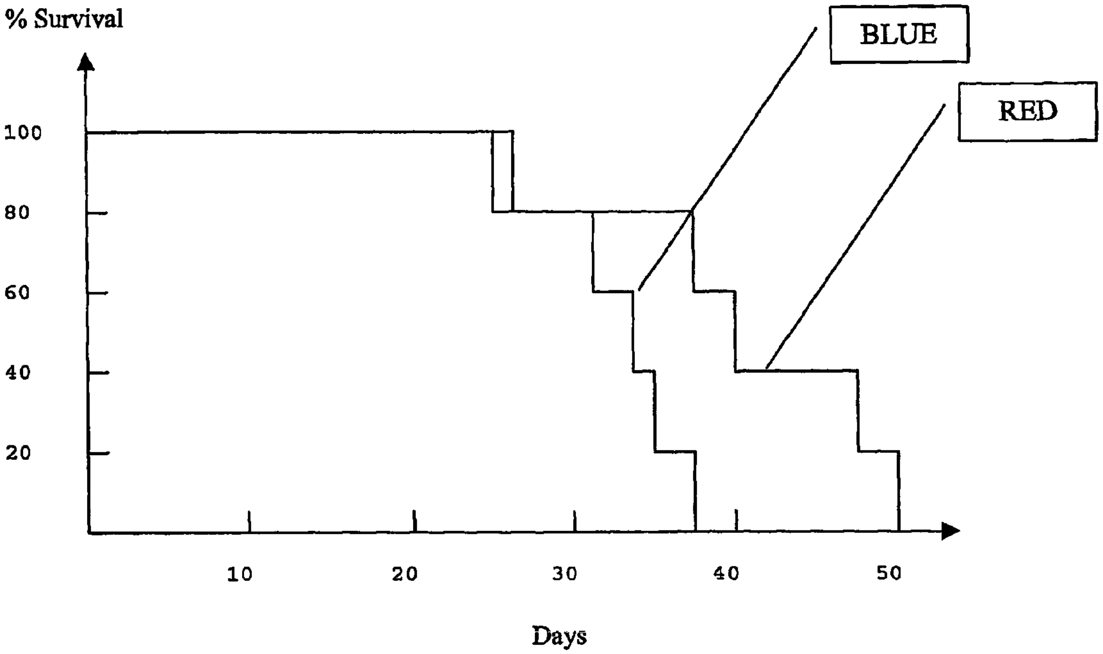

FIG. 36. C57BL/6J mice with EL4 solid tumor have extended mean surviyal time following treatment with the native Fve protein. Eight weeks old female C57BL mice are inoculated with EL4 tumor in the dorsal back Tumor formation is observed 3 days after inoculation. Red line: 100 μg of pCIneo-fve plasmid DNA is intramuscularly injected at the tribilis muscle at days 0 and 7. Mice are received 20 μg of native Fve protein treatment by subcutaneous injection surrounding the tumor site at days 5, 7, 9, 11, 13, 15, and 18, respectively. Blue line: Mice received 100 μg of pCIneo vector alone and 1×PBS as control group.

Figure 37:
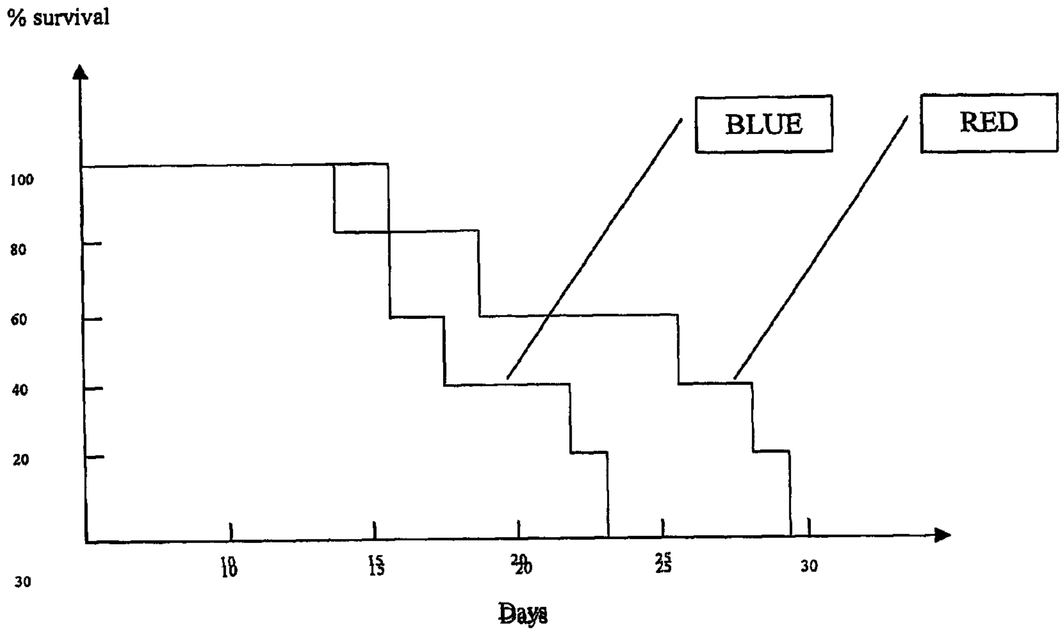

FIG. 37. C57BL/6J mice with B16-F1 melanoma have extended mean survival time following treatment with native Fve protein. Mice are inoculated with B16-F1 tumor cells in the dorsal back. Tumor formation is observed at day 3. Red line: 200 μg of pCIneo-fve plasmid DNA is intramuscularly injected at the tribilis muscle at days −30 and day −1. 50 μg of Fve protein is given by subcutaneous injection surrounding the tumor site at days 4, 7, 9, and 12, respectively. Blue line: Mice received 200 μg of pCIneo vector and 1×PBS as control group.

Figure 38:
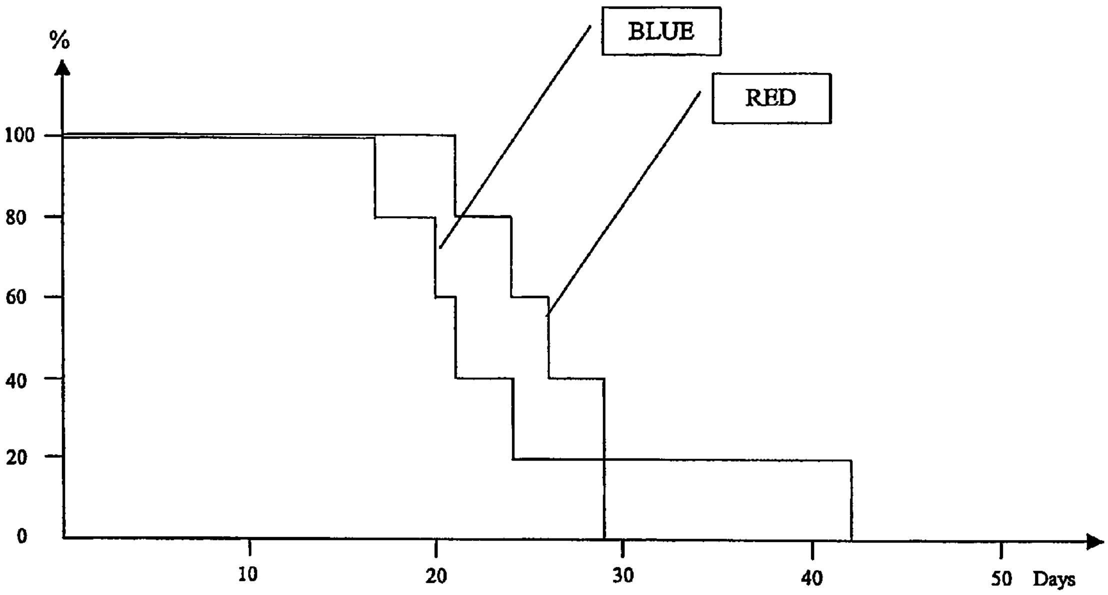

FIG. 38. B16-Fve transfectant has longer survival rate as comparing with B16-vec transfectant. Two groups of C56BL/6J female mice are inoculated either with $5\times10^4$ of B16-Fve (Red line) or $5\times10^4$ of B16-vec (Blue line) transfectants in the right flank. Transfectant melanoma solid tumor is established at days 5-7. The fatal rates of mice are recorded and presented as survival curve.

Figure 39:
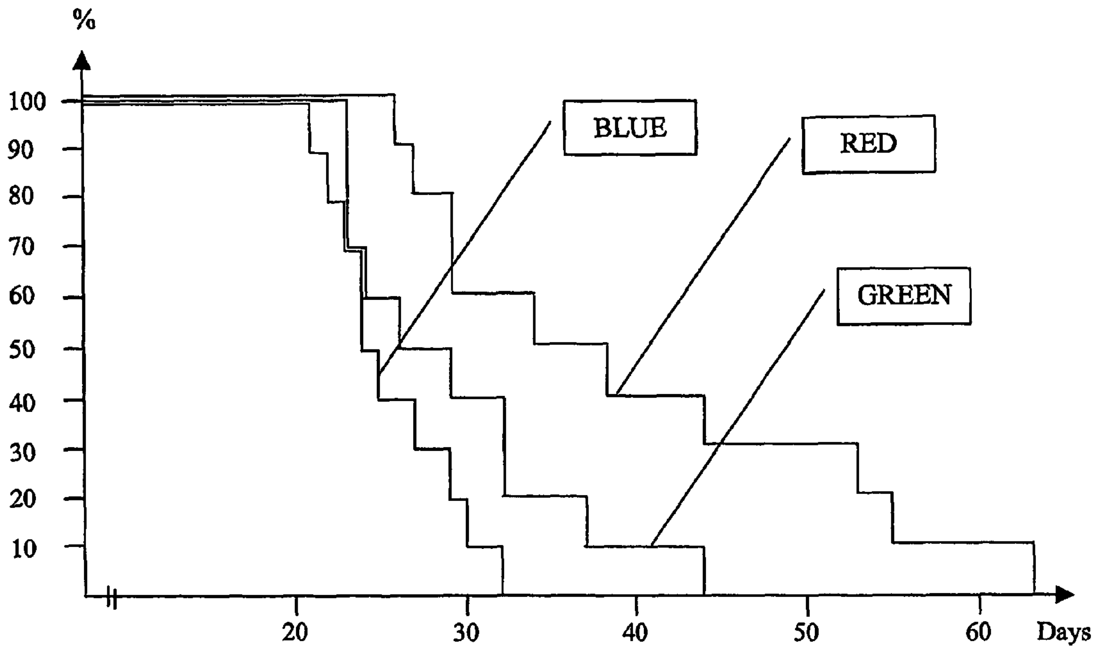

FIG. 39. Combined DNA vaccination and Fve gene-transduced melanoma cells synergizes the extension of life span in solid tumor-established mice. C57BL/6J mice are separated into three groups and each group consisted of ten mice. Mice are inoculated with $5\times10^4$ of B16-F1 tumor transfectants in the dorsal back. Tumor formation is observed at day 5-7. 100 μg of pCIneo-fve plasmid DNA is intramuscularly injected at the right and left tribilis muscle of C57BL/6J at day −77, day −35 and day −21. Mice are subcutaneously injected with $5\times10^4$ of B16-Fve transfectants Red line) and B16-vec transfectant (Green Line) at day 0, respectively. 100 μg of pCIneo plasmid DNA is operated as same experimental procedure and mice are subcutaneously injected with $5\times10^4$ of B16-vec transfectants as negative control (Blue line).

Figure 40:
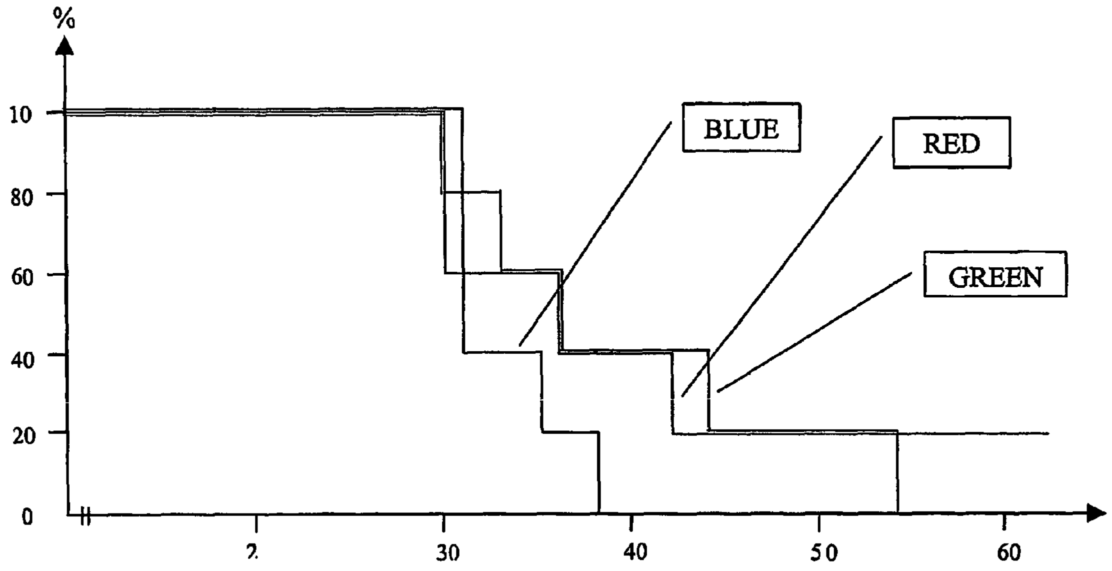

FIG. 40. Strategy of oral primed with Fve protein and intramuscular boosted with plasmid DNA could extend the survival rate of mice with lung metastasis. Two groups of five C57BL/6J mice are given with 10 mg/ml of Fve protein in the drinking water at day −35, −28 and −21, and each water providing is maintained consecutively for one week. Mice are intravenously injected with $2\times10^4$ of B16-F1 (wild type) melanoma cells at day 0. One week after, mice are intramuscularly injected with 100 μg of pCIneo-fve plasmid DNA into the right and left tribilis muscle, respectively. The mixture of $5\times10^4$ of B16-Fve cells lysate plus 10 μg of Fve protein (Red line) or 10 μg of Fve protein alone (Green line) are subcutaneously injected to mice at the following three weeks. Negative control group of mice received same amount of 1×PBS in the drinking water, intravenously injected with $2\times10^4$ of B16-F1 melanoma cells, followed by intramuscularly injected with plasmid DNA vector pCIneo, and finally subcutaneously injected with B16-vec cells lysate plus 1×PBS (Blue line).

Figure 40B:
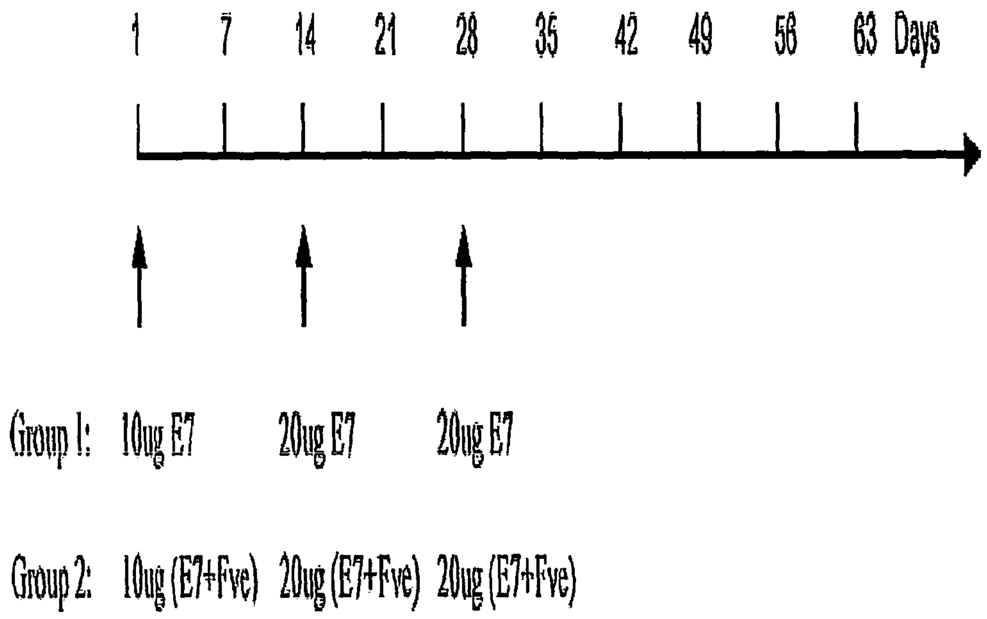

FIG. 40B is a shematic representation of the protocol used in the experiments described in Example 25A.

Figure 40C:
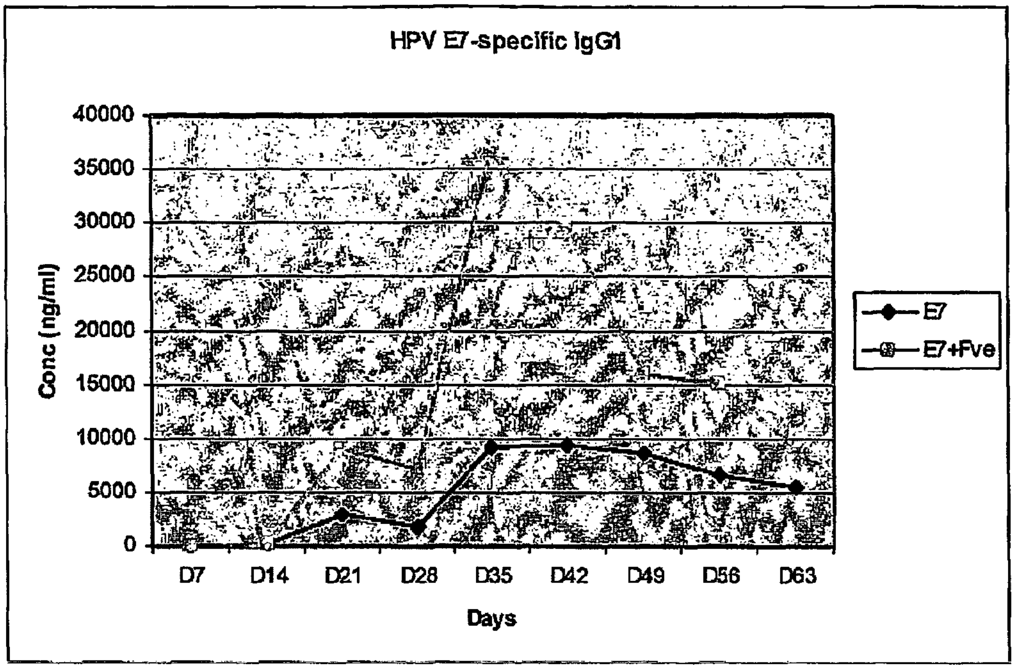
Figure 40C:
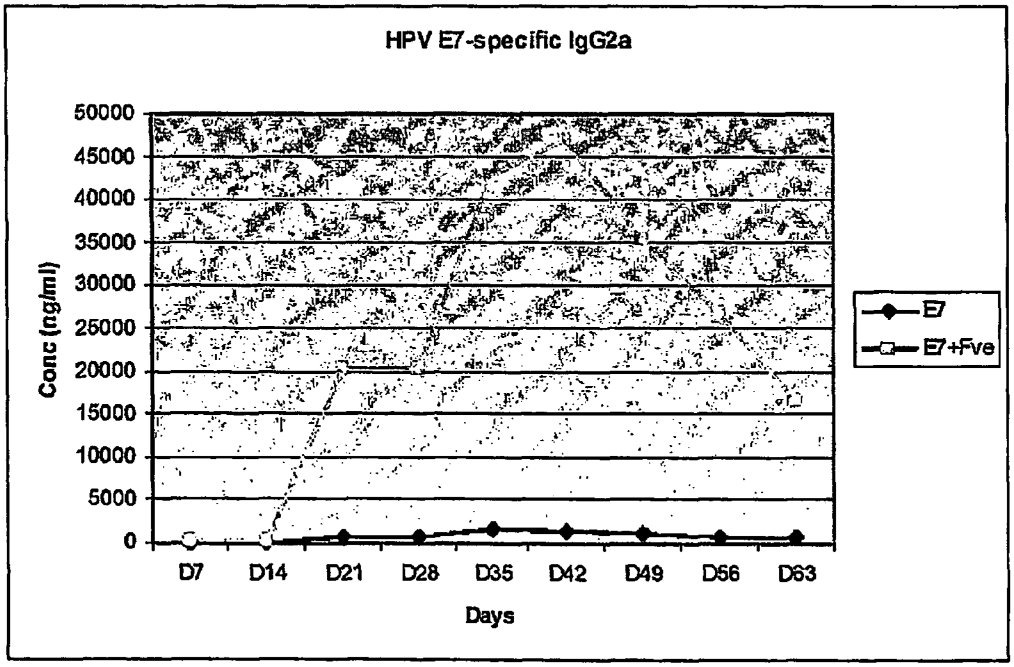

FIG. 40C is a graph showing the results of Example 25A.

Figure 41:
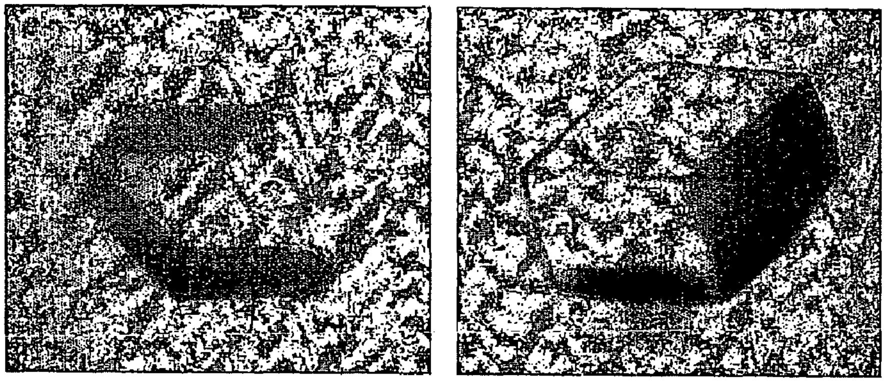

FIG. 41. Two representative crystals of Fve. Tetragonal crystal is grown in 2% PEG 400, 2.0 M Ammonium Sulfate; 0.1 M Tris-HCl pH 8.5. The crystal dimensions are approximately 1 mm×0.9 mm×0.5 mm.

Figure 42:
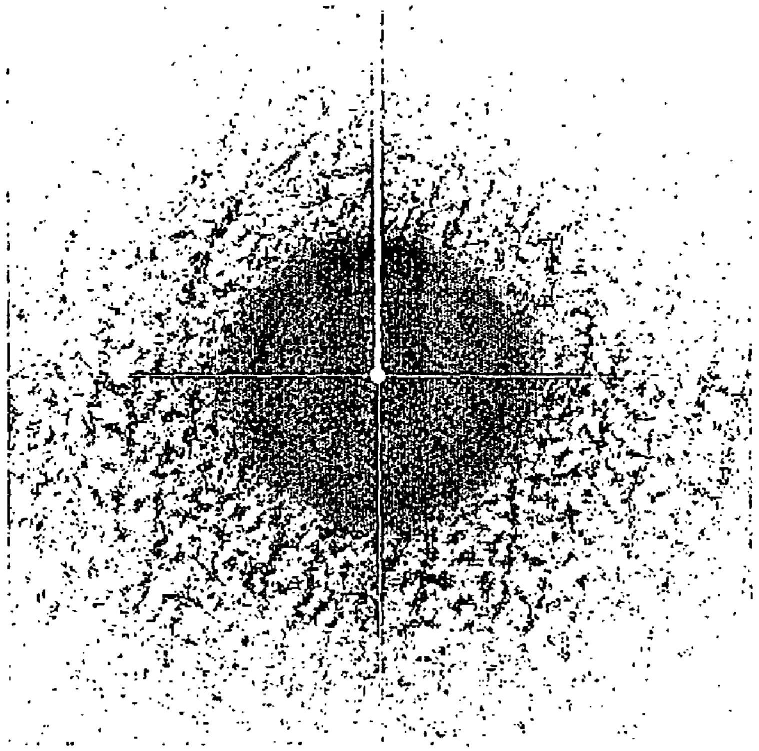
Figure 43:
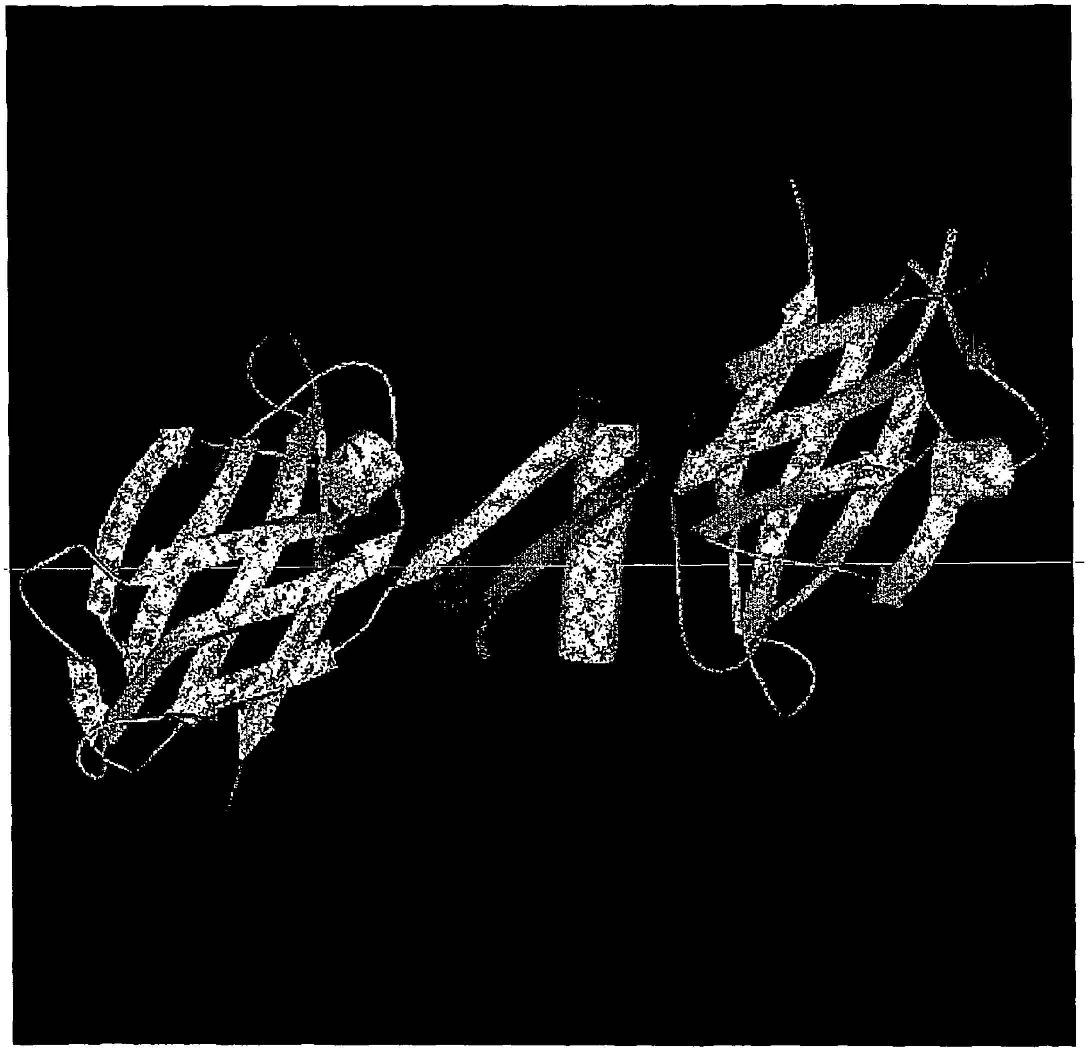

FIG. 42. 1° oscillation image of Fve crystal. The edge of the image corresponds to a resolution of 1.4 Å. Image displayed with Mosflm/Scala.

FIGS. 43, 44A, 44B, 44C, 45A and 45B show structures of Fve.

SEQUENCES

Appendix A shows the nucleic acid and/or aminio acid sequences of the deletiion mutants Fve D6-18, Fve D19-33, Fve D34-46, Fve D47-60, Fve D61-72, Fve D73-84, Fve D85-97, Fve D98-106, Fve D107-115, Fve D61-97, Fve p55-100.

Appendix A also shows the nucleic acid and/or aminio acid sequences of the subsitution mutants Fve R27A, Fve G28A, Fve T29A, as well as the fusion proteins Blo t 5-Fve (two-in-one chimeric wild type), Blo t 5-Fve R27A (two-in-one chimeric mutant), Blo t 5-Fve T29A (two-in-one chimeric mutant), Der p 2-Fve R27A (two-in-one chimeric mutant), Der p 2-Fve T29A(two-in-one chimeric mutant), Blo t 5-Der p 2-Fve R27A(three-in-one chimeric mutant).

Appendix A also shows the nucleic acid and/or aminio acid sequences of the Fusion Proteins of Viral Antigen and Fve, HPV E7-FveT29A and HCV Core23-FveT29A, as well as the nucleic acid and/or aminio acid sequences of the Fusion Proteins of Tumor-Associated Antigen and Fve, MAGE3-FveT29A, MART1-FveT29A and CEA-FveT29A.

Appendix A also shows the sequences of the primers Fd6-18F (36 mer), Fd6-18R (36 mer), Fd19-33F(36 mer), Fd19-33R(36 mer), Fd34-46F(36 mer), Fd34-46R(36 mer), Fd47-60F(36 mer), Fd47-60R(36 mer), Fd61-72F(36 mer), Fd61-72R(36 mer), Fd73-84F(36 mer), Fd73-84R(36 mer), Fd85-97F(36 mer), Fd85-97R(36 mer), Fd98-106F (36 mer), Fd98-106R (36 mer), Fd107-115R(39 mer), d(61-97)-F(36mer), d(61-97)-R(36mer), [Fv55-100]-F(48mer), [Fv55-100]-R (42mer), F(R27A)-F (27 mer), F(R27A)-R (27 mer), F(G28A)-F (27 mer), F(G28A)-R (27 mer), F(129A)-F (27 mer), F(T29A)-R (27 mer), Bt5Fv-F (36mer), Bt5Fv-R (36mer), Dp2Fv-F (36mer), Dp2Fv-R (36mer), Bt5Dp2-F (36mer), Bt5Dp2-R(36mer).

Appendix B shows the sequences of fragments of Fve, which comprise all or part of the RGT motif.

Appendix C shows the crystal coordinates of Fve protein.

The methods and compositions described here may suitably employ any one or more of the sequences shown in the Appendices.

DETAILED DESCRIPTION

We have identified an immunoregulatory protein, designated as native Fve, from *Flammulina velutipes*. The cDNA encoding Fve protein has been isolated and biologically active recombinant Fve has been successfully produced in *E. coli.*

Our studies show that native Fve is capable of inducing high levels of expression of IFN-γ, TNF-α and ICAM-I gene expression in activated human T -and NK cells. It also up-regulates transcription factors IRF-I and NF-κB (c-Rel), but down-regulates 11.-4. In allergic murine model, mice treated with Der p 2, a major house dust mite allergen from *Dermatophagoides pteronyssinus*, plus native Fve show a significant boost of Der p 2-specific IgG2a production. Native Fve also reduces wheel and erythematic flare formation on Der p 2 skin prick test-positive human subject. We also find that fragments, homologues, variants derivatives of native Fve disclosed here (termed "Fve polypeptides") as well as nucleic acids encoding these, also have such activities.

Furthermore, we show in the Examples that Fve polypeptide and native Fve polypeptide is a potent adjuvant that can be codelivered with specific allergens for desensitization of allergic disorders such as asthma, rhinitis and atopic dermatitis. In addition, Fve selectively induces polarization of NK (natural killer) cells and cytotoxic $CD8^+$ T cells in vitro and in vivo. We therefore disclose anti-cancer therapies and methods which employ these immunostimulatory or immunomodulatory effects. We disclose in vivo animal studies which show that this protein prolongs survival rate in solid tumor-transplanted mice.

Fve and its polypeptides may therefore be used for any application where up-regulation of a immune response is desired or necessary. Fve polypeptides may in particular be used in therapy, for example for the treatment of diseases such as infections, cancer, etc.

We further disclose a combination of Fve polypeptide or native Fve, with an allergen, for example in the form of a fusion protein. Such a combination is able to counteract an established allergic reaction. Combinations of Fve polypeptide or native Fve with a tumour associated protein or viral oncogenic protein may be used to prevent or treat cancer, or specifically for preventing tumour progression.

We disclose immunotherapeutic methods and reagents for allergy and virus infections, which take advantage of these immunomodulatory effects of native Fve and Fve polypeptides. We also disclose methods of treatment or prevention of a cancer, tumour, neoplasm or cancerous cell, by use of the Fve polypeptides and nucleic acids described here. DNA vaccines, expression vectors, host cells and transgenic organisms comprising such Fve nucleic acids, or a fragment, homologue, variant or derivative thereof, may also be used for such a purpose. In general, any use of a Fve polypeptide described here may employ a nucleic acid encoding such, or a DNA vaccine, expression vector, host cell and transgenic organism comprising such, and the disclosure should be read accordingly.

We also show that native Fve stimulates gene expression of human IFN-γ, TNF-α, IL-1β, IL-2, IRF-1, c-Rel, $Bcl-X_L$, ICAM-1 and iNOS. In addition, we show that Fve up-regulates a novel subset of $CD8^+$ T cells ($CD3^+$ $CD8^+$ $CD18^{+bright}$), and induces NK cell and $CD8^+$ T cell proliferation in vivo. Animal studies show that Fve prolongs survival rate of tumor-inoculated mice treated with Fve gene and protein We disclose methods and reagents for cancer therapy using the Fve gene, protein and products, for example in the form of cell-based vaccines for cancers.

Fve may be used in vitro to stimulate the proliferation of $CD3^+$ $CD8^{+bright}$ $CD18^{+bright}$ populations, and the amplified populations may then be administered to the individual in need of treatment Thus, while it is possible to stimulate $CD3^+$ $CD8^{+bright}$ $CD18^{+bright}$ populations in the context of the body of the animal, it will be apparent that such amplification is also possible in vitro. We therefore disclose the use of Fve polypeptides to stimulate such cells in vitro. Such amplified populations may then be infused into or otherwise administered to the individual in need of treatment. The starting cell population may come from another individual, but preferably it is derived from the same individual who requires treatment.

We also disclose a crystal of FIP, which has been crystallised for the first time. Such a crystal may be used for modelling, or designing ligands which may interact with Fve. The crystal or model may be stored on a computer, or on a computer readable medium, and manipulated using methods known to the skilled person. A computer readable medium comprising a data representation of the crystal is therefore provided.

The practice of the present invention will employ, unless otherwise indicated, conventional techniques of chemistry, molecular biology, microbiology, recombinant DNA and immunology, which are within the capabilities of a person of ordinary skill in the art. Such techniques are explained in the literature. See, for example, J. Sambrook, E. F. Fritsch, and T. Maniatis, 1989, *Molecular Cloning: A Laboratory Manual*, Second Edition, Books 1-3, Cold Spring Harbor Laboratory Press; Ausubel, F. M. et al. (1995 and periodic supplements; *Current Protocols in Molecular Biology*, ch. 9, 13, and 16, John Wiley & Sons, New York, N.Y.); B. Roe, J. Crabtree, and A. Kahn, 1996, *DNA Isolation and Sequencing: Essential Techniques*, John Wiley & Sons; J. M. Polak and James O'D.

McGee, 1990, *In Situ Hybridization: Principles and Practice*; Oxford University Press; M. J. Gait (Editor), 1984, *Oligonucleotide Synthesis: A Practical Approach*, Irl Press; and, D. M. J. Lilley and J. E. Dahlberg, 1992, *Methods of Enzymology: DNA Structure Part A: Synthesis and Physical Analysis of DNA* Methods in Enzymology, Academic Press. Each of these general texts is herein incorporated by reference.

Native Fve

The terms "native Fve polypeptide" or "native Fve protein", as used in this document, should be taken to refer to the immunoregulatory protein Fve from *Flammulina velutipes*, preferably in isolated form. The term "wild type Fve" should be understood to be synonymous with "native" Fve; furthermore, the term "nFve" is sometimes used to refer to native Fve.

Preferably, "native" Fve has an amino acid sequence set out as as GenBank accession numbers: S69147 immunomodulatory protein FIP-fve—golden needle mushroom gi|7438667|pir||S69147[7438667] and P80412 IMMUNOMODULATORY PROTEIN FIP-FVE gi|729544|sp|P80412|FVE_FLAVE[729544]. A polypeptide and nucleic acid sequence of "native" or "wild type" Fve is also shown in Appendix A, and the term "native FIP" preferably refers to a polypeptide or nucleic acid, as the case may be, having such sequence. Methods of isolating the "native" Fve gene and protein from *Flammulina velutipes* are known in the art, and are also set out in the Examples.

A "native" Fve may comprise a methionine residue at the N terminus; however, a native Fve may include versions which lack the initial methionine. The nucleic acid sequence which encodes such a native Fve may therefore comprise or not comprise an initial ATG codon.

As noted above, we have identified certain previously unknown properties of native Fve, including immunomodulatory and stimulatory properties, and one aspect of the invention is directed to such new uses of native Fve nucleic acid and native Fve polypeptide. These are disclosed in further detail below.

It should be understood, therefore, that the invention preferably does not include wild-type or native Fve protein; however, it does encompass the uses of this in immunomodulation, enhancing immune response and in allergy and cancer treatment. Furthermore, we disclose a fusion protein comprising gluthathione S transferase (GST) and native Fve; such a fusion protein is shown in the Examples to have the beneficial properties of native Fve itself. The sequence of GST-Fve is shown in Appendix A. Therefore, the invention includes this GST-Fve fusion protein (also referred to as rGST-Fve and GST-Fve (wild type)), and nucleic acids encoding it.

We further disclose a nucleic acid sequence encoding native Fve, termed here a "native Fve nucleic acid sequence". The Examples describe the cloning and isolation of a cDNA encoding native Fve protein. The sequence of this is set out as "Fve (Wild type)" in Appendix A. Preferably such a sequence is in isolated form.

Fve Polypeptides

Additionally, we have identified various fragments, homologues, variants and derivatives of "native Fve", which are previously unknown. Such fragments, homologues, variants and derivatives are referred to here as "Fve polypeptides" (as contrasted with "native Fve polypeptides"). We disclose such Fve polypeptides, and their uses.

It will be apparent that the terms "Fve" and "Fve polypeptide", as they is used in this document, preferably exclude the wild type or native Fve protein or gene encoding this, and includes only molecules derived from native Fve, being fragments, homologues, variants and derivatives of native Eve (i.e., Fve polypeptides).

The Fve polypeptides are preferably are at least as biologically active as native Fve. However, they may have 10%, 20%, 30%, 40%, 50%, 60%, 70%, 80%, 90%, 95% or more of the biological activity of native Fve, for example as assayed by any of the tests set out below. As used herein "biologically active" refers to a sequence having a similar structural function (but not necessarily to the same degree), and/or similar regulatory function (but not necessarily to the same degree), and/or similar biochemical function (but not necessarily to the same degree) of the naturally occurring sequence.

"Fve polypeptides" preferably comprise at least one biological activity of native Fve. By "biological activity" in relation to Fve, we refer to at least one of the following activities: up-regulation of expression of Th1 cytokines, preferably IFN-γ and TNF-α, down-regulation of expression of Th2 cytokines, preferably IL-4 and IL-13, hemagglutination activity, cell aggregation activity, lymphocyte aggregation activity, lymphoproliferation activity, up-regulation of expression of IL-2, IFN-γ, TNF-α, but not IL-4 in $CD3^+$ T cells, interaction with T and NK cells, adjuvant activity, stimulation of $CD3^+$ $CD16^+$ $CD56^+$ natural killer (NK) T cells, and up-regulation of expression of allergen specific IgG2a antibody. Further biological activities preferably comprised by Fve polypeptides as described here include prevention of systemic anaphylactic reactions and/or decreased footpad edema, preferably as assayed using the Arthus reaction (Ko et al, 1995). In particular, Fve polypeptides preferably comprise at least some of useful properties, preferably medically or therapeutically useful properties, of native Fve.

Assays for each of these activities are set out in the Examples, and preferably, whether a Fve polypeptide comprises a "biological activity" of Fve is to be assessed according to the relevant assay set out in the Examples.

Preferably, Fve polypeptides comprise at least one or more of the biological activities for the relevant use, preferably use as an immunomodulator, or for upregulating immune response. Preferably, they comprise at least one or more of the biological activities which enable use as a cancer therapy or allergy therapy.

Preferably, Fve polypeptides comprise two or more biological activities of native Fve, preferably substantially all the biological activities of native Fve.

We show in the Examples that the sequence RGT at positions 27-29 of the native Fve polypeptide sequence plays a crucial role in the biological activity of native Fve. In particular, the RGT is shown to mediate the ability of native Fve to cause lymphocyte aggregation and adhesion. This sequence is also shown to mediate lymphoproliferation, and stimulation of IL-2, IFN-γ and TNF-γ secretion in T cells, preferably $CD3^+$ T cells.

Accordingly, in preferred embodiments, the Fve polypeptides comprise at least one, two or all three of the RGT residues (or a functional variant such as RGD) at or about a position corresponding to position 28 of the native Fve polypeptide. By functional variant of RGT, we mean any change in the residues of RGT (or a sequence surrounding it) which does not substantially abolish its function, preferably its function in mediating the activities set out above. Preferably, the Fve polypeptide comprises between 2 to 50, more preferably between 2 to 40, more preferably between 2 to 30, most preferably between 2 to 20 residues of amino acid sequence flanking the glycine residue corresponding to position 28 of native Fve. More preferably, the Fve polypeptide comprises the sequence RGT or the sequence RGD.

However, we show that mutations of R at position 27, as well as mutations of T at position 29, have advantageous effects, in that they independently increase activity of a Fve polypeptide comprising either or both of these mutations. Furthermore, each of the mutations, or in combination, have the potential to increase the solubility of the Fve polypeptide comprising it or them. One, each or both of R27 and T29 may therefore be independently mutated advantageously, by substitution or deletion.

In preferred embodiments, the or each of R27 and T29 are mutated by substitution. The R27 and/or T29 may be substituted by any other residue, but preferably a neutral residue such as G or A. We therefore disclose Fve polypeptides in which R at position 27 is changed to another residue, for example, Fve polypeptides in which R27 is mutated to A, i.e., a Fve polypeptide comprising R27A. We therefore disclose Fve polypeptides in which T at position 29 is changed to another residue, for example, Fve polypeptides in which T29 is mutated to A, i.e., a Fve polypeptide comprising T29A.

Combinations are also possible; hence we disclose Fve polypeptides in which R at position 27 and T at position 29 are independently changed to one or more other residues. For example, we disclose Fve polypeptides in which R27 is mutated to A, and T29 is mutated to A, i.e., a Fve polypeptide comprising R27A and T29A. As noted above, the polypeptide may comprise between 2 to 50, 40, 30 or preferably 20 residues of amino acid flanking the glycine residue at position 28 of native Fve.

Fve polypeptides may comprise fragments of native Fve. For example, Fve D6-18, Fve D19-33, Fve D34-46, Fve D47-60, Fve D61-72, Fve D73-84, Eve D85-97, Fve D98-106, Fve D107-115, Fve D61-97, and Fvep55-100. Fusion proteins comprising these deletion fragments and GST are also disclosed. Fve polypeptides may comprise substitutions, including FveR27A, FveG28A and FveT29A. Further examples of Fve polypeptides are shown in Appendix B, each of which includes at least a portion of the RGT sequence (preferably the whole of the RGT sequence) discussed above. Preferably, the length of such a fragment is 9 amino acid residues or more, e.g., fragment numbers 34-403.

Fve polypeptides may comprise fusion proteins, particularly fusion proteins between an allergen and a Fve polypeptide as defined here. Such allergen-immunomodulator combinations include Blo t 5-Fve(two-in-one chimeric wild type), Blo t 5-FveR27A (two-in-one chimeric mutant), Blo t 5-FveT29A (two-in-one chimeric mutant), Der p 2-FveR27A (two-in-one chimeric mutant), Der p 2-FveT29A (two-in-one chimeric mutant) and Blo t 5-Der p 2-FveR27A (three-in-one chimeric mutant).

Fragments, homologues, variants and derivatives of each of these Fve polypeptides are also included.

The Fve polypeptides may be made by biochemical methods, for example, protein digestion of native Eve, or preferably by recombinant DNA methods as known in the art. Accordingly, it will be understood that Eve polypeptides specifically include recombinant Fve polypeptides. For example, we disclose in the Examples successful production in *E. coli* of biologically active recombinant Fve polypeptide.

The Fve polypeptides disclosed also include homologous sequences obtained from any source, for example related viral/bacterial proteins, cellular homologues and synthetic peptides, as well as variants or derivatives thereof. Thus polypeptides also include those encoding homologues of Fve from other species including other microorganisms. Furthermore, homologues from higher animals such as mammals (e.g. mice, rats or rabbits), especially primates, more especially humans are also included.

Homologues

In the context of this document, a "homologous" sequence is taken to include an amino acid sequence which is at least 15, 20, 25, 30, 40, 50, 60, 70, 80 or 90% identical, preferably at least 95 or 98% identical at the amino acid level over at least 10, 15, 20, 25, 30, 40, 50, 60, 70, 80, 90, 100, 110 or 114 amino acids with the sequence of native Fve shown as "Fve (Wild type)" in Appendix A. In particular, homology should typically be considered with respect to those regions of the sequence known to be essential for protein function rather than non-essential neighbouring sequences. This is especially important when considering homologous sequences from distantly related organisms.

Although homology can also be considered in terms of similarity (i.e. amino acid residues having similar chemical properties/functions), in the context of the present document it is preferred to express homology in terms of sequence identity.

Homology comparisons can be conducted by eye, or more usually, with the aid of readily available sequence comparison programs. These publicly and commercially available computer programs can calculate % homology between two or more sequences.

% homology may be calculated over contiguous sequences, i.e. one sequence is aligned with the other sequence and each amino acid in one sequence directly compared with the corresponding amino acid in the other sequence, one residue at a time. This is called an "ungapped" alignment. Typically, such ungapped alignments are performed only over a relatively short number of residues (for example less than 50 contiguous amino acids).

Although this is a very simple and consistent method, it fails to take into consideration that, for example, in an otherwise identical pair of sequences, one insertion or deletion will cause the following amino acid residues to be put out of alignment, thus potentially resulting in a large reduction in % homology when a global alignment is performed. Consequently, most sequence comparison methods are designed to produce optimal alignments that take into consideration possible insertions and deletions without penalising unduly the overall homology score. This is achieved by inserting "gaps" in the sequence alignment to try to maximise local homology.

However, these more complex methods assign "gap penalties" to each gap that occurs in the alignment so that, for the same number of identical amino acids, a sequence alignment with as few gaps as possible—reflecting higher relatedness between the two compared sequences—will achieve a higher score than one with many gaps. "Affine gap costs" are typically used that charge a relatively high cost for the existence of a gap and a smaller penalty for each subsequent residue in the gap. This is the most commonly used gap scoring system. High gap penalties will of course produce optimised alignments with fewer gaps. Most alignment programs allow the gap penalties to be modified. However, it is preferred to use the default values when using such software for sequence comparisons. For example when using the GCG Wisconsin Bestfit package (see below) the default gap penalty for amino acid sequences is −12 for a gap and −4 for each extension.

Calculation of maximum % homology therefore firstly requires the production of an optimal alignment, taking into consideration gap penalties. A suitable computer program for carrying out such an alignment is the GCG Wisconsin Bestfit package (University of Wisconsin, U.S.A; Devereux et al., 1984, Nucleic Acids Research 12:387). Examples of other software than can perform sequence comparisons include, but are not limited to, the BLAST package (see Ausubel et al., 1999 ibid—Chapter 18), FASTA (Atschul et al., 1990, J. Mol.

Biol., 403-410) and the GENEWORKS suite of comparison tools. Both BLAST and FASTA are available for offline and online searching (see Ausubel et al., 1999 ibid, pages 7-58 to 7-60). However it is preferred to use the GCG Bestfit program.

Although the final % homology can be measured in terms of identity, the alignment process itself is typically not based on an all-or-nothing pair comparison. Instead, a scaled similarity score matrix is generally used that assigns scores to each pairwise comparison based on chemical similarity or evolutionary distance. An example of such a matrix commonly used is the BLOSUM62 matrix—the default matrix for the BLAST suite of programs. GCG Wisconsin programs generally use either the public default values or a custom symbol comparison table if supplied (see user manual for further details). It is preferred to use the public default values for the GCG package, or in the case of other software, the default matrix, such as BLOSUM62.

Advantageously, the BLAST algorithm is employed, with parameters set to default values. The BLAST algorithm is described in detail at http://www.ncbi.nih.gov/BLAST/blast_help.html, which is incorporated herein by reference. The search parameters are defined as follows, can be advantageously set to the defined default parameters.

Advantageously, "substantial identity" when assessed by BLAST equates to sequences which match with an EXPECT value of at least about 7, preferably at least about 9 and most preferably 10 or more. The default threshold for EXPECT in BLAST searching is usually 10.

BLAST (basic Local Alignment Search Tool) is the heuristic search algorithm employed by the programs blastp, blastn, blastx, tblastn, and tblastx; these programs ascribe significance to their findings using the statistical methods of Karlin and Altschul (Karlin and Altschul 1990, *Proc. Natl. Acad. Sci. USA* 87:2264-68; Karlin and Altschul, 1993, *Proc. Natl. Acad. Sci. USA* 90:5873-7; see http://www.ncbi.nih.gov/BLAST/blast_help.html) with a few enhancements. The BLAST programs are tailored for sequence similarity searching, for example to identify homologues to a query sequence. For a discussion of basic issues in similarity searching of sequence databases, see Altschul et al (1994) Nature Genetics 6:119-129.

The five BLAST programs available at http://www.ncbi.nlm.nih.gov perform the following tasks: blastp—compares air amino acid query sequence against a protein sequence database; blastn—compares a nucleotide query sequence against a nucleotide sequence database; blastx—compares the six-frame conceptual translation products of a nucleotide query sequence (both strands) against a protein sequence database; tblastn—compares a protein query sequence against a nucleotide sequence database dynamically translated in all six reading frames (both strands); tblastx—compares the six-frame translations of a nucleotide query sequence against the six-frame translations of a nucleotide sequence database.

BLAST uses the following search parameters:

HISTOGRAM—Display a histogram of scores for each search; default is yes. (See parameter H in the BLAST Manual).

DESCRIPTIONS—Restricts the number of short descriptions of matching sequences reported to the number specified; default limit is 100 descriptions. (See parameter V in the manual page).

EXPECT—The statistical significance threshold for reporting matches against database sequences; the default value is 10, such that 10 matches are expected to be found merely by chance, according to the stochastic model of Karlin and Altschul (1990). If the statistical significance ascribed to a match is greater than the EXPECT threshold, the match will not be reported. Lower EXPECT thresholds are more stringent, leading to fewer chance matches being reported. Fractional values are acceptable. (See parameter E in the BLAST Manual).

CUTOFF—Cutoff score for reporting high-scoring segment pairs. The default value is calculated from the EXPECT value (see above). HSPs are reported for a database sequence only if the statistical significance ascribed to them is at least as high as would be ascribed to a lone HSP having a score equal to the CUTOFF value. Higher CUTOFF values are more stringent, leading to fewer chance matches being reported. (See parameter S in the BLAST Manual). Typically, significance thresholds can be more intuitively managed using EXPECT.

ALIGNMENTS—Restricts database sequences to the number specified for which high-scoring segment pairs (HSPs) are reported; the default limit is 50. If more database sequences than this happen to satisfy the statistical significance threshold for reporting (see EXPECT and CUTOFF below), only the matches ascribed the greatest statistical significance are reported, (See parameter B in the BLAST Manual).

MATRIX—Specify an alternate scoring matrix for BLASTP, BLASTX, TBLASTN and TBLASTX. The default matrix is BLOSUM62 (Henikoff & Henikoff, 1992). The valid alternative choices include: PAM40, PAM120, PAM250 and IDENTITY. No alternate scoring matrices are available for BLASTN; specifying the MATRIX directive in BLASTN requests returns an error response.

STRAND—Restrict a TBLASTN search to just the top or bottom strand of the database sequences; or restrict a BLASTN, BLASTX or TBLASTX search to just reading frames on the top or bottom strand of the query sequence.

FILTER—Mask off segments of the query sequence that have low compositional complexity, as determined by the SEG program of Wootton & Federhen (1993) Computers and Chemistry 17:149-163, or segments consisting of short-periodicity internal repeats, as determined by the XNU program of Claverie & States (1993) Computers and Chemistry 17:191-201, or, for BLASTN, by the DUST program of Tatusov and Lipman (see http://www.ncbi.nlm.nih.gov). Filtering can eliminate statistically significant but biologically uninteresting reports from the blast output (e.g., hits against common acidic-, basic- or proline-rich regions), leaving the more biologically interesting regions of the query sequence available for specific matching against database sequences.

Low complexity sequence found by a filter program is substituted using the letter "N" in nucleotide sequence (e.g., "NNNNNNNNNNNNN") (SEQ ID NO: 1) and the letter "X" in protein sequences (e.g., "XXXXXXXXX") (SEQ ID NO: 2).

Filtering is only applied to the query sequence (or its translation products), not to database sequences. Default filtering is DUST for BLASTN, SEG for other programs.

It is not unusual for nothing at all to be masked by SEG, XNU, or both, when applied to sequences in SWISS-PROT, so filtering should not be expected to always yield an effect. Furthermore, in some cases, sequences are masked in their entirety, indicating that the statistical significance of any matches reported against the unfiltered query sequence should be suspect.

NCBI-gi—Causes NCBI gi identifiers to be shown in the output, in addition to the accession and/or locus name.

Most preferably, sequence comparisons are conducted using the simple BLAST search algorithm provided at http:// www.ncbi.nlm.nih.gov/BLAST. In some embodiments, no gap penalties are used when determining sequence identity.

Once the software has produced an optimal alignment, it is possible to calculate % homology, preferably % sequence identity. The software typically does this as part of the sequence comparison and generates a numerical result.

Variants and Derivatives

The terms "variant" or "derivative" in relation to the amino acid sequences disclosed here includes any substitution of, variation of, modification of, replacement of, deletion of or addition of one (or more) amino acids from or to the sequence providing the resultant amino acid sequence retains substantially the same activity as the unmodified sequence. Preferably, the modified sequence has at least one biological activity as the unmodified sequence, preferably all the biological activities of the unmodified sequence. Preferably, the "variant" or "derivative" has at least one biological activity of native Fve, as described above.

Polypeptides having the amino acid sequence shown in the description and Examples, or fragments or homologues thereof may be modified for use in the methods and compositions described here. Typically, modifications are made that maintain the biological activity of the sequence. Amino acid substitutions may be made, for example from 1, 2 or 3 to 10, 20 or 30 substitutions provided that the modified sequence retains the biological activity of the unmodified sequence. Alternatively, modifications may be made to deliberately inactivate one or more functional domains of the polypeptides described here. Functional domains of native Fve include the a helix at the N terminus, any of the six β helices, as well as the "loop-like" structures at the N and C termini. Preferably, the functional domain of native Fve comprises the N-terminus helix and the loop/strand, which are essential for protein dimerization.

Amino acid substitutions may include the use of non-naturally occurring analogues, for example to increase blood plasma half-life of a therapeutically administered polypeptide.

Conservative substitutions may be made, for example according to the Table below. Amino acids in the same block in the second column and preferably in the same line in the third column may be substituted for each other:

| | | |
|---|---|---|
| ALIPHATIC | Non-polar | G A P |
| | | I L V |
| | Polar - uncharged | C S T M |
| | | N Q |
| | Polar - charged | D E |
| | | K R |
| AROMATIC | | H F W Y |

Polypeptides also include fragments of the full length sequence of native Fve, or any of the Fve polypeptides disclosed here. Preferably fragments comprise at least one epitope. Methods of identifying epitopes are well known in the art. Fragments will typically comprise at least 6 amino acids, more preferably at least 10, 20, 30, 50 or 100 amino acids.

Fve polypeptides, fragments, homologues, variants and derivatives, are typically made by recombinant means, for example as described below in the Examples. However they may also be made by synthetic means using techniques well known to skilled persons such as solid phase synthesis. The proteins may also be produced as fusion proteins, for example to aid in extraction and purification. Examples of fusion protein partners include glutathione-S-transferase (GST), 6×His (SEQ ID NO: 488), GAL4 (DNA binding and/or transcriptional activation domains) and β-galactosidase. It may also be convenient to include a proteolytic cleavage site between the fusion protein partner and the protein sequence of interest to allow removal of fusion protein sequences. Preferably the fusion protein will not hinder the function of the protein of interest sequence. Proteins may also be obtained by purification of cell extracts from animal cells.

The Fve polypeptides, variants, homologues, fragments and derivatives disclosed here may be in a substantially isolated form. It will be understood that such polypeptides may be mixed with carriers or diluents which will not interfere with the intended purpose of the protein and still be regarded as substantially isolated. A Fve variant, homologue, fragment or derivative may also be in a substantially purified form, in which case it will generally comprise the protein in a preparation in which more than 90%, e.g. 95%, 98% or 99% of the protein in the preparation is a protein.

The Fve polypeptides, variants, homologues, fragments and derivatives disclosed here may be labelled with a revealing label. The revealing label may be any suitable label which allows the polypeptide, etc to be detected. Suitable labels include radioisotopes, e.g. $^{125}I$, enzymes, antibodies, polynucleotides and linkers such as biotin. Labelled polypeptides may be used in diagnostic procedures such as immunoassays to determine the amount of a polypeptide in a sample. Polypeptides or labelled polypeptides may also be used in serological or cell-mediated immune assays for the detection of immune reactivity to said polypeptides in animals and humans using standard protocols.

A Fve polypeptide, variant, homologue, fragment or derivative disclosed here, optionally labelled, my also be fixed to a solid phase, for example the surface of an immunoassay well or dipstick. Such labelled and/or immobilised polypeptides may be packaged into kits in a suitable container along with suitable reagents, controls, instructions and the like. Such polypeptides and kits may be used in methods of detection of antibodies to the polypeptides or their allelic or species variants by immunoassay.

Immunoassay methods are well known in the art and will generally comprise: (a) providing a polypeptide comprising an epitope bindable by an antibody against said protein; (b) incubating a biological sample with said polypeptide under conditions which allow for the formation of an antibody-antigen complex; and (c) determining whether antibody-antigen complex comprising said polypeptide is formed.

The Fve polypeptides, variants, homologues, fragments and derivatives disclosed here may be used in in vitro or in vivo cell culture systems to study the role of their corresponding genes and homologues thereof in cell function, including their function in disease. For example, truncated or modified polypeptides may be introduced into a cell to disrupt the normal functions which occur in the cell. The polypeptides may be introduced into the cell by in situ expression of the polypeptide from a recombinant expression vector (see below). The expression vector optionally carries an inducible promoter to control the expression of the polypeptide.

The use of appropriate host cells, such as insect cells or mammalian cells, is expected to provide for such post-translational modifications (e.g. myristolation, glycosylation, truncation, lapidation and tyrosine, serine or threonine phosphorylation) as may be needed to confer optimal biological activity on recombinant expression products. Such cell culture systems in which the Fve polypeptides, variants, homologues, fragments and derivatives disclosed here are expressed maybe used in assay systems to identify candidate substances which interfere with or enhance the functions of the polypeptides in the cell.

Immunomodulator-Antigen Combinations and Conjugates

We show throughout this document (for the first time) that Fve has immunomodulatory properties, and in particular can act to potentiate an immune response. The adjuvant property of Fve may be exploited by administering Fve polypeptide or nucleic acid (or a fragment, homologue, variant or derivative thereof, or a host cell or vector comprising such) as described below, along with a molecule to which an immune response is desired.

The Fve polypeptide, etc may be administered to an individual either in combination, sequentially or simultaneously or in succession with the molecule to which an immune response is desired. We therefore provide for the first time a combination of a Fve polypeptide, etc with an antigenic molecule.

Where the Fve polypeptide, etc and the molecule are administered in combination, this may be achieved by administering a mixture of the Fve polypeptide, etc and the molecule. We therefore provide a simple combination of the Fve polypeptide, etc and the molecule, preferably as a kit. The kit may comprise the Fve polypeptide, etc and the molecule to which an immune response is desired in separate containers, and may optionally comprise instructions to administer these simultaneously, sequentially, etc.

The molecule to which an immune response is desired may comprise an allergen. These are set out in further detail in the following section.

The molecule to which an immune response is desired may comprise a tumour associated antigen. In preferred embodiments, the tumour associated antigen comprises MAGE-1, MAGE-2, MAGE-3, BAGE, GAGE, PRAME, SSX-2, Tyrosinase, MART-1, NY-ESO-1, gp100, TRP-1, TRP-2, A2 melanotope, BCR/ABL, Proteinase-3/Myeloblastin, HER2/neu, CEA, P1A, HK2, PAPA, PSA, PSCA, PSMA, pg75, MUM-1, MUC-1, BTA, GnT-V, β-catenin CDK4, or P15. Nucleic acid and amino acid sequences of these antigens are known in the art, and the skilled person will know how to produce tumour associated antigens, including those set out above. We therefore disclose combinations, preferably in the form of kits, comprising an Fve polypeptide or nucleic acid (or a fragment, homologue, variant or derivative thereof, or a host cell or vector comprising such), together with a tumour associated antigen, for example as set out above.

The molecule to which an immune response is desired may comprise a viral antigen. In preferred embodiments, the viral antigen comprises a protein from an oncogenic virus; such viruses are known in the art. Preferably the oncogenic viral antigen comprises E6 and E7 from HPV; core Ag and E2 from HCV; core and surface antigens from HBV; LMP-1, LMP-2, EBNA-2, EBNA-3 from EBV; or Tax from HTLV-1.

In a further embodiment, the viral antigen comprises an antigen, preferably a protein, more preferably an antigenic protein or fragment thereof from an infectious virus. Such immunomodulator-viral antigen conjugates may be used to treat or prevent a viral infectious disease, i.e., the cognate disease. For example, an immunomodulator-HSV antigen conjugate, for example, a Fve polypeptide-HSV antigen conjugate, may be used to treat or prevent Herpes Simplex Virus infection. Other preferred viral antigens include those from Adenovirus, Parainfluenza 3 virus, Human Immunodeficiency Virus (HIV), Herpes simplex virus, HSV, Respiratory syncytial virus, RSV, and Influenza A, Flu A. These viruses, and the diseases they cause, are well known in the art, and methods for making and purifying antigens from such viruses are also well known. For example, U.S. Pat. No. 4,313,927 (Fridlender) discloses detailed protocols for preparation of rubella and Cytomegalovirus (CMV) antigen.

Nucleic acid and amino acid sequences of these viral antigens are known in the art, and the skilled person will know how to produce viral antigen antigens, including these set out above. We therefore disclose combinations, preferably in the form of kits, comprising an Fve polypeptide or nucleic acid (or a fragment, homologue, variant or derivative thereof, or a host cell or vector comprising such), together with a viral antigen, for example as set out above.

In preferred embodiments, we provide administration of the Fve polypeptide, etc and the molecule to which an immune response is desired, in which there is some degree of association between the Fve polypeptide, etc and the molecule in question.

We therefore disclose for the first time an an agent which comprises an immunomodulator coupled, fused, mixed, combined, or otherwise joined to an allergen. Such a construct is referred to as a "immunomodulator-allergen conjugate" in this document. In particular, we disclose the use of Fve adjuvanted allergen vaccines, as explained in further detail in Examples 13 and 14.

The coupling, etc between the immunomodulator and the allergen may be permanent or transient, and may involve covalent or non-covalent interactions (including ionic interactions, hydrophobic forces, Van der Waals interactions, etc). The exact mode of coupling is not important, so long as the immunomodulator-allergen conjugate. Accordingly, where reference is made to "comprising", "conjugation", "coupling", etc, these references should be taken to include any form of interaction between the immunomodulator and the allergen.

Thus, the immunodulator may be a polypeptide which is provided as a fusion protein with the allergen, for example as shown in Example 13 for Fve/Allergen. An expression vector may be constructed by standard recombinant DNA technology to include a nucleotide sequence capable of expressing a immunodulator, such that a fusion protein is expressed comprising the allergen of interest fused to the immunodulator. The expression vector is transfected or transformed into a suitable host for large scale production of fusion protein, by means known in the art. Purification of the fusion protein may also be carried out by known means. Alternatively, or in addition, and as discussed above, the allergen may be physically associated with the immunomodulator, and attached to it by chemical conjugation. Thus, Example 14 below describes the use of allergen physically conjugated to Fve.

In preferred embodiments, the immunomodulator-allergen conjugate is capable of at least one of the following, preferably two or more, more preferably all: increase the number of human PBMC, to stimulate the proliferation of human lymphocytes, to polarize human $CD8^+$ T cells, and to increase the production of IFN-γ (Th1 response) and IL-10 (Tr response). Preferablly, the immunomodulator-allergen conjugate is capable of inducing both Th1 and Tr immune responses. Preferably, the Th1 response inhibits the development of Th2 cells via IFN-γ, more preferably it is capable of inducing a life-long (or substantially long lasting) protective Th1 memory immune response. Allergen specific Tr cells may in turn dampen the anti-allergic Th1 immune response, ensuring a well-balanced protective but nonpathological TH1 response. Allergen-Fve fusion proteins meet these criteria since they induce cytokine IL-10, and these are therefore preferred.

Where the conjugate comprises Fve, the Fve portion of the conjugate may comprise the whole molecule, or fragments of it. It may for example comprise the native Fve, or any Fve polypeptide as disclosed above. The allergen portion may comprise any allergen, whether proteinaceous or not. Advantageously, proteinaceous allergens are conjugated to the immunomodulator portion by means of covalent bonds, for example, amide bonds (for example, as a fusion protein).

The allergen may comprise for example the whole or a portion of Blo t 5 or Der p 2 allergen. In highly preferred embodiments, the immunomodulator-allergen conjugate comprises Bt5-Fve, Bt5-FveR27 or GST-Dp2-FveR27. Examples of other allergens suitable for use in the immunomodulator-allergen conjugate described here are provided below.

Furthermore, protein-protein conjugation also provides a convenient and alternative choice to develop allergen vaccine. Any suitable means of conjugation, for example, chemical conjugation maybe used to couple the immunomodulator and the allergen. Cross-linkers, for example, heterobifunctional cross linkers are known in the art, and may be used. Furthermore, other conjugation agents, for example, poly-lactic acid (PLA) and polyethylene glycol (PEG) may also be employed.

Allergens

In general, the allergen from which an immunomodulator-allergen conjugate may be constructed may come from any source, for example, a source known to induce allergenic responses in humans. For example, the allergen may comprise a tree pollen allergen, a grass pollen allergen, a weed pollen allergen, a feline antigen, or a fungal allergen. Thus, the allergen may comprise a tree pollen allergen, for example Bet v 1 and Bet v 2 from birch tree. It may comprise a grass pollen allergen, for example, Phl p 1 and Phl p 2 from timothy grass. It may comprise a weed pollen allergen, for example, antigen E from ragweed. It may comprise a major feline antigen, for example, Fel d 1. It may comprise a major fungal allergen, for example, Asp f1, Asp f2, and Asp f3 from *Aspergillus fumigatus*.

In preferred embodiments, the allergen comprises a dust mite allergen, preferably a house dust mite allergen. In particular, the allergen is preferably derived from a mite from Family Glycyphagidae or Family Pyroglyphidae. Dust mites of Family Glycyphagidae include those in the genera Aeroglyphus, Austroglycyphagus, Blomia, Ctenoglyphus, Glycyphagus, Gohieria, Lepidoglyphus. Dust mites of Family Pyroglyphidae include those in the genera Dermatophagoides, Euroglyphus, Pyroglyphus. In preferred embodiments, the allergen is preferably an allergen from a species in any of these genera.

In highly preferred embodiments, the allergen is a group 1 allergen (Der p 1, Der f 1, Blo t 1, Eur m1, Lep d 1), a group 2 allergen (Der p 2, Der f 2, Blo t 2, Eur m 2, Lep d 2), a group 5 allergen (Blo t 5, Der p 5, Der f 5, Eur m 5, Lep d 5) or a group 15 allergen (Der p 15, Der f 15, Blot 15, Eur m 15, Lep d 15) from dust mite. Nucleic acid and amino acid sequences of these allergens are known in the art, and the skilled person will know how to produce allergen-immunomodulator conjugates from any of these allergens using such sequences.

Other Immunomodulator Conjugates

Immunomodulator-Tumour Associated Antigen Conjugates

We also disclose for the first time an an agent which comprises an immunomodulator coupled, fused, mixed, combined, or otherwise joined to an tumour associated antigen. Such a construct is referred to as a "immunomodulator-tumour associated antigen conjugate" in this document.

As the term is used here, "tumour associated antigen" generally includes a cancer protein or a cancer antigen, i.e., a protein which is preferentially expressed in a tumour cell or a transformed cell, compared to a "normal" non-cancerous cell.

In highly preferred embodiments, the tumour associated antigen may comprise MAGE-1, MAGE-2, MAGE-3, BAGE, GAGE, PRAME, SSX-2, Tyrosinase, MART-1, NY-ESO-1, gp100, TRP-1, TRP-2, A2 melanotope, BCR/ABL, Proteinase-3/Myeloblastin, HER2/neu, CEA, P1A, HK2, PAPA, PSA, PSCA, PSMA, pg75, MUM-1, MUC-1, BTA, GnT-V, β-catenin, CDK4, or P15. Nucleic acid and amino acid sequences of these antigens are known in the art, and the skilled person will know how to produce tumour associated antigen-immunomodulator conjugates from any of these allergens using such sequences.

We present in Appendix A the sequences of MAGE3-FveT29A, MART1-FveT29A and CEA-FveT29A, which are preferred Immunomodulator-Tumour Associated Antigen Conjugates suitable for use in the methods and compositions described here.

Immunomodulator-Viral Antigen Conjugates

We further disclose an agent comprising an immunodulator coupled, etc to a viral antigen. In highly preferred embodiments, the viral antigen comprises a protein from an oncogenic virus; such viruses are known in the art. Preferably the oncogenic viral antigen comprises E6 and E7 from HPV; core Ag and E2 from HCV; core and surface antigens from HBV; LMP-1, LMP-2, EBNA-2, EBNA-3 from EBV; or Tax from HTLV-1. Nucleic acid and amino acid sequences of these viral antigens are known in the art, and the skilled person will know how to produce viral antigen-immunomodulator conjugates from any of these allergens using such sequences.

We also provide an agent (for example a polypeptide) comprising a first portion comprising at least a portion of Fve and a second portion comprising at least a portion of a viral antigen, preferably coupled together. The viral antigen may be selected from the group consisting of antigens from Adenovirus, Parainfluenza 3 virus, Herpes simplex virus, HSV, Respiratory syncytial virus, RSV, and Influenza A, Flu A.

The viral antigen may comprise any portion of the native viral antigen, for example, a portion of the HCV core antigen. We have established that a deletion of the HCV core antigen, particularly a deletion of 23 amino acids from residues 141 to 163 of the core antigen leads to an increase in efficiency of protein production. Accordingly, we provide an agent comprising an immunomodulator coupled, etc to a viral antigen, which viral antigen comprises such a deleted core antigen (here referred to as "Core23"), e.g., the fusion protein HCV Core23-FveT29A.

In particular, we find that the polypeptides HCV Core23-FveT29A and HPV E7-FveT29A (the sequences of which are shown in Appendix A) are particularly useful as Immunomodulator-Viral Antigen conjugates.

The coupling, etc between the immunomodulator and the tumour associated antigen, and the viral antigen, may be as described above for the immunomodulator-allergen conjugate.

Fve Nucleic Acids

We provide for a nucleic acid encoding a Fve polypeptide, which we refer to as a "Fve nucleic acid". We also provide nucleic acids encoding variants, homologues, derivatives and fragments of native Fve, as well as fragments, homologues, derivatives and variants of Eve nucleic acids.

Preferably, the Fve nucleic acid is derived from a natural or native Fve sequence, for example, the nucleic sequence shown as "Fve (Wild type)" in Appendix A. In a preferred embodiment, the Fve nucleic acid is a recombinant fragment of native Fve nucleic acid, or any fragment, homologue, variant or derivative thereof. Fragments, homologues, variants and derivatives of each of the above sequences are also included.

"Fve nucleic acids" preferably encode polypeptides which have at least one biological activity of native Fve, as described above. Preferably, Fve nucleic acids encode polypeptides which comprise two or more biological activities of native Eve, preferably substantially all the biological activities of native Fve.

In preferred embodiments, the Fve nucleic acids encode polypeptides which comprise at least one, two or all three of the RGT residues (or a functional variant as defined above, such as RGD) at or about a position corresponding to position 28 of the native Fve polypeptide. In particular, the Fve nucleic acid may comprise the sequence CGTGGTACC. Alternatively, the Fve nucleic acid may comprise the sequence CGTGGTGAT or the sequence CGTGGTGAC. The Fve nucleic acid may comprise a nucleotide sequence which encodes the same amino acids as a result of the redundancy of the genetic code.

The Fve nucleic acid maycomprise a sequence comprising three codons, with a first codon selected from the group consisting of: CGT, CGC, CGA, CGG, AGA and AGG, a second codon selected from the group consisting of: GGT, GGC, GGA and GGG, and a third codon selected from the group consisting of: ACT, ACC, ACA and ACG. Alternatively, the third codon may be selected from the group consisting of: GAT and GAC, Preferably, the Fve polypeptide comprises between 2 to 60 residues of nucleic acid sequence flanking the codon for the glycine residue corresponding to position 28 of native Fve.

In preferred embodiments, Fve nucleic acids may comprise nucleic acids encoding fragments of native Fve. For example, Fve nucleic acids may comprise the nucleic acid sequences depicted in Appendix A as Fve D6-18, Fve D19-33, Fve D34-46, Fve D47-60, Fve D61-72, Fve D73-84, Fve D85-97, Fve D98-106, Fve D107-115, Fve D61-97, and Fvep55-100. Nucleic acids encoding fusion proteins comprising these deletion fragments and GST are also disclosed. Fve nucleic acids may comprise those encoding substitutions, including FveR27A, FveG28A and FveT29A. Fve nucleic acids include those which encode the polypeptide sequences shown in Appendix A.

We also disclose Fve nucleic acids which encode Fve polypeptides comprising fusion proteins, particularly fusion proteins between an allergen and a Fve polypeptide as defined here. We disclose in particular nucleic acid sequences of Blo t 5-Fve(two-in-one chimeric wild type), Blo t 5-FveR27A (two-in-one chimeric mutant), Blo t 5-FveT29A (two-in-one chimeric mutant), Der p 2-FveR27A (two-in-one chimeric mutant), Der p 2-FveT29A (two-in-one chimeric mutant) and Blo t 5-Der p 2-FveR27A (three-in-one chimeric mutant), and shown in Appendix A.

As used here in this document, the terms "polynucleotide", "nucleotide", and nucleic acid are intended to be synonymous with each other. "Polynucleotide" generally refers to any polyribonucleotide or polydeoxribonucleotide, which may be unmodified RNA or DNA or modified RNA or DNA. "Polynucleotides" include, without limitation single- and double-stranded DNA, DNA that is a mixture of single- and double-stranded regions, single- and double-stranded RNA, and RNA that is mixture of single- and double-stranded regions, hybrid molecules comprising DNA and RNA that may be single-stranded or, more typically, double-stranded or a mixture of single- and double-stranded regions. In addition, "polynucleotide" refers to triple-stranded regions comprising RNA or DNA or both RNA and DNA. The term polynucleotide also includes DNAs or RNAs containing one or more modified bases and DNAs or RNAs with backbones modified for stability or for other reasons. "Modified" bases include, for example, tritylated bases and unusual bases such as inosine. A variety of modifications has been made to DNA and RNA; thus, "polynucleotide" embraces chemically, enzymatically or metabolically modified forms of polynucleotides as typically found in nature, as well as the chemical forms of DNA and RNA characteristic of viruses and cells. "Polynucleotide" also embraces relatively short polynucleotides, often referred to as oligonucleotides.

It will be understood by a skilled person that numerous different polynucleotides and nucleic acids can encode the same polypeptide as a result of the degeneracy of the genetic code. In addition, it is to be understood that skilled persons may, using routine techniques, make nucleotide substitutions that do not affect the polypeptide sequence encoded by the polynucleotides described here to reflect the codon usage of any particular host organism in which the polypeptides are to be expressed.

Fve nucleic acids, variants, fragments, derivatives and homologues may comprise DNA or RNA. They may be single-stranded or double-stranded. They may also be polynucleotides which include within them synthetic or modified nucleotides. A number of different types of modification to oligonucleotides are known in the art. These include methylphosphonate and phosphorothioate backbones, addition of acridine or polylysine chains at the 3' and/or 5' ends of the molecule. For the purposes of this document, it is to be understood that the polynucleotides may be modified by any method available in the art. Such modifications may be carried out in order to enhance the in vivo activity or life span of polynucleotides of interest.

The terms "variant", "homologue" or "derivative" in relation to a nucleotide sequence include any substitution of, variation of, modification of, replacement of, deletion of or addition of one (or more) nucleic acid from or to the sequence. Preferably said variant, homologues or derivatives code for a polypeptide having biological activity.

As indicated above, with respect to sequence homology, preferably there is at least 50 or 75%, more preferably at least 85%, more preferably at least 90% homology to the sequences shown in the sequence listing herein. More preferably there is at least 95%, more preferably at least 98%, homology. Nucleotide homology comparisons may be conducted as described above. A preferred sequence comparison program is the GCG Wisconsin Bestfit program described above. The default scoring matrix has a match value of 10 for each identical nucleotide and −9 for each mismatch. The default gap creation penalty is −50 and the default gap extension penalty is −3 for each nucleotide.

We further describe nucleotide sequences that are capable of hybridising selectively to the sequences presented herein, or any variant, fragment or derivative thereof, or to the complement of any of the above. Nucleotide sequences are preferably at least 15 nucleotides in length, more preferably at least 20, 30, 40 or 50 nucleotides in length.

The term "hybridization" as used herein shall include "the process by which a strand of nucleic acid joins with a complementary strand through base pairing" as well as the process of amplification as carried out in polymerase chain reaction technologies.

Polynucleotides capable of selectively hybridising to the nucleotide sequences presented herein, or to their complement, will be generally at least 70%, preferably at least 80 or 90% and more preferably at least 95% or 98% homologous to the corresponding nucleotide sequences presented herein over a region of at least 20, preferably at least 25 or 30, for instance at least 40, 60 or 100 or more contiguous nucleotides.

The term "selectively hybridizable" means that the polynucleotide used as a probe is used under conditions where a target polynucleotide is found to hybridize to the probe at a level significantly above background. The background hybridization may occur because of other polynucleotides present, for example, in the cDNA or genomic DNA library being screening. In this event, background implies a level of signal generated by interaction between the probe and a non-specific DNA member of the library which is less than 10 fold, preferably less than 100 fold as intense as the specific interaction observed with the target DNA. The intensity of interaction may be measured, for example, by radiolabelling the probe, e.g. with $^{32}P$.

Hybridization conditions are based on the melting temperature (Tm) of the nucleic acid binding complex, as taught in Berger and Kimmel (1987, Guide to Molecular Cloning Techniques, Methods in Enzymology, Vol 152, Academic Press, San Diego Calif.), and confer a defined "stringency" as explained below.

Maximum stringency typically occurs at about Tm-5° C. (5° C. below the Tm of the probe); high stringency at about 5° C. to 10° C. below Tm; intermediate stringency at about 10° C. to 20° C. below Tm; and low stringency at about 20° C. to 25° C. below Tm. As will be understood by those of skill in the art, a maximum stringency hybridization can be used to identify or detect identical polynucleotide sequences while an intermediate (or low) stringency hybridization can be used to identify or detect similar or related polynucleotide sequences.

In a preferred aspect, we provide nucleotide sequences that can hybridise to the Fve nucleic acids, fragments, variants, homologues or derivatives dislosed here under stringent conditions (e.g. 65° C. and 0.1×SSC {1×SSC=0.15 M NaCl, 0.015 M $Na_3$ Citrate pH 7.0).

Where the polynucleotide is double-stranded, both strands of the duplex, either individually or in combination, are encompassed by the methods and compositions described here. Where the polynucleotide is single-stranded, it is to be understood that the complementary sequence of that polynucleotide is also included.

Polynucleotides which are not 100% homologous to the Fve sequences disclosed here but which are also included can be obtained in a number of ways. Other variants of the sequences may be obtained for example by probing DNA libraries made from a range of individuals, for example individuals from different populations. For example, Fve homologues may be identified from other individuals, or other species. Further recombinant Fve nucleic acids and polypeptides may be produced by identifying corresponding positions in the homologues, and synthesising or producing the molecule as described elsewhere in this document. Furthermore, the collagen region, neck region and carbohydrate binding domain in such homologues may be identified, for example, by sequence gazing or computer assisted comparisons, and selected for combination into or production of a recombinant Fve which has one or more biological activities of native Fve.

In addition, other viral/bacterial, or cellular homologues of Fve particularly cellular homologues found in mammalian cells (e.g. rat, mouse, bovine and primate cells), may be obtained and such homologues and fragments thereof in general will be capable of selectively hybridising to Fve. Such homologues may be used to design non-human Fve nucleic acids, fragments, variants and homologues. Mutagenesis may be carried out by means known in the art to produce further variety.

Sequences of Fve homologues may be obtained by probing cDNA libraries made from or genomic DNA libraries from other animal or non-animal species, particularly microbial or fungal species, and probing such libraries with probes comprising all or part of any of the Fve nucleic acids, fragments, variants and homologues, or other fragments of Fve under conditions of medium to high stringency.

Similar considerations apply to obtaining species homologues and allelic variants of the polypeptide or nucleotide sequences disclosed here.

Variants and strain/species homologues may also be obtained using degenerate PCR which will use primers designed to target sequences within the variants and homologues encoding conserved amino acid sequences within the sequences of the Fve nucleic acids. Conserved sequences can be predicted, for example, by aligning the amino acid sequences from several variants/homologues. Sequence alignments can be performed using computer software known in the art. For example the GCG Wisconsin PileUp program is widely used.

The primers used in degenerate PCR will contain one or more degenerate positions and will be used at stringency conditions lower than those used for cloning sequences with single sequence primers against known sequences. It will be appreciated by the skilled person that overall nucleotide homology between sequences from distantly related organisms is likely to be very low and thus in these situations degenerate PCR may be the method of choice rather than screening libraries with labelled fragments the Fve sequences.

In addition, homologous sequences may be identified by searching nucleotide and/or protein databases using search algorithms such as the BLAST suite of programs.

Alternatively, such polynucleotides may be obtained by site directed mutagenesis of characterised sequences, for example, Fve nucleic acids, or variants, homologues, derivatives or fragments thereof This may be useful where for example silent codon changes are required to sequences to optimise codon preferences for a particular host cell in which the polynucleotide sequences are being expressed. Other sequence changes may be desired in order to introduce restriction enzyme recognition sites, or to alter the property or function of the polypeptides encoded by the polynucleotides.

The polynucleotides described here may be used to produce a primer, e.g. a PCR primer, a primer for an alternative amplification reaction, a probe e.g. labelled with a revealing label by conventional means using radioactive or non-radioactive labels, or the polynucleotides may be cloned into vectors. Such primers, probes and other fragments will be at least 8, 9, 10, or 15, preferably at least 20, for example at least 25, 30 or 40 nucleotides in length, and are also encompassed by the term "polynucleotides" as used herein.

Polynucleotides such as a DNA polynucleotides and probes may be produced recombinantly, synthetically, or by any means available to those of skill in the art They may also be cloned by standard techniques.

In general, primers will be produced by synthetic means, involving a step wise manufacture of the desired nucleic acid sequence one nucleotide at a time. Techniques for accomplishing this using automated techniques are readily available in the art Longer polynucleotides will generally be produced using recombinant means, for example using a PCR (polymerase chain reaction) cloning techniques. This will involve making a pair of primers (e.g. of about 15 to 30 nucleotides) flanking a region of the lipid targeting sequence which it is desired to clone, bringing the primers into contact with mRNA or cDNA obtained from an animal or human cell, performing a polymerase chain reaction under conditions which bring about amplification of the desired region, isolating the amplified fragment (e.g. by purifying the reaction mixture on an agarose gel) and recovering the amplified DNA. The primers may be designed to contain suitable restriction enzyme recognition sites so that the amplified DNA can be cloned into a suitable cloning vector Polynucleotides or primers may carry a revealing label. Suitable labels include radioisotopes such as $^{32}P$ or $^{35}S$, enzyme labels, or other protein labels such as biotin. Such labels may be added to polynucleotides or primers and may be detected using by techniques known per se. Polynucleotides or primers or fragments thereof labelled or unlabeled may be used by a person skilled in the art in nucleic acid-based tests for detecting or sequencing polynucleotides in the human or animal body.

Such tests for detecting generally comprise bringing a biological sample containing DNA or RNA into contact with a probe comprising a polynucleotide or primer under hybridising conditions and detecting any duplex formed between the probe and nucleic acid in the sample. Such detection may be achieved using techniques such as PCR or by immobilising the probe on a solid support, removing nucleic acid in the sample which is not hybridised to the probe, and then detecting nucleic acid which has hybridised to the probe. Alternatively, the sample nucleic acid may be immobilised on a solid support, and the amount of probe bound to such a support can be detected. Suitable assay methods of this and other formats can be found in for example WO89/03891 and WO90/13667.

Tests for sequencing nucleotides, for example, the Fve nucleic acids, involve bringing a biological sample containing target DNA or RNA into contact with a probe comprising a polynucleotide or primer under hybridising conditions and determining the sequence by, for example the Sanger dideoxy chain termination method (see Sambrook et al.).

Such a method generally comprises elongating, in the presence of suitable reagents, the primer by synthesis of a strand complementary to the target DNA or RNA and selectively terminating the elongation reaction at one or more of an A, C, G or T/U residue; allowing strand elongation and termination reaction to occur; separating out according to size the elongated products to determine the sequence of the nucleotides at which selective termination has occurred. Suitable reagents include a DNA polymerase enzyme, the deoxynucleotides dATP, dCTP, dGTP and dTTP, a buffer and ATP. Dideoxynucleotides are used for selective termination.

Protein Expression and Purification

Host cells comprising polynucleotides may be used to express polypeptides, such as Fve polypeptides, fragments, homologues, variants or derivatives thereof. Host cells may be cultured under suitable conditions which allow expression of the proteins. Expression of the polypeptides may be constitutive such that they are continually produced, or inducible, requiring a stimulus to initiate expression. In the case of inducible expression, protein production can be initiated when required by, for example, addition of an inducer substance to the culture medium, for example dexamethasone or IPTG.

Polypeptides can be extracted from host cells by a variety of techniques known in the art, including enzymatic, chemical and/or osmotic lysis and physical disruption.

Polypeptides may also be produced recombinantly in an in vitro cell-free system, such as the TnT™ (Promega) rabbit reticulocyte system.

Fve Nucleic Acid Molecules

We disclose a nucleic molecule that: a) has a strand that encodes an Fve polypeptide disclosed here, b) has a strand that is complementary with a strand as described in a) above; or c) has a strand that hybridises with a molecule as described in a) or b) above.

Unless the context indicates otherwise, such nucleic acid molecules, which are included within the term “Fve nucleic acid molecule” may have one or more of the following characteristics:

1) They may be DNA or RNA (including variants of naturally occurring DNA or RNA structures, which have non-naturally occurring bases and/or non-naturally occurring backbones).

2) They may be single-stranded or double-stranded (or in some cases higher stranded, e.g. triple-stranded).

3) They may be provided in recombinant form i.e. covalently linked to a heterologous 5' and/or 3' flanking sequence to provide a chimeric molecule (e.g. a vector) that does not occur in nature.

4) They may be provided with or without 5' and/or 3' flanking sequences that normally occur in nature.

5) They may be provided in substantially pure form, e.g. by using probes to isolate cloned molecules having a desired target sequence or by using chemical synthesis techniques. Thus they may be provided in a form that is substantially free from contaminating proteins and/or from other nucleic acids.

6) They may be provided with introns (e.g. as a full-length gene) or without introns (e.g. as DNA).

7) They may be provided in linear or non-linear (e.g. circular) form.

These Fve molecules include not only molecules with classical DNA or RNA structures, but also variants with modified (non-phosphodiester) backbones—e.g. morpholino derivatives and peptide nucleic acids (PNAs), which contain an N-(2-aminoethyl)glycine-based pseudopeptide backbone. (See Nielsen, P. E., Annual Review of Biophysics & Biomolecular Structure, 24:167-83 (1995)). Nucleic acid variants with modified backbones can have increased stability relative to unmodified nucleic acids and are particularly useful where hybridisation is desired over a relatively long period (e.g. in antisense therapy).

Nucleic acid molecules and uses thereof are discussed in further detail below:

a) Coding Nucleic Acid Molecules

The Fve polypeptides can be coded for by a large variety of nucleic acid molecules, taking into account the well-known degeneracy of the genetic code. All of these coding nucleic acid molecules are within the scope of the present document.

The Fve nucleic acids may be administered to an individual and used to express polypeptides disclosed here. Thus, they may be used for the same treatments as the Fve polypeptides.

The Fve nucleic acid molecules may be provided in the form of vectors, although this is not essential. Preferred vectors for use in treatment include replication-deficient adenoviruses, retroviruses and adeno-associated viruses.

Fve nucleic acid molecules may be administered to a patient by physical methods. These methods include topical application of the nucleic acid in an appropriate vehicle, for example in solution in a pharmaceutically acceptable excipient, such as phosphate buffered saline (PBS). They also include particle bombardment (which is sometimes known as “gene gun” technology and is described in U.S. Pat. No. 5,371,015). Here inert particles, such as gold beads coated with a nucleic acid, can be accelerated at speeds sufficient to enable them to penetrate cells. They can be used for example to penetrate the skin of a patient and may be administered by means of discharge under high pressure from a projecting device. Other physical methods of administering the Fve nucleic acid directly to a recipient include ultrasound, electrical stimulation (including iontophoresis) and microseeding (see e.g. U.S. Pat. No. 5,697,901). Alternatively, the Fve nucleic acid molecules may simply be injected at appropriate site (e.g. muscle). They may be incorporated in or on a carrier (which may be a lipid-based carrier, such as a liposome).

Fve nucleic acid molecules may be introduced into host cells (optionally in the form of vectors) to enable the expression of polypeptides. Alternatively, cell-free expression systems may be used. By using an appropriate expression system the Fve polypeptides can be produced in a desired form. For example, the Fve polypeptides can be produced by microorganisms such as bacteria or yeast, by cultured insect cells (which may be baculovirus-infected), by mammalian cells (such as CHO cells) or by transgenic animals that, for instance, secrete the Fve proteins in milk (see e.g. international patent application WO88/00239). Where glycosylation is desired, eukaryotic (e.g. mammalian or insect) expression systems are preferred.

Whatever means is used to obtain expression, transcriptional and translational control sequences will normally be present and will be operatively linked to a sequence encoding a polypeptide to be expressed. These control sequences may be heterologous to the sequence encoding the Fve polypeptide or may be found associated with it in vivo. Promoter, operator and/or enhancer sequences may, for example, be provided, as may polyadenylation sites, splice sites, stop and start codons, upstream and downstream regulatory regions, etc. If desired, a constitutive promoter may be provided. Alternatively, a regulatable promoter may be provided to enable transcription to be controlled by administration of a regulator. The promoter (if present) may be tissue-specific or non tissue-specific.

Polypeptides comprising N-terminal methionine may be produced using certain expression systems, whilst in others the mature polypeptide may lack this residue. Fve polypeptides may initially be expressed so as to include signal sequences. Different signal sequences may be provided for different expression systems. Alternatively, signal sequences may be absent, if not needed.

Once expressed, Fve polypeptides may be purified by a wide variety of techniques. Purification techniques may be used under reducing conditions (in order prevent disulphide bond formation) or non-reducing conditions. Available purification techniques include, for example, electrophoretic techniques, such as SDS PAGE (see e.g. Hunkapiller et al, *Methods Enzymol.* 91:227 (1983), which discloses "Isolation of microgram quantities of proteins from polyacrylamide gels for amino acid sequence analysis."); affinity techniques (e.g. immunoaffinity chromatography); HPLC; gel filtration; ion-exchange chromatography, isoelectric focussing; etc. If desired, combinations of different purification steps may be used and/or individual purification steps may be repeated.

In summary, techniques for cloning, expressing and purifying polypeptides are well known to the skilled person. Various such techniques are disclosed in standard text-books, such as in Sambrook et al [*Molecular Cloning* 2nd Edition, Cold Spring Harbor Laboratory Press (1989)]; in Old & Primrose [*Principles of Gene Manipulation* 5th Edition, Blackwell Scientific Publications (1994)]; and in Stryer [*Biochemistry* 4th Edition, W H Freeman and Company (1995)].

b) Complementary Nucleic Acid Molecules

We also describe nucleic acid strands complementary thereto, whether or not the coding and complementary strands are associated in a duplex. Thus, for example, mRNA and cDNA molecules are included.

c) Hybridising Nucleic Acid Molecules

Nucleic acid molecules that can hybridise to one or more of the Fve nucleic acid molecules discussed above are also disclosed. Such nucleic acid molecules are referred to herein as "hybridising" nucleic acid molecules. Desirably hybridising molecules are at least 10 nucleotides in length and preferably are at least 20, at least 50, at least 100, or at least 200 nucleotides in length.

A hybridising nucleic acid molecule may have a high degree of sequence identity along its length with a nucleic acid molecule within the scope of b) or a) above (e.g. at least 50%, at least 75% or at least 90% sequence identity), although this is not essential. The greater the degree of sequence identity that a given single stranded nucleic acid molecule has with a strand of a nucleic acid molecule, the greater the likelihood that it will hybridise to the complement of said strand.

Most preferably, hybridising nucleic acid molecules hybridise to either DNA strand of a Fve nucleic acid, for example a sequence shown in Appendix A, or to an RNA equivalent thereof, or to a strand that is complementary to either of the aforesaid strands.

Hybridising nucleic acid molecules can be useful as probes or primers, for example.

Probes can be used to purify and/or to identify Fve nucleic acids. They may be used in diagnosis. For example, probes may be used to determine whether or not an organism such as a fungus has a wild-type gene encoding a Fve polypeptide described here, or whether or not one or more deletions, insertions and/or replacements of bases relative to the wild-type sequence are present. It may therefore be used to identify organisms that do not express Fve polypeptides or that express Fve polypeptides having reduced activity (including inactive polypeptides).

Primers are useful in synthesising nucleic acids or parts thereof based upon a template to which a probe hybridises. They can be used in techniques such as PCR to provide large numbers of nucleic acid molecules.

Hybridising molecules also include antisense strands. These hybridise with "sense" strands so as to inhibit transcription and/or translation. An antisense strand can be synthesised based upon knowledge of a sense strand and base pairing rules. It may be exactly complementary with a sense strand, although it should be noted that exact complementarity is not always essential. It may also be produced by genetic engineering, whereby a part of a DNA molecule is provided in an antisense orientation relative to a promoter and is then used to transcribe RNA molecules. Large numbers of antisense molecules can be provided (e.g. by cloning, by transcription, by PCR, by reverse PCR, etc.

Hybridising molecules include ribozymes. Ribozymes can also be used to regulate expression by binding to and cleaving RNA molecules that include particular target sequences recognised by the ribozymes. Ribozymes can be regarded as special types of antisense molecule. They are discussed, for example, by Haselhoff and Gerlach (Nature (1988) 334:585-91).

Antisense molecules may be DNA or RNA molecules. They may be used in antisense therapy to prevent or reduce undesired expression or activity. Antisense molecules may be administered directly to a patient (e.g. by injection). Alternatively, they may be synthesised in situ via a vector that has been administered to a patient.

In addition to the uses described above, the Fve nucleic acid molecules disclosed here (of whatever nature) may be used in screening. Screening can be done to identify moieties that bind to said nucleic acid molecules (e.g. to identify hybridising molecules). It can also be done to identify moieties that affect transcription or translation from said nucleic acid molecules.

It can be used to analyse expression, including analysing expression levels or expression patterns (e.g. by analysing mRNA or cDNA), etc. It can be used to identify particular nucleic acid molecules in a sample. This is useful for in identifying biological material from a given source (e.g. from a human or non-human animal). For example, a reference nucleic acid molecule (or part of it) can be digested with restriction enzymes and the resultant nucleic acid fragments can be run on a gel. This can provide a restriction fragment pattern or "fingerprint" that can be compared with a sample. If the comparison provides a match that is unlikely to have occurred by chance, a conclusion can be reached that the sample and the reference molecule are likely to have originated from a common source. By performing statistical analysis a specific degree of confidence that such a conclusion is correct can be provided.

We also describe a library having a Fve nucleic acid molecule described here, as well as an array comprising such an Fve nucleic acid molecule (which may be a library). Preferably the array is a regular array. The array may have a predetermined pattern. It may have a grid-like pattern. The discussion provided herein in respect of libraries and arrays comprising a polypeptide described here applies *mutatis mutandis* to libraries and arrays comprising the corresponding nucleic acid molecule.

One or more Fve nucleic acid molecules may be immobilised upon a surface (e.g. the surface of a bead or a chip). The surface may, for example, be silicon surface, glass, quartz, a membrane, etc. Techniques for immobilising nucleic acid molecules upon a surface are known and are disclosed, for example, in EP-A-0487104, WO96/04404, WO90/02205, WO96/12014, WO98/44151. In some cases they may include a step of nucleic acid amplification, which may involve PCR. Immobilisation is not however essential. For example nucleic acids may be provided in wells or other containment means (e.g. in a fluid environment).

The Fve nucleic acids may be used in various ways. For example, sequence information can be used in predicting structure and/or function, in homology or identity studies, etc.

Vectors

As indicated above the nucleic acid molecules described here may be provided in the form of vectors.

Vectors comprising such nucleic acid include plasmids, phasmids, cosmids, viruses (including bacteriophages), YACs, PACs, etc. They will usually include an origin of replication and may include one or more selectable markers e.g. drug resistance markers and/or markers enabling growth on a particular medium. A vector may include a marker that is inactivated when a nucleic acid molecule, such as the ones described here, is inserted into the vector. Here a further marker may be provided that is different from the marker that is inactivated (e.g. it encodes a different type of drug resistance).

Vectors may include one or more regions necessary for transcription of RNA encoding a polypeptide. Such vectors are often referred to as expression vectors. They will usually contain a promoter and may contain additional regulatory regions—e.g. operator sequences, enhancer sequences, etc. Translation can be provided by a host cell or by a cell free expression system.

Vectors need not be used for expression. They may be provided for maintaining a given nucleic acid sequence, for replicating that sequence, for manipulating, it or for transferring it between different locations (e.g. between different organisms).

Large nucleic acid molecules may be incorporated into high capacity vectors (e.g. cosmids, phasmids, YACs or PACs). Smaller nucleic acid molecules may be incorporated into a wide variety of vectors.

Fve polynucleotides, for example those described here, can be incorporated into a recombinant replicable vector. The vector may be used to replicate the nucleic acid in a compatible host cell. Thus in a further embodiment, we provide a method of making polynucleotides by introducing a polynucleotide into a replicable vector, introducing the vector into a compatible host cell, and growing the host cell under conditions which bring about replication of the vector. The vector may be recovered from the host cell. Suitable host cells include bacteria such as *E. coli*, yeast, mammalian cell lines and other eukaryotic cell lines, for example insect Sf9 cells.

Preferably, a polynucleotide in a vector is operably linked to a control sequence that is capable of providing for the expression of the coding sequence by the host cell, i.e. the vector is an expression vector. The term "operably linked" means that the components described are in a relationship permitting them to function in their intended manner. A regulatory sequence "operably linked" to a coding sequence is ligated in such a way that expression of the coding sequence is achieved under condition compatible with the control sequences.

The control sequences may be modified, for example by the addition of further transcriptional regulatory elements to make the level of transcription directed by the control sequences more responsive to transcriptional modulators.

Vectors may be transformed or transfected into a suitable host cell as described below to provide for expression of a protein. This process may comprise culturing a host cell transformed with an expression vector as described above under conditions to provide for expression by the vector of a coding sequence encoding the protein, and optionally recovering the expressed protein. Vectors will be chosen that are compatible with the host cell used.

The vectors may be for example, plasmid or virus vectors provided with an origin of replication, optionally a promoter for the expression of the said polynucleotide and optionally a regulator of the promoter. The vectors may contain one or more selectable marker genes, for example an ampicillin resistance gene in the case of a bacterial plasmid or a neomycin resistance gene for a mammalian vector. Vectors may be used, for example, to transfect or transform a host cell.

Control sequences operably linked to sequences encoding the polypeptide include promoters/enhancers and other expression regulation signals. These control sequences may be selected to be compatible with the host cell for which the expression vector is designed to be used in. The term promoter is well-known in the art and encompasses nucleic acid regions ranging in size and complexity from minimal promoters to promoters including upstream elements and enhancers.

The promoter is typically selected from promoters which are functional in mammalian cells, although prokaryotic promoters and promoters functional in other eukaryotic cells, such as insect cells, may be used. The promoter is typically derived from promoter sequences of viral or eukaryotic genes. For example, it may be a promoter derived from the genome of a cell in which expression is to occur. With respect to eukaryotic promoters, they may be promoters that function in a ubiquitous manner (such as promoters of α-actin, β-actin, tubulin) or, alternatively, a tissue-specific manner (such as promoters of the genes for pyruvate kinase). They may also be promoters that respond to specific stimuli, for example promoters that bind steroid hormone receptors. Viral promoters may also be used, for example the Moloney murine leukaemia virus long terminal repeat (MMLV LTR) promoter, the rous sarcoma virus (RSV) LTR promoter or the human cytomegalovirus (CMV) IE promoter.

It may also be advantageous for the promoters to be inducible so that the levels of expression of the heterologous gene can be regulated during the life-time of the cell. Inducible means that the levels of expression obtained using the promoter can be regulated.

In addition, any of these promoters may be modified by the addition of further regulatory sequences, for example enhancer sequences. Chimeric promoters may also be used comprising sequence elements from two or more different promoters described above.

Polynucleotides may also be inserted into the vectors described above in an antisense orientation to provide for the production of antisense RNA. Antisense RNA or other antisense polynucleotides may also be produced by synthetic means. Such antisense polynucleotides may be used in a method of controlling the levels of RNAs transcribed from genes comprising any one of the polynucleotides described here.

Host Cells

Vectors and polynucleotides or nucleic acids comprising or encoding Fve nucleic acids, fragments, homologues, variants or derivatives thereof may be introduced into host cells for the purpose of replicating the vectors/polynucleotides and/or expressing the polypeptides encoded by the polynucleotides. Although the polypeptides may be produced using prokaryotic cells as host cells, it is preferred to use eukaryotic cells, for example yeast, insect or mammalian cells, in particular mammalian cells.

Vectors/polynucleotides may be introduced into suitable host cells using a variety of techniques known in the art, such as transfection, transformation and electroporation. Where vectors/polynucleotides are to be administered to animals, several techniques are known in the art, for example infection with recombinant viral vectors such as retroviruses, herpes simplex viruses and adenoviruses, direct injection of nucleic acids and biolistic transformation.

We therefore further disclose cells comprising Fve nucleic acid molecules or vectors. These may for example be used for expression, as described herein.

A cell capable of expressing a Fve polypeptide described here can be cultured and used to provide the Fve polypeptide, which can then be purified.

Alternatively, the cell may be used in therapy for the same purposes as the Fve polypeptide. For example, cells may be provided from a patient (e.g. via a biopsy), transfected with a nucleic acid molecule or vector and, if desired, cultured in vitro, prior to being returned to the patient (e.g. by injection). The cells can then produce the Fve polypeptide in vivo. Preferably the cells comprise a regulatable promoter enabling transcription to be controlled via administration of one or more regulator molecules. If desired, the promoter may be tissue specific.

Expression is not however essential since the cells may be provided simply for maintaining a given nucleic acid sequence, for replicating the sequence, for manipulating it, etc.

Such cells may be provided in any appropriate form. For example, they may be provided in isolated form, in culture, in stored form, etc. Storage may, for example, involve cryopreservation, buffering, sterile conditions, etc. Such cells may be provided by gene cloning techniques, by stem cell technology or by any other means. They may be part of a tissue or an organ, which may itself be provided in any of the forms discussed above. The cell, tissue or organ may be stored and used later for implantation, if desired. Techniques for providing tissues or organs, include stem cell technology, the provision of cells tissues or organs from transgenic animals, retroviral and non-retroviral techniques for introducing nucleic acids, etc.

In some case cells may be provided together with other material to aid the structure or function or of an implant. For example scaffolds may be provided to hold cells in position, to provide mechanical strength, etc. These may be in the form of matrixes of biodegradable or non-biodegradable material. WO95/01810 describes various materials that can be used for this purpose.

Animals

We also disclose transgenic animals, preferably non-human transgenic animals. Such animals may be useful for producing the particular Fve polypeptides described here (e.g. via secretion in milk, as described herein). Alternatively, they may be useful as test animals for analysing the effect(s) of such Fve polypeptides.

Techniques for producing transgenic animals are well known and are described e.g. in U.S. Pat. Nos. 4,870,009 and 4,873,191. For example, a nucleic acid encoding a Fve polypeptide of interest may be microinjected into a pronucleus of a fertilised oocyte. The oocyte may then be allowed to develop in a pseudopregnant female foster animal. The animal resulting from development of the oocyte can be tested (e.g. with antibodies) to determine whether or not it expresses the particular polypeptide. Alternatively, it can be tested with a probe to determine if it has a transgene (even if there is no expression).

A transgenic animal can be used as a founder animal, which may be bred from in order to produce further transgenic animals. Two transgenic animals may be crossed. For example, in some cases transgenic animals may be haploid for a given gene and it may be desired to try to provide a diploid offspring via crossing.

A transgenic animal may be cloned, e.g. by using the procedures set out in WO97/07668 and WO97/07699 (see also Nature 385:810-813 (1997)). Thus a quiescent cell can be provided and combined with an oocyte from which the nucleus has been removed combined. This can be achieved using electrical discharges. The resultant cell can be allowed to develop in culture and can then be transferred to a pseudopregnant female.

Analytical Tools and Systems

We disclose a moiety comprising a Fve polypeptide, a Fve nucleic acid, a vector comprising Fve, a cell expressing Fve, an Fve binding agent, a moiety identified/identifiable by a screen as described here, when used as an analytical tool or when present in a system suitable for analysis, especially high throughput analysis.

Such an analytical tool or system is useful for a plethora of different purposes. These include diagnosis, forensic science, screening, the identification or characterisation of individuals or populations, preventative medicine, etc.

Libraries comprising such a Fve moiety may be used for the above purposes. A library will generally comprise a plurality of heterologous moieties. Preferred libraries comprise at least 100, at least 10,000, at least 1,000,000, or at least 1,000,000,000 heterologous moieties. Desirably a moiety is provided at a predetermined position within a library. In some cases a plurality of moieties may be present within a library at predetermined positions. A predetermined position may be assigned spatial co-ordinates. These may be stored or processed in a computer in order to assist in analysis.

We further disclose an array comprising such a Fve moiety (whether or not the array is also a library). Preferably the array is a regular array. The array may have a predetermined pattern. It may have a grid-like pattern Preferred arrays comprise at least 100, at least 10,000, at least 1,000,000, or at least 1,000,000,000 components.

A library or array may include naturally occurring moieties, non-naturally occurring moieties, or a mixture of naturally occurring and non-naturally occurring moieties. The moieties may provided in solution, on beads, on chips (see e.g. Fodor (1993) Nature 364:555-556), on bacteria (see e.g. U.S. Pat. No. 5,223,409), on spores (see e.g. U.S. Pat. No. 5,223,409), on phage (see e.g. Scott and Smith (1990) Science 249:386-90 and U.S. Pat. No. 5,223,409), etc.

Such Fve moieties may be immobilised upon a surface, if desired. For example, one or more nucleic acid molecules may be immobilised upon a surface (e.g. the surface of a bead or a chip). The surface may, for example, be silicon, glass, quartz, a membrane, etc. Techniques for immobilising nucleic acid molecules upon a surface are known and are disclosed, for example, in EP-A-0487104, WO96/04404, WO90/02205, WO96/12014, WO98/44151. In some cases they may include a step of nucleic acid amplification, and may involve PCR.

Immobilisation is not however essential, even if moieties are to be used in high throughput analysis. For example, they may be provided in wells, channels, grooves or other containment means.

Whether or not present in a library, an array or in immobilised or non-immobilised form, it is often desirable to locate the position of one or more moieties being analysed or being used in analysis. This can be done by assigning it spatial co-ordinates, which may be provided, stored or processed or provided by a computer. In some cases the location may be determined by a sensor (e.g. a CCD device), which may be operatively linked with a computer.

DNA Vaccines

Any of the Fve nucleic acids disclosed here may be administered to an individual in the form of a DNA vaccine. DNA vaccines are known in the art, and are described in detail in, for example, WO03012117, WO03007986, etc.

The Fve may be administered to an individual in the form of a DNA vaccine. A DNA encoding the Fve, for example, a Fve nucleic acid as disclosed here, may be in any form, for example in the form of a cloned plasmid DNA or a synthetic oligonucleotide. The DNA may be delivered together with a cytokine, for example, IL-2, and/or other co-stimulatory molecules. The cytokines and/or co-stimulatory molecules may themselves be delivered in the form of plasmid or oligonucleotide DNA.

The response to a DNA vaccine has been shown to be increased by the presence of immunostimulatory DNA sequences (ISS). These can take the form of hexameric motifs containing methylated CpG, according to the formula: 5' purine-purine-CG-pyrimidine-pyrimidine-3'. The DNA vaccines may incorporate these or other ISSs, in the DNA encoding the Fve, in the DNA encoding the cytokine or other co-stimulatory molecules, or in both. A review of the advantages of DNA vaccination is provided by Tighe et al (1998, Immunology Today, 19(2), 89-97).

Antibodies

We also provide monoclonal or polyclonal antibodies to polypeptides or fragments thereof Thus, we further provide a process for the production of monoclonal or polyclonal antibodies to an Fve polypeptide, fragment, homologue, variant or derivative thereof If polyclonal antibodies are desired, a selected mammal (e.g., mouse, rabbit, goat, horse, etc.) is immunised with an immunogenic polypeptide bearing an epitope(s) from a polypeptide. Serum from the immunised animal is collected and treated according to known procedures. If serum containing polyclonal antibodies to an epitope from a polypeptide contains antibodies to other antigens, the polyclonal antibodies can be purified by immunoaffinity chromatography. Techniques for producing and processing polyclonal antisera are known in the art. In order that such antibodies may be made, we also provide polypeptides or fragments thereof haptenised to another polypeptide for use as immunogens in animals or humans.

Monoclonal antibodies directed against epitopes in the polypeptides can also be readily produced by one skilled in the art. The general methodology for making monoclonal antibodies by hybridomas is well known. Immortal antibody-producing cell lines can be created by cell fusion, and also by other techniques such as direct transformation of B lymphocytes with oncogenic DNA, or transfection with Epstein-Barr virus. Panels of monoclonal antibodies produced against epitopes in the polypeptides can be screened for various properties; i.e., for isotype and epitope affinity.

An alternative technique involves screening phage display libraries where, for example the phage express scFv fragments on the surface of their coat with a large variety of complementarity determining regions (CDRs). This technique is well known in the art.

Antibodies, both monoclonal and polyclonal, which are directed against epitopes from polypeptides are particularly useful in diagnosis, and those which are neutralising are useful in passive immunotherapy. Monoclonal antibodies, in particular, may be used to raise anti-idiotype antibodies. Anti-idiotype antibodies are immunoglobulins which carry an "internal image" of the antigen of the agent against which protection is desired.

Techniques for raising anti-idiotype antibodies are known in the art. These anti-idiotype antibodies may also be useful in therapy.

For the purposes of this document, the term "antibody", unless specified to the contrary, includes fragments of whole antibodies which retain their binding activity for a target antigen. Such fragments include Fv, F(ab') and $F(ab')_2$ fragments, as well as single chain antibodies (scFv). Furthermore, the antibodies and fragments thereof may be humanised antibodies, for example as described in BP-A-239400.

Antibodies may be used in method of detecting polypeptides present in biological samples by a method which comprises: (a) providing an antibody, (b) incubating a biological sample with said antibody under conditions which allow for the formation of an antibody-antigen complex; and (c) determining whether antibody-antigen complex comprising said antibody is formed.

Suitable samples include extracts tissues such as brain, breast, ovary, lung, colon, pancreas, testes, liver, muscle and bone tissues or from neoplastic growths derived from such tissues.

Antibodies may be bound to a solid support and/or packaged into kits in a suitable container along with suitable reagents, controls, instructions and the like.

Assays

We disclose assays that are suitable for identifying substances which bind to Fve polypeptides, or fragments, homologues, variants or derivatives thereof In general, such binding assays involve exposing a Fve polypeptide, nucleic acid, or a fragment, homologue, variant or derivative thereof to a candidate molecule and detecting an interaction or binding between the Fve polypeptide, nucleic acid, or a fragment, homologue, variant or derivative thereof and the candidate molecule. The binding assay may be conducted in vitro, or in vivo.

We disclose assays for identifying substances which are capable of potentiating the activities of Fve polypeptide. Activities of Fve have been described in detail above. Such compounds may be employed as agonists of Fve polypeptide, and may for example be co-administered to an individual to enhance any desired effect.

In general, an assay to identify such substances or compounds involves providing a cell or organism, exposing the cell or organism to a Fve polypeptide, nucleic acid, or a fragment, homologue, variant or derivative thereof, exposing the cell to a candidate molecule, and detecting an effect associated with Fve. Any Fve polypeptide mediated effect or funciton, as disclosed in this document, particularly the Examples, may be detected.

In particular, the Fve polypeptide mediated effect is preferably chosen from the group consisting of: up-regulation of expression of Th1 cytokines, preferably IFN-γ and TNF-α, down-regulation of expression of Th2 cytokines, preferably IL-4 and IL-13, hemagglutination activity, cell aggregation activity, lymphocyte aggregation activity, lymphoproliferation activity, up-regulation of expression of IL-2, IFN-γ, TNF-α, but not IL-4 in $CD3^+$ T cells, interaction with T and NK cells, adjuvant activity, stimulation of $CD3^+$ $CD16^+$ $CD56^+$ natural killer (NK) T cells, up-regulation of expression of allergen specific IgG2a antibody, prevention of systemic anaphylactic reactions and/or descreased footpad edema, prefereably as assayed using the Arthus reaction (Ko et al, 1995).

In order to identify agonists, an additive or preferably synergistic effect is detected. Thus, while Fve polypeptide on its own is, for example, capable of reducing a level or number, or down-regulation of expression of a molecule, the assays identify molecules which further reduce the level, number or further down-regulate the expression of a molecule. Thus, preferably, the candidate molecule in conjunction with the Fve polypeptide, nucleic acid, or a fragment, homologue, variant or derivative thereof, down-regulates the expression of, or reduces the level or number, by more than 10%, more than 20%, more than 30%, more than 40%, more than 50%, more than 60%, more than 70%, more than 80%, more than 90%, or more compared to an Fve polypeptide on its own. Thus, for example, a candidate molecule suitable for use as an agonist is one which is capable of enhancing by 10% more the up-regulation of expression of Th1 cytokines, preferably IFN-γ and TNF-α, achieved by Fve polypeptide on its own.

Conversely, assays to identify antagonists involve the detection of a reduction in Fve polypeptide mediated effect. Preferably, the down-regulation of expression or reduction in number or level achieved by Fve polypeptide is reduced in the presence of a suitable candidate molecule. Preferably, the reduction is at least 10%, preferably at least 20%, preferably at least 30%, preferably at least 40%, preferably at least 50%, preferably at least 60%, preferably at least 70%, preferably at least 80%, preferably at least 90%, or more compared to an Fve polypeptide on its own. Thus, for example, a candidate molecule suitable for use as an antagonist is one which is capable of reducing by 10% more the up-regulation of expression of Th1 cytokines, preferably IFN-γ and TNF-α, achieved by Fve polypeptide on its own.

As an illustration, if N1 is the expression of Th1 cytokines, in an untreated organism or cell, and N2 the expression in an organism or cell exposed to Fve polypeptide, nucleic acid, or a fragment, homologue, variant or derivative thereof, the expression of Th1 cytoldnes is increased by $R=(N2-N1)/N1\times 100\%$. Agonists increase R, by a factor x, where x is greater than 1 (e.g., x=1, 1.1, 1.2, 1.3, 1.4, 1.5, 2, 3, 4, 5, 10, 20, 50, 100 etc); while antagonists decrease R, by a factor x, where x is less than 1 (e.g., x=0.9, 0.9, 0.7, 0.6, 0.5, 0.4, 0.3, 0.2, 0.1 etc).

For example, an organism may be exposed to a Fve polypeptide, nucleic acid, or a fragment, homologue, variant or derivative thereof and a candidate molecule, and any of the biological activities as set out above, or any combination, detected. Preferred candidate molecules are those which provide an additive or synergistic effect in combination with Fve.

Also disclosed are assays to identify antagonists of Fve polypeptide. Such assays involve detecting a reduced effect on exposure of a cell or organism to an Fve polypeptide, nucleic acid, or a fragment, homologue, variant or derivative thereof in conjunction with a candidate molecule.

In a preferred embodiment, the assays are conducted on whole organisms rather than cells. Preferably, the organism is one which suffers from a disease as disclosed in this document, or exhibits one or more symptoms of such a disease.

Candidate Molecules

Suitable candidate molecules for use in the above assays include peptides, especially of from about 5 to 30 or 10 to 25 amino acids in size. Peptides from panels of peptides comprising random sequences or sequences which have been varied consistently to provide a maximally diverse panel of peptides may be used.

Suitable candidate molecules also include antibody products (for example, monoclonal and polyclonal antibodies, single chain antibodies, chimeric antibodies and CDR-grafted antibodies). Furthermore, combinatorial libraries, peptide and peptide mimetics, defined chemical entities, oligonucleotides, and natural product libraries may be screened for activity. The candidate molecules may be used in an initial screen in batches of, for example 10 types of molecules per reaction, and the molecules of those batches which show enhancement or reduction of a Fve polypeptide mediated effect tested individually.

Libraries

Libraries of candidate molecules, such as libraries of polypeptides or nucleic acids, maybe employed in the methods and compositions described here. Such libraries are exposed a cell or organism in the presence of a Fve polypeptide, nucleic acid, or a fragment, homologue, variant or derivative thereof, and an Fve polypeptide mediated effect detected and assayed as described above.

Selection protocols for isolating desired members of large libraries are known in the art, as typified by phage display techniques. Such systems, in which diverse peptide sequences are displayed on the surface of filamentous bacteriophage (Scott and Smith (1990 supra), have proven useful for creating libraries of antibody fragments (and the nucleotide sequences that encoding them) for the in vitro selection and amplification of specific antibody fragments that bind a target antigen. The nucleotide sequences encoding the $V_H$ and $V_L$ regions are linked to gene fragments which encode leader signals that direct them to the periplasmic space of *E. coli* and as a result the resultant antibody fragments are displayed on the surface of the bacteriophage, typically as fusions to bacteriophage coat proteins (e.g., pIII or pVIII). Alternatively, antibody fragments are displayed externally on lambda phage capsids (phagebodies). An advantage of phage-based display systems is that, because they are biological systems, selected library members can be amplified simply by growing the phage containing the selected library member in bacterial cells. Furthermore, since the nucleotide sequence that encodes the polypeptide library member is contained on a phage or phagemid vector, sequencing, expression and subsequent genetic manipulation is relatively straightforward.

Methods for the construction of bacteriophage antibody display libraries and lambda phage expression libraries are well known in the art (McCafferty et al. (1990) supra; Kang et al. (1991) *Proc. Natl. Acad. Sci. U.S.A.,* 88: 4363; Clackson et al. (1991) *Nature,* 352: 624; Lowman et al. (1991) *Biochemistry,* 30: 10832; Burton et al. (1991) *Proc. Natl. Acad. Sci U.S.A.,* 88: 10134; Hoogenboom et al. (1991) Nucleic Acids Res., 19: 4133; Chang et al. (1991) *J. Immunol.,* 147: 3610; Breitling et al. (1991) *Gene,* 104: 147; Marks et al. (1991) supra; Barbas et al. (1992) supra; Hawkins and Winter (1992) *J. Immunol.,* 22: 867; Marks et al., 1992, *J. Biol. Chem.,* 267: 16007; Lerner et al. (1992) *Science,* 258: 1313, incorporated herein by reference). Such techniques may be modified if necessary for the expression generally of polypeptide libraries.

One particularly advantageous approach has been the use of scFv phage-libraries (Bird, R. E., et al. (1988) *Science* 242: 423-6, Huston et al., 1988, Proc. Natl. Acad. Sci U.S.A., 85: 5879-5883; Chaudhary et al. (1990) Proc. Natl. Acad. Sci U.S.A., 87: 1066-1070; McCafferty et al. (1990) supra; Clackson et al. (1991) supra; Marks et al. (1991) supra; Chiswell et al. (1992) Trends Biotech., 10: 80; Marks et al. (1992) supra). Various embodiments of scFv libraries displayed on bacteriophage coat proteins have been described. Refinements of phage display approaches are also known, for example as described in WO96/06213 and WO92/01047 (Medical Research Council et al.) and WO97/08320 (Morphosys, supra), which are incorporated herein by reference.

Alternative library selection technologies include bacteriophage lambda expression systems, which may be screened directly as bacteriophage plaques or as colonies of lysogens, both as previously described (Huse et al. (1989) *Science,* 246: 1275; Caton and Koprowski (1990) *Proc. Natl. Acad. Sci. U.S.A.,* 87; Mullinax et al. (1990) *Proc. Natl. Acad. Sci. U.S.A.,* 87: 8095; Persson et al. (1991) *Proc. Natl. Acad. Sci. U.S.A.,* 88: 2432) and are of use. These expression systems may be used to screen a large number of different members of a library, in the order of about $10^6$ or even more. Other screening systems rely, for example, on direct chemical synthesis of library members. One early method involves the synthesis of peptides on a set of pins or rods, such as described in WO84/03564. A similar method involving peptide synthesis on beads, which forms a peptide library in which each bead is an individual library member, is described in U.S. Pat. No. 4,631,211 and a related method is described in WO92/00091. A significant improvement of the bead-based methods involves tagging each bead with a unique identifier tag, such as an oligonucleotide, so as to facilitate identification of the amino acid sequence of each library member. These improved bead-based methods are described in WO93/06121.

Another chemical synthesis method involves the synthesis of arrays of peptides (or peptidomimetics) on a surface in a manner that places each distinct library member (e.g., unique peptide sequence) at a discrete, predefined location in the array. The identity of each library member is determined by its spatial location in the array. The locations in the array where binding interactions between a predetermined molecule (e.g.; a receptor) and reactive library members occur is determined, thereby identifying the sequences of the reactive library members on the basis of spatial location. These methods are described in U.S. Pat. No. 5,143,854; WO90/15070 and WO92/10092; Fodor et al. (1991) *Science,* 251: 767; Dower and Fodor (1991) *Ann. Rep. Med. Chem.,* 26: 271.

Other systems for generating libraries of polypeptides or nucleotides involve the use of cell-free enzymatic machinery for the in vitro synthesis of the library members. In one method, RNA molecules are selected by alternate rounds of selection against a target ligand and PCR amplification (Tuerk and Gold (1990) *Science,* 249: 505; Ellington and Szostak (1990) *Nature,* 346: 818). A similar technique may be used to identify DNA sequences which bind a predetermined human transcription factor (Thiesen and Bach (1990) *Nucleic Acids Res.,* 18: 3203; Beaudry and Joyce (1992) *Science,* 257: 635; WO92/05258 and WO92/14843). In a similar way, in vitro translation can be used to synthesise polypeptides as a method for generating large libraries. These methods which generally comprise stabilised polysome complexes, are described further in WO88/08453, WO90/05785, WO90/07003, WO91/02076, WO91/05058, and WO92/02536. Alternative display systems which are not phage-based, such as those disclosed in WO95/22625 and WO95/11922 (Affymax) use the polysomes to display polypeptides for selection. These and all the foregoing documents also are incorporated herein by reference.

Combinatorial Libraries

Libraries, in particular, libraries of candidate molecules, may suitably be in the form of combinatorial libraries (also known as combinatorial chemical libraries).

A "combinatorial library", as the term is used in this document, is a collection of multiple species of chemical compounds that consist of randomly selected subunits. Combinatorial libraries may be screened for molecules which are capable of potentiating, enhancing, reducing or minimising the a Fve polypeptide mediated effect when exposed to a cell or organism.

Various combinatorial libraries of chemical compounds are currently available, including libraries active against proteolytic and non-proteolytic enzymes, libraries of agonists and antagonists of G-protein coupled receptors (GPCRs), libraries active against non-GPCR targets (e.g., integrins, ion channels, domain interactions, nuclear receptors, and transcription factors) and libraries of whole-cell oncology and anti-infective targets, among others. A comprehensive review of combinatorial libraries, in particular their construction and uses is provided in Dolle and Nelson (1999), *Journal of Combinatorial Chemistry*, Vol 1 No 4, 235-282. Reference is also made to *Combinatorial peptide library protocols* (edited by Shmuel Cabilly, Totowa, N.J.: Humana Press, c1998. *Methods in Molecular Biology*; v. 87).

Further references describing chemical combinatorial libraries, their production and use include those available from the URL http://www.netsci.org/Science/Combichem/, including The Chemical Generation of Molecular Diversity. Michael R. Pavia, Sphinx Pharmaceuticals, A Division of Eli Lilly (Published July, 1995); Combinatorial Chemistry: A Strategy for the Future—MDL Information Systems discusses the role its Project Library plays in managing diversity libraries (Published July, 1995); Solid Support Combinatorial Chemistry in Lead Discovery and SAR Optimization, Adnan M: M. Mjalli and Barry E. Toyonaga, Ontogen Corporation (Published July, 1995); Non-Peptidic Bradykinin Receptor Antagonists From a Structurally Directed Non-Peptide Library. Sarvajit Chakravarty, Babu J. Mavunkel, Robin Andy, Donald J. Kyle*, Scios Nova Inc. (Published July, 1995); Combinatorial Chemistry Library Design using Pharmacophore Diversity Keith Davies and Clive Briant, Chemical Design Ltd. (published July, 1995); A Database System for Combinatorial Synthesis Experiments—Craig James and David Weininger, Daylight Chemical Information Systems, Inc. (Published July, 1995); An Information Management Architecture for Combinatorial Chemistry, Keith Davies and Catherine White, Chemical Design Ltd. (Published July, 1995); Novel Software Tools for Addressing Chemical Diversity, R. S. Pearlman, Laboratory for Molecular Graphics and Theoretical Modeling, College of Pharmacy, University of Texas (Published June/July, 1996); Opportunities for Computational Chemists Afforded by the New Strategies in Drug Discovery: An Opinion, Yvonne Connolly Martin, Computer Assisted Molecular Design Project, Abbott Laboratories (Published June/July, 1996); Combinatorial Chemistry and Molecular Diversity Course at the University of Louisville: A Description, Arno F. Spatola, Department of Chemistry, University of Louisville (Published June/July, 1996); Chemically Generated Screening Libraries: Present and Future. Michael R. Pavia, Sphinx Pharmaceuticals, A Division of Eli Lilly (Published June/July, 1996); Chemical Strategies For Introducing Carbohydrate Molecular Diversity Into The Drug Discovery Process., Michael J. Sofia, Transcell Technologies Inc. (Published June/July, 1996); Data Management for Combinatorial Chemistry. Maryjo Zaborowski, Chiron Corporation and Sheila H. DeWitt, Parke-Davis Pharmaceutical Research, Division of Warner-Lambert Company (Published November, 1995); and The Impact of High Throughput Organic Synthesis on R&D in Bio-Based Industries, John P. Devlin (published March, 1996).

Techniques in combinatorial chemistry are gaining wide acceptance among modern methods for the generation of new pharmaceutical leads (Gallop, M. A. et al., 1994, J. Med. Chem. 37:1233-1251; Gordon, E. M. et al., 1994, J. Med. Chem. 37:1385-1401.). One combinatorial approach in use is based on a strategy involving the synthesis of libraries containing a different structure on each particle of the solid phase support, interaction of the library with a soluble receptor, identification of the 'bead' which interacts with the macromolecular target, and determination of the structure carried by the identified 'bead' (Lam, K. S. et al., 1991, Nature 354:82-84). An alternative to this approach is the sequential release of defined aliquots of the compounds from the solid support, with subsequent determination of activity in solution, identification of the particle from which the active compound was released, and elucidation of its structure by direct sequencing (Salmon, S. E. et al., 1993, Proc. Natl. Acad. Sci. USA 90:11708-11712), or by reading its code (Kerr, J. M. et al., 1993, J. Am. Chem. Soc. 115:2529-2531; Nikolaiev, V. et al., 1993, Pept. Res. 6:161-170; Ohlmeyer, M. H. J. et al., 1993, Proc. Natl. Acad. Sci. USA 90:10922-10926).

Soluble random combinatorial libraries may be synthesized using a simple principle for the generation of equimolar mixtures of peptides which was first described by Furka (Furka, A. et al., 1988, Xth International Symposium on Medicinal Chemistry, Budapest 1988; Furka, A. et al., 1988, 14th International Congress of Biochemistry, Prague 1988; Furka, A. et al., 1991, Int. J. Peptide Protein Res. 37:487-493). The construction of soluble libraries for iterative screening has also been described (Houghten, R. A. et al. 1991, Nature 354:84-86). K. S. Lam disclosed the novel and unexpectedly powerful technique of using insoluble random combinatorial libraries. Lam synthesized random combinatorial libraries on solid phase supports, so that each support had a test compound of uniform molecular structure, and screened the libraries without prior removal of the test compounds from the support by solid phase binding protocols (Lam, K. S. et al., 1991, Nature 354:82-84).

Thus, a library of candidate molecules may be a synthetic combinatorial library (e.g., a combinatorial chemical library), a cellular extract, a bodily fluid (e.g., urine, blood, tears, sweat, or saliva), or other mixture of synthetic or natural products (e.g., a library of small molecules or a fermentation mixture).

A library of molecules may include, for example, amino acids, oligopeptides, polypeptides, proteins, or fragments of peptides or proteins; nucleic acids (e.g., antisense; DNA; RNA; or peptide nucleic acids, PNA); aptamers; or carbohydrates or polysaccharides. Each member of the library can be singular or can be a part of a mixture (e.g., a compressed library). The library may contain purified compounds or can be "dirty" (i.e., containing a significant quantity of impurities). Commercially available libraries (e.g., from Affymetrix, ArQule, Neose Technologies, Sarco, Ciddco, Oxford Asymmetry, Maybridge, Aldrich, Panlabs, Pharmacopoeia, Sigma, or Tripose) may also be used with the methods described here.

In addition to libraries as described above, special libraries called diversity files can be used to assess the specificity, reliability, or reproducibility of the new methods. Diversity files contain a large number of compounds (e.g., 1000 or more small molecules) representative of many classes of compounds that could potentially result in nonspecific detection in an assay. Diversity files are commercially available or can also be assembled from individual compounds commercially available from the vendors listed above.

Candidate Substances

Suitable candidate substances include peptides, especially of from about 5 to 30 or 10 to 25 amino acids in size, based on the sequence of the polypeptides described in the Examples, or variants of such peptides in which one or more residues have been substituted. Peptides from panels of peptides comprising random sequences or sequences which have been varied consistently to provide a maximally diverse panel of peptides may be used.

Suitable candidate substances also include antibody products (for example, monoclonal and polyclonal antibodies, single chain antibodies, chimeric antibodies and CDR-grafted antibodies) which are specific for a polypeptide. Furthermore, combinatorial libraries, peptide and peptide mimetics, defined chemical entities, oligonucleotides, and natural product libraries may be screened for activity as inhibitors of binding of a polypeptide to the cell division cycle machinery, for example mitotic/meiotic apparatus (such as microtubules). The candidate substances may be used in an initial screen in batches of, for example 10 substances per reaction, and the substances of those batches which show inhibition tested individually. Candidate substances which show activity in in vitro screens such as those described below can then be tested in whole cell systems, such as mammalian cells which will be exposed to the inhibitor and tested for inhibition of any of the stages of the cell cycle.

Polypeptide Binding Assays

One type of assay for identifying substances that bind to a polypeptide involves contacting a polypeptide, which is immobilised on a solid support, with a non-immobilised candidate substance determining whether and/or to what extent the polypeptide and candidate substance bind to each other. Alternatively, the candidate substance may be immobilised and the polypeptide non-immobilised. This may be used to detect substances capable of binding to Fve polypeptides, or fragments, homologues, variants or derivatives thereof In a preferred assay method, the polypeptide is immobilised on beads such as agarose beads. Typically this is achieved by expressing the Fve polypeptide, or a fragment, homologue, variant or derivative thereof as a GST-fusion protein in bacteria, yeast or higher eukaryotic cell lines and purifying the GST-fusion protein from crude cell extracts using glutathione-agarose beads (Smith and Johnson, 1988). As a control, binding of the candidate substance, which is not a GST-fusion protein, to the immobilised polypeptide is determined in the absence of the polypeptide. The binding of the candidate substance to the immobilised polypeptide is then determined. This type of assay is known in the art as a GST pulldown assay. Again, the candidate substance may be immobilised and the polypeptide non-immobilised.

It is also possible to perform this type of assay using different affinity purification systems for immobilising one of the components, for example Ni-NTA agarose and histidine-tagged components.

Binding of the Fve polypeptide, or a fragment, homologue, variant or derivative thereof to the candidate substance may be determined by a variety of methods well-known in the art. For example, the non-immobilised component may be labeled (with for example, a radioactive label, an epitope tag or an enzyme-antibody conjugate). Alternatively, binding may be determined by immunological detection techniques. For example, the reaction mixture can be Western blotted and the blot probed with an antibody that detects the non-immobilised component. ELISA techniques may also be used.

Candidate substances are typically added to a final concentration of from 1 to 1000 nmol/ml, more preferably from 1 to 100 nmol/ml. In the case of antibodies, the final concentration used is typically from 100 to 500 μg/ml, more preferably from 200 to 300 μg/ml.

Fve Diseases

As disclosed elsewhere in this document, Fve polypeptides, nucleic acids, and fragments, homologues, variants and derivatives thereof, host cells, vectors, DNA vaccines, etc, are suitable for treating or preventing various diseases (here referred to as "Fve diseases"). They may be be administered in an amount in the range of 1 microgram to 1 gramme to an average human patient or individual to be vaccinated. It is preferred to use a smaller dose in the ragne of 1 microgram to 1 milligram for each administration, however.

The Fve polypeptides, etc may be adminisstered togeher, either simultaneously or separately with compounds such as cytokines and/or or growth factors, such as interleukin-2 (IL-2), Interleukin 12 (IL-12), GM-CSF or the like in order to strenghthen the immune response. The Fve polypeptides, etc can be used in a vaccine or a therapeutic composition either alone or in combination with other materials, for example, in the form of a lipopeptide conjugate which is known to induce a high-affinity cytotoxic T cell responses (Deres, 1989, Nature 342).

In particular, Fve diseases include allergies and cancer, described in further detail below.

Cancer

Fve polypeptides, nucleic acids, and fragments, homologues, variants and derivatives thereof, are suitable for treating or preventing cancer.

The terms "cancer" and "cancerous" refer to or describe the physiological condition in mammals that is typically characterized by unregulated cell growth. Examples of cancer include but are not limited to, carcinoma, lymphoma, blastoma, sarcoma, and leukemia. More particular examples of such cancers include squamous cell cancer, small-cell lung cancer, non-small cell lung cancer, gastric cancer, pancreatic cancer, glial cell tumors such as glioblastoma and neurofibromatosis, cervical cancer, ovarian cancer, liver cancer, bladder cancer, hepatoma, breast cancer, colon cancer, colorectal cancer, endometrial carcinoma, salivary gland carcinoma, kidney cancer, renal cancer, prostate cancer, vulval cancer, thyroid cancer, hepatic carcinoma and various types of head and neck cancer. Further examples are solid tumor cancer including colon cancer, breast cancer, lung cancer and prostrate cancer, hematopoietic malignancies including leukemias and lymphomas, Hodgkin's disease, aplastic anemia, skin cancer and familiar adenomatous polyposis. Further examples include brain neoplasms, colorectal neoplasms, breast neoplasms, cervix neoplasms, eye neoplasms, liver neoplasms, lung neoplasms, pancreatic neoplasms, ovarian neoplasms, prostatic neoplasms, skin neoplasms, testicular neoplasms, neoplasms, bone neoplasms, yellow fevertrophoblastic neoplasms, fallopian tube neoplasms, rectal neoplasms, colonic neoplasms, kidney neoplasms, stomach neoplasms, and parathyroid neoplasms. Breast cancer, prostate cancer, pancreatic cancer, colorectal cancer, lung cancer, malignant melanoma, leukaemia, lympyhoma, ovarian cancer, cervical cancer and biliary tract carcinoma are also included.

In preferred embodiments, Fve polypeptide, nucleic acid, and fragments, homologues, variants and derivatives thereof are used to treat T cell lymphoma, melanoma or lung cancer.

The Fve polypeptides and nucleic acids, etc, as described here, may also be used in combination with anticancer agents such as endostatin and angiostatin or cytotoxic agents or chemotherapeutic agent. For example, drugs such as such as adriamycin, daunomycin, cis-platinum, etoposide, taxol, taxotere and alkaloids, such as vincristine, and antimetabolites such as methotrexate. The term "cytotoxic agent" as used herein refers to a substance that inhibits or prevents the function of cells and/or causes destruction of cells. The term is intended to include radioactive isotopes (e.g. I, Y, Pr), chemotherapeutic agents, and toxins such as enzymatically active toxins of bacterial, fungal, plant or animal origin, or fragments thereof.

Also, the term includes oncogene product/tyrosine kinase inhibitors, such as the bicyclic ansamycins disclosed in WO 94/22867; 1,2-bis(arylamino) benzoic acid derivatives disclosed in EP 600832; 6,7-diamino-phthalazin-1-one derivatives disclosed in EP 600831; 4,5-bis(arylamino)-phthalimide derivatives as disclosed in EP 516598; or peptides which inhibit binding of a tyrosine kinase to a SH2-containing substrate protein (see WO 94/07913, for example). A "chemotherapeutic agent" is a chemical compound useful in the treatment of cancer. Examples of chemotherapeutic agents include Adriamycin, Doxorubicin, 5-Fluorouracil (5-FU), Cytosine arabinoside (Ara-C), Cyclophosphamide, Thiotepa, Busulfan, Cytoxin, Taxol, Methotrexate, Cisplatin, Melphalan, Vinblastine, Bleomycin, Etoposide, Ifosfamide, Mitomycin C, Mitoxantrone, Vincristine, VP-16, Vinorelbine, Carboplatin, Teniposide, Daunomycin, Carminomycin, Aminopterin, Dactinomycin, Mitomycins, Nicotinamide, Esperamicins (see U.S. Pat. No. 4,675,187), Melphalan and other related nitrogen mustards, and endocrine therapies (such as diethylstilbestrol (DES), Tamoxifen, LHRH antagonizing drugs, progestins, anti-progestins etc).

Allergies

Existing treatments for allergies typically involve the long-term use of steroids to depress the immune system. There are undesirable side effects with long-term steroid therapy. We demonstrate that Fve polypeptide, nucleic acid, or a fragment, homologue, variant or derivative thereof (as well as DNA vaccines, host cells and transgenic organisms comprising any of these) may be used to alleviate the symptoms of allergy, or to treat allergy. The term "allergy" as used here, refers to any allergic reactions such as allergic contact hypersensitivity.

In general, the allergy may be to an allergen from any source, for example, a source known to induce allergenic responses in humans. For example, the allergy may be to a tree pollen allergen, a grass pollen allergen, a weed pollen allergen, a feline antigen, or a fungal allergen. Thus, the allergy may be to a tree pollen allergen, for example Bet v 1 and Bet v 2 from birch tree. The allergy may be to a grass pollen allergen, for example, Phl p 1 and Phl p 2 from timothy grass. It may be to a weed pollen allergen, for example, antigen E from ragweed. It may be to an animal allergen, for example, a canine or feline antigen. Specifically, it may be to a major feline antigen, for example, Fel d 1. The allergy may be to a fungal allergen, for example a major fungal allergen, for example, Asp f1, Asp f2, and Asp f3 from *Aspergillus fumigatus*.

In preferred embodiments, the allergy is to a dust mite allergen, preferably a house dust mite allergen. In particular, the allergen is preferably derived from a mite from Family Glycyphagidae or Family Pyroglyphidae. Dust mites of Family Glycyphagidae include those in the genera *Aeroglyphus, Austroglycyphagus, Blomia, Ctenoglyphus, Glycyphagus, Gohieria, Lepidoglyphus*. Dust mites of Family Pyroglyphidae include those in the genera *Dermatophagoides, Euroglyphus, Pyroglyphus*. In preferred embodiments, the allergy is preferably to an allergen from a species in any of these genera.

In highly preferred embodiments, the allergy is to an allergen which is a group 1 allergen (Der p 1, Der f 1, Blo t 1, Eur m1, Lep d 1), a group 2 allergen (Der p 2, Der f 2, Blo t 2, Eur m 2, Lep d 2), a group 5 allergen (Blo t 5, Der p 5, Der f 5, Eur m 5, Lep d 5) or a group 15 allergen (Der p 15, Der f 15, Blot 15, Eur m 15, Lep d 15) from dust mite.

Allergies suitable for treatment with Fve polypeptide, nucleic acid, or a fragment, homologue, variant or derivative thereof may therefore include a seasonal respiratory allergy, allergic rhinitis, hayfever, nonallergic rhinitis, vasomotor rhinitis, irritant rhinitis, an allergy against grass pollens, tree pollens or animal danders, an allergy associated with allergic asthma, and food allergies. In particular, and as described elsewhere, Fve polypeptide, nucleic acid, or a fragment, homologue, variant or derivative thereof may be used to treat allergies to house dust mite (*Dermatophagoides* spp), preferably *Dermatophagoides pteronyssinus* or *Dermatophagoides farinae*, or to fungi or fungal spores, preferably *Aspergillus fumigatus*. Preferably, the allergens are comprised in faeces of *Dermatophagoides* spp.

Viral Infections

The immunomodulator-viral infectious antigen combinations, preferably conjugates, may be used to treat or prevent any of a number of viral infectious diseases. The virus concerned may be an RNA virus or a DNA virus. Preferably, the virus is an integrating virus. Preferably, the virus is selected from a lentivirus and a herpesvirus. More preferably, the virus is an HIV virus or a HSV virus.

The methods described here can therefore be used to prevent the development and establishment of diseases caused by or associated with any of the above viruses, including human immunodeficiency virus, such as HIV-1 and HIV-2, and herpesvirus, for example HSV-1, HSV-2, HSV-7 and HSV-8, as well as human cytomegalovirus, varicella-zoster virus, Epstein-Barr virus and human herpesvirus 6.in humans. Human papillomavirus (HPV) is also included, and the immunomodulator as described may be administered in combination (simultaneously or sequentially, etc) together with a viral infectious antigen comprising for example E7 antigen from HPV, as shown in the Examples.

Examples of viruses which may be targeted using the methods and compositions described here are given in the tables below.

Human Immunodeficiency Virus-1 (HIV-1)

| Family | Genus or [Subfamily] | Example | Diseases |
|---|---|---|---|
| | | DNA VIRUSES | |
| Herpesviridae | [*Alphaherpesvirinae*] | Herpes simplex virus type 1 (aka HHV-1) | Encephalitis, cold sores, gingivostomatitis |
| | | Herpes simplex virus type 2 (aka HHV-2) | Genital herpes, encephalitis |
| | | Varicella zoster virus (aka HHV-3) | Chickenpox, shingles |
| | [*Gammaherpesvirinae*] | Epstein Barr virus (aka HHV-4) | Mononucleoisis, hepatitis, tumors (BL, NPC) |
| | | Kaposi's sarcoma associated herpesvirus, KSHV (aka Human herpesvirus 8) | ?Probably: tumors, inc. Kaposi's sarcoma (KS) and some B cell lymphomas |
| | [*Betaherpesvirinae*] | Human cytomegalovirus (aka HHV-5) | Mononucleosis, hepatitis, pneumonitis, congenital |
| | | Human herpesvirus 6 | Roseola (aka E. subitum), pneumonitis |
| Adenoviridae | | Human herpesvirus 7 | Some cases of roseola? |
| Papovaviridae | Mastadenovirus | Human adenoviruses | 50 serotypes (species); respiratory infections |
| | Papillomavirus | Human papillomaviruses | 80 species; warts and tumors |
| Hepadnaviridae | Polyomavirus | JC, BK viruses | Mild usually; JC causes PML in AIDS |
| Poxviridae | Orthohepadnavirus | Hepatitis B virus (HBV) | Hepatitis (chronic), cirrhosis, liver tumors |
| | | Hepatitis C virus (HCV) | Hepatitis (chronic), cirrhosis, liver tumors |
| | Orthopoxvirus | Vaccinia virus | Smallpox vaccine virus |
| | | Monkeypox virus | Smallpox-like disease; a rare zoonosis (recent outbreak in Congo; 92 cases from February 1996-February 1997) |
| Parvoviridae | Parapoxvirus | Orf virus | Skin lesions ("pocks") |
| | Erythrovirus | B19 parvovirus | E. infectiousum (aka Fifth disease), aplastic crisis, fetal loss |
| Circoviridae | Dependovirus | Adeno-associated virus | Useful for gene therapy; integrates into chromosome |
| | Circovirus | TT virus (TTV) | Linked to hepatitis of unknown etiology |

-continued

| Human Immunodeficiency Virus-1 (HIV-1) | | | |
|---|---|---|---|
| Family | Genus or [Subfamily] | Example | Diseases |
| | | RNA VIRUSES | |
| Picornaviridae | Enterovirus | Polioviruses | 3 types; Aseptic meningitis, paralytic poliomyelitis |
| | | Echoviruses | 30 types; Aseptic meningitis, rashes |
| | | Coxsackieviruses | 30 types; Aseptic meningitis, myopericarditis |
| | Hepatovirus | Hepatitis A virus | Acute hepatitis (fecal-oral spread) |
| | Rhinovirus | Human rhinoviruses | 115 types; Common cold |
| Caliciviridae | Calicivirus | Norwalk virus | Gastrointestinal illness |
| Paramyxoviridae | Paramyxovirus | Parainfluenza viruses | 4 types; Common cold, bronchiolitis, pneumonia |
| | Rubulavirus | Mumps virus | Mumps: parotitis, aseptic meningitis (rare: orchitis, encephalitis) |
| | Morbillivirus | Measles virus | Measles: fever, rash (rare: encephalitis, SSPE) |
| | Pneumovirus | Respiratory syncytial virus | Common cold (adults), bronchiolitis, pneumonia (infants) |
| Orthomyxoviridae | Influenzavirus A | Influenza virus A | Flu: fever, myalgia, malaise, cough, pneumonia |
| | Influenzavirus B | Influenza virus B | Flu: fever, myalgia, malaise, cough, pneumonia |
| Rhabdoviridae | Lyssavirus | Rabies virus | Rabies: long incubation, then CNS disease, death |
| Filoviridae | Filovirus | Ebola and Marburg viruses | Hemorrhagic fever, death |
| Bornaviridae | Bornavirus | Borna disease virus | Uncertain; linked to schizophrenia-like disease in some animals |
| Retroviridae | Deltaretrovirus | Human T-lymphotropic virus type-1 | Adult T-cell leukemia (ATL), tropical spastic paraparesis (TSP) |
| | Spumavirus | Human foamy viruses | No disease known |
| | Lentivirus | Human immunodeficiency virus type-1 and -2 | AIDS, CNS disease |
| Togaviridae | Rubivirus | Rubella virus | Mild exanthem; congenital fetal defects |
| | Alphavirus | Equine encephalitis viruses (WEE, EEE, VEE) | Mosquito-born, encephalitis |
| Flaviviridae | Flavivirus | Yellow fever virus | Mosquito-born; fever, hepatitis (yellow fever!) |
| | | Dengue virus | Mosquito-born; hemorrhagic fever |
| | | St. Louis Encephalitis virus | Mosquito-born; encephalitis |
| | Hepacivirus | Hepatitis C virus | Hepatitis (often chronic), liver cancer |
| | | Hepatitis G virus | Hepatitis??? |
| Reoviridae | Rotavirus | Human rotaviruses | Numerous serotypes; Diarrhea |
| | Coltivirus | Colorado Tick Fever virus | Tick-born; fever |
| | Orthoreovirus | Human reoviruses | Minimal disease |
| Bunyaviridae | Hantavirus | Pulmonary Syndrome Hantavirus | Rodent spread; pulmonary illness (can be lethal, "Four Corners" outbreak) |
| | | Hantaan virus | Rodent spread; hemorrhagic fever with renal syndrome |
| | Phlebovirus | Rift Valley Fever virus | Mosquito-born; hemorrhagic fever |
| | Nairovirus | Crimean-Congo Hemorrhagic Fever virus | Mosquito-born; hemorrhagic fever |
| Arenaviridae | Arenavirus | Lymphocytic Choriomeningitis virus | Rodent-born; fever, aseptic meningitis |
| | | Lassa virus | Rodent-born; severe hemorrhagic fever (BL4 agents; also: Machupo, Junin) |
| | Deltavirus | Hepatitis Delta virus | Requires HBV to grow; hepatitis, liver cancer |
| Coronaviridae | Coronavirus | Human coronaviruses | Mild common cold-like illness |
| Astroviridae | Astrovirus | Human astroviruses | Gastroenteritis |
| Unclassified | "Hepatitis E-like viruses" | Hepatitis E virus | Hepatitis (acute); fecal-oral spread |

The combinations and conjugates described here, including Fve polypeptide combinations and conjugates, may be used to treat or prevent Human Immunodeficiency Virus (HIV) infection. The methods described here can therefore be used to prevent the development and establishment of diseases caused by or associated with human immunodeficiency virus, such as HIV-1 and HIV-2.

Human Immunodeficiency Virus (HI) is a retrovirus which infects cells of the immune system, most importantly $CD4^+$ T lymphocytes. $CD4^+$ T lymphocytes are important, not only in terms of their direct role in immune function, but also in stimulating normal function in other components of the immune system, including $CD8^+$ T-lymphocytes. These HIV infected cells have their function disturbed by several mechanisms and/or are rapidly killed by viral replication. The end result of chronic HIV infection is gradual depletion of $CD4^+$ T lymphocytes, reduced immune capacity, and ultimately the development of AIDS, leading to death.

The regulation of HIV gene expression is accomplished by a combination of both cellular and viral factors. HIV gene expression is regulated at both the transcriptional and post-transcriptional levels. The HIV genes can be divided into the early genes and the late genes. The early genes, Tat, Rev, and Nef, are expressed in a Rev-independent manner. The mRNAs encoding the late genes, Gag, Pol, Env, Vpr, Vpu, and Vif require Rev to be cytoplasmically localized and expressed. HIV transcription is mediated by a single promoter in the 5' LTR. Expression from the 5' LTR generates a 9-kb primary transcript that has the potential to encode all nine HIV genes. The primary transcript is roughly 600 bases shorter than the provirus. The primary transcript can be spliced into one of more than 30 mRNA species or packaged without further modification into virion particles (to serve as the viral RNA genome).

Any of the HIV proteins disclosed here may be used as a viral infectious antigen for productions of conjugates and combinations as described above.

Herpes Virus

The combinations and conjugates described here, including Fve polypeptide combinations and conjugates, may be used to treat or prevent Herpesvirus infection. The methods described here can therefore be used to prevent the development and establishment of diseases caused by or associated with herpesvirus, for example HSV-1, HSV-2, HSV-7 and HSV-8.

Particular examples of herpesvirus include: herpes simplex virus 1 (“HSV-1”), herpes simplex virus 2 (“HSV-2”), human cytomegalovirus (“HCMV”), varicella-zoster virus (“VZV”), Epstein-Barr virus (“EBV”), human herpesvirus 6 (“HHV6”), herpes simplex virus 7 (“HSV-7”) and herpes simplex virus 8 (“HSV-8”).

Herpesviruses have also been isolated from horses, cattle, pigs pseudorabies virus (“PSV”) and porcine cytomegalovirus), chickens (infectious larygotracheitis), chimpanzees, birds (Marck’s disease herpesvirus 1 and 2), turkeys and fish (see “Herpesviridae: A Brief Introduction”, Virology, Second Edition, edited by B. N. Fields, Chapter 64, 1787 (1990)).

Herpes simplex viral (“HSV”) infection is generally a recurrent viral infection characterized by the appearance on the skin or mucous membranes of single or multiple clusters of small vesicles, filled with clear fluid, on slightly raised inflammatory bases. The herpes simplex virus is a relatively large-sized virus. HSV-2 commonly causes herpes labialis. HSV-2 is usually, though not always, recoverable from genital lesions. Ordinarily, HSV-2 is transmitted venereally.

Diseases caused by varicella-zoster virus (human herpesvirus 3) include varicella (chickenpox) and zoster (shingles). Cytomegalovirus (human herpesvirus 5) is responsible for cytomegalic inclusion disease in infants. There is presently no specific treatment for treating patients infected with cytomegalovirus. Epstein-Barr virus (human herpesvirus 4) is the causative agent of infectious mononucleosis and has been associated with Burkitt’s lymphoma and nasopharyngeal carcinoma. Animal herpesviruses which may pose a problem for humans include B virus (herpesvirus of Old World Monkeys) and Marmoset herpesvirus (herpesvirus of New World Monkeys).

Herpes simplex virus 1 (HSV-1) is a human pathogen capable of becoming latent in nerve cells. Like all the other members of Herpesviridae it has a complex architecture and double-stranded linear DNA genome which encodes for variety of viral proteins including DNA pol. and TK.

HSV gene expression proceeds in a sequential and strictly regulated manner and can be divided into at least three phases, termed immediate early (IE or α), early (β) and late (γ). The cascade of HSV-1 gene expression starts from IE genes, which are expressed immediately after lytic infection begins. The IE proteins regulate the expression of later classes of genes (early and late) as well as their own expression. The product of IE175k (ICP4) gene is critical for HSV-1 gene regulation and ts mutants in this gene are blocked at IE stage of infection.

The IE genes themselves are activated by a virion structural protein VP16 (expressed late in the replicative cycle and incorporated into HSV particle). All 5 IE genes of HSV-1 (IE110k—2 copies/HSV genome, IE175—2 copies/HSV genome, IE68k, IE63k and IE12k) have at least one copy of a conserved promoter/enhancer sequence—TAATGARAT. This sequence is recognized by the transactivation complex which consists of; Oct-1, HCF and VP16. The GARAT element is required for efficient transactivation by VP16. This mechanism of gene activation is unique for HSV and despite Oct-1 being a common transcription factor, the Oct-1/HCF/VP16 complex activates specifically only HSV IE genes.

Any of the herpesvirus proteins disclosed here may be used as a viral infectious antigen for productions of conjugates and combinations as described above.

Cytokines

In a further embodiment, the Fve polypeptide, nucleic acid, fragment, homologue, variant or derivative thereof is used to modulate cytokine levels in an individual. Preferably, the level of inflammatory cytokines is down-regulated. Examples of inflammatory cytokines include Granulocyte-Macrophage-Colony stimulating factor (GM-CSF), as well as any cytokine that mediates migration of alveolar macrophages into the lung and act to increase cell proliferation.

The term “cytokine” may be used to refer to any of a number of soluble molecules (e.g., glycoproteins) released by sells of the immune system, which act nonenzymatically through specific receptors to regulate immune responses. Cytokines resemble hormones in that they act at low concentrations bound with high affinity to a specific receptor. Preferably, the term “cytokine” refers to a diverse group of soluble proteins and peptides which act as humoral regulators at nano- to picomolar concentrations and which, either under normal or pathological conditions, modulate the functional activities of individual cells and tissues.

Particular examples of cytokines which are suitable for use in the methods and compositions described include interleukins, lymphokine, interferon, Colony Stimulating Factors (CSFs) such as Granulocyte-Colony Stimulating Factor (G-CSF), Macrophage-Colony stimulating factor (N-CSF) and Granulocyte-Macrophage-Colony stimulating factor (GM-CSF), GSF, Platelet-Activating Factors (PAF), Tumor Necrosis Factor (TNF).

Thus, interleukins such as IL1, EL2 and IL4, as well as interferons such as IFN-α, IFN-β and IFN-γ are included. Tumour necrosis factors TNF-α (cachetin), TNF-β (lymphotoxin) may also be suitably employed.

Preferred cytokines are those which are capable of recruiting immune responses, for example, stimulation of dendritic cell or cytotoxic T cell activity, or which are capable of recruiting macrophages to the target site. In a highly preferred embodiment, the cytokine comprises EL-2, GM-CSF or GSF.

Chemical Coupling

As noted above, the immunomodulator may be coupled to the allergen by a number of methods. Crosslinkers are divided into homobifunctional crosslinkers, containing two identical reactive groups, or heterobifunctional crosslinkers, with two different reactive groups. Heterobifunctional crosslinkers allow sequential conjugations, minimizing polymerization.

Any of the homobifunctional or heterobifunctional crosslinkers presented in the table below may be used to couple the allergen with the immunomodulator to produce an immunomodulator-allergen conjugate.

| Reagent | Cat. No. | Modified Group | Solubility | Comments | Refs |
|---|---|---|---|---|---|
| | | | Homobifunctional | | |
| BMME | 442635-Y | —SH | DMF, Acetone | Homobifunctional crosslinker useful for formation of conjugates via thiol groups. | Weston, P. D., et al. 1980. Biochem. Biophys Acta. 612, 40. |
| BSOCOES | 203851-Y | —NH2 | Water | Base cleavable crosslinker useful for studying receptors and mapping surface polypeptide antigens on lymphocytes. | Howard, A. D., et al. 1985. J. Biol. Chem.260, 10833. |
| DSP | 322133-Y | —NH2 | Water | Thiol cleavable crosslinker used to immobilize proteins on supports containing amino groups. | Lee, W. T., and Conrad, D. H. 1985. J. Immunol.134, 518. |
| DSS | 322131-Y | —NH2 | Water | Non-cleavable, membrane impermeable crosslinker widely used for conjugating radiolabeled ligands to cell surface receptors and for detecting conformational changes in membrane proteins. | D'Souza, S. E., et al. 1988. J. Biol. Chem.263, 3943. |
| EGS | 324550-Y | —NH2 | DMSO | Hydroxylamine cleavable reagent for crosslinking and reversible immobilization of proteins through their primary amine groups. Useful for studying structure-function relationships. | Geisler, N., et al. 1992. Eur. J. Biochem.206, 841.14. Moenner, M., et al. 1986. Proc. Natl. Acad. Sci. USA83, 5024. |
| EGS, Water Soluble | 324551-Y | —NH2 | Water | Water soluble version of EGS that reacts rapidly with dilute proteins at neutral pH. Crosslinked proteins are readily cleaved with hydroxylamine at pH 8.5 for 3-6 hours, 37° C. | Yanagi, T., et al. 1989. Agric. Biol. Chem.53, 525. |
| Glutaraldehyde | 354400-Y | —OH | Water | Used for crosslinking proteins and polyhydroxy materials. Conjugates haptens to carrier proteins; also used as a tissue fixative. | Harlow, E., and Lane, D. 1988. Antibodies: A Laboratory Manual, Cold Spring Harbor Publications, N.Y., p. 349. |
| SATA | 573100-Y | —NH2 | DMSO | Introduces protected thiols via primary amines. When treated with hydroxylamine, yields a free sulhydryl group that can be conjugated to maleimide-modified proteins. | Duncan, R. J. S., et al. 1983. Anal. Biochem.132, 68. |
| | | | Heterobifunctional | | |
| GMBS | 442630-Y | —NH2, —SH | DMSO | Heterobifunctional crosslinker useful for preparing enzyme-antibody conjugates (e.g. -gal-IgG) and for immobilizing enzymes on solid supports. | Kitagwa, T., et al. 1983. J. Biochem.94, 1160.19. Rusin, K. M., et al. 1992. Biosens. Bioelectron.7, 367. |
| MBS | 442625-Y 442626-Y | —NH2, —SH —NH2, —SH | DMSO, Water | Thiol cleavable, heterobifunctional reagent especially useful for preparing peptide-carrier conjugates and conjugating toxins to antibodies. | Green, N., et al. 1982. Cell 28, 477. |
| PMPI | 528250-Y | —SH2, —OH | DMSO, DMF | Used in the preparation of alkaline phosphatase conjugates of estradiol, progesterone, serine-enriched peptides, and vitamin B12. | Aithal, H. N., et al. 1988. J. Immunol. Methods112, 63. |
| SMCC | 573114-Y 573115-Y | —NH2, —SH —NH2, —SH | DMF, AN Acetonitrile Water | Heterobifunctional reagent for enzyme labeling of antibodies and antibody fragments. The cyclohexane bridge provides extra stability to the maleimide group. Ideal reagent for preserving enzyme activity and antibody specificity after coupling. | Annunziato, M. E., et al. 1993. Bioconjugate Chem.4, 212. |
| SPDP | 573112-Y | —NH2, —SH | DMF, AN Acetonitrile | Introduces protected thiol groups to amine groups. Thiolated proteins can be coupled to a secondmolecule via an iodoacetamide or maleimide | Caruelle, D., et al. 1988. Anal. Biochem.173, 328. |

-continued

| Reagent | Cat. No. | Modified Group | Solubility | Comments | Refs |
|---|---|---|---|---|---|
| | | | | group, or to a second pyridyldisulfide containing molecule. | |

Each of these reagents may be obtained from a number of manufacturers, for example, from Calbiochem (catalogue number in column 2), or Piece Chemical Company.

Pharmaceutical Compositions

Fve polypeptides may be produced in large amounts at low cost in a bioactive form, allowing the development of Fve containing formulations by aerosolisation, nebulisation, intranasal or intratracheal administration.

While it is possible for the composition comprising the Fve polypeptide or nucleic acid to be administered alone, it is preferable to formulate the active ingredient as a. pharmaceutical formulation. We therefore also disclose pharmaceutical compositions comprising Fve polypeptide or nucleic acid, or a fragment, homologue, variant or derivative thereof. Such pharmaceutical compositions are useful for delivery of Fve polypeptide, nucleic acid, fragment, homologue, variant or derivative thereof to an individual for the treatment or alleviation of symptoms as described.

The composition may include the Fve polypeptide, nucleic acid, fragment, homologue, variant or derivative thereof, a structurally related compound, or an acidic salt thereof. The pharmaceutical formulations comprise an effective amount of Fve polypeptide, nucleic acid, fragment, homologue, variant or derivative thereof, together with one or more pharmaceutically-acceptable carriers. An "effective amount" of an Fve polypeptide, nucleic acid fragment, homologue, variant or derivative thereof is the amount sufficient to alleviate at least one symptom of a disease as described.

The effective amount will vary depending upon the particular disease or syndrome to be treated or alleviated, as well as other factors including the age and weight of the patient, how advanced the disease etc state is, the general health of the patient, the severity of the symptoms, and whether the Fve polypeptide, nucleic acid, fragment, homologue, variant or derivative thereof is being administered alone or in combination with other therapies.

Suitable pharmaceutically acceptable carriers are well known in the art and vary with the desired form and mode of administration of the pharmaceutical formulation. For example, they can include diluents or excipients such as fillers, binders, wetting agents, disintegrators, surface-active agents, lubricants and the like. Typically, the carrier is a solid, a liquid or a vaporizable carrier, or a combination thereof. Each carrier should be "acceptable" in the sense of being compatible with the other ingredients in the formulation and not injurious to the patient. The carrier should be biologically acceptable without eliciting an adverse reaction (e.g. immune response) when administered to the host.

The pharmaceutical compositions disclosed here include those suitable for topical and oral administration, with topical formulations being preferred where the tissue affected is primarily the skin or epidermis (for example, psoriasis, eczema and other epidermal diseases). The topical formulations include those pharmaceutical forms in which the composition is applied externally by direct contact with the skin surface to be treated. A conventional pharmaceutical form for topical application includes a soak, an ointment, a cream, a lotion, a paste, a gel, a stick, a spray, an aerosol, a bath oil, a solution and the like. Topical therapy is delivered by various vehicles, the choice of vehicle can be important and generally is related to whether an acute or chronic disease is to be treated. Other formulations for topical application include shampoos, soaps, shake lotions, and the like, particularly those formulated to leave a residue on the underlying skin, such as the scalp (Arndt et al, in Dermatology In General Medicine 2:2838 (1993)).

In general, the concentration of the Fve polypeptide, nucleic acid, fragment, homologue, variant or derivative thereof composition in the topical formulation is in an amount of about 0.5 to 50% by weight of the composition, preferably about 1 to 30%, more preferably about 2-20%, and most preferably about 5-10%. The concentration used can be in the upper portion of the range initially, as treatment continues, the concentration can be lowered or the application of the formulation may be less frequent. Topical applications are often applied twice daily. However, once-daily application of a larger dose or more frequent applications of a smaller dose may be effective. The stratum corneum may act as a reservoir and allow gradual penetration of a drug into the viable skin layers over a prolonged period of time.

In a topical application, a sufficient amount of active ingredient must penetrate a patient's skin in order to obtain a desired pharmacological effect. It is generally understood that the absorption of drug into the skin is a function of the nature of the drug, the behaviour of the vehicle, and the skin. Three major variables account for differences in the rate of absorption or flux of different topical drugs or the same drug in different vehicles; the concentration of drug in the vehicle, the partition coefficient of drug between the stratum corneum and the vehicle and the diffusion coefficient of drug in the stratum corneum. To be effective for treatment, a drug must cross the stratum corneum which is responsible for the barrier function of the skin. In general, a topical formulation which exerts a high in vitro skin penetration is effective in vivo. Ostrenga et al (J. Pharm. Sci., 60:1175-1179 (1971) demonstrated that in vivo efficacy of topically applied steroids was proportional to the steroid penetration rate into dermatomed human skin in vitro.

A skin penetration enhancer which is dermatologically acceptable and compatible with the agent can be incorporated into the formulation to increase the penetration of the active compound(s) from the skin surface into epidermal keratinocytes. A skin enhancer which increases the absorption of the active compound(s) into the skin reduces the amount of agent needed for an effective treatment and provides for a longer lasting effect of the formulation. Skin penetration enhancers are well known in the art. For example, dimethyl sulfoxide (U.S. Pat. No. 3,711,602); oleic acid, 1,2-butanediol surfactant (Cooper, J. Pharm. Sci., 73:1153-1156 (1984)); a combination of ethanol and oleic acid or oleyl alcohol (EP 267,617), 2-ethyl-1,3-hexanediol (WO 87/03490); decyl methyl sulphoxide and Azone.RTM. (Hadgraft, Eur. J. Drug. Metab. Pharmacokinet, 21:165-173 (1996)); alcohols, sulphoxides, fatty acids, esters, Azone.RTM., pyrrolidones, urea and polyoles (Kalbitz et al, Pharmazie, 51:619-637 (1996));

Terpenes such as 1,8-cineole, menthone, limonene and nerolidol (Yamane, J. Pharmacy & Pharmocology, 47:978-989 (1995)); Azone.RTM. and Transcutol (Harrison et al, Pharmaceutical Res. 13:542-546 (1996)); and oleic acid, polyethylene glycol and propylene glycol (Singh et al, Pharmazie, 51:741-744 (1996)) are known to improve skin penetration of an active ingredient.

Levels of penetration of an agent or composition can be determined by techniques known to those of skill in the art. For example, radiolabeling of the active compound, followed by measurement of the amount of radiolabeled compound absorbed by the skin enables one of skill in the art to determine levels of the composition absorbed using any of several methods of determining skin penetration of the test compound. Publications relating to skin penetration studies include Reinfenrath, W G and G S Hawkins. The Weaning Yorkshire Pig as an Animal Model for Measuring Percutaneous Penetration. In:Swine in Biomedical Research (M. E. Tumbleson, Ed.) Plenum, New York, 1986, and Hawkins, G. S. Methodology for the Execution of In Vitro Skin Penetration Determinations. In: Methods for Skin Absorption, B W Kemppainen and W G Reifenrath, Eds., CRC Press, Boca Raton, 1990, pp. 67-80; and W. G. Reifenrath, Cosmetics & Toiletries, 110:3-9 (1995).

For some applications, it is preferable to administer a long acting form of agent or composition using formulations known in the arts, such as polymers. The agent can be incorporated into a dermal patch (Junginger, H. E., in Acta Pharmaceutica Nordica 4:117 (1992); Thacharodi et al, in Biomaterials 16:145-148 (1995); Niedner R., in Hautarzt 39:761-766 (1988)) or a bandage according to methods known in the arts, to increase the efficiency of delivery of the drug to the areas to be treated.

Optionally, the topical formulations can have additional excipients for example; preservatives such as methylparaben, benzyl alcohol, sorbic acid or quaternary ammonium compound; stabilizers such as EDTA, antioxidants such as butylated hydroxytoluene or butylated hydroxanisole, and buffers such as citrate and phosphate.

The pharmaceutical composition can be administered in an oral formulation in the form of tablets, capsules or solutions. An effective amount of the oral formulation is administered to patients 1 to 3 times daily until the symptoms of the disease alleviated. The effective amount of agent depends on the age, weight and condition of a patient In general, the daily oral dose of agent is less than 1200 mg, and more than 100 mg. The preferred daily oral dose is about 300-600 mg. Oral formulations are conveniently presented in a unit dosage form and may be prepared by any method known in the art of pharmacy. The composition may be formulated together with a suitable pharmaceutically acceptable carrier into any desired dosage form. Typical unit dosage forms include tablets, pills, powders, solutions, suspensions, emulsions, granules, capsules, suppositories. In general, the formulations are prepared by uniformly and intimately bringing into association the agent composition with liquid carriers or finely divided solid carriers or both, and as necessary, shaping the product. The active ingredient can be incorporated into a variety of basic materials in the form of a liquid, powder, tablets or capsules to give an effective amount of active ingredient to treat the disease.

Other therapeutic agents suitable for use herein are any compatible drugs that are effective for the intended purpose, or drugs that are complementary to the agent formulation. The formulation utilized in a combination therapy may be administered simultaneously, or sequentially with other treatment, such that a combined effect is achieved.

The invention is described further, for the purpose of illustration only, in the following examples.

EXAMPLES

In each of the Examples presented below, where an activity is described for a Fve polypeptide comprising a GST (glutathione S fransferase) portion (for example, as a GST-FIP fusion protein), we find that the polypeptide itself, without the GST portion, has substantially the same activity. This is to be expected, as the GST domain does not have any relevant biological activity as far as FIP is concerned.

Example 1

Isolation and Purification of Native Fve Protein from Golden Needle Mushroom Methods and materials Two kilograms of the fruit bodies of *Flammulina velutipes* are homogenized with 2L ice-cold 5% acetic acid in the presence of 0.05 M 2-mercaptoethanol and 0.3 M sodium chloride. The proteins in the supernatant are precipitated by 95% saturated ammonium sulfate.

The precipitate is re-dissolved and dialyzed against 10 mM Tris-HCl pH 8.5 (buffer A) at 4° C. for 48 hours with six to eight changes of dialysis buffer. The protein solution is applied to the Q Sepharose FF column (2.6×10 cm, Pharmacia) that has been previously equilibrated with buffer A. The unbound fraction is collected and dialyzed against 10 mM sodium acetate pH 5.0 (buffer B) at 4° C. for 48 hours with six to eight changes of dialysis buffer and then further purified by applying to the SP Sepharose FF column (2.6×10 cm, Pharmacia) that has been previously equilibrated with buffer B.

The protein is eluted with a gradient of 0-0.5 M NaCl in buffer B. Fractions containing Fve protein are collected and analyzed by a 7.5% Tris-Tricine SDS-PAGE.

Results

High Yield of Native Fve Protein is Purified from *Flammulina velutipes*

Figure 1:
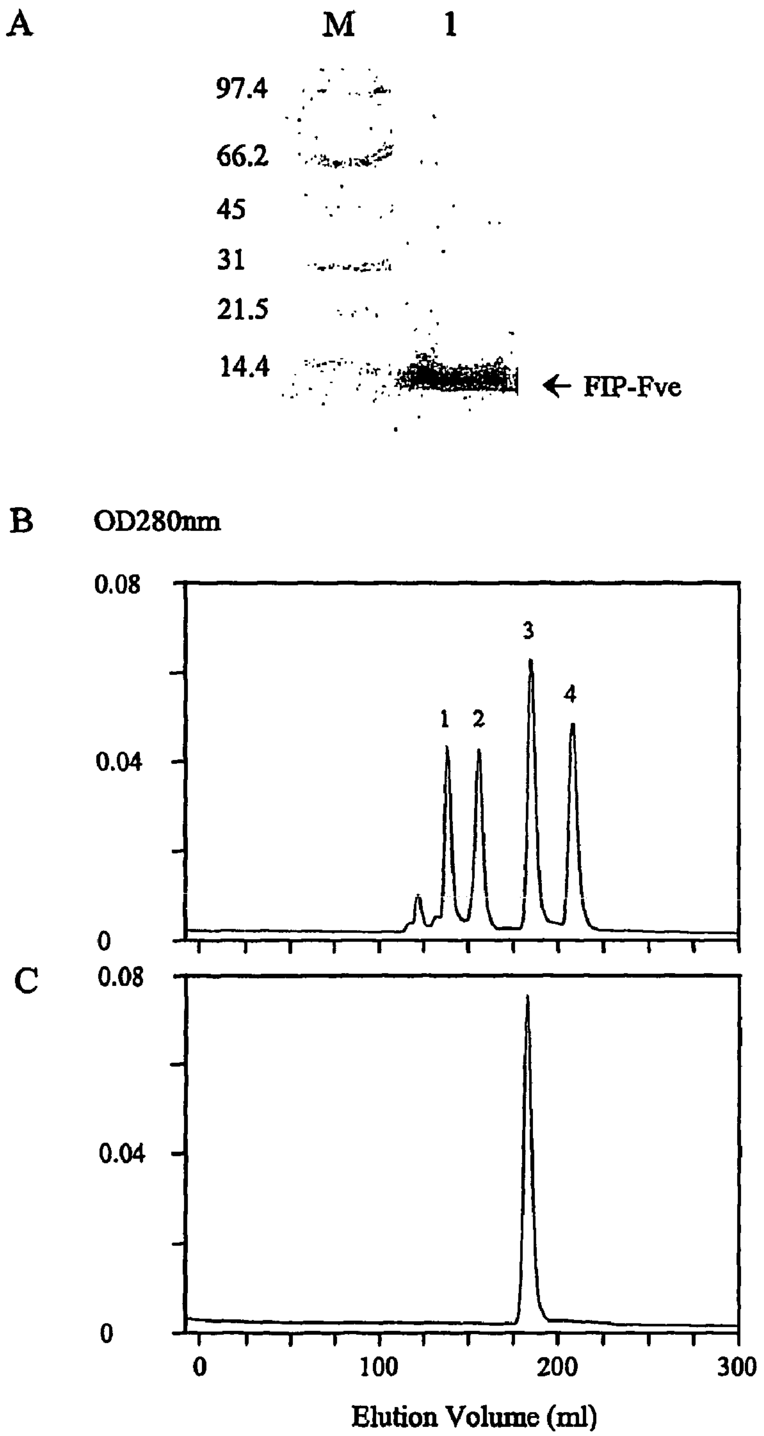
FIG. 1. Analysis of purified native Fve by SDS-PAGE and gel filtration chromatography. (a). The native Fve protein purified by cation and anion exchange chromatography is analyzed by Tricine SDS-PAGE. Fve protein gave a single band with an apparent molecular mass of 12.7 kDa. Lane M, molecular mass markers; lane 1, purified native Fve protein. (b) Elution profile of calibration proteins by Superdex 75 chromatography. Peaks, 1. bovine serum albumin (67 kDa); 2. ovalbumin (43 kDa); 3. chymotrypsinogen A (25 kDa); 4. ribonuclease A (13.7 kDa). (c) Purified native Fve formed homodimer at 25.5 kDa.

The native Fve protein has an apparent molecular weight of 12.7 kDa as determined by SDS-PAGE (FIG. 1A). However, it appears to be a homodimer with a molecular weight of 25.5 kDa as determined by Superdex 75 (26×60 cm, Pharmacia) gel filtration chromatography (FIGS. 1B and 1C). The running buffer for gel filtration is 10 mM Tris-HCl pH 7.5, 0.2 M sodium chloride.

Fve protein is the major component in the crude extract from the mushroom fruit bodies. By removing the cap of the mushroom, we managed to reduce the amount of polysaccharides that cause undesirable interference in the process of protein purification.

The yield of native Fve protein is 40 mg from 1 kg wet-weight of sing material.

Example 2

Measurement of Gene Expression Profile at mRNA Level after Fve Stimulation

Methods and Materials

Two subsets of effector Th cells have been defined on the basis of their distinct cytokine secretion patterns and immunomodulatory effects (Mosmann et al., 1989; Paul and seder, 1994; Abbas et al., 1996). Th1 cells produce inflammatory cytokines, such as IFN-γ, TNF-α, IL-12, IL-15 and IL-18, and enhance cellular immunity mediated by macrophages. In contrast, Th2 cells produce a different group of cytokines, such as IL-4, IL-5, IL-6 and IL-13. The differentiation of precursor T cells into Th1 or Th2 cells has important biologic implication in terms of susceptibility or resistance to a particular disease.

In order to characterize the cytokines expression pattern induced by Fve, human PBMC from healthy donor and splenocytes from 8 week-old BALB/cJ mice are collected and cultured with 20 μg of native Fve. The mRNA is extracted at 48 hours using RNeasy Mini mRNA Purification Kit (QIAGEN). First-strand cDNA is then generated from the mRNA template using oligo-dT primers and MMLV reverse transcriptase (Promega).

PCR reactions are performed with Taq polymerase (Promega) with standard conditions and optimized annealing temperatures. The amplified products are analysed by electrophoresis in 1.5% agarose gel containing ethidium bromide (0.5 μg/ml) and photographed with UV exposure. Messenger RNA for various cytokines and transcription factors are measured. House keeping genes mRNA for hypoxanthine ribosyl-transferase (HPRT) and cyclophilin are used as internal controls.

Results

Enhanced Expression of IFN-γ, TNF-α, IL-1β, IL-2, IRF-1, c-Rel, Bcl-$X_L$, ICAM-1, and iNOS mRNA Human PBMC and spleen cells from BALB/cJ mice are cultured with 20 μg of Fve and analyzed for cytokine mRNA expression at 48 hr. The results indicated that there is an increase in IFN-γ, TNF-α, iNOS mRNA production by spleen cells cultured with Fve protein. Mouse IL-12 remains unchanged. This phenomenon occurred in a dose dependent manner.

Figure 2:
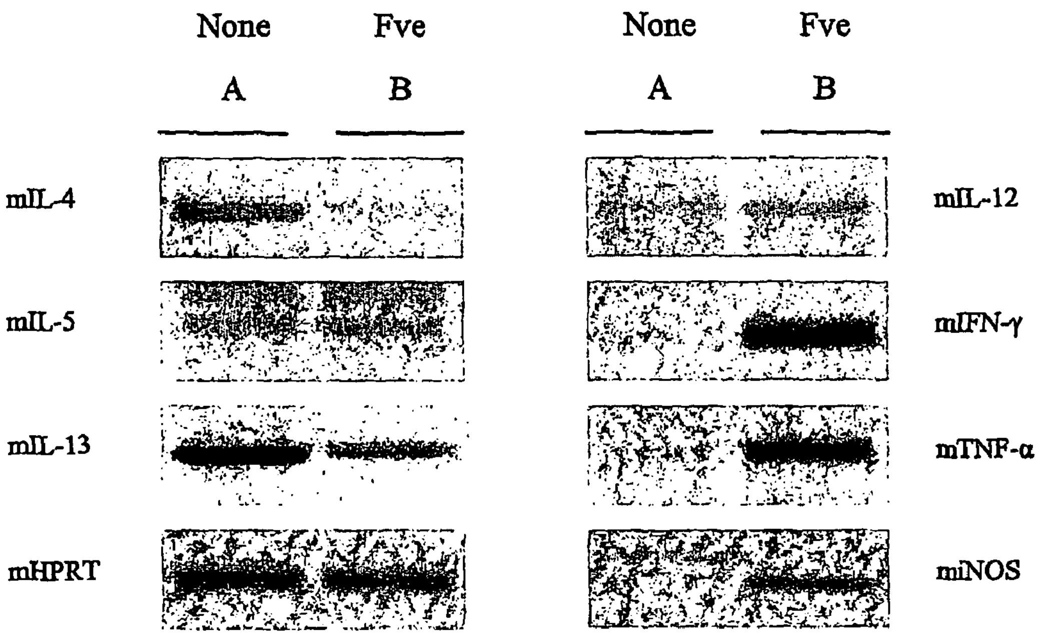
FIG. 2 shows a profile of cytokines and iNOS produced by mouse splenocytes upon stimulation with Fve protein. Mouse spleen cells from Balb/cJ mice are stimulated with 20 μg of Fve. The mRNAs of cytokines are analyzed by RT-PCR after culturing for 48 hours. A: A non-stimulated culture as negative controls, B: A culture stimulated with 20 μg of Fve.
Figure 3:
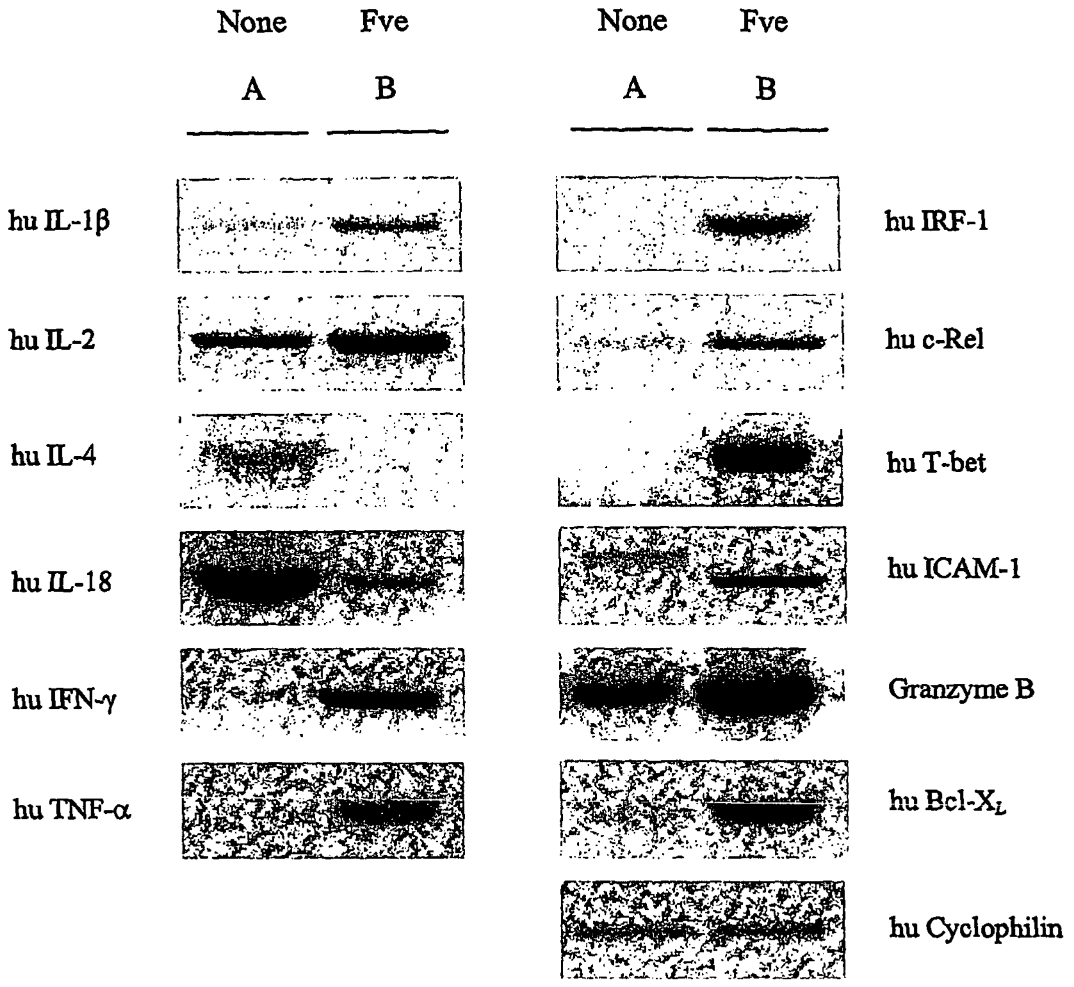
FIG. 3 shows a profile of human cytokines, transcriptional factors, adhesion molecule and anti-apoptotic protein produced by human PBMC upon stimulation with Fve protein. Human PBMC from healthy donor are stimulated with 20 μg of Fve. The mRNA expression is analyzed by RT-PCR after culturing for 48 hours. A: A non-stimulated culture as negative control, B: A culture stimulated with 20 μg of Fve.

Similar results are seen in human PBMC. The mRNA for human cytokines IL-1β, IL-2, IFN-γ and TNF-α; transcription factor IRF-1 and c-Rel; adhesion molecule ICAM-1 and anti-apoptotic protein Bcl-$X_L$ is up regulated after Fve stimulation. FIG. 2 and FIG. 3 show the patterns of mRNA expression for transcription factors, cytokines and adhesion molecules of the splenocytes and PBMC stimulated by Fve.

Example 3

Generation of Fve Mutants By PCR-Based Mutagenesis

Materials and Methods

Figure 4:
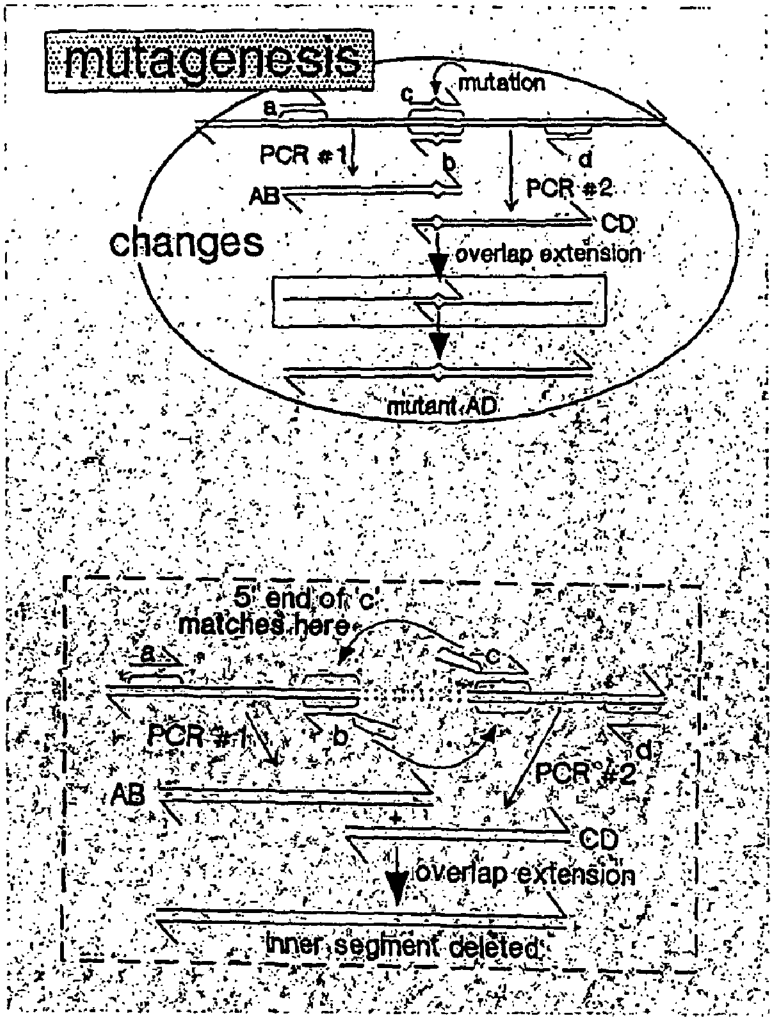
FIG. 4. A schematic representation showing the principle of overlap extension PCR for the generation of single amino acid residue substitution (A) and deletion mutagenesis of DNA (B).
Figure 5:
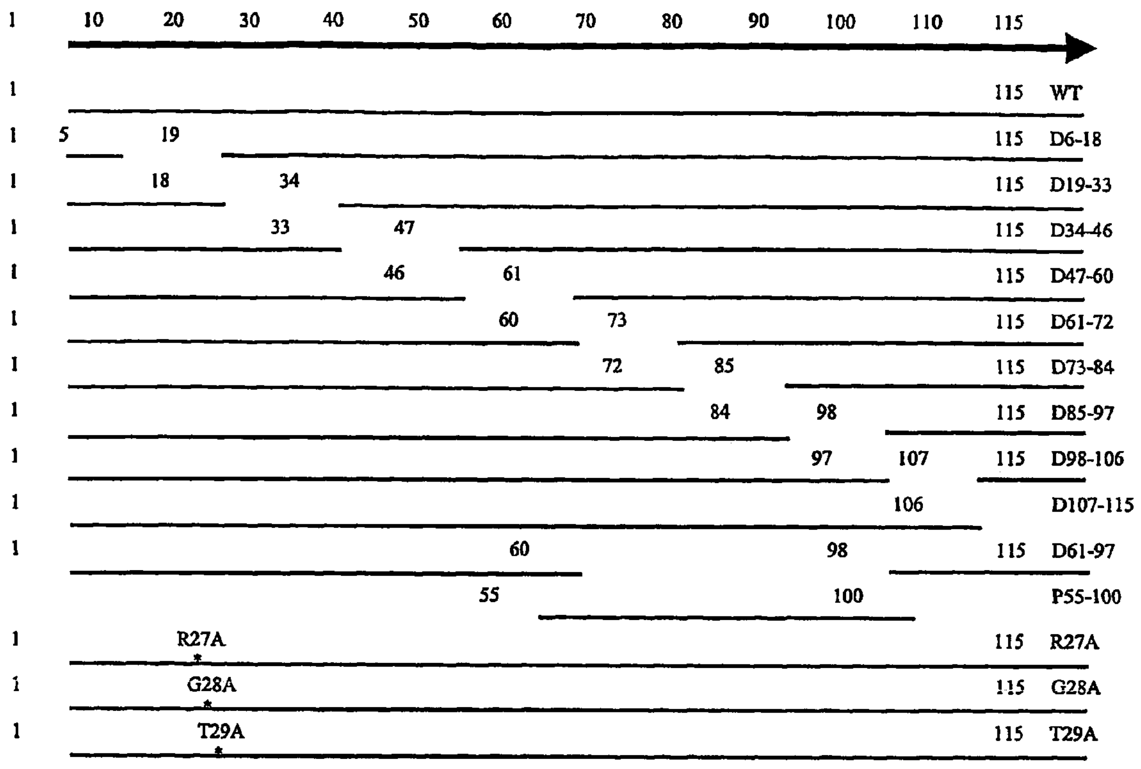
FIG. 5. A schematic representation of the strategy used to generate mutants. On the basis of the structures predicted by PHD prediction program, eleven deletion mutants and three point mutants of Fve plasmid DNA are generated by PCR-based mutagenesis.

A cDNA encoding for the Fve protein is cloned into the BamHI and EcoRI site of pGEX-4T1. This DNA template is used to generate a panel of mutants by recombinant-PCR method (FIG. 4). A schematic representation of the strategy used to generate mutants is shown in FIG. 5.

As predicted by PHD prediction program, Fve contains one α-helix, six β-strands and two β-turns. Each of these predicted secondary structures is serially deleted by recombinant-PCR method. In addition, we also examined the potential function of the R27, G28, T29 residues, which resembles the cell aggregating RGD motif, located in the N-terminal β-turn of Fve protein by point mutation. Each of the amino acid residues of RGT is substituted by alanine residue.

A partial list of fragments of Fve is shown in Appendix B.

Example 4

Production of the Fve-Derived Mutant Proteins

Materials and Methods

Eleven deletion mutants and three point mutants of Fve DNA are generated. Each of the polypeptides is expressed in TG1 *E. coli* cells as fusion protein with GST carrier protein and purified by glutathione affinity column. All the mutants could express protein except insoluble mutant D6-18, in which α-helix has been deleted.

Figure 6:
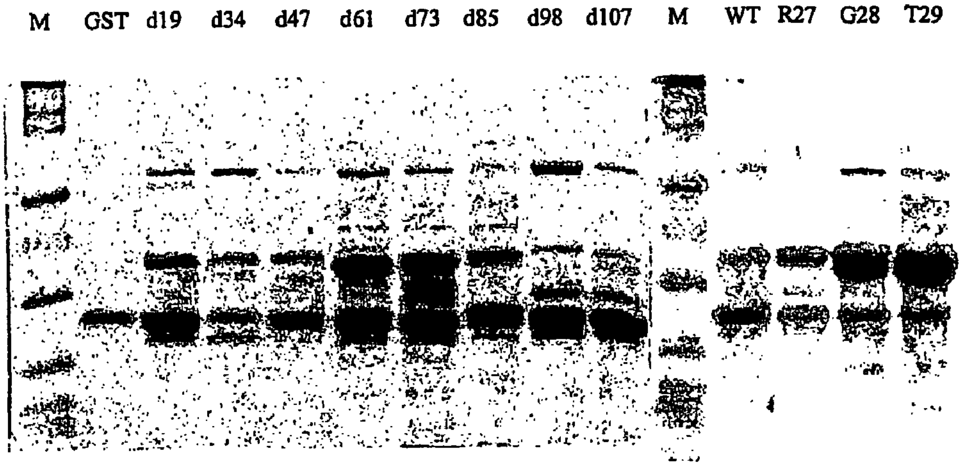
FIG. 6. SDS-PAGE analysis of recombinant Fve mutant proteins.

FIG. 6 shows the panel of the affinity purified mutant proteins on a SDS-PAGE. These purified proteins are used for the cell aggregation, hemagglutination and lymphocytes proliferation assay.

Example 5

Comparison of Hemagglutination Activity of Fve Mutants

Materials and Methods 5 ml of whole human blood obtained from a healthy volunteer is centrifuged at 2500×g for 10 min. The plasma is removed and 2 ml of packed red blood cells are collected from the bottom of the tube.

The red blood cells (RBC) are diluted 5× with 1× PBS buffer and centrifuged at 1200×g for 10 min. RBC pellet is resuspended in 1.5% (v/v) of 1× PBS. 50 ul of 2× serial dilutions (from 64 μg/ml to 0.25 μg/ml) of each Fve mutant protein is added into 50 ul of 0.2% gelatin in 1× PBS (pH 7.4) and then mixed with 100 ul of 1.5% RBC in each well of the 96-well round bottom microtiter plates. Cells are incubated at room temperature and examined for hemagglutination after 2 hours and over night, respectively (Table 1).

Example 6

Lymphocytes Aggregation Activity of Fve and Its Mutants

Materials and Methods

Human peripheral blood mononuclear cells (PBMC) from a healthy donor are isolated and cells are then cultured with 20 μg/ml of various Fve mutants in 24-well plates. Cells aggregation is observed by inverted light microscopy after 24 hours (Table 1).

Results

Mutant GST-FveG28A Lost the Hemagglutination and Lymphocytes Aggregation Activity Native Fve, GST-Fve (wild type) and two point mutants, GST-FveR27A and GST-FveT29A, show positive aggregation and hemagglutination activity. These properties are not seen in all the deletion mutants and a point mutant GST-FveG28A. PHA and ConA are used as positive controls; GST and Blo t 5 are used as negative controls. These results are summarized in Table 1.

The Arg-Gly-Asp (RGD) tripeptide sequence is the most common molecular recognition site implicated in several immunological reactions. Normally RGD motif is located in the β-turn structure. According to the PHD prediction, residue 19 to 33 is β-turn structure. Therefore, we propose that glycine residue of RGT (RGD-like motif) tripeptide sequence at position 28 plays an important role on lymphocyte aggregation/adhesion. The potentially interaction between Fve and the proteins of integrin family will be addressed.

TABLE 1

Lymphocytes aggregation and RBC hemagglutination activities of Fve mutants

| | Cell aggregation | Hemagglutination |
|---|---|---|
| D19-33 | – | – |
| D34-46 | – | – |
| D47-60 | – | – |
| D61-72 | – | – |
| D73-84 | – | – |
| D85-97 | – | – |
| D98-106 | – | – |
| D107-115 | – | – |
| P55-100 | – | – |
| D61-97 | – | – |
| *R27A | + | + |
| **G28A | – | – |
| ***T29A | + | + |
| rGST-Fve | + | + |
| nFve | + | + |
| GST | – | – |
| Blot 5 | – | – |
| ConA | + | + |
| PHA | + | + |

Example 7

Lymphoproliferation Activity of Fve Mutants

Materials and Methods

Splenocytes from Balb/cJ mice and peripheral blood mononuclear cells (PBMC) from a healthy donor are stimulated with 2.5 μg/ml, 5 μg/ml, 10 μg/ml or 20 μg/ml respectively of Fve mutant proteins for 24 hours. Then 1 μCi [$^3$H]-thymidine is added to the culture and further incubated for 18 hours. [$^3$H]-thymidine incorporation is measured in triplicates by a β counter (Beckman).

Results

Figure 7:
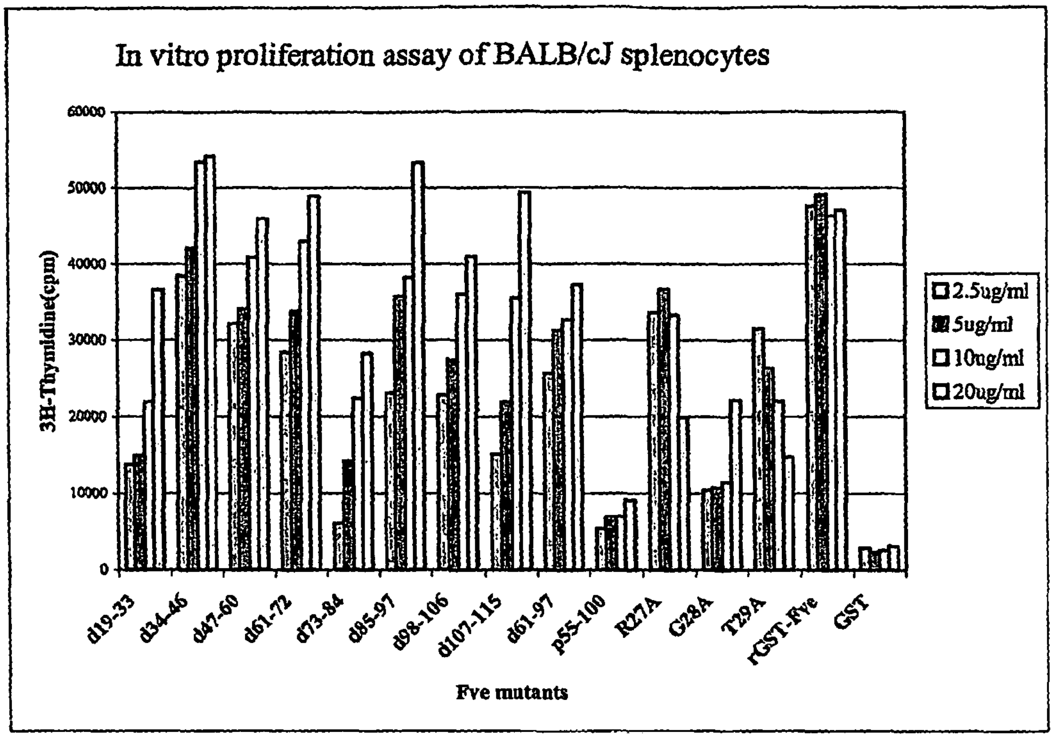
FIG. 7. In vitro proliferation assay of mouse splenocytes. Mouse splenocytes from Balb/cJ is stimulated with 2.5 μg/ml, 5 μg/ml, 10 μg/ml, and 20 μg/ml, respectively, with 13 of Fve mutant proteins for 48 hours. Recombinant GST-Fve is positive control. GST is negative control.
Figure 8:
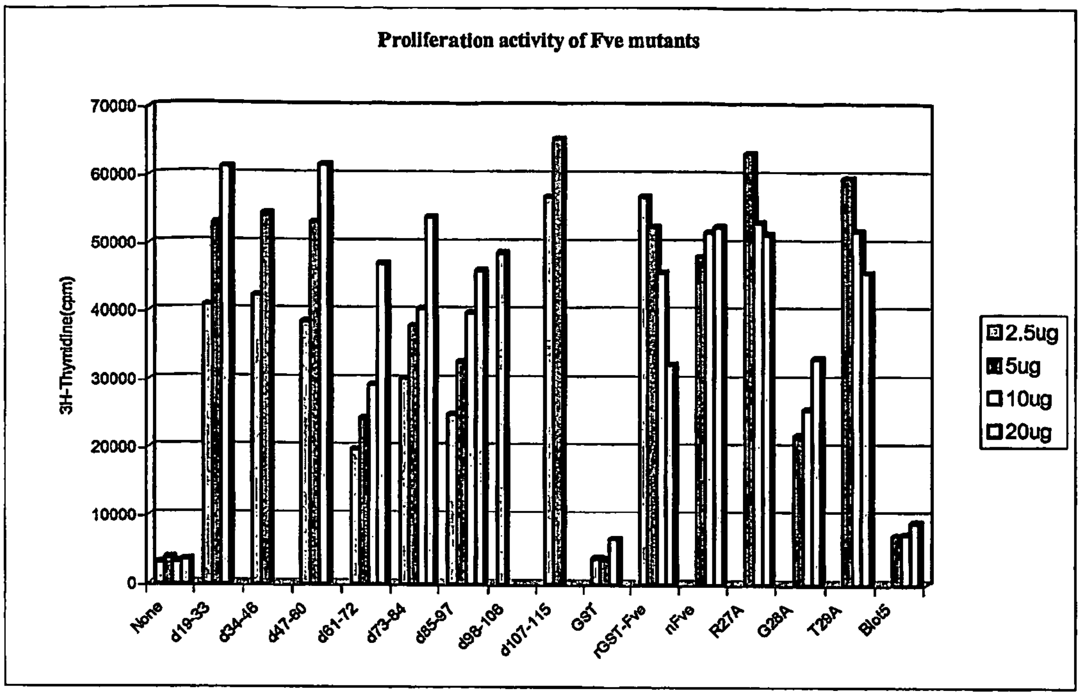
FIG. 8. Lymphoproliferation activity of human PBMC at 48 hours. Human PBMC from a healthy donor is stimulated with 2.5 μg/ml, 5 μg/ml, 10 μg/ml, and 20 μg/ml, respectively, with eleven of Fve mutant proteins for 48 hours. Recombinant GST-Fve and native Fve are positive control. GST and Blo t 5 are negative control.

FIGS. 7 and 8 show the results of the proliferation assay for the panel of proteins tested. Deletion mutants D19-33, D73-84, P55-100, and mutant with single amino acid substitution G28A showed significant reduction in lymphoproliferation activity in mouse splenocytes, whereas, such reduction is less pronounced for the rest of the mutants tested (FIG. 7).

Interestingly, some mutants such as D34-46, D47-60 and D61-72, which show negative hemagglutination and cell aggregation, retain similar lypmphoproliferative activity as the wild type protein. For the result of human PBMC, deletion mutant D61-72 and mutant with single amino acid substitution G28A show more than 50% reduction in lymphoproliferation activity (FIG. 8). Taken together the proliferation results from mouse splenocytes and human PBMC demonstrate that glycine at position 28 plays an key role in lymphocyte proliferation.

Example 8

Recombinant GST-Fve (Wild Type) and GST-FveT79A (Mutant) Show Similar Proliferative Activity of CD3$^+$ T Cells as the Native Fve Materials and Methods Human peripheral blood mononuclear cells (PBMC) from a healthy donor are isolated according to the standard protocol (Coligan et al., 1998). The cells are then cultured with 20 μg/ml of recombinant wild type GST-Fve and mutant GST-FveT29A for 5 days. Cells are stained with anti-CD3$^+$ PerCP monoclonal antibody (Becton Dickinson), and analyzed by FACScan flow cytometry (Becton Dickinson).

Results

Figure 9:
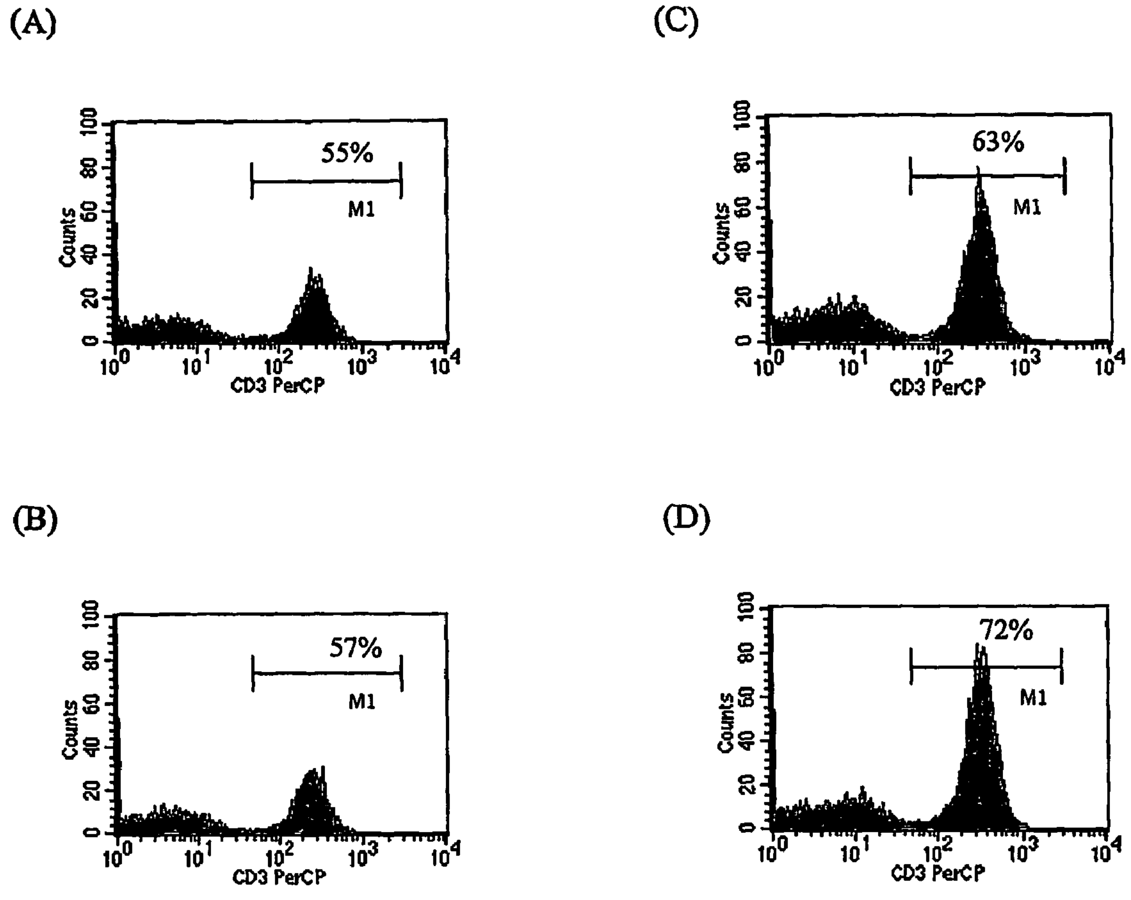
FIG. 9. Recombinant GST-Fve (wild type) and GST-FveT29 mutant protein showed strong lymphoproliferative activity. Human PBMC from healthy donor are cultured with: (A) no antigen, (B) GST, (C) wild type GST-Fve, (D) GST-FveT29, each protein is used at 20 μg/ml. The percentage of $CD3^+$ T lymphocytes is analyzed at day 5 by using flow cytometry.

A histogram shows that 8% and 17% enrichment of T cells are detected after stimulation with recombinant wild type GST-Fve and mutant GST-FveT29A for 5 days (FIG. 9). Results showed that both recombinant wild type GST-Fve and mutant GST-FveT29A showed comparable lymphoproliferative activity of T lymphocytes as well as the native Fve protein.

These data suggest that Fve-mediated T cell polarization and enrichment is detectable at day 5.

Example 9

Detection of IFN-γ and TNF-α by Intracellular Cytokine Staining After Stimulation with Recombinant GST-Fve Protein Methods and Materials Intracellular cytokine staining is done by modification of a standard method from PharMingen. Briefly, human PBMC are stimulated in vitro with 20 μg of native Fve protein, GST, recombinant GST-Fve, GST-R27A, GST-G28A, or with GST-T29A. GlogiPlug™ (PharMingen) is added 48 hr after the cultures are initiated, cells are collected 14 hr later and then stained for T cells surface marker (CD3) in FACS buffer containing GlogiPlug™. Cells are then treated with Cytofix/Cytoperm (PharMingen) for 30 min. Cells are incubated with cytokine antibodies for 30 min after washing with Perm Wash buffer (PharMingen). Finally, cells are washed with PBS containing 1% paraformaldehyde and then analyzed by FACSCalibur flow cytometry (BD Biosciences). CellQuest software (BD Biosciences) is used for data analysis.

Result

Figure 10:
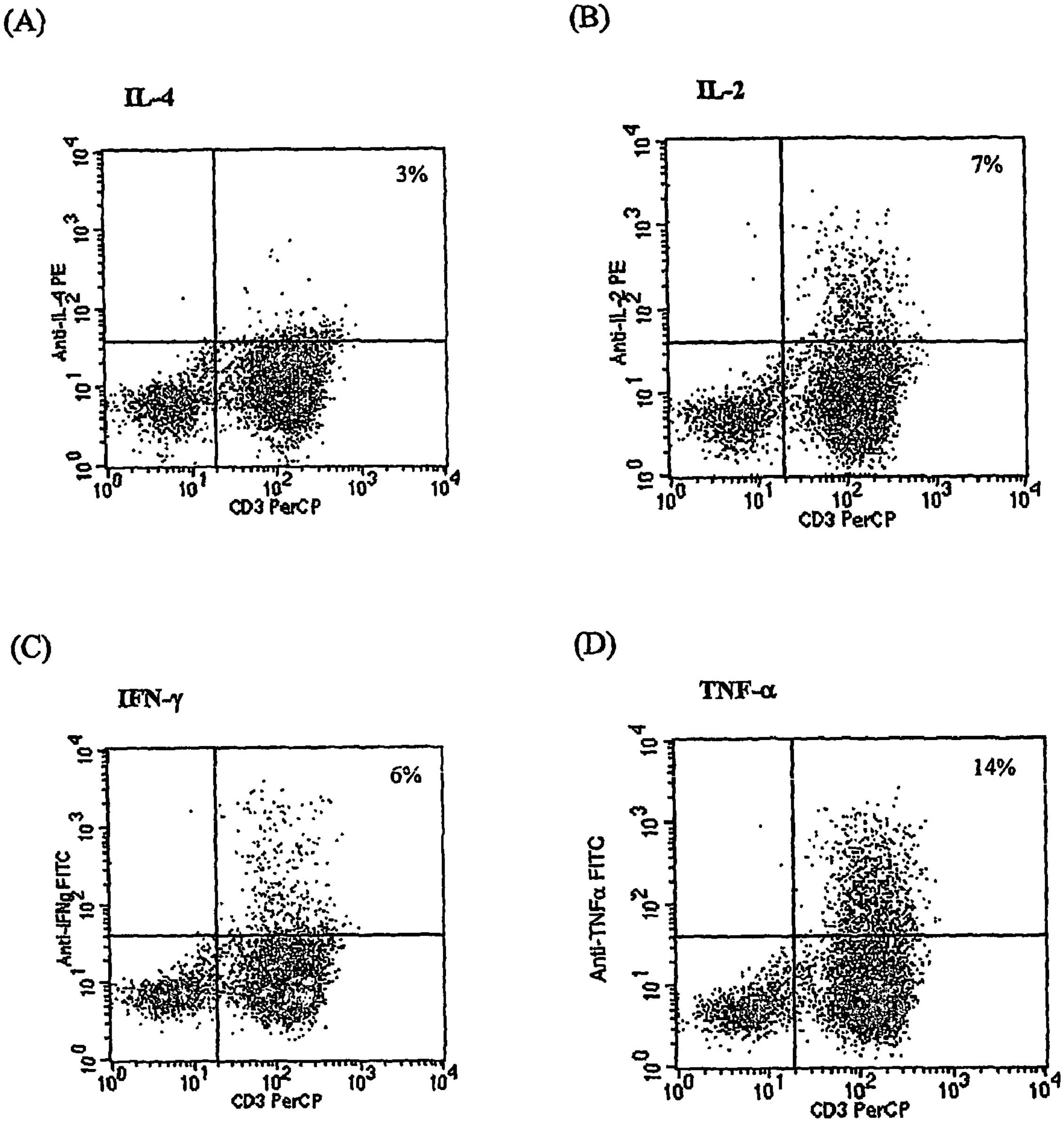
FIG. 10. Increased production of TNF-α, IFN-γ, IL-2 but not IL-4 in $CD3^+$ T lymphocytes after stimulation with native Fve protein. The production of (A) IL-4; (B) IL-2; (C) IFN-γ and (D) TNF-α by human PBMC after stimulation with 20 μg/ml of native Fve protein for three days. The data are analyzed by flow cytometry.
Figure 11:
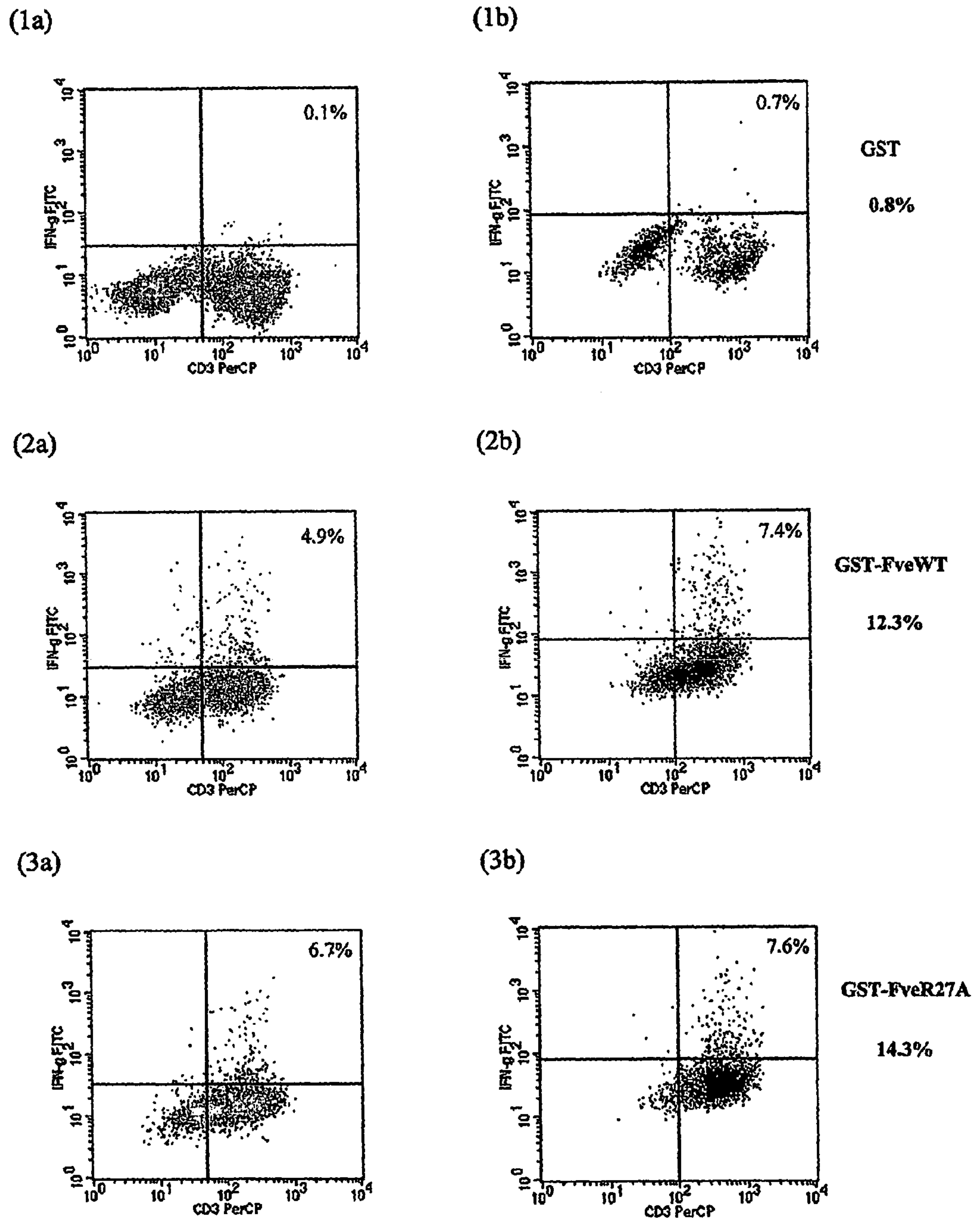
FIG. 11. Recombinant wild type GST-Fve and mutant GST-FveT29A, but not mutant GST-FveG28A, maintained IFN-γ cytokine production activity. Human PBMC from healthy donor are cultured with 20 μg of GST (1); GST-Fve (2); GST-FveR27A (3); GST-FveG28A (4); GST-FveT29A (5). IFN-γ cytokine by T cells is detected at day 3 by staining with anti-CD3 PerCP and anti-IFN-γ FITC specific monoclonal antibody. IFN-γ secretion by small granular lymphocytes and large granular lymphocytes are shown in (a) and (b), respectively. The total amount of IFN-γ production by T cells is the sum of (a) and (b).
Figure 11:
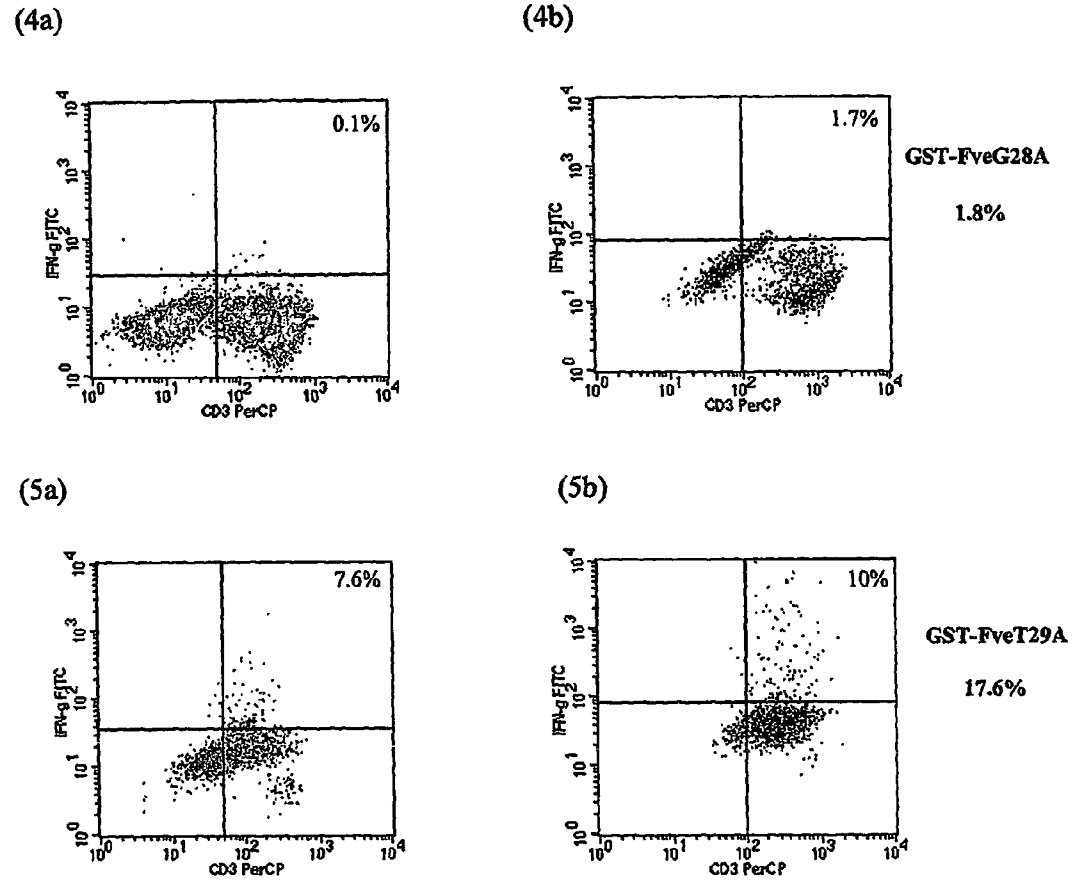
Figure 12:
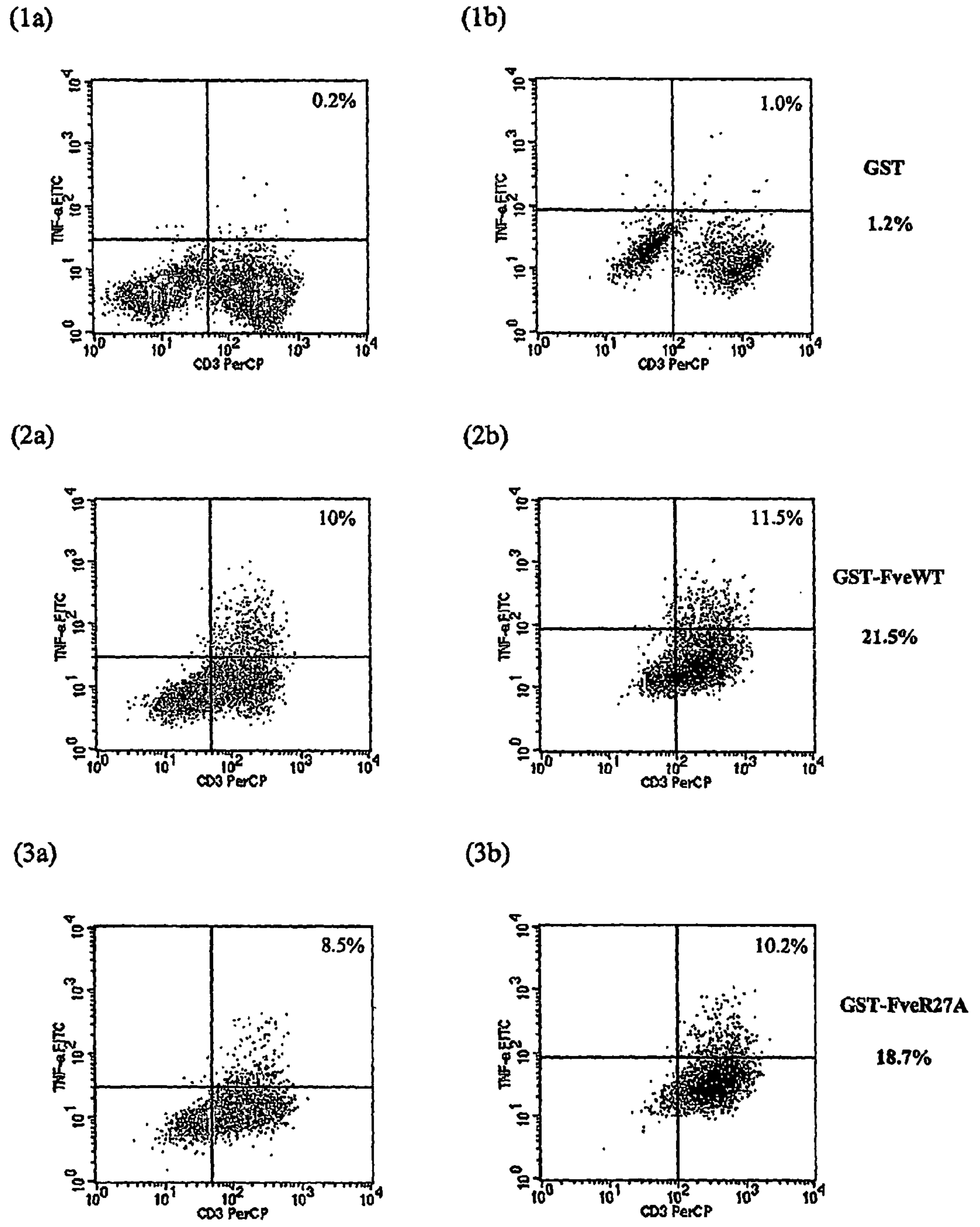
FIG. 12. Recombinant wild type GST-Fve and mutant GST-FveT29A, but not mutant GST-FveG28A, maintained TNF-α production activity. Human PBMC from healthy donor are cultured with 20 μg of GST (1); GST-Fve (2); GST-FveR27A (3); GST-FveG28A (4); GST-FveT29A (5). IFN-γ cytokine by T cells is detected at day 3 by staining with anti-CD3 PerCP and anti-TNF-α FITC specific monoclonal antibody. TNF-α secretion by small granular lymphocytes and large granular lymphocytes are shown in (a) and (b), respectively. The total amount of TNF-α production by T cells is the sum of (a) and (b).
Figure 12:
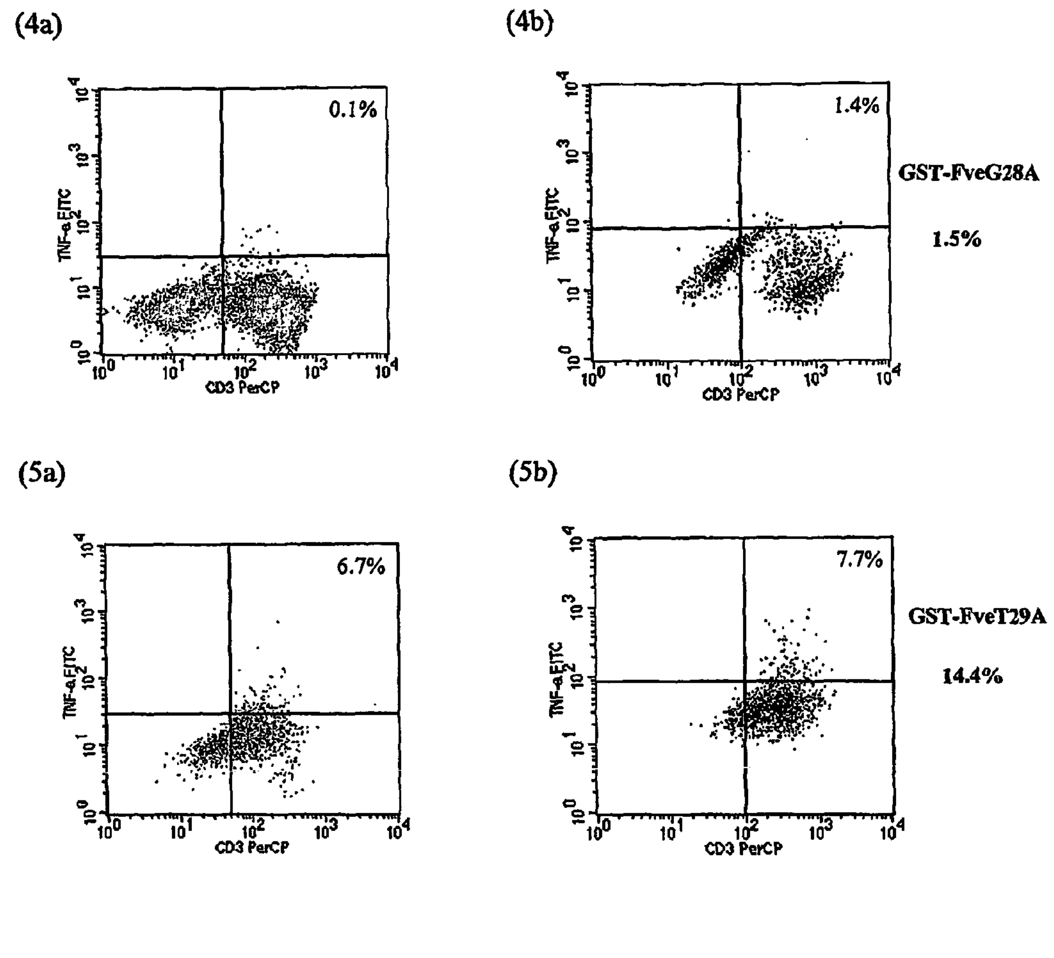

The results show that native Fve protein is able to stimulate production of IL-2, IFN-γ, TNF-α but not IL-4 in CD3$^+$ T cells (FIG. 10). Similar results are seen for the recombinant wild type GST-Fve and two mutants GST-FveR27A, GST-FveT29A. Strikingly, recombinant mutant GST-FveG28A failed to stimulate the production of such cytokines (FIGS. 11 and 12).

The percentages of IFN-γ production induced by GST, GST-Fve, GST-FveR27A, GST-FveG28A, GST-FveT29A are 0.8%, 12.3%,14.3%, 1.8%, 17.6%, respectively. In contrast, the percentages of TNF-α production which induced by GST, GST-Fve, GST-FveR27A, GST-FveG28A, GST-FveT29A are 1.2%, 21.5%, 18.7%, 1.5%, 14.4%, respectively (Table 2). This data provides further evidence that the glycine residue at position 28 of Fve protein plays an important role in the biological function such as aggregation/adhesion, cytokines production, proliferation, and differentiation of lymphocytes. Further examination of the physiological role of RGT sequence in Fve protein by using blocking monoclonal antibodies and peptide inhibition assay are carried out to confirm this function. The possibility of integrin-mediated T/NK-cell adhesion is also investigated.

In summary, mutants FveR27A and FveT29A show enhanced mitogenic activities as compared to that of wild type Fve. In addition, the solubility of both mutant proteins is significantly increased in comparison with that of wild type Fve. This improved solubility will greatly facilitate the large scale production of such recombinant protein.

TABLE 2

The percentage of intracellular cytokines production in $CD3^+$ T lymphocytes during stimulation with three different Fve mutants with single amino acid substitution

| Recombinant proteins | Intracellular IFN-γ | Intracellular TNF-α |
|---|---|---|
| GST | 0.8% | 1.2% |
| GST-FveWT | 12.3% | 21.5% |
| GST-FveR27A | 14.3% | 18.7% |
| GST-FveG28A | 1.8% | 1.5% |
| GST-FveT29A | 17.6% | 14.4% |

Example 10

Applications of Fve in Allergy

The increasing prevalence of atopic diseases such as hay-fever or allergic asthma is a major problem in most developing and developed countries. Accumulating evidence indicates that appropriate immunotherapy prevents the onset of new sensitization and the progress of allergic rhinitis to asthma.

The central role of allergen-specific Th2 cells in the regulation of allergic inflammation has been highlighted. Exploration of novel and effective treatment for atopic diseases is active area of allergy research. Induction of allergen-specific T regulatory immune response, suppression of the effects of IL-4, IL-5 and IL-13 cytokines, and redirecting/balancing Th2 immune response in allergy is an attractive and promising approach to pursue (Akbari et al., 2002; Scanga and Le Gros, 2000; Zuany-Amorim et al., 2002).

Our in vitro and in vivo studies reveal that Fve interacts with T and NK cells.

Fve-activated T cells produce Th1-skewed cytokines in high levels, and suppress Th2 cytokines (IL-4 and IL-13) production. Thus these biological activities of Fve can be exploited to treat Th2-associated diseases such allergic asthma and rhinitis. The use of the immunomodulatory properties of Fve to treat allergic diseases is novel because there are a number of differences between Fve approach and other existing methods such as hexameric motifs, called CpG motifs or DNA immunostimulatory sequences (ISS).

The function of ISS is act as a danger signal to stimulate non-specific innate immune response (Krieg 2000). It is known that ISS is recognized by the toll-like receptor 9 on B cells and $CD123^+$ dendritic cells. It is unexpected that TLR9 is also involved in autoimmunity (Leadbetter et al., 2002; Krieg 2002; Vinuesa and Goodnow, 2002). Upon the detection of CpG motifs or ISS element, B cells are induced to proliferate and secrete immunoglobulin (Ig), and dendritic cells (DCs) secrete a wide array of cytokines, interferons and chemokines that promote T helper type 1 (Th1) cells. Both B and DCs up-regulate costimulatory molecules and have enhanced abilities to induce Th1 cell immune responses. In contrast, Fve is directly target on T and NK cells to involve in the acquire immunity.

Example 11

Co-Administration of Fve with Allergens: In vivo Study of the Adjuvant Effect of Fve Using a Murine Allergic Asthma Model Immunotherapy with recombinant allergen in combination with certain immunomodulator enhancing Th1 but suppressing Th2 immune response is a novel approach to achieve higher efficacies in immunotherapy. Since Fve protein is an activator of Th1/Tc1 immune response, it may be used as such an immunomodulator to provide the adjuvant effects to enhance Th1-skewed immunity.

We investigated the adjuvant effects of Fve for allergy immunotherapy with a combination of a recombinant house dust mite major allergen, Der p 2 and Fve using an animal model.

Methods and Materials

Figure 13:
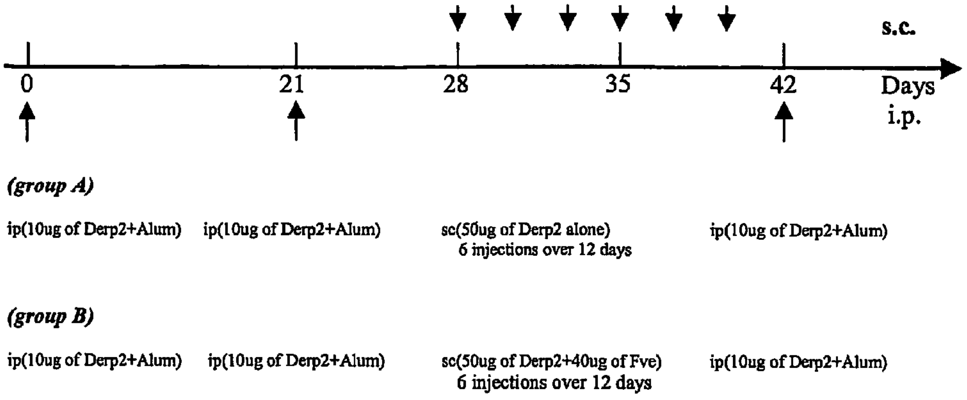
FIG. 13. Schematic representation of the experimental design of the in vivo study Balb/cJ mice are immunized with Der p 2 in aluminum hydroxide at day 0 and boosted at day 21 by intraperitoneal injection. Treatment with Der p 2 alone or Der p 2 plus Fve is started at day 28 by given 6 subcuteneous injections over 12 days. Mice are challenged with Der p 2 at day 42.

A schematic representation of the experimental design is shown in FIG. 13.

8 to 10 week old male BALB/cJ mice obtained from the Sembawang Laboratory Animal Center of Singapore are divided into two groups for each experiment. Mice are sensitized by intraperitoneal injection of 10 μg of recombinant Der p 2 in aluminum hydroxide at day 0 and day 21. Twenty-eight days after the sensitization, each group of mice is subcutaneously injected with 50 μg of Der p 2 and 50 μg of Der p 2 plus 40 μg of Fve, respectively. A total of six injections are performed at every alternative day over a period of 12 days. Mice are then challenged with the third intraperitoneal injection of 10 μg of Der p 2 plus aluminum hydroxide at day 42. Der p 2-specific IgG1 and IgG2a are determined weekly staring at day 14 by ELISA. Since IgG2a is the hallmark of Th1 immunity in mouse, titer of IgG2a is used a measure of Th1 immunity.

Results

Increased Allergen-Specific IgG2a Production in the Treatment Group with Combination of Fve and Allergen Der p 2

Figure 14:
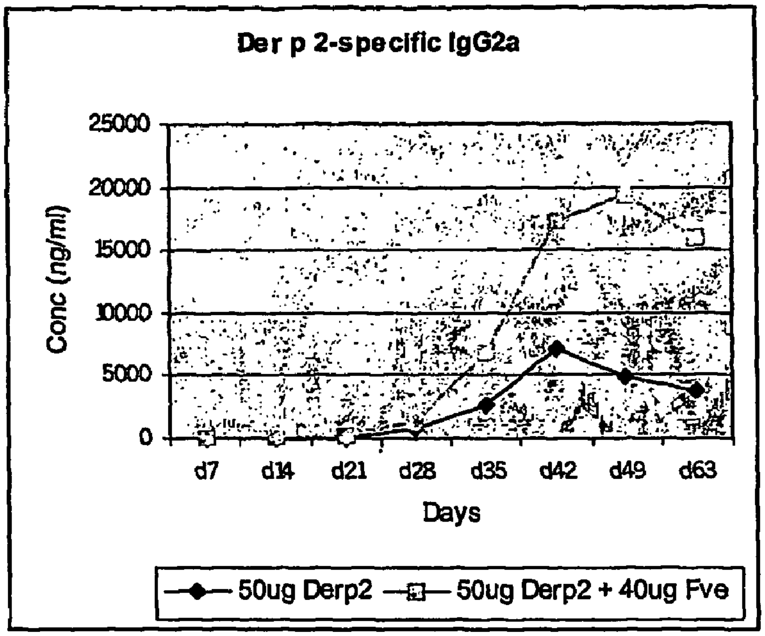
FIG. 14. Enhanced anti-Der p 2 IgG2a by adjuvanicity of Fve protein. IgG2a response in mice that are subcutaneously injected six times with Der p 2 alone (close circle), or Der p 2 plus Fve (close square) twenty-eight days after the initial sensitization with Der p 2 in alum. Mice received third intraperitoneal injection with Der p 2 in alum at day 42. Results are shown as mean titers and error bars indicate the standard deviations from the mean titers.
Figure 14:
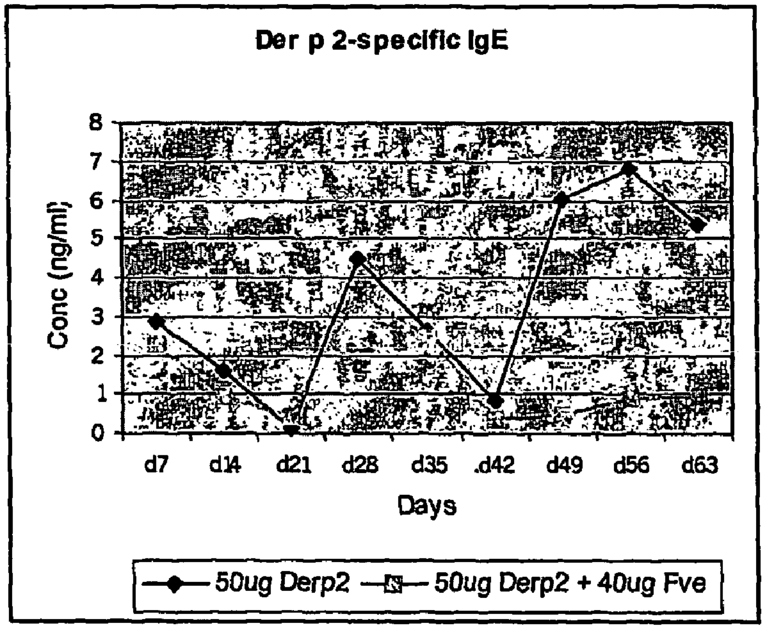

As shown in FIG. 13, mice that are subcutaneously treated with 50 μg of Der p 2 alone produced relatively lower titers of Der p 2-specific IgG2a, whereas mice treated with 50 μg of Der p 2 plus 40 μg of Fve showed a significant boost of Der p 2-specific IgG2a production (FIG. 14).

Upon challenge with intraperitoneal immunization of Der p 2 in alum at day 42, the Der p 2-specific IgG2a in Fve administered mice is further increased at day 49. It is interesting to note that the Fve-specific IgG1 and IgG2a remained low (data not shown).

Increased Allergen-Specific IgG2a Production in the Treatment Group with Combination of Fve and Allergen Blo t 5

Figure 14B:
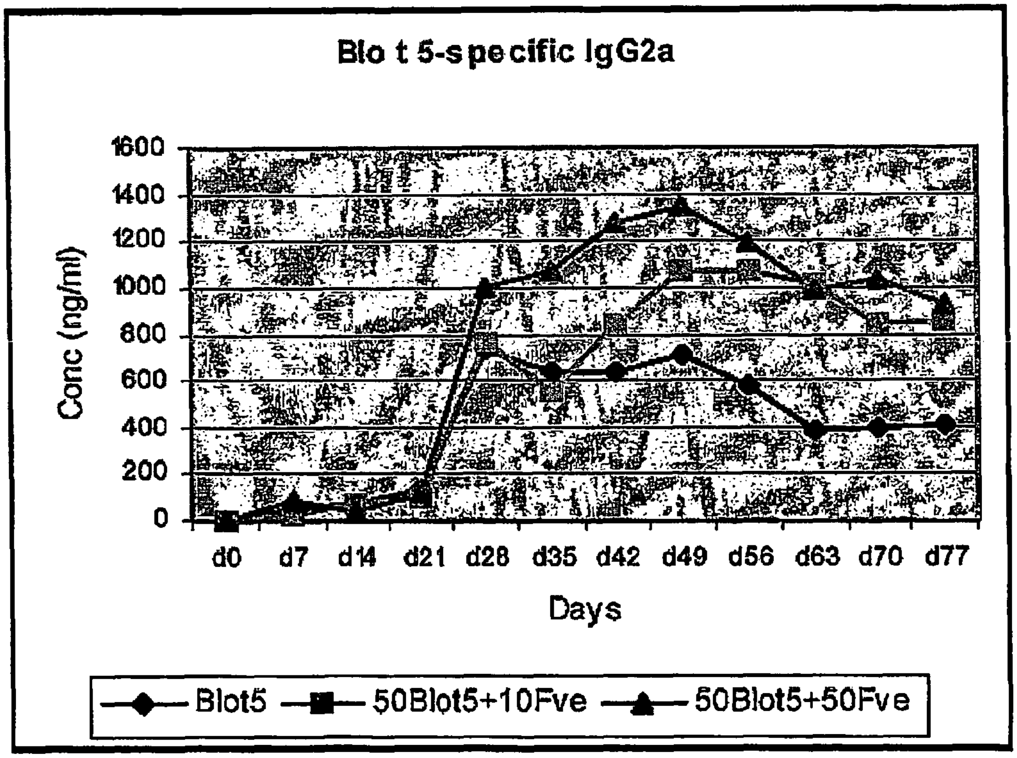
FIG. 14B. Fungal immunomodulatory protein Fve increases allergen-specific IgG2a production in mice sensitized to house dust mite major allergen. All groups of female BALB/cJ (6-8 weeks old) are sensitized intraperitoneally on day 1 with 20 μg of recombinant mite allergen Blo t 5 and boosted at day 14 with same dose of allergen adsorbed to 64 μg/μl of aluminum hydroxide gel in a final volume of 200 μl. Mice treated with six subcutaneous injections of 50 μg of Blo t 5 plus 10 μg of Fve or 50 μg of Blo t 5 plus 50 μg of Fve in 200 μl of PBS at three days interval starting from day 21-35. The negative control mice receive six subcutaneous injections of 50 μg of Blo t 5 alone. All mice are bled weekly and sera were collected for analysis of Blo t 5-specific IgG2a by ELISA. These results show that fungal immunomodulatory protein Fve has the ability to induce Blo t 5-specific IgG2a antibody in allergen-sensitized mice.
Figure 14C:
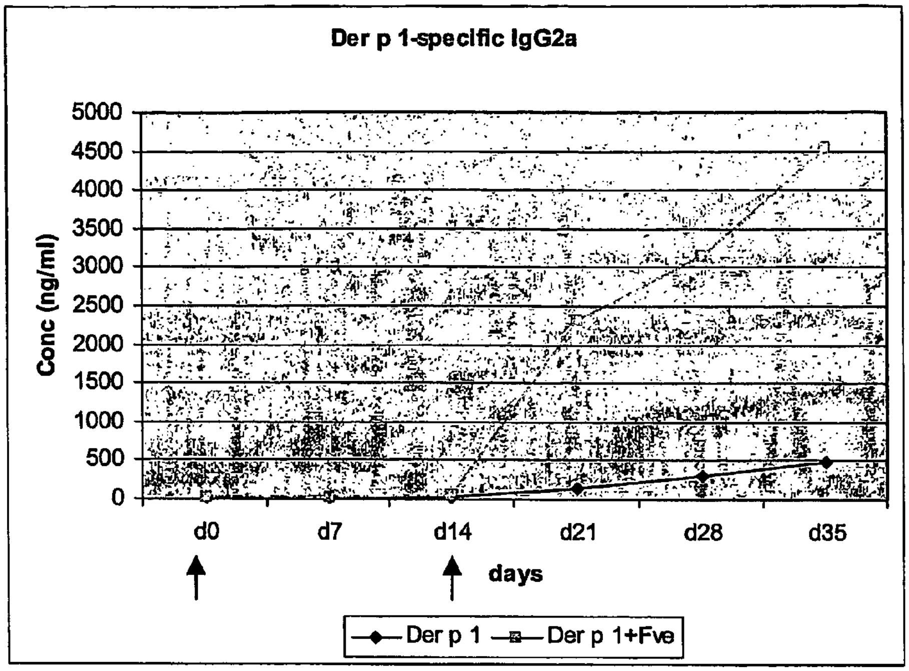

Similar results are observed in similar experiments performed with another house dust mite major allergen, Blo t 5, from *Bromia tropicalis*. These results are shown in FIG. 14B.

Thus we demonstrate mdulation of allergen-specific antibodies responses to the major house dust mite allergen, Blo t 5, by combining treatment with a fungal immunomodulatory protein, Taken together, the data suggested that Fve protein may act as a potent adjuvant/immunomodulator to boost antigen-specific Th1-skewed immune response, therefore it may serves as a useful reagent to improve the efficacies of immunotherapeutic treatment of allergy in humans. The adjuvanticity and immunomodulatory property of Fve protein may be improved by biomolecular engineering.

While not wishing to be bound by theory, it is postulated that this molecule may activate NK cells and $CD8^+$ T cells and thus result in production of IFN-γ. These may induce a strong cellular-mediated immune response and promote isotype switching to specific IgG2a predominantly.

Example 12

Assessment of Erythema Flare and Wheal Diameter Formation Induced by Skin Prick Tests in Human Allergic Subject Materials and Methods The skin prick test is a convenient diagnostic method test for allergy in the clinics. The aim of this study is to evaluate the suppression effect of Fve protein to allergen hypersensitivity. As an in vivo topical challenge method, the skin prick test is administered to a human subject with history of sensitization to house dust mite *Dermatophagoides pteronyssinus*.

25 µg/ml of purified recombinant Der p 2 allergen mixed with same concentration of native Fve protein or Der p 2 allergen alone, is applied to the skin of left and right hand of human subject for 10 minutes. Histamine is used as a positive control. The size of the wheel and erythematic flare diameter is measured manually.

Results

Figure 15A:
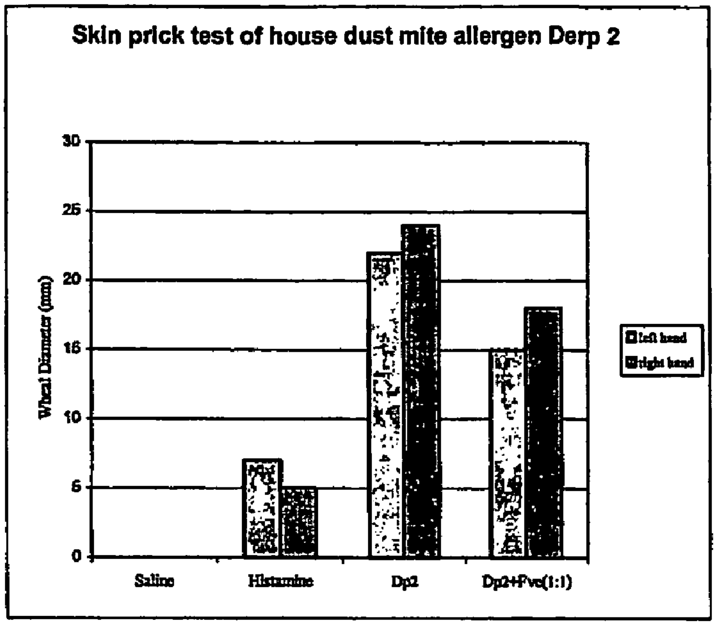
FIG. 15A and FIG. 15B. Fve could reduce wheal and erythematic flare formation on skin prick test-positive human subject. Both the left and right hands of the house dust mite allergen sensitized human subject are challenged with saline, histamine, Der p 2, and mixture of Der p 2 and Fve at the separated sites on hands. The diameter sizes of wheel (A) and erythematic flare (B) are measured after 10 minutes incubation time FIG. 15C. Demonstration of immunomodulatory activity of Fve in allergic subject Quantitative skin-prick tests were performed to evaluate the immunomodulatory function of Fve by co-administration with Der p 2 mite allergen in vivo. A positive reaction (56-130 mm wheel diameter) was shown when Der p 2 alone (20 μg/ml) was applied onto the skin of the fore arm of Dermatophagoides mite allergic subject. There was a Fve-dose-dependent reduction of skin reaction when different amount of Fve was used in combination with Der p2 allergen for skin tests.
Figure 15B:
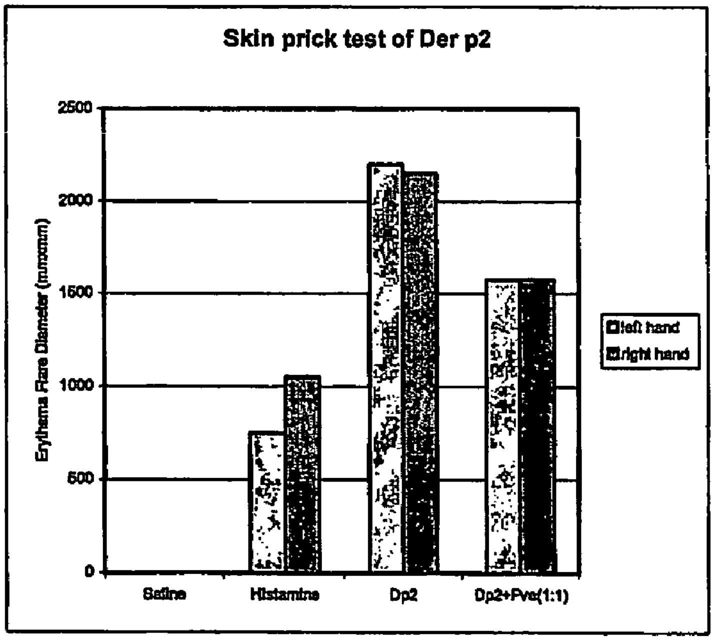

Fve Reduces Wheal and Erythematic Flare Formation on Der p 2 Skin Prick Test-Positive Human Subject The formation of wheal and erythematic flare could be detected in the challenged site of histamine, Der p 2, and Der p 2 combined with Fve. The diameter of the wheals in both left and right hand induced by Der p 2 is 22 mm and 24 mm, respectively. Interestingly, the mixture of Der p 2 and Fve reduces the wheal's diameter in both hands to 15 mm and 18 mm, respectively (FIG. 15A). A similar reduction is also seen in the size of erythematic flare (FIG. 15B, Table 3A and 3B).

The data indicates that there is a suppression of allergic reaction mediated by immunomodulatory effects of Fve protein. The results provide additional evidence that Fve could be used as an adjuvant for allergens immunotherapy.

Besides indoor allergens, outdoor allergens are also important triggering factors that lead to allergic diseases. Hay fever and allergic asthma triggered by grass pollen allergens affect approximately 20% of the population in cool temperate climates. Worldwide more than 200 million individuals are allergic to group 1 grass pollen allergens, and over 100 million individuals exhibit IgE-mediated allergic reactions against Phl p 2, a major allergen from timothy grass (*Phleum pratense*) pollen.

Therefore, we propose that recombinant Fve as well as the native Fve may also be applied in the treatment of other allergies that induced by tree pollen allergen (Bet v 1 and Bet v 2 from birch), grass pollen allergen (Phl p 1 and Phl p 2 from timothy grass), weed pollen allergen (antigen E from ragweed), major feline antigen (Fel d 1), major canine allergen (Der f 15), etc. Other allergens will be known to the person skilled in the art.

Another useful application of Fve protein in allergy is to conjugate or co-deliver with allergenic crude extracts such as mite extracts, pollen extracts, cat and dog extracts, cockroach extracts, fungal and mold extracts for desensitization by immunotherapy.

TABLE 3A

Wheal formation on skin after challenged with Der p 2

| | Wheal Diameter (mm) | |
|---|---|---|
| | Left hand | Right hand |
| Saline (negative control) | 0 | 0 |
| Histamine | 7 | 5 |
| Der p 2 | 22 | 24 |
| Der p 2 + Fve (1:1 w/w) | 15 | 18 |

TABLE 3B

Erythematic flare formation on skin after challenge with Der p 2

| | Erythematic Flare Diameter (mm) | |
|---|---|---|
| | Left hand | Right hand |
| Saline (negative control) | 0 | 0 |
| Histamine | 30 × 25 | 35 × 30 |
| Der p 2 | 55 × 40 | 50 × 43 |
| Der p 2 + Fve (1:1 w/w) | 45 × 35 | 45 × 35 |

Figure 15C:
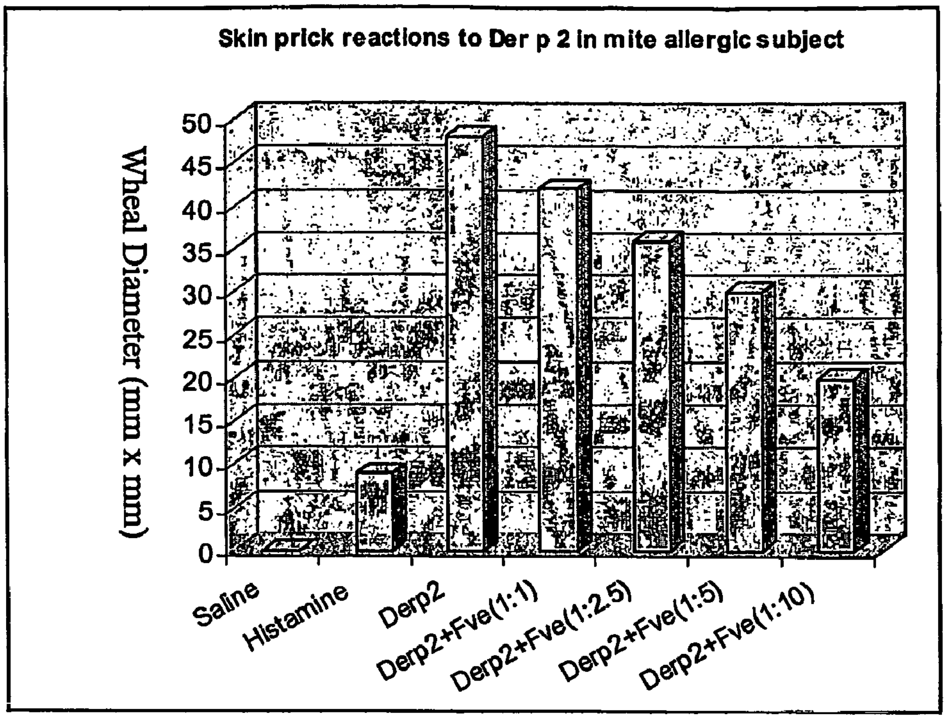

Reference is also made to FIG. 15C, which shows a demonstration of immomodulatory activity of Fve in an allergic subject. Thus, quantitative skin-prick tests are performed to evaluate the immunomodulatory function of Fve by co-administration with Der p 2 mite allergen in vivo.

A positive reaction (56-130 mm wheel diameter) is shown when Der p 2 alone (20 µg/ml) is applied onto the skin of the fore arm of *Dermatophagoides* mite allergic subject There is a Fve-dose-dependent reduction of skin reaction when different amount of Fve are used in combination with Der p2 allergen for skin tests.

Fve Adjuvanted Allergen Vaccines

Example 13

Fusion Proteins of Fve and Allergen

Materials and methods

Treatment of recombinant allergen or vaccination with naked DNA encoding a specific allergen has been shown previously to elevate allergen-specific Th1 immune response against Th2 immune reaction (Maecker et al., 2001). To enhance the effectiveness of immunotherapy or DNA vaccine therapy, we generate several fusion proteins consisting of the complete Fve molecule and the mature form of Blo t 5 or Der p 2 allergen.

Figure 16:
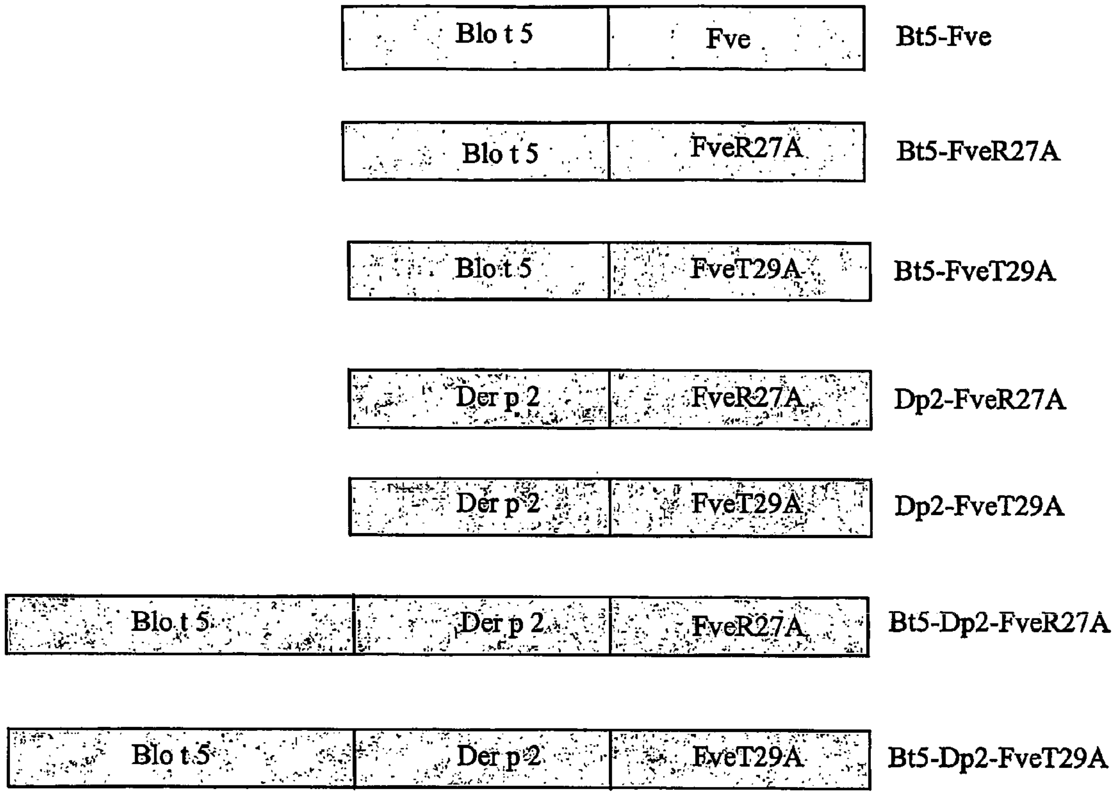
FIG. 16. A schematic representation of the seven fusion proteins of Bt5-Fve (wild type), Bt5-FveR27A, Bt5-FveT29A, Dp2-FveR27A, Dp2-FveT29A, Bt5-Dp2-FveR27A, and Bt5-Dp2-FveT29A.

FIG. 16 shows the construction of seven fusion proteins of Fve and major house dust mite allergen from *Dermatophagoides ptenyssinus* and *Blomia tropicalis*

Figure 17:
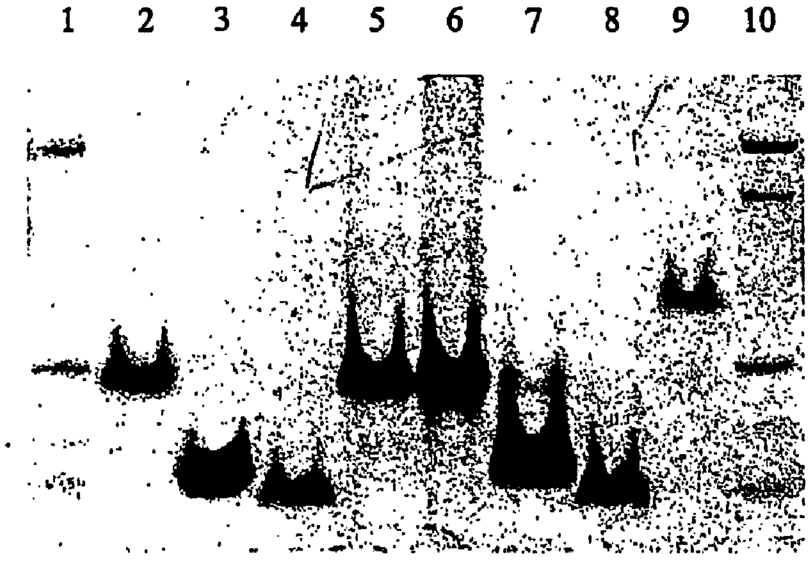
FIG. 17. Expression and purification of recombinant fusion protein Bt5-Fve, Bt5-FveR27A, and GST-Dp2-FveR27A. Lane 1 and 10 are protein marker. Lane 2 to 9 are GST; Blo t 5; Fve; Bt5-Fve; Bt5-FveR27A; Der p 2; Fve; and GST-Bt5, respectively.

The fused cDNAs are successfully expressed in *E coli* (FIG. 17) and the biological properties of the recombinant proteins are examined.

Results

Figure 18:
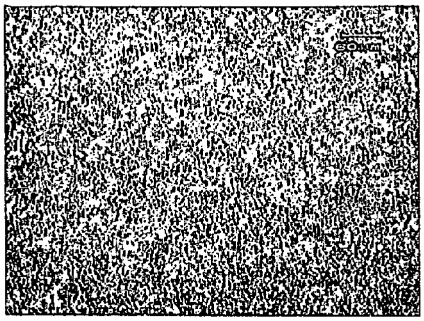
FIG. 18. Functional characterization of recombinant fusion proteins of Fve and allergen. The morphology of human lymphocytes upon stimulation with three different fusion proteins for three days. All photographs are taken at a magnification of ×10 and ×40 with a confocal microscope. 1(a) Control: Non-stimulated (10×10 magnification); 1(b) Control: Non-stimulated (40×10 magnification); 2(a): 20 μg of GST 10×10; 2(b): 20 μg of GST 40×10; 3(a): 20 μg of Blo t 5 10×10; 3(b): 20 μg of Blo t 5 40×10; 4(a): 20 μg of native Fve 10×10; 4(b): 20 μg of native Fve 40×10; 5(a): 20 μg of Bt5-Fve 10×10; 5(b): 20 μg of Bt5-Fve 40×10; 6(a): 40 μg of Bt5-Fve 10×10; 6(b): 40 μg of Bt5-Fve 40×10; 7(a) 40 μg of Bt5-FveR27A 10×10; 7(b): 40 μg of Bt5-FveR27A 40×10; 8(a): 20 μg of Der p 2 10×10; 8(b): 20 μg of Der p 2 40×10; 9(a): 40 μg of GST-Dp2-FveR27A 10×10; 9(b): 40 μg of GST-Dp2-FveR27A 40×10. Human lymphocytes maintained aggregation ability upon stimulation with Bt5-Fve (5a, 5b, 6a, 6b) and Bt5-FveR27A (7a, 7b) for 3 days. Native Fve (4a, 4b) is a positive control. Non-stimulated cells (1a, 1b), GST (2a, 2b), Blo t 5 (3a, 3b), and Der p 2 (8a, 8b) are negative controls. The aggregation ability of GST-Dp2-FveR27A is not apparent at day 3 (9a, 9b).
Figure 18:
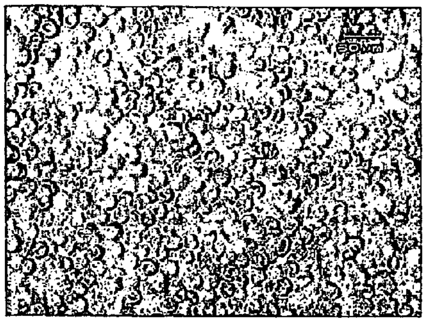
Figure 18:
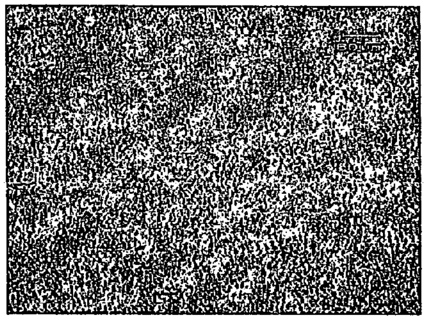
Figure 18:
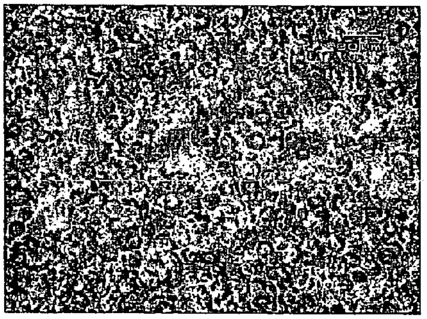
Figure 18:
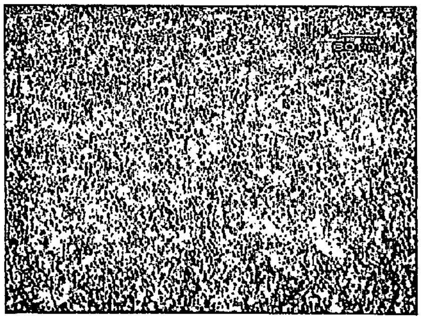
Figure 18:
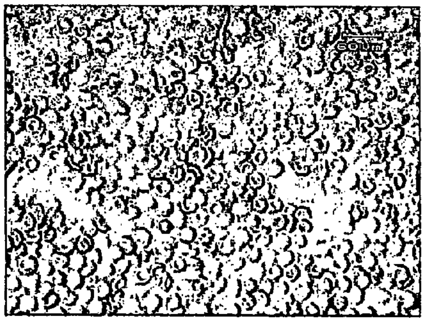
Figure 18:
Figure 18:
Figure 18:
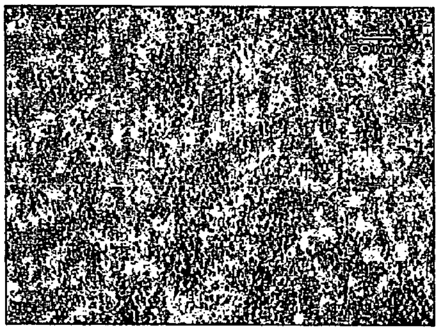
Figure 18:
Figure 18:
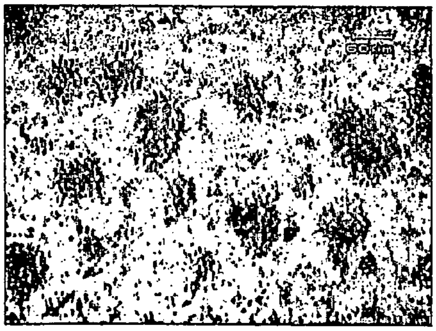
Figure 18:
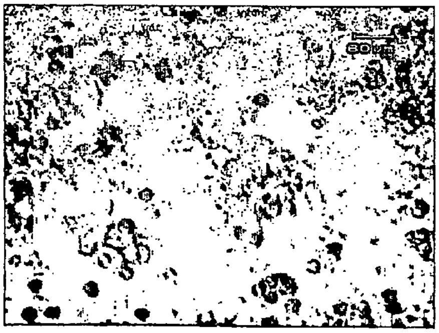
Figure 18:
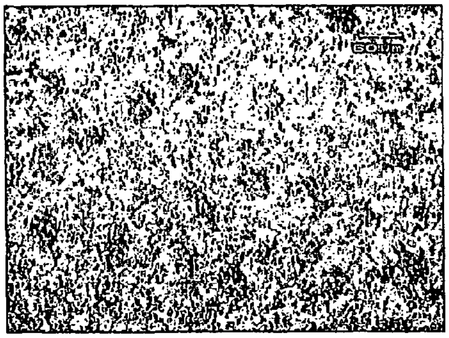
Figure 18:
Figure 18:
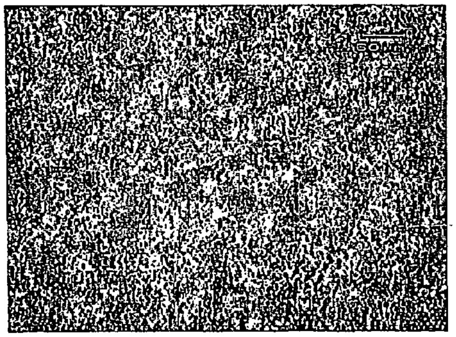
Figure 18:
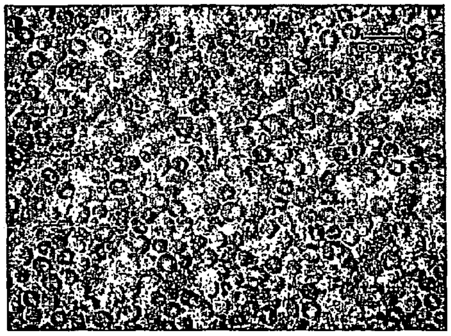
Figure 18:
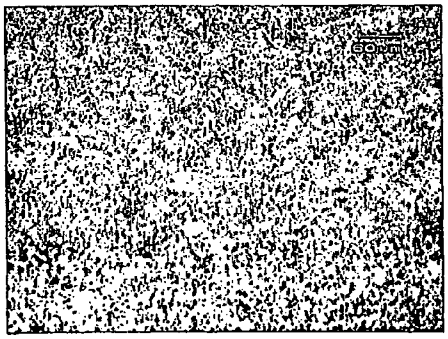
Figure 18:
Figure 19:
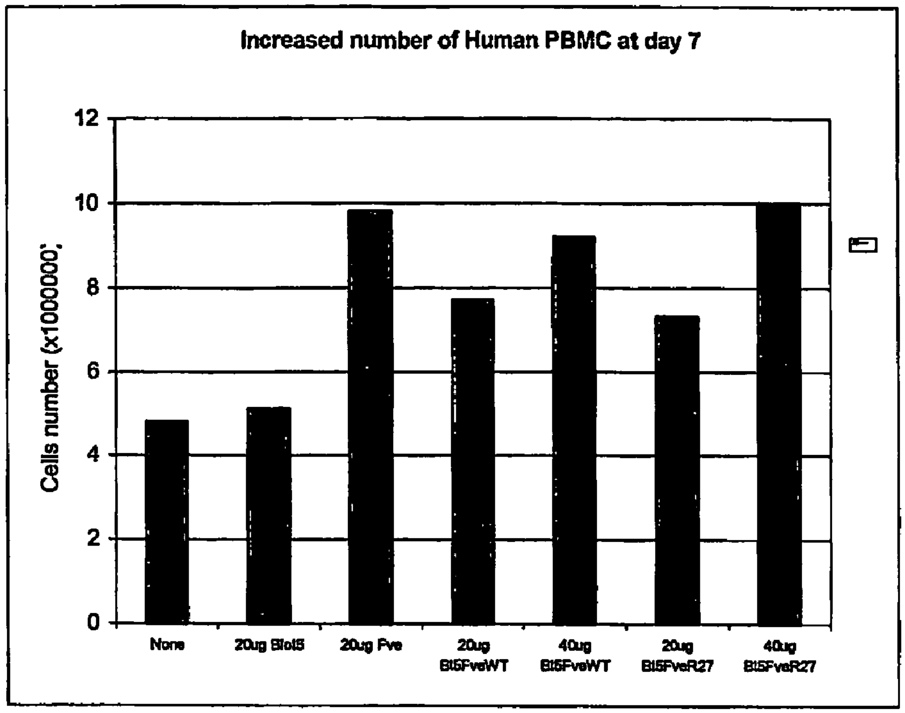
FIG. 19. Cell number comparison of human PBMC after 7 days cultured with tested antigens. Human PBMC are cultured with different doses of recombinant allergen and Fve fusion proteins. Non-stimulated cells and cells stimulated with either 20 μg of Blo t 5; 20 μg of Fve; 20 μg of Bt5-Fve; 40 μg of Bt5-Fve; 20 μg of Bt5-FveR27A; and 40 μg of Bt5-FveR27A are shown in FIG. 19A. Cells stimulated with 20 μg of Der p 2; 20 μg of GST-Dp2-FveR27A; and 40 μg of GST-Dp2-FveR27A are shown in FIG. 19B. The cells are collected and counted at day 7.
Figure 19:
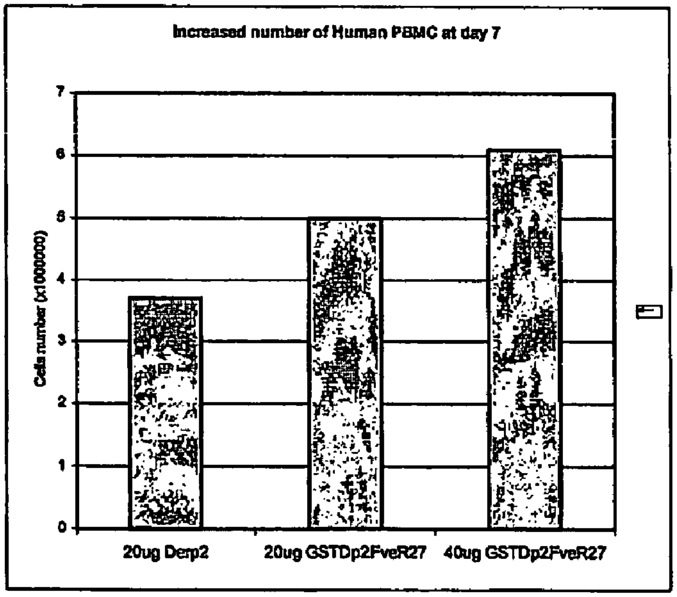
Figure 20:
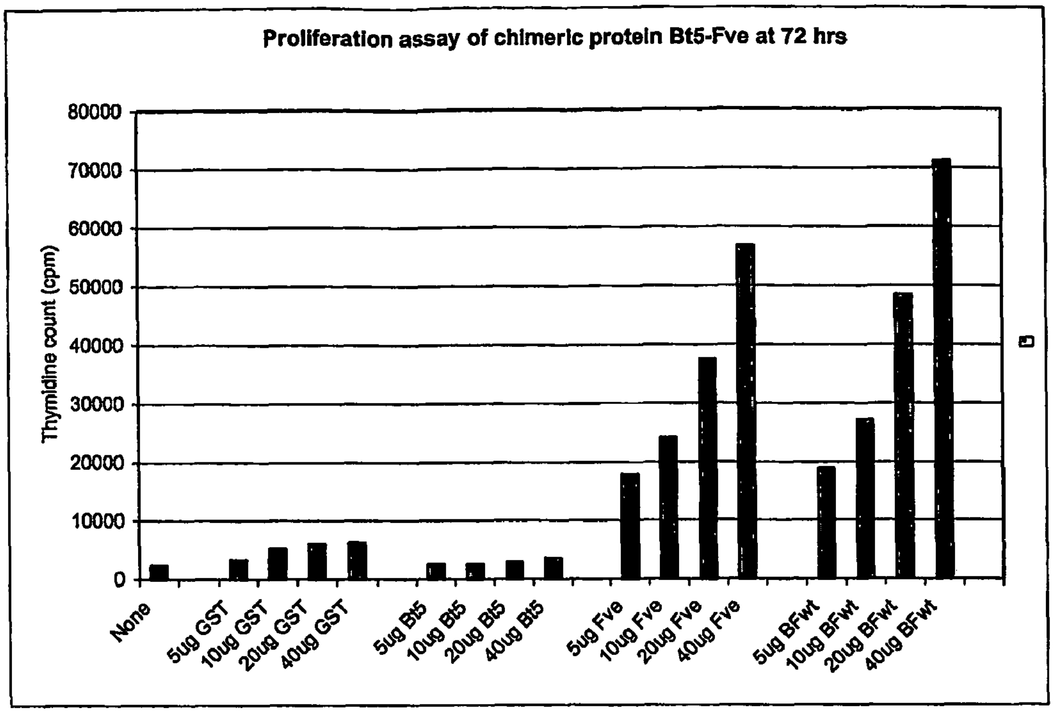
FIG. 20. The lymphoproliferation activity of human lymphocytes upon stimulation with recombinant fusion protein Bt5-Fve for 72 hours. Human PBMC from a healthy donor is co-cultured with 5 μg/ml, 10 μg/ml, 20 μg/ml, and 40 μg/ml, respectively, with fusion protein Bt5-Fve (BFwt). Recombinant GST and Blo t 5 are used as negative controls. Fve is used a positive control.
Figure 21:
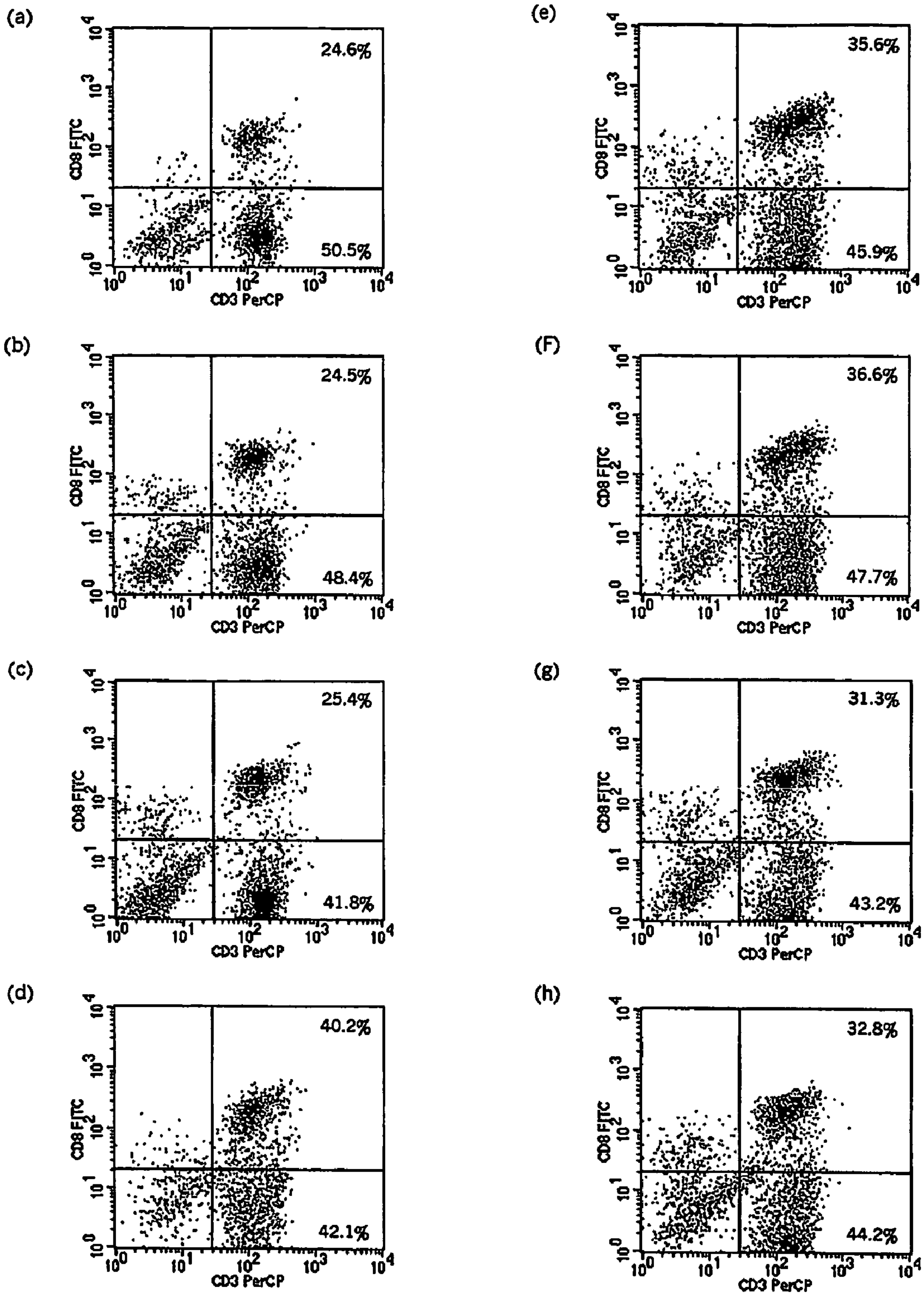
FIG. 21. Bt5Fve fusion protein maintained CD8 T cells polarization activity. Human PBMC are isolated from healthy donar and stimulated with 20 μg of GST (b), 20 μg of Blo t 5 allergen (c), 20 μg of Fve (d), 20 μg of Bt5Fve (e), 40 μg of Bt5Fve (f), 20 μg of Bt5FveR27 (g), and 40 μg of Bt5FveR27 (h) for 5 days. Cells without any stimulation served as negative control (a). Cultured cells are stained with CD3-PerCP and CD8-FITC monoclonal antibodies and analyzed with FACSCalibur cytometry.
Figure 22A:
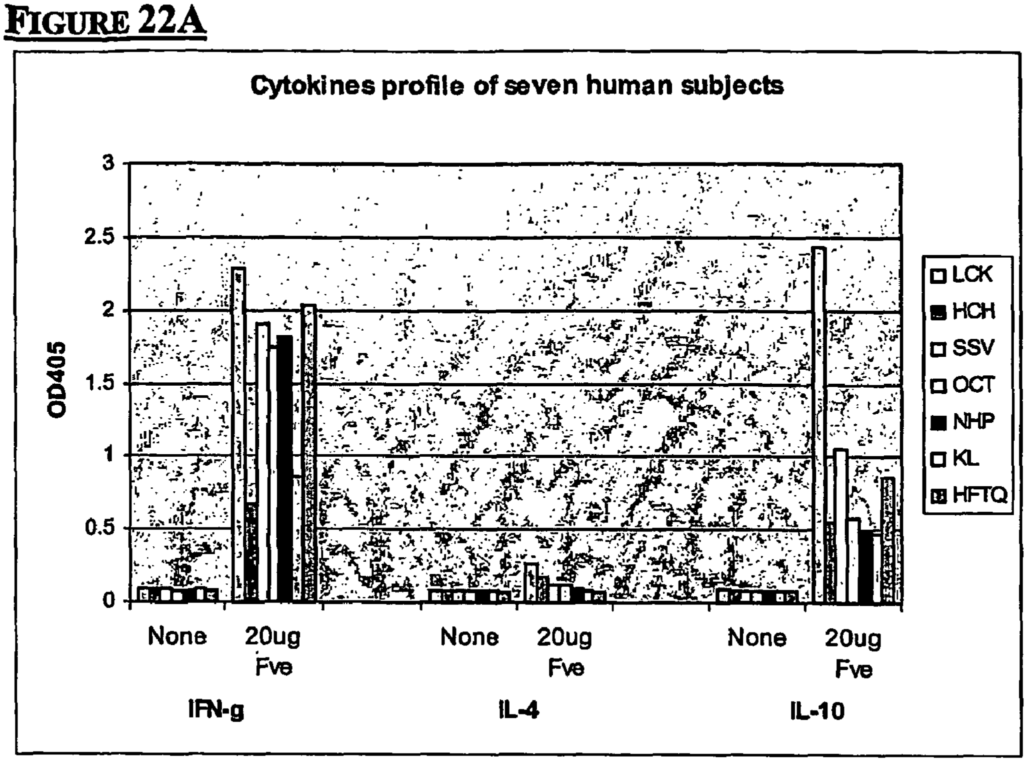
FIG. 22. Fve and allergen-Fve fusion protein are able to induce T helper type 1 and T regulatory immune responses. (A). Fve induced IFN-γ and L-10 production. Human PBMC from seven individuals are cultured with 20 μg of Fve. The production of IFN-γ, IL-4 and IL-10 is assayed by ELISA at day 3. (B). Comparable levels of IFN-γ production are induced by Fve and allergen-Fve fusion protein. Human PBMC are stimulated with Fve, Blot5, Blot5-Fve (wild type) and Blot5-FveR27A (mutant), respectively. The production of IL-4 and IFN-γ is detected by ELISA at day 3 and day 7.
Figure 22B:
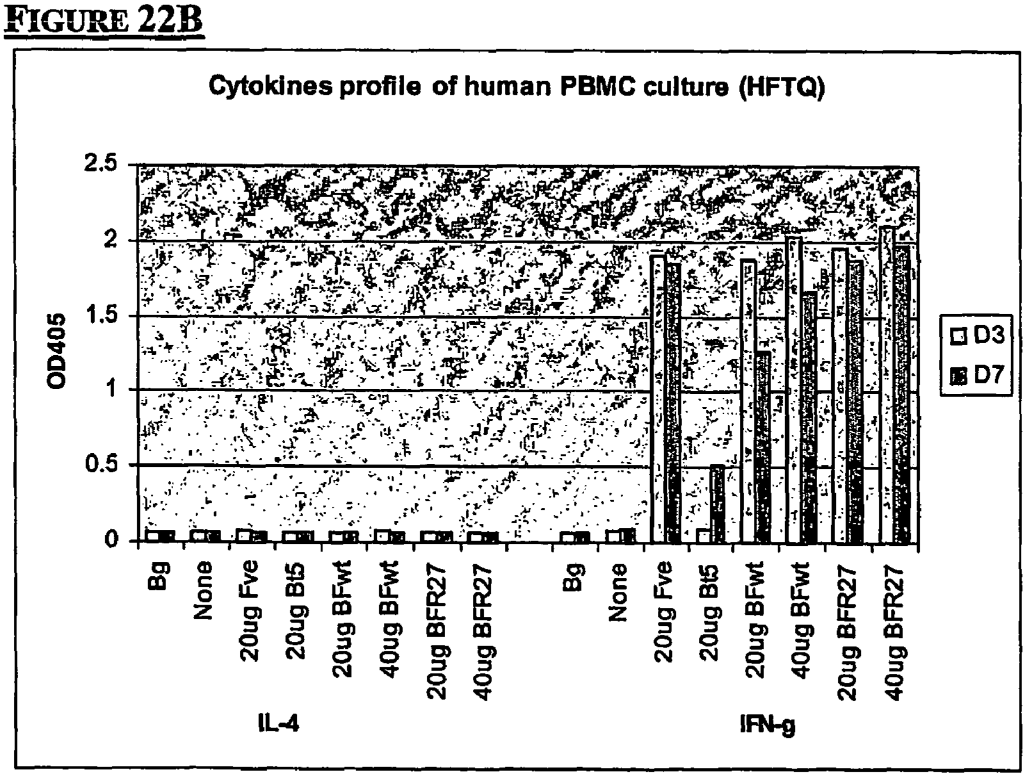

The morphology of lymphocyte culture upon stimulation with three recombinant fusion proteins is photographed with inverted microscope (FIG. 18A-C). Each of Bt5-Fve, Bt5-FveR27, GST-Dp2-FveR27 are able to increase the number of human PBMC (FIGS. 19A and 19B), to stimulate the proliferation of human lymphocytes (FIG. 20), to polarize human $CD8^+$ T cells (FIG. 21), and to increase the production of IFN-γ (Th1 response) and IL-10 (Tr response) (FIG. 22).

A well-balanced vaccine that induces both Th1 and Tr immune response may be the most valuable and desirable. The Th1 response may very efficiently inhibit the development of Th2 cells via IFN-γ, leading to a life-long protective Th1 memory immune response. Allergen specific Tr cells may in turn dampen the anti-allergic Th1 immune response, ensuring a well-balanced protective but nonpathological Th1 response. Allergen-Fve fusion proteins meet these criteria since they induce cytokine IL-10.

Thus, combining Fve protein with allergen in the form of a fusion protein may be used effectively to induce antigen-specific adjuvant effect that augment the Th1 and Tr responses, which in turn down-regulate the Th2 allergic responses.

Figure 23:
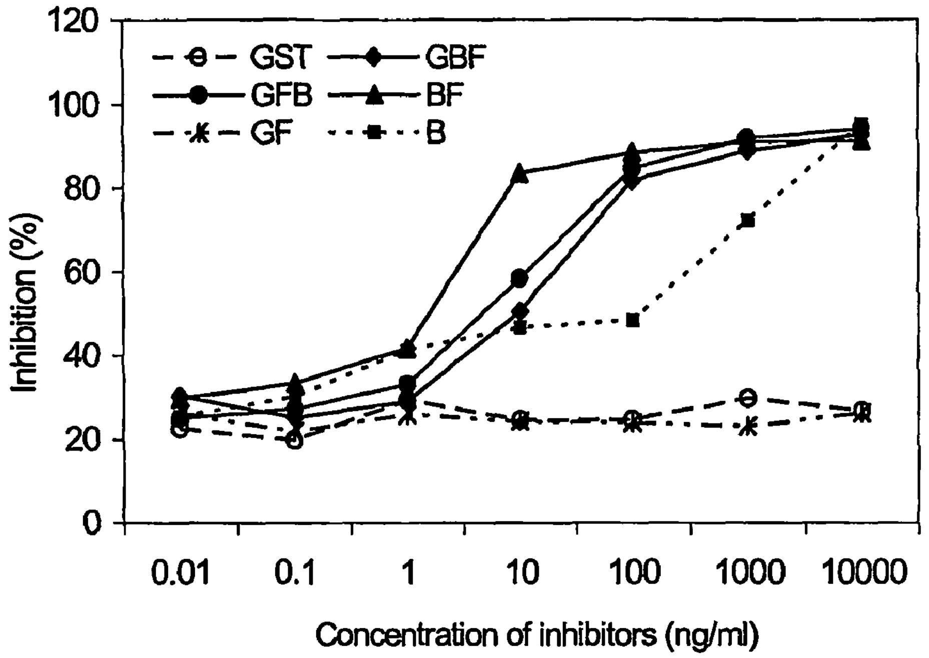
FIG. 23. Competitive inhibition assay. Varying concentrations of inhibitors are used to inhibit the binding of human IgE to GST-Blot5 bound to the Elisa plate. The concentration of different inhibitors ranged from 0.01 ng to 10000 ng/ml. Results are obtained from serum of a representative allergic subject with high IgE reactivity to house dust mite allergens. GST: Glutathione S-transferase. GF: GST-Fve. GFB: GST-Fve-Blot5. GBF: GST-Blot5-Fve. BF: Blot5-Fve. B: Blo t 5.

To test the antigenecity of a Blo t 5-Fve fusion protein, competitive inhibition ELISA is performed using varying concentrations of proteins (GST, GST-Blo t5, GST-Fve, GST-Blo t5-Fve, GST-Fve-Blo t5, Blo t5-Fve). The results show that fusion protein Blo t 5-Fve, un-cleaved GST-Blo t5-Fve and GST-Fve-Blo t5 have lower IgE binding affinity compared to Blo t5 alone and un-cleaved GST-Blo t5 (FIG. 23). The fusion protein Blo t5-Fve inhibited IgE binding to a maximum of 70% whereas Blo t5 is able to inhibit the binding of antibody to GST-Bt5 to 100% at inhibitor concentration of 10 μg/ml. Control GST and GST-Fve are not able to inhibit the binding of IgE to GST-Blo t5 (background levels). In summary, there is a reduction in the IgE binding affinity of Blo t5 when it is in the fusion forms of Blo t5-Fve, GST-Blo t5-Fve and GST-Fve-Blo t5 indicating that the antigenicity of Blo t5 with Fve in fusion forms is lowered.

Experiment B

Five mice per group of female BALB/cJ (6-8 weeks old) are subcutaneous immunized with 10 μg/ml of major house dust mite allergen Blo t 5 alone or fusion protein Blo t 5-FveT29A in tail at day 1. Mice are received similar antigen boosting in footpads at day 14 and day 28. All mice were bled weekly and sera were collected for analysis of Blo t 5 and Fve-specific IgG1, IgG2a and IgE by ELISA.

Figure 23B:
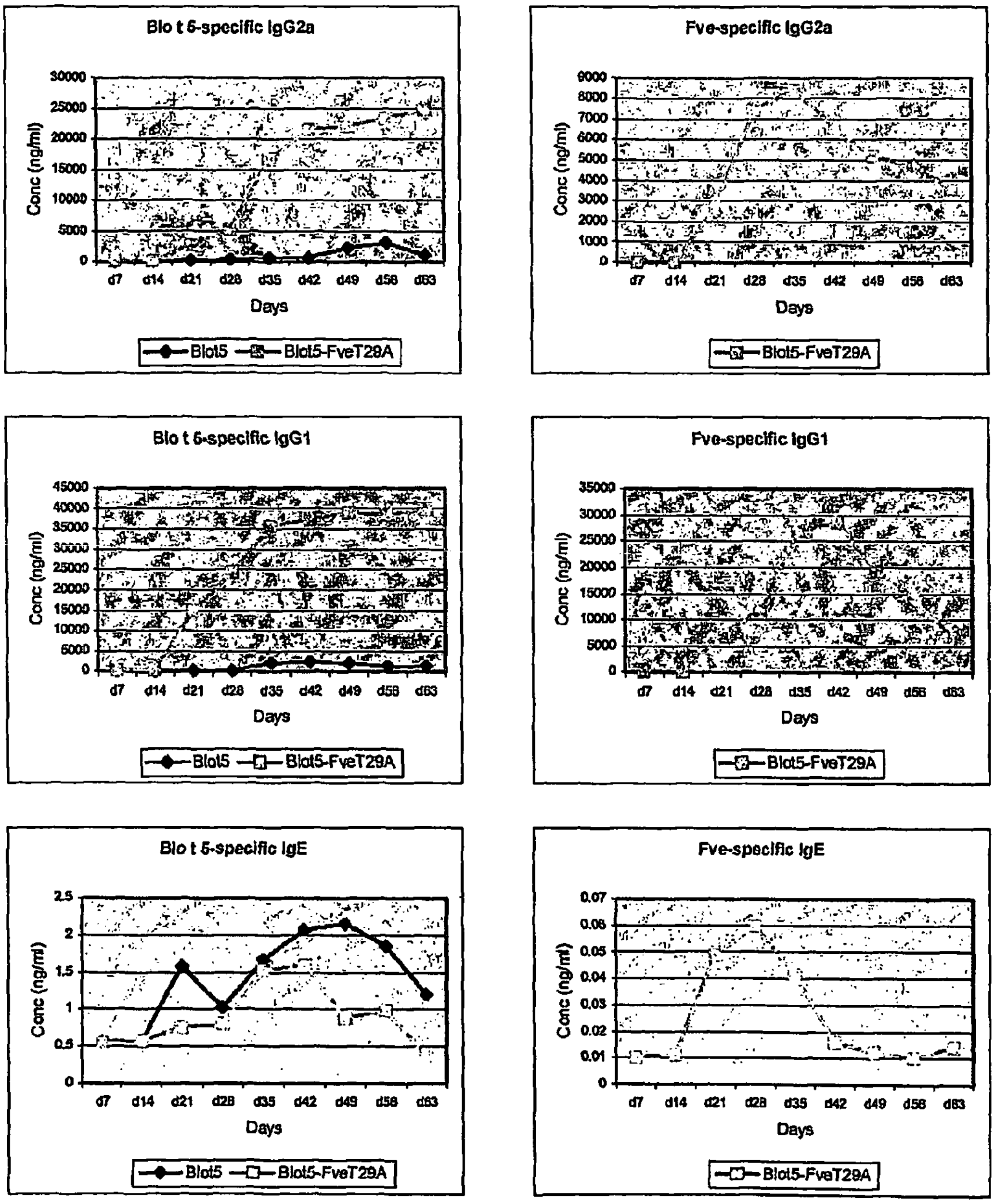
FIG. 23B. Polarized Th1 immune responses by recombinant fusion protein of allergen and fungal immunomodulatory protein Five mice per group of female BALB/cJ (6-8 weeks old) were subcutaneous immunized with 10 μg/ml of major house dust mite allergen Blo t 5 alone or fusion protein Blo t 5-FveT29A in tail at day 1. Mice were received similar antigen boosting in footpads at day 14 and day 28. All mice were bled weekly and sera were collected for analysis of Blo t 5 and Fve-specific IgG1, IgG2a and IgE by ELISA. Results show that recombinant fusion protein of allergen and fungal immunomodulatory protein has the ability to induce Blo t 5-specific IgG2a (2a) and down-regulate IgE production (2c). The overall of Fve-specific IgG1 and IgG2a antibodies are lower than Blo t 5 and decrease gradually after day 42 (2d and 2e), and the induction of Fve-specific IgE is less than 1 ng/ml (2f). Therefore, fungal immunomodulatory protein Fve has the potential to be developed for the immunotherapeutic vaccine of allergy.

The results are presented in FIG. 23B, which shows the concentrations of Blo t 5-specific antibodies (left hand column: top Blo t 5-specific IgG2a, middle: Blo t 5-specific IgG1, bottom: Blo t 5-specific IgE) as well as Fve-specific antibodies (right hand column: top Fve-specific IgG2a, middle: Fve-specific IgG1, bottom: Fve-specific IgE).

The results show that recombinant fusion protein of allergen and fungal immunomodulatory protein has the ability to induce Blo t 5-specific IgG2a (2a) and down-regulate IgE production (2c). The overall of Fve-specific IgG1 and IgG2a antibodies are lower than Blo t 5 and decrease gradually after day 42 (2d and 2e), and the induction of Fve-specific IgE is less than 1 ng/ml (2f).

Therefore, fungal immunomodulatory protein Fve has the potential to be developed for the immunotherapeutic vaccine of allergy.

Experiment C

All groups of female BALB/cJ (6-8 weeks old) are sensitized intraperitoneally on day 1 with 5 μg of recombinant mite allergen Blo t 5 and boosted at day 14 with 1 μg of Blo t 5 adsorbed to 64 μg/μl of aluminum hydroxide gel in a final volume of 200 μl. Mice treated with six subcutaneous injections of 20 μg of Blo t 5-FveWT or Blo t 5-FveT29A fusion protein in 200 μl of PBS at three days interval started from day 21-35. The negative control mice receive six subcutaneous injections of 20 μg of Blo t 5 alone. All mice are bled weekly and sera were collected for analysis of Blo t 5 and Fve-specific IgG1, IgG2a, and IgE by ELISA.

Figure 23C:
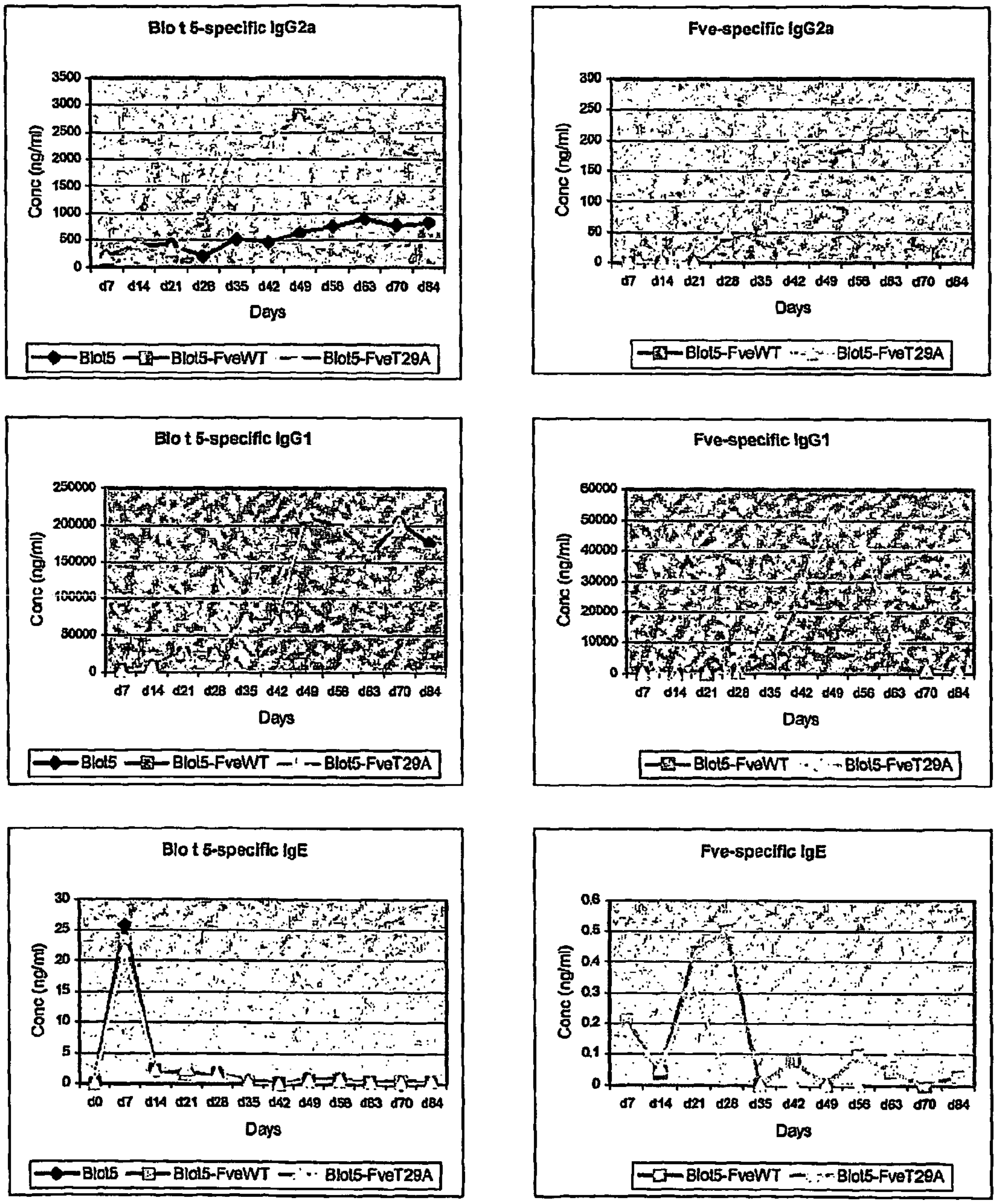
FIG. 23C. Efficient induction of Th1-mediated immune responses in mite allergeninduced mice by recombinant fusion protein Blo t 5-Fve All groups of female BALB/cJ (6-8 weeks old) were sensitized intraperitoneally on day 1 with 5 μg of recombinant mite allergen Blo t 5 and boosted at day 14 with 1 μg of Blo t 5 adsorbed to 64 μg/μl of aluminum hydroxide gel in a final volume of 200 μl. Mice treated with six subcutaneous injections of 20 μg of Blo t 5-FveWT or Blo t 5-FveT29A fusion protein in 200 μl of PBS at three days interval started from day 21-35. The negative control mice received six subcutaneous injections of 20 μg of Blo t 5 alone. All mice were bled weekly and sera were collected for analysis of Blo t 5 and Fve-specific IgG1, IgG2a, and IgE by ELISA. Result show that recombinant fusion protein Blo t 5-FveT29A has the ability to induce Blo t 5-specific IgG2a antibody (3a) in allergensensitized mice.

The results are presented in FIG. 23C which shows the concentrations of Blo t 5-specific antibodies (left hand column: top Blo t 5-specific IgG2a, middle: Blo t 5-specific IgG1, bottom: Blo t 5-specific IgE) as well as Fve-specific antibodies (right hand column: top Fve-specific IgG2a, middle: Fve-specific IgG1, bottom: Fve-specific IgE).

These results show that recombinant fusion protein Blo t 5-FveT29A has the ability to induce Blo t 5-specific IgG2a antibody (3a) in allergensensitized mice.

Discussion

It is well recognized that a vaccine that induces both Th1 and Tr immune response is highly desirable for treatment of allergy, and the allergen-Fve fusion proteins seem to meet these criteria since it could induce both cytokines IFN-γ(Th1) and IL-10 (Tr). It is anticipated that Fve protein with allergen in the form of a fusion protein could be an effective way to induce antigen-specific adjuvant effect that augment the Th1 and Tr responses, which in turns can down-regulate the Th2 allergic responses. Besides, it is known that in the inductive phase of allergen sensitization, Th1 cytokines can inhibit the development of Th2 cells via IFN-γ, leading to a life-long protective Th1 memory immune response. Allergen specific Tr cells may in turn dampen the anti-allergic Th1 immune response, ensuring a well-balanced protective but nonpathological Th1 response.

Therefore, Fve-allergen fusion proteins can be exploited to develop vaccine for prophylactic of allergic disorders.

Example 14

Allergen Conjugated to Fve

Beside the use of gene fusions to produce fusion proteins, protein-protein conjugation also provides a convenient and alternative choice to develop allergen vaccine.

To date, allergen conjugated adjuvants which have been reported include crystalline bacteria cell surface layer (S-layers) (Jahn-Schmid et al., 1996), CpG oligodeoxynucleotides (CpG motifs) (Shirota et al., 2000), cholera toxin B subunit (CTB) (Rask et al., 2000), and *Brucella abortus* (Scharf et al., 2001).

Here we disclose Fve protein which is isolated from edible mushroom can also be an ideal adjuvant coupling to allergen vaccine. Poly-lactic acid (PLA) and polyethylene glycol (PEG) are two materials which may be used to couple Fve and house dust mite allergen (Der p 2 or Blo t 5), although other materials will be evident to the skilled reader.

Particular coss-linking reagents which may be used to conjugate an allergen and immumodulator, such as Fve, include N,N'-dicyclohexylcarbodiimide (DCC), N-succinimidyl-S-acetyl-thioacetate (SATA), N-succinimidyl-3-2-pyridyldithio)propionate (SPDP), ortho-phenylenedimaleimide (o-PDM), and sulfosuccinimidyl 4-(N-maleimidomethyl)cyclohexane-1-carboxylate (sulfo-SMCC). A chemical conjugation protocol which may be used is that provided in the Protein-Protein Crosslinking Kit (P6305) from Molecular Probes, Eugene, USA. Protocols for conjugation using SPDP are disclosed in Clinical Experimental Allergy 30: 1024-1032, 2000 and European Journal of Immunology 28: 424-432, 1998.

For example, native Fve or recombinant Fve from *E coli* is conjugated with N-succinimidyl 3-(2-pyridyldithio) propionate (SPDP, Molecular Probes) as a bifunctional coupling reagent. The resulting Allergen-Fve conjugates are purified by gel filtration and characterized for their allergenicity and adjuvanicity by in vitro and in vivo assays.

Example 15

Human Cytokine Assay in Purified $CD4^+$ and $CD8^+$ T Cell Subsets

Materials and Methods

To elucidate and identify subsets of human T lymphocytes responding to Fve stimulation, purified $CD4^+$ T cells and $CD8^+$ T cells from four human tonsillectomy patients (subject 1, 6 yrs-old Chinese; subject 2, 16 yrs-old Indian; subject 3, 17 yrs-old Malay, subject 4, 27 yrs-old Malay) are stimulated with 20 μg of Fve after AutoMACS seperation. AutoMACS is an automated magnetic cell sorter from Miltenyi-Biotec, Germany. The differential cytokine production profiles of these subsets are determined by intracellular cytokines staining after 48 hours in vitro culture.

Results

Fve Triggers Th1/Tc1 Cytokine Production in Human T Cells

The human cytokines induction studies show that Fve stimulates the production of IL-2, IFN-γ, TNF-α whereas IL-4 and IL-10 are nearly undetectable. In addition, purified $CD4^+$ T cells produce higher levels of TNF-α than purified $CD8^+$ T cells ($CD4^+$ vs $CD8^+$: 11.4% vs 2.5%), whereas purified $CD8^+$ T cells produce higher levels of IFN-γ than purified $CD4^+$ T cells ($CD4^+$ vs $CD8^+$: 3.6% vs 8.5%) upon Fve stimulation (Table 4). Therefore, the enrichment of $CD8^+$ T cells seems to derive from a protein-cell direct interaction. Taken together, this data supported that Fve could trigger Th1/TC1 cytokines production in human T lymphocytes.

TABLE 4

Cytokines profile of purified human T cells subsets

| Intracellular Cytokines Scretion | Purified $CD8^+$ T cells from human tonsil | | Purified $CD4^+$ T cells from human tonsil | |
|---|---|---|---|---|
| | None | Fve | None | Fve |
| IL-2 | 0.1% | 0.6% | 0.2% | 6.8% |
| IL-4 | 0.1% | 0.3% | 0.1% | 0.9% |
| IL-10 | 0.6% | 0.5% | 2.3% | 0.9% |
| IFN-γ | 0.1% | 8.5% | 0.6% | 3.6% |
| TNF-α | 0.2% | 2.5% | 0.4% | 11.4% |

Example 16

Lymphocyte Aggregation Activity of Fve

Materials and Methods

Human $CD4^+$ and $CD8^+$ T cells subset are purified from AutoMACS (an automated magnetic cell sorter from Miltenyi-Biotec, Germany). The morphology of the cells is observed by light microscope at day 3.

Six human cell lines are also used for the cell aggregation study. Promyelocytic HL-60 cells, Jurkat-T cells, monocytic leukemia U937 cells, myeloid leukemia K562 cells, Raji B cells, natural killer NK-92 cells are cultured with native Fve protein with 2.5 μg/ml, 5 μg/ml, 10 μg/ml, 20 μg/ml and 40 μg/ml, respectively. Cells aggregation is observed by inverted light microscopy after 24 hours.

Results

Fve Induced Aggregation of Human $CD4^+$ and $CD8^+$ T cells subsets, HL-60, Jurkat-T cells, and NK-92 Cells Human $CD4^+$ and $CD8^+$ T cells subset are purified from the tonsil of human 5 subject The aggregation of $CD4^+$ and $CD8^+$ T cells upon stimulation with 20 μg of Fve protein is observed by confocal microscope at day 3 (photographed data not shown).

From the human cell line study, we found that Fve could induce HL-60 aggregation at low concentration of 2.5 μg/ml. Jurkats-T cells and NK-92 also induced aggregation by Fve at concentration of 10 μg/ml and 20 μg/ml, respectively, where as U937, K562 and Raji didn't induce cell aggregation (Table 5). From the result, it seems that the level of cell aggregation correlates with the level of certain surface protein(s) expression in different cell lines. Promyelocytic cell line HL60 seems to be an idea cell line to identify Fve receptor.

TABLE 5

Cell aggregation activity of human cell lines

| Human Cell Lines | Fve | | | | |
|---|---|---|---|---|---|
| | 2.5 μg/ml | 5 μg/ml | 10 μg/ml | 20 μg/ml | 40 μg/ml |
| HL-60 | + | + | + | + | + |
| Jurkat T | +/− | +/− | + | + | + |
| U937 | − | − | − | − | +/− |
| K562 | − | − | − | − | +/− |
| Raji | − | − | − | − | − |
| NK-92 | − | − | +/− | + | + |

Example 17

In Vitro Polarization of Human NK Cells and $CD8^+$ T Cells

Materials and Methods

Human peripheral blood mononuclear cells (PBMC) from a healthy donor are isolated as standard protocol (Coligan et al., 1998). The cells are then cultured in 24-well plates with native Fve (5 μg/ml or 25 μg/ml). At days 5 and 10, cell culture are stained with anti-$CD4^+$ FITC, anti-$CD8^+$ PE, anti-$CD16^+$ PE plus anti-$CD56^+$ PE monoclonal antibodies (Becton Dickinson), and analyzed by FACScan flow cytometry (Becton Dickinson).

Results

Sequential Polarization of Cells by Fve, NK Cells and NKT Cells are Proportionally Increased at Day 5 Whereas $CD8^+$ T Cells are Increased at Day 10

Figure 24:
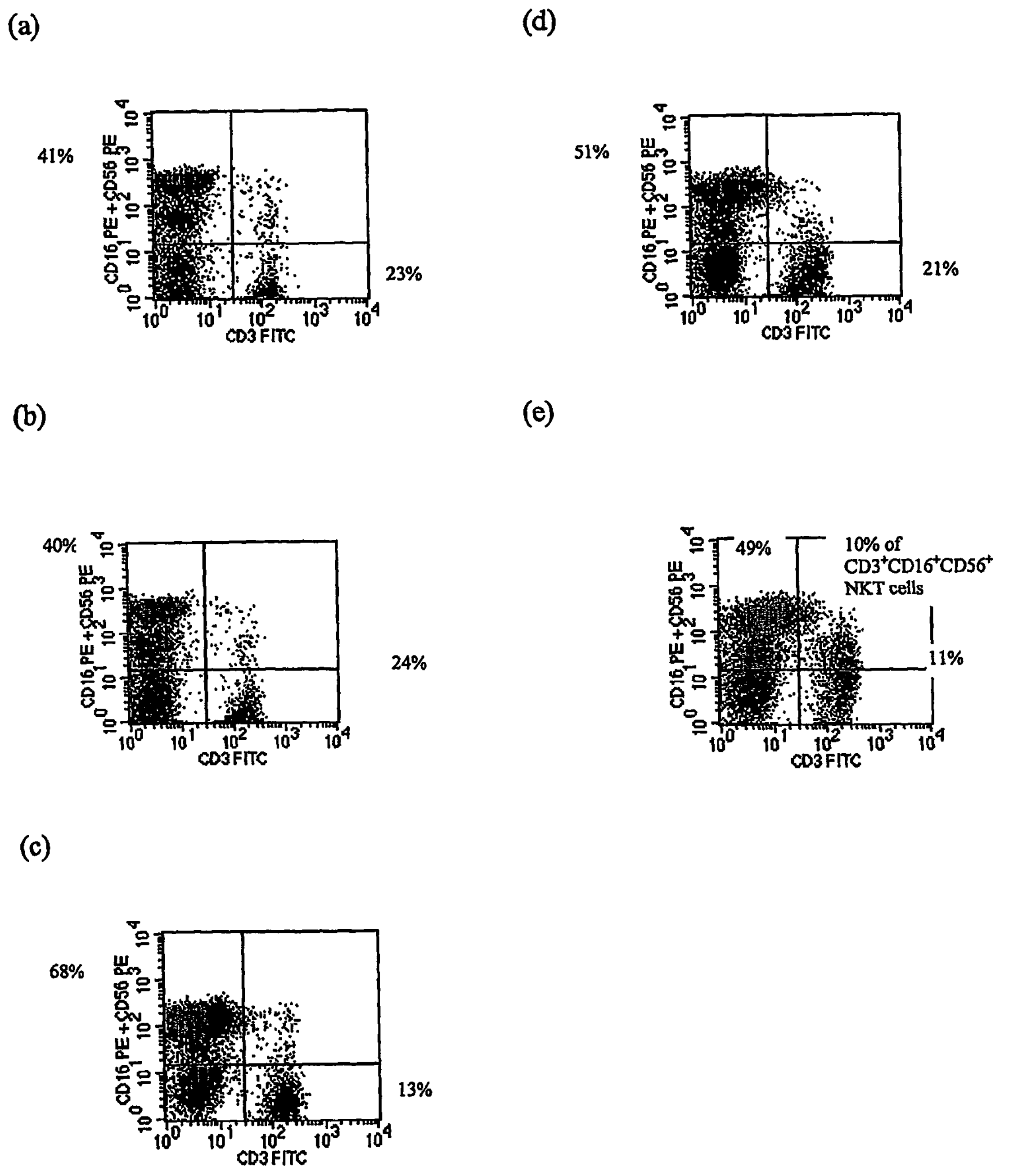
FIG. 24. Human PBMC stimulated with native Fve protein for five days showed a significant increase in $CD16^+$ and $CD56^+$cells. The $CD3^+$ cells and $CD16^+$+$CD56^+$ cells are analyzed by FACScan after staining with anti-CD3 FITC, anti-CD16 PE and anti-CD56 PE conjugated mouse anti-human specific monoclonal antibody. Cells stimulated with (a) no antigen; (b). 5 μg of Der p 2 house dust mite allergen as negative control; (c). 5 μg of PHA; (d). 5 μg of Fve; (e). 25 μg of Fve.
Figure 25:
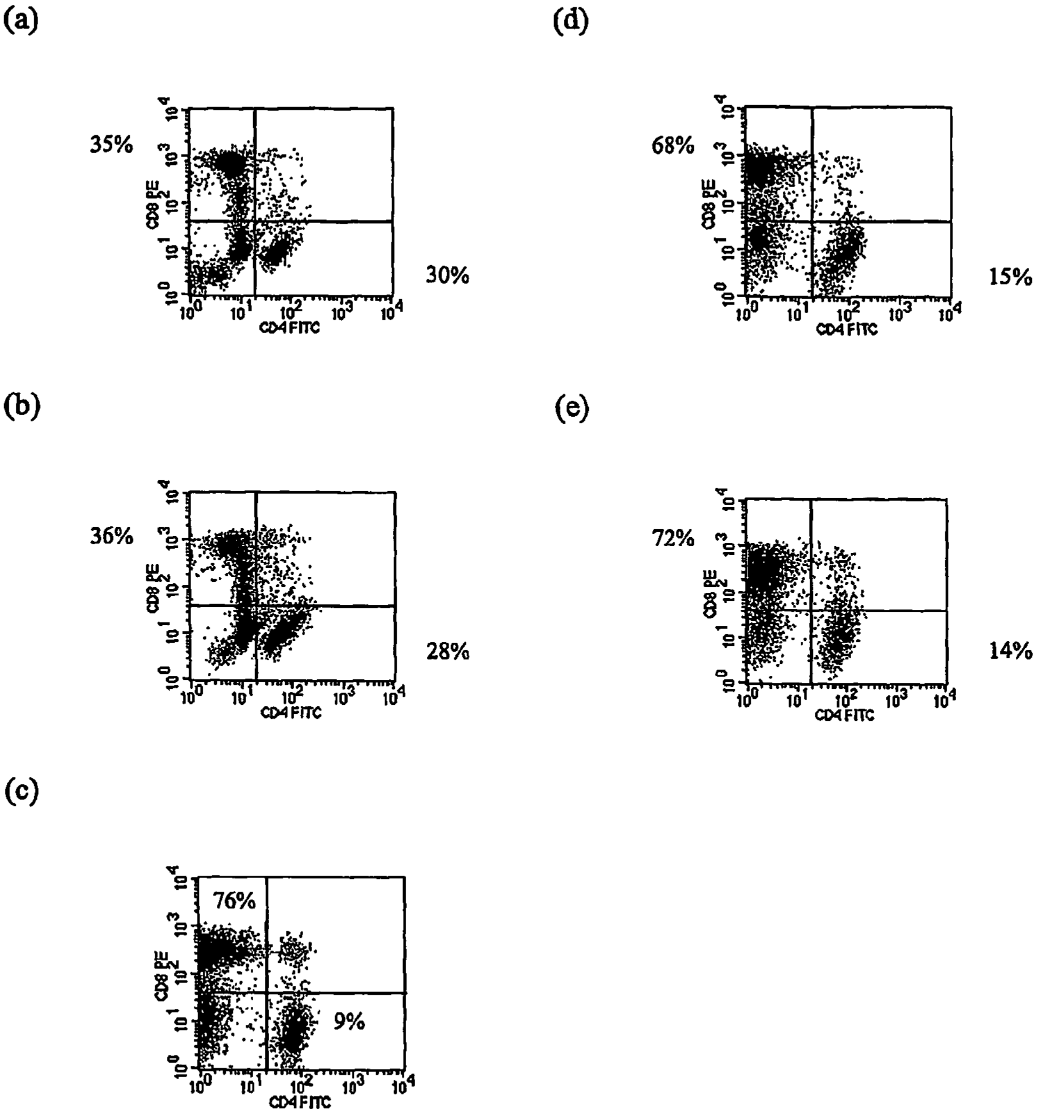
FIG. 25. Human PBMC stimulated with Fve protein for ten days showed a significant increase in $CD8^+$ cells. The proportion of $CD4^+$ and $CD8^+$ T cells are analyzed by FACScan after staining with anti-CD4 FITC and anti-CD8 PE conjugated mouse anti-human specific monoclonal antibody. Cells are stimulated with (a). no antigen; (b). 5 μg of Der p 2 house dust mite allergen as negative control; (c). 5 μg of PHA; (d). 5 μg of Fve; (e). 25 μg of Fve.

The results show a 10% increase of $CD16^+$ and $CD56^+$ double positive cells (Natural Killer cells) after stimulation with Fve protein for 5 days (FIG. 24). In addition, $CD8^+$ T cells but not $CD4^+$ cells are increased up to 35% after culturing for 10 days FIG. 25). This result showed that native Fve protein could stimulate both natural killer cells and $CD8^+$ T cells and the stimulation of these cells occurred sequentially with polarization of NK cells and $CD8^+$ T cells peaked at day 5 and day 10, respectively.

The data also showed that cell culture consisted of 10% of $CD3^+CD16^+CD56^+$ NKT cells after stimulation with 25 μg/ml of native Fve protein (FIG. 24E). This subset of cytotoxic NKT cells has a unique feature in that they mediate non-MHC-restricted cytotoxicity (Lanier et al., 1986).

Example 18

Up-Regulation of a Novel Subset of $CD8^+$ T Cells ($CD3^+$ $CD8^+$ $CD18^{+bright}$)

Materials and Methods

Repeated subcutaneous injection of IL-12 in patients with cancer resulted in the selective expansion of a unique subset of peripheral blood $CD8^+$ T cells. This subset expressed high levels of $CD18^+$ and up-regulated IL-12 receptor expression after IL-12 treatment in vivo. They appeared morphologically as large granular lymphocytes, increased high IFN-γ production and enhanced non-MHC-restricted cytolytic activity. Thus, these T cells may play an important role in innate as well as acquired immunity to tumors and infectious pathogens.

To determine whether $CD3^+$ $CD8^+$ $CD18^{+bright}$ T cells can be enriched by native Fve protein, human peripheral blood mononuclear cells (PBMC) from a healthy donor are isolated and cultured with 20 μg/ml of native Fve protein. Cell culture are stained with anti-CD18 FITC, anti-CD8 PE, anti-CD3

PerCP monoclonal antiboodies (Becton Dickinson) at day 5, and then analyzed by FACSCalibur flow cytometry (Becton Dickinson).

Results

Figure 26:
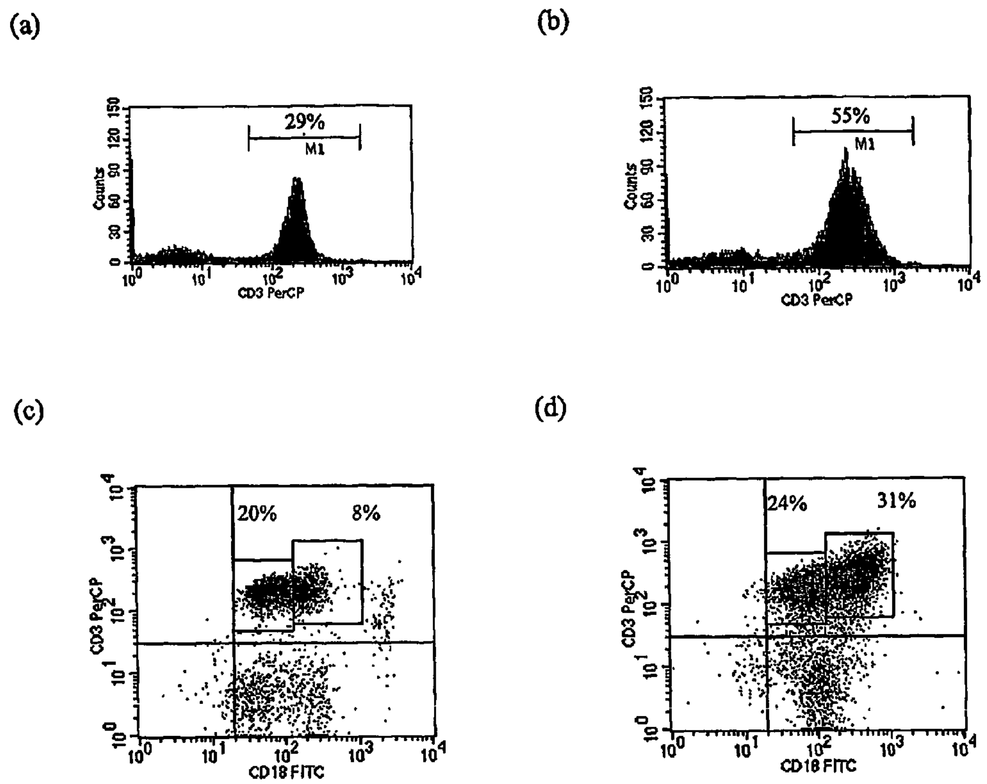
FIG. 26. Expanded human $CD3^+CD18^{+Bright}$ T cells subset in human PBMC after stimulation with Fve protein for five days. Human PBMC from healthy donor are cultured alone (a and c) or with 20 μg of native Fve protein (b and d) for 5 days. Cells are then analyzed by flow cytometry after staining with anti-CD3 PerCP, anti-CD8 PE and anti-CD18 FITC.
Figure 27:
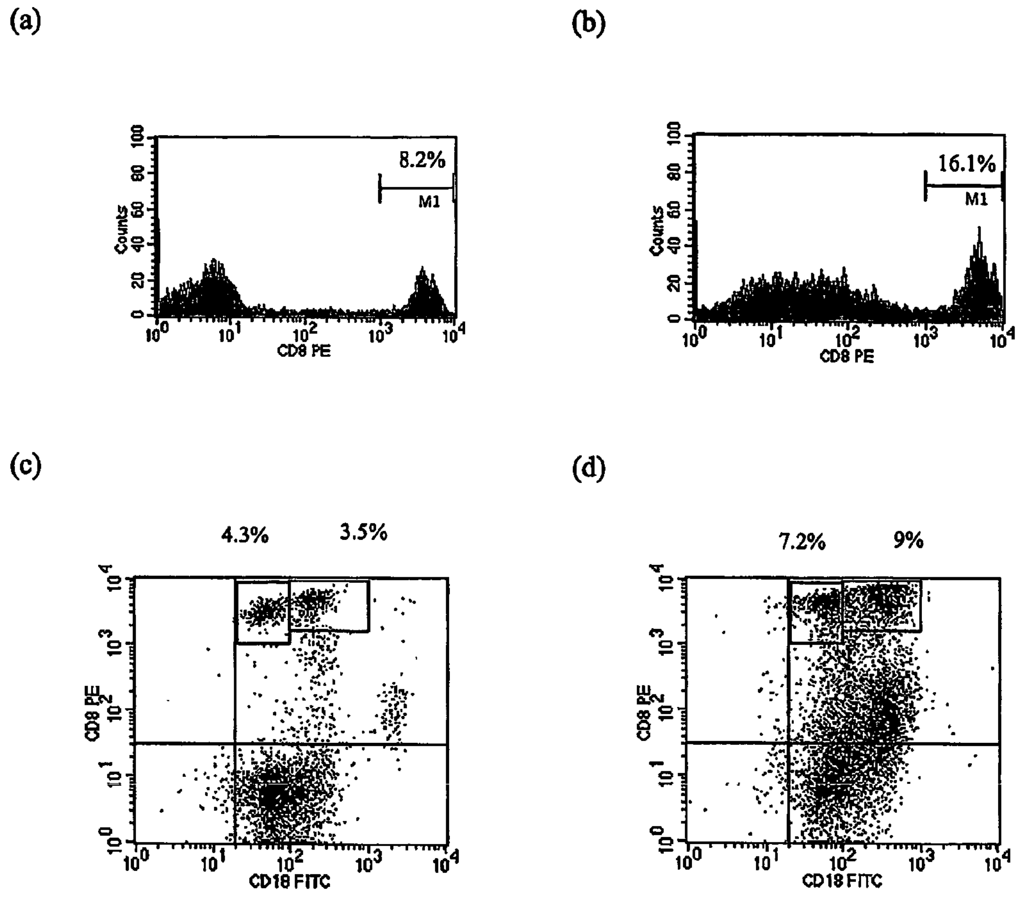
FIG. 27. Expanded $CD3^+CD8^{+Bright}CD18^{+Bright}$ T cells in human PBMC after cultured with Fve protein for five days. Human PBMC from healthy donor are cultured alone (a and c) or with 20 μg of native Fve protein (b and d) for five days. Cells are analyzed by flow cytometry after staining with anti-CD3 PerCP, anti-CD8 PE and anti-CD18 FITC.

Result showed that $CD3^{+}CD18^{+bright}$ T cells are increased from 8% to 31% of total cell population (FIG. 26), and $CD3^{+}CD8^{+bright}CD18^{+bright}$ T cells are increased nearly three times, from 3.5% to 9% of the total cell population (FIG. 27) after stimulation with 20 μg/ml of native Fve protein. Furthermore, some $CD18^{+}$ CD8− cells started to differentiate into $CD18^{+}CD8^{+dim}$ cells after stimulated with native Fve protein (FIG. 27B). This data suggested that Fve protein from the golden needle mushroom has a potential ability to stimulate cellular immune responses directed against malignancies in human.

Example 19

In Vivo Lymphocyte Proliferation Assays

Materials and Methods

Since Fve protein can activate human NK cells and $CD8^{+}$ T cells in vitro, we sought to determine whether Fve would enhance activation of these cells in vivo. Mouse provides a good model system for such a study.

A group of three C57BL/6J mice are subcutaneously injected with 10 μg, 50 μg or 250 μg Fve protein consecutively for three days, respectively. Another three BALB/cJ mice are treated with 125 μg of Fve protein each for seven days by subcutaneous injection. For continuous BrdU labeling, mice are given 0.5 mg/ml BrdU (Sigma) in the drinking water, which is changed every 3 days and then each mouse received one intraperitoneal injection of 1 mg of BrdU in PBS at 6 hours before being sacrificed. PBMC, lymph node and spleen are isolated and resuspended in 200 ul of washing buffer (1× PBS containing 1% bovine calf serum), then stained with anti $CD4^{+}$-FITC, anti $CD8^{+}$-PE, anti $CD19^{+}$-PE or anti PanNK-PE monoclonal antibody (Pharmingen) for 30 minutes on ice. After two washings with washing-buffer, the samples are fixed with FACS Permeabilizing Solution (Becton Dickinson) for 16 hours. After that samples are treated with 50U DNase I (Sigma) for 1 hr at room temperature. The cells are washed and stained with anti BrdU-FITC mAb (Becton Dickinson) in PBS for 30 minutes. 1-5×$10^{5}$ viable (forward and side scatter gated) PBMC, lymphocytes in lymph nodes or splenocytes per sample are analyzed with FACScan (Becton Dickinson) and data are processed using the CellQuest software (Becton Dickinson).

Results

Fve Induced NK Cells and $CD8^{+}$ T Cells Proliferation in Vivo

Figure 28:
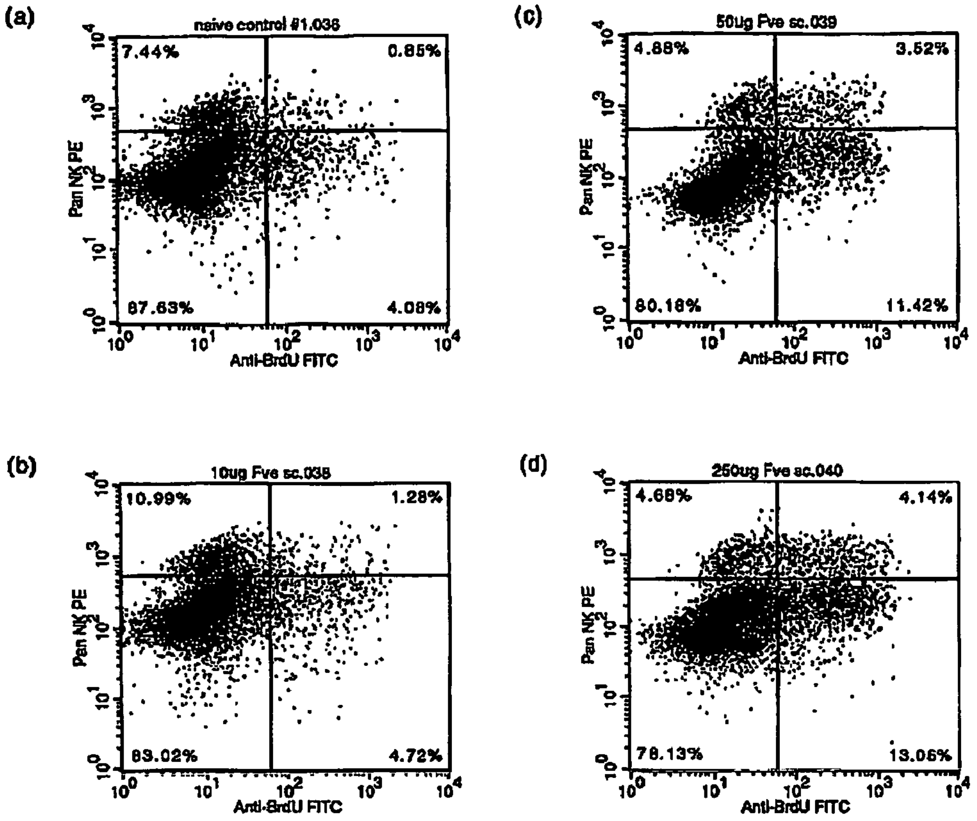
FIG. 28. Proportion of in vivo BrdU incorporated natural killer (NK) cells from spleen of C57BL/6J naïve mice (a), or mouse received three consecutive subcutaneous injections with 10 μg of Fve (b), 50 μg of Fve (c), 250 μg of Fve (d).

FACScan analysis data showed that Fve could induce increased proliferation of NK cells and $CD8^{+}$ T cells in a dose-dependent manner in C57BL/6J mice (FIG. 28 and FIG. 29). In contrast, $CD4^{+}$ T cells and $CD19^{+}$ B cells showed no significant increase (FIG. 30 and FIG. 31). Similar $CD8^{+}$ T cell polarization is also seen in lymph nodes of C57BL/6J mice FIG. 32) and so the peripheral blood mononuclear cells (PBMC) of Balb/cJ mice that are subcutaneous injected for seven consecutive days with 125 μg of Fve protein. The $CD8^{+}$ versus $CD4^{+}$ T cells ratio is significantly increased in each of the Fve-treated BALB/cJ mouse as compared to the naive control (FIG. 33). Data from the experiment are presented in Table 6 below.

TABLE 6

Data showing results of FIG. 33.

| Naïve | PBMC | | |
|---|---|---|---|
| Balb/cJ mouse | $CD4^{+}$ T cells | $CD8^{+}$ T cells | $CD8^{+}/CD4^{+}$ ratio |
| #1 None | 40.3% | 15.7% | 0.389 |
| #2 125 μg nFve | 40.2% | 26.2% | 0.651 |
| #3 125 μg nFve | 40.7% | 21.8% | 0.535 |
| #4 125 μg nFve | 33.3% | 19.6% | 0.588 |

In summary, for NK cells in spleen, 10 g Fve caused one fold increase proliferation. The proliferation increased to 5-6 fold when 50 μg and 250 μg of Fve protein is added. Similar finding is observed in CD8 positive T cells in spleen and lymph nodes. 250 μg Fve protein caused 2-3 fold increase proliferation as compared to non-treated mouse. By contrast, Fve failed to stimulate CD4 positive T cells and has very mild stimulation to CD19 B cells (Table 7). Similar phenomenon is also seen in the peripheral blood mononuclear cells. The proportional of CD8 T cells increased up to 6-10% after 125 μg of Fve protein are subcutaneous injected to Balb/cJ mice for seven days (Table 8).

These in vitro data are in concordance with those derived from in vitro studies, which clearly indicate that Fve induces selective polarization of NK cells and $CD8^{+}$ T cells. Furthermore, these immunostimulatory effects of Fve are independent of the genetic background of mouse strains. Thus, Fve appears to be a potent immunostimulator for cellular mediated immune response. Purified NK cells and $CD8^{+}$ T cells will be used for future studies to examine the molecular and cellular basis for the polarization of cell subsets.

TABLE 7

In vivo stimulation of C57BL/6J mouse lymphocytes

| | Spleen | | | | |
|---|---|---|---|---|---|
| Naïve C57BL/6J mouse | BrdU incorporated NK cells | BrdU incorporated $CD4^{+}$ T cells | BrdU incorporated $CD8^{+}$ T cells | BrdU incorporated $CD19^{+}$ B cells | Lymph nodes BrdU incorporated $CD8^{+}$ T cells |
| #1 None | 0.63% | 3.49% | 2.22% | 3.48% | 5.83% |
| #2 10 μg Fve | 1.20% | 3.32% | 2.81% | 3.43% | 5.72% |
| #3 50 μg Fve | 3.53% | 3.47% | 3.34% | 4.11% | 9.19% |
| #4 250 μg Fve | 4.00% | 2.55% | 7.31% | 4.55% | 12.05% |

TABLE 8

In vivo stimulation of Balb/cJ mouse lymphocytes

| Naïve | PBMC | | |
|---|---|---|---|
| Balb/cJ mouse | $CD4^+$ T cells | $CD8^+$ T cells | $CD8^+/CD4^+$ ratio |
| #1 None | 40.3% | 15.7% | 0.389 |
| #2 125 μg Fve | 40.2% | 26.2% | 0.651 |
| #3 125 μg Fve | 40.7% | 21.8% | 0.535 |
| #4 125 μg Fve | 33.3% | 19.6% | 0.588 |

Example 20

In Vivo Evaluation of the Potential Use of Fve for Immunotherapy of Solid Tumors There are several approaches to treat cancer such as surgery; radiation therapy, given tumor cell arrested drugs; induced apoptosis in cancerous cells; inhibited angiogenesis; elevated tumor recognition and specific killing ability of immune system to eliminate cancerous cells.

Previous data have indicated that Fve protein stimulate enhanced production of various cytokines, particularly IFN-γ, TNF-α and IL-2; induced polarization of natural killer cells and $CD8^+$ T lymphocytes; and triggered a Th1/Tc1-like cellular-mediated immune response. Each of these biological properties may contribute to suppression of tumor growth and to prevent the risk of cancer recurrence by inducing various forms of nonspecific or even specific immunity after surgery.

Malignant melanoma is a very common cancer in the western world. A subset of patient with metastatic melanoma can be successfully treated by the administration of recombinant IL-2, sometimes given together with autologous melanoma-reactive lymphocytes that have been expanded ex vivo. Since melanocyte differentiation antigens, including MART-1/Melan-A, gp100, tyrosinase, TRP-1, and TRP-2, and cancer-testis antigens, including MAGE-3, BAGE, GAGE, NY-ESO-1, are recognized by human T lymphocytes, therefore they become the attractive targets for melanoma vaccines. However, from an immunological point of view, these melanocytes differentiation antigens and cancer-testis antigens are "self" antigens. It may induce central or peripheral tolerance, and thus potentially hampering the induction of powerful anti-melanoma immune responses. Therefore, induction of a strong tumor specific immunity with an immunopotentiator or novel adjuvant could be a useful treatment strategy to overcome immune ignorance and tolerance.

In order to investigate the anti-tumor effect of Fve, C57BL6J mice are subcutaneously inoculated either with T cell lymphoma EL4 or melanoma B16-F1, the later is a well established and widely used tumor model for which treatment is notoriously difficult. The tumor growth and survival rate of mice are monitored.

Materials and Methods

Construction of pCIneo-Fve and pDisplay-Fve Recombinant Plasmid DNA

The pCIneo vector is designed for high level and constitutive expression of cloned DNA inserts in mammalian cells (FIG. 34A). Fve DNA is amplified from pGEX-fve and subcloned into the Xho I and EcoR I restriction enzyme cutting sites of pCIneo vector. The pCIneo-fve is used for priming the immune response by intramuscular injection.

The pDisplay vector is a mammalian expression vector that is designed to target and to display recombinant proteins to the surface of mammalian cells (FIG. 34B). Fusion DNA of Fve and murine Ig kappa chain V-J2C signal peptide without hemagglutinin A epitope is generated by recombinant PCR and subcloned into the EcoR I and Pst I restriction enzyme cutting sites of pDisplay vector. The Fve protein expressed from the pDisplay-fve acts as triggering signal for immune system and recruiting T lymphocytes to recognize tumor cells.

Transfection of B16-F1 Cells with pDisplay-Fve

The murine melanoma cells B16-F1 is purchased from ATCC, USA. Tumor cells are grown in DMEM supplemented with 10% FBS in 5% $CO_2$. Cells in the exponential growth phase within four passages are used in this investigation. To obtain stable transfectants, endotoxin free plasmid pDisplay-fve is mixed with polyfect transfection reagent (QIAGEN, Germany) and transfected into B16-F1 cells. Colonies resistant to G418 (Geneticin, GIBCO BRL) at 1000 μg/ml for 25-30 days are isolated and designated as B16-Fve. The control B16-F1 cells which are transfected with pDisplay vector alone are designated as B16-vec.

EL4 Protection Assay

Six to eight weeks old C57BL/6J mice are inoculated with $8\times10^6$ EL4 cells. Tumor formation is observed at day 3. 100 μg of pCIneo-fve recombinant plasmid DNA is intramuscularly injected into the tibialis muscle at day 0 and day 7. 20 μg of Fve protein is given by subcutaneous injection surrounding the tumor site at day 5, 7, 9, 11, 13, 15, and 18, respectively. The diameters of tumors are measured with a caliper and tumor volume is calculated by long diameter time short diameter. Finally the survival rate is recorded.

DNA Vaccination and B16-F1 Tumor Protection Experiments

Endotoxin free pCIneo and pCIneo-fve are purified from the QIAGEN plasmid DNA extraction and purification kits. 100 μg of pCIneo-fve is intramuscularly injected into the tibialis muscle of C57BL/6 mice at day-30 and day-1. Muscles are pulsed with Electro Square Porator ECM830 (BTX, Genetronics, USA) equipped with a two needle array electrode after DNA injection. Mice are inoculated with $5\times10^5$ B16-F1 cells. Small tumor nodule developed at day 3. 50 μg of Fve protein is given by subcutaneous injection surrounding the tumor site at day 4, 7, 9, and 12, respectively.

Experimental Lung Metastasis

B16-F1 cells are trypsinized from monolayer cultures, counted and spun down at 1,200 rpm for 5 min and resuspended with DMEM. Five C57BL/6 syngenic 6-week-old female mice are intravenously injected with $2\times10^4$ of B16-F1 melanoma cells in a final volume of 120 μl. About 4 weeks after injection, tumor nodules are established in lung. Mice are kept until they died to assess survival.

Example 21

Prolonged Survival Rate of Tumor-Inoculated Mice Receiving with Fve Gene and Protein Our results show that tumor established mice that received pCIneo-fve DNA and Fve protein had shown a reduction of T cell lymphoma growth rate (FIG. 35) and an extension of survival time (FIG. 36). Similar results are also seen in melanoma B16-F1 inoculated C57BL/6J mice FIG. 37).

These data indicate that Fve induces some protection against the solid EL4 tumor and B16-F1 melanoma, suggesting that Fve could be a potential candidate molecule for the development of the immunotherapeutic reagents for treatment of some cancers. The results also show that DNA vaccine-mediated treatment using the gene of Fve can be further exploited for effective cancer treatment. Nowadays, DNA vaccination is being explored as a potential strategy for combating cancer. However, tumor antigens are often weak and the immune system of patients may be compromised. Like the concept of allergen-Fve fusion protein, fusion of Fve to specific tumor antigen may an effective way to activate protective anti-tumor immune response. Genetic immunization with chemeric gene encoding Fve and tumor antigen may augment and direct immune attack on a range of target tumor antigens.

Example 22

Life Span in Solid Tumor Model is Extended in Fve Transfectant

In previous study, we have proved that using Fve plasmid DNA primed in muscle and Fve protein boosted in tumor region could initiate anti-tumor immune response and thus prolong the survival time of tumor-inoculated mice. Instead of injection Fve surrounding the tumor, we specifically targeted Fve gene into tumor cells and tried to create an inducible-antigenic tumor for cancer therapy. This genetically modified tumor cells may provide signals for antigen presenting cells and both helper and cytotoxic T cells.

To determine whether introduction of the Fve gene into malignant cells would result in enhanced tumor recognition ability via Fve display and lead to extended survival rate in solid tumor experiment. Recombinant plasmid DNA pDisplay-fve is transfected into wild type B16-F1 mouse melanoma and then G418 resistant colonies are selected. Five female of C57BL/6J mice are inoculated with $5\times10^4$ of B16-Fve transfectant. The antigenicity of B16-vec and B16-Fve transfectants are compared through the life span of two groups of tumor-inoculated mice.

Result demonstrated that artificially expressed Fve on the surface of B16-F1 mouse melanoma extended survival rate as compared to B16-vec inoculated mice (FIG. 38). We propose that the characteristics of highly antigenecity and lymphocytes mitogenecity of Fve may elevate immune function to fight against tumor when it displayed on the surface of melanoma. Therefore, Fve may use as immune response activator and enhancer especially for those poorly recognized and low immunogenic tumor, which escaped from cancer surveillance and immune clearance by altering immune recognition and modulating cytotoxic response.

Example 23

Fve DNA Vaccination Retards Tumor Progression

Cancer vaccines are designed to prevent and treat cancer. In general, research has shown that the most effective anti-tumor immune responses are achieved by stimulating T cells, which can recognize and kill tumor cells directly. Most current cancer vaccines try to activate T cells directly, try to enlist APCs to activate T cells, or both. Some novel ways in which researchers are attempting to better activate T cells are: (1) Altering tumor cells so molecules that are normally only express on APCs are now express on the tumor cell. These molecules are capable of giving T cells a stronger activating signal than the original tumor cells. (2) Testing more cytokines and adjuvants to determine which are best candidates for recruiting APCs to areas where they are needed. (3) Using dendritic cells and other APCs fused with tumor cells as the cancer vaccines. These cells go into the body carrying tumor antigen and ready to activate T cells. Early cancer vaccine clinical trials involved mainly patients with melanoma. Currently, cancer vaccines are also being tested in the treatment of many other types of cancer, including prostate cancer, breast cancer, colon cancer, and lymphoma.

Here, we accessed tumor immunity that stimulated by recombinant Fve DNA vaccination alone and the combination of Fve DNA vaccination and Fve-transduced tumor cells. C57BL/6J mice are separated into three groups and each group consisted of ten mice. Mice are inoculated either with $5\times10^4$ of B16-Fve or B16-vec tumor transfectants in the dorsal back. Tumor formation is observed at day 5-7. 100 μg of pCIneo-fve plasmid DNA is intramuscularly injected at the right and left tribilis muscle of C57BL/6J at day-77, day-35 and day-21. Mice are subcutaneously injected with $5\times10^4$ of B16-Fve transfectant and B16-vec transfectant at day 0, respectively. 100 μg of pCIneo plasmid DNA is administered following similar experimental procedure and mice are subcutaneously injected with $5\times10^4$ of B16-vec transfectant as negative control. The fatal rate of mice are recorded and data are presented as survival curves.

Result showed that Fve DNA vaccination contained certain degree of tumor protection (Green line in FIG. 39) as compared with vector DNA vaccination (Blue line in FIG. 39). In addition, the combination of Fve DNA vaccination and B16-Fve transfectant exerted a stronger tumor protection effect (Red line in FIG. 39). Based on the result, we propose Fve is a novel protein to activate T cells directly. This protein is capable of giving T cells a strong activating signal when it is displayed on the surface of poorly immunogenic tumor cells. Therefore, the phenomenon of extended survival rate is observed in the experimental tumor-inoculated mice.

In future, the adjuvant effect of fusion proteins between Fve and tumor antigens to enhance tumor immunity will be determined. In particular, DNA fusion vaccine strategy, whereby target tumor antigen is genetically linked to immunostimulatory molecules such as Fve, is currently being explored. The introduction of fusion gene encoding tumor-associated antigen with Fve into antigen-presenting cells hold considerable promise for the treatment of patients with cancer. The ease of DNA manipulation has allowed incorporation of a wide variety of molecules able to promote antigen uptake, processing and presentation by professional antigen-presenting cells, to provide critical $CD4^+$ T-cell help and to activate more effective immune effector pathways (Zhu and Stevenson 2002). The concept of DNA fusion vaccine strategy is particularly important for cancer vaccines to increase their immunogenicity and to overcome tolerance.

Example 24

Fve Extends the Survival Rate of Lung Metastatic Mice $2\times10^4$ of B16-F1 melanoma cells is delivered to C57BL/6J via tail vein injection. The effect of combination of distill water and DNA vector pCIneo versus Fve protein and plasmid DNA pCIneo-fve administration on survival after the establishment of lung metastasis is determined. Survival extended in both metastatic experimental groups undergoing Fve protein orally primed and DNA intramuscularly boosted strategy.

Two groups of five C57BL/6J mice are given with 10 mg/ml of Fve protein in the drinking water at days-35, -28 and -21, and each water providing is maintained consecutively for one week. Mice are intravenously injected with $2\times10^4$ of B16-F1 (wild type) melanoma cells at day 0. One week after, mice are intramuscularly injected with 100 μg of pCIneo-fve plasmid DNA into the right and left tribilis muscle, respectively. The mixture of $5\times10^4$ of B16-Fve cells lysate plus 10

μg of Fve protein (Red line in FIG. 40) or 10 μg of Fve protein alone (Green line in FIG. 40) are subcutaneously injected into mice at the following three weeks. Negative control group of mice received same amount of 1× PBS in the drinking water, intravenously injected with $2\times10^4$ of B16-F1 melanoma cells, followed by intramuscularly injected with plasmid DNA vector pCIneo, and finally subcutaneously injected with B16-vec cells lysate plus 1× PBS (Blue line in FIG. 40).

Results showed that the strategy of orally primed with Fve protein before tumor introduced into the lung and intramuscularly boosted the immune response with the plasmid DNA pCIneo-fve after tumor established in lung could extend the survival rate of mice as compared with the control group (FIG. 40). This data provided another evidence suggesting Fve could augment anti-tumor immune response against developing or metastatic tumor cells. The inhibition of B16-F1 melanoma experimental lung metastasis by Fve may go through induction of IFN-γ, TNF-α and activation of anti-tumor host mechanisms. IFN-$\gamma^{-/-}$ and TNF-$\alpha^{-/-}$ gene knockout mice and in vivo depletions of $CD4^+$, $CD8^+$, or $NK1.1^+$ cells may provide supportive evidence to this phenomenon.

Example 25

Global Gene Expression Profiling of Human T Cells and NK Cells After Activation with Fve The invention of microarray technology allows the simultaneous monitoring of the transcriptional behavior of thousands of genes. This technology has been repeatedly shown to be useful in the analysis of the response of a variety of cellular systems to stimuli, in the classification of human cancer, and in the analysis of animal models of human disease (Churchill 2002; Slonim 2002; van Berkum and Holstege, 2001). To characterize the transcriptional profile of Fve, we analyzed gene expression patterns in T and NK cells from either healthy donor or human cell lines stimulation with Fve by using oligonucleotide microarrays and compared them with gene expression patterns in non-stimulation cells. In future, protein microarray assays would also be used to study protein-protein interactions on a genome-wide scale (Templin et al., 2002; Zhu et al., 2001).

Materials and Methods

Cells Collection and Total RNA Purification

Peripheral blood mononuclear cells (PBMC) are collected from healthy donors. CD8-positive T lymphocytes and natural killer cells isolation are performed by immunomagnetic bead selection with monoclonal mouse anti-human CD8 antibodies and monoclonal mouse anti-human CD56 antibodies using the AutoMACS automated separation system (Miltenyi-Biotec, Germany). CD8-positive T cells and CD56-positive natural killer cells purity of more than 94% and 88% homogeneity are confirmed by two-color flow cytometry using $CD3^+/CD8^+$ and $CD56^+$ criteria (Becton Dickinson, USA). Human T cell lines (Jurkat T cell, MOLT-4) and NK cell line (NK-92) are grown as recommended (ATCC, USA). Cells are stimulated with Fve and total RNA is isolated with RNeasy Mini Kit (Qiagen, Germany) after 2 and 48 hours, respectively.

Preparation of Labeled Complementary RNA and Hybridization to High-Density Microarray Double-stranded complementary DNA (cDNA) and biotinylated complementary RNA (cRNA) are synthesized from total RNA and hybridized to human GeneChip microarray (Affymetrix, USA), which are washed and scanned according to procedures developed by the manufacturer. The arrays are scanned using laser scanner and visualized using Affymetrix 3.3 software (Affymetrix).

GeneChip Data Analysis

Differentially expressed genes are analysed by functional assays

Example 25A

Th1 Adjuvant Effect of Fve on HPV E7 Antigen

Th1 Adjuvant Effect of Fve on HPV E7 Antigen

Introduction

Fve protein, which is isolated from the fruit bodies of edible mushroom *Flammulina velutipes*, belongs to a new family of fungal immunomodulatory protein. Previous studies showed that Fve could stimulate gene expression of human IFN-γ, TNF-α, IL-1β, IL-2. In allergic murine model, mice treated with Der p 2 plus Fve showed a significant Der p 2-specific IgG2a production. Taken together, Fve may act as a strong adjuvant to drive immune responses toward Th1-type responses. Human papillomavirus (HPV) infection is a major cause of cervical cancer worldwide. The HPV oncogenic proteins, E6 and E7 are required for tumorigenesis and maintenance of tumor state. Clinical study found that E7-specific immune responses are detected in cervical cancer patient, suggesting that E7 could be a specific target for immunotherapy against HPV-derived cervical cancer. In this animal study, we demonstrated that the production of HPV E7-specific IgG1 and IgG2a is greatly enhanced when E7 is co-administrated injection with the fungal immunomoodulatory protein Fve. Result suggests that Fve can be used as a potent adjuvant for viral vaccines development Materials And Methods 1. Construction of Plasmid DNA pGEX-4T1-E7

The DNA fragment encoding E7 of HPV type 16 is subcloned into pGEX-4T1 protein expression vector. E7 DNA fragment is amplified by polymerase chain reaction (PCR) using a set of primers: 5'-TTGTTGGATCCCATGGAGATACACCTACATTG-3' (SEQ ID NO: 3) and 5'-TTACTGAATTCTTATGGTTTCTGAGAACAGATG-3' (SEQ ID NO: 4). The amplified DNA is digested with BamH1 and EcoR1, and the resulting fragment is then cloned into the BamH1 and EcoR1 sites of pGEX-4T1 vector. The presence of the inserted E7 is confirmed by and restriction enzyme digestion and gel electrophoresis. The accuracy of the constructs is further confirmed by DNA sequencing. The plasmid construct is transformed into Escherichia coli TG-1 for protein expression.

2. Expression and Purification of Recombinant GST-E7 Protein

E7 is expressed as GST-fusions protein from pEGX-4T1 (Invitrogen, CA, USA). Small scale of pGEX4T1-E7 transformed TG1 bacteria is seeded in LB medium. The overnight culture is transferred to 1L of LB medium containing ampicillin (100 μg/ml) in 1 in 40 proportion and grown at 37. C with 250 rpm vigorous shaking until the $OD_{600}$ reach to 0.6-0.8 (approximately 2-3 hours). The recombinant protein is induced by 0.1 mM isopropyl-β-D-thiogalactopyranoside (Gold Biotechnology, Missouri, USA) at final concentration and further incubation of 4-6 hours at 35. C with 200 rpm shaking. Cells are harvested by centrifugation at 6000 rpm for 10 minutes and the pellets are used for protein extraction. The pellets of E7 transformed bacteria are resuspended in 250 ml ice-cold lysis buffer (1× TBS pH 7.5, 1 mM PMSF (Sigma, Missouri, USA), 20 μg/ml DNase I and 1% Tween 20). The cell suspension is then sonicated at 4. C for 50 seconds, 18 cycles with 30 seconds intervals. Total cell lysate is centrifuged at 16000 rpm for 25 min, 4. C and the supernatant is collected for further affinity purification on glutathione agarose beads. Glutathione agarose beads (Sigma, Missouri, USA) is dispensed into a chromatography column and then washed with 1×TBS (pH 7.5). Supernatant from the total cell lysate is then loaded onto the column and subsequently washed with 1× TBS. GST-E7 is eluted with elution buffer (Glutathione 0.15 g, Tris-base in a total volume of 50 ml $dH_2O$) and then analyzed by SDS-PAGE. Pure fractions of GST-E7 protein are pooled together and cleaved with thrombin. Purified E7 is dialyzed against 1× PBS (pH 7.4) and used in further studies.

3. Isolation and Purification of Fve Protein from *Flammulina velutipes*

Two kilo grams of *Flammulina velutipes* (Golden needle mushroom) is purchased from Taiwan. The fresh fruit bodies of mushroom are homogenized with 2 L 5% acetic acid (v/v) in the presence of 0.1% (v/v) 2-mercaptoetheanol. The homogenate are centrifuged for 20 min and soluble proteins in the supernatant are precipitated by addition of ammonium sulphate to 95% saturation. After stirring for an overnight, the precipitates are collected by centrifuge for 20 min again. The pellets are dialyzed against 4.5 L of 10 mM Tris/HCl (PH 8.0) at 4° C. for 4 days with 9 changes of dialysis solution. The dialysate is firstly applied to Q column which is previously equilibrated with 10 mM Tris/HCl (PH 8.0). The flowthrough factions are then further purified by application to SP column which is previously equilibrated with 10 mM sodium acetate (PH 5.0). The column is first washed with 10 mM equilibration buffer and then eluted with a linear gradient of 0-1 M NaCl in 10 mM sodium acetate (PH 5.0). The fractions are then further purified on a Q column (PH 8.0) and SP column (PH 5.0). After purification, we combined them and dialyzed with 2 L 10 mM PBS (PH 7.4), then stores Fve protein at −20° C.

4. SDS-PAGE and Western Blot

Purified Fve and E7 are run in a 7.5% Tricine SDS-PAGE. After electrophoresis has completed, the proteins in the gel are stained with Coomassie plus Reagent (Pierce, IL, USA). For western blotting, the proteins are transfer from the gel to a bio-blot nitrocellulose membrane and probed with either Fve polyclonal antibody or E7 monoclonal antibody (Southern Biotechnology, USA).

5. Mice

Female C57BL/6 mice are purchased from the Laboratory Animal Center (Sembawang, Singapore) and kept in the National University of Singapore (NUS) Animal Holding Unit. All animal procedures are performed according to approved protocols and in accordance with the Institutional Guidelines for Animal Care and Handling, NUS.

6. Protein Immunization of Mice

Two groups of eight-to ten-week-old female C57BL/6 mice (5 mice per group) are injected subcutaneously at the tail base with 10 μg of E7 alone or combination with 10 μg of Fve in a final volume of 100 μg of PBS at day 1. Mice are boosted with 20 μg of E7 alone or mixture with 20 μg of Fve at day 14 and day 28. Blood are collected weekly from the orbital sinus of the immunized mice and the collect sera are used for antibodies analysis using ELISA.

7. ELISA

In all ELISA experiments, samples are assayed in duplicates and 50 μg per well of reagents and samples are used. 96-well plates (Costar 9018, Corning, NY, USA) are incubated overnight at 4° C. with 5 μg/ml of purified E7 proteins in 0.1 M $NaHCO_3$, pH 8.3 coating buffer. Wells are washed three times with washing buffer TBST (0.05% Tween 20 (Sigma) in 1×(0.01 M) TBS, pH 7.4) using the automated Columbus washer (TECAN, Austria) and blocked with 100 μl/well of blocking buffer (1% BSA; bovine serum albumin in TBST) for 2 hours at room temperature. Plates are washed three times and diluted sera appropriately and incubated overnight at 4° C. For quantification and internal control purposes, known serial dilutions of purified mouse IgG1, IgG2a and ê light chain isotype standard (Pharmingen, California, USA) is used on wells coated with anti-mouse ê light chain (Pharmingen, California, USA).

Plates are again washed 6 times before adding biotin-conjugated anti-mouse isotypic antibodies IgG1, IgG2a (Southern Biotech, Alabamba, USA) at 1:1000 dilution are added. The plates are then incubated for 1 hour at room temperature, followed by 6 times washing and 1 hour incubation at room temperature with ExtrAvidin alkaline-phosphatase conjugate Sigma, Missouri USA). The plates are then washed 6 times and developed in paranitrophenyl phosphate (pNPP) substrate Sigma, Missouri USA) at room temperature in the dark. The binding of specific antibodies is measured as absorbance at 405 nm with the Sectra (Shell) reader TECAN, Austria). The antibody production units of antigen-specific antibodies are determined from the $OD_{405}$ using the plot of absorbance versus concentration of the standard.

Two groups of female BALB/cJ mice aged 6 to 8 weeks are given subcuteneous injection of either 10 μg of HPV E7 antigen alone (group 1) or mixture of 10 μg of E7 with 10 μg of Fve (group 2) at day 1. Mice are boosted with 20 μg of same antigen at day 14 and 28. Sera are collected weekly and E7-specific IgG1and IgG2a antibodies are analyzed using Elisa.

A schematic protocol of the animal study is shown in FIG. 40B.

Results

Combinations of E7 and Fve Enhance E7-Specific Immune Response

The results are shown in FIG. 40C. These results show that the production of E7-specific IgG1and IgG2a are dramatically increased when E7 is co-administrated injection with Fve, as compared with E7 alone. The induction of IgG2a is 17-fold higher in the experimental mice as compare with the control group. This demonstrates that Fve displays an adjuvant effect and therefore enhance specific immune response to viral antigen. Co-administration of fungal immunomodulatory protein Fve and viral antigen HPV E7 increases the production of neutralizing antibodies.

Example 26

X-Ray Crystallographic Study of Fve: Materials and Methods

The three dimensional structural of Fve provides a good basis for the understanding of protein functions, immunomodulations and therapeutic applications in allergy and other diseases. We have crystallized the well-diffracting crystals of Fve and show that it diffracts to 1.4 Å resolution when exposed to synchrotron radiation.

This and the follwing Examples describe a 1.6 A° x-ray structure of Fve, determined by Single Anomalous Diffraction (SAD) using the anomalous signal of bromide ions present in the crystal for phasing. Fve represents a novel structure, wherein each monomer consists of an N-terminal α-helix followed by an immunoglobulin fold (beta-sandwich). The structure strongly suggests that dimerization, critical for the activity of FIP proteins, occurs by 3-D domain swapping of these helices and is stabilized predominantly by strong hydrophobic interactions between them.

Crystallization

Fve protein is obtained as described above. It is concentrated to 4 mg/ml in 10 mM Tris-HCl pH 7.5. Initial crystallization screening is done by the sparse matrix crystallization screening kit 1 & 2 from Hampton Research (Jancarik and Kim, 1991; Cudney, et al., 1994). All the screening and crystals growth are accomplished by hanging drops vapor diffusion method at 21° C. in VDX multi-well plates with 650 μl reservoir solutions. Drops consisting of 4 μl precipitant buffer from reservoirs and 4 μl protein sample (4 mg/ml) are equilibrated over the well solution for one week.

After extensive screening, plates-like crystals are obtained at two different low salt conditions: (1) 30% PEG 4000, 0.1 M Tris-HCl pH 8.5, 0.2 M $MgCl_2$; (2) 30% PEG 4000, 0.1 M Tris-HCl pH 8.5, 0.2 M NaOAc. 3D cubic-shaped and octahedral crystals also appeared after 3 days at two different high salt conditions: (1) 2.0 M $(NH_4)_2SO_4$, 0.1 M Tris-HCl pH 8.5; (2) 2% PEG 400; 0.1 M Na Hepes pH 7.5, 2.0 M $(NH_4)_2SO_4$. To optimize the crystallization condition, combinations of varied protein and salt concentrations, different molecular weights of PEG, and different pH are screened.

The best crystals formed at the high salt condition is optimized to 2.5% PEG 400, 2.0 M $(NH_4)_2SO_4$, 0.1 M Tris-HCl pH 8.5 at 21° C. They grew to the approximate dimensions of 1.0×0.9×0.5 nm within five days. The micrographs of Fve crystals are captured by inverted light microscope (FIG. 41).

High resolution protein crystals are therefore grown by vapor diffusion from hanging drop at 2.0% PEG 400, 2.0 M $(NH_4)_2SO_4$, 0.1 M Tris-Base, pH 8.5 for 1-2 weeks. Heavy atom derivatives are prepared by soaking the crystals in mother liquor containing 25% glycerol and 1M NaBr. The crystals are flash-frozen at 100 K after a 1-min soak in the heavy atom (Br) solution. SAD data from a derivatized crystal are collected at the National Synchrotron Light Source (NSLS) beam line X12C) at one wavelength (***) around the Br absorption edge. The crystal diffracted to 1.7 Å.

X-Ray Analysis

The X-ray diffraction intensities from Fve crystals are measured at 100 K on beamline BL9-2 from the Stanford Synchrotron Radiation Laboratory facility with ADSC Quantum-315 CCD detector. Data are collected at a wavelength of 1.07 Å. All the data are processed by MOSFLM (Leslie, 1992) and X-ray intensities are scaled with SCALA (CCP4, 1994). Well-ordered diffraction data at 1.4 Å resolution are collected from larger crystals (FIG. 42).

Analysis of the collected data (Table 9) indicated that Fve crystals belong to the tetragonal space group $P4_32_12$ with unit cell dimensions of a=b=96.92 Å, c=61.42 Å. The Matthews parameter ($V_M$) of these crystals is 2.84 $Å^3$ per Da and thus the solvent content is 56.37% assuming two molecules of Fve per asymmetric unit (Matthews, 1968). A total of 344079 observations are obtained at 1.4 Å resolution giving approximate 56993 unique reflections (99.7% complete, $R_{merge}$=0.047).

TABLE 9

| Data Collection and Statistics of Fve Crystal | |
|---|---|
| X-ray source, beamline | SSRL, BL9-2 |
| Wavelength | 1.07 Å |
| Detector distance | 99.97 mm, Q-315 CCD Detector |
| Cell angles (°) | 90.00, 90.00, 90.00 |
| Unit cell dimensions (Å) | 96.92, 96.92, 61.42 |
| Space group | $P4_32_12$ |
| Number of molecules per ASU | 2 |
| Number of observed reflections | 344079 |
| Number of unique reflections | 56993 |
| Solvent (%) | 56.37 |
| $V_M$ ($Å^3Da^{-1}$) | 2.84 |
| Resolution range (Å) | 33.5-1.4 |
| Average I/σ(I) | 10.1 |
| $R_{merge}^a$ | 0.047 |
| Completeness (%) | 99.7 |

[a]$R_{merge}$ = $|I_i - \langle I\rangle|/I_i$, where $I_i$ is the mean intensity of symmetry-related measurements of this reflection.

Data Processing

The SAD data are processed and scaled using DENZO and SCALEPACK from the HKL2000 suite of programs (Otwinowski and Minor, 1997).

The crystal of Fve belongs to the tetragonal space group P43212 and has unit cell dimensions a=b=97.12, c=61.41 and α=β=γ=90.0. All of the bromine heavy atom positions are located and refined by the program SOLVE at 1.7 Å (Terwilliger and Berendzen, 1999) and solvent flattened map is calculated using RESOLVE (Terwilliger, 2001). The resulting electron density map reveals secondary structure elements and side chains. In principle, it is possible to build an initial model by standard protein map-tracing methods. However, the phases obtained from RESOLVE are directly used in ARP/wARP (Morris et al., 2001) for automated main chains tracing, result in 4 continuous fragments that contained 97% of model. The rest of the model and side chains are fitted manually using XtalView (McRee, 1999). The refinement is carried out in REFMAC 5 (Murshudov et al., 1999) using resolution range 30.02-1.7 and water molecules are picked up by ARP/WARP later in the refinement.

In chain A, C-terminal residue 114 is modeled as Ala residue, whereas in chain B, C-terminal residue 113 and 114 are omitted from the final model, due to the poor interpretable density. The quality of the final model is verified with PROCHECK (Laskowski et al., 1993). However, the Ramachandran plot shows that Lys 14 in both A and B chains is in the disallowed region, although this residue fits very well in the 2fo-fc map.

Example 27

X-Ray Crystallographic Study of Fve: Results

The crystal structure is solved by single anomalous scattering using Br as the heavy-atom, and is refined to a resolution of 1.7. The atomic coordinates are presented in Appendix C.

In total, two chains with a total of 226 residues, 16 bromine atoms and 136 solvent molecules are built into a high quality electron density map. Fve comprises almost exclusively of β-sheet structure with an Ig-like fold, which is formed by seven major antiparallel β-strands arranged into two sheets of four (D, E, H and I) and three (B, C and F) strands packed again each other. The N-terminal domain is composed of a α-helix which spans a length of 12 residues from Ala2 to Val13 and a β-sheet (A). The N-terminal serine residue is blocked by an acetyl group the density of which is also observed. Six loops connect the two main β-sheets and one loop connects the N-terminal domain with β-sheet structure. The loop between the β-sheets F and H contains a short β-strand and a $3_{10}$ helix.

The structure of Fve (FIG. 43) reveals that exists as a dimer. This is corroborated experimentally by running Fve on a gel filtration column against standard molecular weight markers (data not shown). From the structure, there are two extended regions of subunit-subunit interactions: between the two N-terminal α-helical regions (residues 2 to 13) and the β-stranded region (A and A').

Figure 44A:
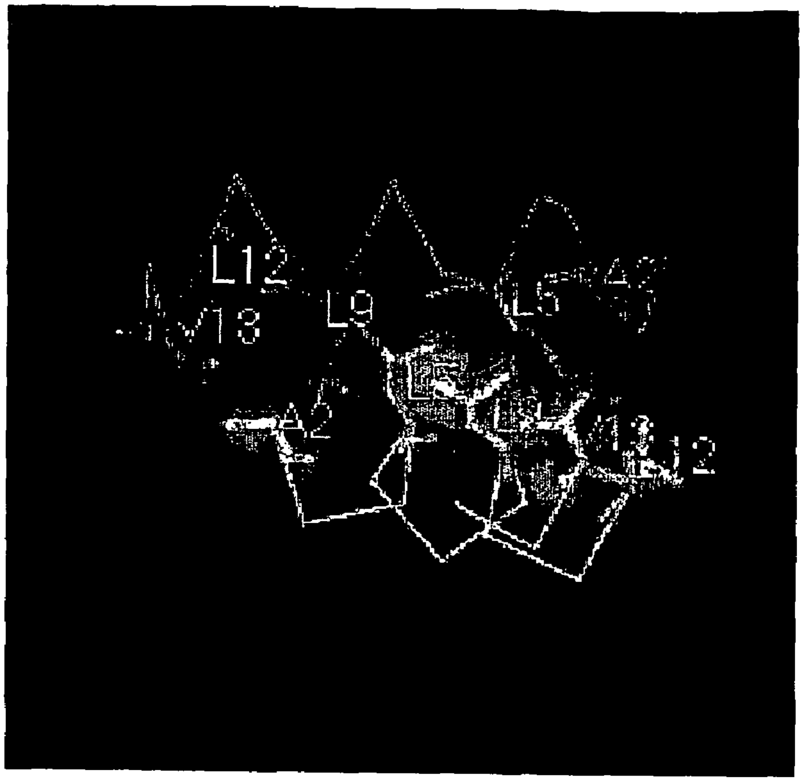
Figure 44B:
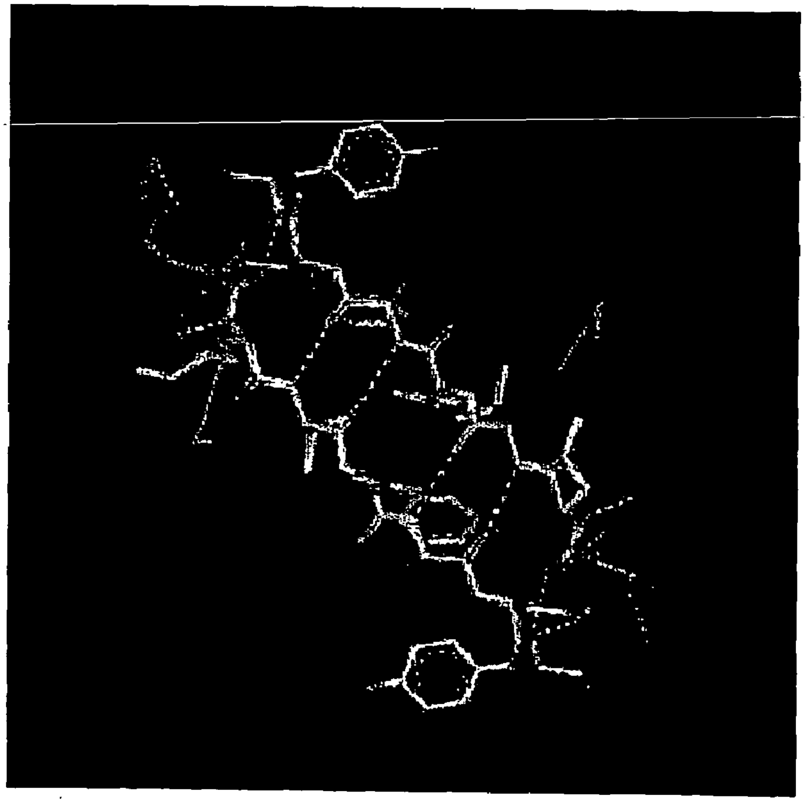
Figure 44C:
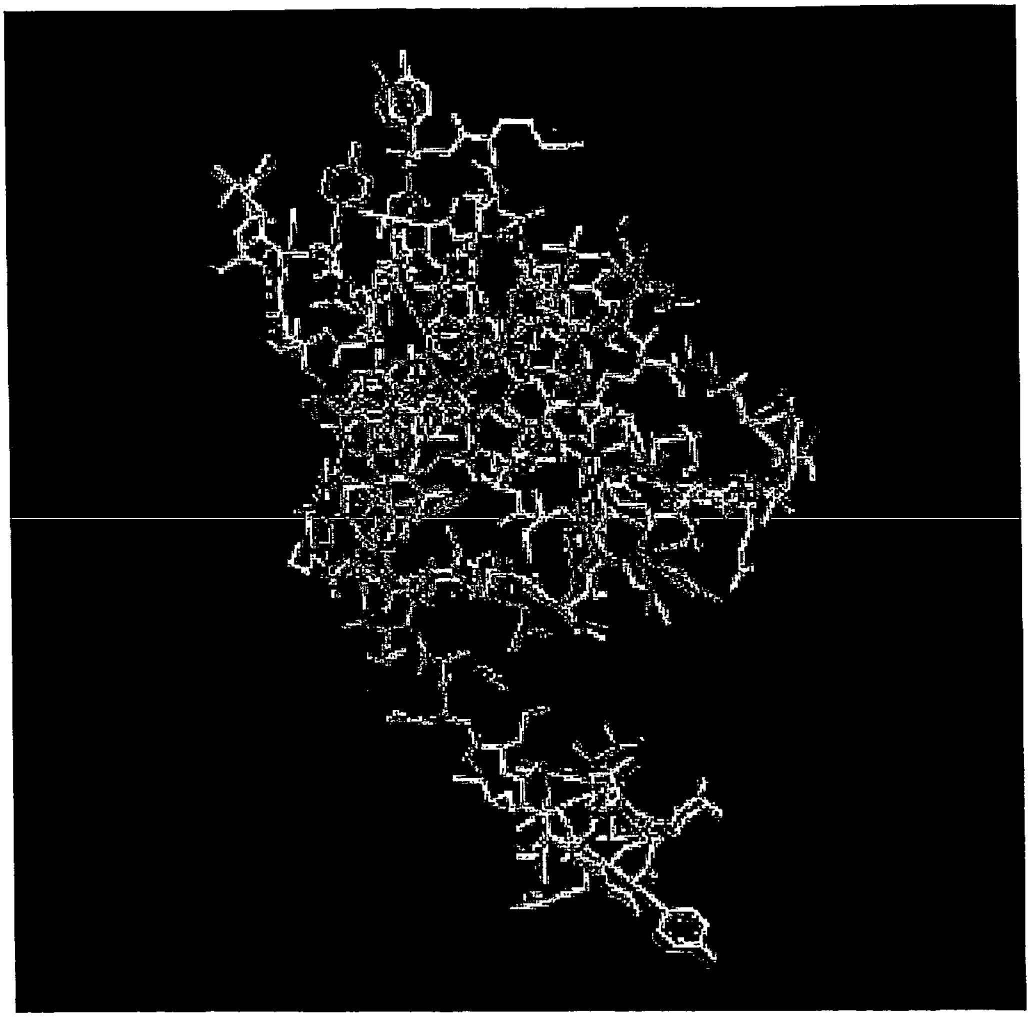

The buried side chains of the α-helical regions form a hydrophobic core (FIG. 44A), containing residues Ala 2, Leu 5, Leu 9 and Val 13 whereas the side chains of β-strand (A and A') make inter-subunit hydrogen bonds (FIG. 44B). These hydrophobic interactions and hydrogen bonds are responsible for dimer formation. The two monomers, A and B chains, of Fve can be closely superimposed: the RMSD between corresponding $C_\alpha$positions of 112 residues is 0.29 Å (FIG. 44C).

Domain Swapping

Domain swapping is a very efficient method of forming oligomers since the interactions within the monomer are reused in the dimer. There is thus no need to evolve a new site on the surface which in one monomer mutually recognizes the corresponding site on the other monomer, since in the domain swapped dimer the recognition requirement has already largely been accounted for (Bennett et al., 1995).

Domain-swapped proteins have a C-interface generally with many specifics interaction, formed between domains linked by a hinge loop (Bennett et al., 1995). In p13suc1, two proline residues, located in the hinge region, have been shown to be essential and control the domain-swapping process (Rousseau et al., 2001).

Figures 45A, 45B:
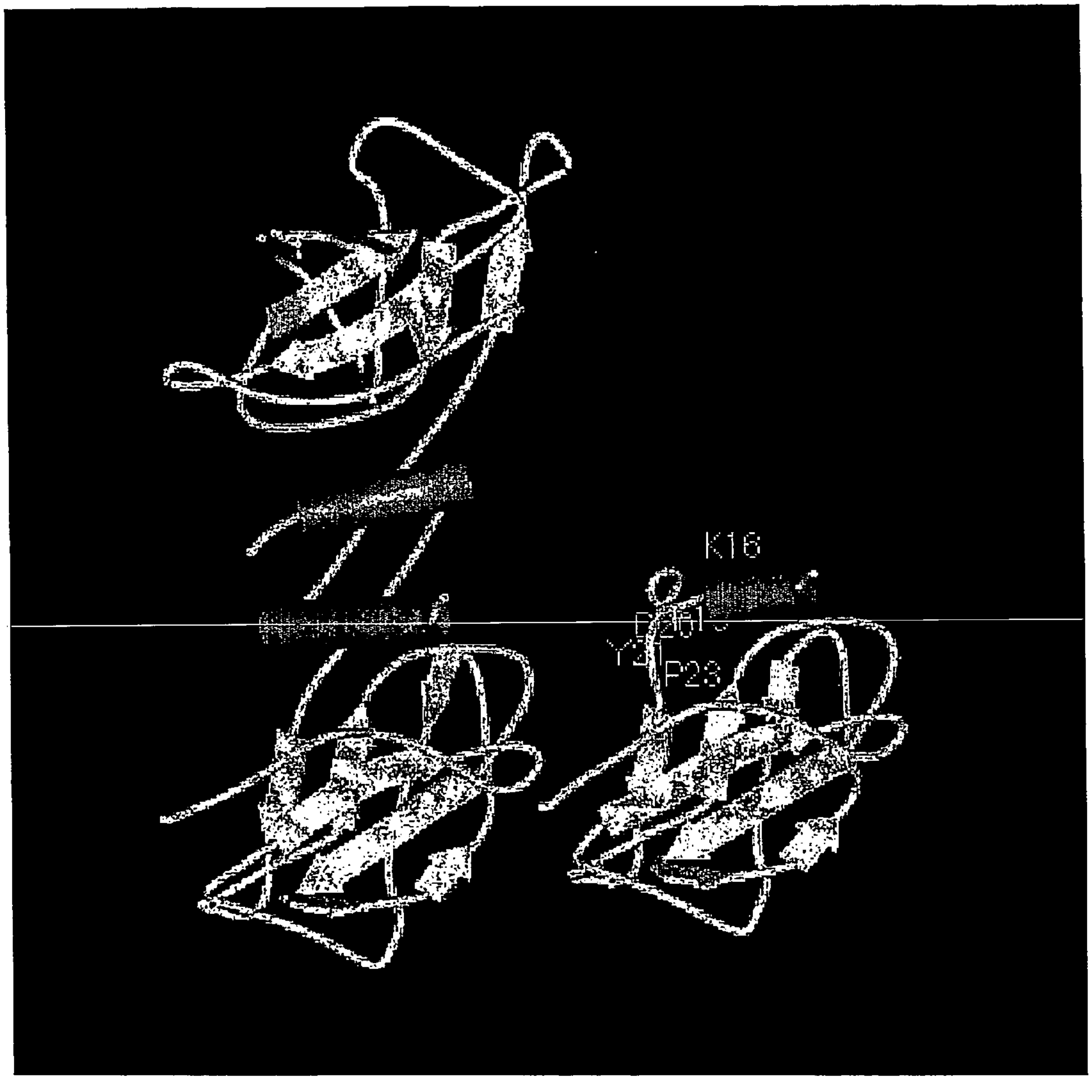

As shown in FIG. 45A, half of the dimer of Fve contains one N-terminal helix, forming a C-interface with hydrophobic core, which is linked to rest of its subunit by a hinge loop, stretching from residue Val 13 to Pro 22. Furthermore, Fve contains a proline residue at the end of the hinge region, which could adopt alternative conformation in the dimer by releasing the tension in the monomer. These observations suggest that domain-swapping swapping could be the mechanism for forming dimer protein from its monomer. The monomer is modeled (FIG. 45B).

Structural Similarity with Other Proteins

Fve has no sequence homology to any other non-FIP proteins. However, a search for similar structure in the DALI database (Holm and Sander, 1993) reveals that the protein has a significantly similar fold to 140 proteins but none with the significant sequence similarity to Fve. Among 140 similar fold protein, fibronectin type III family emerged with less topology diversity to Fve β-sandwich fold: the heparin and integrin binding segment of human fibronectin (FN12-15; PDB entry 1FNH), the fragment of human fibronectin type III repeat (FN7-10; 1FNF), The p40 domain of human interlukin-12 (p40; 1F42) and the antibody a6 fragment interferon-gamma receptor alpha chain (IFNγR1-108; 1JRH). An alignment of FN12-15, FN7-10, p40, IFNγR1-108 and Fve on the basis of structural similarity shows topology diversity in the range 11-17, calculated by Topp program (Lu, 1996) (Table 10).

TABLE 10

| | Name | PDB ID | Z-Score | RM SD | Length of aligned segment | Topological Diversity | Superfamily (Family) | Species |
|---|---|---|---|---|---|---|---|---|
| 1 | interleukin-4 receptor alpha chain fragment: b:1-96 | 1iar-B | 5.8 | 3 | 78 | 8.5 | Fn III (FNIII) | *Homo sapiens* |
| 2 | mhc class ii i-ak: a:82-181 | 1iak-A | 5.8 | 4.7 | 83 | 18.6 | Ig (C1) | *Mus musculus* |
| 3 | mhc class ii i-ak: b:93-190 | 1iak-B | 5.6 | 3.5 | 74 | 17.8 | Ig (C1) | *Mus musculus* |
| 4 | igg2a intact antibody - mab23, kappa L chain: a:1-108 | 1igt-B | 5.5 | 3.8 | 86 | 18.4 | Ig (V) | *Mus musculus* |
| 5 | class ii histocompatibility antigen, HLA-DM: a:94-196 | 1hdm-B | 5.3 | 4.7 | 82 | 18.4 | Ig (C1) | *Homo sapiens* |
| 6 | fibronectin fragment, heparin & integrin binding segment: a:93-182 | 1fnh-A | 5.3 | 3 | 73 | 11.1 | Fn III (FNIII) | *Homo sapiens* |
| 7 | ch3 domain of mak33 antibody fragment: chain a | 1cqk-A | 5.3 | 3.3 | 76 | 18.5 | Ig (C1) | *Mus musculus* |
| 8 | CD1, beta2-microglobulin and alpha-3 domain:d | 1cid | 5.3 | 2.8 | 76 | 17.8 | Ig (V) | *Rattus rattus* |
| 9 | fibronectin fragment, ED-B domain: chain a | 2fnb-A | 5.2 | 3.9 | 72 | 17 | Fn III (FNIII) | *Homo sapiens* |
| 10 | hiv-1 gag peptide: a:182-276 | 1agd-A | 5.2 | 3.8 | 84 | 20.1 | Ig (C1) | *Homo sapiens* |
| 11 | iggl antibody 32c2 fragment: a:1-110 | 32c2-A | 5.1 | 5.6 | 80 | 19.4 | Ig (V) | *Mus musculus* |
| 12 | fibronectin repeat 7: 1142-1235 | 1fnf | 5.1 | 2.7 | 71 | 10.8 | Fn III (FNIII) | *Homo sapiens* |
| 13 | interleukin-12 beta chain fragment: a:88-211. | 1f42-A | 5.1 | 2.8 | 70 | 12.8 | Fn III (FNIII) | *Homo sapiens* |
| 14 | Mutant growth hormone receptor fragment: b:131-236 | 1axi-B | 5.1 | 3.2 | 72 | 14.7 | Fn III (FNIII) | *Homo sapiens* |

REFERFENCES

Akbari O, Freeman G J, Meyer E H, Greenfield E A, Chang T T, Sharpe A H, Berry G, DeKruyff R H, and Umetsu D T. (2002) Antigen-specific regulatory T cells develop via the ICOS-ICOS-ligand pathway and inhibit allergen-induced airway hyperreactivity. Nat. Med. 8:1024-1032.

Arkwright P D and David T J. (2001) Intradermal administration of a killed *Mycobacterium vaccae* suspension (SRL 172) is associated with improvement in atopic dermatitis in children with moderate-to-severe disease. J. Allergy Clin. Immunol. 107:531-534.

Banos, V., Gomez, J., Garcia, A., Ruiz, J., Alvarez, R., Lorenzo, M., Canteras, M., and Valdes, M. (1997) Effectiveness of immunomodulating treatment (thymostimulin) in chronic obstructive pulmonary disease. *Respiration.* 64, 220-223.

Bennett, M. J., Schlunegger, M. P. & Eisenberg, D. 3D domain swapping—a mechanism for oligomer assembly, *Protein Science,* 4, 2455-2468, (1995).

Bonde, J., Dahl, R., Edelstein, R., Kok-Jensen, A., Lazer, L., Punakivi, L., Seppala, A., Soes-Petersen, U., and Viskum, K. (1986) The effect of RU 41.740, an immune modulating compound, in the prevention of acute exacerbations in patients with chronic bronchitis. *Eur. J. Respir. Dis.* 69, 235-241.

Braga, P. C., Dal Sasso, M., Maci, S., Piatti, G., Palmieri, R., Bruno, L., and Albanese, C. (1994) Restoration of polymorphonuclear leukocyte function in elderly subjects by thymomodulin. *J. Chemother.* 6, 354-359.

Chihara, G., Maeda, Y., Hamuro, J., Sasaki, T., and Fukuoka, F. (1969) Inhibition of mouse sarcoma 180 by polysaccharide from *Lentinus edodes* (Berk) sing. *Nature.* 222, 687-688.

Churchill G A. (2002) Fundamentals of experimental design for cDNA microarrays. Nat. Genet. 32 Suppl 2:490-495. Collaborative Computational Computor Project 4. (1994) The CCP4 suite: programs for protein crystallography. *Acta Crystallogr.* D50, 760-763.

Cross M L and Gill H S. (2001) Can immunoregulatory Lactic acid bacteria be used as dietary supplements to Limit Allergies? lit. Arch. Allergy Immunol. 125:112-119.

Cudney, B., Patel, S., Weisgraber, K., and Newhouse, Y. (1994) Screening and optimization strategies for macromolecular crystal growth. *Acta Crystallogr.* D50, 414-423.

Daniell H, Streatfield S J, and Wycoff K. (2001) Medical molecular farming: production of antibodies, biopharmaceuticals and edible vaccines in plants. Trends Plant Sci. 6:219-226.

Darji A, Guzman C A, Gerstel B, Wachholz P, Timmis K N, Wehland J, Chakraborty T, and Weiss S. (1997) Oral somatic transgene vaccination using attenuated *S. typhimurium.* Cell 91:765-775.

Donnelly J J, Ulmer J B, Shiver J W, and Liu M A. (1997) DNA vaccines. Annu. Rev. Immunol. 15:617-648.

During M Y, Symes C W, Lawlor P A, Lin J, Dunning J, Fitzsimons H L, Poulsen D, Leone P, Xu R, Dicker B L, Lipski J, and Young D. (2000) An oral vaccine against NMDAR1 with efficacy in experimental stroke and epilepsy. Science 287:1453-1460.

Erbacher, P., Zou, S., Bettinger, T., Steffan, A. M. & Remy, J. S. Chitosan-based vector/DNA complexes for gene delivery: biophysical characteristics and transfection ability. *Pharm. Res.* 15: 1332-1339, 1998.

Eriksson K and Holmgren J. (2002) Recent advances in mucosal vaccines and adjuvants. Curr. Opin. Immunol. 14:666-672.

Federico, M., Gobbi, P. G., Moretti, G., Avanzini, P., Di Renzo, N., Cavanna, L., Ascari, E., and Silingardi, V. (1995) Effects of thymostimulin with combination chemotherapy in patients with aggressive non-Hodgkin's lymphoma. A report from the Italian Lymphoma Study Group (GISL). *Am. J. Clin. Oncol.* 18, 8-14.

Fenske D B, MacLachlan I, and Cullis P R. (2002) Stabilized plasmid-lipid particles: a systemic gene therapy vector. Methods Enzymol. 346:36-71.

Fischer R and Emans N. (2000) Molecular farming of pharmaceutical proteins. Transgenic Res. 9:279-99.

Fisher, M., and Yang, L. X. (2002) Anticancer effects and mechanisms of polysaccharide-K (PSK): implications of cancer immunotherapy. *Anticancer Res.* 22, 1737-1754.

Fujimiya, Y., Suzuki, Y., Katakura, R., and Ebina, T. (1999) Tumor-specific cytocidal and immunopotentiating effects of relatively low molecular weight products derived from the basidiomycete, *Agaricus blazei* Murill. *Anticancer Res.* 19, 113-118.

Giddings G, Allison G, Brooks D, and Carter A. (2000) Transgenic plants as factories for biopharmaceuticals. Nat. Biotechnol. 18:1151-1155.

Hirasawa, M., Shouji, N., Neta, T., Fukushima, K., and Takada, K. (1999) Three kinds of antibacterial substances from *Lentinus edodes* (Berk.) Sing. (Shiitake, an edible mushroom). *Int. J. Antimicrobial Agents.* 11, 151-157.

Holm, L & Sander, C. Protein structure comparison by alignment of distance matrices. *J. Mol. Biol.* 233, 123-138 (1993).

Holm, L & Sander, C. Protein structure comparison by alignment of distance matrices. *J. Mol. Biol.* 233, 123-138 (1993).

Hsu C H, Chua K Y, Tao M H, Lai Y L, Wu H D, Huang S K, and Hsieh K H. (1996) Immunoprophylaxis of allergen-induced immunoglobulin E synthesis and airway hyperresponsiveness in vivo by genetic immunization. Nat. Med. 2:540-544.

Hsu, H. C., Hsu, C. I., Lin, R. H., Kao, C. L., and Lin, J. Y. (1997) Fip-vvo, a new fungal immunomodulatory protein isolated from *Volvariella volvacea. Biochem. J.* 323, 557-565.

Iguchi, C., Nio, Y., Takeda, H., Yamasawa, K., Hirahara, N., Toga, T., Itakura, M., and Tamura, K. (2001) Plant polysaccharide PSK: cytostatic effects on growth and invasion; modulating effect on the expression of HLA and adhesion molecules on human gastric and colonic tumor cell surface. *Anticancer Res.* 21, 1007-1013.

Illum L, Jabbal-Gill I, Hinchcliffe M, Fisher A N, and Davis S S. (2001) Chitosan as a novel nasal delivery system for vaccines. Adv. Drug Deliv. Rev. 51:81-96.

Jahn-Schmid B, Graninger M, Glozik M, Kupcu S, Ebner C, Unger F M, Sleytr U B, and Messner P. (1996) Imunoreactivity of allergen (Bet v 1) conjugated to crystalline bacterial cell surface layers (S-layers). Immunotechnology 1996 2:103-113.

Jancarik, J., and Kim, S. H. (1991) Sparse matrix sampling: a screening method for crystallization of proteins. *J. Appl. Crystallogr.* 24, 409-411.

Johnson-Saliba M, and Jans D A. (2001) Gene therapy: optimising DNA delivery to the nucleus. Curr. Drug Targets 2:371-399.

Jones D H, Corris S, McDonald S, Clegg J C, and Farrar G H. (1997) Poly(DL-lactide-co-glycolide)-encapsulated plasmid DNA elicits systemic and mucosal antibody responses to encoded protein after oral administration. Vaccine 15:814-817.

Jong, et al. Immunomodulatory Substances of Fungal Origin, J. Immunol. Immunopharmacol., Vol. XI, No. 3, 1991. pp. 115-122.

Kakuta S, Tagawa Y, Shibata S, Nanno M, and Iwakura Y. (2002) Inhibition of B16 melanoma experimental metastasis by interferon-gamma through direct inhibition of cell proliferation and activation of antitumour host mechanisms. Immunology 105:92-100.

Kamat, A. M., and Lamm, D. L. (2001) Immunotherapy for bladder cancer. *Curr. Urol. Rep.* 2, 62-69.

Kas, H. S. Chitosan: properties, preparations and application to microparticulate systems. *J. Microencapsul.* 14: 689-711, 1997.

Kino, K., Yamashita, A., Yamaoka, K., Watanabe, J., Tanaka, S., Ko, K., Shimizu, K., and Tsunoo, H. (1989) Isolation and characterization of a new immunomodulatory protein, Ling Zhi-8 (LZ-8), from *Ganoderma lucidium, J. Biol. Chem.* 264, 472-478.

Klaenhammer T R. (1995) Genetics of intestinal lactobacilli. Int. Dairy J. 5:1019-1058.

Ko J L, Hsu C I, Lin R H, Kao C L, Lin J Y, A new fungal immunomodulatory protein, FIP-fve isolated from the edible mushroom, *Flammulina velutipes* and its complete amino acid sequence. *Eur. J. Biochem.* 228(2):244-9 (1995)

Ko, J. L., Lin, S. J., Hsu, C. I., Kao, C. L & Lin, J. Y. Molecular cloning and expression of a fungal immunomodulatory protein, FIP-fve, from *flammulina velutipes. J Forms Med Assoc.* 96, 517-524, (1997).

Komatsu, N., Okuto, S., Kikumoto, S., Kimura, K., Saito, G., and Sakai, S. (1969) Host mediated antitumor action of Schizophyllan, a glucan produced by Schizophyllaum commune. *Gann.* 60, 137-144.

Kong Q, Richter L, Yang Y F, Arntzen C J, Mason H S, and Thanavala Y. (2001) Oral immunization with hepatitis B surface antigen expressed in transgenic plants. Proc. Natl. Acad. Sci. USA 98:11539-11544.

Kraulis, P. J. A program to produce both detailed and schematic plots of protein. *J. Appl. Crystallogr.* 24, 946-950 (1991).

Krieg A M. (2000) The role of CpG motifs in innate immunity. Curr. Opin. Immunol. 12:35-43.

Krieg A M. (2002) A role for toll in autoimmunity. Nat. Immunol. 3: 423-424.

Kruger C, Hu Y, Pan Q, Marcotte H, Hultberg A, Delwar D, Van Dalen P J, Pouwels P H, Leer R J, Kelly C G, Van Dollenweerd C, Ma J K, and Hammarstrom L. (2002) In situ delivery of passive immunity by lactobacilli producing single-chain antibodies. Nat. Biotechnol. 20:702-706.

La Mantia, I., Grillo, C., Mattina, T., Zaccone, P., Xiang, M., Di Mauro, M., Meroni, P. L., and Nicoletti, F. (1999) Prophylaxis with the novel immunomodulator pidotimod reduces the frequency and severity of upper respiratory tract infections in children with Down's syndrome. *J. Chemother.* 11, 126-130.

Laskowski, R. A., MacArthur, M. W., Moss, D. S. & Thorton, J. M. PROCHECK: a program to check the stereochemical quality of protein structures. *J. Appl. Crystallogr.* 26, 283-290 (1993).

Leadbetter E A, Rifkin I R, Hohlbaum A M, Beaudette B C, Shlomchik M J, Marshak-Rothstein A. (2002) Chromatin-IgG complexes activate B cells by dual engagement of IgM and Toll-like receptors. Nature 416:603-607.

Leslie, A. G. W. (1992) Recent changes to the Mosflm package for processing film and image plate data. *Joint CCP4 and ESF-EACBM Newsletter on Protein Crystallography*. No. 26. SERC Daresbury Laboratory, Warrington, UK.

Liao, H. F., Chou, C. J., Wu, S. H., Khoo, K. H., Chen, C. F., and Wang, S. Y. (2001) Isolation and characterization of an active compound from black soybean [Glycine max (L.) Merr.] and its effect on proliferation and differentiation of human leukemic U937 cells. *Anticancer Drugs.* 12, 841-846.

Lin, W. H., Hung, C. H., Hsu, C. I., and Lin, J. Y. (1997) Dimerization of the N-terminal amphipathic α-helix domain of the fungal immunomodulatory protein from *Ganoderma tsugae* (Fip-gts) defined by a yeast two-hybrid system and site-directed mutagenesis. *J. Biol. Chem.* 272, 20044-20048.

Lu G., A WWW service system for automatic comparison of protein structures. *Protein* Data Bank Quarterly Newsletter. 78, 10-11 (1996).

Maassen C B. A rapid and safe plasmid isolation method for efficient engineering of recombinant lactobacilli expressing immunogenic or tolerogenic epitopes for oral administration. J. Immunol. Methods 223: 131-136, 1999.

MacLaughlin, F. C., Mumper, R. J., Wang, J., Tagliaferri, J. M., Gill, I., Hinchcliffe, M. & Rolland, A. P. Chitosan and depolymerized chitosan oligomers as condensing carriers for in vivo plasmid delivery. *J. Controlled Release* 56: 259-272, 1998.

Maecker H T, Hansen G, Walter D M, DeKruyff R H, Levy S, and Umetsu D T. (2001) Vaccination with allergen-IL-18 fusion DNA protects against, and reverses established, airway hyperreactivity in a murine asthma model. J. Immunol. 166:959-965.

Maeda, Y. Y. and Chihara, G. (1971) Lentinan, a new immuno-accelerator of cell-mediated responses. *Nature.* 229, 634.

Matthews, B. W. (1968) Solvent content of protein crystals. *J. Mol. Biol.* 33, 491-497.

McRee, D. E. XtalView/Xfit—A Versatile Program for Manipulating Atomic Coordinates and Electron Density. *Journal Structural Biology,* 125, 156-165 (1999)

Meneses, G., Delgado, M. A., Perez-Machado, M. A., Prieto, A., Alonso, R., Carrion, F., Lanzos, E., and Alvarez-Mon, M. (1997) Thymostimulin increases natural cytotoxic activity in patients with breast cancer. *Int. J. Immunopharmacol.* 19, 187-193.

Mercenier A, Muller-Alouf H, and Grangette C. (2000) Lactic acid bacteria as live vaccines. Curr. Issues Mol. Biol. 2:17-25.

Merrit, E. A. & Bacon, D. J. RASTER3D. *Methods Enzymol.* 277, 505-524 (1997).

Morales, A. (1984) Long term results and complications of intracavitary *bacillus* Calmette-Guerin therapy for bladder cancer. *J. Urol.* 132, 457-459.

Morris, R. J., Perrakis, A. & Lamzin, V. S. Arp/warp's model-building algorithms. i. the main chain. *Acta Crystallogr. D* 58, 968-975 (2002)

Murshudov, G. N., Lebedev, A., Vagin, A. A., Wilson, K. S. & Dodson, E. J. Efficient anisotropic-refinement of Macromolecular structures using FFT *Acta Crystallogr. D* 55, 247-255 (1999)

Nakamura, K., Yamaguchi, Y., Kagota, S., Kwon, Y. M., Shinozuka, K., and Kunitomo, M. (1999) Inhibitory effect of Cordyceps sinensis on spontaneous liver metastasis of Lewis lung carcinoma and B16 melanoma cells in syngeneic mice. *Jpn. J. Pharmacol.* 79, 335-341.

Namba, K., Yamamura, E., Nitanai, H., Otani, T., and Azuma, I. (1997) Romurtide, a synthetic muramyl dipeptide derivative, promotes megakaryocytopoiesis through stimulation of cytokine production in nonnuman primates with myelosuppression. *Vaccine.* 15,405-413.

Okamoto, M., Kaji, R., Kasetani, H., Yoshida, H., Moriya, Y., Saito, M., and Sato, M. (1993) Purification and characterization of interferon-gamma-inducing molecule of OK-432, a penicillin-killed streptococcal preparation, by monoclonal antibody neutralizing interferon-gamma-inducing activity of OK432. *J. Immunother.* 13, 232-242.

Otwinowski, Z. M. & Minor, W. Processing of X-ray diffraction data collected in oscillation mode. *Methods Enzymol.* 276, 307-326 (1997).

Piraino, F. and Brandt, C. R. (1999) Isolation and partial characterization of an antiviral, RC-183, from the edible mushroom *Rozites caperata. Antiviral Res.* 43, 67-78.

Pochard P, Gosset P, Grangette C, Andre C, Tonnel A B, Pestel J, and Mercenier A. (2002) Lactic acid bacteria inhibit TH2 cytokine production by mononuclear cells from allergic patients. J. Allergy Clin. Immunol. 110:617-623.

Rask C, Holmgren J, Fredriksson M, Lindblad M, Nordstrom I, Sun J B, and Czerlinsky C. (2000) Prolonged oral treatment with low doses of allergen conjugated to cholera toxin B subunit suppresses immunoglobulin E antibody responses in sensitized mice. Clin. Exp. Allergy 30:1024-32.

Rost, B. (2001) Review: protein secondary structure prediction continues to rise. *J. Struct. Biol.* 134, 204-218.

Rousseau, F., Schymkowitz, J. W. H., Wilkinson, H. R., & Itzhaki, L. S. Three-dimensional domain swapping in p13suc1 occurs in the unfolded and controlled by conserved proline residues. *Proc. Natl. Acad. Sci. USA.* 98, 5596-5601, (2001).

Roy, K., Mao, H. Q., Huang, S. K. & Leong, K. W. Oral gene delivery with chitosan-DNA nanoparticles generates immunologic protection in a murine model of peanut allergy. *Nat. Med.* 5: 387-391, 1999.

Scanga C B and Le Gros G. (2000) Development of an asthma vaccine: research into BCG. Drugs 59:1217-1221.

Scharf O, Agranovich I, Lee K, Eller N L, Levy L, Imman J, Scott D E, and Golding B. (2001) Ontogeny of Th1 memory responses against a *Brucella abortus* conjugate. Infect Immun 69:5417-5422.

Scheppler L, Vogel M, Zuercher A W, Zuercher M, Germond J E, Miescher S M, and Stadler B M. (2002) Recombinant *Lactobacillus johnsonii* as a mucosal vaccine delivery vehicle. Vaccine 20:2913-2920.

Shea L D, Smiley E, Bonadio J, and Mooney D J. (1999) DNA delivery from polymer matrices for tissue engineering. Nat. Biotechnol. 17:551-554.

Shimizu, Y., Hasumi, K., and Masubuchi, K. (1992) Augmenting effect of sizofiran on the immunofunction of regional lymph nodes in cervical cancer. *Cancer.* 69, 1184-1194.

Shirota H, Sano K, Kikuchi T, Tamura G, and Shirato K. (2000) Regulation of murine airway eosinophilia and Th2 cells by antigen-conjugated CpG oligodeoxynucleotides as a novel antigen-specific immunomodulator. J. Immunol. 2000 164:5575-5582.

Singh, V. K., Biswas, S., Mathur, K. B., Haq, W., Garg, S. K., and Agarwal, S. S. (1998) Thymopentin and splenopentin as immunomodulators. Current status. *Immunol Res.* 17, 345-368.

Slonim D K (2002) From patterns to pathways: gene expression data analysis comes of age. Nat. Genet. 32 Suppl 2:502-508.

Solomon, P., Wasser & Alexander, L. W. Therapeutic effect of substance occurring in higher *Basidiomycetes* Mushroom: A modern perspective. Critical Review in Immunology.19, 65-96 (1999).

Taal, B. G., Van Tinteren, H., Zoetmulder, F. A., and NACCP group. (2001) Adjuvant 5FU plus levamisole in colonic or rectal cancer: improved survival in stage II and III. *Br. J. Cancer.* 85, 1437-1443.

Tacket C O, Mason H S, Losonsky G, Clements J D, Levine M M, and Arntzen C J. (1998) Immunogenicity in humans of a recombinant bacterial antigen delivered in a transgenic potato. Nat. Med. 4:607-609.

Templin M F, Stoll D, Schrenk M, Traub P C, Vohringer C F, and Joos T O. (2002) Protein microarray technology. Trends Biotechnol. 20:160-166.

Terwilliger, T. C. & Berendzen, J. *Acta Crystallogr. D* 55, 849-861 (1999).

Terwilliger. Map-likelihood phasing *Acta Crysallogr. D* 57, 1763-1775 (2001)

van Berkum N L and Holstege F C. (2001) DNA microarrays: raising the profile. Curr. Opin. Biotechnol.12:48-52.

Viland, H. and Blomgren, H. (1987) Augmentation of spontaneous cytotoxicity of human lymphocytes by RU 41.740, a glucoprotein extract of *Klebsiella pneumoniae. Anticancer Res.* 7, 17-22.

Vinuesa C G and Goodnow C C. (2002) Immunology: DNA drives autoimmunity. Nature 416:595-598.

Wasson, V. P & Wasson, R. G. Mushroom, Russia and History, Pantheon Books, New York, 433, 1957.

Wohlleben G and Erb K J. (2001) Atopic disorders: a vaccine around the corner? Trends Immunol. 22:618-626.

Yoshino, S., Tabata, T., Hazama, S., Iizuka, N., Yamamoto, K., Hirayama, M., Tangoku, A., and Oka, M. (2000) Immunoregulatory effects of the antitumor polysaccharide lentinan on Th1/Th2 balance in patients with digestive cancers. *Anticancer Res.* 20, 4707-4711.

Zhu D and Stevenson F K. (2002) DNA gene fusion vaccines against cancer. Curr. Opin. Mol. Ther. 4:41-48.

Zhu H, Bilgin M, Bangham R, Hall D, Casamayor A, Bertone P, Lan N, Jansen R, Bidlingmaier S, Houfek T, Mitchell T, Miller P, Dean R A, Gerstein M, and Snyder M. (2001) Global analysis of protein activities using proteome chips. Science 293: 2101-2105.

Zuany-Amorim C, Sawicka E, Manlius C, Le Moine A, Brunet L R, Kemeny D M, Bowen G, Rook G, and Walker C. (2002) Suppression of airway eosinophilia by killed *Mycobacterium vaccae*-induced allergen-specific regulatory T-cells. Nat. Med. 8:625-629.

Each of the applications and patents mentioned in this document, and each document cited or referenced in each of the above applications and patents, including during the prosecution of each of the applications and patents ("application cited documents") and any manufacturer's instructions or catalogues for any products cited or mentioned in each of the applications and patents and in any of the application cited documents, are hereby incorporated herein by reference. Furthermore, all documents cited in this text, and all documents cited or referenced in documents cited in this text, and any manufacturer's instructions or catalogues for any products cited or mentioned in this text, are hereby incorporated herein by reference.

Various modifications and variations of the described methods and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for caring out the invention which are obvious to those skilled in molecular biology or related fields are intended to be within the scope of the claims.

| Appendix A: Sequences |
|---|
| Fve is isolated from Golden Needle Mushroom (*Flammulina velutipes*). ORGANISM: *Flammulina velutipes*. Eukaryota; Fungi; Basidiomycota; Hymenomycetes; Agaricales; Tricholomataceae; Flammulina. |

Fve (Wild type)

ATGTCCGCCACGTCGCTCACCTTCCAGCTTGCCTACTTGGTGAAGAAGATCGACTTCGACTACACCCC

CAACTGGGGCCGTGGTACCCCAAGCAGCTACATCGACAACCTTACCTTCCCCAAGGTTCTCACCGACA

AAAAATACTCGTACCGCGTCGTGGTCAATGGCTCTGACCTTGGCGTCGAGTCCAACTTCGCAGTGACA

CCGTCCGGTGGGCAGACCATCAACTTCCTCCAGTACAACAAGGGGTATGGTGTCGCGGACACCAAAAC

GATTCAAGTTTTCGTTGTCATTCCAGATACCGGCAACTCGGAGGAGTACATCATCGCTGAGTGGAAGA

AGACTTGA (SEQ ID NO: 5)

msatsltfqlaylvkkidfdytpnwgrgtpssyidnitfpkvitdkkysyrvvvngsdlgvesnfav tpsggqtinflqynkgygvadtktiqvfvvipdtgnseeyiiaewkkt (SEQ ID NO: 6)

ATG/TCC/GCc/ACG/TCG/CTC/ACC/TTC/CAG/CTT/GCC/TAC/TTG/GTG/AAG/AAG/ATC/

GAC/TTC/GAC/TAC/ACC/CCC/AAC/TGG/GGC/CGT/GGT/ACC/CCA/AGC/AGC/TAC/ATC/

GAC/AAC/CTT/ACC/TTC/CCC/AAG/GTT/CTC/ACC/GAC/AAA/AAA/TAC/TCG/TAC/CGC/

GTC/GTG/GTC/AAT/GGC/TCT/GAC/CTT/GGC/GTC/GAG/TCC/AAC/TTC/GCA/GTG/ACA/

CCG/TCC/GGT/GGG/CAG/ACC/ATC/AAC/TTC/CTC/CAG/TAC/AAC/AAG/GGG/TAT/GGT/

GTC/GCG/GAC/ACC/AAA/ACG/ATT/CAA/GTT/TTC/GTT/GTC/ATT/CCA/GAT/ACC/GGC/

AAC/TCG/GAG/GAG/TAC/ATC/ATC/GCT/GAG/TGG/AAG/AAG/ACT/TGA (SEQ ID NO: 5)

A Fve (Wild type) sequence may also comprise a sequence as set out above, but lacking the initial methionine (M) in the amino acid sequence, or lacking the initial ATG in the nucleic acid sequence.

GST-Fve (Wild type) Nucleotide Sequence

ATGTCCCCTATACTAGGTTATTGGAAAATTAAGGGCCTTGTGCAACCCACTCGACTTCTTTT

GGAATATCTTGAAGAAAAATATGAAGAGCATTTGTATGAGCGCGATGAAGGTGATAAATGGC

GAAACAAAAAGTTTGAATTGGGTTTGGAGTTTCCCAATCTTCCTTATTATATTGATGGTGAT

GTTAAATTAACACAGTCTATGGCCATCATACGTTATATAGCTGACAAGCACAACATGTTGGG

TGGTTGTCCAAAAGAGCGTGCAGAGATTTCAATGCTTGAAGGAGCGGTTTTGGATATTAGAT

ACGGTGTTTCGAGAATTGCATATAGTAAAGACTTTGAAACTCTCAAAGTTGATTTTCTTAGC

AAGCTACCTGAAATGCTGAAAATGTTCGAAGATCGTTTATGTCATAAAACATATTTAAATGG

TGATCATGTAACCCATCCTGACTTCATGTTGTATGACGCTCTTGATGTTGTTTTATACATGG

ACCCAATGTGCCTGGATGCGTTCCCAAAATTAGTTTGTTTTAAAAAACGTATTGAAGCTATC

CCACAAATTGATAAGTACTTGAAATCCAGCAAGTATATAGCATGGCCTTTGCAGGGCTGGCA

AGCCACGTTTGGTGGTGGCGACCATCCTCCAAAATCGGATCTGGAAGTTCTGTTCCAGGGGC

CCCTGGGATCCTCCGCCACGTCGCTCACCTTCCAGCTTGCCTACTTGGTGAAGAAGATCGAC

TTCGACTACACCCCCAACTGGGGCCGTGGTACCCCAAGCAGCTACATCGACAACCTTACCTT

CCCCAAGGTTCTCACCGACAAAAAATACTCGTACCGCGTCGTGGTCAATGGCTCTGACCTTG

GCGTCGAGTCCAACTTCGCAGTGACACCGTCCGGTGGGCAGACCATCAACTTCCTCCAGTAC

AACAAGGGGTATGGTGTCGCGGACACCAAAACGATTCAAGTTTTCGTTGTCATTCCAGATAC

CGGCAACTCGGAGGAGTACATCATCGCTGAGTGGAAGAAGACTTGA (SEQ ID NO: 7)

-continued

| Appendix A: Sequences |
|---|

GST-Fve (Wild type) Amino Acid Sequence
MSPILGYWKIKGLVQPTRLLLEYLEEKYEEHLYERDEGDKWRNKKFELGLEFPNLPYYIDGDVKLTQS

MAIIRYIADKHNMLGGCPKERAEISMLEGAVLDIRYGVSRIAYSKDFETLKVDFLSKLPEMLKMFEDR

LCHKTYLNGDHVTHPDFMLYDALDVVLYMDPMCLDAFPKLVCFKKRIEAIPQIDKYLKSSKYIAWPLQ

GWQATFGGGDHPPKSDLEVLFQGPLGSSATSLTFQLAYLVKKIDFDYTPNWGRGTPSSYIDNLTFPKV

LTDKKYSYRVVVNGSDLGVESNFAVTPSGGQTINFLQYNKGYGVADTKTIQVFVVIPDTGNSEEYIIA

EWKKT (SEQ ID NO: 8)

FVE DELETION MUTANTS

Fve D6-18
ATG/TCC/GCC/ACG/TCG/TTC/GAC/TAC/ACC/CCC/AAC/TGG/GGC/CGT/GGT/ACC/CCA/

AGC/AGC/TAC/ATC/GAC/AAC/CTT/ACC/TTC/CCC/AAG/GTT/CTC/ACC/GAC/AAA/AAA/

TAC/TCG/TAC/CGC/GTC/GTG/GTC/AAT/GGC/TCT/GAC/CTT/GGC/GTC/GAG/TCC/AAC/

TTC/GCA/GTG/ACA/CCG/TCC/GGT/GGG/CAG/ACC/ATC/AAC/TTC/CTC/CAG/TAC/AAC/

AAG/GGG/TAT/GGT/GTC/GCG/GAC/ACC/AAA/ACG/ATT/CAA/GTT/TTC/GTT/GTC/ATT/

CCA/GAT/ACC/GGC/AAC/TCG/GAG/GAG/TAC/ATC/ATC/GCT/GAG/TGG/AAG/AAG/ACT/

TGA (SEQ ID NO: 9)

msats/fdytpnwgrgtpssyidnitfpkvltdkkysyrvvvngsdlgvesnfavtpsggqtinflqy nkgygvadtktiqvfvvipdtgnseeyiiaewkkt (SEQ ID NO: 10)

Fve D19-33
ATG/TCC/GCC/ACG/TCG/CTC/ACC/TTC/CAG/CTT/GCC/TAC/TTG/GTG/AAG/AAG/ATC/

GAC/ATC/GAC/AAC/CTT/ACC/TTC/CCC/AAG/GTT/CTC/ACC/GAC/AAA/AAA/TAC/TCG/

TAC/CGC/GTC/GTG/GTC/AAT/GGC/TCT/GAC/CTT/GGC/GTC/GAG/TCC/AAC/TTC/GCA/

GTG/ACA/CCG/TCC/GGT/GGG/CAG/ACC/ATC/AAC/TTC/CTC/CAG/TAC/AAC/AAG/GGG/

TAT/GGT/GTC/GCG/GAC/ACC/AAA/ACG/ATT/CAA/GTT/TTC/GTT/GTC/ATT/CCA/GAT/

ACC/GGC/AAC/TCG/GAG/GAG/TAC/ATC/ATC/GCT/GAG/TGG/AAG/AAG/ACT/TGA
(SEQ ID NO: 11)

msatsltfqlaylvidcid/idnitfpkvltdkkysyrvvvngsdlgvesnfavtpsggqtinflqynk gygvadtktiqvfvvipdtgnseeyiiaewkkt (SEQ ID NO: 12)

Fve D34-46
ATG/TCC/GCC/ACG/TCG/CTC/ACC/TTC/CAG/CTT/GCC/TAC/TTG/GTG/AAG/AAG/ATC/

GAC/TTC/GAC/TAC/ACC/CCC/AAC/TGG/GGC/CGT/GGT/ACC/CCA/AGC/AGC/TAC/AAA/

TAC/TCG/TAC/CGC/GTC/GTG/GTC/AAT/GGC/TCT/GAC/CTT/GGC/GTC/GAG/TCC/AAC/

TTC/GCA/GTG/ACA/CCG/TCC/GGT/GGG/CAG/ACC/ATC/AAC/TTC/CTC/CAG/TAC/AAC/

AAG/GGG/TAT/GGT/GTC/GCG/GAC/ACC/AAA/ACG/ATT/CAA/GTT/TTC/GTT/GTC/ATT/

CCA/GAT/ACC/GGC/AAC/TCG/GAG/GAG/TAC/ATC/ATC/GCT/GAG/TGG/AAG/AAG/ACT/

TGA (SEQ ID NO: 131 msatsltfqlaylvkkidfdytpnwgrgtpssy/kysyrvvvngsdlgvesnfavtpsggqtinflqy nkgygvadtktiqvfvvipdtgnseeyiiaewkkt (SEQ ID NO: 14)

Fve D47-60
ATG/TCC/GCC/ACG/TCG/CTC/ACC/TTC/CAG/CTT/GCC/TAC/TTG/GTG/AAG/AAG/ATC/

GAC/TTC/GAC/TAC/ACC/CCC/AAC/TGG/GGC/CGT/GGT/ACC/CCA/AGC/AGC/TAC/ATC/

GAC/AAC/CTT/ACC/TTC/CCC/AAG/GTT/CTC/ACC/GAC/AAA/GTC/GAG/TCC/AAC/TTC/

-continued

Appendix A: Sequences

GCA/GTG/ACA/CCG/TCC/GGT/GGG/CAG/ACC/ATC/AAC/TTC/CTC/CAG/TAC/AAC/AAG/

GGG/TAT/GGT/GTC/GCG/GAC/ACC/AAA/ACG/ATT/CAA/GTT/TTC/GTT/GTC/ATT/CCA/

GAT/ACC/GGC/AAC/TCG/GAG/GAG/TAC/ATC/ATC/GCT/GAG/TGG/AAG/AAG/ACT/TGA
(SEQ ID NO: 15)

msatsltfqlaylvkkidfdytpnwgrgtpssyidnitfpkvltdk/vesnfavtpsggqtinflqyn kgygvadtktiqvfvvipdtgnseeyiiaewkkt (SEQ ID NO: 16)

Fve D61-72
ATG/TCC/GCC/ACG/TCG/CTC/ACC/TTC/CAG/CTT/GCC/TAC/TTG/GTG/AAG/AAG/ATC/

GAC/TTC/GAC/TAC/ACC/CCC/AAC/TGG/GGC/CGT/GGT/ACC/CCA/AGC/AGC/TAC/ATC/

GAC/AAC/CTT/ACC/TTC/CCC/AAG/GTT/CTC/ACC/GAC/AAA/AAA/TAC/TCG/TAC/CGC/

GTC/GTG/GTC/AAT/GGC/TCT/GAC/CTT/GGC/CAG/ACC/ATC/AAC/TTC/CTC/CAG/TAC/

AAC/AAG/GGG/TAT/GGT/GTC/GCG/GAC/ACC/AAA/ACG/ATT/CAA/GTT/TTC/GTT/GTC/

ATT/CCA/GAT/ACC/GGC/AAC/TCG/GAG/GAG/TAC/ATC/ATC/GCT/GAG/TGG/AAG/AAG/

ACT/TGA (SEQ ID NO: 17)

msatsltfqlaylvkkidfdytpnwgrgtpssyidnitfpkvltdldcysyrvvvngsdlg/qtinflq ynkgygvadtktiqvfvvipdtgnseeyiiaewkkt (SEQ ID NO: 18)

Fve 073-84
ATG/TCC/GCC/ACG/TCG/CTC/ACC/TTC/CAG/CTT/GCC/TAC/TTG/GTG/AAG/AAG/ATC/

GAC/TTC/GAC/TAC/ACC/CCC/AAC/TGG/GGC/CGT/GGT/ACC/CCA/AGC/AGC/TAC/ATC/

GAC/AAC/CTT/ACC/TTC/CCC/AAG/GTT/CTC/ACC/GAC/AAA/AAA/TAC/TCG/TAC/CGC/

GTC/GTG/GTC/AAT/GGC/TCT/GAC/CTT/GGC/GTC/GAG/TCC/AAC/TTC/GCA/GTG/ACA/

CCG/TCC/GGT/GGG/GGT/GTC/GCG/GAC/ACC/AAA/ACG/ATT/CAA/GTT/TTC/GTT/GTC/

ATT/CCA/GAT/ACC/GGC/AAC/TCG/GAG/GAG/TAC/ATC/ATC/GCT/GAG/TGG/AAG/AAG/

ACT/TGA (SEQ ID NO: 19)

msatsltfqlaylvklcidfdytpnwgrgtpssyidnitfpkyltdkkysyrvvvngsdlgvesnfavt psgg/gvadtktiqvfvvipdtgnseeynaewIckt (SEQ ID NO: 20)

Fve D85-97
ATG/TCC/GCC/ACG/TCG/CTC/ACC/TTC/CAG/CTT/GCC/TAC/TTG/GTG/AAG/AAG/ATC/

GAC/TTC/GAC/TAC/ACC/CCC/AAC/TGG/GGC/CGT/GGT/ACC/CCA/AGC/AGC/TAC/ATC/

GAC/AAC/CTT/ACC/TTC/CCC/AAG/GTT/CTC/ACC/GAC/AAA/AAA/TAC/TCG/TAC/CGC/

GTC/GTG/GTC/AAT/GGC/TCT/GAC/CTT/GGC/GTC/GAG/TCC/AAC/TTC/GCA/GTG/ACA/

CCG/TCC/GGT/GGG/CAG/ACC/ATC/AAC/TTC/CTC/CAG/TAC/AAC/AAG/GGG/TAT/GTC/

ATT/CCA/GAT/ACC/GGC/AAC/TCG/GAG/GAG/TAC/ATC/ATC/GCT/GAG/TGG/AAG/AAG/

ACT/TGA (SEQ ID NO: 21)

msatsltfqlaylvkkidfdytpnwgrgtpssyidnitfpkvltdkkysyrvvvngsdlgvesnfavt psggqtinflqynkgy/ipdtgnseeyiiaewlckt (SEQ ID NO: 22)

Fve 098-106
ATG/TCC/GCC/ACG/TCG/CTC/ACC/TTC/CAG/CTT/GCC/TAC/TTG/GTG/AAG/AAG/ATC/

GAC/TTC/GAC/TAC/ACC/CCC/AAC/TGG/GGC/CGT/GGT/ACC/CCA/AGC/AGC/TAC/ATC/

GAC/AAC/CTT/ACC/TTC/CCC/AAG/GTT/CTC/ACC/GAC/AAA/AAA/TAC/TCG/TAC/CGC/

GTC/GTG/GTC/AAT/GGC/TCT/GAC/CTT/GGC/GTC/GAG/TCC/AAC/TTC/GCA/GTG/ACA/

-continued

Appendix A: Sequences

CCG/TCC/GGT/GGG/CAG/ACC/ATC/AAC/TTC/CTC/CAG/TAC/AAC/AAG/GGG/TAT/GGT/

GTC/GCG/GAC/ACC/AAA/ACG/ATT/CAA/GTT/TTC/GTT/GTC/TAC/ATC/ATC/GCT/GAG/

TGG/AAG/AAG/ACT/TGA (SEQ ID NO: 23)

msatsltfglaylvkkidfdytpnwgrgtpssyidnitfplcvltdkkysyrvvvngsdlgvesnfavt psggqtinflqynkgygvadtktiqvfvv/yiiaewkkt (SEQ ID NO: 24)

Fve D107-115

ATG/TCC/GCC/ACG/TCG/CTC/ACC/TTC/CAG/CTT/GCC/TAC/TTG/GTG/AAG/AAG/ATC/

GAC/TTC/GAC/TAC/ACC/CCC/AAC/TGG/GGC/CGT/GGT/ACC/CCA/AGC/AGC/TAC/ATC/

GAC/AAC/CTT/ACC/TTC/CCC/AAG/GTT/CTC/ACC/GAC/AAA/AAA/TAC/TCG/TAC/CGC/

GTC/GTG/GTC/AAT/GGC/TCT/GAC/CTT/GGC/GTC/GAG/TCC/AAC/TTC/GCA/GTG/ACA/

CCG/TCC/GGT/GGG/CAG/ACC/ATC/AAC/TTC/CTC/CAG/TAC/AAC/AAG/GGG/TAT/GGT/

GTC/GCG/GAC/ACC/AAA/ACG/ATT/CAA/GTT/TTC/GTT/GTC/ATT/CCA/GAT/ACC/GGC/

AAC/TCG/GAG/GAG/TGA (SEQ ID NO: 25)

msatsltfqlaylvkkidfdytpnwgrgtpssyidnitfpkvltdkkysyrvvvngsdlgvesnfavt psggqtinflqynIcgygvadtktiqvfvvipdtgnsee/ (SEQ ID NO: 26)

Fve D61-97

ATG/TCC/GCC/ACG/TCG/CTC/ACC/TTC/CAG/CTT/GCC/TAC/TTG/GTG/AAG/AAG/ATC/

GAC/TTC/GAC/TAC/ACC/CCC/AAC/TGG/GGC/CGT/GGT/ACC/CCA/AGC/AGC/TAC/ATC/

GAC/AAC/CTT/ACC/TTC/CCC/AAG/GTT/CTC/ACC/GAC/AAA/AAA/TAC/TCG/TAC/CGC/

GTC/GTG/GTC/AAT/GGC/TCT/GAC/CTT/GGC/ATT/CCA/GAT/ACC/GGC/AAC/TCG/GAG/

GAG/TAC/ATC/ATC/GCT/GAG/TGG/AAG/AAG/ACT/TGA (SEQ ID NO: 27)

msatsltfqlaylvkkidfdytpnwgrgtpssyidnitfpkvltdIckysyrvvvngsdlg/ipdtgns eeyiiaewkkt (SEQ ID NO: 28)

Fve p55-100

AAT/GGC/TCT/GAC/CTT/GGC/GTC/GAG/TCC/AAC/TTC/GCA/GTG/ACA/CCG/TCC/GGT/

GGG/CAG/ACC/ATC/AAC/TTC/CTC/CAG/TAC/AAC/AAG/GGG/TAT/GGT/GTC/GCG/GAC/

ACC/AAA/ACG/ATT/CAA/GTT/TTC/GTT/GTC/ATT/CCA/GAT/ (SEQ ID NO: 29)

Ngsdlgvesnfavtpsggqtinflqynkgygvadtktiqvfvvipd (SEQ ID NO: 30)

FVE MUTANTS WITH SINGLE AMINO ACID SUBSTITUTIONS

FveR27A

ATG/TCC/GCC/ACG/TCG/CTC/ACC/TTC/CAG/CTT/GCC/TAC/TTG/GTG/AAG/AAG/ATC/

GAC/TTC/GAC/TAC/ACC/CCC/AAC/TGG/GGC/GCA/GGT/ACC/CCA/AGC/AGC/TAC/ATC/

GAC/AAC/CTT/ACC/TTC/CCC/AAG/GTT/CTC/ACC/GAC/AAA/AAA/TAC/TCG/TAC/CGC/

GTC/GTG/GTC/AAT/GGC/TCT/GAC/CTT/GGC/GTC/GAG/TCC/AAC/TTC/GCA/GTG/ACA/

CCG/TCC/GGT/GGG/CAG/ACC/ATC/AAC/TTC/CTC/CAG/TAC/AAC/AAG/GGG/TAT/GGT/

GTC/GCG/GAC/ACC/AAAJACG/ATT/CAA/GTT/TTC/GTT/GTC/ATT/CCA/GAT/ACC/GGC/

AAC/TCG/GAG/GAG/TAC/ATC/ATC/GCT/GAG/TGG/AAG/AAG/ACT/TGA(SEQ ID NO: 31)

msatsltfqlaylvkkidfdytpnwgagtpssyidnitfpkvltdkkysyrvvvngsdlgvesnfavt psggqtinflqynkgygvadtktiqvfvvipdtgnseeyiiaewkkt (SEQ ID NO: 32)

FveG28A

ATG/TCC/GCC/ACG/TCG/CTC/ACC/TTC/CAG/CTT/GCC/TAC/TTG/GTG/AAG/AAG/ATC/

GAC/TTC/GAC/TAC/ACC/CCC/AAC/TGG/GGC/CGT/GCA/ACC/CCA/AGC/AGC/TAC/ATC/

-continued

| Appendix A: Sequences |
|---|
| GAC/AAC/CTT/ACC/TTC/CCC/AAG/GTT/CTC/ACC/GAC/AAA/AAA/TAC/TCG/TAC/CGC/ |
| GTC/GTG/GTC/AAT/GGC/TCT/GAC/CTT/GGC/GTC/GAG/TCC/AAC/TTC/GCA/GTG/ACA/ |
| CCG/TCC/GGT/GGG/CAG/ACC/ATC/AAC/TTC/CTC/CAG/TAC/AAC/AAG/GGG/TAT/GGT/ |
| GTC/GCG/GAC/ACC/AAA/ACG/ATT/CAA/GTT/TTC/GTT/GTC/ATT/CCA/GAT/ACC/GGC/ |
| AAC/TCG/GAG/GAG/TAC/ATC/ATC/GCT/GAG/TGG/AAG/AAG/ACT/TGA (SEQ ID NO: 33) |
| msatsltfqlaylvkkidfdytpnwgratpssyidnitfpkvltdkkysyrvvvngsdlgvesnfavt |
| psggqtinflqynkgygvadtktiqvfvvipdtgnseeyiiaewkkt (SEQ ID NO: 34) |
| FveT29A |
| ATG/TCc/GCC/ACG/TcG/CTC/ACC/TTC/CAG/CTT/GCC/TAC/TTG/GTG/AAG/AAG/ATC/ |
| GAC/TTC/GAC/TAC/ACC/CCC/AAC/TGG/GGC/CGT/GGT/GCA/CCA/AGC/AGC/TAC/ATC/ |
| GAC/AAC/CTT/ACC/TTC/CCC/AAG/GTT/CTC/ACC/GAC/AAA/AAA/TAC/TCG/TAC/CGC/ |
| GTC/GTG/GTC/AAT/GGC/TCT/GAC/CTT/GGC/GTC/GAG/TCC/AAC/TTC/GCA/GTG/ACA/ |
| CCG/TCC/GGT/GGG/CAG/ACC/ATC/AAC/TTC/CTC/CAG/TAC/AAC/AAG/GGG/TAT/GGT/ |
| GTC/GCG/GAC/ACC/AAA/ACG/ATT/CAA/GTT/TTC/GTT/GTC/ATT/CCA/GAT/ACC/GGC/ |
| AAC/TCG/GAG/GAG/TAC/ATC/ATC/GCT/GAG/TGG/AAG/AAG/ACT/TGA (SEQ ID NO: 35) |
| msatsltfqlaylvkkidfdytpnwgrgapssyidnitfpkvltdkkysyrvvvngsdlgvesnfavt |
| psggqtinflqynkgygvadtktiqvfvvipdtgnseeyiiaewkkt (SEQ ID NO: 36) |

| FUSION PROTEINS OF MAJOR HOUSE DUST MITE ALLERGEN (BLO T 5 OR DER P 2) AND FUNGAL IMMUNOMODULATORY PROTEIN FVE |
|---|
| Blo t 5-Fve (two-in-one chimeric wild type) |
| caagagcacaagccaaagaaggatgatttccgaaacgaattcgatcacttgttgatcgaacaggcaaa |
| ccatgctatcgaaaagggagaacatcaattgctttacttgcaacaccaactcgacgaattgaatgaaa |
| acaagagcaaggaattgcaagagaaaatcattcgagaacttgatgttgtttgcgccatgatcgaagga |
| gcccaaggagctttggaacgtgaattgaagcgaactgatcttaacattttggaacgattcaactacga |
| agaggctcaaactctcagcaagatcttgcttaaggatttgaaggaaaccgaacaaaaagtgaaggata |
| ttcaaacccaaTCCGCCACGTCGCTCACCTTCCAGCTTGCCTACTTGGTGAAGAAGATCGACTTCGAC |
| TACACCCCCAACTGGGGCCGTGGTACCCCAAGCAGCTACATCGACAACCTTACCTTCCCCAAGGTTCT |
| CACCGACAAAAAATACTCGTACCGCGTCGTGGTCAATGGCTCTGACCTTGGCGTCGAGTCCAACTTCG |
| CAGTGACACCGTCCGGTGGGCAGACCATCAACTTCCTCCAGTACAACAAGGGGTATGGTGTCGCGGAC |
| ACCAAAACGATTCAAGTTTTCGTTGTCATTCCAGATACCGGCAACTCGGAGGAGTACATCATCGCTGA |
| GTGGAAGAAGACTTGA (SEQ ID NO: 37) |
| QEHKPKKDDFRNEFDHLLIEQANHAIEKGEHQLLYLQHQLDELNENKSKELQEKIIRELDVVCAMIEG |
| AQGALERELKRTDLNILERFNYEEAQTLSKILLKDLKETEQKVKDIQTQsatsltfqlaylvkkidfd |
| ytpnwgrgtpssyidnitfpkvltdkkysyrvvvngsdlgvesnfavtpsggqtinflqynkgygvad |
| tktiqvfvvipdtgnseeyiiaewkkt (SEQ ID NO: 38) |
| Blo t 5-FveR27 A (two-in-one chimeric mutant) |
| caagagcacaagccaaagaaggatgatttccgaaacgaattcgatcacttgttgatcgaacaggcaaa |
| ccatgctatcgaaaagggagaacatcaattgctttacttgcaacaccaactcgacgaattgaatgaaa |
| acaagagcaaggaattgcaagagaaaatcattcgagaacttgatgttgtttgcgccatgatcgaagga |
| gcccaaggagctttggaacgtgaattgaagcgaactgatcttaacattttggaacgattcaactacga |

-continued

Appendix A: Sequences agaggctcaaactctcagcaagatcttgcttaaggatttgaaggaaaccgaacaaaaagtgaaggata ttcaaacccaaTCCGCCACGTCGCTCACCTTCCAGCTTGCCTACTTGGTGAAGAAGATCGACTTCGAC

TACACCCCCAACTGGGGCGCAGGTACCCCAAGCAGCTACATCGACAACCTTACCTTCCCCAAGGTTC

TCACCGACAAAAAATACTCGTACCGCGTCGTGGTCAATGGCTCTGACCTTGGCGTCGAGTCCAACTTC

GCAGTGACACCGTCCGGTGGGCAGACCATCAACTTCCTCCAGTACAACAAGGGGTATGGTGTCGCGGA

CACCAAAACGATTCAAGTTTTCGTTGTCATTCCAGATACCGGCAACTCGGAGGAGTACATCATCGCTG

AGTGGAAGAAGACTTGA (SEQ ID NO: 39)

QEHKPKKDDFRNEFDHLLIEQANHAIEKGEHQLLYLQHQLDELNENKSKELQEKIIRELDVVCAMIEG

AWALERELKRTDLNILERFNYEEAQTLSKILLKDLKETEQKVKDIQTQsatsltfqlaylvkkidfd ytpnwgagtpssyidnitfpkvltdkkysyrvvvngsdlgvesnfavtpsggqtinflqynkgygvad tktiqvfvvipdtgnseeyiiaewkkt (SEQ ID NO: 40)

Blo t 5-Fve T29,4 (two-in-one chimeric mutant)

caagagcacaagccaaagaaggatgatttccgaaacgaattcgatcacttgttgatcgaacaggcaaa ccatgctatcgaaaagggagaacatcaattgctttacttgcaacaccaactcgacgaattgaatgaaa acaagagcaaggaattgcaagagaaaatcattcgagaacttgatgttgtttgcgccatgatcgaagga gcccaaggagctttggaacgtgaattgaagcgaactgatcttaacattttggaacgattcaactacga agaggctcaaactctcagcaagatcttgcttaaggatttgaaggaaaccgaacaaaaagtgaaggata ttcaaacccaaTCCGCCACGTCGCTCACCTTCCAGCTTGCCTACTTGGTGAAGAAGATCGACTTCGAC

TACACCCCCAACTGGGGCCGTGGTGCACCAAGCAGCTACATCGACAACCTTACCTTCCCCAAGGTTC

TCACCGACAAAAAATACTCGTACCGCGTCGTGGTCAATGGCTCTGACCTTGGCGTCGAGTCCAACTTC

GCAGTGACACCGTCCGGTGGGCAGACCATCAACTTCCTCCAGTACAACAAGGGGTATGGTGTCGCGGA

CACCAAAACGATTCAAGTTTTCGTTGTCATTCCAGATACCGGCAACTCGGAGGAGTACATCATCGCTG

AGTGGAAGAAGACTTGA (SEQ ID NO: 41)

QEHKPKKDDFRNEFDHLLIEQANHAIEKGEHQLLYLQHQLDELNENKSKELQEKIIRELDVVCAMIEG

AQGALERELKRTDLNILERFNYEEAQTLSKILLKDLKETEQKVKDIQTQsatsltfqlaylvkkidfd ytpnwgrgapssyidnitfpkvltdkkysyrvvvngsdlgvesnfavtpsggqtinflqynkgygvad tktiqvfvvipdtgnseeyiiaewkkt (SEQ ID NO: 42)

Der p 2-FveR27A (two-in-one chimeric mutant)

gatcaagtcgatgtcaaagattgtgccaatcatgaaatcaaaaaagttt tggtaccaggatgccatgg ttcagaaccatgtatcattcatcgtggtaaaccattccaattggaagccgttttcgaagccaaccaaa acacaaaaacggctaaaattgaaatcaaagcctcaatcgatggtttagaagttgatgttcccggtatc gatccaaatgcatgccattacatgaaatgcccattggttaaaggacaacaatatgatattaaatatac atggaatgttccgaaaattgcaccaaaatctgaaaatgttgtcgtcactgttaaagttatgggtgatg atggtgttttggcctgtgctattgctactcatgctaaaatccgcgatTCCGCCACGTCGCTCACCTTC

CAGCTTGCCTACTTGGTGAAGAAGATCGACTTCGACTACACCCCCAACTGGGGCGCAGGTACCCCAA

GCAGCTACATCGACAACCTTACCTTCCCCAAGGTTCTCACCGACAAAAAATACTCGTACCGCGTCGTG

GTCAATGGCTCTGACCTTGGCGTCGAGTCCAACTTCGCAGTGACACCGTCCGGTGGGCAGACCATCAA

CTTCCTCCAGTACAACAAGGGGTATGGTGTCGCGGACACCAAAACGATTCAAGTTTTCGTTGTCATTC

CAGATACCGGCAACTCGGAGGAGTACATCATCGCTGAGTGGAAGAAGACTTGA (SEQ ID NO: 43)

DQVDVKDCANHEIKKVLVPGCHGSEPCIIHRGKPFQLEAVFEANQNTKTAKIEIKASIDGLEVDVPGI

-continued

Appendix A: Sequences

DPNACHYMKCPLVKGQQYDIKYTWNVPKIAPKSENVVVTVKVMGDDGVLACAIATHAKIRDsatsltf qlaylvkkidfdytpnwgagtpssyidnitfpkvltdkkysyrvvvngsdlgvesnfavtpsggqtin flgynkgygvadtktiqvfvvipdtgnseeynaewkkt (SEQ ID NO: 44)

Der p 2-FveT29A (two-in-one chimeric mutant)

gatcaagtcgatgtcaaagattgtgccaatcatgaaatcaaaaaagttttggtaccaggatgccatgg ttcagaaccatgtatcattcatcgtggtaaaccattccaattggaagccgttttcgaagccaaccaaa acacaaaaacggctaaaattgaaatcaaagcctcaatcgatggtttagaagttgatgttcccggtatc gatccaaatgcatgccattacatgaaatgcccattggttaaaggacaacaatatgatattaaatatac atggaatgttccgaaaattgcaccaaaatctgaaaatgttgtcgtcactgttaaagttatgggtgatg atggtgttttggcctgtgctattgctactcatgctaaaatccgcgatTCCGCCACGTCGCTCACCTTC

CAGCTTGCCTACTTGGTGAAGAAGATCGACTTCGACTACACCCCCAACTGGGGCCGTGGTGCACCAA

GCAGCTACATCGACAACCTTACCTTCCCCAAGGTTCTCACCGACAAAAAATACTCGTACCGCGTCGTG

GTCAATGGCTCTGACCTTGGCGTCGAGTCCAACTTCGCAGTGACACCGTCCGGTGGGCAGACCATCAA

CTTCCTCCAGTACAACAAGGGGTATGGTGTCGCGGACACCAAAACGATTCAAGTTTTCGTTGTCATTC

CAGATACCGGCAACTCGGAGGAGTACATCATCGCTGAGTGGAAGAAGACTTGA (SEQ ID NO: 45)

DQVDVKDCANHEIKKVLVPGCHGSEPCIIHRGKPFQLEAVFEANQNTKTAKIEIKASIDGLEVDVPGI

DPNACHYMKCPLVKGQQYDIKYTWNVPKIAPKSENVVVTVKVMGDDGVLACAIATHAKIRDsatsltf glaylvkkidfdytpnwgrgapssyidnitfpkvltdkkysyrvvvngsdlgvesnfavtpsggqtin flgynkgygvadtktiqvfvvipdtgnseeynaewkkt (SEQ ID NO: 46)

Blo t 5-Der p 2-FveR27A (three-in-one chimeric mutant)

caagagcacaagccaaagaaggatgatttccgaaacgaattcgatcacttgttgatcgaacaggcaaa ccatgctatcgaaaagggagaacatcaattgctttacttgcaacaccaactcgacgaattgaatgaaa acaagagcaaggaattgcaagagaaaatcattcgagaacttgatgttgtttgcgccatgatcgaagga gcccaaggagctttggaacgtgaattgaagcgaactgatcttaacattttggaacgattcaactacga agaggctcaaactctcagcaagatcttgcttaaggatttgaaggaaaccgaacaaaaagtgaaggata ttcaaacccaagatcaagtcgatgtcaaagattgtgccaatcatgaaatcaaaaaagttttggtacca ggatgccatggttcagaaccatgtatcattcatcgtggtaaaccattccaattggaagccgttttcga agccaaccaaaacacaaaaacggctaaaattgaaatcaaagcctcaatcgatggtttagaagttgatg ttcccggtatcgatccaaatgcatgccattacatgaaatgcccattggttaaaggacaacaatatgat attaaatatacatggaatgttccgaaaattgcaccaaaatctgaaaatgttgtcgtcactgttaaagt tatgggtgatgatggtgttttggcctgtgctattgctactcatgctaaaatccgcgatTCCGCCACGT

CGCTCACCTTCCAGCTTGCCTACTTGGTGAAGAAGATCGACTTCGACTACACCCCCAACTGGGGCGC

AGGTACCCCAAGCAGCTACATCGACAACCTTACCTTCCCCAAGGTTCTCACCGACAAAAAATACTCGT

ACCGCGTCGTGGTCAATGGCTCTGACCTTGGCGTCGAGTCCAACTTCGCAGTGACACCGTCCGGTGGG

CAGACCATCAACTTCCTCCAGTACAACAAGGGGTATGGTGTCGCGGACACCAAAACGATTCAAGTTTT

CGTTGTCATTCCAGATACCGGCAACTCGGAGGAGTACATCATCGCTGAGTGGAAGAAGACTTGA
(SEQ ID NO: 47)

QEHKPKKDDFRNEFDHLLIEQANHAIEKGEHQLLYLQHQLDELNENKSKELQEKIIRELDVVCAMIEG

AQGALERELKRTDLNILERFNYEEAQTLSKILLKDLKETEQKVKDIQTQDQVDVKDCANHEIKKVLVP

GCHGSEPCIIHRGKPFQLEAVFEANQNTKTAKIEIKASIDGLEVDVPGIDPNACHYMKCPLVKGQQYD

IKYTWNVPKIAPKSENVVVTVKVMGDDGVLACAIATHAKIRDsatsitfcilaylvkkidfdytpnwg

-continued

Appendix A: Sequences agtpssyidnitfpkvltdkkysyrvvvngsdlgvesnfavtpsggqtinflgynkgygvadtktiqv fvvipdtgnseeyiiaewkkt (SEQ ID NO: 48)

FUSION PROTEINS OF VIRAL ANTIGEN AND FVE

HPV E7-FveT29A
MHGDTPTLHEYMLDLQPETTDLYCYEQLNDSSEEEDEIDGPAGQAEPDRAHYNIVTFCCKCDSTLRLC

VQSTHVDIRTLEDLLMGTLGIVCPICSQKPsatsltfqlaylvlckidfdytpnwgrgapssyidnit fpkvltdkkysyrvvvngsdlgvesnfavtpsggqtinflqynkgygvadtktiqvfvvipdtgnsee yiiaewkkt (SEQ ID NO: 49)

atgcatggagatacacctacattgcatgaatatatgttagatttgcaaccagagacaactgatctcta ctgttatgagcaattaaatgacagctcagaggaggaggatgaaatagatggtccagctggacaagcag aaccggacagagcccattacaatattgtaaccttttgttgcaagtgtgactctacgcttcggttgtgc gtacaaagcacacacgtagacattcgtactttggaagacctgttaatgggcacactaggaattgtgtg ccccatctgttctcagaaaccaTCCGCCACGTCGCTCACCTTCCAGCTTGCCTACTTGGTGAAGAAGA

TCGACTTCGACTACACCCCCAACTGGGGCCGTGGTGCACCAAGCAGCTACATCGACAACCTTACCTTC

CCCAAGGTTCTCACCGACAAAAAATACTCGTACCGCGTCGTGGTCAATGGCTCTGACCTTGGCGTCGA

GTCCAACTTCGCAGTGACACCGTCCGGTGGGCAGACCATCAACTTCCTCCAGTACAACAAGGGGTATG

GTGTCGCGGACACCAAAACGATTCAAGTTTTCGTTGTCATTCCAGATACCGGCAACTCGGAGGAGTAC

ATCATCGCTGAGTGGAAGAAGACTTGA (SEQ ID NO: 50)

HCV Core23-FveT29A
Deletion of the 23 amino acids of core antigen from 141-163 amino acid residues leads to increased protein production efficiency
MSTNPKPQRKTKRNTNRRPQDVKFPGGGQIVGGVYLLPRRGPRLGVRATRKTSERSQPRGRRQPIPKA

RQPEGRAWAQPGYPWPLYGNEGLGWAGWLLSPRGSRPSWGPTDPRRRSRNLGKVIDTLTCGFADLMGY

LPLVYATGNLPGCSFSIFLLALLSCLTIPASAsatsltfcilaylvkkidfdytpnwgrgapssyidn ltfpkvltdkkysyrvvvngsdlgvesnfavtpsggqtinflgynkgygvadtktiqvfvvipdtgns eeyiiaewkkt (SEQ ID NO: 51)

atgagcacgaatcctaaacctcaaagaaaaaccaaacgtaacaccaaccgccgcccacaggacgtcaa gttcccgggcggtggtcagatcgtcggtggagtttacctgttgccgcgcaggggccccaggttgggtg tgcgcgcgactaggaagacttccgagcggtcgcaacctcgtggaaggcgacaacctatccccaaggct cgccagcccgagggtagggcctgggctcagcccgggtacccctggcccctctatggcaatgagggctt ggggtgggcaggatggctcctgtcaccccgtggctctcggcctagttggggccccacggacccccggc gtaggtcgcgcaatttgggtaaggtcatcgataccctcacgtgcggcttcgccgatctcatggggtac cttccgctcgtcggcgcaacagggaatctgcccggttgctcctttttctatcttccttttggctttgct gtcctgtttgaccatcccagcttccgcttatgaagTCCGCCACGTCGCTCACCTTCCAGCTTGCCTAC

TTGGTGAAGAAGATCGACTTCGACTACACCCCCAACTGGGGCCGTGGTGCACCAAGCAGCTACATCGA

CAACCTTACCTTCCCCAAGGTTCTCACCGACAAAAAATACTCGTACCGCGTCGTGGTCAATGGCTCTG

ACCTTGGCGTCGAGTCCAACTTCGCAGTGACACCGTCCGGTGGGCAGACCATCAACTTCCTCCAGTAC

AACAAGGGGTATGGTGTCGCGGACACCAAAACGATTCAAGTTTTCGTTGTCATTCCAGATACCGGCAA

CTCGGAGGAGTACATCATCGCTGAGTGGAAGAAGACTTGA (SEQ ID NO: 52)

-continued

Appendix A: Sequences

FUSION PROTEINS OF TUMOR-ASSOCIATED ANTIGEN AND FVE

MAGE-3-FtreT29A mpleqrsqhckpeegleargealglvgaqapateeqeaasssstivevtlgevpaaespdppqspqga sslpttmnyplwsqsyedssnqeeegpstfpdlesefqaalsrkvaelvhflllkyrarepvtkaeml gsvvgnwqyffpvifskassslqlvfgielmevdpighlyifatclglsydgllgdnqimpkagllii vlaiiaregdcapeekiweelsvlevfegredsilgdpkklltqhfvqenyleyrqvpgsdpacyefl wgpralvetsyvkvlhhmvkisggphisypplhewvlregeesatsltfqlaylvkkidfdytpnwgr gapssyidnitfpkvltdkkysyrvvvngsdlgvesnfavtpsgggtinflgynkgygvadtktigvf vvipdtgnseeyiiaewkkt (SEQ ID NO: 53)

atgcctcttgagcagaggagtcagcactgcaagcctgaagaaggccttgaggcccgaggagaggccct gggcctggtgggtgcgcaggctcctgctactgaggagcaggaggctgcctcctcctcttctactctag ttgaagtcaccctgggggaggtgcctgctgccgagtcaccagatcctccccagagtcctcagggagcc tccagcctccccactaccatgaactaccctctctggagccaatcctatgaggactccagcaaccaaga agaggaggggccaagcaccttccctgacctggagtccgagttccaagcagcactcagtaggaaggtgg ccgagttggttcattttctgctcctcaagtatcgagccagggagccggtcacaaaggcagaaatgctg gggagtgtcgtcggaaattggcagtatttctttcctgtgatcttcagcaaagcttccagttccttgca gctggtctttggcatcgagctgatggaagtggaccccatcggccacttgtacatctttgccacctgcc tgggcctctcctacgatggcctgctgggtgacaatcagatcatgcccaaggcaggcctcctgataatc gtcctggccataatcgcaagagagggcgactgtgcccctgaggagaaaatctgggaggagctgagtgt gttagaggtgtttgaggggagggaagacagtatcttgggggatcccaagaagctgctcacccaacatt tcgtgcaggaaaactacctggagtaccggcaggtccccggcagtgatcctgcatgttatgaattcctg tggggtccaagggccctcgttgaaaccagctatgtgaaagtcctgcaccatatggtaaagatcagtgg aggacctcacatttcctacccacccctgcatgagtgggttttgagagagggggaagagTCCGCCACGT

CGCTCACCTTCCAGCTTGCCTACTTGGTGAAGAAGATCGACTTCGACTACACCCCCAACTGGGGCCGT

GGTGCACCAAGCAGCTACATCGACAACCTTACCTTCCCCAAGGTTCTCACCGACAAAAAATACTCGTA

CCGCGTCGTGGTCAATGGCTCTGACCTTGGCGTCGAGTCCAACTTCGCAGTGACACCGTCCGGTGGGC

AGACCATCAACTTCCTCCAGTACAACAAGGGGTATGGTGTCGCGGACACCAAAACGATTCAAGTTTTC

GTTGTCATTCCAGATACCGGCAACTCGGAGGAGTACATCATCGCTGAGTGGAAGAAGACTTGA
(SEQ ID NO: 54)

MART1-1-FveT29A mpredahfiygypkkghghsyttaeeaagigiltvilgvnligcwycrrrngyralmdkslhvgtqc altrrcpolegfdhrdskvslqekncepvvpnappayeklsaeqspppyspsatsltfqlaylvkki dfdytpnwgrgapssyidnitfpkvltdkkysyrvvvngsdlgvesnfavtpsgggtinflgynkgy gvadtktigvfvvipdtgnseeyiiaewkkt (SEQ ID NO: 55)

atgccaagagaagatgctcacttcatctatggttaccccaagaaggggcacggccactcttacaccac ggctgaagaggccgctgggatcggcatcctgacagtgatcctgggagtcttactgctcatcggctgtt ggtattgtagaagacgaaatggatacagagccttgatggataaaagtcttcatgttggcactcaatgt gccttaacaagaagatgcccacaagaagggtttgatcatcgggacagcaaagtgtctcttcaagagaa aaactgtgaacctgtggttcccaatgctccacctgcttatgagaaactctctgcagaacagtcaccac caccttattcaccTCCGCCACGTCGCTCACCTTCCAGCTTGCCTACTTGGTGAAGAAGATCGACTTC

GACTACACCCCCAACTGGGGCCGTGGTGCACCAAGCAGCTACATCGACAACCTTACCTTCCCCAAGGT

-continued

Appendix A: Sequences

TCTCACCGACAAAAAATACTCGTACCGCGTCGTGGTCAATGGCTCTGACCTTGGCGTCGAGTCCAACT
TCGCAGTGACACCGTCCGGTGGGCAGACCATCAACTTCCTCCAGTACAACAAGGGGTATGGTGTCGCG
GACACCAAAACGATTCAAGTTTTCGTTGTCATTCCAGATACCGGCAACTCGGAGGAGTACATCATCGC
TGAGTGGAAGAAGACTTGA (SEQ ID NO: 56)

CEA-Fve T29A kltiestpfnvaegkevillvhnlpqhlfgyswykgervdgnrqiigyvigtqqatpgpaysgreily
pnaslliciniiqndtgfytlhviksdlyneeatgqfrvypelpkpsissnnskporedkdavaftcepe
tqdatylwwwincislpvsprlqlsngnrtltlfnvtrndtasykcetqnpvsarrsdsvillivlygpd
aptispintsyrsgenlnlschaasnppaaffswfvngtfqqstclelfipnitynnsgsytcqahnsdt
glnrttlittitvyaeppkpfitsnnsnpvededavaltcepeignttylwidynnqslpvsprlqlsnd
nrtltllsvtrndvgpyecgicinelsvdhsdpvilmilygpddptispsytyyrpgvnlslschaasn
ppagyswlidgniqqhtclelfisniteknsglytcgannsasghsrttyktitirsaelpkpsissnns
kpvedkdavaftcepeacinttylwwvngqslpvsprlqlsngnrtltlfnvtrndarayvcgiqnsys
anrsdpvtldvlygpdtpiisppdssylsganlnlschsasnpsmyswringipqqhtqvlfiakit
pnnngtyacfvsnlatgrnnsivksitysasgtspglsagatvgimigylvgvalisatsltfqlayl
vkkidfdytpnwgrgapssyidnitfpkvltdkkysyrvvvngsdlgvesnfavtpsggqtinflqyn
kgygvadtktiqvfvvipdtgnseeyiiaewkkt (SEQ ID NO: 57)

aagctcactattgaatccacgccgttcaatgtcgcagaggggaaggaggtgcttctacttgtccacaa
tctgccccagcatctttttggctacagctggtacaaaggtgaaagagtggatggcaaccgtcaaatta
taggatatgtaataggaactcaacaagctaccccagggcccgcatacagtggtcgagagataatatac
cccaatgcatccctgctgatccagaacatcatccagaatgacacaggattctacaccctacacgtcat
aaagtcagatcttgtgaatgaagaagcaactggccagttccgggtatacccggagctgcccaagccct
ccatctccagcaacaactccaaacccgtggaggacaaggatgctgtggccttcacctgtgaacctgag
actcaggacgcaacctacctgtggtgggtaaacaatcagagcctcccggtcagtcccaggctgcagct
gtccaatggcaacaggaccctcactctattcaatgtcacaagaaatgacacagcaagctacaaatgtg
aaacccagaacccagtgagtgccaggcgcagtgattcagtcatcctgaatgtcctctatggcccggat
gcccccaccatttcccctctaaacacatcttacagatcaggggaaaatctgaacctctcctgccatgc
agcctctaacccacctgcacagtactcttggtttgtcaatgggactttccagcaatccacccaagagc
tctttatccccaacatcactgtgaataatagtggatcctatacgtgccaagcccataactcagacact
ggcctcaataggaccacagtcacgacgatcacagtctatgcagagccacccaaacccttcatcaccag
caacaactccaaccccgtggaggatgaggatgctgtagccttaacctgtgaacctgagattcagaaca
caacctacctgtggtgggtaaataatcagagcctcccggtcagtcccaggctgcagctgtccaatgac
aacaggaccctcactctactcagtgtcacaaggaatgatgtaggaccctatgagtgtggaatccagaa
cgaattaagtgttgaccacagcgacccagtcatcctgaatgtcctctatggcccagacgaccccacca
tttccccctcatacacctattaccgtccaggggtgaacctcagcctctcctgccatgcagcctctaac
ccacctgcacagtattcttggctgattgatgggaacatccagcaacacacacaagagctctttatctc
caacatcactgagaagaacagcggactctatacctgccaggccaataactcagccagtggccacagca
ggactacagtcaagacaatcacagtctctgcggagctgcccaagccctccatctccagcaacaactcc
aaacccgtggaggacaaggatgctgtggccttcacctgtgaacctgaggctcagaacacaacctacct

Appendix A: Sequences gtggtgggtaaatggtcagagcctcccagtcagtcccaggctgcagctgtccaatggcaacaggaccc tcactctattcaatgtcacaagaaatgacgcaagagcctatgtatgtggaatccagaactcagtgagt gcaaaccgcagtgacccagtcaccctggatgtcctctatgggccggacaccccatcatttccccccc agactcgtcttacctttcgggagcgaacctcaacctctcctgccactcggcctctaacccatccccgc agtattcttggcgtatcaatgggataccgcagcaacacacacaagttctctttatcgccaaaatcacg ccaaataataacgggacctatgcctgttttgtctctaacttggctactggccgcaataattccatagt caagagcatcacagtctctgcatctggaacttctcctggtctctcagctggggccactgtcggcatca tgattggagtgctggttggggttgctctgataTCCGCCACGTCGCTCACCTTCCAGCTTGCCTACTTG

GTGAAGAAGATCGACTTCGACTACACCCCCAACTGGGGCCGTGGTGCACCAAGCAGCTACATCGACAA

CCTTACCTTCCCCAAGGTTCTCACCGACAAAAAATACTCGTACCGCGTCGTGGTCAATGGCTCTGACC

TTGGCGTCGAGTCCAACTTCGCAGTGACACCGTCCGGTGGGCAGACCATCAACTTCCTCCAGTACAAC

AAGGGGTATGGTGTCGCGGACACCAAAACGATTCAAGTTTTCGTTGTCATTCCAGATACCGGCAACTC

GGAGGAGTACATCATCGCTGAGTGGAAGAAGACTTGA (SEQ ID NO: 58)

PRIMERS FOR CONSTRUCTION OF FVE DELETION MUTANTS

Fd6-18F (36 mer)
5'-ggA/TCC/TCC/gCC/ACg/TCg/TTC/gAC/TAC/ACC/CCC/AAC-3' (SEQ ID NO: 59)

Fd6-18R (36 mer)
5'-gTT/ggg/ggT/gTA/gTC/gAA/CgA/CgT/ggC/ggA/ggA/TCC-3' (SEQ ID NO: 60)

Fd19-33F (36 mer)
5'-TTg/gTg/AAg/AAg/ATC/gAC/ATC/gAC/AAC/CTT/ACC/TTC-3' (SEQ ID NO: 61)

Fd19-33R (36 mer)
5'-gAA/ggT/AAg/gTT/gTC/gAT/gTC/gAT/CTT/CTT/CAC/CAA-3' (SEQ ID NO: 62)

Fd34-46F (36 mer)
5'-ggT/ACC/CCA/AgC/AgC/TAC/AAA/TAC/TCg/TAC/CgC/gTC-3' (SEQ ID NO: 63)

Fd34-46R (36 mer)
5'-gAC/gCg/gTA/CgA/gTA/TTT/gTA/gCT/gCT/Tgg/ggT/ACC-3' (SEQ ID NO: 64)

Fd47-60F (36 mer)
5'-AAg/gTT/CTC/ACC/gAC/AAA/gTC/gAg/TCC/AAC/TTC/gCA-3' (SEQ ID NO: 65)

Fd47-60R (36 mer)
5'-TgC/gAA/gTT/ggA/CTC/gAC/TTT/gTC/ggT/gAg/AAC/CTT-3' (SEQ ID NO: 66)

Fd61-72F (36 mer)
5'-AAT/ggC/TCT/gAC/CTT/ggC/CAg/ACC/ATC/AAC/TTC/CTC-3' (SEQ ID NO: 67)

Fd61-72R (36 mer)
5'-gAg/gAA/gTT/gAT/ggT/CTg/gCC/AAg/gTC/AgA/gCC/ATT-3' (SEQ ID NO: 68)

Fd73-84F (36 mer)
5'-gTg/ACA/CCg/TCC/ggT/ggg/ggT/gTC/gCg/gAC/ACC/AAA-3' (SEQ ID NO: 69)

Fd73-84R (36 mer)
5'-TTT/ggT/gTC/CgC/gAC/ACC/CCC/ACC/ggA/Cgg/TgT/CAC-3' (SEQ ID NO: 70)

Fd85-97F (36 mer)
5'-CAg/TAC/AAC/AAg/ggg/TAT/ATT/CCA/gAT/ACC/ggC/AAC-3' (SEQ ID NO: 71)

Fd85-97R (36 mer)
5'-gTT/gCC/ggT/ATC/Tgg/AAT/ATA/CCC/CTT/gTT/gTA/CTg-3' (SEQ ID NO: 72)

Fd98-106F (36 mer)
5'-ATT/CAA/gTT/TTC/gTT/gTC/TAC/ATC/ATC/gCT/gAg/Tgg-3' (SEQ ID NO: 731

Fd98-106R (36 mer)
5'-CCA/CTC/AgC/gAT/gAT/gTA/gAC/AAC/gAA/AAC/TTg/AAT-3' (SEQ ID NO: 74)

Fd107-115R (39 mer)
5'-gAT/gCA/ACT/gAA/TTC/TTA/TTA/CTC/CTC/CgA/gTT/gCC/ggT-3' (SEQ ID NO: 75)

-continued

Appendix A: Sequences

PRIMERS FOR CONSTRUCTION OF LARGE FRAGMENT DELETION OF FVE d(61-97)-F (36mer)
5'-/AAT/ggC/TCT/gAC/CTT/ggC/ATT/CCA/gAT/ACC/ggC/AAC/-3' (SEQ ID NO: 76)

d(61-97)-R (36mer)
5'-/gTT/gCC/ggT/ATC/Tgg/AAT/gCC/AAg/gTC/AgA/gCC/ATT/-3' (SEQ ID NO: 77)

PRIMERS FOR CONSTRUCTION OF SMALL FRAGMENT OF FVE (FROM 55AA TO 100AA)

[Fv55-100]-F (48mer)
5'-/gTT/CCg/CgT/ggA/TCC/ATC/gAA/ggT/CgT/AAT/ggC/TCT/gAC/CTT/ggC/gTC/-3' (SEQ ID NO: 78)

[Fv55-100]-R (42mer)
5'-/gAT/gCA/ACT/gAA/TTC/TTA/TCA/ATC/Tgg/AAT/gAC/AAC/gAA/AAC/-3' (SEQ ID NO: 79)

PRIMERS FOR CONSTRUCTION OF POINT MUTANTS OF FVE

F(R27A)-F (27 mer)
5'-CCC/AAC/Tgg/ggC/gCA/ggT/ACC/CCA/AgC-3' (SEQ ID NO: 80)

F(R27A)-R (27 mer)
5'-gCT/Tgg/ggT/ACC/TgC/gCC/CCA/gTT/ggg-3' (SEQ ID NO: 81)

F(G28A)-F (27 mer)
5'-AAC/Tgg/ggC/CgT/gCA/ACC/CCA/AgC/AgC-3' (SEQ ID NO: 82)

F(G28A)-R (27 mer)
5'-gCT/gCT/Tgg/ggT/TgC/ACg/gCC/CCA/gTT-3' (SEQ ID NO: 83)

F(T29A)-F (27 mer)
5'-Tgg/ggC/CgT/ggT/gCA/CCA/AgC/AgC/TAC-3' (SEQ ID NO: 84)

F(T29A)-R (27 mer)
5'-gTA/gCT/gCT/Tgg/TgC/ACC/ACg/gCC/CCA-3' (SEQ ID NO: 85)

PRIMERS FOR BLO T 5-FVE FUSION PROTEIN

Bt5Fv-F (36mer)
5'-/AAg/gAT/ATT/CAA/ACC/CAA/TCC/gCC/ACg/TCg/CTC/ACC/-3' (SEQ ID NO: 86)

Bt5Fv-R (36mer)
5'-/ggT/gAg/CgA/CgT/ggC/ggA/TTg/ggT/TTg/AAT/ATC/CTT/-3' (SEQ ID NO: 87)

PRIMERS FOR DER P 2-FVE FUSION PROTEIN

Dp2Fv-F (36mer)
5'-/CAT/gCT/AAA/ATC/CgC/gAT/TCC/gCC/ACg/TCg/CTC/ACC-3' (SEQ ID NO: 88)

Dp2Fv-R (36mer)
5'-/ggT/gAg/CgA/CgT/ggC/ggA/ATC/gCg/gAT/TTT/AgC/ATg-3' (SEQ ID NO: 89)

PRIMERS FOR BLO T 5-DER P 2-FVE FUSION PROTEIN

Bt5Dp2-F (36mer)
5' -/aag/gat/att/caa/acc/caa/gat/caa/gtc/gat/gtc/aaa/-3' (SEQ ID NO: 90)

Bt5Dp2-R (36mer)
5'-/ttt/gac/atc/gac/ttg/atc/ttg/ggt/ttg/aat/atc/ctt/-3' (SEQ ID NO: 91)

APPENDIX B

FVE FRAGMENTS (RGT TRIPLET HIGHLIGHTED)
(APPENDIX DICLOSES SEQ ID NOS: 92-487, RESPECTIVELY, IN ORDER OF APPEARANCE.)

| Fragment Number | Residues | Sequence |
|---|---|---|
| 1 | 24-28 | WGRGT |
| 2 | 25-29 | GRGTP |
| 3 | 26-30 | RGTPS |
| 4 | 27-31 | GTPSS |
| 5 | 28-32 | TPSSY |
| 6 | 23-28 | NWGRGT |
| 7 | 24-29 | WGRGTP |

APPENDIX B-continued

FVE FRAGMENTS (RGT TRIPLET HIGHLIGHTED)
(APPENDIX DICLOSES SEQ ID NOS: 92-487, RESPECTIVELY, IN ORDER OF APPEARANCE.)

| Fragment Number | Residues | Sequence |
|---|---|---|
| 8 | 25-30 | GRGTPS |
| 9 | 26-31 | RGTPSS |
| 10 | 27-32 | GTPSSY |
| 11 | 28-33 | TPSSYI |
| 12 | 22-28 | PNWGRGT |
| 13 | 23-29 | NWGRGTP |
| 14 | 24-30 | WGRGTPS |

APPENDIX B-continued

FVE FRAGMENTS (RGT TRIPLET HIGHLIGHTED) (APPENDIX DICLOSES SEQ ID NOS: 92-487, RESPECTIVELY, IN ORDER OF APPEARANCE.)

| Fragment Number | Residues | Sequence |
|---|---|---|
| 15 | 25-31 | GRGTPSS |
| 16 | 26-32 | RGTPSSY |
| 17 | 27-33 | GTPSSYI |
| 18 | 28-34 | TPSSYID |
| 19 | 21-28 | TPNWGRGT |
| 20 | 22-29 | PNWGRGTP |
| 21 | 23-30 | NWGRGTPS |
| 22 | 24-31 | WGRGTPSS |
| 23 | 25-32 | GRGTPSSY |
| 24 | 26-33 | RGTPSSYI |
| 25 | 27-34 | GTPSSYID |
| 26 | 28-35 | TPSSYIDN |
| 27 | 20-28 | YTPNWGRGT |
| 28 | 21-29 | TPNWGRGTP |
| 29 | 22-30 | PNWGRGTPS |
| 30 | 23-31 | NWGRGTPSS |
| 31 | 24-32 | WGRGTPSSY |
| 32 | 25-33 | GRGTPSSYI |
| 33 | 26-34 | RGTPSSYID |
| 34 | 27-35 | GTPSSYIDN |
| 35 | 28-36 | TPSSYIDNL |
| 36 | 19-28 | DYTPNWGRGT |
| 37 | 20-29 | YTPNWGRGTP |
| 38 | 21-30 | TPNWGRGTPS |
| 39 | 22-31 | PNWGRGTPSS |
| 40 | 23-32 | NWGRGTPSSY |
| 41 | 24-33 | WGRGTPSSYI |
| 42 | 25-34 | GRGTPSSYID |
| 43 | 26-35 | RGTPSSYIDN |
| 44 | 27-36 | GTPSSYIDNL |
| 45 | 28-37 | TPSSYIDNLT |
| 46 | 18-28 | FDYTPNWGRGT |
| 47 | 19-29 | DYTPNWGRGTP |
| 48 | 20-30 | YTPNWGRGTPS |
| 49 | 21-31 | TPNWGRGTPSS |
| 50 | 22-32 | PNWGRGTPSSY |
| 51 | 23-33 | NWGRGTPSSYI |
| 52 | 24-34 | WGRGTPSSYID |
| 53 | 25-35 | GRGTPSSYIDN |
| 54 | 26-36 | RGTPSSYIDNL |
| 55 | 27-37 | GTPSSYIDNLT |
| 56 | 28-38 | TPSSYIDNLTF |
| 57 | 17-28 | DFDYTPNWGRGT |
| 58 | 18-29 | FDYTPNWGRGTP |
| 59 | 19-30 | DYTPNWGRGTPS |
| 60 | 20-31 | YTPNWGRGTPSS |
| 61 | 21-32 | TPNWGRGTPSSY |
| 62 | 22-33 | PNWGRGTPSSYI |
| 63 | 23-34 | NWGRGTPSSYID |
| 64 | 24-35 | WGRGTPSSYIDN |
| 65 | 25-36 | GRGTPSSYIDNL |
| 66 | 26-37 | RGTPSSYIDNLT |
| 67 | 27-38 | GTPSSYIDNLTF |
| 68 | 28-39 | TPSSYIDNLTFP |
| 69 | 16-28 | IDFDYTPNWGRGT |
| 70 | 17-29 | DFDYTPNWGRGTP |
| 71 | 18-30 | FDYTPNWGRGTPS |
| 72 | 19-31 | DYTPNWGRGTPSS |
| 73 | 20-32 | YTPNWGRGTPSSY |
| 74 | 21-33 | TPNWGRGTPSSYI |
| 75 | 22-34 | PNWGRGTPSSYID |
| 76 | 23-35 | NWGRGTPSSYIDN |
| 77 | 24-36 | WGRGTPSSYIDNL |
| 78 | 25-37 | GRGTPSSYIDNLT |
| 79 | 26-38 | RGTPSSYIDNLTF |
| 80 | 27-39 | GTPSSYIDNLTFP |
| 81 | 28-40 | TPSSYIDNLTFPK |
| 82 | 15-28 | KIDFDYTPNWGRGT |
| 83 | 16-29 | IDFDYTPNWGRGTP |
| 84 | 17-30 | DFDYTPNWGRGTPS |
| 85 | 18-31 | FDYTPNWGRGTPSS |
| 86 | 19-32 | DYTPNWGRGTPSSY |
| 87 | 20-33 | YTPNWGRGTPSSYI |

APPENDIX B-continued

FVE FRAGMENTS (RGT TRIPLET HIGHLIGHTED) (APPENDIX DICLOSES SEQ ID NOS: 92-487, RESPECTIVELY, IN ORDER OF APPEARANCE.)

| Fragment Number | Residues | Sequence |
|---|---|---|
| 88 | 21-34 | TPNWGRGTPSSYID |
| 89 | 22-35 | PNWGRGTPSSYIDN |
| 90 | 23-36 | NWGRGTPSSYIDNL |
| 91 | 24-37 | WGRGTPSSYIDNLT |
| 92 | 25-38 | GRGTPSSYIDNLTF |
| 93 | 26-39 | RGTPSSYIDNLTFP |
| 94 | 27-40 | GTPSSYIDNLTFPK |
| 95 | 28-41 | TPSSYIDNLTFPKV |
| 96 | 14-28 | KKIDFDYTPNWGRGT |
| 97 | 15-29 | KIDFDYTPNWGRGTP |
| 98 | 16-30 | IDFDYTPNWGRGTPS |
| 99 | 17-31 | DFDYTPNWGRGTPSS |
| 100 | 18-32 | FDYTPNWGRGTPSSY |
| 101 | 19-33 | DYTPNWGRGTPSSYI |
| 102 | 20-34 | YTPNWGRGTPSSYID |
| 103 | 21-35 | TPNWGRGTPSSYIDN |
| 104 | 22-36 | PNWGRGTPSSYIDNL |
| 105 | 23-37 | NWGRGTPSSYIDNLT |
| 106 | 24-38 | WGRGTPSSYIDNLTF |
| 107 | 25-39 | GRGTPSSYIDNLTFP |
| 108 | 26-40 | RGTPSSYIDNLTFPK |
| 109 | 27-41 | GTPSSYIDNLTFPKV |
| 110 | 28-42 | TPSSYIDNLTFPKVL |
| 111 | 13-28 | VKKIDFDYTPNWGRGT |
| 112 | 14-29 | KKIDFDYTPNWGRGTP |
| 113 | 15-30 | KIDFDYTPNWGRGTPS |
| 114 | 16-31 | IDFDYTPNWGRGTPSS |
| 115 | 17-32 | DFDYTPNWGRGTPSSY |
| 116 | 18-33 | FDYTPNWGRGTPSSYI |
| 117 | 19-34 | DYTPNWGRGTPSSYID |
| 118 | 20-35 | YTPNWGRGTPSSYIDN |
| 119 | 21-36 | TPNWGRGTPSSYIDNL |
| 120 | 22-37 | PNWGRGTPSSYIDNLT |
| 121 | 23-38 | NWGRGTPSSYIDNLTF |
| 122 | 24-39 | WGRGTPSSYIDNLTFP |
| 123 | 25-40 | GRGTPSSYIDNLTFPK |
| 124 | 26-41 | RGTPSSYIDNLTFPKV |
| 125 | 27-42 | GTPSSYIDNLTFPKVL |
| 126 | 28-43 | TPSSYIDNLTFPKVLT |
| 127 | 12-28 | LVKKIDFDYTPNWGRGT |
| 128 | 13-29 | VKKIDFDYTPNWGRGTP |
| 129 | 14-30 | KKIDFDYTPNWGRGTPS |
| 130 | 15-31 | KIDFDYTPNWGRGTPSS |
| 131 | 16-32 | IDFDYTPNWGRGTPSSY |
| 132 | 17-33 | DFDYTPNWGRGTPSSYI |
| 133 | 18-34 | FDYTPNWGRGTPSSYID |
| 134 | 19-35 | DYTPNWGRGTPSSYIDN |
| 135 | 20-36 | YTPNWGRGTPSSYIDNL |
| 136 | 21-37 | TPNWGRGTPSSYIDNLT |
| 137 | 22-38 | PNWGRGTPSSYIDNLTF |
| 138 | 23-39 | NWGRGTPSSYIDNLTFP |
| 139 | 24-40 | WGRGTPSSYIDNLTFPK |
| 140 | 25-41 | GRGTPSSYIDNLTFPKV |
| 141 | 26-42 | RGTPSSYIDNLTFPKVL |
| 142 | 27-43 | GTPSSYIDNLTFPKVLT |
| 143 | 28-44 | TPSSYIDNLTFPKVLTD |
| 144 | 11-28 | YLVKKIDFDYTPNWGRGT |
| 145 | 12-29 | LVKKIDFDYTPNWGRGTP |
| 146 | 13-30 | VKKIDFDYTPNWGRGTPS |
| 147 | 14-31 | KKIDFDYTPNWGRGTPSS |
| 148 | 15-32 | KIDFDYTPNWGRGTPSSY |
| 149 | 16-33 | IDFDYTPNWGRGTPSSYI |
| 150 | 17-34 | DFDYTPNWGRGTPSSYID |
| 151 | 18-35 | FDYTPNWGRGTPSSYIDN |
| 152 | 19-36 | DYTPNWGRGTPSSYIDNL |
| 153 | 20-37 | YTPNWGRGTPSSYIDNLT |
| 154 | 21-38 | TPNWGRGTPSSYIDNLTF |
| 155 | 22-39 | PNWGRGTPSSYIDNLTFP |
| 156 | 23-40 | NWGRGTPSSYIDNLTFPK |
| 157 | 24-41 | WGRGTPSSYIDNLTFPKV |
| 158 | 25-42 | GRGTPSSYIDNLTFPKVL |
| 159 | 26-43 | RGTPSSYIDNLTFPKVLT |
| 160 | 27-44 | GTPSSYIDNLTFPKVLTD |

APPENDIX B-continued

FVE FRAGMENTS (RGT TRIPLET HIGHLIGHTED)
(APPENDIX DICLOSES SEQ ID NOS: 92-487,
RESPECTIVELY, IN ORDER OF APPEARANCE.)

| Fragment Number | Residues | Sequence |
|---|---|---|
| 161 | 28-45 | TPSSYIDNLTFPKVLTDK |
| 162 | 10-28 | AYLVKKIDFDYTPNWGRGT |
| 163 | 11-29 | YLVKKIDFDYTPNWGRGTP |
| 164 | 12-30 | LVKKIDFDYTPNWGRGTPS |
| 165 | 13-31 | VKKIDFDYTPNWGRGTPSS |
| 166 | 14-32 | KKIDFDYTPNWGRGTPSSY |
| 167 | 15-33 | KIDFDYTPNWGRGTPSSYI |
| 168 | 16-34 | IDFDYTPNWGRGTPSSYID |
| 169 | 17-35 | DFDYTPNWGRGTPSSYIDN |
| 170 | 18-36 | FDYTPNWGRGTPSSYIDNL |
| 171 | 19-37 | DYTPNWGRGTPSSYIDNLT |
| 172 | 20-38 | YTPNWGRGTPSSYIDNLTF |
| 173 | 21-39 | TPNWGRGTPSSYIDNLTFP |
| 174 | 22-40 | PNWGRGTPSSYIDNLTFPK |
| 175 | 23-41 | NWGRGTPSSYIDNLTFPKV |
| 176 | 24-42 | WGRGTPSSYIDNLTFPKVL |
| 177 | 25-43 | GRGTPSSYIDNLTFPKVLT |
| 178 | 26-44 | RGTPSSYIDNLTFPKVLTD |
| 179 | 27-45 | GTPSSYIDNLTFPKVLTDK |
| 180 | 28-46 | TPSSYIDNLTFPKVLTDKK |
| 181 | 9-28 | LAYLVKKIDFDYTPNWGRGT |
| 182 | 10-29 | AYLVKKIDFDYTPNWGRGTP |
| 183 | 11-30 | YLVKKIDFDYTPNWGRGTPS |
| 184 | 12-31 | LVKKIDFDYTPNWGRGTPSS |
| 185 | 13-32 | VKKIDFDYTPNWGRGTPSSY |
| 186 | 14-33 | KKIDFDYTPNWGRGTPSSYI |
| 187 | 15-34 | KIDFDYTPNWGRGTPSSYID |
| 188 | 16-35 | IDFDYTPNWGRGTPSSYIDN |
| 189 | 17-36 | DFDYTPNWGRGTPSSYIDNL |
| 190 | 18-37 | FDYTPNWGRGTPSSYIDNLT |
| 191 | 19-38 | DYTPNWGRGTPSSYIDNLTF |
| 192 | 20-39 | YTPNWGRGTPSSYIDNLTFP |
| 193 | 21-40 | TPNWGRGTPSSYIDNLTFPK |
| 194 | 22-41 | PNWGRGTPSSYIDNLTFPKV |
| 195 | 23-42 | NWGRGTPSSYIDNLTFPKVL |
| 196 | 24-43 | WGRGTPSSYIDNLTFPKVLT |
| 197 | 25-44 | GRGTPSSYIDNLTFPKVLTD |
| 198 | 26-45 | RGTPSSYIDNLTFPKVLTDK |
| 199 | 27-46 | GTPSSYIDNLTFPKVLTDKK |
| 200 | 28-47 | TPSSYIDNLTFPKVLTDKKY |
| 201 | 8-28 | QLAYLVKKIDFDYTPNWGRGT |
| 202 | 9-29 | LAYLVKKIDFDYTPNWGRGTP |
| 203 | 10-30 | AYLVKKIDFDYTPNWGRGTPS |
| 204 | 11-31 | YLVKKIDFDYTPNWGRGTPSS |
| 205 | 12-32 | LVKKIDFDYTPNWGRGTPSSY |
| 206 | 13-33 | VKKIDFDYTPNWGRGTPSSYI |
| 207 | 14-34 | KKIDFDYTPNWGRGTPSSYID |
| 208 | 15-35 | KIDFDYTPNWGRGTPSSYIDN |
| 209 | 16-36 | IDFDYTPNWGRGTPSSYIDNL |
| 210 | 17-37 | DFDYTPNWGRGTPSSYIDNLT |
| 211 | 18-38 | FDYTPNWGRGTPSSYIDNLTF |
| 212 | 19-39 | DYTPNWGRGTPSSYIDNLTFP |
| 213 | 20-40 | YTPNWGRGTPSSYIDNLTFPK |
| 214 | 21-41 | TPNWGRGTPSSYIDNLTFPKV |
| 215 | 22-42 | PNWGRGTPSSYIDNLTFPKVL |
| 216 | 23-43 | NWGRGTPSSYIDNLTFPKVLT |
| 217 | 24-44 | WGRGTPSSYIDNLTFPKVLTD |
| 218 | 25-45 | GRGTPSSYIDNLTFPKVLTDK |
| 219 | 26-46 | RGTPSSYIDNLTFPKVLTDKK |
| 220 | 27-47 | GTPSSYIDNLTFPKVLTDKKY |
| 221 | 28-48 | TPSSYIDNLTFPKVLTDKKYS |
| 222 | 7-28 | FQLAYLVKKIDFDYTPNWGRGT |
| 223 | 8-29 | QLAYLVKKIDFDYTPNWGRGTP |
| 224 | 9-30 | LAYLVKKIDFDYTPNWGRGTPS |
| 225 | 10-31 | AYLVKKIDFDYTPNWGRGTPSS |
| 226 | 11-32 | YLVKKIDFDYTPNWGRGTPSSY |
| 227 | 12-33 | LVKKIDFDYTPNWGRGTPSSYI |
| 228 | 13-34 | VKKIDFDYTPNWGRGTPSSYID |
| 229 | 14-35 | KKIDFDYTPNWGRGTPSSYIDN |
| 230 | 15-36 | KIDFDYTPNWGRGTPSSYIDNL |
| 231 | 16-37 | IDFDYTPNWGRGTPSSYIDNLT |
| 232 | 17-38 | DFDYTPNWGRGTPSSYIDNLTF |
| 233 | 18-39 | FDYTPNWGRGTPSSYIDNLTFP |

APPENDIX B-continued

FVE FRAGMENTS (RGT TRIPLET HIGHLIGHTED)
(APPENDIX DICLOSES SEQ ID NOS: 92-487,
RESPECTIVELY, IN ORDER OF APPEARANCE.)

| Fragment Number | Residues | Sequence |
|---|---|---|
| 234 | 19-40 | DYTPNWGRGTPSSYIDNLTFPK |
| 235 | 20-41 | YTPNWGRGTPSSYIDNLTFPKV |
| 236 | 21-42 | TPNWGRGTPSSYIDNLTFPKVL |
| 237 | 22-43 | PNWGRGTPSSYIDNLTFPKVLT |
| 238 | 23-44 | NWGRGTPSSYIDNLTFPKVLTD |
| 239 | 24-45 | WGRGTPSSYIDNLTFPKVLTDK |
| 240 | 25-46 | GRGTPSSYIDNLTFPKVLTDKK |
| 241 | 26-47 | RGTPSSYIDNLTFPKVLTDKKY |
| 242 | 27-48 | GTPSSYIDNLTFPKVLTDKKYS |
| 243 | 28-49 | TPSSYIDNLTFPKVLTDKKYSY |
| 244 | 6-28 | TFQLAYLVKKIDFDYTPNWGRGT |
| 245 | 7-29 | FQLAYLVKKIDFDYTPNWGRGTP |
| 246 | 8-30 | QLAYLVKKIDFDYTPNWGRGTPS |
| 247 | 9-31 | LAYLVKKIDFDYTPNWGRGTPSS |
| 248 | 10-32 | AYLVKKIDFDYTPNWGRGTPSSY |
| 249 | 11-33 | YLVKKIDFDYTPNWGRGTPSSYI |
| 250 | 12-34 | LVKKIDFDYTPNWGRGTPSSYID |
| 251 | 13-35 | VKKIDFDYTPNWGRGTPSSYIDN |
| 252 | 14-36 | KKIDFDYTPNWGRGTPSSYIDNL |
| 253 | 15-37 | KIDFDYTPNWGRGTPSSYIDNLT |
| 254 | 16-38 | IDFDYTPNWGRGTPSSYIDNLTF |
| 255 | 17-39 | DFDYTPNWGRGTPSSYIDNLTFP |
| 256 | 18-40 | FDYTPNWGRGTPSSYIDNLTFPK |
| 257 | 19-41 | DYTPNWGRGTPSSYIDNLTFPKV |
| 258 | 20-42 | YTPNWGRGTPSSYIDNLTFPKVL |
| 259 | 21-43 | TPNWGRGTPSSYIDNLTFPKVLT |
| 260 | 22-44 | PNWGRGTPSSYIDNLTFPKVLTD |
| 261 | 23-45 | NWGRGTPSSYIDNLTFPKVLTDK |
| 262 | 24-46 | WGRGTPSSYIDNLTFPKVLTDKK |
| 263 | 25-47 | GRGTPSSYIDNLTFPKVLTDKKY |
| 264 | 26-48 | RGTPSSYIDNLTFPKVLTDKKYS |
| 265 | 27-49 | GTPSSYIDNLTFPKVLTDKKYSY |
| 266 | 28-50 | TPSSYIDNLTFPKVLTDKKYSYR |
| 267 | 5-28 | LTFQLAYLVKKIDFDYTPNWGRGT |
| 268 | 6-29 | TFQLAYLVKKIDFDYTPNWGRGTP |
| 269 | 7-30 | FQLAYLVKKIDFDYTPNWGRGTPS |
| 270 | 8-31 | QLAYLVKKIDFDYTPNWGRGTPSS |
| 271 | 9-32 | LAYLVKKIDFDYTPNWGRGTPSSY |
| 272 | 10-33 | AYLVKKIDFDYTPNWGRGTPSSYI |
| 273 | 11-34 | YLVKKIDFDYTPNWGRGTPSSYID |
| 274 | 12-35 | LVKKIDFDYTPNWGRGTPSSYIDN |
| 275 | 13-36 | VKKIDFDYTPNWGRGTPSSYIDNL |
| 276 | 14-37 | KKIDFDYTPNWGRGTPSSYIDNLT |
| 277 | 15-38 | KIDFDYTPNWGRGTPSSYIDNLTF |
| 278 | 16-39 | IDFDYTPNWGRGTPSSYIDNLTFP |
| 279 | 17-40 | DFDYTPNWGRGTPSSYIDNLTFPK |
| 280 | 18-41 | FDYTPNWGRGTPSSYIDNLTFPKV |
| 281 | 19-42 | DYTPNWGRGTPSSYIDNLTFPKVL |
| 282 | 20-43 | YTPNWGRGTPSSYIDNLTFPKVLT |
| 283 | 21-44 | TPNWGRGTPSSYIDNLTFPKVLTD |
| 284 | 22-45 | PNWGRGTPSSYIDNLTFPKVLTDK |
| 285 | 23-46 | NWGRGTPSSYIDNLTFPKVLTDKK |
| 286 | 24-47 | WGRGTPSSYIDNLTFPKVLTDKKY |
| 287 | 25-48 | GRGTPSSYIDNLTFPKVLTDKKYS |
| 288 | 26-49 | RGTPSSYIDNLTFPKVLTDKKYSY |
| 289 | 27-50 | GTPSSYIDNLTFPKVLTDKKYSYR |
| 290 | 28-51 | TPSSYIDNLTFPKVLTDKKYSYRV |
| 291 | 4-28 | SLTFQLAYLVKKIDFDYTPNWGRGT |
| 292 | 5-29 | LTFQLAYLVKKIDFDYTPNWGRGTP |
| 293 | 6-30 | TFQLAYLVKKIDFDYTPNWGRGTPS |
| 294 | 7-31 | FQLAYLVKKIDFDYTPNWGRGTPSS |
| 295 | 8-32 | QLAYLVKKIDFDYTPNWGRGTPSSY |
| 296 | 9-33 | LAYLVKKIDFDYTPNWGRGTPSSYI |
| 297 | 10-34 | AYLVKKIDFDYTPNWGRGTPSSYID |
| 298 | 11-35 | YLVKKIDFDYTPNWGRGTPSSYIDN |
| 299 | 12-36 | LVKKIDFDYTPNWGRGTPSSYIDNL |
| 300 | 13-37 | VKKIDFDYTPNWGRGTPSSYIDNLT |
| 301 | 14-38 | KKIDFDYTPNWGRGTPSSYIDNLTF |
| 302 | 15-39 | KIDFDYTPNWGRGTPSSYIDNLTFP |
| 303 | 16-40 | IDFDYTPNWGRGTPSSYIDNLTFPK |
| 304 | 17-41 | DFDYTPNWGRGTPSSYIDNLTFPKV |
| 305 | 18-42 | FDYTPNWGRGTPSSYIDNLTFPKVL |
| 306 | 19-43 | DYTPNWGRGTPSSYIDNLTFPKVLT |

APPENDIX B-continued

FVE FRAGMENTS (RGT TRIPLET HIGHLIGHTED)
(APPENDIX DICLOSES SEQ ID NOS: 92-487,
RESPECTIVELY, IN ORDER OF APPEARANCE.)

| Fragment Number | Residues | Sequence |
|---|---|---|
| 307 | 20-44 | YTPNWGRGTPSSYIDNLTFPKVLTD |
| 308 | 21-45 | TPNWGRGTPSSYIDNLTFPKVLTDK |
| 309 | 22-46 | PNWGRGTPSSYIDNLTFPKVLTDKK |
| 310 | 23-47 | NWGRGTPSSYIDNLTFPKVLTDKKY |
| 311 | 24-48 | WGRGTPSSYIDNLTFPKVLTDKKYS |
| 312 | 25-49 | GRGTPSSYIDNLTFPKVLTDKKYSY |
| 313 | 26-50 | RGTPSSYIDNLTFPKVLTDKKYSYR |
| 314 | 27-51 | GTPSSYIDNLTFPKVLTDKKYSYRV |
| 315 | 28-52 | TPSSYIDNLTFPKVLTDKKYSYRVV |
| 316 | 3-28 | TSLTFQLAYLVKKIDFDYTPNWGRGT |
| 317 | 4-29 | SLTFQLAYLVKKIDFDYTPNWGRGTP |
| 318 | 5-30 | LTFQLAYLVKKIDFDYTPNWGRGTPS |
| 319 | 6-31 | TFQLAYLVKKIDFDYTPNWGRGTPSS |
| 320 | 7-32 | FQLAYLVKKIDFDYTPNWGRGTPSSY |
| 321 | 8-33 | QLAYLVKKIDFDYTPNWGRGTPSSYI |
| 322 | 9-34 | LAYLVKKIDFDYTPNWGRGTPSSYID |
| 323 | 10-35 | AYLVKKIDFDYTPNWGRGTPSSYIDN |
| 324 | 11-36 | YLVKKIDFDYTPNWGRGTPSSYIDNL |
| 325 | 12-37 | LVKKIDFDYTPNWGRGTPSSYIDNLT |
| 326 | 13-38 | VKKIDFDYTPNWGRGTPSSYIDNLTF |
| 327 | 14-39 | KKIDFDYTPNWGRGTPSSYIDNLTFP |
| 328 | 15-40 | KIDFDYTPNWGRGTPSSYIDNLTFPK |
| 329 | 16-41 | IDFDYTPNWGRGTPSSYIDNLTFPKV |
| 330 | 17-42 | DFDYTPNWGRGTPSSYIDNLTFPKVL |
| 331 | 18-43 | FDYTPNWGRGTPSSYIDNLTFPKVLT |
| 332 | 19-44 | DYTPNWGRGTPSSYIDNLTFPKVLTD |
| 333 | 20-45 | YTPNWGRGTPSSYIDNLTFPKVLTDK |
| 334 | 21-46 | TPNWGRGTPSSYIDNLTFPKVLTDKK |
| 335 | 22-47 | PNWGRGTPSSYIDNLTFPKVLTDKKY |
| 336 | 23-48 | NWGRGTPSSYIDNLTFPKVLTDKKYS |
| 337 | 24-49 | WGRGTPSSYIDNLTFPKVLTDKKYSY |
| 338 | 25-50 | GRGTPSSYIDNLTFPKVLTDKKYSYR |
| 339 | 26-51 | RGTPSSYIDNLTFPKVLTDKKYSYRV |
| 340 | 27-52 | GTPSSYIDNLTFPKVLTDKKYSYRVV |
| 341 | 28-53 | TPSSYIDNLTFPKVLTDKKYSYRVVV |
| 342 | 2-28 | ATSLTFQLAYLVKKIDFDYTPNWGRGT |
| 343 | 3-29 | TSLTFQLAYLVKKIDFDYTPNWGRGTP |
| 344 | 4-30 | SLTFQLAYLVKKIDFDYTPNWGRGTPS |
| 345 | 5-31 | LTFQLAYLVKKIDFDYTPNWGRGTPSS |
| 346 | 6-32 | TFQLAYLVKKIDFDYTPNWGRGTPSSY |
| 347 | 7-33 | FQLAYLVKKIDFDYTPNWGRGTPSSYI |
| 348 | 8-34 | QLAYLVKKIDFDYTPNWGRGTPSSYID |
| 349 | 9-35 | LAYLVKKIDFDYTPNWGRGTPSSYIDN |
| 350 | 10-36 | AYLVKKIDFDYTPNWGRGTPSSYIDNL |
| 351 | 11-37 | YLVKKIDFDYTPNWGRGTPSSYIDNLT |
| 352 | 12-38 | LVKKIDFDYTPNWGRGTPSSYIDNLTF |
| 353 | 13-39 | VKKIDFDYTPNWGRGTPSSYIDNLTFP |
| 354 | 14-40 | KKIDFDYTPNWGRGTPSSYIDNLTFPK |
| 355 | 15-41 | KIDFDYTPNWGRGTPSSYIDNLTFPKV |
| 356 | 16-42 | IDFDYTPNWGRGTPSSYIDNLTFPKVL |
| 357 | 17-43 | DFDYTPNWGRGTPSSYIDNLTFPKVLT |
| 358 | 18-44 | FDYTPNWGRGTPSSYIDNLTFPKVLTD |
| 359 | 19-45 | DYTPNWGRGTPSSYIDNLTFPKVLTDK |
| 360 | 20-46 | YTPNWGRGTPSSYIDNLTFPKVLTDKK |
| 361 | 21-47 | TPNWGRGTPSSYIDNLTFPKVLTDKKY |
| 362 | 22-48 | PNWGRGTPSSYIDNLTFPKVLTDKKYS |
| 363 | 23-49 | NWGRGTPSSYIDNLTFPKVLTDKKYSY |
| 364 | 24-50 | WGRGTPSSYIDNLTFPKVLTDKKYSYR |
| 365 | 25-51 | GRGTPSSYIDNLTFPKVLTDKKYSYRV |
| 366 | 26-52 | RGTPSSYIDNLTFPKVLTDKKYSYRVV |
| 367 | 27-53 | GTPSSYIDNLTFPKVLTDKKYSYRVVV |
| 368 | 28-54 | TPSSYIDNLTFPKVLTDKKYSYRVVVN |
| 369 | 1-28 | SATSLTFQLAYLVKKIDFDYTPNWGRGT |
| 370 | 2-29 | ATSLTFQLAYLVKKIDFDYTPNWGRGTP |
| 371 | 3-30 | TSLTFQLAYLVKKIDFDYTPNWGRGTPS |
| 372 | 4-31 | SLTFQLAYLVKKIDFDYTPNWGRGTPSS |
| 373 | 5-32 | LTFQLAYLVKKIDFDYTPNWGRGTPSSY |
| 374 | 6-33 | TFQLAYLVKKIDFDYTPNWGRGTPSSYI |
| 375 | 7-34 | FQLAYLVKKIDFDYTPNWGRGTPSSYID |
| 376 | 8-35 | QLAYLVKKIDFDYTPNWGRGTPSSYIDN |
| 377 | 9-36 | LAYLVKKIDFDYTPNWGRGTPSSYIDNL |
| 378 | 10-37 | AYLVKKIDFDYTPNWGRGTPSSYIDNLT |
| 379 | 11-38 | YLVKKIDFDYTPNWGRGTPSSYIDNLTF |
| 380 | 12-39 | LVKKIDFDYTPNWGRGTPSSYIDNLTFP |
| 381 | 13-40 | VKKIDFDYTPNWGRGTPSSYIDNLTFPK |
| 382 | 14-41 | KKIDFDYTPNWGRGTPSSYIDNLTFPKV |
| 383 | 15-42 | KIDFDYTPNWGRGTPSSYIDNLTFPKVL |
| 384 | 16-43 | IDFDYTPNWGRGTPSSYIDNLTFPKVLT |
| 385 | 17-44 | DFDYTPNWGRGTPSSYIDNLTFPKVLTD |
| 386 | 18-45 | FDYTPNWGRGTPSSYIDNLTFPKVLTDK |
| 387 | 19-46 | DYTPNWGRGTPSSYIDNLTFPKVLTDKK |
| 388 | 20-47 | YTPNWGRGTPSSYIDNLTFPKVLTDKKY |
| 389 | 21-48 | TPNWGRGTPSSYIDNLTFPKVLTDKKYS |
| 390 | 22-49 | PNWGRGTPSSYIDNLTFPKVLTDKKYSY |
| 391 | 23-50 | NWGRGTPSSYIDNLTFPKVLTDKKYSYR |
| 392 | 24-51 | WGRGTPSSYIDNLTFPKVLTDKKYSYRV |
| 393 | 25-52 | GRGTPSSYIDNLTFPKVLTDKKYSYRVV |
| 394 | 26-53 | RGTPSSYIDNLTFPKVLTDKKYSYRVVV |
| 395 | 27-54 | GTPSSYIDNLTFPKVLTDKKYSYRVVVN |
| 396 | 28-55 | TPSSYIDNLTFPKVLTDKKYSYRVVVNG |

Appendix C: Crystal Coordinates of Fve Protein

HEADER - - -XX-XXX-XX xxxx

COMPND - - -

REMARK 3

REMARK 3 REFINEMENT.

REMARK 3 PROGRAM: REFMAC 5.0

REMARK 3 AUTHORS: MURSHUDOV, VAGIN, DODSON

REMARK 3

REMARK 3 REFINEMENT TARGET: MAXIMUM LIKELIHOOD

REMARK 3

REMARK 3 DATA USED IN REFINEMENT.

REMARK 3 RESOLUTION RANGE HIGH (ANGSTROMS): 1.70

REMARK 3 RESOLUTION RANGE LOW (ANGSTROMS): 30.02

REMARK 3 DATA CUTOFF (SIGMA(F)): NONE

REMARK 3 COMPLETENESS FOR RANGE (%): 98.80

REMARK 3 NUMBER OF REFLECTIONS: 30783

REMARK 3

REMARK 3 FIT TO DATA USED IN REFINEMENT.

REMARK 3 CROSS-VALIDATION METHOD: THROUGHOUT

REMARK 3 FREE R VALUE TEST SET SELECTION: RANDOM

REMARK 3 R VALUE (WORKING+TEST SET): 0.18358

REMARK 3 R VALUE (WORKING SET): 0.18218

REMARK 3 FREE R VALUE: 0.21016

REMARK 3 FREE R VALUE TEST SET SIZE (%): 5.1

REMARK 3 FREE R VALUE TEST SET COUNT: 1650

REMARK 3

REMARK 3 FIT IN THE HIGHEST RESOLUTION BIN.

REMARK 3 TOTAL NUMBER OF BINS USED: 20

REMARK 3 BIN RESOLUTION RANGE HIGH: 1.701

REMARK 3 BIN RESOLUTION RANGE LOW: 1.745

REMARK 3 REFLECTION IN BIN (WORKING SET): 2183

REMARK 3 BIN R VALUE (WORKING SET): 0.160

REMARK 3 BIN FREE R VALUE SET COUNT: 114

REMARK 3 BIN FREE R VALUE: 0.197

REMARK 3

REMARK 3 NUMBER OF NON-HYDROGEN ATOMS USED IN REFINEMENT.

REMARK 3 ALL ATOMS: 1940
REMARK 3
REMARK 3 B VALUES.
REMARK 3 FROM WILSON PLOT (A**2): NULL
REMARK 3 MEAN B VALUE (OVERALL, A**2): 13.666
REMARK 3 OVERALL ANISOTROPIC B VALUE.
REMARK 3 B11 (A**2): −0.02
REMARK 3 B22 (A**2): −0.02
REMARK 3 B33 (A**2): 0.03
REMARK 3 B12 (A**2): 0.00
REMARK 3 B13 (A**2): 0.00
REMARK 3 B23 (A**2): 0.00
REMARK 3
REMARK 3 ESTIMATED OVERALL COORDINATE ERROR.
REMARK 3 ESU BASED ON R VALUE (A): 0.092
REMARK 3 ESU BASED ON FREE R VALUE (A): 0.092
REMARK 3 ESU BASED ON MAXIMUM LIKELIHOOD (A): 0.075
REMARK 3 ESU FOR B VALUES BASED ON MAXIMUM LIKELIHOOD (A**2): 2.208
REMARK 3
REMARK 3 CORRELATION COEFFICIENTS.
REMARK 3 CORRELATION COEFFICIENT FO-FC: 0.947
REMARK 3 CORRELATION COEFFICIENT FO-FC FREE: 0.933
REMARK 3
REMARK 3 RMS DEVIATIONS FROM IDEAL VALUES COUNT RMS WEIGHT
REMARK 3 BOND LENGTHS REFINED ATOMS (A): 1830; 0.010; 0.022
REMARK 3 BOND LENGTHS OTHERS (A): 1593; 0.001; 0.020
REMARK 3 BOND ANGLES REFINED ATOMS (DEGREES): 2490; 1.466; 1.941
REMARK 3 BOND ANGLES OTHERS (DEGREES): 3724; 0.921; 3.000
REMARK 3 TORSION ANGLES, PERIOD 1 (DEGREES): 224; 4.899; 3.000
REMARK 3 TORSION ANGLES, PERIOD 3 (DEGREES): 311; 16.844; 15.000
REMARK 3 CHIRAL-CENTER RESTRAINTS (A**3): 280; 0.231; 0.200
REMARK 3 GENERAL PLANES REFINED ATOMS (A): 2026; 0.006; 0.020
REMARK 3 GENERAL PLANES OTHERS (A): 374; 0.003; 0.020
REMARK 3 NON-BONDED CONTACTS REFINED ATOMS (A): 327; 0.271; 0.300
REMARK 3 NON-BONDED CONTACTS OTHERS (A): 1447; 0.212; 0.300
REMARK 3 H-BOND (X . . . Y) REFINED ATOMS (A): 131; 0.131; 0.500
REMARK 3 SYMMETRY VDW REFINED ATOMS (A): 8; 0.310; 0.300
REMARK 3 SYMMETRY VDW OTHERS (A): 17; 0.291; 0.300
REMARK 3 SYMMETRY H-BOND REFINED ATOMS (A): 14; 0.144; 0.500
REMARK 3
REMARK 3 ISOTROPIC THERMAL FACTOR RESTRAINTS. COUNT RMS WEIGHT
REMARK 3 MAIN-CHAIN BOND REFINED ATOMS (A**2): 1124; 0.898; 1.500
REMARK 3 MAIN-CHAIN ANGLE REFINED ATOMS (A**2): 1827; 1.603; 2.000
REMARK 3 SIDE-CHAIN BOND REFINED ATOMS (A**2): 706; 2.292; 3.000
REMARK 3 SIDE-CHAIN ANGLE REFINED ATOMS (A**2): 663; 3.839; 4.500
REMARK 3
REMARK 3 NCS RESTRAINTS STATISTICS
REMARK 3 NUMBER OF NCS GROUPS: NULL
REMARK 3
REMARK 3
REMARK 3 TLS DETAILS
REMARK 3 NUMBER OF TLS GROUPS: 2
REMARK 3
REMARK 3 TLS GROUP: 1
REMARK 3 NUMBER OF COMPONENTS GROUP: 1
REMARK 3 COMPONENTS C SSSEQI TO C SSSEQI
REMARK 3 RESIDUE RANGE: A 1 A 113
REMARK 3 ORIGIN FOR THE GROUP (A): 31.8380 34.4130 15.9540
REMARK 3 T TENSOR
REMARK 3 T11: 0.0826 T22: 0.0528
REMARK 3 T33: 0.0022 T12: 0.0085
REMARK 3 T13: 0.0118 T23: 0.0066
REMARK 3 L TENSOR
REMARK 3 L11: 0.3236 L22: 1.6346
REMARK 3 L33: 0.0319 L12: −0.4538
REMARK 3 L13: −0.1060 L23: −0.1134
REMARK 3 S TENSOR
REMARK 3 S11: 0.0668 S12: 0.0317 S13: 0.0266
REMARK 3 S21: −0.0158 S22: −0.0508 S23: −0.0656
REMARK 3 S31: −0.0111 S32: 0.0027 S33: −0.0160
REMARK 3
REMARK 3 TLS GROUP: 2
REMARK 3 NUMBER OF COMPONENTS GROUP: 1
REMARK 3 COMPONENTS C SSSEQI TO C SSSEQI
REMARK 3 RESIDUE RANGE: B 1 B 112
REMARK 3 ORIGIN FOR THE GROUP (A): 33.7580 2.5150 18.4210
REMARK 3 T TENSOR
REMARK 3 T11: 0.0638 T22: 0.0608
REMARK 3 T33: 0.0227 T12: 0.0019
REMARK 3 T13: −0.0064 T23: −0.0055
REMARK 3 L TENSOR
REMARK 3 L11: 0.0923 L22: 0.6926
REMARK 3 L33: 0.1427 L12: −0.1092
REMARK 3 L13: −0.1135 L23: −0.0160
REMARK 3 S TENSOR
REMARK 3 S11: 0.0096 S12: 0.0276 S13: −0.0212
REMARK 3 S21: −0.0046 S22: −0.0327 S23: 0.0279
REMARK 3 S31: −0.0061 S32: −0.0095 S33: 0.0231
REMARK 3
REMARK 3
REMARK 3 BULK SOLVENT MODELLING.
REMARK 3 METHOD USED: BABINET MODEL WITH MASK
REMARK 3 PARAMETERS FOR MASK CALCULATION
REMARK 3 VDW PROBE RADIUS: 1.40
REMARK 3 ION PROBE RADIUS: 0.80
REMARK 3 SHRINKAGE RADIUS: 0.80
REMARK 3
REMARK 3 OTHER REFINEMENT REMARKS:
REMARK 3 HYDROGENS HAVE BEEN ADDED IN THE RIDING POSITIONS
REMARK 3
CISPEP 1 THR A 28 PRO A 29 0.00
CISPEP 2 THR B 28 PRO B 29 0.00
CRYST1 97.118 97.118 61.413 90.00 90.00 90.00 P 43 21 2
SCALE1 0.010297 0.000000 0.000000 0.00000

SCALE2 0.000000 0.010297 0.000000 0.00000
SCALE3 0.000000 0.000000 0.016283 0.00000
ATOM 1 O ACE A 0 39.758 17.815 6.621 1.00 32.04 O
ATOM 2 C ACE A 0 38.470 17.959 6.297 1.00 30.44 C
ATOM 3 CA ACE A 0 37.841 19.332 5.940 1.00 30.13 C
ATOM 4 N SER A 1 37.877 16.775 5.643 1.00 19.18 N
ATOM 6 CA SER A 1 36.408 16.741 5.468 1.00 17.19 C
ATOM 8 CB SER A 1 35.991 15.421 4.841 1.00 17.15 C
ATOM 11 OG SER A 1 36.194 14.363 5.768 1.00 16.56 O
ATOM 13 C SER A 1 35.748 16.842 6.834 1.00 16.94 C
ATOM 14 O SER A 1 36.412 16.630 7.854 1.00 16.93 O
ATOM 17 N ALA A 2 34.500 17.297 6.850 1.00 17.11 N
ATOM 19 CA ALA A 2 33.637 17.247 8.031 1.00 16.12 C
ATOM 21 CB ALA A 2 32.200 17.465 7.619 1.00 16.40 C
ATOM 25 C ALA A 2 33.762 15.907 8.757 1.00 15.10 C
ATOM 26 O ALA A 2 33.901 15.848 9.975 1.00 13.93 O
ATOM 27 N THR A 3 33.680 14.823 8.009 1.00 14.66 N
ATOM 29 CA THR A 3 33.773 13.515 8.630 1.00 13.12 C
ATOM 31 CB THR A 3 33.497 12.440 7.599 1.00 13.38 C
ATOM 33 OG1 THR A 3 32.154 12.599 7.122 1.00 13.50 O
ATOM 35 CG2 THR A 3 33.517 11.067 8.238 1.00 14.13 C
ATOM 39 C THR A 3 35.111 13.272 9.307 1.00 12.51 C
ATOM 40 O THR A 3 35.141 12.780 10.440 1.00 10.83 O
ATOM 41 N SER A 4 36.216 13.578 8.632 1.00 11.39 N
ATOM 43 CA SER A 4 37.538 13.356 9.244 1.00 12.60 C
ATOM 45 CB SER A 4 38.694 13.609 8.266 1.00 13.31 C
ATOM 48 OG SER A 4 38.566 14.874 7.668 1.00 19.57 O
ATOM 50 C SER A 4 37.726 14.223 10.471 1.00 11.69 C
ATOM 51 O SER A 4 38.223 13.765 11.484 1.00 10.87 O
ATOM 52 N LEU A 5 37.331 15.484 10.379 1.00 11.95 N
ATOM 54 CA LEU A 5 37.478 16.382 11.515 1.00 11.00 C
ATOM 56 CB LEU A 5 37.047 17.801 11.149 1.00 11.44 C
ATOM 59 CG LEU A 5 37.928 18.509 10.117 1.00 13.46 C
ATOM 61 CD1 LEU A 5 37.267 19.790 9.651 1.00 15.05 C
ATOM 65 CD2 LEU A 5 39.270 18.807 10.731 1.00 15.52 C
ATOM 69 C LEU A 5 36.658 15.900 12.698 1.00 10.25 C
ATOM 70 O LEU A 5 37.114 15.947 13.852 1.00 9.79 O
ATOM 71 N THR A 6 35.440 15.446 12.417 1.00 9.51 N
ATOM 73 CA THR A 6 34.547 14.953 13.459 1.00 9.80 C
ATOM 75 CB THR A 6 33.250 14.425 12.840 1.00 9.84 C
ATOM 77 OG1 THR A 6 32.454 15.510 12.319 1.00 10.30 O
ATOM 79 CG2 THR A 6 32.388 13.749 13.859 1.00 9.40 C
ATOM 83 C THR A 6 35.186 13.816 14.236 1.00 9.72 C
ATOM 84 O THR A 6 35.215 13.845 15.451 1.00 9.30 O
ATOM 85 N PHE A 7 35.679 12.796 13.545 1.00 9.95 N
ATOM 87 CA PHE A 7 36.185 11.642 14.278 1.00 8.92 C
ATOM 89 CB PHE A 7 35.993 10.367 13.490 1.00 8.90 C
ATOM 92 CG PHE A 7 34.552 9.988 13.365 1.00 8.19 C
ATOM 93 CD1 PHE A 7 33.848 9.583 14.485 1.00 10.40 C
ATOM 95 CE1 PHE A 7 32.512 9.267 14.407 1.00 10.95 C
ATOM 97 CZ PHE A 7 31.848 9.370 13.217 1.00 11.35 C
ATOM 99 CE2 PHE A 7 32.532 9.791 12.080 1.00 10.55 C
ATOM 101 CD2 PHE A 7 33.872 10.127 12.165 1.00 10.65 C
ATOM 103 C PHE A 7 37.603 11.819 14.812 1.00 9.58 C
ATOM 104 O PHE A 7 37.970 11.203 15.811 1.00 9.17 O
ATOM 105 N GLN A 8 38.405 12.669 14.177 1.00 9.36 N
ATOM 107 CA GLN A 8 39.683 12.999 14.778 1.00 10.36 C
ATOM 109 CB GLN A 8 40.476 13.937 13.891 1.00 10.90 C
ATOM 112 CG GLN A 8 41.097 13.322 12.692 1.00 14.14 C
ATOM 115 CD GLN A 8 41.805 14.419 11.894 1.00 16.75 C
ATOM 116 OE1 GLN A 8 41.409 14.742 10.787 1.00 21.77 O
ATOM 117 NE2 GLN A 8 42.799 15.056 12.517 1.00 20.28 N
ATOM 120 C GLN A 8 39.409 13.716 16.116 1.00 10.53 C
ATOM 121 O GLN A 8 40.049 13.416 17.118 1.00 10.95 O
ATOM 122 N LEU A 9 38.457 14.654 16.122 1.00 9.95 N
ATOM 124 CA LEU A 9 38.145 15.413 17.332 1.00 9.62 C
ATOM 126 CB LEU A 9 37.162 16.537 17.057 1.00 9.66 C
ATOM 129 CG LEU A 9 36.767 17.375 18.278 1.00 9.80 C
ATOM 131 CD1 LEU A 9 37.974 18.098 18.862 1.00 10.08 C
ATOM 135 CD2 LEU A 9 35.701 18.397 17.886 1.00 12.75 C
ATOM 139 C LEU A 9 37.541 14.467 18.346 1.00 9.58 C
ATOM 140 O LEU A 9 37.935 14.484 19.514 1.00 9.46 O
ATOM 141 N ALA A 10 36.588 13.637 17.917 1.00 9.20 N
ATOM 143 CA ALA A 10 35.952 12.701 18.856 1.00 9.03 C
ATOM 145 CB ALA A 10 34.875 11.850 18.154 1.00 8.72 C
ATOM 149 C ALA A 10 36.949 11.802 19.605 1.00 8.50 C
ATOM 150 O ALA A 10 36.855 11.615 20.825 1.00 8.50 O
ATOM 151 N TYR A 11 37.918 11.242 18.899 1.00 9.18 N
ATOM 153 CA TYR A 11 38.865 10.359 19.541 1.00 8.12 C
ATOM 155 CB TYR A 11 39.716 9.664 18.491 1.00 8.30 C
ATOM 158 CG TYR A 11 40.642 8.638 19.075 1.00 7.61 C
ATOM 159 CD1 TYR A 11 40.156 7.495 19.699 1.00 9.07 C
ATOM 161 CE1 TYR A 11 41.008 6.560 20.229 1.00 10.41 C
ATOM 163 CZ TYR A 11 42.359 6.768 20.170 1.00 13.73 C
ATOM 164 OH TYR A 11 43.210 5.831 20.740 1.00 15.09 O
ATOM 166 CE2 TYR A 11 42.868 7.898 19.571 1.00 10.94 C
ATOM 168 CD2 TYR A 11 42.014 8.827 19.027 1.00 10.00 C
ATOM 170 C TYR A 11 39.752 11.139 20.530 1.00 8.66 C
ATOM 171 O TYR A 11 40.158 10.596 21.550 1.00 8.96 O
ATOM 172 N LEU A 12 40.012 12.412 20.245 1.00 8.35 N
ATOM 174 CA LEU A 12 40.899 13.238 21.081 1.00 9.68 C
ATOM 176 CB LEU A 12 41.501 14.374 20.257 1.00 10.19 C
ATOM 179 CG LEU A 12 42.469 13.943 19.152 1.00 15.33 C
ATOM 181 CD1 LEU A 12 43.187 15.145 18.549 1.00 18.28 C
ATOM 185 CD2 LEU A 12 43.464 12.905 19.653 1.00 18.55 C
ATOM 189 C LEU A 12 40.242 13.812 22.351 1.00 9.19 C
ATOM 190 O LEU A 12 40.851 13.776 23.445 1.00 10.13 O
ATOM 191 N VAL A 13 39.010 14.301 22.232 1.00 8.92 N
ATOM 193 CA VAL A 13 38.357 14.969 23.368 1.00 8.52 C
ATOM 195 CB VAL A 13 38.013 16.426 23.050 1.00 8.78 C
ATOM 197 CG1 VAL A 13 39.251 17.141 22.537 1.00 10.74 C
ATOM 201 CG2 VAL A 13 36.864 16.560 22.057 1.00 9.49 C
ATOM 205 C VAL A 13 37.131 14.252 23.904 1.00 8.44 C
ATOM 206 O VAL A 13 36.592 14.631 24.947 1.00 8.60 O
ATOM 207 N LYS A 14 36.709 13.218 23.178 1.00 8.48 N
ATOM 209 CA LYS A 14 35.583 12.339 23.536 1.00 8.98 C
ATOM 211 CB LYS A 14 35.771 11.687 24.909 1.00 8.33 C
ATOM 214 CG LYS A 14 37.127 11.029 25.118 1.00 7.66 C
ATOM 217 CD LYS A 14 37.513 10.044 23.992 1.00 8.44 C
ATOM 220 CE LYS A 14 38.818 9.318 24.229 1.00 7.68 C
ATOM 223 NZ LYS A 14 39.160 8.416 23.087 1.00 7.55 N
ATOM 227 C LYS A 14 34.187 12.932 23.465 1.00 10.23 C
ATOM 228 O LYS A 14 33.306 12.332 22.864 1.00 9.28 O
ATOM 229 N LYS A 15 33.976 14.083 24.089 1.00 10.78 N
ATOM 231 CA LYS A 15 32.636 14.648 24.202 1.00 12.04 C
ATOM 233 CB LYS A 15 32.058 14.428 25.615 1.00 13.87 C
ATOM 236 CG LYS A 15 30.626 14.970 25.767 1.00 18.29 C
ATOM 239 CD LYS A 15 30.411 15.838 26.991 1.00 25.35 C
ATOM 242 CE LYS A 15 29.648 17.144 26.648 1.00 26.80 C
ATOM 245 NZ LYS A 15 30.479 18.398 26.848 1.00 28.04 N
ATOM 249 C LYS A 15 32.701 16.124 23.876 1.00 11.99 C
ATOM 250 O LYS A 15 33.603 16.825 24.333 1.00 12.92 O
ATOM 251 N ILE A 16 31.770 16.587 23.054 1.00 11.71 N

ATOM 253 CA ILE A 16 31.631 18.011 22.795 1.00 11.45 C
ATOM 255 CB ILE A 16 32.644 18.502 21.769 1.00 12.21 C
ATOM 257 CG1 ILE A 16 32.966 19.980 22.019 1.00 12.61 C
ATOM 260 CD1 ILE A 16 34.167 20.459 21.239 1.00 16.67 C
ATOM 264 CG2 ILE A 16 32.154 18.226 20.357 1.00 12.62 C
ATOM 268 C ILE A 16 30.193 18.273 22.375 1.00 11.19 C
ATOM 269 O ILE A 16 29.515 17.396 21.835 1.00 10.05 O
ATOM 270 N ASP A 17 29.729 19.495 22.614 1.00 11.77 N
ATOM 272 CA ASP A 17 28.357 19.861 22.315 1.00 11.36 C
ATOM 274 CB ASP A 17 27.503 19.570 23.548 1.00 12.18 C
ATOM 277 CG ASP A 17 26.019 19.854 23.363 1.00 13.83 C
ATOM 278 OD1 ASP A 17 25.558 20.190 22.262 1.00 14.93 O
ATOM 279 OD2 ASP A 17 25.207 19.726 24.327 1.00 17.34 O
ATOM 280 C ASP A 17 28.354 21.342 22.018 1.00 10.94 C
ATOM 281 O ASP A 17 28.505 22.158 22.930 1.00 12.08 O
ATOM 282 N PHE A 18 28.220 21.709 20.754 1.00 9.97 N
ATOM 284 CA PHE A 18 28.208 23.121 20.420 1.00 9.42 C
ATOM 286 CB PHE A 18 29.621 23.630 20.070 1.00 9.10 C
ATOM 289 CG PHE A 18 30.262 22.990 18.849 1.00 9.30 C
ATOM 290 CD1 PHE A 18 31.457 22.269 18.966 1.00 11.84 C
ATOM 292 CE1 PHE A 18 32.069 21.704 17.850 1.00 11.09 C
ATOM 294 CZ PHE A 18 31.520 21.860 16.619 1.00 10.73 C
ATOM 296 CE2 PHE A 18 30.335 22.573 16.470 1.00 11.19 C
ATOM 298 CD2 PHE A 18 29.725 23.157 17.586 1.00 8.90 C
ATOM 300 C PHE A 18 27.226 23.431 19.299 1.00 9.78 C
ATOM 301 O PHE A 18 26.794 22.537 18.568 1.00 9.84 O
ATOM 302 N ASP A 19 26.899 24.711 19.156 1.00 10.97 N
ATOM 304 CA ASP A 19 26.059 25.169 18.060 1.00 10.37 C
ATOM 306 CB ASP A 19 24.575 25.130 18.429 1.00 10.87 C
ATOM 309 CG ASP A 19 23.674 25.452 17.267 1.00 11.55 C
ATOM 310 OD1 ASP A 19 24.180 25.843 16.178 1.00 11.30 O
ATOM 311 OD2 ASP A 19 22.418 25.322 17.350 1.00 12.10 O
ATOM 312 C ASP A 19 26.497 26.590 17.705 1.00 10.71 C
ATOM 313 O ASP A 19 26.136 27.575 18.388 1.00 10.19 O
ATOM 314 N TYR A 20 27.297 26.678 16.646 1.00 10.10 N
ATOM 316 CA TYR A 20 27.788 27.942 16.103 1.00 9.68 C
ATOM 318 CB TYR A 20 29.308 27.879 15.911 1.00 9.82 C
ATOM 321 CG TYR A 20 30.089 28.043 17.181 1.00 8.36 C
ATOM 322 CD1 TYR A 20 30.459 26.943 17.934 1.00 9.01 C
ATOM 324 CE1 TYR A 20 31.175 27.087 19.115 1.00 9.44 C
ATOM 326 CZ TYR A 20 31.514 28.335 19.546 1.00 10.02 C
ATOM 327 OH TYR A 20 32.228 28.469 20.703 1.00 9.07 O
ATOM 329 CE2 TYR A 20 31.167 29.441 18.804 1.00 10.02 C
ATOM 331 CD2 TYR A 20 30.451 29.303 17.648 1.00 8.62 C
ATOM 333 C TYR A 20 27.054 28.282 14.786 1.00 10.92 C
ATOM 334 O TYR A 20 27.600 28.930 13.878 1.00 11.60 O
ATOM 335 N THR A 21 25.800 27.857 14.694 1.00 12.18 N
ATOM 337 CA THR A 21 24.980 28.261 13.567 1.00 12.37 C
ATOM 339 CB THR A 21 23.584 27.692 13.676 1.00 12.82 C
ATOM 341 OG1 THR A 21 23.623 26.259 13.737 1.00 12.95 O
ATOM 343 CG2 THR A 21 22.832 27.997 12.401 1.00 13.70 C
ATOM 347 C THR A 21 24.871 29.776 13.598 1.00 12.58 C
ATOM 348 O THR A 21 24.445 30.332 14.595 1.00 12.57 O
ATOM 349 N PRO A 22 25.259 30.460 12.528 1.00 12.83 N
ATOM 350 CA PRO A 22 25.263 31.917 12.549 1.00 12.54 C
ATOM 352 CB PRO A 22 26.214 32.276 11.409 1.00 12.71 C
ATOM 355 CG PRO A 22 26.064 31.150 10.423 1.00 12.51 C
ATOM 358 CD PRO A 22 25.773 29.925 11.259 1.00 12.22 C
ATOM 361 C PRO A 22 23.890 32.509 12.337 1.00 12.87 C
ATOM 362 O PRO A 22 23.281 32.302 11.282 1.00 14.33 O
ATOM 363 N ASN A 23 23.405 33.202 13.363 1.00 12.69 N
ATOM 365 CA ASN A 23 22.145 33.920 13.285 1.00 12.96 C
ATOM 367 CB ASN A 23 21.290 33.568 14.497 1.00 13.22 C
ATOM 370 CG ASN A 23 20.761 32.141 14.427 1.00 16.73 C
ATOM 371 OD1 ASN A 23 19.705 31.904 13.821 1.00 22.06 O
ATOM 372 ND2 ASN A 23 21.511 31.174 14.977 1.00 18.52 N
ATOM 375 C ASN A 23 22.449 35.415 13.208 1.00 12.31 C
ATOM 376 O ASN A 23 22.904 36.007 14.185 1.00 12.34 O
ATOM 377 N TRP A 24 22.216 36.016 12.048 1.00 12.92 N
ATOM 379 CA TRP A 24 22.554 37.408 11.814 1.00 12.37 C
ATOM 381 CB TRP A 24 22.990 37.612 10.367 1.00 13.22 C
ATOM 384 CG TRP A 24 24.130 36.740 9.944 1.00 12.12 C
ATOM 385 CD1 TRP A 24 24.039 35.556 9.279 1.00 11.86 C
ATOM 387 NE1 TRP A 24 25.292 35.046 9.042 1.00 13.92 N
ATOM 389 CE2 TRP A 24 26.230 35.904 9.547 1.00 11.19 C
ATOM 390 CD2 TRP A 24 25.536 36.989 10.123 1.00 10.96 C
ATOM 391 CE3 TRP A 24 26.276 38.003 10.726 1.00 11.62 C
ATOM 393 CZ3 TRP A 24 27.660 37.925 10.707 1.00 13.20 C
ATOM 395 CH2 TRP A 24 28.317 36.833 10.136 1.00 11.66 C
ATOM 397 CZ2 TRP A 24 27.619 35.814 9.545 1.00 10.81 C
ATOM 399 C TRP A 24 21.343 38.268 12.120 1.00 12.73 C
ATOM 400 O TRP A 24 20.282 38.076 11.532 1.00 13.03 O
ATOM 401 N GLY A 25 21.488 39.222 13.029 1.00 12.00 N
ATOM 403 CA GLY A 25 20.370 40.074 13.398 1.00 11.21 C
ATOM 406 C GLY A 25 20.495 41.423 12.706 1.00 11.71 C
ATOM 407 O GLY A 25 21.592 41.969 12.603 1.00 11.26 O
ATOM 408 N ARG A 26 19.375 41.957 12.233 1.00 11.79 N
ATOM 410 CA ARG A 26 19.388 43.192 11.486 1.00 12.49 C
ATOM 412 CB ARG A 26 18.460 43.083 10.267 1.00 12.94 C
ATOM 415 CG ARG A 26 18.999 42.137 9.202 1.00 16.01 C
ATOM 418 CD ARG A 26 18.019 41.888 8.062 1.00 20.32 C
ATOM 421 NE ARG A 26 18.565 41.043 6.998 1.00 24.78 N
ATOM 423 CZ ARG A 26 19.426 41.460 6.071 1.00 25.04 C
ATOM 424 NH1 ARG A 26 19.860 40.607 5.149 1.00 29.16 N
ATOM 427 NH2 ARG A 26 19.863 42.715 6.057 1.00 19.47 N
ATOM 430 C ARG A 26 19.010 44.365 12.357 1.00 12.60 C
ATOM 431 O ARG A 26 18.369 44.206 13.398 1.00 12.88 O
ATOM 432 N GLY A 27 19.411 45.549 11.917 1.00 12.77 N

ATOM 434 CA GLY A 27 19.173 46.761 12.675 1.00 12.32 C
ATOM 437 C GLY A 27 18.090 47.628 12.071 1.00 13.21 C
ATOM 438 O GLY A 27 17.167 47.128 11.435 1.00 11.98 O
ATOM 439 N THR A 28 18.203 48.928 12.316 1.00 14.26 N
ATOM 441 CA THR A 28 17.261 49.925 11.819 1.00 14.60 C
ATOM 443 CB THR A 28 16.523 50.576 13.006 1.00 13.94 C
ATOM 445 OG1 THR A 28 15.801 49.590 13.761 1.00 12.38 O
ATOM 447 CG2 THR A 28 15.460 51.569 12.517 1.00 14.06 C
ATOM 451 C THR A 28 18.039 51.002 11.041 1.00 15.60 C
ATOM 452 O THR A 28 18.823 51.756 11.636 1.00 15.37 O
ATOM 453 N PRO A 29 17.874 51.082 9.718 1.00 17.62 N
ATOM 454 CA PRO A 29 17.025 50.182 8.928 1.00 17.21 C
ATOM 456 CB PRO A 29 16.956 50.887 7.570 1.00 17.70 C
ATOM 459 CG PRO A 29 18.211 51.657 7.483 1.00 17.48 C
ATOM 462 CD PRO A 29 18.513 52.109 8.878 1.00 17.56 C
ATOM 465 C PRO A 29 17.586 48.772 8.752 1.00 17.76 C
ATOM 466 O PRO A 29 18.751 48.525 9.061 1.00 16.07 O
ATOM 467 N SER A 30 16.742 47.873 8.242 1.00 18.81 N
ATOM 469 CA SER A 30 17.050 46.450 8.184 1.00 18.37 C
ATOM 471 CB SER A 30 15.805 45.644 7.833 1.00 18.99 C
ATOM 474 OG SER A 30 15.343 45.991 6.543 1.00 20.21 O
ATOM 476 C SER A 30 18.169 46.068 7.246 1.00 17.73 C
ATOM 477 O SER A 30 18.593 44.925 7.249 1.00 17.30 O
ATOM 478 N SER A 31 18.638 47.019 6.442 1.00 17.71 N
ATOM 480 CA SER A 31 19.762 46.788 5.545 1.00 16.65 C
ATOM 482 CB SER A 31 19.806 47.894 4.489 1.00 16.79 C
ATOM 485 OG SER A 31 19.921 49.171 5.094 1.00 17.30 O
ATOM 487 C SER A 31 21.098 46.709 6.297 1.00 16.11 C
ATOM 488 O SER A 31 22.127 46.365 5.704 1.00 15.78 O
ATOM 489 N TYR A 32 21.086 47.032 7.597 1.00 14.64 N
ATOM 491 CA TYR A 32 22.271 46.896 8.439 1.00 14.65 C
ATOM 493 CB TYR A 32 22.375 48.046 9.422 1.00 14.98 C
ATOM 496 CG TYR A 32 22.739 49.334 8.714 1.00 18.51 C
ATOM 497 CD1 TYR A 32 24.066 49.674 8.496 1.00 21.23 C
ATOM 499 CE1 TYR A 32 24.407 50.838 7.829 1.00 23.56 C
ATOM 501 CZ TYR A 32 23.413 51.669 7.369 1.00 24.54 C
ATOM 502 OH TYR A 32 23.739 52.830 6.706 1.00 26.67 O
ATOM 504 CE2 TYR A 32 22.087 51.341 7.555 1.00 23.37 C
ATOM 506 CD2 TYR A 32 21.758 50.174 8.225 1.00 21.68 C
ATOM 508 C TYR A 32 22.237 45.591 9.229 1.00 13.62 C
ATOM 509 O TYR A 32 21.188 45.198 9.725 1.00 13.16 O
ATOM 510 N ILE A 33 23.380 44.911 9.286 1.00 13.61 N
ATOM 512 CA ILE A 33 23.586 43.751 10.157 1.00 12.63 C
ATOM 514 CB ILE A 33 24.578 42.754 9.534 1.00 12.46 C
ATOM 516 CG1 ILE A 33 24.075 42.259 8.180 1.00 15.30 C
ATOM 519 CD1 ILE A 33 22.722 41.668 8.218 1.00 17.61 C
ATOM 523 CG2 ILE A 33 24.827 41.551 10.448 1.00 12.99 C
ATOM 527 C ILE A 33 24.190 44.290 11.450 1.00 12.11 C
ATOM 528 O ILE A 33 25.296 44.828 11.452 1.00 11.53 O
ATOM 529 N ASP A 34 23.471 44.131 12.551 1.00 12.39 N
ATOM 531 CA ASP A 34 23.884 44.688 13.831 1.00 11.42 C
ATOM 533 CB ASP A 34 22.658 45.171 14.607 1.00 11.00 C
ATOM 536 CG ASP A 34 22.217 46.584 14.234 1.00 12.48 C
ATOM 537 OD1 ASP A 34 22.658 47.096 13.183 1.00 13.04 O
ATOM 538 OD2 ASP A 34 21.399 47.223 14.951 1.00 13.34 O
ATOM 539 C ASP A 34 24.580 43.675 14.723 1.00 10.32 C
ATOM 540 O ASP A 34 25.317 44.056 15.621 1.00 10.05 O
ATOM 541 N ASN A 35 24.321 42.394 14.504 1.00 10.16 N
ATOM 543 CA ASN A 35 24.851 41.393 15.433 1.00 9.67 C
ATOM 545 CB ASN A 35 24.030 41.450 16.727 1.00 10.07 C
ATOM 548 CG ASN A 35 22.554 41.273 16.471 1.00 10.85 C
ATOM 549 OD1 ASN A 35 22.107 40.167 16.176 1.00 12.45 O
ATOM 550 ND2 ASN A 35 21.783 42.374 16.550 1.00 9.57 N
ATOM 553 C ASN A 35 24.840 39.977 14.875 1.00 9.80 C
ATOM 554 O ASN A 35 24.247 39.693 13.824 1.00 10.06 O
ATOM 555 N LEU A 36 25.504 39.087 15.604 1.00 9.45 N
ATOM 557 CA LEU A 36 25.636 37.689 15.262 1.00 9.51 C
ATOM 559 CB LEU A 36 27.042 37.442 14.753 1.00 9.66 C
ATOM 562 CG LEU A 36 27.470 36.000 14.536 1.00 9.35 C
ATOM 564 CD1 LEU A 36 26.605 35.300 13.482 1.00 10.39 C
ATOM 568 CD2 LEU A 36 28.951 35.986 14.161 1.00 10.50 C
ATOM 572 C LEU A 36 25.419 36.881 16.535 1.00 10.20 C
ATOM 573 O LEU A 36 26.105 37.111 17.539 1.00 10.03 O
ATOM 574 N THR A 37 24.482 35.941 16.502 1.00 10.24 N
ATOM 576 CA THR A 37 24.190 35.099 17.661 1.00 10.84 C
ATOM 578 CB THR A 37 22.716 35.234 18.063 1.00 11.04 C
ATOM 580 OG1 THR A 37 22.440 36.591 18.421 1.00 12.32 O
ATOM 582 CG2 THR A 37 22.397 34.382 19.308 1.00 11.78 C
ATOM 586 C THR A 37 24.484 33.647 17.365 1.00 10.36 C
ATOM 587 O THR A 37 24.103 33.128 16.314 1.00 11.69 O
ATOM 588 N PHE A 38 25.183 33.002 18.288 1.00 10.33 N
ATOM 590 CA PHE A 38 25.435 31.568 18.220 1.00 10.67 C
ATOM 592 CB PHE A 38 26.892 31.285 18.520 1.00 10.97 C
ATOM 595 CG PHE A 38 27.844 31.792 17.480 1.00 9.37 C
ATOM 596 CD1 PHE A 38 28.952 32.543 17.835 1.00 10.78 C
ATOM 598 CE1 PHE A 38 29.844 32.982 16.879 1.00 10.42 C
ATOM 600 CZ PHE A 38 29.659 32.667 15.590 1.00 12.03 C
ATOM 602 CE2 PHE A 38 28.559 31.898 15.215 1.00 10.68 C
ATOM 604 CD2 PHE A 38 27.660 31.476 16.146 1.00 10.68 C
ATOM 606 C PHE A 38 24.595 30.912 19.303 1.00 11.13 C
ATOM 607 O PHE A 38 24.678 31.328 20.444 1.00 11.20 O
ATOM 608 N PRO A 39 23.777 29.911 18.995 1.00 11.41 N
ATOM 609 CA PRO A 39 22.920 29.317 20.033 1.00 11.03 C
ATOM 611 CB PRO A 39 22.047 28.347 19.251 1.00 11.55 C
ATOM 614 CG PRO A 39 22.138 28.792 17.827 1.00 11.41 C
ATOM 617 CD PRO A 39 23.501 29.337 17.671 1.00 10.69 C
ATOM 620 C PRO A 39 23.593 28.585 21.186 1.00 10.78 C
ATOM 621 O PRO A 39 23.007 28.537 22.272 1.00 11.13 O
ATOM 622 N LYS A 40 24.756 27.986 20.961 1.00 10.03 N
ATOM 624 CA LYS A 40 25.420 27.246 22.033 1.00 11.35 C
ATOM 626 CB LYS A 40 24.930 25.808 22.100 1.00 11.81 C
ATOM 629 CG LYS A 40 25.329 25.153 23.413 1.00 15.47 C
ATOM 632 CD LYS A 40 25.020 23.673 23.445 1.00 21.03 C
ATOM 635 CE LYS A 40 25.654 23.024 24.665 1.00 26.85 C
ATOM 638 NZ LYS A 40 24.928 23.362 25.917 1.00 35.22 N
ATOM 642 C LYS A 40 26.939 27.297 21.877 1.00 11.13 C

ATOM 643 O LYS A 40 27.540 26.454 21.211 1.00 11.86 O
ATOM 644 N VAL A 41 27.549 28.310 22.479 1.00 10.84 N
ATOM 646 CA VAL A 41 28.995 28.462 22.410 1.00 10.68 C
ATOM 648 CB VAL A 41 29.449 29.903 22.641 1.00 10.07 C
ATOM 650 CG1 VAL A 41 28.907 30.826 21.533 1.00 10.33 C
ATOM 654 CG2 VAL A 41 29.040 30.419 24.007 1.00 10.45 C
ATOM 658 C VAL A 41 29.690 27.564 23.425 1.00 11.85 C
ATOM 659 O VAL A 41 29.093 27.111 24.425 1.00 12.38 O
ATOM 660 N LEU A 42 30.957 27.305 23.165 1.00 13.03 N
ATOM 662 CA LEU A 42 31.803 26.664 24.159 1.00 15.12 C
ATOM 664 CB LEU A 42 33.126 26.219 23.556 1.00 14.97 C
ATOM 667 CG LEU A 42 32.873 25.139 22.491 1.00 15.42 C
ATOM 669 CD1 LEU A 42 34.128 24.763 21.705 1.00 16.85 C
ATOM 673 CD2 LEU A 42 32.303 23.917 23.125 1.00 17.26 C
ATOM 677 C LEU A 42 32.012 27.709 25.245 1.00 17.87 C
ATOM 678 O LEU A 42 32.083 28.897 24.974 1.00 17.12 O
ATOM 679 N THR A 43 32.171 27.279 26.476 1.00 21.75 N
ATOM 681 CA THR A 43 32.188 28.272 27.549 1.00 24.61 C
ATOM 683 CB THR A 43 30.761 28.365 28.043 1.00 24.82 C
ATOM 685 OG1 THR A 43 29.883 29.292 27.424 1.00 27.15 O
ATOM 687 CG2 THR A 43 30.199 27.229 28.835 1.00 24.68 C
ATOM 691 C THR A 43 33.197 27.863 28.620 1.00 26.54 C
ATOM 692 O THR A 43 33.185 28.377 29.738 1.00 27.45 O
ATOM 693 N ASP A 44 34.103 26.963 28.249 1.00 28.93 N
ATOM 695 CA ASP A 44 35.103 26.469 29.179 1.00 29.14 C
ATOM 697 CB ASP A 44 35.855 25.271 28.602 1.00 28.74 C
ATOM 700 CG ASP A 44 36.401 25.521 27.217 1.00 28.34 C
ATOM 701 OD1 ASP A 44 37.572 25.172 26.990 1.00 26.28 O
ATOM 702 OD2 ASP A 44 35.734 26.028 26.286 1.00 24.46 O
ATOM 703 C ASP A 44 36.063 27.575 29.547 1.00 30.53 C
ATOM 704 O ASP A 44 36.513 27.663 30.699 1.00 30.19 O
ATOM 705 N LYS A 45 36.372 28.422 28.568 1.00 31.95 N
ATOM 707 CA LYS A 45 37.275 29.547 28.790 1.00 31.72 C
ATOM 709 CB LYS A 45 38.701 29.244 28.320 1.00 31.90 C
ATOM 712 CG LYS A 45 38.971 29.445 26.860 1.00 32.28 C
ATOM 715 CD LYS A 45 39.201 28.149 26.171 1.00 33.73 C
ATOM 718 CE LYS A 45 40.448 27.462 26.609 1.00 33.84 C
ATOM 721 NZ LYS A 45 40.509 26.190 25.855 1.00 36.70 N
ATOM 725 C LYS A 45 36.715 30.803 28.140 1.00 31.38 C
ATOM 726 O LYS A 45 35.679 30.756 27.482 1.00 31.01 O
ATOM 727 N LYS A 46 37.399 31.925 28.352 1.00 31.71 N
ATOM 729 CA LYS A 46 36.910 33.224 27.903 1.00 29.44 C
ATOM 731 CB LYS A 46 37.338 34.330 28.875 1.00 30.08 C
ATOM 734 CG LYS A 46 38.819 34.397 29.144 1.00 32.08 C
ATOM 737 CD LYS A 46 39.083 34.836 30.591 1.00 35.03 C
ATOM 740 CB LYS A 46 40.571 34.941 30.910 1.00 36.79 C
ATOM 743 NZ LYS A 46 40.827 34.716 32.367 1.00 37.85 N
ATOM 747 C LYS A 46 37.335 33.551 26.488 1.00 26.70 C
ATOM 748 O LYS A 46 38.347 34.201 26.240 1.00 26.57 O
ATOM 749 N TYR A 47 36.542 33.083 25.544 1.00 24.74 N
ATOM 751 CA TYR A 47 36.802 33.387 24.144 1.00 20.86 C
ATOM 753 CB TYR A 47 35.966 32.476 23.252 1.00 19.97 C
ATOM 756 CG TYR A 47 36.251 31.026 23.482 1.00 17.82 C
ATOM 757 CD1 TYR A 47 35.393 30.240 24.244 1.00 17.29 C
ATOM 759 CE1 TYR A 47 35.654 28.910 24.468 1.00 17.53 C
ATOM 761 CZ TYR A 47 36.797 28.346 23.956 1.00 16.67 C
ATOM 762 OH TYR A 47 37.076 27.005 24.174 1.00 20.90 O
ATOM 764 CE2 TYR A 47 37.670 29.109 23.205 1.00 17.26 C
ATOM 766 CD2 TYR A 47 37.395 30.446 22.984 1.00 16.93 C
ATOM 768 C TYR A 47 36.482 34.836 23.806 1.00 18.65 C
ATOM 769 O TYR A 47 35.575 35.432 24.361 1.00 19.20 O
ATOM 770 N SER A 48 37.229 35.388 22.863 1.00 16.14 N
ATOM 772 CA SER A 48 36.957 36.716 22.329 1.00 14.79 C
ATOM 774 CB SER A 48 38.168 37.624 22.472 1.00 15.65 C
ATOM 777 OG SER A 48 38.434 37.890 23.830 1.00 17.92 O
ATOM 779 C SER A 48 36.638 36.586 20.852 1.00 12.87 C
ATOM 780 O SER A 48 36.836 35.525 20.255 1.00 11.78 O
ATOM 781 N TYR A 49 36.173 37.675 20.249 1.00 10.68 N
ATOM 783 CA TYR A 49 35.870 37.671 18.822 1.00 11.65 C
ATOM 785 CB TYR A 49 34.362 37.641 18.580 1.00 11.29 C
ATOM 788 CG TYR A 49 33.668 36.471 19.256 1.00 10.85 C
ATOM 789 CD1 TYR A 49 33.098 36.593 20.510 1.00 10.38 C
ATOM 791 CE1 TYR A 49 32.475 35.517 21.131 1.00 10.61 C
ATOM 793 CZ TYR A 49 32.404 34.310 20.480 1.00 12.03 C
ATOM 794 OH TYR A 49 31.781 33.238 21.072 1.00 13.62 O
ATOM 796 CE2 TYR A 49 32.980 34.163 19.239 1.00 10.96 C
ATOM 798 CD2 TYR A 49 33.598 35.240 18.631 1.00 11.17 C
ATOM 800 C TYR A 49 36.446 38.895 18.119 1.00 11.93 C
ATOM 801 O TYR A 49 36.259 40.028 18.564 1.00 12.07 O
ATOM 802 N ARG A 50 37.122 38.649 17.004 1.00 13.41 N
ATOM 804 CA ARG A 50 37.603 39.714 16.134 1.00 13.03 C
ATOM 806 CB ARG A 50 38.983 39.376 15.561 1.00 13.84 C
ATOM 809 CG ARG A 50 39.542 40.479 14.661 1.00 15.89 C
ATOM 812 CD ARG A 50 40.799 40.094 13.892 1.00 19.76 C
ATOM 815 NE ARG A 50 41.825 39.658 14.809 1.00 22.85 N
ATOM 817 CZ ARG A 50 42.474 40.468 15.643 1.00 29.33 C
ATOM 818 NH1 ARG A 50 43.391 39.966 16.456 1.00 35.65 N
ATOM 821 NH2 ARG A 50 42.224 41.779 15.666 1.00 30.97 N
ATOM 824 C ARG A 50 36.632 39.865 14.982 1.00 12.87 C
ATOM 825 O ARG A 50 36.175 38.857 14.420 1.00 12.78 O
ATOM 826 N VAL A 51 36.338 41.108 14.605 1.00 12.80 N
ATOM 828 CA VAL A 51 35.419 41.393 13.506 1.00 13.04 C
ATOM 830 CB VAL A 51 34.206 42.194 13.983 1.00 12.62 C
ATOM 832 CG1 VAL A 51 33.343 42.630 12.809 1.00 12.65 C

ATOM 836 CG2 VAL A 51 33.389 41.356 14.936 1.00 12.04 C
ATOM 840 C VAL A 51 36.167 42.170 12.438 1.00 13.60 C
ATOM 841 O VAL A 51 36.851 43.153 12.738 1.00 13.27 O
ATOM 842 N VAL A 52 36.074 41.685 11.206 1.00 14.90 N
ATOM 844 CA VAL A 52 36.768 42.287 10.070 1.00 14.99 C
ATOM 846 CB VAL A 52 37.834 41.307 9.534 1.00 15.36 C
ATOM 848 CG1 VAL A 52 38.577 41.908 8.360 1.00 15.94 C
ATOM 852 CG2 VAL A 52 38.819 40.945 10.636 1.00 15.62 C
ATOM 856 C VAL A 52 35.733 42.590 8.981 1.00 15.27 C
ATOM 857 O VAL A 52 35.001 41.691 8.577 1.00 14.98 O
ATOM 858 N VAL A 53 35.680 43.840 8.506 1.00 15.37 N
ATOM 860 CA VAL A 53 34.663 44.255 7.542 1.00 16.36 C
ATOM 862 CB VAL A 53 33.805 45.395 8.090 1.00 16.50 C
ATOM 864 CG1 VAL A 53 32.827 45.905 7.043 1.00 16.92 C
ATOM 868 CG2 VAL A 53 33.037 44.923 9.314 1.00 16.68 C
ATOM 872 C VAL A 53 35.366 44.712 6.284 1.00 17.90 C
ATOM 873 O VAL A 53 36.121 45.670 6.321 1.00 17.86 O
ATOM 874 N ASN A 54 35.099 44.024 5.182 1.00 19.87 N
ATOM 876 CA ASN A 54 35.764 44.316 3.916 1.00 20.93 C
ATOM 878 CB ASN A 54 35.225 45.606 3.324 1.00 20.73 C
ATOM 881 CG ASN A 54 33.946 45.408 2.504 1.00 20.64 C
ATOM 882 OD1 ASN A 54 33.395 46.382 1.976 1.00 22.37 O
ATOM 883 ND2 ASN A 54 33.474 44.168 2.388 1.00 18.46 N
ATOM 886 C ASN A 54 37.281 44.421 4.100 1.00 22.08 C
ATOM 887 O ASN A 54 37.924 45.291 3.513 1.00 22.88 O
ATOM 888 N GLY A 55 37.851 43.545 4.924 1.00 23.68 N
ATOM 890 CA GLY A 55 39.288 43.532 5.134 1.00 22.59 C
ATOM 893 C GLY A 55 39.767 44.478 6.212 1.00 22.03 C
ATOM 894 O GLY A 55 40.936 44.441 6.586 1.00 22.03 O
ATOM 895 N SER A 56 38.883 45.332 6.712 1.00 21.22 N
ATOM 897 CA SER A 56 39.268 46.257 7.764 1.00 20.83 C
ATOM 899 CB SER A 56 38.434 47.521 7.666 1.00 21.16 C
ATOM 902 OG SER A 56 38.925 48.496 8.556 1.00 24.04 O
ATOM 904 C SER A 56 39.068 45.628 9.138 1.00 19.96 C
ATOM 905 O SER A 56 37.961 45.229 9.477 1.00 18.84 O
ATOM 906 N ASP A 57 40.129 45.590 9.937 1.00 19.21 N
ATOM 908 CA ASP A 57 40.100 44.953 11.252 1.00 19.05 C
ATOM 910 CB ASP A 57 41.547 44.599 11.610 1.00 19.38 C
ATOM 913 CG ASP A.57 41.704 43.926 12.947 1.00 20.67 C
ATOM 914 OD1 ASP A 57 40.717 43.476 13.545 1.00 19.91 O
ATOM 915 OD2 ASP A 57 42.833 43.786 13.472 1.00 25.20 O
ATOM 916 C ASP A 57 39.483 45.908 12.263 1.00 18.66 C
ATOM 917 O ASP A 57 40.031 46.992 12.524 1.00 17.62 O
ATOM 918 N LEU A 58 38.337 45.517 12.823 1.00 18.14 N
ATOM 920 CA LEU A 58 37.660 46.339 13.821 1.00 17.44 C
ATOM 922 CB LEU A 58 36.140 46.283 13.638 1.00 17.54 C
ATOM 925 CG LEU A 58 35.587 46.711 12.271 1.00 18.21 C
ATOM 927 CD1 LEU A 58 34.067 46.915 12.314 1.00 18.79 C
ATOM 931 CD2 LEU A 58 36.271 47.970 11.777 1.00 20.33 C
ATOM 935 C LEU A 58 38.058 45.955 15.248 1.00 17.13 C
ATOM 936 O LEU A 58 37.539 46.510 16.221 1.00 17.54 O
ATOM 937 N GLY A 59 38.978 45.010 15.381 1.00 16.87 N
ATOM 939 CA GLY A 59 39.503 44.667 16.686 1.00 16.43 C
ATOM 942 C GLY A 59 38.781 43.524 17.361 1.00 16.14 C
ATOM 943 O GLY A 59 37.953 42.845 16.768 1.00 13.91 O
ATOM 944 N VAL A 60 39.070 43.377 18.641 1.00 16.63 N
ATOM 946 CA VAL A 60 38.664 42.216 19.409 1.00 16.80 C
ATOM 948 CB VAL A 60 39.909 41.452 19.859 1.00 17.07 C
ATOM 950 CG1 VAL A 60 39.536 40.267 20.694 1.00 17.82 C
ATOM 954 CG2 VAL A 60 40.719 40.997 18.636 1.00 17.98 C
ATOM 958 C VAL A 60 37.883 42.635 20.638 1.00 17.13 C
ATOM 959 O VAL A 60 38.254 43.594 21.331 1.00 17.22 O
ATOM 960 N GLU A 61 36.806 41.913 20.913 1.00 16.81 N
ATOM 962 CA GLU A 61 35.954 42.215 22.058 1.00 17.72 C
ATOM 964 CB GLU A 61 34.759 43.060 21.623 1.00 18.26 C
ATOM 967 CG GLU A 61 35.079 44.412 20.956 1.00 20.64 C
ATOM 970 CD GLU A 61 35.548 45.510 21.912 1.00 24.07 C
ATOM 971 OE1 GLU A 61 35.294 45.417 23.142 1.00 25.24 O
ATOM 972 OE2 GLU A 61 36.174 46.484 21.416 1.00 24.17 O
ATOM 973 C GLU A 61 35.477 40.897 22.667 1.00 18.17 C
ATOM 974 O GLU A 61 35.387 39.870 21.972 1.00 15.50 O
ATOM 975 N SER A 62 35.171 40.917 23.964 1.00 19.13 N
ATOM 977 CA SER A 62 34.710 39.697 24.634 1.00 20.18 C
ATOM 979 CB SER A 62 35.838 39.109 25.479 1.00 20.45 C
ATOM 982 OG SER A 62 36.229 40.016 26.499 1.00 21.81 O
ATOM 984 C SER A 62 33.488 39.884 25.537 1.00 20.19 C
ATOM 985 O SER A 62 32.920 38.912 26.038 1.00 20.33 O
ATOM 986 N ASN A 63 33.073 41.120 25.735 1.00 20.95 N
ATOM 988 CA ASN A 63 32.043 41.388 26.729 1.00 21.35 C
ATOM 990 CB ASN A 63 32.310 42.725 27.418 1.00 22.62 C
ATOM 993 CG ASN A 63 31.947 43.893 26.582 1.00 26.10 C
ATOM 994 OD1 ASN A 63 31.697 44.985 27.106 1.00 33.95 O
ATOM 995 ND2 ASN A 63 31.936 43.704 25.268 1.00 38.69 N
ATOM 998 C ASN A 63 30.655 41.248 26.135 1.00 19.66 C
ATOM 999 O ASN A 63 29.954 42.221 25.801 1.00 20.53 O
ATOM 1000 N PHE A 64 30.318 39.982 25.925 1.00 17.32 N
ATOM 1002 CA PHE A 64 29.024 39.592 25.437 1.00 15.47 C
ATOM 1004 CB PHE A 64 29.125 39.076 23.995 1.00 14.91 C
ATOM 1007 CG PHE A 64 29.885 40.014 23.077 1.00 13.87 C
ATOM 1008 CD1 PHE A 64 29.388 41.270 22.792 1.00 14.13 C
ATOM 1010 CE1 PHE A 64 30.091 42.136 21.982 1.00 14.78 C
ATOM 1012 CZ PHE A 64 31.299 41.748 21.441 1.00 12.67 C
ATOM 1014 CE2 PHE A 64 31.808 40.511 21.723 1.00 13.44 C
ATOM 1016 CD2 PHE A 64 31.108 39.644 22.529 1.00 13.11 C
ATOM 1018 C PHE A 64 28.561 38.496 26.376 1.00 14.27 C
ATOM 1019 O PHE A 64 29.242 37.490 26.585 1.00 12.73 O
ATOM 1020 N ALA A 65 27.382 38.708 26.928 1.00 14.30 N
ATOM 1022 CA ALA A 65 26.782 37.806 27.875 1.00 14.41 C

ATOM 1024 CB ALA A 65 25.441 38.380 28.300 1.00 14.45 C
ATOM 1028 C ALA A 65 26.581 36.424 27.282 1.00 14.66 C
ATOM 1029 O ALA A 65 26.244 36.311 26.098 1.00 15.01 O
ATOM 1030 N VAL A 66 26.796 35.389 28.086 1.00 15.36 N
ATOM 1032 CA VAL A 66 26.427 34.049 27.683 1.00 15.61 C
ATOM 1034 CB VAL A 66 27.484 32.994 27.972 1.00 15.66 C
ATOM 1036 CG1 VAL A 66 26.958 31.609 27.592 1.00 17.06 C
ATOM 1040 CG2 VAL A 66 28.754 33.275 27.215 1.00 16.50 C
ATOM 1044 C VAL A 66 25.158 33.766 28.476 1.00 15.70 C
ATOM 1045 O VAL A 66 25.098 33.936 29.705 1.00 17.12 O
ATOM 1046 N THR A 67 24.115 33.379 27.777 1.00 15.06 N
ATOM 1048 CA THR A 67 22.854 33.106 28.439 1.00 15.98 C
ATOM 1050 CB THR A 67 21.681 33.345 27.491 1.00 15.54 C
ATOM 1052 OG1 THR A 67 21.794 32.535 26.311 1.00 14.59 O
ATOM 1054 CG2 THR A 67 21.718 34.774 26.958 1.00 15.99 C
ATOM 1058 C THR A 67 22.910 31.687 29.016 1.00 16.78 C
ATOM 1059 O THR A 67 23.742 30.885 28.620 1.00 16.89 O
ATOM 1060 N PRO A 68 22.150 31.418 30.062 1.00 18.84 N
ATOM 1061 CA PRO A 68 22.093 30.058 30.617 1.00 19.21 C
ATOM 1063 CB PRO A 68 20.997 30.168 31.683 1.00 19.65 C
ATOM 1066 CG PRO A 68 21.101 31.602 32.125 1.00 18.30 C
ATOM 1069 CD PRO A 68 21.436 32.395 30.897 1.00 18.90 C
ATOM 1072 C PRO A 68 21.826 28.955 29.582 1.00 20.21 C
ATOM 1073 O PRO A 68 22.274 27.827 29.790 1.00 19.65 O
ATOM 1074 N SER A 69 21.145 29.278 28.485 1.00 22.19 N
ATOM 1076 CA SER A 69 20.918 28.325 27.390 1.00 21.01 C
ATOM 1078 CB SER A 69 19.822 28.847 26.463 1.00 21.48 C
ATOM 1081 OG SER A 69 20.198 30.084 25.869 1.00 21.75 O
ATOM 1083 C SER A 69 22.189 28.062 26.582 1.00 20.29 C
ATOM 1084 O SER A 69 22.276 27.090 25.825 1.00 20.29 O
ATOM 1085 N GLY A 70 23.185 28.926 26.742 1.00 18.45 N
ATOM 1087 CA GLY A 70 24.455 28.736 26.089 1.00 16.37 C
ATOM 1090 C GLY A 70 24.635 29.701 24.941 1.00 14.59 C
ATOM 1091 O GLY A 70 25.655 29.678 24.275 1.00 14.71 O
ATOM 1092 N GLY A 71 23.655 30.564 24.707 1.00 12.55 N
ATOM 1094 CA GLY A 71 23.758 31.485 23.587 1.00 11.79 C
ATOM 1097 C GLY A 71 24.646 32.689 23.872 1.00 11.04 C
ATOM 1098 O GLY A 71 24.827 33.109 25.024 1.00 11.27 O
ATOM 1099 N GLN A 72 25.209 33.247 22.807 1.00 10.97 N
ATOM 1101 CA GLN A 72 26.016 34.462 22.914 1.00 10.54 C
ATOM 1103 CB GLN A 72 27.497 34.125 23.115 1.00 10.98 C
ATOM 1106 CG GLN A 72 28.414 35.293 23.430 1.00 12.20 C
ATOM 1109 CD GLN A 72 29.834 34.862 23.853 1.00 15.65 C

ATOM 1110 OE1 GLN A 72 30.449 35.487 24.742 1.00 17.66 O
ATOM 1111 NE2 GLN A 72 30.354 33.820 23.222 1.00 10.29 N
ATOM 1114 C GLN A 72 25.807 35.312 21.675 1.00 11.06 C
ATOM 1115 O GLN A 72 25.877 34.821 20.533 1.00 11.31 O
ATOM 1116 N THR A 73 25.535 36.589 21.904 1.00 10.95 N
ATOM 1118 CA THR A 73 25.337 37.526 20.830 1.00 9.80 C
ATOM 1120 CB THR A 73 24.021 38.290 21.035 1.00 10.73 C
ATOM 1122 OG1 THR A 73 22.912 37.385 21.013 1.00 11.04 O
ATOM 1124 CG2 THR A 73 23.786 39.270 19.891 1.00 10.78 C
ATOM 1128 C THR A 73 26.475 38.540 20.782 1.00 9.92 C
ATOM 1129 O THR A 73 26.722 39.283 21.745 1.00 10.19 O
ATOM 1130 N ILE A 74 27.161 38.554 19.643 1.00 9.37 N
ATOM 1132 CA ILE A 74 28.232 39.493 19.364 1.00 10.19 C
ATOM 1134 CB ILE A 74 29.235 38.855 18.371 1.00 10.48 C
ATOM 1136 CG1 ILE A 74 29.843 37.581 18.972 1.00 12.71 C
ATOM 1139 CD1 ILE A 74 30.471 36.666 17.946 1.00 16.05 C
ATOM 1143 CG2 ILE A 74 30.296 39.860 17.986 1.00 10.70 C
ATOM 1147 C ILE A 74 27.609 40.733 18.756 1.00 10.18 C
ATOM 1148 O ILE A 74 27.052 40.677 17.660 1.00 11.08 O
ATOM 1149 N ASN A 75 27.674 41.851 19.489 1.00 9.17 N
ATOM 1151 CA ASN A 75 27.079 43.102 19.040 1.00 9.50 C
ATOM 1153 CB ASN A 75 26.600 43.849 20.274 1.00 9.51 C
ATOM 1156 CG ASN A 75 25.994 45.177 19.950 1.00 10.45 C
ATOM 1157 OD1 ASN A 75 25.558 45.424 18.827 1.00 9.62 O
ATOM 1158 ND2 ASN A 75 25.931 46.046 20.959 1.00 12.30 N
ATOM 1161 C ASN A 75 28.050 43.975 18.248 1.00 9.58 C
ATOM 1162 O ASN A 75 28.992 44.543 18.807 1.00 10.09 O
ATOM 1163 N PHE A 76 27.817 44.088 16.945 1.00 10.23 N
ATOM 1165 CA PHE A 76 28.751 44.809 16.087 1.00 10.31 C
ATOM 1167 CB PHE A 76 28.464 44.552 14.610 1.00 10.82 C
ATOM 1170 CG PHE A 76 28.596 43.096 14.199 1.00 11.07 C
ATOM 1171 CD1 PHE A 76 29.568 42.277 14.737 1.00 13.37 C
ATOM 1173 CE1 PHE A 76 29.681 40.936 14.328 1.00 10.49 C
ATOM 1175 CZ PHE A 76 28.820 40.441 13.411 1.00 10.42 C
ATOM 1177 CE2 PHE A 76 27.856 41.259 12.865 1.00 11.96 C
ATOM 1179 CD2 PHE A 76 27.746 42.568 13.258 1.00 12.00 C
ATOM 1181 C PHE A 76 28.780 46.301 16.409 1.00 10.53 C
ATOM 1182 O PHE A 76 29.743 46.978 16.059 1.00 10.34 O
ATOM 1183 N LEU A 77 27.746 46.826 17.073 1.00 10.19 N
ATOM 1185 CA LEU A 77 27.754 48.242 17.446 1.00 11.27 C

ATOM 1187 CB LEU A 77 26.443 48.652 18.120 1.00 11.26 C
ATOM 1190 CG LEU A 77 25.267 48.913 17.154 1.00 12.41 C
ATOM 1192 CD1 LEU A 77 24.989 47.774 16.232 1.00 12.55 C
ATOM 1196 CD2 LEU A 77 23.977 49.223 17.911 1.00 13.90 C
ATOM 1200 C LEU A 77 28.933 48.577 18.368 1.00 12.07 C
ATOM 1201 O LEU A 77 29.399 49.717 18.371 1.00 13.10 O
ATOM 1202 N GLN A 78 29.416 47.580 19.112 1.00 12.87 N
ATOM 1204 CA GLN A 78 30.562 47.741 20.011 1.00 13.30 C
ATOM 1206 CB GLN A 78 30.588 46.602 21.048 1.00 13.42 C
ATOM 1209 CG GLN A 78 29.408 46.690 22.022 1.00 14.19 C
ATOM 1212 CD GLN A 78 29.251 45.560 23.009 1.00 17.92 C
ATOM 1213 OE1 GLN A 78 28.141 45.045 23.165 1.00 20.68 O
ATOM 1214 NE2 GLN A 78 30.316 45.212 23.726 1.00 21.02 N
ATOM 1217 C GLN A 78 31.892 47.837 19.231 1.00 14.14 C
ATOM 1218 O GLN A 78 32.905 48.303 19.774 1.00 16.34 O
ATOM 1219 N TYR A 79 31.896 47.398 17.979 1.00 13.44 N
ATOM 1221 CA TYR A 79 33.101 47.443 17.143 1.00 13.76 C
ATOM 1223 CB TYR A 79 33.220 46.165 16.311 1.00 13.39 C
ATOM 1226 CG TYR A 79 33.402 44.856 17.041 1.00 12.44 C
ATOM 1227 CD1 TYR A 79 34.649 44.249 17.117 1.00 11.93 C
ATOM 1229 CE1 TYR A 79 34.816 43.040 17.755 1.00 11.71 C
ATOM 1231 CZ TYR A 79 33.712 42.414 18.310 1.00 12.16 C
ATOM 1232 OH TYR A 79 33.873 41.215 18.929 1.00 13.43 O
ATOM 1234 CE2 TYR A 79 32.463 43.002 18.239 1.00 10.82 C
ATOM 1236 CD2 TYR A 79 32.319 44.204 17.607 1.00 11.32 C
ATOM 1238 C TYR A 79 33.092 48.571 16.111 1.00 14.75 C
ATOM 1239 O TYR A 79 34.154 48.964 15.600 1.00 14.73 O
ATOM 1240 N ASN A 80 31.899 49.072 15.786 1.00 15.93 N
ATOM 1242 CA ASN A 80 31.702 49.928 14.614 1.00 15.93 C
ATOM 1244 CB ASN A 80 30.814 49.164 13.619 1.00 15.91 C
ATOM 1247 CG ASN A 80 30.884 49.703 12.203 1.00 17.60 C
ATOM 1248 OD1 ASN A 80 29.863 49.757 11.507 1.00 22.84 O
ATOM 1249 ND2 ASN A 80 32.067 50.104 11.767 1.00 16.39 N
ATOM 1252 C ASN A 80 31.101 51.293 14.941 1.00 16.30 C
ATOM 1253 O ASN A 80 30.238 51.789 14.220 1.00 16.27 O
ATOM 1254 N LYS A 81 31.559 51.881 16.042 1.00 16.66 N
ATOM 1256 CA LYS A 81 31.166 53.238 16.448 1.00 17.75 C
ATOM 1258 CB LYS A 81 31.753 54.274 15.485 1.00 18.72 C
ATOM 1261 CG LYS A 81 33.275 54.164 15.279 1.00 22.17 C
ATOM 1264 CD LYS A 81 34.098 53.637 16.494 1.00 28.26 C
ATOM 1267 CE LYS A 81 33.999 54.432 17.816 1.00 31.88 C
ATOM 1270 NZ LYS A 81 34.916 53.895 18.908 1.00 34.98 N
ATOM 1274 C LYS A 81 29.660 53.445 16.590 1.00 17.22 C
ATOM 1275 O LYS A 81 29.139 54.507 16.230 1.00 16.93 O
ATOM 1276 N GLY A 82 28.969 52.429 17.115 1.00 16.00 N
ATOM 1278 CA GLY A 82 27.546 52.523 17.393 1.00 16.21 C
ATOM 1281 C GLY A 82 26.612 52.249 16.232 1.00 16.87 C
ATOM 1282 O GLY A 82 25.406 52.461 16.362 1.00 16.37 O
ATOM 1283 N TYR A 83 27.152 51.772 15.111 1.00 16.99 N
ATOM 1285 CA TYR A 83 26.342 51.425 13.958 1.00 17.84 C
ATOM 1287 CB TYR A 83 26.751 52.240 12.735 1.00 18.95 C
ATOM 1290 CG TYR A 83 26.375 53.678 12.816 1.00 24.21 C
ATOM 1291 CD1 TYR A 83 25.138 54.103 12.373 1.00 29.21 C
ATOM 1293 CE1 TYR A 83 24.775 55.428 12.440 1.00 31.15 C
ATOM 1295 CZ TYR A 83 25.660 56.351 12.956 1.00 32.63 C
ATOM 1296 OH TYR A 83 25.291 57.680 13.016 1.00 35.54 O
ATOM 1298 CE2 TYR A 83 26.906 55.954 13.404 1.00 31.21 C
ATOM 1300 CD2 TYR A 83 27.258 54.618 13.327 1.00 28.33 C
ATOM 1302 C TYR A 83 26.576 49.990 13.590 1.00 16.45 C
ATOM 1303 O TYR A 83 27.652 49.438 13.854 1.00 16.18 O
ATOM 1304 N GLY A 84 25.570 49.372 12.982 1.00 14.45 N
ATOM 1306 CA GLY A 84 25.761 48.049 12.430 1.00 14.93 C
ATOM 1309 C GLY A 84 26.514 48.187 11.109 1.00 15.19 C
ATOM 1310 O GLY A 84 27.001 49.273 10.757 1.00 15.50 O
ATOM 1311 N VAL A 85 26.565 47.099 10.353 1.00 15.19 N
ATOM 1313 CA VAL A 85 27.352 47.043 9.112 1.00 15.08 C
ATOM 1315 CB VAL A 85 28.332 45.860 9.143.1.00 15.27 C
ATOM 1317 CG1 VAL A 85 29.157 45.794 7.872 1.00 15.21 C
ATOM 1321 CG2 VAL A 85 29.255 45.956 10.329 1.00 15.25 C
ATOM 1325 C VAL A 85 26.438 46.873 7.911 1.00 15.53 C
ATOM 1326 O VAL A 85 25.551 46.025 7.910 1.00 14.72 O
ATOM 1327 N ALA A 86 26.648 47.673 6.875 1.00 15.80 N
ATOM 1329 CA ALA A 86 25.802 47.548 5.698 1.00 16.04 C
ATOM 1331 CB ALA A 86 26.250 48.488 4.631 1.00 16.32 C
ATOM 1335 C ALA A 86 25.861 46.128 5.186 1.00 15.57 C
ATOM 1336 O ALA A 86 26.941 45.575 5.059 1.00 15.01 O
ATOM 1337 N ASP A 87 24.708 45.558 4.842 1.00 16.64 N
ATOM 1339 CA ASP A 87 24.658 44.160 4.402 1.00 16.37 C
ATOM 1341 CB ASP A 87 23.253 43.550 4.495 1.00 16.92 C
ATOM 1344 CG ASP A 87 22.293 44.088 3.472 1.00 17.15 C
ATOM 1345 OD1 ASP A 87 21.117 43.677 3.520 1.00 17.33 O
ATOM 1346 OD2 ASP A 87 22.615 44.920 2.605 1.00 17.89 O
ATOM 1347 C ASP A 87 25.316 43.899 3.046 1.00 16.95 C
ATOM 1348 O ASP A 87 25.392 42.753 2.623 1.00 16.19 O

ATOM 1349 N THR A 88 25.812 44.949 2.398 1.00 18.29 N
ATOM 1351 CA THR A 88 26.566 44.803 1.146 1.00 17.50 C
ATOM 1353 CB THR A 88 26.427 46.084 0.327 1.00 17.73 C
ATOM 1355 OG1 THR A 88 26.702 47.225 1.150 1.00 16.82 O
ATOM 1357 CG2 THR A 88 25.020 46.269 −0.109 1.00 18.14 C
ATOM 1361 C THR A 88 28.052 44.563 1.361 1.00 17.57 C
ATOM 1362 O THR A 88 28.820 44.404 0.409 1.00 16.74 O
ATOM 1363 N LYS A 89 28.477 44.594 2.609 1.00 17.46 N
ATOM 1365 CA LYS A 89 29.871 44.389 2.919 1.00 17.25 C
ATOM 1367 CB LYS A 89 30.312 45.388 3.978 1.00 17.22 C
ATOM 1370 CG LYS A 89 30.058 46.844 3.579 1.00 18.92 C
ATOM 1373 CD LYS A 89 30.818 47.788 4.471 1.00 22.27 C
ATOM 1376 CB LYS A 89 30.590 49.242 4.055 1.00 25.20 C
ATOM 1379 NZ LYS A 89 31.208 50.160 5.042 1.00 29.86 N
ATOM 1383 C LYS A 89 30.069 42.968 3.411 1.00 17.09 C
ATOM 1384 O LYS A 89 29.122 42.311 3.818 1.00 16.84 O
ATOM 1385 N THR A 90 31.300 42.493 3.343 1.00 17.10 N
ATOM 1387 CA THR A 90 31.662 41.181 3.842 1.00 16.27 C
ATOM 1389 CB THR A 90 32.860 40.644 3.086 1.00 17.13 C
ATOM 1391 OG1 THR A 90 32.533 40.515 1.704 1.00 15.79 O
ATOM 1393 CG2 THR A 90 33.199 39.226 3.543 1.00 17.35 C
ATOM 1397 C THR A 90 32.068 41.322 5.296 1.00 15.60 C
ATOM 1398 O THR A 90 32.930 42.137 5.613 1.00 14.66 O
ATOM 1399 N ILE A 91 31.451 40.543 6.170 1.00 15.11 N
ATOM 1401 CA ILE A 91 31.823 40.561 7.577 1.00 14.05 C
ATOM 1403 CB ILE A 91 30.596 40.777 8.475 1.00 14.05 C
ATOM 1405 CG1 ILE A 91 29.771 41.971 7.995 1.00 13.77 C
ATOM 1408 CD1 ILE A 91 28.482 42.119 8.725 1.00 15.25 C
ATOM 1412 CG2 ILE A 91 31.039 40.924 9.949 1.00 13.82 C
ATOM 1416 C ILE A 91 32.435 39.221 7.914 1.00 14.03 C
ATOM 1417 O ILE A 91 31.795 38.191 7.702 1.00 14.85 O
ATOM 1418 N GLN A 92 33.679 39.230 8.382 1.00 12.86 N
ATOM 1420 CA GLN A 92 34.298 38.028 8.919 1.00 13.25 C
ATOM 1422 CB GLN A 92 35.678 37.818 8.338 1.00 14.29 C
ATOM 1425 CG GLN A 92 35.645 37.428 6.904 1.00 16.51 C
ATOM 1428 CD GLN A 92 37.020 37.515 6.275 1.00 21.30 C
ATOM 1429 OE1 GLN A 92 37.536 36.517 5.775 1.00 25.59 O
ATOM 1430 NE2 GLN A 92 37.627 38.701 6.319 1.00 23.68 N
ATOM 1433 C GLN A 92 34.443 38.120 10.423 1.00 12.74 C
ATOM 1434 O GLN A 92 34.914 39.127 10.940 1.00 12.27 O
ATOM 1435 N VAL A 93 34.072 37.051 11.115 1.00 11.90 N
ATOM 1437 CA VAL A 93 34.217 36.985 12.564 1.00 11.73 C
ATOM 1439 CB VAL A 93 32.865 36.841 13.257 1.00 11.43 C
ATOM 1441 CG1 VAL A 93 33.048 36.856 14.771 1.00 12.22 C
ATOM 1445 CG2 VAL A 93 31.925 37.956 12.809 1.00 12.10 C
ATOM 1449 C VAL A 93 35.118 35.797 12.912 1.00 11.97 C
ATOM 1450 O VAL A 93 34.953 34.707 12.379 1.00 11.23 O
ATOM 1451 N PHE A 94 36.096 36.055 13.773 1.00 11.48 N
ATOM 1453 CA PHE A 94 37.069 35.064 14.188 1.00 12.22 C
ATOM 1455 CB PHE A 94 38.473 35.563 13.871 1.00 12.62 C
ATOM 1458 CG PHE A 94 38.736 35.743 12.404 1.00 12.77 C
ATOM 1459 CD1 PHE A 94 38.345 36.900 11.763 1.00 14.64 C
ATOM 1461 CE1 PHE A 94 38.598 37.083 10.420 1.00 16.13 C
ATOM 1463 CZ PHE A 94 39.255 36.106 9.711 1.00 15.54 C
ATOM 1465 CE2 PHE A 94 39.660 34.948 10.345 1.00 16.06 C
ATOM 1467 CD2 PHE A 94 39.409 34.768 11.682 1.00 13.20 C
ATOM 1469 C PHE A 94 36.984 34.837 15.681 1.00 12.26 C
ATOM 1470 O PHE A 94 36.882 35.794 16.458 1.00 11.72 O
ATOM 1471 N VAL A 95 36.998 33.581 16.097 1.00 12.66 N
ATOM 1473 CA VAL A 95 37.063 33.304 17.530 1.00 13.63 C
ATOM 1475 CB VAL A 95 36.390 31.976 17.924 1.00 13.74 C
ATOM 1477 CG1 VAL A 95 37.054 30.809 17.246 1.00 15.18 C
ATOM 1481 CG2 VAL A 95 36.397 31.814 19.473 1.00 15.16 C
ATOM 1485 C VAL A 95 38.554 33.362 17.882 1.00 13.85 C
ATOM 1486 O VAL A 95 39.399 32.777 17.203 1.00 13.33 O
ATOM 1487 N VAL A 96 38.862 34.116 18.924 1.00 14.98 N
ATOM 1489 CA VAL A 96 40.231 34.355 19.364 1.00 16.25 C
ATOM 1491 CB VAL A 96 40.478 35.868 19.524 1.00 16.70 C
ATOM 1493 CG1 VAL A 96 41.904 36.141 20.002 1.00 17.91 C
ATOM 1497 CG2 VAL A 96 40.202 36.576 18.209 1.00 17.10 C
ATOM 1501 C VAL A 96 40.466 33.634 20.691 1.00 17.27 C
ATOM 1502 O VAL A 96 39.695 33.788 21.641 1.00 16.34 O
ATOM 1503 N ILE A 97 41.522 32.830 20.726 1.00 18.96 N
ATOM 1505 CA ILE A 97 41.842 32.001 21.883 1.00 20.35 C
ATOM 1507 CB ILE A 97 42.745 30.808 21.453 1.00 20.22 C
ATOM 1509 CG1 ILE A 97 42.107 30.040 20.289 1.00 19.14 C
ATOM 1512 CD1 ILE A 97 40.750 29.510 20.588 1.00 18.75 C
ATOM 1516 CG2 ILE A 97 43.031 29.889 22.639 1.00 20.66 C
ATOM 1520 C ILE A 97 42.545 32.863 22.925 1.00 22.26 C
ATOM 1521 O ILE A 97 43.457 33.599 22.579 1.00 22.69 O
ATOM 1522 N PRO A 98 42.099 32.814 24.176 1.00 24.62 N
ATOM 1523 CA PRO A 98 42.733 33.599 25.240 1.00 26.52 C
ATOM 1525 CB PRO A 98.41.778 33.441 26.426 1.00 25.97 C
ATOM 1528 CG PRO A 98 40.990 32.213 26.153 1.00 25.73 C
ATOM 1531 CD PRO A 98 40.942 32.054 24.669 1.00 24.63 C
ATOM 1534 C PRO A 98 44.114 33.108 25.621 1.00 28.91 C
ATOM 1535 O PRO A 98 44.507 31.975 25.313 1.00 28.13 O
ATOM 1536 N ASP A 99 44.838 33.999 26.295 1.00 32.98 N

ATOM 1538 CA ASP A 99 46.175 33.735 26.804 1.00 34.16 C
ATOM 1540 CB ASP A 99 46.090 32.683 27.897 1.00 34.51 C
ATOM 1543 CG ASP A 99 45.238 33.162 29.064 1.00 36.30 C
ATOM 1544 OD1 ASP A 99 45.547 34.247 29.608 1.00 39.17 O
ATOM 1545 OD2 ASP A 99 44.222 32.559 29.481 1.00 39.73 O
ATOM 1546 C ASP A 99 47.083 33.361 25.645 1.00 35.01 C
ATOM 1547 O ASP A 99 47.925 32.468 25.733 1.00 35.21 O
ATOM 1548 N THR A 100 46.914 34.118 24.568 1.00 36.50 N
ATOM 1550 CA THR A 100 47.559 33.836 23.307 1.00 35.94 C
ATOM 1552 CB THR A 100 46.536 33.051 22.457 1.00 36.18 C
ATOM 1554 OG1 THR A 100 47.151 31.891 21.882 1.00 36.31 O
ATOM 1556 CG2 THR A 100 46.021 33.845 21.282 1.00 35.16 C
ATOM 1560 C THR A 100 48.034 35.115 22.606 1.00 36.08 C
ATOM 1561 O THR A 100 48.650 35.058 21.542 1.00 35.70 O
ATOM 1562 N GLY A 101 47.776 36.267 23.220 1.00 36.43 N
ATOM 1564 CA GLY A 101 48.151 37.550 22.636 1.00 36.52 C
ATOM 1567 C GLY A 101 47.365 37.850 21.368 1.00 36.69 C
ATOM 1568 O GLY A 101 47.842 38.551 20.467 1.00 36.66 O
ATOM 1569 N ASN A 102 46.149 37.309 21.305 1.00 37.04 N
ATOM 1571 CA ASN A 102 45.279 37.436 20.135 1.00 35.46 C
ATOM 1573 CB ASN A 102 44.881 38.904 19.889 1.00 35.74 C
ATOM 1576 CG ASN A 102 44.070 39.509 21.044 1.00 36.19 C
ATOM 1577 OD1 ASN A 102 43.556 38.795 21.914 1.00 36.82 O
ATOM 1578 ND2 ASN A 102 43.948 40.836 21.046 1.00 38.45 N
ATOM 1581 C ASN A 102 45.884 36.813 18.855 1.00 34.28 C
ATOM 1582 O ASN A 102 45.401 37.081 17.757 1.00 34.09 O
ATOM 1583 N SER A 103 46.919 35.978 18.997 1.00 32.94 N
ATOM 1585 CA SER A 103 47.608 35.359 17.852 1.00 30.99 C
ATOM 1587 CB SER A 103 49.068 35.070 18.214 1.00 31.29 C
ATOM 1590 OG SER A 103 49.175 34.552 19.532 1.00 32.26 O
ATOM 1592 C SER A 103 46.981 34.072 17.315 1.00 28.93 C
ATOM 1593 O SER A 103 47.135 33.752 16.140 1.00 29.01 O
ATOM 1594 N GLU A 104 46.308 33.320 18.173 1.00 26.74 N
ATOM 1596 CA GLU A 104 45.648 32.098 17.739 1.00 23.55 C
ATOM 1598 CB GLU A 104 45.821 30.969 18.759 1.00 23.10 C
ATOM 1601 CG GLU A 104 45.217 29.652 18.294 1.00 22.29 C
ATOM 1604 CD GLU A 104 45.267 28.539 19.335 1.00 20.79 C
ATOM 1605 OE1 GLU A 104 44.705 27.459 19.063 1.00 18.27 O
ATOM 1606 OE2 GLU A 104 45.872 28.735 20.405 1.00 19.73 O
ATOM 1607 C GLU A 104 44.166 32.431 17.527 1.00 21.26 C
ATOM 1608 O GLU A 104 43.463 32.788 18.468 1.00 20.20 O
ATOM 1609 N GLU A 105 43.706 32.342 16.286 1.00 19.27 N
ATOM 1611 CA GLU A 105 42.310 32.652 15.989 1.00 17.92 C
ATOM 1613 CB GLU A 105 42.119 34.141 15.658 1.00 18.34 C
ATOM 1616 CG GLU A 105 42.614 34.515 14.283 1.00 19.41 C
ATOM 1619 CD GLU A 105 42.443 35.986 13.960 1.00 21.46 C
ATOM 1620 OE1 GLU A 105 42.657 36.346 12.779 1.00 22.55 O
ATOM 1621 OE2 GLU A 105 42.097 36.770 14.872 1.00 19.79 O
ATOM 1622 C GLU A 105 41.807 31.788 14.851 1.00 16.31 C
ATOM 1623 O GLU A 105 42.589 31.268 14.050 1.00 16.35 O
ATOM 1624 N TYR A 106 40.489 31.642 14.779 1.00 14.92 N
ATOM 1626 CA TYR A 106 39.856 30.789 13.784 1.00 13.70 C
ATOM 1628 CB TYR A 106 39.466 29.416 14.400 1.00 12.91 C
ATOM 1631 CG TYR A 106 40.630 28.705 15.037 1.00 13.45 C
ATOM 1632 CD1 TYR A 106 41.441 27.863 14.296 1.00 15.31 C
ATOM 1634 CE1 TYR A 106 42.517 27.226 14.869 1.00 15.32 C
ATOM 1636 CZ TYR A 106 42.812 27.428 16.186 1.00 15.25 C
ATOM 1637 OH TYR A 106 43.904 26.776 16.728 1.00 16.78 O
ATOM 1639 CE2 TYR A 106 42.027 28.251 16.961 1.00 15.05 C
ATOM 1641 CD2 TYR A 106 40.934 28.890 16.379 1.00 13.75 C
ATOM 1643 C TYR A 106 38.605 31.460 13.230 1.00 13.16 C
ATOM 1644 O TYR A 106 37.789 31.993 14.001 1.00 12.90 O
ATOM 1645 N ILE A 107 38.432 31.416 11.911 1.00 12.87 N
ATOM 1647 CA ILE A 107 37.219 31.954 11.296 1.00 13.04 C
ATOM 1649 CB ILE A 107 37.271 31.865 9.734 1.00 13.61 C
ATOM 1651 CG1 ILE A 107 36.049 32.531 9.105 1.00 16.08 C
ATOM 1654 CD1 ILE A 107 36.054 33.996 9.131 1.00 19.25 C

ATOM 1658 CG2 ILE A 107 37.277 30.431 9.234 1.00 14.39 C
ATOM 1662 C ILE A 107 36.026 31.203 11.890 1.00 12.69 C
ATOM 1663 O ILE A 107 36.050 29.967 11.991 1.00 12.26 O
ATOM 1664 N ILE A 108 34.994 31.931 12.314 1.00 10.96 N
ATOM 1666 CA ILE A 108 33.831 31.283 12.892 1.00 11.58 C
ATOM 1668 CB ILE A 108 33.823 31.470 14.438 1.00 11.47 C
ATOM 1670 CG1 ILE A 108 32.825 30.527 15.117 1.00 12.45 C
ATOM 1673 CD1 ILE A 108 33.138 29.042 14.913 1.00 14.07 C
ATOM 1677 CG2 ILE A 108 33.541 32.903 14.825 1.00 11.20 C
ATOM 1681 C ILE A 108 32.516 31.695 12.234 1.00 11.67 C
ATOM 1682 O ILE A 108 31.510 31.041 12.437 1.00 13.19 O
ATOM 1683 N ALA A 109 32.512 32.756 11.438 1.00 11.35 N
ATOM 1685 CA ALA A 109 31.319 33.139 10.675 1.00 12.23 C
ATOM 1687 CB ALA A 109 30.290 33.798 11.582 1.00 12.13 C
ATOM 1691 C ALA A 109 31.699 34.113 9.557 1.00 12.08 C
ATOM 1692 O ALA A 109 32.648 34.879 9.714 1.00 12.05 O
ATOM 1693 N GLU A 110 30.956 34.090 8.448 1.00 13.59 N
ATOM 1695 CA GLU A 110 31.147 35.085 7.399 1.00 13.30 C
ATOM 1697 CB GLU A 110 32.149 34.594 6.336 1.00 14.11 C
ATOM 1700 CG GLU A 110 32.258 35.509 5.123 1.00 15.16 C
ATOM 1703 CD GLU A 110 33.187 34.947 4.059 1.00 18.76 C
ATOM 1704 OE1 GLU A 110 34.393 35.270 4.085 1.00 20.47 O
ATOM 1705 OE2 GLU A 110 32.706 34.165 3.204 1.00 21.90 O
ATOM 1706 C GLU A 110 29.814 35.470 6.762 1.00 13.12 C
ATOM 1707 O GLU A 110 29.028 34.608 6.372 1.00 13.60 O
ATOM 1708 N TRP A 111 29.559 36.772 6.709 1.00 12.93 N
ATOM 1710 CA TRP A 111 28.420 37.335 6.032 1.00 14.60 C
ATOM 1712 CB TRP A 111 27.809 38.507 6.808 1.00 15.14 C
ATOM 1715 CG TRP A 111 26.726 39.127 5.988 1.00 15.69 C
ATOM 1716 CD1 TRP A 111 26.858 40.164 5.110 1.00 16.10 C
ATOM 1718 NE1 TRP A 111 25.661 40.419 4.489 1.00 16.03 N
ATOM 1720 CE2 TRP A 111 24.727 39.530 4.949 1.00 18.16 C
ATOM 1721 CD2 TRP A 111 25.367 38.695 5.891 1.00 18.12 C
ATOM 1722 CE3 TRP A 111 24.618 37.689 6.510 1.00 19.20 C
ATOM 1724 CZ3 TRP A 111 23.277 37.560 6.189 1.00 21.05 C
ATOM 1726 CH2 TRP A 111 22.673 38.410 5.255 1.00 20.77 C
ATOM 1728 CZ2 TRP A 111 23.382 39.397 4.626 1.00 19.73 C
ATOM 1730 C TRP A 111 28.912 37.854 4.684 1.00 16.60 C
ATOM 1731 O TRP A 111 29.813 38.692 4.621 1.00 15.60 O
ATOM 1732 N LYS A 112 28.344 37.323 3.618 1.00 18.75 N
ATOM 1734 CA LYS A 112 28.630 37.843 2.288 1.00 21.69 C
ATOM 1736 CB LYS A 112 29.829 37.176 1.651 1.00 21.83 C
ATOM 1739 CG LYS A 112 30.317 37.972 0.444 1.00 24.07 C
ATOM 1742 CD LYS A 112 31.330 37.217 −0.360 1.00 26.81 C
ATOM 1745 CE LYS A 112 32.648 37.120 0.351 1.00 28.67 C
ATOM 1748 NZ LYS A 112 33.684 36.627 −0.601 1.00 31.60 N
ATOM 1752 C LYS A 112 27.394 37.622 1.452 1.00 23.68 C
ATOM 1753 O LYS A 112 27.097 36.495 1.042 1.00 24.51 O
ATOM 1754 N LYS A 113 26.678 38.708 1.226 1.00 26.48 N
ATOM 1756 CA LYS A 113 25.423 38.686 0.536 1.00 29.15 C
ATOM 1758 CB LYS A 113 24.840 40.091 0.501 1.00 29.56 C
ATOM 1761 CG LYS A 113 23.349 40.115 0.396 1.00 31.24 C
ATOM 1764 CD LYS A 113 22.790 41.488 0.542 1.00 33.22 C
ATOM 1767 CE LYS A 113 21.264 41.332 0.752 1.00 34.56 C
ATOM 1770 NZ LYS A 113 20.811 40.425 1.911 1.00 34.61 N
ATOM 1774 C LYS A 113 25.589 38.215 −0.870 1.00 30.92 C
ATOM 1775 O LYS A 113 26.581 38.511 −1.536 1.00 31.06 O
ATOM 1776 N ALA A 114 24.575 37.490 −1.308 1.00 33.51 N
ATOM 1778 CA ALA A 114 24.484 37.015 −2.669 1.00 34.75 C
ATOM 1780 CB ALA A 114 25.336 35.792 −2.859 1.00 35.33 C
ATOM 1784 C ALA A 114 23.016 36.693 −2.918 1.00 35.91 C
ATOM 1785 O ALA A 114 22.275 36.373 −1.973 1.00 37.33 O
ATOM 1786 O ACE B 0 45.942 19.784 14.579 1.00 39.31 O
ATOM 1787 C ACE B 0 45.727 19.383 15.830 1.00 38.58 C
ATOM 1788 CA ACE B 0 44.966 18.078 16.167 1.00 38.68 C
ATOM 1789 N SER B 1 45.689 20.569 16.659 1.00 19.77 N
ATOM 1791 CA SER B 1 45.431 20.583 18.122 1.00 17.98 C
ATOM 1793 CB SER B 1 45.842 21.915 18.761 1.00 18.61 C
ATOM 1796 OG SER B 1 44.965 22.977 18.387 1.00 16.99 O
ATOM 1798 C SER B 1 43.950 20.368 18.350 1.00 17.78 C
ATOM 1799 O SER B 1 43.169 20.531 17.414 1.00 17.20 O
ATOM 1802 N ALA B 2 43.575 19.905 19.539 1.00 16.87 N
ATOM 1804 CA ALA B 2 42.161 19.821 19.902 1.00 16.13 C
ATOM 1806 CB ALA B 2 41.991 19.439 21.370 1.00 16.68 C
ATOM 1810 C ALA B 2 41.405 21.112 19.611 1.00 15.41 C
ATOM 1811 O ALA B 2 40.278 21.088 19.118 1.00 14.56 O
ATOM 1812 N THR B 3 42.018 22.234 19.952 1.00 15.22 N
ATOM 1814 CA THR B 3 41.391 23.526 19.766 1.00 14.31 C

ATOM 1816 CB THR B 3 42.264 24.598 20.403 1.00 14.74 C
ATOM 1818 OG1 THR B 3 42.272 24.402 21.826 1.00 16.14 O
ATOM 1820 CG2 THR B 3 41.660 25.961 20.217 1.00 14.49 C
ATOM 1824 C THR B 3 41.194 23.813 18.295 1.00 13.68 C
ATOM 1825 O THR B 3 40.111 24.227 17.861 1.00 13.01 O
ATOM 1826 N SER B 4 42.231 23.568 17.505 1.00 12.92 N
ATOM 1828 CA SER B 4 42.114 23.823 16.074 1.00 12.63 C
ATOM 1830 CB SER B 4 43.466 23.637 15.389 1.00 13.31 C
ATOM 1833 OG SER B 4 43.349 23.779 13.980 1.00 15.34 O
ATOM 1835 C SER B 4 41.042 22.939 15.427 1.00 11.99 C
ATOM 1836 O SER B 4 40.232 23.408 14.613 1.00 11.15 O
ATOM 1837 N LEU B 5 41.045 21.652 15.755 1.00 11.62 N
ATOM 1839 CA LEU B 5 40.036 20.744 15.224 1.00 10.95 C
ATOM 1841 CB LEU B 5 40.253 19.326 15.755 1.00 11.58 C
ATOM 1844 CG LEU B 5 41.493 18.602 15.191 1.00 13.26 C
ATOM 1846 CD1 LEU B 5 41.671 17.274 15.878 1.00 14.30 C
ATOM 1850 CD2 LEU B 5 41.430 18.388 13.679 1.00 16.20 C
ATOM 1854 C LEU B 5 38.633 21.207 15.621 1.00 10.05 C
ATOM 1855 O LEU B 5 37.713 21.115 14.830 1.00 9.60 O
ATOM 1856 N THR B 6 38.482 21.669 16.858 1.00 9.83 N
ATOM 1858 CA THR B 6 37.187 22.108 17.359 1.00 10.01 C
ATOM 1860 CB THR B 6 37.300 22.622 18.794 1.00 9.92 C
ATOM 1862 OG1 THR B 6 37.622 21.536 19.681 1.00 10.43 O
ATOM 1864 CG2 THR B 6 35.965 23.168 19.289 1.00 9.67 C
ATOM 1868 C THR B 6 36.616 23.197 16.490 1.00 10.19 C
ATOM 1869 O THR B 6 35.478 23.121 16.047 1.00 10.13 O
ATOM 1870 N PHE B 7 37.416 24.217 16.232 1.00 10.95 N
ATOM 1872 CA PHE B 7 36.898 25.372 15.532 1.00 10.37 C
ATOM 1874 CB PHE B 7 37.576 26.643 16.024 1.00 10.33 C
ATOM 1877 CG PHE B 7 37.149 27.021 17.415 1.00 10.12 C
ATOM 1878 CD1 PHE B 7 35.833 27.366 17.673 1.00 10.88 C
ATOM 1880 CE1 PHE B 7 35.417 27.659 18.945 1.00 11.19 C
ATOM 1882 CZ PHE B 7 36.296 27.605 19.969 1.00 11.18 C
ATOM 1884 CE2 PHE B 7 37.605 27.245 19.734 1.00 12.59 C
ATOM 1886 CD2 PHE B 7 38.021 26.936 18.466 1.00 11.83 C
ATOM 1888 C PHE B 7 36.909 25.194 14.025 1.00 10.94 C
ATOM 1889 O PHE B 7 36.103 25.820 13.353 1.00 11.93 O
ATOM 1890 N GLN B 8 37.767 24.329 13.489 1.00 11.93 N
ATOM 1892 CA GLN B 8 37.647 24.010 12.067 1.00 11.34 C
ATOM 1894 CB GLN B 8.38.761 23.087 11.621 1.00 12.48 C
ATOM 1897 CG GLN B 8 40.113 23.720 11.528 1.00 14.22 C
ATOM 1900 CD GLN B 8 41.117 22.698 11.051 1.00 15.81 C
ATOM 1901 OE1 GLN B 8 42.036 22.331 11.781 1.00 19.91 O
ATOM 1902 NE2 GLN B 8 40.902 22.184 9.843 1.00 17.92 N
ATOM 1905 C GLN B 8 36.316 23.286 11.855 1.00 10.37 C
ATOM 1906 O GLN B 8 35.580 23.546 10.908 1.00 10.98 O
ATOM 1907 N LEU B 9 36.006 22.360 12.758 1.00 10.06 N
ATOM 1909 CA LEU B 9 34.757 21.608 12.648 1.00 9.71 C
ATOM 1911 CB LEU B 9 34.726 20.455 13.634 1.00 9.51 C
ATOM 1914 CG LEU B 9 33.493 19.574 13.606 1.00 10.41 C
ATOM 1916 CD1 LEU B 9 33.447 18.825 12.265 1.00 11.23 C
ATOM 1920 CD2 LEU B 9 33.561 18.587 14.753 1.00 9.36 C
ATOM 1924 C LEU B 9 33.552 22.498 12.880 1.00 9.33 C
ATOM 1925 O LEU B 9 32.566 22.409 12.160 1.00 10.21 O
ATOM 1926 N ALA B 10 33.618 23.376 13.874 1.00 9.78 N
ATOM 1928 CA ALA B 10 32.476 24.246 14.138 1.00 9.75 C
ATOM 1930 CB ALA B 10 32.727 25.091 15.353 1.00 10.03 C
ATOM 1934 C ALA B 10 32.145 25.126 12.919 1.00 9.57 C
ATOM 1935 O ALA B 10 30.982 25.275 12.554 1.00 8.63 O
ATOM 1936 N TYR B 11 33.155 25.688 12.269 1.00 9.75 N
ATOM 1938 CA TYR B 11 32.885 26.566 11.136 1.00 10.72 C
ATOM 1940 CB TYR B 11 34.159 27.237 10.688 1.00 10.48 C
ATOM 1943 CG TYR B 11 33.979 28.188 9.535 1.00 11.27 C
ATOM 1944 CD1 TYR B 11 34.664 27.988 8.352 1.00 11.30 C
ATOM 1946 CE1 TYR B 11 34.534 28.867 7.292 1.00 13.85 C
ATOM 1948 CZ TYR B 11 33.706 29.949 7.409 1.00 14.97 C
ATOM 1949 OH TYR B 11 33.579 30.827 6.350 1.00 16.32 O
ATOM 1951 CE2 TYR B 11 33.022 30.183 8.582 1.00 14.29 C
ATOM 1953 CD2 TYR B 11 33.159 29.300 9.640 1.00 12.05 C
ATOM 1955 C TYR B 11 32.250 25.801 9.987 1.00 11.09 C
ATOM 1956 O TYR B 11 31.380 26.310 9.272 1.00 11.19 O
ATOM 1957 N LEU B 12 32.672 24.556 9.823 1.00 12.21 N
ATOM 1959 CA LEU B 12 32.179 23.730 8.742 1.00 12.45 C
ATOM 1961 CB LEU B 12 33.187 22.614 8.470 1.00 12.95 C
ATOM 1964 CG LEU B 12 33.011 21.779 7.209 1.00 16.64 C
ATOM 1966 CD1 LEU B 12 32.907 22.662 5.962 1.00 17.27 C
ATOM 1970 CD2 LEU B 12 34.193 20.804 7.093 1.00 18.06 C
ATOM 1974 C LEU B 12 30.767 23.156 8.956 1.00 12.37 C
ATOM 1975 O LEU B 12 29.914 23.302 8.071 1.00 13.09 O
ATOM 1976 N VAL B 13 30.514 22.525 10.103 1.00 12.47 N
ATOM 1978 CA VAL B 13 29.256 21.805 10.335 1.00 12.51 C
ATOM 1980 CB VAL B 13 29.485 20.381 10.894 1.00 13.37 C
ATOM 1982 CG1 VAL B 13 30.492 19.620 10.042 1.00 15.30 C
ATOM 1986 CG2 VAL B 13 29.922 20.398 12.336 1.00 14.08 C
ATOM 1990 C VAL B 13 28.273 22.541 11.237 1.00 12.00 C
ATOM 1991 O VAL B 13 27.106 22.172 11.319 1.00 11.68 O
ATOM 1992 N LYS B 14 28.775 23.558 11.917 1.00 11.40 N

ATOM 1994 CA LYS B 14 27.991 24.459 12.764 1.00 11.19 C
ATOM 1996 CB LYS B 14 26.759 25.042 12.035 1.00 11.48 C
ATOM 1999 CG LYS B 14 27.039 25.761 10.731 1.00 11.14 C
ATOM 2002 CD LYS B 14 28.190 26.750 10.824 1.00 9.92 C
ATOM 2005 CE LYS B 14 28.422 27.540 9.526 1.00 10.31 C
ATOM 2008 NZ LYS B 14 29.602 28.448 9.653 1.00 12.24 N
ATOM 2012 C LYS B 14 27.549 23.850 14.104 1.00 10.98 C
ATOM 2013 O LYS B 14 27.795 24.432 15.165 1.00 10.55 O
ATOM 2014 N LYS B 15 26.914 22.684 14.069 1.00 10.86 N
ATOM 2016 CA LYS B 15 26.282 22.127 15.256 1.00 12.66 C
ATOM 2018 CB LYS B 15 24.753 22.337 15.149 1.00 13.78 C
ATOM 2021 CG LYS B 15 23.878 21.739 16.237 1.00 18.00 C
ATOM 2024 CD LYS B 15 22.382 22.146 16.068 1.00 23.19 C
ATOM 2027 CE LYS B 15 21.671 21.394 14.921 1.00 27.17 C
ATOM 2030 NZ LYS B 15 20.279 21.902 14.547 1.00 34.39 N
ATOM 2034 C LYS B 15 26.637 20.640 15.355 1.00 12.47 C
ATOM 2035 O LYS B 15 26.526 19.913 14.363 1.00 13.03 O
ATOM 2036 N ILE B 16 27.094 20.207 16.526 1.00 13.16 N
ATOM 2038 CA ILE B 16 27.368 18.784 16.760 1.00 12.11 C
ATOM 2040 CB ILE B 16 28.707 18.380 16.149 1.00 12.61 C
ATOM 2042 CG1 ILE B 16 28.660 16.894 15.756 1.00 13.09 C
ATOM 2045 CD1 ILE B 16 29.822 16.447 14.941 1.00 14.91 C
ATOM 2049 CG2 ILE B 16 29.831 18.704 17.105 1.00 12.04 C
ATOM 2053 C ILE B 16 27.276 18.487 18.258 1.00 12.09 C
ATOM 2054 O ILE B 16 27.516 19.360 19.098 1.00 11.30 O
ATOM 2055 N ASP B 17 26.903 17.257 18.587 1.00 11.37 N
ATOM 2057 CA ASP B 17 26.701 16.850 19.977 1.00 11.97 C
ATOM 2059 CB ASP B 17 25.238 17.060 20.347 1.00 12.19 C
ATOM 2062 CG ASP B 17 24.929 16.770 21.795 1.00 15.47 C
ATOM 2063 OD1 ASP B 17 25.834 16.488 22.602 1.00 15.71 O
ATOM 2064 OD2 ASP B 17 23.746 16.838 22.212 1.00 21.94 O
ATOM 2065 C ASP B 17 27.026 15.373 20.040 1.00 11.79 C
ATOM 2066 O ASP B 17 26.246 14.552 19.554 1.00 12.85 O
ATOM 2067 N PHE B 18 28.190 15.029 20.566 1.00 10.57 N
ATOM 2069 CA PHE B 18 28.552 13.620 20.686 1.00 10.47 C
ATOM 2071 CB PHE B 18 29.385 13.115 19.479 1.00 9.71 C
ATOM 2074 CG PHE B 18 30.728 13.797 19.316 1.00 9.88 C
ATOM 2075 CD1 PHE B 18 31.732 13.663 20.275 1.00 7.77 C
ATOM 2077 CE1 PHE B 18 32.936 14.318 20.131 1.00 9.85 C
ATOM 2079 CZ PHE B 18 33.172 15.094 19.013 1.00 10.47 C
ATOM 2081 CE2 PHE B 18 32.194 15.226 18.062 1.00 9.60 C
ATOM 2083 CD2 PHE B 18 30.979 14.584 18.211 1.00 9.21 C
ATOM 2085 C PHE B 18 29.281 13.324 21.983 1.00 9.72 C
ATOM 2086 O PHE B 18 29.760 14.220 22.691 1.00 10.09 O
ATOM 2087 N ASP B 19 29.326 12.041 22.306 1.00 9.08 N
ATOM 2089 CA ASP B 19 30.050 11.562 23.459 1.00 9.72 C
ATOM 2091 CB ASP B 19 29.193 11.549 24.716 1.00 9.54 C
ATOM 2094 CG ASP B 19 29.999 11.225 25.937 1.00 11.36 C
ATOM 2095 OD1 ASP B 19 29.498 11.408 27.093 1.00 13.80 O
ATOM 2096 OD2 ASP B 19 31.149 10.767 25.834 1.00 10.64 O
ATOM 2097 C ASP B 19 30.543 10.155 23.160 1.00 9.57 C
ATOM 2098 O ASP B 19 29.765 9.177 23.218 1.00 10.53 O
ATOM 2099 N TYR B 20 31.830 10.085 22.813 1.00 9.01 N
ATOM 2101 CA TYR B 20 32.505 8.831 22.518 1.00 8.11 C
ATOM 2103 CB TYR B 20 33.232 8.896 21.163 1.00 7.80 C
ATOM 2106 CG TYR B 20 32.292 8.800 19.966 1.00 7.18 C
ATOM 2107 CD1 TYR B 20 31.765 9.933 19.381 1.00 8.23 C
ATOM 2109 CE1 TYR B 20 30.897 9.849 18.286 1.00 8.63 C
ATOM 2111 CZ TYR B 20 30.570 8.623 17.777 1.00 8.76 C
ATOM 2112 OH TYR B 20 29.690 8.504 16.698 1.00 7.11 O
ATOM 2114 CE2 TYR B 20 31.081 7.492 18.358 1.00 7.59 C
ATOM 2116 CD2 TYR B 20 31.929 7.580 19.435 1.00 8.21 C
ATOM 2118 C TYR B 20 33.453 8.446 23.657 1.00 7.82 C
ATOM 2119 O TYR B 20 34.453 7.777 23.416 1.00 8.72 O
ATOM 2120 N THR B 21 33.128 8.834 24.892 1.00 8.34 N
ATOM 2122 CA THR B 21 33.897 8.365 26.046 1.00 8.81 C
ATOM 2124 CB THR B 21 33.320 8.922 27.334 1.00 9.96 C
ATOM 2126 OG1 THR B 21 33.372 10.363 27.299 1.00 10.43 O
ATOM 2128 CG2 THR B 21 34.222 8.512 28.491 1.00 9.86 C
ATOM 2132 C THR B 21 33.804 6.831 26.040 1.00 9.35 C
ATOM 2133 O THR B 21 32.692 6.291 26.011 1.00 9.22 O
ATOM 2134 N PRO B 22 34.922 6.111 26.025 1.00 9.19 N
ATOM 2135 CA PRO B 22 34.844 4.647 25.905 1.00 9.50 C
ATOM 2137 CB PRO B 22 36.209 4.280 25.352 1.00 9.82 C
ATOM 2140 CG PRO B 22 37.138 5.334 25.941 1.00 9.26 C
ATOM 2143 CD PRO B 22 36.320 6.589 26.015 1.00 9.34 C
ATOM 2146 C PRO B 22 34.616 3.930 27.227 1.00 10.16 C
ATOM 2147 O PRO B 22 35.520 3.898 28.070 1.00 10.91 O
ATOM 2148 N ASN B 23 33.413 3.394 27.413 1.00 10.40 N
ATOM 2150 CA ASN B 23 33.082 2.645 28.614 1.00 10.53 C
ATOM 2152 CB ASN B 23 31.680 3.014 29.089 1.00 11.14 C
ATOM 2155 CG ASN B 23 31.595 4.472 29.590 1.00 13.44 C
ATOM 2156 OD1 ASN B 23 31.816 4.721 30.763 1.00 19.39 O
ATOM 2157 ND2 ASN B 23 31.342 5.441 28.685 1.00 14.28 N
ATOM 2160 C ASN B 23 33.228 1.143 28.312 1.00 9.85 C
ATOM 2161 O ASN B 23 32.489 0.595 27.483 1.00 10.11 O
ATOM 2162 N TRP B 24 34.208 0.502 28.942 1.00 8.96 N
ATOM 2164 CA TRP B 24 34.524 −0.899 28.684 1.00 8.99 C
ATOM 2166 CB TRP B 24 36.032 −1.117 28.760 1.00 8.98 C
ATOM 2169 CG TRP B 24 36.799 −0.256 27.823 1.00 8.22 C
ATOM 2170 CD1 TRP B 24 37.375 0.965 28.116 1.00 9.52 C
ATOM 2172 NE1 TRP B 24 38.003 1.469 27.000 1.00 9.37 N
ATOM 2174 CE2 TRP B 24 37.860 0.574 25.967 1.00 9.60 C
ATOM 2175 CD2 TRP B 24 37.099 −0.517 26.446 1.00 9.21 C

ATOM 2176 CE3 TRP B 24 36.824 −1.577 25.560 1.00 9.09 C
ATOM 2178 CZ3 TRP B 24 37.292 −1.502 24.264 1.00 9.03 C
ATOM 2180 CH2 TRP B 24 38.045 −0.414 23.829 1.00 7.76 C
ATOM 2182 CZ2 TRP B 24 38.337 0.636 24.661 1.00 8.73 C
ATOM 2184 C TRP B 24 33.806 −1.771 29.715 1.00 10.09 C
ATOM 2185 O TRP B 24 34.024 −1.610 30.922 1.00 11.35 O
ATOM 2186 N GLY B 25 32.931 −2.655 29.234 1.00 10.43 N
ATOM 2188 CA GLY B 25 32.143 −3.516 30.098 1.00 9.95 C
ATOM 2191 C GLY B 25 32.749 −4.894 30.176 1.00 10.10 C
ATOM 2192 O GLY B 25 33.220 −5.444 29.184 1.00 10.44 O
ATOM 2193 N ARG B 26 32.721 −5.470 31.372 1.00 9.91 N
ATOM 2195 CA ARG B 26 33.393 −6.738 31.594 1.00 10.74 C
ATOM 2197 CB ARG B 26 34.185 −6.692 32.897 1.00 11.28 C
ATOM 2200 CG ARG B 26 35.418 −5.792 32.764 1.00 14.61 C
ATOM 2203 CD ARG B 26 36.168 −5.505 34.025 1.00 18.47 C
ATOM 2206 NE ARG B 26 37.353 −4.694 33.713 1.00 22.81 N
ATOM 2208 CZ ARG B 26 38.526 −5.167 33.274 1.00 20.92 C
ATOM 2209 NH1 ARG B 26 38.730 −6.471 33.093 1.00 16.47 N
ATOM 2212 NH2 ARG B 26 39.522 −4.318 33.028 1.00 21.83 N
ATOM 2215 C ARG B 26 32.431 −7.898 31.604 1.00 11.12 C
ATOM 2216 O ARG B 26 31.227 −7.721 31.802 1.00 11.55 O
ATOM 2217 N GLY B 27 32.990 −9.082 31.405 1.00 10.76 N
ATOM 2219 CA GLY B 27 32.203 −10.305 31.337 1.00 11.53 C
ATOM 2222 C GLY B 27 32.382 −11.170 32.553 1.00 12.49 C
ATOM 2223 O GLY B 27 32.588 −10.677 33.664 1.00 11.38 O
ATOM 2224 N THR B 28 32.285 −12.468 32.308 1.00 14.02 N
ATOM 2226 CA THR B 28 32.361 −13.494 33.325 1.00 14.82 C
ATOM 2228 CB THR B 28 30.965 −14.118 33.495 1.00 14.80 C
ATOM 2230 OG1 THR B 28 30.052 −13.151 34.032 1.00 15.92 O
ATOM 2232 CG2 THR B 28 30.974 −15.235 34.519 1.00 16.05 C
ATOM 2236 C THR B 28 33.327 −14.552 32.828 1.00 15.01 C
ATOM 2237 O THR B 28 33.037 −15.215 31.838 1.00 15.21 O
ATOM 2238 N PRO B 29 34.490 −14.700 33.454 1.00 16.30 N
ATOM 2239 CA PRO B 29 34.948 −13.877 34.569 1.00 16.04 C
ATOM 2241 CB PRO B 29 36.219 −14.575 35.028 1.00 16.47 C
ATOM 2244 CG PRO B 29 36.636 −15.376 33.917 1.00 16.57 C
ATOM 2247 CD PRO B 29 35.467 −15.724 33.083 1.00 16.58 C
ATOM 2250 C PRO B 29 35.286 −12.472 34.156 1.00 15.67 C
ATOM 2251 O PRO B 29 35.396 −12.161 32.977 1.00 14.52 O
ATOM 2252 N SER B 30 35.477 −11.643 35.164 1.00 15.56 N
ATOM 2254 CA SER B 30 35.592 −10.188 34.990 1.00 15.79 C
ATOM 2256 CB SER B 30 35.368 −9.479 36.338 1.00 16.72 C
ATOM 2259 OG SER B 30 36.454 −9.647 37.224 1.00 19.27 O
ATOM 2261 C SER B 30 36.886 −9.718 34.319 1.00 15.13 C
ATOM 2262 O SER B 30 37.028 −8.535 33.981 1.00 14.89 O
ATOM 2263 N SER B 31 37.813 −10.644 34.117 1.00 15.18 N
ATOM 2265 CA SER B 31 39.073 −10.365 33.451 1.00 14.92 C
ATOM 2267 CB SER B 31 40.078 −11.489 33.743 1.00 15.53 C
ATOM 2270 OG SER B 31 39.588 −12.751 33.330 1.00 16.71 O
ATOM 2272 C SER B 31 38.833 −10.220 31.958 1.00 14.13 C
ATOM 2273 O SER B 31 39.704 −9.755 31.247 1.00 14.11 O
ATOM 2274 N TYR B 32 37.655 −10.629 31.492 1.00 13.25 N
ATOM 2276 CA TYR B 32 37.263 −10.430 30.088 1.00 12.84 C
ATOM 2278 CB TYR B 32 36.386 −11.579 29.595 1.00 13.42 C
ATOM 2281 CG TYR B 32 37.194 −12.849 29.494 1.00 17.98 C
ATOM 2282 CD1 TYR B 32 37.301 −13.710 30.586 1.00 22.94 C
ATOM 2284 CE1 TYR B 32 38.065 −14.852 30.521 1.00 23.98 C
ATOM 2286 CZ TYR B 32 38.746 −15.143 29.354 1.00 25.27 C
ATOM 2287 OR TYR B 32 39.505 −16.288 29.289 1.Q0 27.54 O
ATOM 2289 CE2 TYR B 32 38.663 −14.298 28.266 1.00 23.63 C
ATOM 2291 CD2 TYR B 32 37.895 −13.159 28.344 1.00 21.29 C
ATOM 2293 C TYR B 32 36.533 −9.112 29.846 1.00 11.60 C
ATOM 2294 O TYR B 32 35.685 −8.695 30.647 1.00 10.60 O
ATOM 2295 N ILE B 33 36.880 −8.444 28.745 1.00 10.45 N
ATOM 2297 CA ILE B 33 36.165 −7.242 28.298 1.00 10.39 C
ATOM 2299 CB ILE B 33 37.144 −6.198 27.724 1.00 10.57 C
ATOM 2301 CG1 ILE B 33 38.031 −5.676 28.860 1.00 13.06 C
ATOM 2304 CD1 ILE B 33 39.008 −4.662 28.440 1.00 16.01 C
ATOM 2308 CG2 ILE B 33 36.395 −5.062 26.975 1.00 10.92 C
ATOM 2312 C ILE B 33 35.178 −7.715 27.237 1.00 9.65 C
ATOM 2313 O ILE B 33 35.595 −8.249 26.202 1.00 8.88 O
ATOM 2314 N ASP B 34 33.883 −7.580 27.498 1.00 9.91 N
ATOM 2316 CA ASP B 34 32.857 −8.063 26.583 1.00 9.11 C
ATOM 2318 CB ASP B 34 31.665 −8.615 27.367 1.00 9.19 C
ATOM 2321 CG ASP B 34 31.881 −10.030 27.892 1.00 11.22 C
ATOM 2322 OD1 ASP B 34 33.013 −10.576 27.882 1.00 10.96 O

ATOM 2323 OD2 ASP B 34 30.916 −10.660 28.362 1.00 11.64 O
ATOM 2324 C ASP B 34 32.306 −7.017 25.640 1.00 9.26 C
ATOM 2325 O ASP B 34 31.726 −7.362 24.616 1.00 8.27 O
ATOM 2326 N ASN B 35 32.465 −5.740 25.959 1.00 9.55 N
ATOM 2328 CA ASN B 35 31.791 −4.730 25.152 1.00 8.99 C
ATOM 2330 CB ASN B 35 30.278 −4.762 25.446 1.00 9.72 C
ATOM 2333 CG ASN B 35 29.970 −4.723 26.949 1.00 11.37 C
ATOM 2334 OD1 ASN B 35 29.559 −5.741 27.574 1.00 14.30 O
ATOM 2335 ND2 ASN B 35 30.186 −3.573 27.551 1.00 7.97 N
ATOM 2338 C ASN B 35 32.351 −3.341 25.400 1.00 9.17 C
ATOM 2339 O ASN B 35 33.129 −3.115 26.332 1.00 9.29 O
ATOM 2340 N LEU B 36 31.917 −2.413 24.552 1.00 9.41 N
ATOM 2342 CA LEU B 36 32.345 −1.026 24.581 1.00 9.12 C
ATOM 2344 CB LEU B 36 33.308 −0:779 23.414 1.00 8.17 C
ATOM 2347 CG LEU B 36 33.652 0.670 23.053 1.00 9.08 C
ATOM 2349 CD1 LEU B 36 34.294 1.387 24.199 1.00 9.44 C
ATOM 2353 CD2 LEU B 36 34.560 0.729 21.837 1.00 10.64 C
ATOM 2357 C LEU B 36 31.099 −0.186 24.369 1.00 9.10 C
ATOM 2358 O LEU B 36 30.382 −0.391 23.385 1.00 8.92 O
ATOM 2359 N THR B 37 30.824 0.737 25.279 1.00 9.13 N
ATOM 2361 CA THR B 37 29.653 1.596 25.151 1.00 8.93 C
ATOM 2363 CB THR B 37 28.725 1.447 26.372 1.00 9.51 C
ATOM 2365 OG1 THR B 37 28.238 0.095 26.458 1.00 10.29 O
ATOM 2367 CG2 THR B 37 27.474 2.316 26.234 1.00 10.22 C
ATOM 2371 C THR B 37 30.041 3.056 25.034 1.00 8.89 C
ATOM 2372 O THR B 37 30.857 3.557 25.814 1.00 8.97 O
ATOM 2373 N PHE B 38 29.450 3.724 24.042 1.00 7.97 N
ATOM 2375 CA PHE B 38 29.584 5.161 23.853 1.00 8.58 C
ATOM 2377 CB PHE B 38 29.827 5.456 22.386 1.00 8.85 C
ATOM 2380 CG PHE B 38 31.134 4.951 21.847 1.00 7.28 C
ATOM 2381 CD1 PHE B 38 32.340 5.237 22.482 1.00 7.91 C
ATOM 2383 CE1 PHE B 38 33.544 4.811 21.942 1.00 8.72 C
ATOM 2385 CZ PHE B 38 33.555 4.102 20.756 1.00 11.58 C
ATOM 2387 CE2 PHE B 38 32.366 3.817 20.120 1.00 9.53 C
ATOM 2389 CD2 PHE B 38 31.163 4.243 20.661 1.00 7.95 C
ATOM 2391 C PHE B 38 28.269 5.844 24.273 1.00 8.73 C
ATOM 2392 O PHE B 38 27.216 5.431 23.811 1.00 9.98 O
ATOM 2393 N PRO B 39 28.293 6.842 25.163 1.00 8.76 N
ATOM 2394 CA PRO B 39 27.036 7.460 25.636 1.00 8.86 C
ATOM 2396 CB PRO B 39 27.497 8.386 26.780 1.00 9.34 C
ATOM 2399 CG PRO B 39 28.785 7.866 27.199 1.00 9.35 C
ATOM 2402 CD PRO B 39 29.448 7.348 25.916 1.00 9.58 C
ATOM 2405 C PRO B 39 26.209 8.230 24.627 1.00 9.13 C
ATOM 2406 O PRO B 39 24.991 8.328 24.796 1.00 8.44 O
ATOM 2407 N LYS B 40 26.834 8.794 23.602 1.00 9.49 N
ATOM 2409 CA LYS B 40 26.061 9.548 22.618 1.00 9.43 C
ATOM 2411 CB LYS B 40 25.784 10.967 23.094 1.00 10.36 C
ATOM 2414 CG LYS B 40 24.760 11.685 22.232 1.00 12.43 C
ATOM 2417 CD LYS B 40 24.661 13.182 22.550 1.00 16.76 C
ATOM 2420 CE LYS B 40 24.030 13.456 23.916 1.00 22.56 C
ATOM 2423 NZ LYS B 40 24.148 14.904 24.336 1.00 28.45 N
ATOM 2427 C LYS B 40 26.748 9.529 21.265 1.00 9.14 C
ATOM 2428 O LYS B 40 27.597 10.355 20.962 1.00 9.57 O
ATOM 2429 N VAL B 41 26.393 8.544 20.458 1.00 9.12 N
ATOM 2431 CA VAL B 41 26.969 8.438 19.131 1.00 9.08 C
ATOM 2433 CB VAL B 41 26.967 6.970 18.603 1.00 9.12 C
ATOM 2435 CG1 VAL B 41 27.769 6.059 19.553 1.00 8.74 C
ATOM 2439 CG2 VAL B 41 25.556 6.453 18.410 1.00 8.61 C
ATOM 2443 C VAL B 41 26.243 9.323 18.136 1.00 9.87 C
ATOM 2444 O VAL B 41 25.107 9.759 18.350 1.00 9.30 O
ATOM 2445 N LEU B 42 26.907 9.582 17.022 1.00 10.23 N
ATOM 2447 CA LEU B 42 26.261 10.288 15.932 1.00 11.90 C
ATOM 2449 CB LEU B 42 27.303 10.820 14.948 1.00 11.82 C
ATOM 2452 CG LEU B 42 28.246 11.835 15.604 1.00 13.37 C
ATOM 2454 CD1 LEU B 42 29.484 12.076 14.765 1.00 17.49 C
ATOM 2458 CD2 LEU B 42 27.504 13.150 15.923 1.00 13.74 C
ATOM 2462 C LEU B 42 25.303 9.312 15.257 1.00 13.53 C
ATOM 2463 O LEU B 42 25.559 8.103 15.208 1.00 13.30 O
ATOM 2464 N THR B 43 24.203 9.824 14.717 1.00 16.10 N
ATOM 2466 CA THR B 43 23.223 8.949 14.082 1.00 17.45 C
ATOM 2468 CB THR B 43 21.953 8.828 14.935 1.00 17.82 C
ATOM 2470 OG1 THR B 43 21.431 10.123 15.252 1.00 20.64 O
ATOM 2472 CG2 THR B 43 22.241 8.193 16.296 1.00 18.56 C
ATOM 2476 C THR B 43 22.842 9.433 12.691 1.00 18.34 C
ATOM 2477 O THR B 43 21.866 8.947 12.117 1.00 18.70 O
ATOM 2478 N ASP B 44 23.614 10.367 12.148 1.00 18.36 N
ATOM 2480 CA ASP B 44 23.349 10.867 10.776 1.00 19.37 C
ATOM 2482 CB ASP B 44 24.158 12.130 10.514 1.00 18.75 C
ATOM 2485 CG ASP B 44 25.649 11.906 10.660 1.00 20.65 C
ATOM 2486 OD1 ASP B 44 26.435 12.599 9.975 1.00 22.24 O
ATOM 2487 OD2 ASP B 44 26.119 11.081 11.464 1.00 18.51 O
ATOM 2488 C ASP B 44 23.632 9.875 9.640 1.00 20.76 C
ATOM 2489 O ASP B 44 23.120 10.045 8.516 1.00 20.73 O
ATOM 2490 N LYS B 45 24.451 8.858 9.910 1.00 22.30 N
ATOM 2492 CA LYS B 45 24.845 7.850 8.930 1.00 22.65 C
ATOM 2494 CB LYS B 45 26.271 8.089 8.416 1.00 23.02 C
ATOM 2497 CG LYS B 45 26.515 9.467 7.807 1.00 25.19 C
ATOM 2500 CD LYS B 45 27.968 9.681 7.419 1.00 29.05 C
ATOM 2503 CE LYS B 45 28.158 10.993 6.672 1.00 32.51 C
ATOM 2506 NZ LYS B 45 29.514 11.592 6.878 1.00 36.79 N
ATOM 2510 C LYS B 45 24.790 6.500 9.640 1.00 23.32 C
ATOM 2511 O LYS B 45 24.775 6.441 10.878 1.00 23.05 O
ATOM 2512 N LYS B 46 24.771 5.425 8.856 1.00 24.20 N
ATOM 2514 CA LYS B 46 24.712 4.075 9.398 1.00 23.77 C
ATOM 2516 CB LYS B 46 24.033 3.132 8.406 1.00 23.95 C
ATOM 2519 CG LYS B 46 22.685 3.632 7.903 1.00 24.89 C
ATOM 2522 CD LYS B 46 22.803 4.957 7.139 1.00 24.88 C
ATOM 2525 CE LYS B 46 23.693 4.858 5.919 1.00 24.51 C
ATOM 2528 NZ LYS B 46 24.316 6.162 5.572 1.00 20.23 N
ATOM 2532 C LYS B 46 26.127 3.598 9.655 1.00 22.13 C

ATOM 2533 O LYS B 46 26.717 2.916 8.828 1.00 23.19 O
ATOM 2534 N TYR B 47 26.678 3.932 10.814 1.00 21.82 N
ATOM 2536 CA TYR B 47 28.065 3.580 11.084 1.00 17.30 C
ATOM 2538 CB TYR B 47 28.630 4.461 12.199 1.00 16.73 C
ATOM 2541 CG TYR B 47 28.584 5.926 11.880 1.00 14.44 C
ATOM 2542 CD1 TYR B 47 29.504 6.494 11.022 1.00 14.82 C
ATOM 2544 CE1 TYR B 47 29.475 7.842 10.736 1.00 15.44 C
ATOM 2546 CZ TYR B 47 28.502 8.629 11.305 1.00 14.96 C
ATOM 2547 OH TYR B 47 28.457 9.966 11.010 1.00 16.74 O
ATOM 2549 CE2 TYR B 47 27.572 8.078 12.165 1.00 15.51 C
ATOM 2551 CD2 TYR B 47 27.616 6.748 12.446 1.00 15.33 C
ATOM 2553 C TYR B 47 28.239 2.119 11.467 1.00 15.49 C
ATOM 2554 O TYR B 47 27.349 1.501 12.055 1.00 15.48 O
ATOM 2555 N SER B 48 29.376 1.550 11.086 1.00 12.97 N
ATOM 2557 CA SER B 48 29.731 0.219 11.553 1.00 12.31 C
ATOM 2559 CB SER B 48 29.852 −0.787 10.419 1.00 13.21 C
ATOM 2562 OG SER B 48 30.688 −0.272 9.425 1.00 17.27 O
ATOM 2564 C SER B 48 31.064 0.343 12.277 1.00 10.66 C
ATOM 2565 O SER B 48 31.687 1.401 12.295 1.00 9.38 O
ATOM 2566 N TYR B 49 31.478 −0.754 12.890 1.00 9.05 N
ATOM 2568 CA TYR B 49 32.700 −0.772 13.663 1.00 8.64 C
ATOM 2570 CB TYR B 49 32.345 −0.790 15.142 1.00 8.24 C
ATOM 2573 CG TYR B 49 31.547 0.419 15.574 1.00 7.93 C
ATOM 2574 CD1 TYR B 49 30.173 0.348 15.704 1.00 9.31 C
ATOM 2576 CE1 TYR B 49 29.444 1.443 16.089 1.00 10.10 C
ATOM 2578 CZ TYR B 49 30.076 2.635 16.361 1.00 9.43 C
ATOM 2579 OH TYR B 49 29.321 3.726 16.755 1.00 11.22 O
ATOM 2581 CE2 TYR B 49 31.442 2.741 16.222 1.00 7.22 C
ATOM 2583 CD2 TYR B 49 32.169 1.629 15.833 1.00 7.22 C
ATOM 2585 C TYR B 49 33.542 −1.997 13.338 1.00 8.84 C
ATOM 2586 O TYR B 49 33.035 −3.120 13.301 1.00 8.75 O
ATOM 2587 N ARG B 50 34.838 −1.764 13.149 1.00 8.80 N
ATOM 2589 CA ARG B 50 35.811 −2.821 12.915 1.00 8.50 C
ATOM 2591 CB ARG B 50 36.725 −2.427 11.771 1.00 8.52 C
ATOM 2594 CG ARG B 50 37.615 −3.545 11.308 1.00 9.29 C
ATOM 2597 CD ARG B 50 38.349 −3.220 10.048 1.00 9.53 C
ATOM 2600 NE ARG B 50 39.382 −2.205 10.191 1.00 8.80 N
ATOM 2602 CZ ARG B 50 40.631 −2.476 10.566 1.00 11.23 C
ATOM 2603 NH1 ARG B 50 40.986 −3.721 10.901 1.00 11.51 N
ATOM 2606 NH2 ARG B 50 41.533 −1.506 10.650 1.00 13.88 N
ATOM 2609 C ARG B 50 36.627 −2.987 14.186 1.00 8.77 C
ATOM 2610 O ARG B 50 37.063 −2.001 14.787 1.00 8.89 O
ATOM 2611 N VAL B 51 36.797 −4.230 14.609 1.00 9.25 N
ATOM 2613 CA VAL B 51 37.467 −4.543 15.860 1.00 9.05 C
ATOM 2615 CB VAL B 51 36.503 −5.312 16.778 1.00 9.51 C
ATOM 2617 CG1 VAL B 51 37.193 −5.808 18.029 1.00 10.94 C
ATOM 2621 CG2 VAL B 51 35.356 −4.425 17.179 1.00 9.48 C
ATOM 2625 C VAL B 51 38.729 −5.378 15.614 1.00 9.31 C
ATOM 2626 O VAL B 51 38.692 −6.344 14.865 1.00 9.58 O
ATOM 2627 N VAL B 52 39.827 −5.004 16.274 1.00 8.69 N
ATOM 2629 CA VAL B 52 41.136 −5.638 16.112 1.00 8.61 C
ATOM 2631 CB VAL B 52 42.132 −4.664 15.406 1.00 8.82 C
ATOM 2633 CG1 VAL B 52 43.432 −5.350 15.057 1.00 8.22 C
ATOM 2637 CG2 VAL B 52 41.503 −4.031 14.166 1.00 8.20 C
ATOM 2641 C VAL B 52 41.680 −6.010 17.490 1.00 8.96 C
ATOM 2642 O VAL B 52 41.759 −5.166 18.367 1.00 9.37 O
ATOM 2643 N VAL B 53 42.050 −7.276 17.677 1.00 8.28 N
ATOM 2645 CA VAL B 53 42.521 −7.758 18.973 1.00 9.11 C
ATOM 2647 CB VAL B 53 41.645 −8.918 19.482 1.00 9.88 C
ATOM 2649 CG1 VAL B 53 42.248 −9.531 20.746 1.00 10.11 C
ATOM 2653 CG2 VAL B 53 40.207 −8.420 19.731 1.00 10.75 C
ATOM 2657 C VAL B 53 43.965 −8.214 18.850 1.00 9.11 C
ATOM 2658 O VAL B 53 44.254 −9.170 18.105 1.00 9.06 O
ATOM 2659 N ASN B 54 44.873 −7.543 19.563 1.00 8.85 N
ATOM 2661 CA ASN B 54 46.310 −7.827 19.435 1.00 9.61 C
ATOM 2663 CB ASN B 54 46.676 −9.140 20.109 1.00 10.03 C
ATOM 2666 CG ASN B 54 47.031 −8.996 21.586 1.00 11.16 C
ATOM 2667 OD1 ASN B 54 47.247 −10.014 22.267 1.00 16.89 O
ATOM 2668 ND2 ASN B 54 47.126 −7.781 22.076 1.00 9.72 N
ATOM 2671 C ASN B 54 46.747 −7.870 17.956 1.00 10.26 C
ATOM 2672 O ASN B 54 47.522 −8.745 17.548 1.00 11.02 O
ATOM 2673 N GLY B 55 46.238 −6.928 17.168 1.00 10.54 N
ATOM 2675 CA GLY B 55 46.575 −6.793 15.760 1.00 9.95 C
ATOM 2678 C GLY B 55 45.844 −7.707 14.792 1.00 9.84 C
ATOM 2679 O GLY B 55 45.998 −7.522 13.579 1.00 9.89 O
ATOM 2680 N SER B 56 45.036 −8.629 15.310 1.00 9.14 N
ATOM 2682 CA SER B 56 44.226 −9.538 14.506 1.00 9.52 C
ATOM 2684 CB SER B 56 44.022 −10.867 15.235 1.00 10.16 C
ATOM 2687 OG SER B 56 43.162 −11.730 14.503 1.00 10.98 O
ATOM 2689 C SER B 56 42.858 −8.888 14.232 1.00 9.17 C
ATOM 2690 O SER B 56 42.065 −8.653 15.148 1.00 8.64 O
ATOM 2691 N ASP B 57 42.613 −8.558 12.976 1.00 9.04 N
ATOM 2693 CA ASP B 57 41.358 −7.950 12.530 1.00 8.46 C
ATOM 2695 CB ASP B 57 41.559 −7.526 11.067 1.00 8.57 C
ATOM 2698 CG ASP B 57 40.364 −6.842 10.457 1.00 9.39 C
ATOM 2699 OD1 ASP B 57 40.383 −6.708 9.193 1.00 9.52 O
ATOM 2700 OD2 ASP B 57 39.385 −6.414 11.106 1.00 9.56 O
ATOM 2701 C ASP B 57 40.201 −8.950 12.628 1.00 8.72 C
ATOM 2702 O ASP B 57 40.218 −10.003 11.966 1.00 8.92 O
ATOM 2703 N LEU B 58 39.217 −8.665 13.478 1.00 9.29 N

ATOM 2705 CA LEU B 58 38.021 −9.508 13.542 1.00 9.33 C
ATOM 2707 CB LEU B 58 37.508 −9.582 14.977 1.00 9.53 C
ATOM 2710 CG LEU B 58 38.564 −9.973 16.005 1.00 9.47 C
ATOM 2712 CD1 LEU B 58 37.925 −10.156 17.379 1.00 11.17 C
ATOM 2716 CD2 LEU B 58 39.325 −11.242 15.604 1.00 11.86 C
ATOM 2720 C LEU B 58 36.897 −9.037 12.608 1.00 9.41 C
ATOM 2721 O LEU B 58 35.797 −9.607 12.608 1.00 10.79 O
ATOM 2722 N GLY B 59 37.166 −8.006 11.826 1.00 9.53 N
ATOM 2724 CA GLY B 59 36.245 −7.517 10.815 1.00 9.73 C
ATOM 2727 C GLY B 59 35.209 −6.570 11.375 1.00 9.94 C
ATOM 2728 O GLY B 59 35.355 −6.046 12.482 1.00 9.32 O
ATOM 2729 N VAL B 60 34.133 −6.407 10.614 1.00 10.86 N
ATOM 2731 CA VAL B 60 33.165 −5.356 10.840 1.00 11.57 C
ATOM 2733 CB VAL B 60 33.048 −4.476 9.571 1.00 11.80 C
ATOM 2735 CG1 VAL B 60 32.330 −3.170 9.845 1.00 13.91 C
ATOM 2739 CG2 VAL B 60 32.361 −5.227 8.443 1.00 13.46 C
ATOM 2743 C VAL B 60 31.806 −5.894 11.230 1.00 11.41 C
ATOM 2744 O VAL B 60 31.409 −7.016 10.849 1.00 11.80 O
ATOM 2745 N GLU B 61 31.090 −5.084 11.998 1.00 10.41 N
ATOM 2747 CA GLU B 61 29.728 −5.416 12.391 1.00 11.68 C
ATOM 2749 CB GLU B 61 29.701 −6.352 13.600 1.00 11.99 C
ATOM 2752 CG GLU B 61 28.316 −6.803 14.051 1.00 16.37 C
ATOM 2755 CD GLU B 61 27.469 −7.353 12.931 1.00 18.62 C
ATOM 2756 OE1 GLU B 61 26.499 −6.673 12.533 1.00 19.03 O
ATOM 2757 OE2 GLU B 61 27.791 −8.452 12.418 1.00 20.11 O
ATOM 2758 C GLU B 61 28.994 −4.105 12.643 1.00 12.02 C
ATOM 2759 O GLU B 61 29.616 −3.087 12.944 1.00 10.24 O
ATOM 2760 N SER B 62 27.673 −4.129 12.540 1.00 13.34 N
ATOM 2762 CA SER B 62 26.908 −2.919 12.741 1.00 13.52 C
ATOM 2764 CB SER B 62 26.526 −2.289 11.407 1.00 14.00 C
ATOM 2767 OG SER B 62 25.717 −3.176 10.647 1.00 13.96 O
ATOM 2769 C SER B 62 25.631 −3.142 13.513 1.00 13.46 C
ATOM 2770 O SER B 62 24.940 −2.159 13.807 1.00 14.34 O
ATOM 2771 N ASN B 63 25.333 −4.389 13.869 1.00 12.74 N
ATOM 2773 CA ASN B 63 24.037 −4.692 14.474 1.00 14.23 C
ATOM 2775 CB ASN B 63 23.557 −6.123 14.156 1.00 15.00 C
ATOM 2778 CG ASN B 63 22.193 −6.441 14.798 1.00 16.84 C
ATOM 2779 OD1 ASN B 63 21.441 −5.531 15.129 1.00 21.06 O
ATOM 2780 ND2 ASN B 63 21.895 −7.727 15.010 1.00 21.14 N
ATOM 2783 C ASN B 63 24.089 −4.438 15.971 1.00 13.99 C
ATOM 2784 O ASN B 63 24.093 −5.385 16.770 1.00 13.96 O
ATOM 2785 N PHE B 64 24.126 −3.143 16.308 1.00 13.92 N
ATOM 2787 CA PHE B 64 24.126 −2.622 17.673 1.00 12.95 C
ATOM 2789 CB PHE B 64 25.518 −2.121 18.080 1.00 12.24 C
ATOM 2792 CG PHE B 64 26.621 −3.056 17.698 1.00 10.08 C
ATOM 2793 CD1 PHE B 64 26.707 −4.313 18.267 1.00 9.82 C
ATOM 2795 CE1 PHE B 64 27.717 −5.176 17.900 1.00 10.20 C
ATOM 2797 CZ PHE B 64 28.622 −4.784 16.947 1.00 10.37 C
ATOM 2799 CE2 PHE B 64 28.533 −3.542 16.383 1.00 10.15 C
ATOM 2801 CD2 PHE B 64 27.547 −2.689 16.752 1.00 9.91 C
ATOM 2803 C PHE B 64 23.135 −1.462 17.777 1.00 12.85 C
ATOM 2804 O PHE B 64 23.282 −0.433 17.128 1.00 12.07 O
ATOM 2805 N ALA B 65 22.124 −1.637 18.613 1.00 13.52 N
ATOM 2807 CA ALA B 65 21.038 −0.677 18.719 1.00 13.11 C
ATOM 2809 CB ALA B 65 19.990 −1.165 19.701 1.00 13.88 C
ATOM 2813 C ALA B 65 21.554 0.641 19.215 1.00 13.59 C
ATOM 2814 O ALA B 65 22.471 0.668 20.026 1.00 13.52 O
ATOM 2815 N VAL B 66 20.985 1.727 18.716 1.00 13.44 N
ATOM 2817 CA VAL B 66 21.223 3.015 19.337 1.00 13.23 C
ATOM 2819 CB VAL B 66 21.412 4.126 18.322 1.00 13.46 C
ATOM 2821 CG1 VAL B 66 21.554 5.453 19.053 1.00 14.25 C
ATOM 2825 CG2 VAL B 66 22.634 3.839 17.457 1.00 12.99 C
ATOM 2829 C VAL B 66 20.007 3.276 20.232 1.00 13.98 C
ATOM 2830 O VAL B 66 18.860 3.239 19.765 1.00 14.47 O
ATOM 2831 N THR B 67 20.241 3.517 21.512 1.00 13.83 N
ATOM 2833 CA THR B 67 19.134 3.762 22.438 1.00 15.29 C
ATOM 2835 CB THR B 67 19.577 3.436 23.873 1.00 15.38 C
ATOM 2837 OG1 THR B 67 20.710 4.246 24.225 1.00 13.23 O
ATOM 2839 CG2 THR B 67 20.111 2.014 23.990 1.00 15.32 C
ATOM 2843 C THR B 67 18.644 5.220 22.269 1.00 16.76 C
ATOM 2844 O THR B 67 19.300 6.037 21.642 1.00 16.95 O
ATOM 2845 N PRO B 68 17.459 5.547 22.766 1.00 20.60 N
ATOM 2846 CA PRO B 68 16.921 6.907 22.635 1.00 20.58 C
ATOM 2848 CB PRO B 68 15.605 6.822 23.400 1.00 21.01 C
ATOM 2851 CG PRO B 68 15.218 5.414 23.278 1.00 21.24 C
ATOM 2854 CD PRO B 68 16.507 4.646 23.423 1.00 19.89 C
ATOM 2857 C PRO B 68 17.814 8.029 23.188 1.00 21.33 C
ATOM 2858 O PRO B 68 17.759 9.162 22.687 1.00 21.25 O
ATOM 2859 N SER B 69 18.616 7.701 24.199 1.00 22.75 N
ATOM 2861 CA SER B 69 19.587 8.608 24.826 1.00 21.20 C
ATOM 2863 CB SER B 69 20.082 7.995 26.138 1.00 21.30 C
ATOM 2866 OG SER B 69 20.644 6.705 25.953 1.00 22.43 O
ATOM 2868 C SER B 69 20.769 8.877 23.909 1.00 20.23 C
ATOM 2869 O SER B 69 21.553 9.820 24.111 1.00 20.71 O
ATOM 2870 N GLY B 70 20.897 8.016 22.908 1.00 18.48 N
ATOM 2872 CA GLY B 70 21.923 8.132 21.904 1.00 15.60 C

ATOM 2875 C GLY B 70 23.049 7.151 22.179 1.00 13.15 C
ATOM 2876 O GLY B 70 24.061 7.186 21.524 1.00 12.69 O
ATOM 2877 N GLY B 71 22.876 6.276 23.162 1.00 10.24 N
ATOM 2879 CA GLY B 71 23.942 5.354 23.525 1.00 10.32 C
ATOM 2882 C GLY B 71 24.044 4.180 22.570 1.00 10.01 C
ATOM 2883 O GLY B 71 23.067 3.830 21.893 1.00 9.06 O
ATOM 2884 N GLN B 72 25.221 3.567 22.513 1.00 9.21 N
ATOM 2886 CA GLN B 72 25.427 2.402 21.654 1.00 9.07 C
ATOM 2888 CB GLN B 72 25.841 2.818 20.242 1.00 9.26 C
ATOM 2891 CG GLN B 72 25.762 1.671 19.241 1.00 10.65 C
ATOM 2894 CD GLN B 72 25.989 2.078 17.779 1.00 11.82 C
ATOM 2895 OE1 GLN B 72 25.420 1.465 16.838 1.00 14.64 O
ATOM 2896 NE2 GLN B 72 26.832 3.043 17.578 1.00 8.39 N
ATOM 2899 C GLN B 72 26.482 1.500 22.251 1.00 8.92 C
ATOM 2900 O GLN B 72 27.562 1.958 22.606 1.00 9.57 O
ATOM 2901 N THR B 73 26.154 0.216 22.363 1.00 8.86 N
ATOM 2903 CA THR B 73 27.059 −0.781 22.906 1.00 9.09 C
ATOM 2905 CB THR B 73 26.344 −1.572 24.005 1.00 9.39 C
ATOM 2907 OG1 THR B 73 25.995 −0.692 25.072 1.00 9.52 O
ATOM 2909 CG2 THR B 73 27.270 −2.612 24.627 1.00 10.72 C
ATOM 2913 C THR B 73 27.509 −1.748 21.809 1.00 9.41 C
ATOM 2914 O THR B 73 26.680 −2.437 21.200 1.00 10.31 O
ATOM 2915 N ILE B 74 28.812 −1.757 21.563 1.00 9.66 N
ATOM 2917 CA ILE B 74 29.458 −2.662 20.630 1.00 9.26 C
ATOM 2919 CB ILE B 74 30.716 −2.000 20.065 1.00 9.30 C
ATOM 2921 CG1 ILE B 74 30.322 −0.764 19.234 1.00 10.63 C
ATOM 2924 CD1 ILE B 74 31.405 0.279 19.094 1.00 13.52 C
ATOM 2928 CG2 ILE B 74 31.494 −2.996 19.212 1.00 9.71 C
ATOM 2932 C ILE B 74 29.779 −3.915 21.441 1.00 8.04 C
ATOM 2933 O ILE B 74 30.553 −3.873 22.389 1.00 8.84 O
ATOM 2934 N ASN B 75 29.117 −5.012 21.103 1.00 8.10 N
ATOM 2936 CA ASN B 75 29.257 −6.266 21.819 1.00 7.89 C
ATOM 2938 CB ASN B 75 27.908 −6.975 21.781 1.00 8.13 C
ATOM 2941 CG ASN B 75 27.942 −8.323 22.426 1.00 8.20 C
ATOM 2942 OD1 ASN B 75 28.856 −8.662 23.195 1.00 7.74 O
ATOM 2943 ND2 ASN B 75 26.946 −9.120 22.108 1.00 11.67 N
ATOM 2946 C ASN B 75 30.324 −7.129 21.149 1.00 8.35 C
ATOM 2947 O ASN B 75 30.128 −7.635 20.029 1.00 7.57 O
ATOM 2948 N PHE B 76 31.449 −7.309 21.831 1.00 8.93 N
ATOM 2950 CA PHE B 76 32.572 −8.022 21.228 1.00 9.24 C
ATOM 2952 CB PHE B 76 33.846 −7.826 22.054 1.00 9.38 C
ATOM 2955 CG PHE B 76 34.319 −6.391 22.076 1.00 9.36 C
ATOM 2956 CD1 PHE B 76 34.307 −5.628 20.921 1.00 10.05 C
ATOM 2958 CE1 PHE B 76 34.715 −4.318 20.939 1.00 9.26 C
ATOM 2960 CZ PHE B 76 35.131 −3.763 22.112 1.00 8.99 C
ATOM 2962 CE2 PHE B 76 35.143 −4.500 23.259 1.00 10.57 C
ATOM 2964 CD2 PHE B 76 34.745 −5.806 23.246 1.00 10.62 C
ATOM 2966 C PHE B 76 32.260 −9.502 20.999 1.00 9.01 C
ATOM 2967 O PHE B 76 32.893 −10.149 20.169 1.00 9.14 O
ATOM 2968 N LEU B 77 31.268 −10.038 21.708 1.00 9.74 N
ATOM 2970 CA LEU B 77 30.894 −11.444 21.525 1.00 9.62 C
ATOM 2972 CB LEU B 77 29.844 −11.840 22.565 1.00 9.60 C
ATOM 2975 CG LEU B 77 30.361 −12.157 23.981 1.00 11.85 C
ATOM 2977 CD1 LEU B 77 31.102 −11.029 24.640 1.00 13.22 C
ATOM 2981 CD2 LEU B 77 29.174 −12.593 24.854 1.00 12.68 C
ATOM 2985 C LEU B 77 30.400 −11.713 20.077 1.00 9.32 C
ATOM 2986 O LEU B 77 30.481 −12.843 19.574 1.00 10.46 O
ATOM 2987 N GLN B 78 29.907 −10.671 19.415 1.00 9.10 N
ATOM 2989 CA GLN B 78 29.450 −10.748 18.032 1.00 10.10 C
ATOM 2991 CB GLN B 78 28.517 −9.569 17.697 1.00 10.43 C
ATOM 2994 CG GLN B 78 27.143 −9.734 18.379 1.00 9.66 C
ATOM 2997 CD GLN B 78 26.224 −8.538 18.295 1.00 11.71 C
ATOM 2998 OE1 GLN B 78 25.803 −8.019 19.329 1.00 11.16 O
ATOM 2999 NE2 GLN B 78 25.871 −8.113 17.071 1.00 13.17 N
ATOM 3002 C GLN B 78 30.612 −10.816 17.042 1.00 11.05 C
ATOM 3003 O GLN B 78 30.379 −11.128 15.859 1.00 13.23 O
ATOM 3004 N TYR B 79 31.826 −10.506 17.500 1.00 10.96 N
ATOM 3006 CA TYR B 79 33.026 −10.570 16.654 1.00 12.02 C
ATOM 3008 CB TYR B 79 33.915 −9.339 16.842 1.00 11.81 C
ATOM 3011 CG TYR B 79 33.345 −8.005 16.481 1.00 10.03 C
ATOM 3012 CD1 TYR B 79 33.681 −7.372 15.280 1.00 8.25 C
ATOM 3014 CE1 TYR B 79 33.169 −6.116 14.965 1.00 8.39 C
ATOM 3016 CZ TYR B 79 32.322 −5.483 15.842 1.00 8.21 C
ATOM 3017 OH TYR B 79 31.827 −4.250 15.505 1.00 8.87 O
ATOM 3019 CE2 TYR B 79 31.972 −6.104 17.033 1.00 10.02 C
ATOM 3021 CD2 TYR B 79 32.487 −7.347 17.345 1.00 9.93 C
ATOM 3023 C TYR B 79 33.940 −11.728 16.985 1.00 13.56 C
ATOM 3024 O TYR B 79 34.689 −12.190 16.120 1.00 13.49 O
ATOM 3025 N ASN B 80 33.919 −12.162 18.242 1.00 15.17 N
ATOM 3027 CA ASN B 80 34.925 −13.076 18.751 1.00 14.48 C

ATOM 3029 CB ASN B 80 35.582 −12.444 19.978 1.00 14.14 C
ATOM 3032 CG ASN B 80 36.890 −13.105 20.361 1.00 14.62 C
ATOM 3033 OD1 ASN B 80 37.651 −13.558 19.509 1.00 16.67 O
ATOM 3034 ND2 ASN B 80 37.153 −13.163 21.664 1.00 13.88 N
ATOM 3037 C ASN B 80 34.352 −14.437 19.084 1.00 14.66 C
ATOM 3038 O ASN B 80 34.712 −15.056 20.083 1.00 13.88 O
ATOM 3039 N LYS B 81 33.412 −14.879 18.257 1.00 15.51 N
ATOM 3041 CA LYS B 81 32.859 −16.233 18.368 1.00 16.46 C
ATOM 3043 CB LYS B 81 33.943 −17.263 17.992 1.00 16.91 C
ATOM 3046 CG LYS B 81 34.644 −16.962 16.663 1.00 20.41 C
ATOM 3049 CD LYS B 81 35.616 −18.076 16.175 1.00 26.52 C
ATOM 3052 CE LYS B 81 36.392 −18.798 17.293 1.00 31.18 C
ATOM 3055 NZ LYS B 81 37.525 −19.720 16.822 1.00 38.55 N
ATOM 3059 C LYS B 81 32.216 −16.559 19.735 1.00 15.91 C
ATOM 3060 O LYS B 81 32.322 −17.678 20.227 1.00 16.16 O
ATOM 3061 N GLY B 82 31.522 −15.575 20.307 1.00 15.03 N
ATOM 3063 CA GLY B 82 30.735 −15.736 21.512 1.00 15.26 C
ATOM 3066 C GLY B 82 31.492 −15.553 22.800 1.00 15.69 C
ATOM 3067 O GLY B 82 30.960 −15.833 23.857 1.00 15.34 O
ATOM 3068 N TYR B 83 32.721 −15.052 22.708 1.00 16.90 N
ATOM 3070 CA TYR B 83 33.550 −14.806 23.873 1.00 17.19 C
ATOM 3072 CB TYR B 83 34.815 −15.667 23.808 1.00 18.20 C
ATOM 3075 CG TYR B 83 34.583 −17.155 23.934 1.00 23.38 C
ATOM 3076 CD1 TYR B 83 34.448 −17.745 25.181 1.00 28.89 C
ATOM 3078 CE1 TYR B 83 34.239 −19.105 25.310 1.00 31.05 C
ATOM 3080 CZ TYR B 83 34.170 −19.896 24.184 1.00 32.68 C
ATOM 3081 OH TYR B 83 33.962 −21.259 24.329 1.00 36.36 O
ATOM 3083 CE2 TYR B 83 34.305 −19.340 22.930 1.00 30.78 C
ATOM 3085 CD2 TYR B 83 34.506 −17.972 22.810 1.00 28.62 C
ATOM 3087 C TYR B 83 34.006 −13.355 23.925 1.00 16.15 C
ATOM 3088 O TYR B 83 34.169 −12.715 22.894 1.00 15.94 O
ATOM 3089 N GLY B 84 34.190 −12.828 25.134 1.00 15.91 N
ATOM 3091 CA GLY B 84 34.842 −11.539 25.278 1.00 14.80 C
ATOM 3094 C GLY B 84 36.359 −11.675 25.047 1.00 13.96 C
ATOM 3095 O GLY B 84 36.882 −12.737 24.675 1.00 14.24 O
ATOM 3096 N VAL B 85 37.071 −10.586 25.311 1.00 11.64 N
ATOM 3098 CA VAL B 85 38.497 −10.478 25.027 1.00 12.19 C
ATOM 3100 CB VAL B 85 38.761 −9.214 24.159 1.00 11.76 C
ATOM 3102 CG1 VAL B 85 40.254 −9.019 23.892 1.00 12.27 C
ATOM 3106 CG2 VAL B 85 37.970 −9.236 22.852 1.00 12.61 C
ATOM 3110 C VAL B 85 39.258 −10.315 26.329 1.00 12.06 C
ATOM 3111 O VAL B 85 38.954 −9.435 27.133 1.00 11.39 O
ATOM 3112 N ALA B 86 40.263 −11.154 26.554 1.00 11.94 N
ATOM 3114 CA ALA B 86 41.077 −11.026 27.752 1.00 12.43 C
ATOM 3116 CB ALA B 86 42.221 −12.031 27.709 1.00 12.46 C
ATOM 3120 C ALA B 86 41.630 −9.606 27.895 1.00 12.58 C
ATOM 3121 O ALA B 86 42.145 −9.034 26.921 1.00 11.12 O
ATOM 3122 N ASP B 87 41.542 −9.046 29.101 1.00 12.96 N
ATOM 3124 CA ASP B 87 41.977 −7.664 29.319 1.00 13.26 C
ATOM 3126 CB ASP B 87 41.413 −7.038 30.599 1.00 12.94 C
ATOM 3129 CG ASP B 87 41.973 −7.621 31.863 1.00 15.55 C
ATOM 3130 OD1 ASP B 87 42.925 −8.435 31.811 1.00 16.54 O
ATOM 3131 OD2 ASP B 87 41.478 −7.304 32.971 1.00 17.64 O
ATOM 3132 C ASP B 87 43.473 −7.446 29.177 1.00 13.14 C
ATOM 3133 O ASP B 87 43.923 −6.303 29.211 1.00 13.88 O
ATOM 3134 N THR B 88 44.222 −8.529 28.986 1.00 13.35 N
ATOM 3136 CA THR B 88 45.648 −8.426 28.770 1.00 13.89 C
ATOM 3138 CB THR B 88 46.376 −9.702 29.223 1.00 13.97 C
ATOM 3140 OG1 THR B 88 45.720 −10.853 28.692 1.00 14.23 O
ATOM 3142 CG2 THR B 88 46.312 −9.865 30.728 1.00 15.70 C
ATOM 3146 C THR B 88 45.972 −8.179 27.308 1.00 14.14 C
ATOM 3147 O THR B 88 47.138 −7.960 26.978 1.00 16.23 O
ATOM 3148 N LYS B 89 44.961 −8.217 26.444 1.00 13.28 N
ATOM 3150 CA LYS B 89 45.163 −7.962 25.021 1.00 13.04 C
ATOM 3152 CB LYS B 89 44.317 −8.922 24.185 1.00 13.74 C
ATOM 3155 CG LYS B 89 44.531 −10.371 24.562 1.00 15.15 C
ATOM 3158 CD LYS B 89 43.821 −11.309 23.612 1.00 18.37 C
ATOM 3161 CE LYS B 89 43.980 −12.771 24.006 1.00 20.95 C
ATOM 3164 NZ LYS B 89 43.412 −13.640 22.933 1.00 24.82 N
ATOM 3168 C LYS B 89 44.798 −6.531 24.667 1.00 12.47 C
ATOM 3169 O LYS B 89 44.022 −5.884 25.369 1.00 12.82 O
ATOM 3170 N THR B 90 45.377 −6.023 23.589 1.00 11.85 N

ATOM 3172 CA THR B 90 45.017 −4.714 23.072 1.00 11.57 C
ATOM 3174 CB THR B 90 46.177 −4.184 22.273 1.00 11.83 C
ATOM 3176 OG1 THR B 90 47.280 −3.912 23.164 1.00 14.04 O
ATOM 3178 CG2 THR B 90 45.838 −2.872 21.626 1.00 13.14 C
ATOM 3182 C THR B 90 43.780 −4.827 22.180 1.00 11.03 C
ATOM 3183 O THR B 90 43.684 −5.748 21.355 1.00 10.60 O
ATOM 3184 N ILE B 91 42.839 −3.893 22.344 1.00 10.28 N
ATOM 3186 CA ILE B 91 41.640 −3.871 21.530 1.00 10.28 C
ATOM 3188 CB ILE B 91 40.361 −4.011 22.361 1.00 10.29 C
ATOM 3190 CG1 ILE B 91 40.407 −5.261 23.238 1.00 11.66 C
ATOM 3193 CD1 ILE B 91 39.298 −5.354 24.285 1.00 13.60 C
ATOM 3197 CG2 ILE B 91 39.141 −4.060 21.408 1.00 10.59 C
ATOM 3201 C ILE B 91 41.597 −2.536 20.815 1.00 10.62 C
ATOM 3202 O ILE B 91 41.700 −1.489 21.442 1.00 10.66 O
ATOM 3203 N GLN B 92 417.490 −2.563 19.497 1.00 10.49 N
ATOM 3205 CA GLN B 92 41.313 −1.326 18.764 1.00 10.71 C
ATOM 3207 CB GLN B 92 42.410 −1.146 17.719 1.00 11.65 C
ATOM 3213 CD GLN B 92 44.809 −1.227 17.215 1.00 21.75 C
ATOM 3214 OE1 GLN B 92 45.030 −2.382 16.855 1.00 23.06 O
ATOM 3215 NE2 GLN B 92 45.388 −0.176 16.654 1.00 29.53 N
ATOM 3218 C GLN B 92 39.964 −1.384 18.063 1.00 9.76 C
ATOM 3219 O GLN B 92 39.599 −2.416 17.499 1.00 9.52 O
ATOM 3220 N VAL B 93 39.225 −0.286 18.109 1.00 8.49 N
ATOM 3222 CA VAL B 93 37.922 −0.204 17.447 1.00 8.46 C
ATOM 3224 CB VAL B 93 36.754 −0.031 18.452 1.00 8.40 C
ATOM 3226 CG1 VAL B 93 35.408 −0.068 17.715 1.00 8.33 C
ATOM 3230 CG2 VAL B 93 36.818 −1.110 19.565 1.00 9.21 C
ATOM 3234 C VAL B 93 37.954 0.979 16.498 1.00 8.80 C
ATOM 3235 O VAL B 93 38.313 2.100 16.913 1.00 9.38 O
ATOM 3236 N PHE B 94 37.585 0.735 15.235 1.00 7.89 N
ATOM 3238 CA PHE B 94 37.514 1.756 14.207 1.00 8.32 C
ATOM 3240 CB PHE B 94 38.303 1.336 12.954 1.00 8.53 C
ATOM 3243 CG PHE B 94 39.774 1.165 13.207 1.00 8.61 C
ATOM 3244 CD1 PHE B 94 40.658 2.188 12.898 1.00 10.93 C
ATOM 3246 CE1 PHE B 94 42.001 2.046 13.153 1.00 11.25 C
ATOM 3248 CZ PHE B 94 42.482 0.899 13.732 1.00 10.46 C
ATOM 3250 CE2 PHE B 94 41.644 −0.131 14.027 1.00 10.75 C
ATOM 3252 CD2 PHE B 94 40.273 0.003 13.776 1.00 10.71 C
ATOM 3254 C PHE B 94 36.070 1.974 13.819 1.00 8.61 C
ATOM 3255 O PHE B 94 35.314 1.013 13.648 1.00 9.56 O
ATOM 3256 N VAL B 95 35.687 3.231 13.647 1.00 8.45 N
ATOM 3258 CA VAL B 95 34.370 3.546 13.104 1.00 9.19 C
ATOM 3260 CB VAL B 95 33.767 4.834 13.699 1.00 9.11 C
ATOM 3262 CG1 VAL B 95 34.614 6.052 13.439 1.00 11.33 C
ATOM 3266 CG2 VAL B 95 32.342 5.013 13.203 1.00 10.43 C
ATOM 3270 C VAL B 95 34.535 3.607 11.594 1.00 9.06 C
ATOM 3271 O VAL B 95 35.480 4.251 11.094 1.00 9.36 O
ATOM 3272 N VAL B 96 33.660 2.896 10.888 1.00 10.07 N
ATOM 3274 CA VAL B 96 33.731 2.760 9.435 1.00 10.75 C
ATOM 3276 CB VAL B 96 33.633 1.287 9.027 1.00 11.31 C
ATOM 3278 CG1 VAL B 96 33.699 1.117 7.507 1.00 12.23 C
ATOM 3282 CG2 VAL B 96 34.726 0.475 9.716 1.00 11.29 C
ATOM 3286 C VAL B 96 32.598 3.544 8.811 1.00 11.08 C
ATOM 3287 O VAL B 96 31.425 3.388 9.170 1.00 11.36 O
ATOM 3288 N ILE B 97 32.948 4.403 7.866 1.00 11.39 N
ATOM 3290 CA ILE B 97 31.959 5.265 7.236 1.00 12.42 C
ATOM 3292 CB ILE B 97 32.677 6.496 6.644 1.00 12.48 C
ATOM 3294 CG1 ILE B 97 33.614 7.145 7.677 1.00 12.52 C
ATOM 3297 CD1 ILE B 97 32.936 7.612 8.958 1.00 14.19 C
ATOM 3301 CG2 ILE B 97 31.669 7.488 6.082 1.00 12.90 C
ATOM 3305 C ILE B 97 31.234 4.501 6.130 1.00 13.56 C
ATOM 3306 O ILE B 97 31.898 3.883 5.308 1.00 13.06 O
ATOM 3307 N PRO B 98 29.898 4.524 6.113 1.00 15.09 N
ATOM 3308 CA PRO B 98 29.132 3.809 5.086 1.00 16.07 C
ATOM 3310 CB PRO B 98 27.696 3.899 5.600 1.00 15.86 C
ATOM 3313 CG PRO B 98 27.661 5.122 6.370 1.00 16.80 C
ATOM 3316 CD PRO B 98 29.007 5.184 7.076 1.00 14.97 C
ATOM 3319 C PRO B 98 29.267 4.451 3.718 1.00 17.70 C
ATOM 3320 O PRO B 98 29.605 5.631 3.592 1.00 17.04 O
ATOM 3321 N ASP B 99 29.014 3.649 2.696 1.00 20.10 N
ATOM 3323 CA ASP B 99 29.082 4.091 1.303 1.00 20.04 C
ATOM 3325 CB ASP B 99 28.029 5.172 1.061 1.00 21.12 C
ATOM 3328 CG ASP B 99 26.612 4.657 1.337 1.00 23.44 C
ATOM 3329 OD1 ASP B 99 26.291 3.537 0.874 1.00 27.92 O
ATOM 3330 OD2 ASP B 99 25.761 5.269 2.020 1.00 28.30 O
ATOM 3331 C ASP B 99 30.494 4.496 0.860 1.00 19.38 C
ATOM 3332 O ASP B 99 30.646 5.358 −0.015 1.00 19.12 O
ATOM 3333 N THR B 100 31.521 3.879 1.460 1.00 17.96 N
ATOM 3335 CA THR B 100 32.917 4.061 1.030 1.00 18.27 C
ATOM 3337 CB THR B 100 33.757 4.812 2.091 1.00 18.29 C
ATOM 3339 OG1 THR B 100 33.964 3.969 3.249 1.00 16.21 O
ATOM 3341 CG2 THR B 100 33.041 6.065 2.595 1.00 18.22 C
ATOM 3345 C THR B 100 33.606 2.725 0.744 1.00 18.55 C
ATOM 3346 O THR B 100 34.839 2.644 0.724 1.00 18.17 O
ATOM 3347 N GLY B 101 32.813 1.676 0.537 1.00 19.93 N
ATOM 3349 CA GLY B 101 33.346 0.341 0.306 1.00 19.59 C
ATOM 3352 C GLY B 101 34.217 −0.119 1.467 1.00 19.66 C
ATOM 3353 O GLY B 101 35.181 −0.861 1.285 1.00 19.57 O
ATOM 3354 N ASN B 102 33.856 0.343 2.661 1.00 19.84 N
ATOM 3356 CA ASN B 102 34.580 0.071 3.906 1.00 19.99 C
ATOM 3358 CB ASN B 102 34.517 −1.406 4.266 1.00 20.27 C
ATOM 3361 CG ASN B 102 33.148 −1.823 4.683 1.00 22.54 C
ATOM 3362 OD1 ASN B 102 32.856 −1.970 5.871 1.00 26.86 O
ATOM 3363 ND2 ASN B 102 32.293 −2.035 3.709 1.00 25.85 N
ATOM 3366 C ASN B 102 36.016 0.557 3.943 1.00 19.98 C
ATOM 3367 O ASN B 102 36.805 0.124 4.782 1.00 19.09 O
ATOM 3368 N SER B 103 36.343 1.504 3.076 1.00 20.60 N
ATOM 3370 CA SER B 103 37.707 1.990 2.986 1.00 19.63 C
ATOM 3372 CB SER B 103 38.016 2.353 1.541 1.00 20.16 C

ATOM 3375 OG SER B 103 37.253 3.481 1.156 1.00 22.36 O
ATOM 3377 C SER B 103 37.979 3.214 3.870 1.00 18.01 C
ATOM 3378 O SER B 103 39.137 3.525 4.144 1.00 18.98 O
ATOM 3379 N GLU B 104 36.936 3.918 4.294 1.00 15.67 N
ATOM 3381 CA GLU B 104 37.L35 5.116 5.120 1.00 13.43 C
ATOM 3383 CB GLU B 104 36.265 6.297 4.656 1.00 12.81 C
ATOM 3386 CG GLU B 104 36.679 7.618 5.313 1.00 13.27 C
ATOM 3389 CD GLU B 104 35.732 8.776 5.029 1.00 14.64 C
ATOM 3390 OE1 GLU B 104 34.919 8.679 4.069 1.00 15.08 O
ATOM 3391 OE2 GLU B 104 35.814 9.803 5.742 1.00 14.12 O
ATOM 3392 C GLU B 104 36.797 4.780 6.558 1.00 12.23 C
ATOM 3393 O GLU B 104 35.659 4.435 6.855 1.00 11.79 O
ATOM 3394 N GLU B 105 37.793 4.856 7.439 1.00 11.65 N
ATOM 3396 CA GLU B 105 37.573 4.534 8.845 1.00 10.60 C
ATOM 3398 CB GLU B 105 37.830 3.047 9.102 1.00 10.23 C
ATOM 3401 CG GLU B 105 39.288 2.653 8.998 1.00 11.51 C
ATOM 3404 CD GLU B 105 39.569 1.177 9.250 1.00 13.25 C
ATOM 3405 OE1 GLU B 105 40.772 0.827 9.367 1.00 14.63 O
ATOM 3406 OE2 GLU B 105 38.617 0.366 9.341 1.00 11.87 O
ATOM 3407 C GLU B 105 38.476 5.381 9.732 1.00 9.65 C
ATOM 3408 O GLU B 105 39.492 5.931 9.272 1.00 10.58 O
ATOM 3409 N TYR B 106 38.112 5.465 11.014 1.00 9.46 N
ATOM 3411 CA TYR B 106 38.842 6.260 12.004 1.00 9.17 C
ATOM 3413 CB TYR B 106 38.119 7.593 12.258 1.00 9.00 C
ATOM 3416 CG TYR B 106 37.989 8.388 10.990 1.00 9.70 C
ATOM 3417 CD1 TYR B 106 39.000 9.227 10.565 1.00 10.02 C
ATOM 3419 CE1 TYR B 106 38.900 9.908 9.378 1.00 11.83 C
ATOM 3421 CZ TYR B 106 37.797 9.755 8.584 1.00 10.67 C
ATOM 3422 OH TYR B 106 37.719 10.438 7.368 1.00 13.02 O
ATOM 3424 CE2 TYR B 106 36.784 8.909 8.958 1.00 10.26 C
ATOM 3426 CD2 TYR B 106 36.887 8.224 10.166 1.00 9.29 C
ATOM 3428 C TYR B 106 38.949 5.516 13.318 1.00 9.17 C
ATOM 3429 O TYR B 106 37.963 4.945 13.774 1.00 8.39 O
ATOM 3430 N ILE B 107 40.116 5.546 13.955 1.00 8.89 N
ATOM 3432 CA ILE B 107 40.211 4.966 15.288 1.00 8.90 C
ATOM 3434 CB ILE B 107 41.652 5.037 15.848 1.00 9.24 C
ATOM 3436 CG1 ILE B 107 41.770 4.245 17.155 1.00 10.76 C
ATOM 3439 CD1 ILE B 107 41.571 2.765 16.979 1.00 12.64 C
ATOM 3443 CG2 ILE B 107 42.088 6.484 16.051 1.00 9.73 C
ATOM 3447 C ILE B 107 39.211 5.679 16.194 1.00 9.06 C
ATOM 3448 O ILE B 107 39.102 6.912 16.171 1.00 9.11 O
ATOM 3449 N ILE B 108 38.448 4.908 16.958 1.00 8.10 N
ATOM 3451 CA ILE B 108 37.466 5.505 17.858 1.00 8.46 C
ATOM 3453 CB ILE B 108 36.038 5.362 17.263 1.00 7.92 C
ATOM 3455 CG1 ILE B 108 35.058 6.318 17.933 1.00 8.44 C
ATOM 3458 CD1 ILE B 108 35.451 7.735 17.791 1.00 10.51 C
ATOM 3462 CG2 ILE B 108 35.548 3.943 17.367 1.00 7.73 C
ATOM 3466 C ILE B 108 37.577 5.032 19.315 1.00 9.21 C
ATOM 3467 O ILE B 108 37.028 5.675 20.206 1.00 9.94 O
ATOM 3468 N ALA B 109 38.295 3.939 19.566 1.00 8.98 N
ATOM 3470 CA ALA B 109 38.565 3.467 20.929 1.00 8.87 C
ATOM 3472 CB ALA B 109 37.358 2.771 21.525 1.00 9.01 C
ATOM 3476 C ALA B 109 39.744 2.507 20.935 1.00 8.73 C
ATOM 3477 O ALA B 109 39.957 1.757 19.994 1.00 9.76 O
ATOM 3478 N GLU B 110 40.533 2.576 21.998 1.00 9.54 N
ATOM 3480 CA GLU B 110 41.607 1.634 22.215 1.00 9.46 C
ATOM 3482 CB GLU B 110 42.946 2.257 21.824 1.00 10.74 C
ATOM 3485 CG GLU B 110 44.120 1.290 21.888 1.00 14.55 C
ATOM 3488 CD GLU B 110 45.414 1.938 21.419 1.00 21.68 C
ATOM 3489 OE1 GLU B 110 45.950 2.812 22.134 1.00 25.49 O
ATOM 3490 OE2 GLU B 110 45.877 1.587 20.321 1.00 27.22 O
ATOM 3491 C GLU B 110 41.678 1.209 23.680 1.00 9.73 C
ATOM 3492 O GLU B 110 41.720 2.056 24.582 1.00 10.15 O
ATOM 3493 N TRP B 111 41.703 −0.098 23.894 1.00 9.39 N
ATOM 3495 CA TRP B 111 41.990 −0.671 25.187 1.00 10.20 C
ATOM 3497 CB TRP B 111 41.076 −1.840 25.491 1.00 9.67 C
ATOM 3500 CG TRP B 111 41.470 −2.528 26.787 1.00 8.52 C
ATOM 3501 CD1 TRP B 111 −42.308 −3.581 26.928 1.00 9.95 C
ATOM 3503 NE1 TRP B 111 42.456 −3.906 28.256 1.00 13.10 N
ATOM 3505 CE2 TRP B 111 41.728 −3.017 29.010 1.00 10.98 C
ATOM 3506 CD2 TRP B 111 41.102 −2.128 28.116 1.00 9.50 C
ATOM 3507 CE3 TRP B 111 40.282 −1.123 28.636 1.00 10.62 C
ATOM 3509 CZ3 TRP B 111 40.114 −1.040 30.002 1.00 12.26 C
ATOM 3511 CH2 TRP B 111 40.756 −1.929 30.857 1.00 9.96 C
ATOM 3513 CZ2 TRP B 111 41.561 −2.926 30.385 1.00 12.41 C
ATOM 3515 C TRP B 111 43.423 −1.193 25.169 1.00 13.35 C
ATOM 3516 O TRP B 111 43.775 −2.031 24.344 1.00 11.63 O
ATOM 3517 N LYS B 112 44.263 −0.666 26.056 1.00 16.48 N
ATOM 3519 CA LYS B 112 45.593 −1.223 26.244 1.00 20.35 C
ATOM 3521 CB LYS B 112 46.627 −0.459 25.436 1.00 22.00 C
ATOM 3524 CG LYS B 112 47.926 −1.228 25.265 1.00 26.13 C

ATOM 3527 CD LYS B 112 49.024 −0.337 24.701 1.00 31.80 C
ATOM 3530 CE LYS B 112 48.724 0.098 23.278 1.00 34.89 C
ATOM 3533 NZ LYS B 112 49.811 0.945 22.716 1.00 40.47 N
ATOM 3537 C LYS B 112 45.946 −1.177 27.725 1.00 22.27 C
ATOM 3538 O LYS B 112 46.204 −0.081 28.253 1.00 23.96 O
ATOM 3539 BR BR1 C 1 32.421 56.008 18.617 1.00 7.69 B
ATOM 3540 BR BR1 C 2 29.535 49.785 7.652 1.00 7.89 B
ATOM 3541 BR BR1 C 3 14.888 42.517 9.414 1.00 6.57 B
ATOM 3542 BR BR1 C 4 25.062 15.958 16.407 1.00 10.90 B
ATOM 3543 BR BR1 C 5 33.144 18.262 4.026 1.00 20.03 B
ATOM 3544 BR BR1 C 6 40.800 30.559 10.185 1.00 12.36 B
ATOM 3545 BR BR1 C 7 30.248 54.190 19.852 1.00 14.74 B
ATOM 3546 BR BR1 C 8 38.772 41.003 24.687 1.00 22.37 B
ATOM 3547 BR BR1 C 9 26.990 5.115 28.326 1.00 15.47 B
ATOM 3548 BR BR1 C 10 40.148 5.267 23.548 1.00 2.00 B
ATOM 3549 BR BR1 C 11 40.494 −13.035 23.333 1.00 14.97 B
ATOM 3550 BR BR1 C 12 26.318 −12.293 15.448 1.00 14.38 B
ATOM 3551 BR BR1 C 13 31.199 −18.188 15.135 1.00 9.41 B
ATOM 3552 BR BR1 C 14 32.035 −14.040 15.742 1.00 12.63 B
ATOM 3553 BR BR1 C 15 29.171 31.139 8.101 1.00 2.00 B
ATOM 3554 BR BR1 C 16 28.318 −4.326 9.061 1.00 2.00 B
ATOM 3555 O HOH D 1 45.016 −8.481 11.093 1.00 14.02 O
ATOM 3558 O HOH D 2 39.945 9.187 15.069 1.00 13.06 O
ATOM 3561 O HOH D 3 37.478 27.672 11.707 1.00 16.80 O
ATOM 3564 O HOH D 4 44.772 −4.577 18.363 1.00 14.26 O
ATOM 3567 O HOH D 5 28.336 −7.855 25.862 1.00 13.43 O
ATOM 3570 O HOH D 6 23.544 0.467 24.663 1.00 16.56 O
ATOM 3573 O HOH D 7 29.531 −5.991 30.538 1.00 15.82 O
ATOM 3576 O HOH D 8 24.673 37.622 24.477 1.00 15.51 O
ATOM 3579 O HOH D 9 33.907 51.248 18.235 1.00 18.02 O
ATOM 3582 O HOH D 10 29.468 6.207 15.500 1.00 14.54 O
ATOM 3585 O HOH D 11 33.083 30.830 21.409 1.00 17.28 O
ATOM 3588 O HOH D 12 22.901 44.556 18.335 1.00 14.73 O
ATOM 3591 O HOH D 13 31.027 20.428 25.544 1.00 16.68 O
ATOM 3594 O HOH D 14 30.995 8.205 30.208 1.00 19.66 O
ATOM 3597 O HOH D 15 28.108 −13.792 35.951 1.00 20.73 O
ATOM 3600 O HOH D 16 42.527 6.434 12.302 1.00 18.94 O
ATOM 3603 O HOH D 17 32.508 14.749 4.982 1.00 23.91 O
ATOM 3606 O HOH D 18 23.468 6.955 26.616 1.00 18.06 O
ATOM 3609 O HOH D 19 22.712 2.972 25.766 1.00 20.00 O
ATOM 3612 O HOH D 20 13.244 50.277 14.738 1.00 18.37 O
ATOM 3615 O HOH D 21 36.790 15.994 26.963 1.00 17.85 O
ATOM 3618 O HOH D 22 22.367 36.375 23.529 1.00 17.11 O
ATOM 3621 O HOH D 23 18.911 31.260 28.272 1.00 26.39 O
ATOM 3624 O HOH D 24 31.505 1.688 3.641 1.00 20.97 O
ATOM 3627 O HOH D 25 21.210 33.851 24.000 1.00 21.28 O
ATOM 3630 O HOH D 26 23.386 −0.715 22.103 1.00 15.14 O
ATOM 3633 O HOH D 27 29.074 −11.945 31.532 1.00 24.32 O
ATOM 3636 O HOH D 28 25.268 40.455 23.574 1.00 23.95 O
ATOM 3639 O HOH D 29 33.156 −9.344 11.616 1.00 20.79 O
ATOM 3642 O HOH D 30 38.478 −5.911 7.639 1.00 21.26 O
ATOM 3645 O HOH D 31 24.308 53.095 18.780 1.00 19.70 O
ATOM 3648 O HOH D 32 17.754 48.477 15.499 1.00 20.76 O
ATOM 3651 O HOH D 33 42.790 5.854 23.394 1.00 23.30 O
ATOM 3654 O HOH D 34 27.861 15.691 24.120 1.00 23.40 O
ATOM 3657 O HOH D 35 35.797 12.184 4.416 1.00 21.31 O
ATOM 3660 O HOH D 36 30.360 −0.992 28.013 1.00 16.72 O
ATOM 3663 O HOH D 37 28.276 −16.367 24.146 1.00 20.65 O
ATOM 3666 O HOH D 38 32.226 24.366 27.005 1.00 23.68 O
ATOM 3669 O HOH D 39 20.858 29.760 23.162 1.00 21.99 O
ATOM 3672 O HOH D 40 49.235 18.819 15.583 1.00 25.35 O
ATOM 3675 O HOH D 41 24.467 −3.793 21.863 1.00 22.04 O
ATOM 3678 O HOH D 42 26.332 −5.940 25.774 1.00 16.62 O
ATOM 3681 O HOH D 43 40.578 4.994 6.108 1.00 25.58 O
ATOM 3684 O HOH D 44 20.863 46.163 17.522 1.00 25.28 O
ATOM 3687 O HOH D 45 42.794 2.619 9.388 1.00 23.00 O
ATOM 3690 O HOH D 46 20.611 25.977 15.514 1.00 25.08 O
ATOM 3693 O HOH D 47 24.778 21.030 19.875 1.00 21.37 O
ATOM 3696 O HOH D 48 24.759 −5.920 23.503 1.00 16.11 O
ATOM 3699 O HOH D 49 36.889 24.475 8.631 1.00 23.03 O
ATOM 3702 O HOH D 50 20.215 49.361 14.399 1.00 22.50 O
ATOM 3705 O HOH D 51 47.164 −5.215 12.615 1.00 22.87 O
ATOM 3708 O HOH D 52 46.004 25.078 19.448 1.00 25.71 O
ATOM 3711 O HOH D 53 20.097 31.594 19.238 1.00 27.29 O
ATOM 3714 O HOH D 54 19.046 1.435 16.404 1.00 27.34 O
ATOM 3717 O HOH D 55 39.089 23.057 7.816 1.00 28.18 O
ATOM 3720 O HOH D 56 22.799 49.789 12.926 1.00 27.76 O
ATOM 3723 O HOH D 57 21.681 37.631 15.807 1.00 23.46 O
ATOM 3726 O HOH D 58 44.307 22.404 22.181 1.00 23.37 O
ATOM 3729 O HOH D 59 46.170 −13.085 20.941 1.00 17.48 O
ATOM 3732 O HOH D 60 36.365 41.071 5.729 1.00 27.02 O
ATOM 3735 O HOH D 61 36.990 7.023 22.512 1.00 22.71 O
ATOM 3738 O HOH D 62 19.169 −8.584 16.372 1.00 23.92 O
ATOM 3741 O HOH D 63 20.055 28.469 14.698 1.00 26.12 O
ATOM 3744 O HOH D 64 30.998 −12.907 29.623 1.00 25.28 O
ATOM 3747 O HOH D 65 37.347 −1.150 7.121 1.00 22.93 O

ATOM 3750 O HOH D 66 33.031 −13.258 27.775 1.00 32.50 O
ATOM 3753 O HOH D 67 22.945 −4.003 11.274 1.00 30.88 O
ATOM 3756 O HOH D 68 27.701 41.270 1.720 1.00 29.57 O
ATOM 3759 O HOH D 69 25.980 −9.896 14.868 1.00 27.31 O
ATOM 3762 O HOH D 70 23.821 12.814 14.658 1.00 24.54 O
ATOM 3765 O HOH D 71 35.006 43.534 25.083 1.00 28.85 O
ATOM 3768 O HOH D 72 35.312 36.253 1.522 1.00 29.21 O
ATOM 3771 O HOH D 73 48.598 −9.901 24.935 1.00 25.55 O
ATOM 3774 O HOH D 74 42.294 −13.685 16.218 1.00 25.18 O
ATOM 3777 O HOH D 75 42.607 12.387 16.515 1.00 31.10 O
ATOM 3780 O HOH D 76 26.330 35.006 4.050 1.00 31.74 O
ATOM 3783 O HOH D 77 32.850 10.209 3.504 1.00 27.19 O
ATOM 3786 O HOH D 78 30.508 10.747 29.512 1.00 25.87 O
ATOM 3789 O HOH D 79 45.693 19.098 22.237 1.00 30.36 O
ATOM 3792 O HOH D 80 15.634 44.761 11.710 1.00 26.02 O
ATOM 3795 O HOH D 81 18.085 50.959 3.872 1.00 35.51 O
ATOM 3798 O HOH D 82 29.549 1.503 7.572 1.00 29.19 O
ATOM 3801 O HOH D 83 39.725 31.841 30.695 1.00 40.77 O
ATOM 3804 O HOH D 84 20.283 36.188 −4.205 1.00 39.38 O
ATOM 3807 O HOH D 85 34.763 −11.883 13.146 1.00 21.47 O
ATOM 3810 O HOH D 86 26.410 32.901 7.289 1.00 24.64 O
ATOM 3813 O HOH D 87 44.314 −2.758 11.932 1.00 23.95 O
ATOM 3816 O HOH D 88 30.034 −14.313 17.413 1.00 29.20 O
ATOM 3819 O HOH D 89 26.961 12.263 27.391 1.00 30.17 O
ATOM 3822 O HOH D 90 28.249 0.678 3.312 1.00 28.11 O
ATOM 3825 O HOH D 91 45.718 32.030 14.220 1.00 34.46 O
ATOM 3828 O HOH D 92 28.299 −9.696 27.995 1.00 24.79 O
ATOM 3831 O HOH D 93 13.832 48.982 7.768 1.00 33.46 O
ATOM 3834 O HOH D 94 43.000 −11.174 31.241 1.00 28.43 O
ATOM 3837 O HOH D 95 35.944 8.335 1.385 1.00 29.40 O
ATOM 3840 O HOH D 96 29.165 29.895 11.877 1.00 24.28 O
ATOM 3843 O HOH D 97 32.349 31.864 24.473 1.00 30.09 O
ATOM 3846 O HOH D 98 22.954 24.601 11.686 1.00 28.72 O
ATOM 3849 O HOH D 99 31.154 51.462 19.574 1.00 25.81 O
ATOM 3852 O HOH D 100 43.443 12.360 23.615 1.00 24.55 O
ATOM 3855 O HOH D 101 15.670 52.252 4.362 1.00 34.13 O
ATOM 3858 O HOH D 102 25.701 41.081 26.231 1.00 27.56 O
ATOM 3861 O HOH D 103 37.527 21.694 22.195 1.00 32.29 O

ATOM 3864 O HOH D 104 33.325 −12.660 37.738 1.00 35.18 O
ATOM 3867 O HOH D 105 26.319 5.217 15.262 1.00 26.13 O
ATOM 3870 O HOH D 106 33.848 22.140 26.173 1.00 31.07 O
ATOM 3873 O HOH D 107 35.489 18.857 24.618 1.00 27.43 O
ATOM 3876 O HOH D 108 42.855 46.462 8.947 1.00 33.41 O
ATOM 3879 O HOH D 109 42.188 5.317 9.853 1.00 30.90 O
ATOM 3882 O HOH D 110 41.401 45.084 19.630 1.00 35.22 O
ATOM 3885 O HOH D 111 45.990 −4.685 27.447 1.00 36.33 O
ATOM 3888 O HOH D 112 44.969 4.979 13.641 1.00 30.89 O
ATOM 3891 O HOH D 113 21.231 24.488 19.771 1.00 29.91 O
ATOM 3894 O HOH D 114 28.991 22.460 25.768 1.00 32.28 O
ATOM 3897 O HOH D 115 30.182 42.704 28.664 1.00 34.73 O
ATOM 3900 O HOH D 116 38.457 26.788 9.301 1.00 28.25 O
ATOM 3903 O HOH D 117 33.010 8.247 32.080 1.00 30.38 O
ATOM 3906 O HOH D 118 40.296 −12.388 19.763 1.00 29.43 O
ATOM 3909 O HOH D 119 26.522 44.371 25.621 1.00 29.51 O
ATOM 3912 O HOH D 120 43.804 −4.826 10.570 1.00 33.46 O
ATOM 3915 O HOH D 121 47.448 −11.680 26.748 1.00 37.40 O
ATOM 3918 O HOH D 122 40.716 −13.572 24.920 1.00 24.40 O
ATOM 3921 O HOH D 123 41.998 −1.274 34.849 1.00 32.74 O
ATOM 3924 O HOH D 124 45.154 42.318 18.028 1.00 36.95 O
ATOM 3927 O HOH D 125 30.324 −11.134 10.862 1.00 29.46 O
ATOM 3930 O HOH D 126 42.517 10.179 15.159 1.00 30.78 O
ATOM 3933 O HOH D 127 48.214 −11.222 16.932 1.00 31.45 O
ATOM 3936 O HOH D 128 23.815 −9.373 14.042 1.00 33.96 O
ATOM 3939 O HOH D 129 31.988 24.965 29.884 1.00 32.47 O
ATOM 3942 O HOH D 130 35.266 30.662 4.339 1.00 37.13 O
ATOM 3945 O HOH D 131 42.057 38.530 10.976 1.00 38.75 O
ATOM 3948 O HOH D 132 24.900 3.888 13.671 1.00 41.30 O
ATOM 3951 O HOH D 133 44.797 −11.819 18.372 1.00 31.27 O
ATOM 3954 O HOH D 134 31.380 27.561 6.462 1.00 38.93 O
ATOM 3957 O HOH D 135 24.585 −2.131 6.886 1.00 36.52 O
ATOM 3960 O HOH D 136 44.178 14.598 21.666 1.00 49.82 O

The invention claimed is:

1. A method for producing a fusion protein of SEQ ID NO: 44 or 46, the method comprising:

(a) providing a host cell comprising an expression vector containing a nucleic acid sequence encoding the fusion protein of SEQ ID NO: 44 or 46;

(b) expressing the encoded fusion protein; and (c) recovering the fusion protein.

2. The method of claim 1, wherein the fusion protein further comprises a glutathione S transferase (GST) moiety.

* * * * *

SEQUENCE LISTING

<160> NUMBER OF SEQ ID NOS: 488

<210> SEQ ID NO 1
<211> LENGTH: 13
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<221> NAME/KEY: modified_base
<222> LOCATION: (1)..(13)
<223> OTHER INFORMATION: a, c, g, t, unknown or other

<400> SEQUENCE: 1
nnnnnnnnnn nnn 13

<210> SEQ ID NO 2
<211> LENGTH: 9
<212> TYPE: PRT
<213> ORGANISM: Artificial Sequence
<220> FEATURE:
<223> OTHER INFORMATION: Description of Artificial Sequence: Synthetic peptide
<220> FEATURE:
<221> NAME/KEY: MOD_RES
<222> LOCATION: (1)..(9)
<223> OTHER INFORMATION: Variable amino acid

<400> SEQUENCE: 2

Xaa Xaa Xaa Xaa Xaa Xaa Xaa Xaa Xaa
1 5

<210> SEQ ID NO 3
<211> LENGTH: 32
<212> TYPE: DNA
<213> ORGANISM: Artificial Sequence
<220> FEATURE:
<223> OTHER INFORMATION: Description of Artificial Sequence: Synthetic primer

<400> SEQUENCE: 3
ttgttggatc ccatggagat acacctacat tg 32

<210> SEQ ID NO 4
<211> LENGTH: 33
<212> TYPE: DNA
<213> ORGANISM: Artificial Sequence
<220> FEATURE:
<223> OTHER INFORMATION: Description of Artificial Sequence: Synthetic primer

<400> SEQUENCE: 4
ttactgaatt cttatggttt ctgagaacag atg 33

<210> SEQ ID NO 5
<211> LENGTH: 348
<212> TYPE: DNA
<213> ORGANISM: Flammulina velutipes

<400> SEQUENCE: 5
atgtccgcca cgtcgctcac cttccagctt gcctacttgg tgaagaagat cgacttcgac 60
tacaccccca actggggccg tggtacccca agcagctaca tcgacaacct taccttcccc 120
aaggttctca ccgacaaaaa atactcgtac cgcgtcgtgg tcaatggctc tgaccttggc 180
gtcgagtcca acttcgcagt gacaccgtcc ggtgggcaga ccatcaactt cctccagtac 240

```
aacaaggggt atggtgtcgc ggacaccaaa acgattcaag ttttcgttgt cattccagat    300

accggcaact cggaggagta catcatcgct gagtggaaga agacttga                 348


<210> SEQ ID NO 6
<211> LENGTH: 115
<212> TYPE: PRT
<213> ORGANISM: Flammulina velutipes

<400> SEQUENCE: 6

Met Ser Ala Thr Ser Leu Thr Phe Gln Leu Ala Tyr Leu Val Lys Lys
1               5                   10                  15

Ile Asp Phe Asp Tyr Thr Pro Asn Trp Gly Arg Gly Thr Pro Ser Ser
            20                  25                  30

Tyr Ile Asp Asn Leu Thr Phe Pro Lys Val Leu Thr Asp Lys Lys Tyr
        35                  40                  45

Ser Tyr Arg Val Val Val Asn Gly Ser Asp Leu Gly Val Glu Ser Asn
    50                  55                  60

Phe Ala Val Thr Pro Ser Gly Gly Gln Thr Ile Asn Phe Leu Gln Tyr
65                  70                  75                  80

Asn Lys Gly Tyr Gly Val Ala Asp Thr Lys Thr Ile Gln Val Phe Val
                85                  90                  95

Val Ile Pro Asp Thr Gly Asn Ser Glu Glu Tyr Ile Ile Ala Glu Trp
            100                 105                 110

Lys Lys Thr
        115


<210> SEQ ID NO 7
<211> LENGTH: 1038
<212> TYPE: DNA
<213> ORGANISM: Flammulina velutipes

<400> SEQUENCE: 7

atgtccccta tactaggtta ttggaaaatt aagggccttg tgcaacccac tcgacttctt     60

ttggaatatc ttgaagaaaa atatgaagag catttgtatg agcgcgatga aggtgataaa    120

tggcgaaaca aaaagtttga attgggtttg gagtttccca atcttcctta ttatattgat    180

ggtgatgtta aattaacaca gtctatggcc atcatacgtt atatagctga caagcacaac    240

atgttgggtg gttgtccaaa agagcgtgca gagatttcaa tgcttgaagg agcggttttg    300

gatattagat acggtgtttc gagaattgca tatagtaaag actttgaaac tctcaaagtt    360

gattttctta gcaagctacc tgaaatgctg aaaatgttcg aagatcgttt atgtcataaa    420

acatatttaa atggtgatca tgtaacccat cctgacttca tgttgtatga cgctcttgat    480

gttgttttat acatggaccc aatgtgcctg gatgcgttcc caaaattagt ttgttttaaa    540

aaacgtattg aagctatccc acaaattgat aagtacttga aatccagcaa gtatatagca    600

tggcctttgc agggctggca agccacgttt ggtggtggcg accatcctcc aaaatcggat    660

ctggaagttc tgttccaggg gcccctggga tcctccgcca cgtcgctcac cttccagctt    720

gcctacttgg tgaagaagat cgacttcgac tacaccccca actggggccg tggtacccca    780

agcagctaca tcgacaacct taccttcccc aaggttctca ccgacaaaaa atactcgtac    840

cgcgtcgtgg tcaatggctc tgaccttggc gtcgagtcca acttcgcagt gacaccgtcc    900

ggtgggcaga ccatcaactt cctccagtac aacaaggggt atggtgtcgc ggacaccaaa    960

acgattcaag ttttcgttgt cattccagat accggcaact cggaggagta catcatcgct   1020

gagtggaaga agacttga                                                 1038
```

<210> SEQ ID NO 8
<211> LENGTH: 345
<212> TYPE: PRT
<213> ORGANISM: Flammulina velutipes

<400> SEQUENCE: 8

```
Met Ser Pro Ile Leu Gly Tyr Trp Lys Ile Lys Gly Leu Val Gln Pro
1               5                   10                  15

Thr Arg Leu Leu Leu Glu Tyr Leu Glu Glu Lys Tyr Glu Glu His Leu
            20                  25                  30

Tyr Glu Arg Asp Glu Gly Asp Lys Trp Arg Asn Lys Lys Phe Glu Leu
        35                  40                  45

Gly Leu Glu Phe Pro Asn Leu Pro Tyr Tyr Ile Asp Gly Asp Val Lys
    50                  55                  60

Leu Thr Gln Ser Met Ala Ile Ile Arg Tyr Ile Ala Asp Lys His Asn
65                  70                  75                  80

Met Leu Gly Gly Cys Pro Lys Glu Arg Ala Glu Ile Ser Met Leu Glu
                85                  90                  95

Gly Ala Val Leu Asp Ile Arg Tyr Gly Val Ser Arg Ile Ala Tyr Ser
            100                 105                 110

Lys Asp Phe Glu Thr Leu Lys Val Asp Phe Leu Ser Lys Leu Pro Glu
        115                 120                 125

Met Leu Lys Met Phe Glu Asp Arg Leu Cys His Lys Thr Tyr Leu Asn
    130                 135                 140

Gly Asp His Val Thr His Pro Asp Phe Met Leu Tyr Asp Ala Leu Asp
145                 150                 155                 160

Val Val Leu Tyr Met Asp Pro Met Cys Leu Asp Ala Phe Pro Lys Leu
                165                 170                 175

Val Cys Phe Lys Lys Arg Ile Glu Ala Ile Pro Gln Ile Asp Lys Tyr
            180                 185                 190

Leu Lys Ser Ser Lys Tyr Ile Ala Trp Pro Leu Gln Gly Trp Gln Ala
        195                 200                 205

Thr Phe Gly Gly Gly Asp His Pro Pro Lys Ser Asp Leu Glu Val Leu
    210                 215                 220

Phe Gln Gly Pro Leu Gly Ser Ser Ala Thr Ser Leu Thr Phe Gln Leu
225                 230                 235                 240

Ala Tyr Leu Val Lys Lys Ile Asp Phe Asp Tyr Thr Pro Asn Trp Gly
                245                 250                 255

Arg Gly Thr Pro Ser Ser Tyr Ile Asp Asn Leu Thr Phe Pro Lys Val
            260                 265                 270

Leu Thr Asp Lys Lys Tyr Ser Tyr Arg Val Val Val Asn Gly Ser Asp
        275                 280                 285

Leu Gly Val Glu Ser Asn Phe Ala Val Thr Pro Ser Gly Gly Gln Thr
    290                 295                 300

Ile Asn Phe Leu Gln Tyr Asn Lys Gly Tyr Gly Val Ala Asp Thr Lys
305                 310                 315                 320

Thr Ile Gln Val Phe Val Val Ile Pro Asp Thr Gly Asn Ser Glu Glu
                325                 330                 335

Tyr Ile Ile Ala Glu Trp Lys Lys Thr
            340                 345
```

<210> SEQ ID NO 9
<211> LENGTH: 309
<212> TYPE: DNA
<213> ORGANISM: Artificial Sequence
<220> FEATURE:
<223> OTHER INFORMATION: Description of Artificial Sequence: Synthetic
nucleotide sequence

<400> SEQUENCE: 9
atgtccgcca cgtcgttcga ctacaccccc aactggggcc gtggtacccc aagcagctac 60
atcgacaacc ttaccttccc caaggttctc accgacaaaa aatactcgta ccgcgtcgtg 120
gtcaatggct ctgaccttgg cgtcgagtcc aacttcgcag tgacaccgtc cggtgggcag 180
accatcaact tcctccagta caacaagggg tatggtgtcg cggacaccaa aacgattcaa 240
gttttcgttg tcattccaga taccggcaac tcggaggagt acatcatcgc tgagtggaag 300
aagacttga 309

<210> SEQ ID NO 10
<211> LENGTH: 102
<212> TYPE: PRT
<213> ORGANISM: Artificial Sequence
<220> FEATURE:
<223> OTHER INFORMATION: Description of Artificial Sequence: Synthetic
protein sequence

<400> SEQUENCE: 10

Met Ser Ala Thr Ser Phe Asp Tyr Thr Pro Asn Trp Gly Arg Gly Thr
1 5 10 15

Pro Ser Ser Tyr Ile Asp Asn Leu Thr Phe Pro Lys Val Leu Thr Asp
20 25 30

Lys Lys Tyr Ser Tyr Arg Val Val Val Asn Gly Ser Asp Leu Gly Val
35 40 45

Glu Ser Asn Phe Ala Val Thr Pro Ser Gly Gly Gln Thr Ile Asn Phe
50 55 60

Leu Gln Tyr Asn Lys Gly Tyr Gly Val Ala Asp Thr Lys Thr Ile Gln
65 70 75 80

Val Phe Val Val Ile Pro Asp Thr Gly Asn Ser Glu Glu Tyr Ile Ile
85 90 95

Ala Glu Trp Lys Lys Thr
100

<210> SEQ ID NO 11
<211> LENGTH: 303
<212> TYPE: DNA
<213> ORGANISM: Artificial Sequence
<220> FEATURE:
<223> OTHER INFORMATION: Description of Artificial Sequence: Synthetic
nucleotide sequence

<400> SEQUENCE: 11
atgtccgcca cgtcgctcac cttccagctt gcctacttgg tgaagaagat cgacatcgac 60
aaccttacct tccccaaggt tctcaccgac aaaaaatact cgtaccgcgt cgtggtcaat 120
ggctctgacc ttggcgtcga gtccaacttc gcagtgacac cgtccggtgg gcagaccatc 180
aacttcctcc agtacaacaa ggggtatggt gtcgcggaca ccaaaacgat tcaagttttc 240
gttgtcattc cagataccgg caactcggag gagtacatca tcgctgagtg gaagaagact 300
tga 303

<210> SEQ ID NO 12
<211> LENGTH: 100
<212> TYPE: PRT
<213> ORGANISM: Artificial Sequence
<220> FEATURE:
<223> OTHER INFORMATION: Description of Artificial Sequence: Synthetic protein sequence

<400> SEQUENCE: 12

```
Met Ser Ala Thr Ser Leu Thr Phe Gln Leu Ala Tyr Leu Val Lys Lys
1               5                   10                  15

Ile Asp Ile Asp Asn Leu Thr Phe Pro Lys Val Leu Thr Asp Lys Lys
            20                  25                  30

Tyr Ser Tyr Arg Val Val Val Asn Gly Ser Asp Leu Gly Val Glu Ser
        35                  40                  45

Asn Phe Ala Val Thr Pro Ser Gly Gly Gln Thr Ile Asn Phe Leu Gln
    50                  55                  60

Tyr Asn Lys Gly Tyr Gly Val Ala Asp Thr Lys Thr Ile Gln Val Phe
65                  70                  75                  80

Val Val Ile Pro Asp Thr Gly Asn Ser Glu Glu Tyr Ile Ile Ala Glu
                85                  90                  95

Trp Lys Lys Thr
            100
```

<210> SEQ ID NO 13
<211> LENGTH: 309
<212> TYPE: DNA
<213> ORGANISM: Artificial Sequence
<220> FEATURE:
<223> OTHER INFORMATION: Description of Artificial Sequence: Synthetic nucleotide sequence

<400> SEQUENCE: 13

```
atgtccgcca cgtcgctcac cttccagctt gcctacttgg tgaagaagat cgacttcgac      60

tacacccccca actggggccg tggtacccca agcagctaca aatactcgta ccgcgtcgtg    120

gtcaatggct ctgaccttgg cgtcgagtcc aacttcgcag tgacaccgtc cggtgggcag    180

accatcaact tcctccagta caacaagggg tatggtgtcg cggacaccaa aacgattcaa    240

gttttcgttg tcattccaga taccggcaac tcggaggagt acatcatcgc tgagtggaag    300

aagacttga                                                             309
```

<210> SEQ ID NO 14
<211> LENGTH: 102
<212> TYPE: PRT
<213> ORGANISM: Artificial Sequence
<220> FEATURE:
<223> OTHER INFORMATION: Description of Artificial Sequence: Synthetic protein sequence

<400> SEQUENCE: 14

```
Met Ser Ala Thr Ser Leu Thr Phe Gln Leu Ala Tyr Leu Val Lys Lys
1               5                   10                  15

Ile Asp Phe Asp Tyr Thr Pro Asn Trp Gly Arg Gly Thr Pro Ser Ser
            20                  25                  30

Tyr Lys Tyr Ser Tyr Arg Val Val Val Asn Gly Ser Asp Leu Gly Val
        35                  40                  45

Glu Ser Asn Phe Ala Val Thr Pro Ser Gly Gly Gln Thr Ile Asn Phe
    50                  55                  60

Leu Gln Tyr Asn Lys Gly Tyr Gly Val Ala Asp Thr Lys Thr Ile Gln
65                  70                  75                  80

Val Phe Val Val Ile Pro Asp Thr Gly Asn Ser Glu Glu Tyr Ile Ile
                85                  90                  95

Ala Glu Trp Lys Lys Thr
            100
```

<210> SEQ ID NO 15
<211> LENGTH: 306
<212> TYPE: DNA
<213> ORGANISM: Artificial Sequence
<220> FEATURE:
<223> OTHER INFORMATION: Description of Artificial Sequence: Synthetic nucleotide sequence

<400> SEQUENCE: 15
atgtccgcca cgtcgctcac cttccagctt gcctacttgg tgaagaagat cgacttcgac 60
tacaccccca actggggccg tggtacccca agcagctaca tcgacaacct taccttcccc 120
aaggttctca ccgacaaagt cgagtccaac ttcgcagtga caccgtccgg tgggcagacc 180
atcaacttcc tccagtacaa caaggggtat ggtgtcgcgg acaccaaaac gattcaagtt 240
ttcgttgtca ttccagatac cggcaactcg gaggagtaca tcatcgctga gtggaagaag 300
acttga 306

<210> SEQ ID NO 16
<211> LENGTH: 101
<212> TYPE: PRT
<213> ORGANISM: Artificial Sequence
<220> FEATURE:
<223> OTHER INFORMATION: Description of Artificial Sequence: Synthetic protein sequence

<400> SEQUENCE: 16

Met Ser Ala Thr Ser Leu Thr Phe Gln Leu Ala Tyr Leu Val Lys Lys
1 5 10 15

Ile Asp Phe Asp Tyr Thr Pro Asn Trp Gly Arg Gly Thr Pro Ser Ser
20 25 30

Tyr Ile Asp Asn Leu Thr Phe Pro Lys Val Leu Thr Asp Lys Val Glu
35 40 45

Ser Asn Phe Ala Val Thr Pro Ser Gly Gly Gln Thr Ile Asn Phe Leu
50 55 60

Gln Tyr Asn Lys Gly Tyr Gly Val Ala Asp Thr Lys Thr Ile Gln Val
65 70 75 80

Phe Val Val Ile Pro Asp Thr Gly Asn Ser Glu Glu Tyr Ile Ile Ala
85 90 95

Glu Trp Lys Lys Thr
100

<210> SEQ ID NO 17
<211> LENGTH: 312
<212> TYPE: DNA
<213> ORGANISM: Artificial Sequence
<220> FEATURE:
<223> OTHER INFORMATION: Description of Artificial Sequence: Synthetic nucleotide sequence

<400> SEQUENCE: 17
atgtccgcca cgtcgctcac cttccagctt gcctacttgg tgaagaagat cgacttcgac 60
tacaccccca actggggccg tggtacccca agcagctaca tcgacaacct taccttcccc 120
aaggttctca ccgacaaaaa atactcgtac cgcgtcgtgg tcaatggctc tgaccttggc 180
cagaccatca acttcctcca gtacaacaag gggtatggtg tcgcggacac caaaacgatt 240
caagttttcg ttgtcattcc agataccggc aactcggagg agtacatcat cgctgagtgg 300
aagaagactt ga 312

<210> SEQ ID NO 18

<211> LENGTH: 103
<212> TYPE: PRT
<213> ORGANISM: Artificial Sequence
<220> FEATURE:
<223> OTHER INFORMATION: Description of Artificial Sequence: Synthetic protein sequence

<400> SEQUENCE: 18

```
Met Ser Ala Thr Ser Leu Thr Phe Gln Leu Ala Tyr Leu Val Lys Lys
1               5                   10                  15

Ile Asp Phe Asp Tyr Thr Pro Asn Trp Gly Arg Gly Thr Pro Ser Ser
            20                  25                  30

Tyr Ile Asp Asn Leu Thr Phe Pro Lys Val Leu Thr Asp Lys Lys Tyr
        35                  40                  45

Ser Tyr Arg Val Val Val Asn Gly Ser Asp Leu Gly Gln Thr Ile Asn
    50                  55                  60

Phe Leu Gln Tyr Asn Lys Gly Tyr Gly Val Ala Asp Thr Lys Thr Ile
65                  70                  75                  80

Gln Val Phe Val Val Ile Pro Asp Thr Gly Asn Ser Glu Glu Tyr Ile
                85                  90                  95

Ile Ala Glu Trp Lys Lys Thr
            100
```

<210> SEQ ID NO 19
<211> LENGTH: 312
<212> TYPE: DNA
<213> ORGANISM: Artificial Sequence
<220> FEATURE:
<223> OTHER INFORMATION: Description of Artificial Sequence: Synthetic nucleotide sequence

<400> SEQUENCE: 19

```
atgtccgcca cgtcgctcac cttccagctt gcctacttgg tgaagaagat cgacttcgac     60

tacaccccca actggggccg tggtacccca agcagctaca tcgacaacct taccttcccc    120

aaggttctca ccgacaaaaa atactcgtac cgcgtcgtgg tcaatggctc tgaccttggc    180

gtcgagtcca acttcgcagt gacaccgtcc ggtgggggtg tcgcggacac caaaacgatt    240

caagttttcg ttgtcattcc agataccggc aactcggagg agtacatcat cgctgagtgg    300

aagaagactt ga                                                        312
```

<210> SEQ ID NO 20
<211> LENGTH: 103
<212> TYPE: PRT
<213> ORGANISM: Artificial Sequence
<220> FEATURE:
<223> OTHER INFORMATION: Description of Artificial Sequence: Synthetic protein sequence

<400> SEQUENCE: 20

```
Met Ser Ala Thr Ser Leu Thr Phe Gln Leu Ala Tyr Leu Val Lys Lys
1               5                   10                  15

Ile Asp Phe Asp Tyr Thr Pro Asn Trp Gly Arg Gly Thr Pro Ser Ser
            20                  25                  30

Tyr Ile Asp Asn Leu Thr Phe Pro Lys Val Leu Thr Asp Lys Lys Tyr
        35                  40                  45

Ser Tyr Arg Val Val Val Asn Gly Ser Asp Leu Gly Val Glu Ser Asn
    50                  55                  60

Phe Ala Val Thr Pro Ser Gly Gly Gly Val Ala Asp Thr Lys Thr Ile
65                  70                  75                  80

Gln Val Phe Val Val Ile Pro Asp Thr Gly Asn Ser Glu Glu Tyr Ile
```

```
                85                  90                  95

Ile Ala Glu Trp Lys Lys Thr
            100


<210> SEQ ID NO 21
<211> LENGTH: 312
<212> TYPE: DNA
<213> ORGANISM: Artificial Sequence
<220> FEATURE:
<223> OTHER INFORMATION: Description of Artificial Sequence: Synthetic
      nucleotide sequence

<400> SEQUENCE: 21

atgtccgcca cgtcgctcac cttccagctt gcctacttgg tgaagaagat cgacttcgac     60

tacaccccca actggggccg tggtacccca agcagctaca tcgacaacct taccttcccc    120

aaggttctca ccgacaaaaa atactcgtac cgcgtcgtgg tcaatggctc tgaccttggc    180

gtcgagtcca acttcgcagt gacaccgtcc ggtgggcaga ccatcaactt cctccagtac    240

aacaaggggt atgtcattcc agataccggc aactcggagg agtacatcat cgctgagtgg    300

aagaagactt ga                                                        312


<210> SEQ ID NO 22
<211> LENGTH: 102
<212> TYPE: PRT
<213> ORGANISM: Artificial Sequence
<220> FEATURE:
<223> OTHER INFORMATION: Description of Artificial Sequence: Synthetic
      protein sequence

<400> SEQUENCE: 22

Met Ser Ala Thr Ser Leu Thr Phe Gln Leu Ala Tyr Leu Val Lys Lys
1               5                   10                  15

Ile Asp Phe Asp Tyr Thr Pro Asn Trp Gly Arg Gly Thr Pro Ser Ser
            20                  25                  30

Tyr Ile Asp Asn Leu Thr Phe Pro Lys Val Leu Thr Asp Lys Lys Tyr
        35                  40                  45

Ser Tyr Arg Val Val Val Asn Gly Ser Asp Leu Gly Val Glu Ser Asn
    50                  55                  60

Phe Ala Val Thr Pro Ser Gly Gly Gln Thr Ile Asn Phe Leu Gln Tyr
65                  70                  75                  80

Asn Lys Gly Tyr Ile Pro Asp Thr Gly Asn Ser Glu Glu Tyr Ile Ile
                85                  90                  95

Ala Glu Trp Lys Lys Thr
            100


<210> SEQ ID NO 23
<211> LENGTH: 321
<212> TYPE: DNA
<213> ORGANISM: Artificial Sequence
<220> FEATURE:
<223> OTHER INFORMATION: Description of Artificial Sequence: Synthetic
      nucleotide sequence

<400> SEQUENCE: 23

atgtccgcca cgtcgctcac cttccagctt gcctacttgg tgaagaagat cgacttcgac     60

tacaccccca actggggccg tggtacccca agcagctaca tcgacaacct taccttcccc    120

aaggttctca ccgacaaaaa atactcgtac cgcgtcgtgg tcaatggctc tgaccttggc    180

gtcgagtcca acttcgcagt gacaccgtcc ggtgggcaga ccatcaactt cctccagtac    240

aacaaggggt atggtgtcgc ggacaccaaa acgattcaag ttttcgttgt ctacatcatc    300
```

gctgagtgga agaagacttg a 321

<210> SEQ ID NO 24
<211> LENGTH: 106
<212> TYPE: PRT
<213> ORGANISM: Artificial Sequence
<220> FEATURE:
<223> OTHER INFORMATION: Description of Artificial Sequence: Synthetic
protein sequence

<400> SEQUENCE: 24

Met Ser Ala Thr Ser Leu Thr Phe Gln Leu Ala Tyr Leu Val Lys Lys
1 5 10 15

Ile Asp Phe Asp Tyr Thr Pro Asn Trp Gly Arg Gly Thr Pro Ser Ser
20 25 30

Tyr Ile Asp Asn Leu Thr Phe Pro Lys Val Leu Thr Asp Lys Lys Tyr
35 40 45

Ser Tyr Arg Val Val Val Asn Gly Ser Asp Leu Gly Val Glu Ser Asn
50 55 60

Phe Ala Val Thr Pro Ser Gly Gly Gln Thr Ile Asn Phe Leu Gln Tyr
65 70 75 80

Asn Lys Gly Tyr Gly Val Ala Asp Thr Lys Thr Ile Gln Val Phe Val
85 90 95

Val Tyr Ile Ile Ala Glu Trp Lys Lys Thr
100 105

<210> SEQ ID NO 25
<211> LENGTH: 321
<212> TYPE: DNA
<213> ORGANISM: Artificial Sequence
<220> FEATURE:
<223> OTHER INFORMATION: Description of Artificial Sequence: Synthetic
nucleotide sequence

<400> SEQUENCE: 25
atgtccgcca cgtcgctcac cttccagctt gcctacttgg tgaagaagat cgacttcgac 60
tacaccccca actggggccg tggtacccca agcagctaca tcgacaacct taccttcccc 120
aaggttctca ccgacaaaaa atactcgtac cgcgtcgtgg tcaatggctc tgaccttggc 180
gtcgagtcca acttcgcagt gacaccgtcc ggtgggcaga ccatcaactt cctccagtac 240
aacaaggggt atggtgtcgc ggacaccaaa acgattcaag ttttcgttgt cattccagat 300
accggcaact cggaggagtg a 321

<210> SEQ ID NO 26
<211> LENGTH: 106
<212> TYPE: PRT
<213> ORGANISM: Artificial Sequence
<220> FEATURE:
<223> OTHER INFORMATION: Description of Artificial Sequence: Synthetic
protein sequence

<400> SEQUENCE: 26

Met Ser Ala Thr Ser Leu Thr Phe Gln Leu Ala Tyr Leu Val Lys Lys
1 5 10 15

Ile Asp Phe Asp Tyr Thr Pro Asn Trp Gly Arg Gly Thr Pro Ser Ser
20 25 30

Tyr Ile Asp Asn Leu Thr Phe Pro Lys Val Leu Thr Asp Lys Lys Tyr
35 40 45

Ser Tyr Arg Val Val Val Asn Gly Ser Asp Leu Gly Val Glu Ser Asn
50 55 60

Phe Ala Val Thr Pro Ser Gly Gly Gln Thr Ile Asn Phe Leu Gln Tyr
65 70 75 80

Asn Lys Gly Tyr Gly Val Ala Asp Thr Lys Thr Ile Gln Val Phe Val
85 90 95

Val Ile Pro Asp Thr Gly Asn Ser Glu Glu
100 105

<210> SEQ ID NO 27
<211> LENGTH: 237
<212> TYPE: DNA
<213> ORGANISM: Artificial Sequence
<220> FEATURE:
<223> OTHER INFORMATION: Description of Artificial Sequence: Synthetic nucleotide sequence

<400> SEQUENCE: 27
atgtccgcca cgtcgctcac cttccagctt gcctacttgg tgaagaagat cgacttcgac 60
tacaccccca actggggccg tggtacccca agcagctaca tcgacaacct taccttcccc 120
aaggttctca ccgacaaaaa atactcgtac cgcgtcgtgg tcaatggctc tgaccttggc 180
attccagata ccggcaactc ggaggagtac atcatcgctg agtggaagaa gacttga 237

<210> SEQ ID NO 28
<211> LENGTH: 78
<212> TYPE: PRT
<213> ORGANISM: Artificial Sequence
<220> FEATURE:
<223> OTHER INFORMATION: Description of Artificial Sequence: Synthetic protein sequence

<400> SEQUENCE: 28

Met Ser Ala Thr Ser Leu Thr Phe Gln Leu Ala Tyr Leu Val Lys Lys
1 5 10 15

Ile Asp Phe Asp Tyr Thr Pro Asn Trp Gly Arg Gly Thr Pro Ser Ser
20 25 30

Tyr Ile Asp Asn Leu Thr Phe Pro Lys Val Leu Thr Asp Lys Lys Tyr
35 40 45

Ser Tyr Arg Val Val Val Asn Gly Ser Asp Leu Gly Ile Pro Asp Thr
50 55 60

Gly Asn Ser Glu Glu Tyr Ile Ile Ala Glu Trp Lys Lys Thr
65 70 75

<210> SEQ ID NO 29
<211> LENGTH: 138
<212> TYPE: DNA
<213> ORGANISM: Artificial Sequence
<220> FEATURE:
<223> OTHER INFORMATION: Description of Artificial Sequence: Synthetic nucleotide sequence

<400> SEQUENCE: 29
aatggctctg accttggcgt cgagtccaac ttcgcagtga caccgtccgg tgggcagacc 60
atcaacttcc tccagtacaa caaggggtat ggtgtcgcgg acaccaaaac gattcaagtt 120
ttcgttgtca ttccagat 138

<210> SEQ ID NO 30
<211> LENGTH: 46
<212> TYPE: PRT
<213> ORGANISM: Artificial Sequence
<220> FEATURE:
<223> OTHER INFORMATION: Description of Artificial Sequence: Synthetic protein sequence

<400> SEQUENCE: 30

Asn Gly Ser Asp Leu Gly Val Glu Ser Asn Phe Ala Val Thr Pro Ser
1 5 10 15

Gly Gly Gln Thr Ile Asn Phe Leu Gln Tyr Asn Lys Gly Tyr Gly Val
20 25 30

Ala Asp Thr Lys Thr Ile Gln Val Phe Val Val Ile Pro Asp
35 40 45

<210> SEQ ID NO 31
<211> LENGTH: 348
<212> TYPE: DNA
<213> ORGANISM: Artificial Sequence
<220> FEATURE:
<223> OTHER INFORMATION: Description of Artificial Sequence: Synthetic nucleotide sequence

<400> SEQUENCE: 31
atgtccgcca cgtcgctcac cttccagctt gcctacttgg tgaagaagat cgacttcgac 60
tacaccccca actggggcgc aggtaccca agcagctaca tcgacaacct taccttcccc 120
aaggttctca ccgacaaaaa atactcgtac cgcgtcgtgg tcaatggctc tgaccttggc 180
gtcgagtcca acttcgcagt gacaccgtcc ggtgggcaga ccatcaactt cctccagtac 240
aacaaggggt atggtgtcgc ggacaccaaa acgattcaag ttttcgttgt cattccagat 300
accggcaact cggaggagta catcatcgct gagtggaaga agacttga 348

<210> SEQ ID NO 32
<211> LENGTH: 115
<212> TYPE: PRT
<213> ORGANISM: Artificial Sequence
<220> FEATURE:
<223> OTHER INFORMATION: Description of Artificial Sequence: Synthetic protein sequence

<400> SEQUENCE: 32

Met Ser Ala Thr Ser Leu Thr Phe Gln Leu Ala Tyr Leu Val Lys Lys
1 5 10 15

Ile Asp Phe Asp Tyr Thr Pro Asn Trp Gly Ala Gly Thr Pro Ser Ser
20 25 30

Tyr Ile Asp Asn Leu Thr Phe Pro Lys Val Leu Thr Asp Lys Lys Tyr
35 40 45

Ser Tyr Arg Val Val Val Asn Gly Ser Asp Leu Gly Val Glu Ser Asn
50 55 60

Phe Ala Val Thr Pro Ser Gly Gly Gln Thr Ile Asn Phe Leu Gln Tyr
65 70 75 80

Asn Lys Gly Tyr Gly Val Ala Asp Thr Lys Thr Ile Gln Val Phe Val
85 90 95

Val Ile Pro Asp Thr Gly Asn Ser Glu Glu Tyr Ile Ile Ala Glu Trp
100 105 110

Lys Lys Thr
115

<210> SEQ ID NO 33
<211> LENGTH: 348
<212> TYPE: DNA
<213> ORGANISM: Artificial Sequence
<220> FEATURE:
<223> OTHER INFORMATION: Description of Artificial Sequence: Synthetic nucleotide sequence

<400> SEQUENCE: 33
atgtccgcca cgtcgctcac cttccagctt gcctacttgg tgaagaagat cgacttcgac 60
tacaccccca actggggccg tgcaacccca agcagctaca tcgacaacct taccttcccc 120
aaggttctca ccgacaaaaa atactcgtac cgcgtcgtgg tcaatggctc tgaccttggc 180
gtcgagtcca acttcgcagt gacaccgtcc ggtgggcaga ccatcaactt cctccagtac 240
aacaaggggt atggtgtcgc ggacaccaaa acgattcaag ttttcgttgt cattccagat 300
accggcaact cggaggagta catcatcgct gagtggaaga agacttga 348

<210> SEQ ID NO 34
<211> LENGTH: 115
<212> TYPE: PRT
<213> ORGANISM: Artificial Sequence
<220> FEATURE:
<223> OTHER INFORMATION: Description of Artificial Sequence: Synthetic
protein sequence

<400> SEQUENCE: 34

Met Ser Ala Thr Ser Leu Thr Phe Gln Leu Ala Tyr Leu Val Lys Lys
1 5 10 15

Ile Asp Phe Asp Tyr Thr Pro Asn Trp Gly Arg Ala Thr Pro Ser Ser
20 25 30

Tyr Ile Asp Asn Leu Thr Phe Pro Lys Val Leu Thr Asp Lys Lys Tyr
35 40 45

Ser Tyr Arg Val Val Val Asn Gly Ser Asp Leu Gly Val Glu Ser Asn
50 55 60

Phe Ala Val Thr Pro Ser Gly Gly Gln Thr Ile Asn Phe Leu Gln Tyr
65 70 75 80

Asn Lys Gly Tyr Gly Val Ala Asp Thr Lys Thr Ile Gln Val Phe Val
85 90 95

Val Ile Pro Asp Thr Gly Asn Ser Glu Glu Tyr Ile Ile Ala Glu Trp
100 105 110

Lys Lys Thr
115

<210> SEQ ID NO 35
<211> LENGTH: 348
<212> TYPE: DNA
<213> ORGANISM: Artificial Sequence
<220> FEATURE:
<223> OTHER INFORMATION: Description of Artificial Sequence: Synthetic
nucleotide sequence

<400> SEQUENCE: 35
atgtccgcca cgtcgctcac cttccagctt gcctacttgg tgaagaagat cgacttcgac 60
tacaccccca actggggccg tggtgcacca agcagctaca tcgacaacct taccttcccc 120
aaggttctca ccgacaaaaa atactcgtac cgcgtcgtgg tcaatggctc tgaccttggc 180
gtcgagtcca acttcgcagt gacaccgtcc ggtgggcaga ccatcaactt cctccagtac 240
aacaaggggt atggtgtcgc ggacaccaaa acgattcaag ttttcgttgt cattccagat 300
accggcaact cggaggagta catcatcgct gagtggaaga agacttga 348

<210> SEQ ID NO 36
<211> LENGTH: 115
<212> TYPE: PRT
<213> ORGANISM: Artificial Sequence
<220> FEATURE:
<223> OTHER INFORMATION: Description of Artificial Sequence: Synthetic
protein sequence

<400> SEQUENCE: 36

Met Ser Ala Thr Ser Leu Thr Phe Gln Leu Ala Tyr Leu Val Lys Lys
1 5 10 15

Ile Asp Phe Asp Tyr Thr Pro Asn Trp Gly Arg Gly Ala Pro Ser Ser
20 25 30

Tyr Ile Asp Asn Leu Thr Phe Pro Lys Val Leu Thr Asp Lys Lys Tyr
35 40 45

Ser Tyr Arg Val Val Val Asn Gly Ser Asp Leu Gly Val Glu Ser Asn
50 55 60

Phe Ala Val Thr Pro Ser Gly Gly Gln Thr Ile Asn Phe Leu Gln Tyr
65 70 75 80

Asn Lys Gly Tyr Gly Val Ala Asp Thr Lys Thr Ile Gln Val Phe Val
85 90 95

Val Ile Pro Asp Thr Gly Asn Ser Glu Glu Tyr Ile Ile Ala Glu Trp
100 105 110

Lys Lys Thr
115

<210> SEQ ID NO 37
<211> LENGTH: 696
<212> TYPE: DNA
<213> ORGANISM: Artificial Sequence
<220> FEATURE:
<223> OTHER INFORMATION: Description of Artificial Sequence: Synthetic nucleotide sequence

<400> SEQUENCE: 37
caagagcaca agccaaagaa ggatgatttc cgaaacgaat tcgatcactt gttgatcgaa 60
caggcaaacc atgctatcga aaagggagaa catcaattgc tttacttgca acaccaactc 120
gacgaattga atgaaaacaa gagcaaggaa ttgcaagaga aaatcattcg agaacttgat 180
gttgtttgcg ccatgatcga aggagcccaa ggagctttgg aacgtgaatt gaagcgaact 240
gatcttaaca ttttggaacg attcaactac gaagaggctc aaactctcag caagatcttg 300
cttaaggatt tgaaggaaac cgaacaaaaa gtgaaggata ttcaaaccca atccgccacg 360
tcgctcacct tccagcttgc ctacttggtg aagaagatcg acttcgacta cacccccaac 420
tggggccgtg gtaccccaag cagctacatc gacaacctta ccttccccaa ggttctcacc 480
gacaaaaaat actcgtaccg cgtcgtggtc aatggctctg accttggcgt cgagtccaac 540
ttcgcagtga caccgtccgg tggcagacc atcaacttcc tccagtacaa caaggggtat 600
ggtgtcgcgg acaccaaaac gattcaagtt ttcgttgtca ttccagatac cggcaactcg 660
gaggagtaca tcatcgctga gtggaagaag acttga 696

<210> SEQ ID NO 38
<211> LENGTH: 231
<212> TYPE: PRT
<213> ORGANISM: Artificial Sequence
<220> FEATURE:
<223> OTHER INFORMATION: Description of Artificial Sequence: Synthetic protein sequence

<400> SEQUENCE: 38

Gln Glu His Lys Pro Lys Lys Asp Asp Phe Arg Asn Glu Phe Asp His
1 5 10 15

Leu Leu Ile Glu Gln Ala Asn His Ala Ile Glu Lys Gly Glu His Gln
20 25 30

Leu Leu Tyr Leu Gln His Gln Leu Asp Glu Leu Asn Glu Asn Lys Ser
35 40 45

```
Lys Glu Leu Gln Glu Lys Ile Ile Arg Glu Leu Asp Val Val Cys Ala
    50                  55                  60

Met Ile Glu Gly Ala Gln Gly Ala Leu Glu Arg Glu Leu Lys Arg Thr
65                  70                  75                  80

Asp Leu Asn Ile Leu Glu Arg Phe Asn Tyr Glu Glu Ala Gln Thr Leu
                85                  90                  95

Ser Lys Ile Leu Leu Lys Asp Leu Lys Glu Thr Glu Gln Lys Val Lys
            100                 105                 110

Asp Ile Gln Thr Gln Ser Ala Thr Ser Leu Thr Phe Gln Leu Ala Tyr
        115                 120                 125

Leu Val Lys Lys Ile Asp Phe Asp Tyr Thr Pro Asn Trp Gly Arg Gly
    130                 135                 140

Thr Pro Ser Ser Tyr Ile Asp Asn Leu Thr Phe Pro Lys Val Leu Thr
145                 150                 155                 160

Asp Lys Lys Tyr Ser Tyr Arg Val Val Val Asn Gly Ser Asp Leu Gly
                165                 170                 175

Val Glu Ser Asn Phe Ala Val Thr Pro Ser Gly Gly Gln Thr Ile Asn
            180                 185                 190

Phe Leu Gln Tyr Asn Lys Gly Tyr Gly Val Ala Asp Thr Lys Thr Ile
        195                 200                 205

Gln Val Phe Val Val Ile Pro Asp Thr Gly Asn Ser Glu Glu Tyr Ile
    210                 215                 220

Ile Ala Glu Trp Lys Lys Thr
225                 230
```

<210> SEQ ID NO 39
<211> LENGTH: 696
<212> TYPE: DNA
<213> ORGANISM: Artificial Sequence
<220> FEATURE:
<223> OTHER INFORMATION: Description of Artificial Sequence: Synthetic nucleotide sequence

<400> SEQUENCE: 39

```
caagagcaca agccaaagaa ggatgatttc cgaaacgaat tcgatcactt gttgatcgaa     60

caggcaaacc atgctatcga aaagggagaa catcaattgc tttacttgca acaccaactc    120

gacgaattga atgaaaacaa gagcaaggaa ttgcaagaga aaatcattcg agaacttgat    180

gttgtttgcg ccatgatcga aggagcccaa ggagctttgg aacgtgaatt gaagcgaact    240

gatcttaaca ttttggaacg attcaactac gaagaggctc aaactctcag caagatcttg    300

cttaaggatt tgaaggaaac cgaacaaaaa gtgaaggata ttcaaaccca atccgccacg    360

tcgctcacct tccagcttgc ctacttggtg aagaagatcg acttcgacta cacccccaac    420

tggggcgcag gtaccccaag cagctacatc gacaacctta ccttccccaa ggttctcacc    480

gacaaaaaat actcgtaccg cgtcgtggtc aatggctctg accttggcgt cgagtccaac    540

ttcgcagtga caccgtccgg tgggcagacc atcaacttcc tccagtacaa caaggggtat    600

ggtgtcgcgg acaccaaaac gattcaagtt ttcgttgtca ttccagatac cggcaactcg    660

gaggagtaca tcatcgctga gtggaagaag acttga                              696
```

<210> SEQ ID NO 40
<211> LENGTH: 231
<212> TYPE: PRT
<213> ORGANISM: Artificial Sequence
<220> FEATURE:
<223> OTHER INFORMATION: Description of Artificial Sequence: Synthetic protein sequence

<400> SEQUENCE: 40

Gln Glu His Lys Pro Lys Lys Asp Asp Phe Arg Asn Glu Phe Asp His
1               5                   10                  15

Leu Leu Ile Glu Gln Ala Asn His Ala Ile Glu Lys Gly Glu His Gln
            20                  25                  30

Leu Leu Tyr Leu Gln His Gln Leu Asp Glu Leu Asn Glu Asn Lys Ser
        35                  40                  45

Lys Glu Leu Gln Glu Lys Ile Ile Arg Glu Leu Asp Val Val Cys Ala
    50                  55                  60

Met Ile Glu Gly Ala Gln Gly Ala Leu Glu Arg Glu Leu Lys Arg Thr
65                  70                  75                  80

Asp Leu Asn Ile Leu Glu Arg Phe Asn Tyr Glu Glu Ala Gln Thr Leu
                85                  90                  95

Ser Lys Ile Leu Leu Lys Asp Leu Lys Glu Thr Glu Gln Lys Val Lys
            100                 105                 110

Asp Ile Gln Thr Gln Ser Ala Thr Ser Leu Thr Phe Gln Leu Ala Tyr
        115                 120                 125

Leu Val Lys Lys Ile Asp Phe Asp Tyr Thr Pro Asn Trp Gly Ala Gly
    130                 135                 140

Thr Pro Ser Ser Tyr Ile Asp Asn Leu Thr Phe Pro Lys Val Leu Thr
145                 150                 155                 160

Asp Lys Lys Tyr Ser Tyr Arg Val Val Val Asn Gly Ser Asp Leu Gly
                165                 170                 175

Val Glu Ser Asn Phe Ala Val Thr Pro Ser Gly Gly Gln Thr Ile Asn
            180                 185                 190

Phe Leu Gln Tyr Asn Lys Gly Tyr Gly Val Ala Asp Thr Lys Thr Ile
        195                 200                 205

Gln Val Phe Val Val Ile Pro Asp Thr Gly Asn Ser Glu Glu Tyr Ile
    210                 215                 220

Ile Ala Glu Trp Lys Lys Thr
225                 230

<210> SEQ ID NO 41
<211> LENGTH: 696
<212> TYPE: DNA
<213> ORGANISM: Artificial Sequence
<220> FEATURE:
<223> OTHER INFORMATION: Description of Artificial Sequence: Synthetic nucleotide sequence

<400> SEQUENCE: 41
caagagcaca agccaaagaa ggatgatttc cgaaacgaat tcgatcactt gttgatcgaa 60
caggcaaacc atgctatcga aaagggagaa catcaattgc tttacttgca acaccaactc 120
gacgaattga atgaaaacaa gagcaaggaa ttgcaagaga aaatcattcg agaacttgat 180
gttgtttgcg ccatgatcga aggagcccaa ggagctttgg aacgtgaatt gaagcgaact 240
gatcttaaca ttttggaacg attcaactac gaagaggctc aaactctcag caagatcttg 300
cttaaggatt tgaaggaaac cgaacaaaaa gtgaaggata ttcaaaccca atccgccacg 360
tcgctcacct tccagcttgc ctacttggtg aagaagatcg acttcgacta cacccccaac 420
tggggccgtg gtgcaccaag cagctacatc gacaacctta ccttccccaa ggttctcacc 480
gacaaaaaat actcgtaccg cgtcgtggtc aatggctctg accttggcgt cgagtccaac 540
ttcgcagtga caccgtccgg tgggcagacc atcaacttcc tccagtacaa caaggggtat 600
ggtgtcgcgg acaccaaaac gattcaagtt ttcgttgtca ttccagatac cggcaactcg 660
gaggagtaca tcatcgctga gtggaagaag acttga 696

<210> SEQ ID NO 42
<211> LENGTH: 231
<212> TYPE: PRT
<213> ORGANISM: Artificial Sequence
<220> FEATURE:
<223> OTHER INFORMATION: Description of Artificial Sequence: Synthetic protein sequence

<400> SEQUENCE: 42

```
Gln Glu His Lys Pro Lys Lys Asp Asp Phe Arg Asn Glu Phe Asp His
1               5                   10                  15

Leu Leu Ile Glu Gln Ala Asn His Ala Ile Glu Lys Gly Glu His Gln
            20                  25                  30

Leu Leu Tyr Leu Gln His Gln Leu Asp Glu Leu Asn Glu Asn Lys Ser
        35                  40                  45

Lys Glu Leu Gln Glu Lys Ile Ile Arg Glu Leu Asp Val Val Cys Ala
    50                  55                  60

Met Ile Glu Gly Ala Gln Gly Ala Leu Glu Arg Glu Leu Lys Arg Thr
65                  70                  75                  80

Asp Leu Asn Ile Leu Glu Arg Phe Asn Tyr Glu Glu Ala Gln Thr Leu
                85                  90                  95

Ser Lys Ile Leu Leu Lys Asp Leu Lys Glu Thr Glu Gln Lys Val Lys
            100                 105                 110

Asp Ile Gln Thr Gln Ser Ala Thr Ser Leu Thr Phe Gln Leu Ala Tyr
        115                 120                 125

Leu Val Lys Lys Ile Asp Phe Asp Tyr Thr Pro Asn Trp Gly Arg Gly
    130                 135                 140

Ala Pro Ser Ser Tyr Ile Asp Asn Leu Thr Phe Pro Lys Val Leu Thr
145                 150                 155                 160

Asp Lys Lys Tyr Ser Tyr Arg Val Val Val Asn Gly Ser Asp Leu Gly
                165                 170                 175

Val Glu Ser Asn Phe Ala Val Thr Pro Ser Gly Gly Gln Thr Ile Asn
            180                 185                 190

Phe Leu Gln Tyr Asn Lys Gly Tyr Gly Val Ala Asp Thr Lys Thr Ile
        195                 200                 205

Gln Val Phe Val Val Ile Pro Asp Thr Gly Asn Ser Glu Glu Tyr Ile
    210                 215                 220

Ile Ala Glu Trp Lys Lys Thr
225                 230
```

<210> SEQ ID NO 43
<211> LENGTH: 732
<212> TYPE: DNA
<213> ORGANISM: Artificial Sequence
<220> FEATURE:
<223> OTHER INFORMATION: Description of Artificial Sequence: Synthetic nucleotide sequence

<400> SEQUENCE: 43
gatcaagtcg atgtcaaaga ttgtgccaat catgaaatca aaaaagtttt ggtaccagga 60
tgccatggtt cagaaccatg tatcattcat cgtggtaaac cattccaatt ggaagccgtt 120
ttcgaagcca accaaaacac aaaaacggct aaaattgaaa tcaaagcctc aatcgatggt 180
ttagaagttg atgttcccgg tatcgatcca aatgcatgcc attacatgaa atgcccattg 240
gttaaaggac aacaatatga tattaaatat acatggaatg ttccgaaaat tgcaccaaaa 300

```
tctgaaaatg ttgtcgtcac tgttaaagtt atgggtgatg atggtgtttt ggcctgtgct    360

attgctactc atgctaaaat ccgcgattcc gccacgtcgc tcaccttcca gcttgcctac    420

ttggtgaaga agatcgactt cgactacacc cccaactggg gcgcaggtac cccaagcagc    480

tacatcgaca accttacctt ccccaaggtt ctcaccgaca aaaaatactc gtaccgcgtc    540

gtggtcaatg gctctgacct tggcgtcgag tccaacttcg cagtgacacc gtccggtggg    600

cagaccatca acttcctcca gtacaacaag ggtatggtg tcgcggacac caaaacgatt    660

caagttttcg ttgtcattcc agataccggc aactcggagg agtacatcat cgctgagtgg    720

aagaagactt ga                                                         732
```

<210> SEQ ID NO 44
<211> LENGTH: 243
<212> TYPE: PRT
<213> ORGANISM: Artificial Sequence
<220> FEATURE:
<223> OTHER INFORMATION: Description of Artificial Sequence: Synthetic protein sequence

<400> SEQUENCE: 44

```
Asp Gln Val Asp Val Lys Asp Cys Ala Asn His Glu Ile Lys Lys Val
1               5                   10                  15

Leu Val Pro Gly Cys His Gly Ser Glu Pro Cys Ile Ile His Arg Gly
            20                  25                  30

Lys Pro Phe Gln Leu Glu Ala Val Phe Glu Ala Asn Gln Asn Thr Lys
        35                  40                  45

Thr Ala Lys Ile Glu Ile Lys Ala Ser Ile Asp Gly Leu Glu Val Asp
    50                  55                  60

Val Pro Gly Ile Asp Pro Asn Ala Cys His Tyr Met Lys Cys Pro Leu
65                  70                  75                  80

Val Lys Gly Gln Gln Tyr Asp Ile Lys Tyr Thr Trp Asn Val Pro Lys
                85                  90                  95

Ile Ala Pro Lys Ser Glu Asn Val Val Val Thr Val Lys Val Met Gly
            100                 105                 110

Asp Asp Gly Val Leu Ala Cys Ala Ile Ala Thr His Ala Lys Ile Arg
        115                 120                 125

Asp Ser Ala Thr Ser Leu Thr Phe Gln Leu Ala Tyr Leu Val Lys Lys
    130                 135                 140

Ile Asp Phe Asp Tyr Thr Pro Asn Trp Gly Ala Gly Thr Pro Ser Ser
145                 150                 155                 160

Tyr Ile Asp Asn Leu Thr Phe Pro Lys Val Leu Thr Asp Lys Lys Tyr
                165                 170                 175

Ser Tyr Arg Val Val Val Asn Gly Ser Asp Leu Gly Val Glu Ser Asn
            180                 185                 190

Phe Ala Val Thr Pro Ser Gly Gly Gln Thr Ile Asn Phe Leu Gln Tyr
        195                 200                 205

Asn Lys Gly Tyr Gly Val Ala Asp Thr Lys Thr Ile Gln Val Phe Val
    210                 215                 220

Val Ile Pro Asp Thr Gly Asn Ser Glu Glu Tyr Ile Ile Ala Glu Trp
225                 230                 235                 240

Lys Lys Thr
```

<210> SEQ ID NO 45
<211> LENGTH: 732
<212> TYPE: DNA
<213> ORGANISM: Artificial Sequence
<220> FEATURE:

<223> OTHER INFORMATION: Description of Artificial Sequence: Synthetic
      nucleotide sequence

<400> SEQUENCE: 45

```
gatcaagtcg atgtcaaaga ttgtgccaat catgaaatca aaaaagtttt ggtaccagga     60

tgccatggtt cagaaccatg tatcattcat cgtggtaaac cattccaatt ggaagccgtt    120

ttcgaagcca accaaaacac aaaaacggct aaaattgaaa tcaaagcctc aatcgatggt    180

ttagaagttg atgttcccgg tatcgatcca aatgcatgcc attacatgaa atgcccattg    240

gttaaaggac aacaatatga tattaaatat acatggaatg ttccgaaaat tgcaccaaaa    300

tctgaaaatg ttgtcgtcac tgttaaagtt atgggtgatg atggtgtttt ggcctgtgct    360

attgctactc atgctaaaat ccgcgattcc gccacgtcgc tcaccttcca gcttgcctac    420

ttggtgaaga agatcgactt cgactacacc cccaactggg gccgtggtgc accaagcagc    480

tacatcgaca accttacctt ccccaaggtt ctcaccgaca aaaaatactc gtaccgcgtc    540

gtggtcaatg gctctgacct tggcgtcgag tccaacttcg cagtgacacc gtccggtggg    600

cagaccatca acttcctcca gtacaacaag ggtatggtg tcgcggacac caaaacgatt    660

caagttttcg ttgtcattcc agataccggc aactcggagg agtacatcat cgctgagtgg    720

aagaagactt ga                                                        732
```

<210> SEQ ID NO 46
<211> LENGTH: 243
<212> TYPE: PRT
<213> ORGANISM: Artificial Sequence
<220> FEATURE:
<223> OTHER INFORMATION: Description of Artificial Sequence: Synthetic
      protein sequence

<400> SEQUENCE: 46

```
Asp Gln Val Asp Val Lys Asp Cys Ala Asn His Glu Ile Lys Lys Val
1               5                   10                  15

Leu Val Pro Gly Cys His Gly Ser Glu Pro Cys Ile Ile His Arg Gly
            20                  25                  30

Lys Pro Phe Gln Leu Glu Ala Val Phe Glu Ala Asn Gln Asn Thr Lys
        35                  40                  45

Thr Ala Lys Ile Glu Ile Lys Ala Ser Ile Asp Gly Leu Glu Val Asp
    50                  55                  60

Val Pro Gly Ile Asp Pro Asn Ala Cys His Tyr Met Lys Cys Pro Leu
65                  70                  75                  80

Val Lys Gly Gln Gln Tyr Asp Ile Lys Tyr Thr Trp Asn Val Pro Lys
                85                  90                  95

Ile Ala Pro Lys Ser Glu Asn Val Val Val Thr Val Lys Val Met Gly
            100                 105                 110

Asp Asp Gly Val Leu Ala Cys Ala Ile Ala Thr His Ala Lys Ile Arg
        115                 120                 125

Asp Ser Ala Thr Ser Leu Thr Phe Gln Leu Ala Tyr Leu Val Lys Lys
    130                 135                 140

Ile Asp Phe Asp Tyr Thr Pro Asn Trp Gly Arg Gly Ala Pro Ser Ser
145                 150                 155                 160

Tyr Ile Asp Asn Leu Thr Phe Pro Lys Val Leu Thr Asp Lys Lys Tyr
                165                 170                 175

Ser Tyr Arg Val Val Val Asn Gly Ser Asp Leu Gly Val Glu Ser Asn
            180                 185                 190

Phe Ala Val Thr Pro Ser Gly Gly Gln Thr Ile Asn Phe Leu Gln Tyr
        195                 200                 205
```

-continued

```
Asn Lys Gly Tyr Gly Val Ala Asp Thr Lys Thr Ile Gln Val Phe Val
    210                 215                 220

Val Ile Pro Asp Thr Gly Asn Ser Glu Glu Tyr Ile Ile Ala Glu Trp
225                 230                 235                 240

Lys Lys Thr
```

<210> SEQ ID NO 47
<211> LENGTH: 1083
<212> TYPE: DNA
<213> ORGANISM: Artificial Sequence
<220> FEATURE:
<223> OTHER INFORMATION: Description of Artificial Sequence: Synthetic nucleotide sequence

<400> SEQUENCE: 47

```
caagagcaca agccaaagaa ggatgatttc cgaaacgaat tcgatcactt gttgatcgaa      60

caggcaaacc atgctatcga aaagggagaa catcaattgc tttacttgca acaccaactc     120

gacgaattga atgaaaacaa gagcaaggaa ttgcaagaga aaatcattcg agaacttgat     180

gttgtttgcg ccatgatcga aggagcccaa ggagctttgg aacgtgaatt gaagcgaact     240

gatcttaaca ttttggaacg attcaactac gaagaggctc aaactctcag caagatcttg     300

cttaaggatt tgaaggaaac cgaacaaaaa gtgaaggata ttcaaaccca agatcaagtc     360

gatgtcaaag attgtgccaa tcatgaaatc aaaaaagttt tggtaccagg atgccatggt     420

tcagaaccat gtatcattca tcgtggtaaa ccattccaat tggaagccgt tttcgaagcc     480

aaccaaaaca caaaaacggc taaaattgaa atcaaagcct caatcgatgg tttagaagtt     540

gatgttcccg gtatcgatcc aaatgcatgc cattacatga aatgcccatt ggttaaagga     600

caacaatatg atattaaata tacatggaat gttccgaaaa ttgcaccaaa atctgaaaat     660

gttgtcgtca ctgttaaagt tatgggtgat gatggtgttt tggcctgtgc tattgctact     720

catgctaaaa tccgcgattc cgccacgtcg ctcaccttcc agcttgccta cttggtgaag     780

aagatcgact tcgactacac ccccaactgg ggcgcaggta ccccaagcag ctacatcgac     840

aaccttacct tccccaaggt tctcaccgac aaaaaatact cgtaccgcgt cgtggtcaat     900

ggctctgacc ttggcgtcga gtccaacttc gcagtgacac cgtccggtgg gcagaccatc     960

aacttcctcc agtacaacaa ggggtatggt gtcgcggaca ccaaaacgat tcaagttttc    1020

gttgtcattc cagataccgg caactcggag gagtacatca tcgctgagtg gaagaagact    1080

tga                                                                  1083
```

<210> SEQ ID NO 48
<211> LENGTH: 360
<212> TYPE: PRT
<213> ORGANISM: Artificial Sequence
<220> FEATURE:
<223> OTHER INFORMATION: Description of Artificial Sequence: Synthetic protein sequence

<400> SEQUENCE: 48

```
Gln Glu His Lys Pro Lys Lys Asp Asp Phe Arg Asn Glu Phe Asp His
1               5                   10                  15

Leu Leu Ile Glu Gln Ala Asn His Ala Ile Glu Lys Gly Glu His Gln
            20                  25                  30

Leu Leu Tyr Leu Gln His Gln Leu Asp Glu Leu Asn Glu Asn Lys Ser
        35                  40                  45

Lys Glu Leu Gln Glu Lys Ile Ile Arg Glu Leu Asp Val Val Cys Ala
    50                  55                  60
```

Met Ile Glu Gly Ala Gln Gly Ala Leu Glu Arg Glu Leu Lys Arg Thr
65 70 75 80

Asp Leu Asn Ile Leu Glu Arg Phe Asn Tyr Glu Glu Ala Gln Thr Leu
85 90 95

Ser Lys Ile Leu Leu Lys Asp Leu Lys Glu Thr Glu Gln Lys Val Lys
100 105 110

Asp Ile Gln Thr Gln Asp Gln Val Asp Val Lys Asp Cys Ala Asn His
115 120 125

Glu Ile Lys Lys Val Leu Val Pro Gly Cys His Gly Ser Glu Pro Cys
130 135 140

Ile Ile His Arg Gly Lys Pro Phe Gln Leu Glu Ala Val Phe Glu Ala
145 150 155 160

Asn Gln Asn Thr Lys Thr Ala Lys Ile Glu Ile Lys Ala Ser Ile Asp
165 170 175

Gly Leu Glu Val Asp Val Pro Gly Ile Asp Pro Asn Ala Cys His Tyr
180 185 190

Met Lys Cys Pro Leu Val Lys Gly Gln Gln Tyr Asp Ile Lys Tyr Thr
195 200 205

Trp Asn Val Pro Lys Ile Ala Pro Lys Ser Glu Asn Val Val Val Thr
210 215 220

Val Lys Val Met Gly Asp Asp Gly Val Leu Ala Cys Ala Ile Ala Thr
225 230 235 240

His Ala Lys Ile Arg Asp Ser Ala Thr Ser Leu Thr Phe Gln Leu Ala
245 250 255

Tyr Leu Val Lys Lys Ile Asp Phe Asp Tyr Thr Pro Asn Trp Gly Ala
260 265 270

Gly Thr Pro Ser Ser Tyr Ile Asp Asn Leu Thr Phe Pro Lys Val Leu
275 280 285

Thr Asp Lys Lys Tyr Ser Tyr Arg Val Val Val Asn Gly Ser Asp Leu
290 295 300

Gly Val Glu Ser Asn Phe Ala Val Thr Pro Ser Gly Gly Gln Thr Ile
305 310 315 320

Asn Phe Leu Gln Tyr Asn Lys Gly Tyr Gly Val Ala Asp Thr Lys Thr
325 330 335

Ile Gln Val Phe Val Val Ile Pro Asp Thr Gly Asn Ser Glu Glu Tyr
340 345 350

Ile Ile Ala Glu Trp Lys Lys Thr
355 360

<210> SEQ ID NO 49
<211> LENGTH: 212
<212> TYPE: PRT
<213> ORGANISM: Artificial Sequence
<220> FEATURE:
<223> OTHER INFORMATION: Description of Artificial Sequence: Synthetic protein sequence

<400> SEQUENCE: 49

Met His Gly Asp Thr Pro Thr Leu His Glu Tyr Met Leu Asp Leu Gln
1 5 10 15

Pro Glu Thr Thr Asp Leu Tyr Cys Tyr Glu Gln Leu Asn Asp Ser Ser
20 25 30

Glu Glu Glu Asp Glu Ile Asp Gly Pro Ala Gly Gln Ala Glu Pro Asp
35 40 45

Arg Ala His Tyr Asn Ile Val Thr Phe Cys Cys Lys Cys Asp Ser Thr
50 55 60

```
Leu Arg Leu Cys Val Gln Ser Thr His Val Asp Ile Arg Thr Leu Glu
65                  70                  75                  80

Asp Leu Leu Met Gly Thr Leu Gly Ile Val Cys Pro Ile Cys Ser Gln
                85                  90                  95

Lys Pro Ser Ala Thr Ser Leu Thr Phe Gln Leu Ala Tyr Leu Val Lys
            100                 105                 110

Lys Ile Asp Phe Asp Tyr Thr Pro Asn Trp Gly Arg Gly Ala Pro Ser
        115                 120                 125

Ser Tyr Ile Asp Asn Leu Thr Phe Pro Lys Val Leu Thr Asp Lys Lys
    130                 135                 140

Tyr Ser Tyr Arg Val Val Val Asn Gly Ser Asp Leu Gly Val Glu Ser
145                 150                 155                 160

Asn Phe Ala Val Thr Pro Ser Gly Gly Gln Thr Ile Asn Phe Leu Gln
                165                 170                 175

Tyr Asn Lys Gly Tyr Gly Val Ala Asp Thr Lys Thr Ile Gln Val Phe
            180                 185                 190

Val Val Ile Pro Asp Thr Gly Asn Ser Glu Glu Tyr Ile Ile Ala Glu
        195                 200                 205

Trp Lys Lys Thr
    210


<210> SEQ ID NO 50
<211> LENGTH: 639
<212> TYPE: DNA
<213> ORGANISM: Artificial Sequence
<220> FEATURE:
<223> OTHER INFORMATION: Description of Artificial Sequence: Synthetic
      nucleotide sequence

<400> SEQUENCE: 50

atgcatggag atacacctac attgcatgaa tatatgttag atttgcaacc agagacaact     60

gatctctact gttatgagca attaaatgac agctcagagg aggaggatga aatagatggt    120

ccagctggac aagcagaacc ggacagagcc cattacaata ttgtaacctt ttgttgcaag    180

tgtgactcta cgcttcggtt gtgcgtacaa agcacacacg tagacattcg tactttggaa    240

gacctgttaa tgggcacact aggaattgtg tgccccatct gttctcagaa accatccgcc    300

acgtcgctca ccttccagct tgcctacttg gtgaagaaga tcgacttcga ctacaccccc    360

aactggggcc gtggtgcacc aagcagctac atcgacaacc ttaccttccc caaggttctc    420

accgacaaaa aatactcgta ccgcgtcgtg gtcaatggct ctgaccttgg cgtcgagtcc    480

aacttcgcag tgacaccgtc cggtgggcag accatcaact tcctccagta caacaagggg    540

tatggtgtcg cggacaccaa aacgattcaa gttttcgttg tcattccaga taccggcaac    600

tcggaggagt acatcatcgc tgagtggaag aagacttga                           639


<210> SEQ ID NO 51
<211> LENGTH: 282
<212> TYPE: PRT
<213> ORGANISM: Artificial Sequence
<220> FEATURE:
<223> OTHER INFORMATION: Description of Artificial Sequence: Synthetic
      protein sequence

<400> SEQUENCE: 51

Met Ser Thr Asn Pro Lys Pro Gln Arg Lys Thr Lys Arg Asn Thr Asn
1               5                   10                  15

Arg Arg Pro Gln Asp Val Lys Phe Pro Gly Gly Gly Gln Ile Val Gly
            20                  25                  30
```

```
Gly Val Tyr Leu Leu Pro Arg Arg Gly Pro Arg Leu Gly Val Arg Ala
        35                  40                  45

Thr Arg Lys Thr Ser Glu Arg Ser Gln Pro Arg Gly Arg Arg Gln Pro
    50                  55                  60

Ile Pro Lys Ala Arg Gln Pro Glu Gly Arg Ala Trp Ala Gln Pro Gly
65                  70                  75                  80

Tyr Pro Trp Pro Leu Tyr Gly Asn Glu Gly Leu Gly Trp Ala Gly Trp
                85                  90                  95

Leu Leu Ser Pro Arg Gly Ser Arg Pro Ser Trp Gly Pro Thr Asp Pro
            100                 105                 110

Arg Arg Arg Ser Arg Asn Leu Gly Lys Val Ile Asp Thr Leu Thr Cys
        115                 120                 125

Gly Phe Ala Asp Leu Met Gly Tyr Leu Pro Leu Val Tyr Ala Thr Gly
    130                 135                 140

Asn Leu Pro Gly Cys Ser Phe Ser Ile Phe Leu Leu Ala Leu Leu Ser
145                 150                 155                 160

Cys Leu Thr Ile Pro Ala Ser Ala Ser Ala Thr Ser Leu Thr Phe Gln
                165                 170                 175

Leu Ala Tyr Leu Val Lys Lys Ile Asp Phe Asp Tyr Thr Pro Asn Trp
            180                 185                 190

Gly Arg Gly Ala Pro Ser Ser Tyr Ile Asp Asn Leu Thr Phe Pro Lys
        195                 200                 205

Val Leu Thr Asp Lys Lys Tyr Ser Tyr Arg Val Val Val Asn Gly Ser
    210                 215                 220

Asp Leu Gly Val Glu Ser Asn Phe Ala Val Thr Pro Ser Gly Gly Gln
225                 230                 235                 240

Thr Ile Asn Phe Leu Gln Tyr Asn Lys Gly Tyr Gly Val Ala Asp Thr
                245                 250                 255

Lys Thr Ile Gln Val Phe Val Val Ile Pro Asp Thr Gly Asn Ser Glu
            260                 265                 270

Glu Tyr Ile Ile Ala Glu Trp Lys Lys Thr
        275                 280
```

```
<210> SEQ ID NO 52
<211> LENGTH: 856
<212> TYPE: DNA
<213> ORGANISM: Artificial Sequence
<220> FEATURE:
<223> OTHER INFORMATION: Description of Artificial Sequence: Synthetic
      nucleotide sequence

<400> SEQUENCE: 52

atgagcacga atcctaaacc tcaaagaaaa accaaacgta acaccaaccg ccgcccacag      60

gacgtcaagt tcccgggcgg tggtcagatc gtcggtggag tttacctgtt gccgcgcagg     120

ggccccaggt tgggtgtgcg cgcgactagg aagacttccg agcggtcgca acctcgtgga     180

aggcgacaac ctatccccaa ggctcgccag cccgagggta gggcctgggc tcagcccggg     240

tacccctggc ccctctatgg caatgagggc ttggggtggg caggatggct cctgtcaccc     300

cgtggctctc ggcctagttg gggccccacg gacccccggc gtaggtcgcg caatttgggt     360

aaggtcatcg ataccctcac gtgcggcttc gccgatctca tggggtacct tccgctcgtc     420

ggcgcaacag ggaatctgcc cggttgctcc ttttctatct tcctttggc tttgctgtcc      480

tgtttgacca tcccagcttc cgcttatgaa gtccgccacg tcgctcacct tccagcttgc     540

ctacttggtg aagaagatcg acttcgacta cacccccaac tggggccgtg gtgcaccaag     600
```

-continued

```
cagctacatc gacaacctta ccttccccaa ggttctcacc gacaaaaaat actcgtaccg    660

cgtcgtggtc aatggctctg accttggcgt cgagtccaac ttcgcagtga caccgtccgg    720

tgggcagacc atcaacttcc tccagtacaa caaggggtat ggtgtcgcgg acaccaaaac    780

gattcaagtt ttcgttgtca ttccagatac cggcaactcg gaggagtaca tcatcgctga    840

gtggaagaag acttga                                                    856


<210> SEQ ID NO 53
<211> LENGTH: 428
<212> TYPE: PRT
<213> ORGANISM: Artificial Sequence
<220> FEATURE:
<223> OTHER INFORMATION: Description of Artificial Sequence: Synthetic
      protein sequence

<400> SEQUENCE: 53

Met Pro Leu Glu Gln Arg Ser Gln His Cys Lys Pro Glu Glu Gly Leu
1               5                   10                  15

Glu Ala Arg Gly Glu Ala Leu Gly Leu Val Gly Ala Gln Ala Pro Ala
            20                  25                  30

Thr Glu Glu Gln Glu Ala Ala Ser Ser Ser Ser Thr Leu Val Glu Val
        35                  40                  45

Thr Leu Gly Glu Val Pro Ala Ala Glu Ser Pro Asp Pro Pro Gln Ser
    50                  55                  60

Pro Gln Gly Ala Ser Ser Leu Pro Thr Thr Met Asn Tyr Pro Leu Trp
65                  70                  75                  80

Ser Gln Ser Tyr Glu Asp Ser Ser Asn Gln Glu Glu Glu Gly Pro Ser
                85                  90                  95

Thr Phe Pro Asp Leu Glu Ser Glu Phe Gln Ala Ala Leu Ser Arg Lys
            100                 105                 110

Val Ala Glu Leu Val His Phe Leu Leu Leu Lys Tyr Arg Ala Arg Glu
        115                 120                 125

Pro Val Thr Lys Ala Glu Met Leu Gly Ser Val Val Gly Asn Trp Gln
    130                 135                 140

Tyr Phe Phe Pro Val Ile Phe Ser Lys Ala Ser Ser Ser Leu Gln Leu
145                 150                 155                 160

Val Phe Gly Ile Glu Leu Met Glu Val Asp Pro Ile Gly His Leu Tyr
                165                 170                 175

Ile Phe Ala Thr Cys Leu Gly Leu Ser Tyr Asp Gly Leu Leu Gly Asp
            180                 185                 190

Asn Gln Ile Met Pro Lys Ala Gly Leu Leu Ile Ile Val Leu Ala Ile
        195                 200                 205

Ile Ala Arg Glu Gly Asp Cys Ala Pro Glu Glu Lys Ile Trp Glu Glu
    210                 215                 220

Leu Ser Val Leu Glu Val Phe Glu Gly Arg Glu Asp Ser Ile Leu Gly
225                 230                 235                 240

Asp Pro Lys Lys Leu Leu Thr Gln His Phe Val Gln Glu Asn Tyr Leu
                245                 250                 255

Glu Tyr Arg Gln Val Pro Gly Ser Asp Pro Ala Cys Tyr Glu Phe Leu
            260                 265                 270

Trp Gly Pro Arg Ala Leu Val Glu Thr Ser Tyr Val Lys Val Leu His
        275                 280                 285

His Met Val Lys Ile Ser Gly Gly Pro His Ile Ser Tyr Pro Pro Leu
    290                 295                 300

His Glu Trp Val Leu Arg Glu Gly Glu Glu Ser Ala Thr Ser Leu Thr
305                 310                 315                 320
```

```
Phe Gln Leu Ala Tyr Leu Val Lys Lys Ile Asp Phe Asp Tyr Thr Pro
                325                 330                 335

Asn Trp Gly Arg Gly Ala Pro Ser Ser Tyr Ile Asp Asn Leu Thr Phe
            340                 345                 350

Pro Lys Val Leu Thr Asp Lys Lys Tyr Ser Tyr Arg Val Val Val Asn
        355                 360                 365

Gly Ser Asp Leu Gly Val Glu Ser Asn Phe Ala Val Thr Pro Ser Gly
    370                 375                 380

Gly Gln Thr Ile Asn Phe Leu Gln Tyr Asn Lys Gly Tyr Gly Val Ala
385                 390                 395                 400

Asp Thr Lys Thr Ile Gln Val Phe Val Val Ile Pro Asp Thr Gly Asn
                405                 410                 415

Ser Glu Glu Tyr Ile Ile Ala Glu Trp Lys Lys Thr
            420                 425
```

<210> SEQ ID NO 54
<211> LENGTH: 1287
<212> TYPE: DNA
<213> ORGANISM: Artificial Sequence
<220> FEATURE:
<223> OTHER INFORMATION: Description of Artificial Sequence: Synthetic nucleotide sequence

<400> SEQUENCE: 54

```
atgcctcttg agcagaggag tcagcactgc aagcctgaag aaggccttga ggcccgagga     60

gaggccctgg gcctggtggg tgcgcaggct cctgctactg aggagcagga ggctgcctcc    120

tcctcttcta ctctagttga agtcaccctg gggggaggtgc ctgctgccga gtcaccagat    180

cctccccaga gtcctcaggg agcctccagc ctccccacta ccatgaacta ccctctctgg    240

agccaatcct atgaggactc cagcaaccaa gaagaggagg ggccaagcac cttccctgac    300

ctggagtccg agttccaagc agcactcagt aggaaggtgg ccgagttggt tcattttctg    360

ctcctcaagt atcgagccag ggagccggtc acaaaggcag aaatgctggg gagtgtcgtc    420

ggaaattggc agtatttctt tcctgtgatc ttcagcaaag cttccagttc cttgcagctg    480

gtctttggca tcgagctgat ggaagtggac cccatcggcc acttgtacat ctttgccacc    540

tgcctgggcc tctcctacga tggcctgctg ggtgacaatc agatcatgcc caaggcaggc    600

ctcctgataa tcgtcctggc cataatcgca agagagggcg actgtgcccc tgaggagaaa    660

atctgggagg agctgagtgt gttagaggtg tttgaggggga gggaagacag tatcttgggg    720

gatcccaaga agctgctcac ccaacatttc gtgcaggaaa actacctgga gtaccggcag    780

gtccccggca gtgatcctgc atgttatgaa ttcctgtggg gtccaagggc cctcgttgaa    840

accagctatg tgaaagtcct gcaccatatg gtaaagatca gtggaggacc tcacatttcc    900

tacccacccc tgcatgagtg ggttttgaga gagggggaag agtccgccac gtcgctcacc    960

ttccagcttg cctacttggt gaagaagatc gacttcgact acacccccaa ctggggccgt   1020

ggtgcaccaa gcagctacat cgacaacctt accttcccca aggttctcac cgacaaaaaa   1080

tactcgtacc gcgtcgtggt caatggctct gaccttggcg tcgagtccaa cttcgcagtg   1140

acaccgtccg gtgggcagac catcaacttc ctccagtaca acaaggggta tggtgtcgcg   1200

gacaccaaaa cgattcaagt tttcgttgtc attccagata ccggcaactc ggaggagtac   1260

atcatcgctg agtggaagaa gacttga                                        1287
```

<210> SEQ ID NO 55
<211> LENGTH: 232

<212> TYPE: PRT
<213> ORGANISM: Artificial Sequence
<220> FEATURE:
<223> OTHER INFORMATION: Description of Artificial Sequence: Synthetic
protein sequence

<400> SEQUENCE: 55

```
Met Pro Arg Glu Asp Ala His Phe Ile Tyr Gly Tyr Pro Lys Lys Gly
1               5                   10                  15

His Gly His Ser Tyr Thr Thr Ala Glu Glu Ala Ala Gly Ile Gly Ile
            20                  25                  30

Leu Thr Val Ile Leu Gly Val Leu Leu Leu Ile Gly Cys Trp Tyr Cys
        35                  40                  45

Arg Arg Arg Asn Gly Tyr Arg Ala Leu Met Asp Lys Ser Leu His Val
    50                  55                  60

Gly Thr Gln Cys Ala Leu Thr Arg Arg Cys Pro Gln Glu Gly Phe Asp
65                  70                  75                  80

His Arg Asp Ser Lys Val Ser Leu Gln Glu Lys Asn Cys Glu Pro Val
                85                  90                  95

Val Pro Asn Ala Pro Pro Ala Tyr Glu Lys Leu Ser Ala Glu Gln Ser
            100                 105                 110

Pro Pro Pro Tyr Ser Pro Ser Ala Thr Ser Leu Thr Phe Gln Leu Ala
        115                 120                 125

Tyr Leu Val Lys Lys Ile Asp Phe Asp Tyr Thr Pro Asn Trp Gly Arg
    130                 135                 140

Gly Ala Pro Ser Ser Tyr Ile Asp Asn Leu Thr Phe Pro Lys Val Leu
145                 150                 155                 160

Thr Asp Lys Lys Tyr Ser Tyr Arg Val Val Val Asn Gly Ser Asp Leu
                165                 170                 175

Gly Val Glu Ser Asn Phe Ala Val Thr Pro Ser Gly Gly Gln Thr Ile
            180                 185                 190

Asn Phe Leu Gln Tyr Asn Lys Gly Tyr Gly Val Ala Asp Thr Lys Thr
        195                 200                 205

Ile Gln Val Phe Val Val Ile Pro Asp Thr Gly Asn Ser Glu Glu Tyr
    210                 215                 220

Ile Ile Ala Glu Trp Lys Lys Thr
225                 230
```

<210> SEQ ID NO 56
<211> LENGTH: 699
<212> TYPE: DNA
<213> ORGANISM: Artificial Sequence
<220> FEATURE:
<223> OTHER INFORMATION: Description of Artificial Sequence: Synthetic
nucleotide sequence

<400> SEQUENCE: 56

```
atgccaagag aagatgctca cttcatctat ggttacccca agaaggggca cggccactct     60

tacaccacgg ctgaagaggc cgctgggatc ggcatcctga cagtgatcct gggagtctta    120

ctgctcatcg gctgttggta ttgtagaaga cgaaatggat acagagcctt gatggataaa    180

agtcttcatg ttggcactca atgtgcctta acaagaagat gcccacaaga agggtttgat    240

catcgggaca gcaaagtgtc tcttcaagag aaaaactgtg aacctgtggt tcccaatgct    300

ccacctgctt atgagaaact ctctgcagaa cagtcaccac caccttattc accttccgcc    360

acgtcgctca ccttccagct tgcctacttg gtgaagaaga tcgacttcga ctacaccccc    420

aactggggcc gtggtgcacc aagcagctac atcgacaacc ttaccttccc caaggttctc    480
```

-continued

```
accgacaaaa aatactcgta ccgcgtcgtg gtcaatggct ctgaccttgg cgtcgagtcc    540

aacttcgcag tgacaccgtc cggtgggcag accatcaact tcctccagta caacaagggg    600

tatggtgtcg cggacaccaa aacgattcaa gttttcgttg tcattccaga taccggcaac    660

tcggaggagt acatcatcgc tgagtggaag aagacttga                           699


<210> SEQ ID NO 57
<211> LENGTH: 782
<212> TYPE: PRT
<213> ORGANISM: Artificial Sequence
<220> FEATURE:
<223> OTHER INFORMATION: Description of Artificial Sequence: Synthetic
      protein sequence

<400> SEQUENCE: 57

Lys Leu Thr Ile Glu Ser Thr Pro Phe Asn Val Ala Glu Gly Lys Glu
1               5                   10                  15

Val Leu Leu Leu Val His Asn Leu Pro Gln His Leu Phe Gly Tyr Ser
            20                  25                  30

Trp Tyr Lys Gly Glu Arg Val Asp Gly Asn Arg Gln Ile Ile Gly Tyr
        35                  40                  45

Val Ile Gly Thr Gln Gln Ala Thr Pro Gly Pro Ala Tyr Ser Gly Arg
    50                  55                  60

Glu Ile Ile Tyr Pro Asn Ala Ser Leu Leu Ile Gln Asn Ile Ile Gln
65                  70                  75                  80

Asn Asp Thr Gly Phe Tyr Thr Leu His Val Ile Lys Ser Asp Leu Val
                85                  90                  95

Asn Glu Glu Ala Thr Gly Gln Phe Arg Val Tyr Pro Glu Leu Pro Lys
            100                 105                 110

Pro Ser Ile Ser Ser Asn Asn Ser Lys Pro Val Glu Asp Lys Asp Ala
        115                 120                 125

Val Ala Phe Thr Cys Glu Pro Glu Thr Gln Asp Ala Thr Tyr Leu Trp
    130                 135                 140

Trp Val Asn Asn Gln Ser Leu Pro Val Ser Pro Arg Leu Gln Leu Ser
145                 150                 155                 160

Asn Gly Asn Arg Thr Leu Thr Leu Phe Asn Val Thr Arg Asn Asp Thr
                165                 170                 175

Ala Ser Tyr Lys Cys Glu Thr Gln Asn Pro Val Ser Ala Arg Arg Ser
            180                 185                 190

Asp Ser Val Ile Leu Asn Val Leu Tyr Gly Pro Asp Ala Pro Thr Ile
        195                 200                 205

Ser Pro Leu Asn Thr Ser Tyr Arg Ser Gly Glu Asn Leu Asn Leu Ser
    210                 215                 220

Cys His Ala Ala Ser Asn Pro Pro Ala Gln Tyr Ser Trp Phe Val Asn
225                 230                 235                 240

Gly Thr Phe Gln Gln Ser Thr Gln Glu Leu Phe Ile Pro Asn Ile Thr
                245                 250                 255

Val Asn Asn Ser Gly Ser Tyr Thr Cys Gln Ala His Asn Ser Asp Thr
            260                 265                 270

Gly Leu Asn Arg Thr Thr Val Thr Thr Ile Thr Val Tyr Ala Glu Pro
        275                 280                 285

Pro Lys Pro Phe Ile Thr Ser Asn Asn Ser Asn Pro Val Glu Asp Glu
    290                 295                 300

Asp Ala Val Ala Leu Thr Cys Glu Pro Glu Ile Gln Asn Thr Thr Tyr
305                 310                 315                 320

Leu Trp Trp Val Asn Asn Gln Ser Leu Pro Val Ser Pro Arg Leu Gln
```

-continued

```
                325                 330                 335

Leu Ser Asn Asp Asn Arg Thr Leu Thr Leu Leu Ser Val Thr Arg Asn
            340                 345                 350

Asp Val Gly Pro Tyr Glu Cys Gly Ile Gln Asn Glu Leu Ser Val Asp
        355                 360                 365

His Ser Asp Pro Val Ile Leu Asn Val Leu Tyr Gly Pro Asp Asp Pro
    370                 375                 380

Thr Ile Ser Pro Ser Tyr Thr Tyr Tyr Arg Pro Gly Val Asn Leu Ser
385                 390                 395                 400

Leu Ser Cys His Ala Ala Ser Asn Pro Pro Ala Gln Tyr Ser Trp Leu
                405                 410                 415

Ile Asp Gly Asn Ile Gln Gln His Thr Gln Glu Leu Phe Ile Ser Asn
            420                 425                 430

Ile Thr Glu Lys Asn Ser Gly Leu Tyr Thr Cys Gln Ala Asn Asn Ser
        435                 440                 445

Ala Ser Gly His Ser Arg Thr Thr Val Lys Thr Ile Thr Val Ser Ala
    450                 455                 460

Glu Leu Pro Lys Pro Ser Ile Ser Ser Asn Asn Ser Lys Pro Val Glu
465                 470                 475                 480

Asp Lys Asp Ala Val Ala Phe Thr Cys Glu Pro Glu Ala Gln Asn Thr
                485                 490                 495

Thr Tyr Leu Trp Trp Val Asn Gly Gln Ser Leu Pro Val Ser Pro Arg
            500                 505                 510

Leu Gln Leu Ser Asn Gly Asn Arg Thr Leu Thr Leu Phe Asn Val Thr
        515                 520                 525

Arg Asn Asp Ala Arg Ala Tyr Val Cys Gly Ile Gln Asn Ser Val Ser
    530                 535                 540

Ala Asn Arg Ser Asp Pro Val Thr Leu Asp Val Leu Tyr Gly Pro Asp
545                 550                 555                 560

Thr Pro Ile Ile Ser Pro Pro Asp Ser Ser Tyr Leu Ser Gly Ala Asn
                565                 570                 575

Leu Asn Leu Ser Cys His Ser Ala Ser Asn Pro Ser Pro Gln Tyr Ser
            580                 585                 590

Trp Arg Ile Asn Gly Ile Pro Gln Gln His Thr Gln Val Leu Phe Ile
        595                 600                 605

Ala Lys Ile Thr Pro Asn Asn Asn Gly Thr Tyr Ala Cys Phe Val Ser
    610                 615                 620

Asn Leu Ala Thr Gly Arg Asn Asn Ser Ile Val Lys Ser Ile Thr Val
625                 630                 635                 640

Ser Ala Ser Gly Thr Ser Pro Gly Leu Ser Ala Gly Ala Thr Val Gly
                645                 650                 655

Ile Met Ile Gly Val Leu Val Gly Val Ala Leu Ile Ser Ala Thr Ser
            660                 665                 670

Leu Thr Phe Gln Leu Ala Tyr Leu Val Lys Lys Ile Asp Phe Asp Tyr
        675                 680                 685

Thr Pro Asn Trp Gly Arg Gly Ala Pro Ser Ser Tyr Ile Asp Asn Leu
    690                 695                 700

Thr Phe Pro Lys Val Leu Thr Asp Lys Lys Tyr Ser Tyr Arg Val Val
705                 710                 715                 720

Val Asn Gly Ser Asp Leu Gly Val Glu Ser Asn Phe Ala Val Thr Pro
                725                 730                 735

Ser Gly Gly Gln Thr Ile Asn Phe Leu Gln Tyr Asn Lys Gly Tyr Gly
            740                 745                 750
```

```
Val Ala Asp Thr Lys Thr Ile Gln Val Phe Val Val Ile Pro Asp Thr
        755                 760                 765

Gly Asn Ser Glu Glu Tyr Ile Ile Ala Glu Trp Lys Lys Thr
    770                 775                 780
```

<210> SEQ ID NO 58
<211> LENGTH: 2349
<212> TYPE: DNA
<213> ORGANISM: Artificial Sequence
<220> FEATURE:
<223> OTHER INFORMATION: Description of Artificial Sequence: Synthetic nucleotide sequence

<400> SEQUENCE: 58

```
aagctcacta ttgaatccac gccgttcaat gtcgcagagg ggaaggaggt gcttctactt     60
gtccacaatc tgccccagca tctttttggc tacagctggt acaaaggtga aagagtggat    120
ggcaaccgtc aaattatagg atatgtaata ggaactcaac aagctacccc agggcccgca    180
tacagtggtc gagagataat ataccccaat gcatccctgc tgatccagaa catcatccag    240
aatgacacag gattctacac cctacacgtc ataaagtcag atcttgtgaa tgaagaagca    300
actggccagt tccgggtata cccggagctg cccaagccct ccatctccag caacaactcc    360
aaacccgtgg aggacaagga tgctgtggcc ttcacctgtg aacctgagac tcaggacgca    420
acctacctgt ggtgggtaaa caatcagagc ctcccggtca gtcccaggct gcagctgtcc    480
aatggcaaca ggaccctcac tctattcaat gtcacaagaa atgacacagc aagctacaaa    540
tgtgaaaccc agaacccagt gagtgccagg cgcagtgatt cagtcatcct gaatgtcctc    600
tatggcccgg atgcccccac catttcccct ctaaacacat cttacagatc aggggaaaat    660
ctgaacctct cctgccatgc agcctctaac ccacctgcac agtactcttg gtttgtcaat    720
gggactttcc agcaatccac ccaagagctc tttatcccca acatcactgt gaataatagt    780
ggatcctata cgtgccaagc ccataactca gacactggcc tcaataggac cacagtcacg    840
acgatcacag tctatgcaga gccacccaaa cccttcatca ccagcaacaa ctccaacccc    900
gtggaggatg aggatgctgt agccttaacc tgtgaacctg agattcagaa cacaacctac    960
ctgtggtggg taaataatca gagcctcccg gtcagtccca ggctgcagct gtccaatgac   1020
aacaggaccc tcactctact cagtgtcaca aggaatgatg taggacccta tgagtgtgga   1080
atccagaacg aattaagtgt tgaccacagc gacccagtca tcctgaatgt cctctatggc   1140
ccagacgacc ccaccatttc cccctcatac acctattacc gtccaggggt gaacctcagc   1200
ctctcctgcc atgcagcctc taacccacct gcacagtatt cttggctgat tgatgggaac   1260
atccagcaac acacacaaga gctctttatc tccaacatca ctgagaagaa cagcggactc   1320
tatacctgcc aggccaataa ctcagccagt ggccacagca ggactacagt caagacaatc   1380
acagtctctg cggagctgcc caagccctcc atctccagca acaactccaa acccgtggag   1440
gacaaggatg ctgtggcctt cacctgtgaa cctgaggctc agaacacaac ctacctgtgg   1500
tgggtaaatg gtcagagcct cccagtcagt cccaggctgc agctgtccaa tggcaacagg   1560
accctcactc tattcaatgt cacaagaaat gacgcaagag cctatgtatg tggaatccag   1620
aactcagtga gtgcaaaccg cagtgaccca gtcaccctgg atgtcctcta tgggccggac   1680
acccccatca tttccccccc agactcgtct tacctttcgg gagcgaacct caacctctcc   1740
tgccactcgg cctctaaccc atccccgcag tattcttggc gtatcaatgg gataccgcag   1800
caacacacac aagttctctt tatcgccaaa atcacgccaa ataataacgg gacctatgcc   1860
tgttttgtct ctaacttggc tactggccgc aataattcca tagtcaagag catcacagtc   1920
```

-continued

```
tctgcatctg gaacttctcc tggtctctca gctggggcca ctgtcggcat catgattgga   1980

gtgctggttg gggttgctct gatatccgcc acgtcgctca ccttccagct tgcctacttg   2040

gtgaagaaga tcgacttcga ctacaccccc aactggggcc gtggtgcacc aagcagctac   2100

atcgacaacc ttaccttccc caaggttctc accgacaaaa aatactcgta ccgcgtcgtg   2160

gtcaatggct ctgaccttgg cgtcgagtcc aacttcgcag tgacaccgtc cggtgggcag   2220

accatcaact tcctccagta caacaagggg tatggtgtcg cggacaccaa aacgattcaa   2280

gttttcgttg tcattccaga taccggcaac tcggaggagt acatcatcgc tgagtggaag   2340

aagacttga                                                           2349


<210> SEQ ID NO 59
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 59

ggatcctccg ccacgtcgtt cgactacacc cccaac                               36


<210> SEQ ID NO 60
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 60

gttgggggtg tagtcgaacg acgtggcgga ggatcc                               36


<210> SEQ ID NO 61
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 61

ttggtgaaga agatcgacat cgacaacctt accttc                               36


<210> SEQ ID NO 62
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 62

gaaggtaagg ttgtcgatgt cgatcttctt caccaa                               36


<210> SEQ ID NO 63
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 63
```

-continued ggtaccccaa gcagctacaa atactcgtac cgcgtc 36

<210> SEQ ID NO 64
<211> LENGTH: 36
<212> TYPE: DNA
<213> ORGANISM: Artificial Sequence
<220> FEATURE:
<223> OTHER INFORMATION: Description of Artificial Sequence: Synthetic primer

<400> SEQUENCE: 64
gacgcggtac gagtatttgt agctgcttgg ggtacc 36

<210> SEQ ID NO 65
<211> LENGTH: 36
<212> TYPE: DNA
<213> ORGANISM: Artificial Sequence
<220> FEATURE:
<223> OTHER INFORMATION: Description of Artificial Sequence: Synthetic primer

<400> SEQUENCE: 65
aaggttctca ccgacaaagt cgagtccaac ttcgca 36

<210> SEQ ID NO 66
<211> LENGTH: 36
<212> TYPE: DNA
<213> ORGANISM: Artificial Sequence
<220> FEATURE:
<223> OTHER INFORMATION: Description of Artificial Sequence: Synthetic primer

<400> SEQUENCE: 66
tgcgaagttg gactcgactt tgtcggtgag aacctt 36

<210> SEQ ID NO 67
<211> LENGTH: 36
<212> TYPE: DNA
<213> ORGANISM: Artificial Sequence
<220> FEATURE:
<223> OTHER INFORMATION: Description of Artificial Sequence: Synthetic primer

<400> SEQUENCE: 67
aatggctctg accttggcca gaccatcaac ttcctc 36

<210> SEQ ID NO 68
<211> LENGTH: 36
<212> TYPE: DNA
<213> ORGANISM: Artificial Sequence
<220> FEATURE:
<223> OTHER INFORMATION: Description of Artificial Sequence: Synthetic primer

<400> SEQUENCE: 68
gaggaagttg atggtctggc caaggtcaga gccatt 36

<210> SEQ ID NO 69
<211> LENGTH: 36
<212> TYPE: DNA
<213> ORGANISM: Artificial Sequence
<220> FEATURE:
<223> OTHER INFORMATION: Description of Artificial Sequence: Synthetic primer

<400> SEQUENCE: 69
gtgacaccgt ccggtggggg tgtcgcggac accaaa 36

<210> SEQ ID NO 70
<211> LENGTH: 36
<212> TYPE: DNA
<213> ORGANISM: Artificial Sequence
<220> FEATURE:
<223> OTHER INFORMATION: Description of Artificial Sequence: Synthetic primer

<400> SEQUENCE: 70
tttggtgtcc gcgacacccc caccggacgg tgtcac 36

<210> SEQ ID NO 71
<211> LENGTH: 36
<212> TYPE: DNA
<213> ORGANISM: Artificial Sequence
<220> FEATURE:
<223> OTHER INFORMATION: Description of Artificial Sequence: Synthetic primer

<400> SEQUENCE: 71
cagtacaaca aggggtatat tccagatacc ggcaac 36

<210> SEQ ID NO 72
<211> LENGTH: 36
<212> TYPE: DNA
<213> ORGANISM: Artificial Sequence
<220> FEATURE:
<223> OTHER INFORMATION: Description of Artificial Sequence: Synthetic primer

<400> SEQUENCE: 72
gttgccggta tctggaatat accccttgtt gtactg 36

<210> SEQ ID NO 73
<211> LENGTH: 36
<212> TYPE: DNA
<213> ORGANISM: Artificial Sequence
<220> FEATURE:
<223> OTHER INFORMATION: Description of Artificial Sequence: Synthetic primer

<400> SEQUENCE: 73
attcaagttt tcgttgtcta catcatcgct gagtgg 36

<210> SEQ ID NO 74
<211> LENGTH: 36
<212> TYPE: DNA
<213> ORGANISM: Artificial Sequence
<220> FEATURE:
<223> OTHER INFORMATION: Description of Artificial Sequence: Synthetic primer

<400> SEQUENCE: 74
ccactcagcg atgatgtaga caacgaaaac ttgaat 36

<210> SEQ ID NO 75
<211> LENGTH: 39
<212> TYPE: DNA
<213> ORGANISM: Artificial Sequence
<220> FEATURE:
<223> OTHER INFORMATION: Description of Artificial Sequence: Synthetic primer

<400> SEQUENCE: 75
gatgcaactg aattcttatt actcctccga gttgccggt 39

<210> SEQ ID NO 76

<211> LENGTH: 36
<212> TYPE: DNA
<213> ORGANISM: Artificial Sequence
<220> FEATURE:
<223> OTHER INFORMATION: Description of Artificial Sequence: Synthetic
primer

<400> SEQUENCE: 76
aatggctctg accttggcat tccagatacc ggcaac 36

<210> SEQ ID NO 77
<211> LENGTH: 36
<212> TYPE: DNA
<213> ORGANISM: Artificial Sequence
<220> FEATURE:
<223> OTHER INFORMATION: Description of Artificial Sequence: Synthetic
primer

<400> SEQUENCE: 77
gttgccggta tctggaatgc caaggtcaga gccatt 36

<210> SEQ ID NO 78
<211> LENGTH: 48
<212> TYPE: DNA
<213> ORGANISM: Artificial Sequence
<220> FEATURE:
<223> OTHER INFORMATION: Description of Artificial Sequence: Synthetic
primer

<400> SEQUENCE: 78
gttccgcgtg gatccatcga aggtcgtaat ggctctgacc ttggcgtc 48

<210> SEQ ID NO 79
<211> LENGTH: 42
<212> TYPE: DNA
<213> ORGANISM: Artificial Sequence
<220> FEATURE:
<223> OTHER INFORMATION: Description of Artificial Sequence: Synthetic
primer

<400> SEQUENCE: 79
gatgcaactg aattcttatc aatctggaat gacaacgaaa ac 42

<210> SEQ ID NO 80
<211> LENGTH: 27
<212> TYPE: DNA
<213> ORGANISM: Artificial Sequence
<220> FEATURE:
<223> OTHER INFORMATION: Description of Artificial Sequence: Synthetic
primer

<400> SEQUENCE: 80
cccaactggg gcgcaggtac cccaagc 27

<210> SEQ ID NO 81
<211> LENGTH: 27
<212> TYPE: DNA
<213> ORGANISM: Artificial Sequence
<220> FEATURE:
<223> OTHER INFORMATION: Description of Artificial Sequence: Synthetic
primer

<400> SEQUENCE: 81
gcttggggta cctgcgcccc agttggg 27

<210> SEQ ID NO 82
<211> LENGTH: 27
<212> TYPE: DNA

<213> ORGANISM: Artificial Sequence
<220> FEATURE:
<223> OTHER INFORMATION: Description of Artificial Sequence: Synthetic
primer

<400> SEQUENCE: 82
aactggggcc gtgcaacccc aagcagc 27

<210> SEQ ID NO 83
<211> LENGTH: 27
<212> TYPE: DNA
<213> ORGANISM: Artificial Sequence
<220> FEATURE:
<223> OTHER INFORMATION: Description of Artificial Sequence: Synthetic
primer

<400> SEQUENCE: 83
gctgcttggg gttgcacggc cccagtt 27

<210> SEQ ID NO 84
<211> LENGTH: 27
<212> TYPE: DNA
<213> ORGANISM: Artificial Sequence
<220> FEATURE:
<223> OTHER INFORMATION: Description of Artificial Sequence: Synthetic
primer

<400> SEQUENCE: 84
tggggccgtg gtgcaccaag cagctac 27

<210> SEQ ID NO 85
<211> LENGTH: 27
<212> TYPE: DNA
<213> ORGANISM: Artificial Sequence
<220> FEATURE:
<223> OTHER INFORMATION: Description of Artificial Sequence: Synthetic
primer

<400> SEQUENCE: 85
gtagctgctt ggtgcaccac ggcccca 27

<210> SEQ ID NO 86
<211> LENGTH: 36
<212> TYPE: DNA
<213> ORGANISM: Artificial Sequence
<220> FEATURE:
<223> OTHER INFORMATION: Description of Artificial Sequence: Synthetic
primer

<400> SEQUENCE: 86
aaggatattc aaacccaatc cgccacgtcg ctcacc 36

<210> SEQ ID NO 87
<211> LENGTH: 36
<212> TYPE: DNA
<213> ORGANISM: Artificial Sequence
<220> FEATURE:
<223> OTHER INFORMATION: Description of Artificial Sequence: Synthetic
primer

<400> SEQUENCE: 87
ggtgagcgac gtggcggatt gggtttgaat atcctt 36

<210> SEQ ID NO 88
<211> LENGTH: 36
<212> TYPE: DNA
<213> ORGANISM: Artificial Sequence
<220> FEATURE:

<223> OTHER INFORMATION: Description of Artificial Sequence: Synthetic
primer

<400> SEQUENCE: 88
catgctaaaa tccgcgattc cgccacgtcg ctcacc 36

<210> SEQ ID NO 89
<211> LENGTH: 36
<212> TYPE: DNA
<213> ORGANISM: Artificial Sequence
<220> FEATURE:
<223> OTHER INFORMATION: Description of Artificial Sequence: Synthetic
primer

<400> SEQUENCE: 89
ggtgagcgac gtggcggaat cgcggatttt agcatg 36

<210> SEQ ID NO 90
<211> LENGTH: 36
<212> TYPE: DNA
<213> ORGANISM: Artificial Sequence
<220> FEATURE:
<223> OTHER INFORMATION: Description of Artificial Sequence: Synthetic
primer

<400> SEQUENCE: 90
aaggatattc aaacccaaga tcaagtcgat gtcaaa 36

<210> SEQ ID NO 91
<211> LENGTH: 36
<212> TYPE: DNA
<213> ORGANISM: Artificial Sequence
<220> FEATURE:
<223> OTHER INFORMATION: Description of Artificial Sequence: Synthetic
primer

<400> SEQUENCE: 91
tttgacatcg acttgatctt gggtttgaat atcctt 36

<210> SEQ ID NO 92
<211> LENGTH: 5
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 92

Trp Gly Arg Gly Thr
1 5

<210> SEQ ID NO 93
<211> LENGTH: 5
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 93

Gly Arg Gly Thr Pro
1 5

<210> SEQ ID NO 94
<211> LENGTH: 5
<212> TYPE: PRT
<213> ORGANISM: Artificial Sequence
<220> FEATURE:

<223> OTHER INFORMATION: Description of Artificial Sequence: Synthetic
      peptide

<400> SEQUENCE: 94

Arg Gly Thr Pro Ser
1               5

<210> SEQ ID NO 95
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 95

Gly Thr Pro Ser Ser
1               5

<210> SEQ ID NO 96
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 96

Thr Pro Ser Ser Tyr
1               5

<210> SEQ ID NO 97
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 97

Asn Trp Gly Arg Gly Thr
1               5

<210> SEQ ID NO 98
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 98

Trp Gly Arg Gly Thr Pro
1               5

<210> SEQ ID NO 99
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 99

Gly Arg Gly Thr Pro Ser
1               5

<210> SEQ ID NO 100

<211> LENGTH: 6
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 100

Arg Gly Thr Pro Ser Ser
1 5

<210> SEQ ID NO 101
<211> LENGTH: 6
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 101

Gly Thr Pro Ser Ser Tyr
1 5

<210> SEQ ID NO 102
<211> LENGTH: 6
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 102

Thr Pro Ser Ser Tyr Ile
1 5

<210> SEQ ID NO 103
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 103

Pro Asn Trp Gly Arg Gly Thr
1 5

<210> SEQ ID NO 104
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 104

Asn Trp Gly Arg Gly Thr Pro
1 5

<210> SEQ ID NO 105
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 105

Trp Gly Arg Gly Thr Pro Ser 1 5

<210> SEQ ID NO 106
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 106

Gly Arg Gly Thr Pro Ser Ser
1 5

<210> SEQ ID NO 107
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 107

Arg Gly Thr Pro Ser Ser Tyr
1 5

<210> SEQ ID NO 108
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 108

Gly Thr Pro Ser Ser Tyr Ile
1 5

<210> SEQ ID NO 109
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 109

Thr Pro Ser Ser Tyr Ile Asp
1 5

<210> SEQ ID NO 110
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 110

Thr Pro Asn Trp Gly Arg Gly Thr
1 5

<210> SEQ ID NO 111
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 111

Pro Asn Trp Gly Arg Gly Thr Pro
1 5

<210> SEQ ID NO 112
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 112

Asn Trp Gly Arg Gly Thr Pro Ser
1 5

<210> SEQ ID NO 113
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 113

Trp Gly Arg Gly Thr Pro Ser Ser
1 5

<210> SEQ ID NO 114
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 114

Gly Arg Gly Thr Pro Ser Ser Tyr
1 5

<210> SEQ ID NO 115
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 115

Arg Gly Thr Pro Ser Ser Tyr Ile
1 5

<210> SEQ ID NO 116
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 116

Gly Thr Pro Ser Ser Tyr Ile Asp
1 5

<210> SEQ ID NO 117
<211> LENGTH: 8
<212> TYPE: PRT

<213> ORGANISM: Artificial Sequence
<220> FEATURE:
<223> OTHER INFORMATION: Description of Artificial Sequence: Synthetic
peptide

<400> SEQUENCE: 117

Thr Pro Ser Ser Tyr Ile Asp Asn
1 5

<210> SEQ ID NO 118
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 118

Tyr Thr Pro Asn Trp Gly Arg Gly Thr
1 5

<210> SEQ ID NO 119
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 119

Thr Pro Asn Trp Gly Arg Gly Thr Pro
1 5

<210> SEQ ID NO 120
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 120

Pro Asn Trp Gly Arg Gly Thr Pro Ser
1 5

<210> SEQ ID NO 121
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 121

Asn Trp Gly Arg Gly Thr Pro Ser Ser
1 5

<210> SEQ ID NO 122
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 122

Trp Gly Arg Gly Thr Pro Ser Ser Tyr
1 5

<210> SEQ ID NO 123
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 123

Gly Arg Gly Thr Pro Ser Ser Tyr Ile
1 5

<210> SEQ ID NO 124
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 124

Arg Gly Thr Pro Ser Ser Tyr Ile Asp
1 5

<210> SEQ ID NO 125
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 125

Gly Thr Pro Ser Ser Tyr Ile Asp Asn
1 5

<210> SEQ ID NO 126
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 126

Thr Pro Ser Ser Tyr Ile Asp Asn Leu
1 5

<210> SEQ ID NO 127
<211> LENGTH: 10
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 127

Asp Tyr Thr Pro Asn Trp Gly Arg Gly Thr
1 5 10

<210> SEQ ID NO 128
<211> LENGTH: 10
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 128

Tyr Thr Pro Asn Trp Gly Arg Gly Thr Pro
1 5 10

<210> SEQ ID NO 129
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 129

Thr Pro Asn Trp Gly Arg Gly Thr Pro Ser
1 5 10

<210> SEQ ID NO 130
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 130

Pro Asn Trp Gly Arg Gly Thr Pro Ser Ser
1 5 10

<210> SEQ ID NO 131
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 131

Asn Trp Gly Arg Gly Thr Pro Ser Ser Tyr
1 5 10

<210> SEQ ID NO 132
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 132

Trp Gly Arg Gly Thr Pro Ser Ser Tyr Ile
1 5 10

<210> SEQ ID NO 133
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 133

Gly Arg Gly Thr Pro Ser Ser Tyr Ile Asp
1 5 10

<210> SEQ ID NO 134
<211> LENGTH: 10
<212> TYPE: PRT
<213> ORGANISM: Artificial Sequence
<220> FEATURE:

<223> OTHER INFORMATION: Description of Artificial Sequence: Synthetic
peptide

<400> SEQUENCE: 134

Arg Gly Thr Pro Ser Ser Tyr Ile Asp Asn
1 5 10

<210> SEQ ID NO 135
<211> LENGTH: 10
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 135

Gly Thr Pro Ser Ser Tyr Ile Asp Asn Leu
1 5 10

<210> SEQ ID NO 136
<211> LENGTH: 10
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 136

Thr Pro Ser Ser Tyr Ile Asp Asn Leu Thr
1 5 10

<210> SEQ ID NO 137
<211> LENGTH: 11
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 137

Phe Asp Tyr Thr Pro Asn Trp Gly Arg Gly Thr
1 5 10

<210> SEQ ID NO 138
<211> LENGTH: 11
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 138

Asp Tyr Thr Pro Asn Trp Gly Arg Gly Thr Pro
1 5 10

<210> SEQ ID NO 139
<211> LENGTH: 11
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 139

Tyr Thr Pro Asn Trp Gly Arg Gly Thr Pro Ser
1 5 10

<210> SEQ ID NO 140

<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 140

Thr Pro Asn Trp Gly Arg Gly Thr Pro Ser Ser
1               5                   10

<210> SEQ ID NO 141
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 141

Pro Asn Trp Gly Arg Gly Thr Pro Ser Ser Tyr
1               5                   10

<210> SEQ ID NO 142
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 142

Asn Trp Gly Arg Gly Thr Pro Ser Ser Tyr Ile
1               5                   10

<210> SEQ ID NO 143
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 143

Trp Gly Arg Gly Thr Pro Ser Ser Tyr Ile Asp
1               5                   10

<210> SEQ ID NO 144
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 144

Gly Arg Gly Thr Pro Ser Ser Tyr Ile Asp Asn
1               5                   10

<210> SEQ ID NO 145
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 145

Arg Gly Thr Pro Ser Ser Tyr Ile Asp Asn Leu 1 5 10

<210> SEQ ID NO 146
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 146

Gly Thr Pro Ser Ser Tyr Ile Asp Asn Leu Thr
1 5 10

<210> SEQ ID NO 147
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 147

Thr Pro Ser Ser Tyr Ile Asp Asn Leu Thr Phe
1 5 10

<210> SEQ ID NO 148
<211> LENGTH: 12
<212> TYPE: PRT
<213> ORGANISM: Artificial Sequence
<220> FEATURE:
<223> OTHER INFORMATION: Description of Artificial Sequence: Synthetic peptide

<400> SEQUENCE: 148

Asp Phe Asp Tyr Thr Pro Asn Trp Gly Arg Gly Thr
1 5 10

<210> SEQ ID NO 149
<211> LENGTH: 12
<212> TYPE: PRT
<213> ORGANISM: Artificial Sequence
<220> FEATURE:
<223> OTHER INFORMATION: Description of Artificial Sequence: Synthetic peptide

<400> SEQUENCE: 149

Phe Asp Tyr Thr Pro Asn Trp Gly Arg Gly Thr Pro
1 5 10

<210> SEQ ID NO 150
<211> LENGTH: 12
<212> TYPE: PRT
<213> ORGANISM: Artificial Sequence
<220> FEATURE:
<223> OTHER INFORMATION: Description of Artificial Sequence: Synthetic peptide

<400> SEQUENCE: 150

Asp Tyr Thr Pro Asn Trp Gly Arg Gly Thr Pro Ser
1 5 10

<210> SEQ ID NO 151
<211> LENGTH: 12
<212> TYPE: PRT
<213> ORGANISM: Artificial Sequence
<220> FEATURE:
<223> OTHER INFORMATION: Description of Artificial Sequence: Synthetic peptide

<400> SEQUENCE: 151

Tyr Thr Pro Asn Trp Gly Arg Gly Thr Pro Ser Ser
1 5 10

<210> SEQ ID NO 152
<211> LENGTH: 12
<212> TYPE: PRT
<213> ORGANISM: Artificial Sequence
<220> FEATURE:
<223> OTHER INFORMATION: Description of Artificial Sequence: Synthetic peptide

<400> SEQUENCE: 152

Thr Pro Asn Trp Gly Arg Gly Thr Pro Ser Ser Tyr
1 5 10

<210> SEQ ID NO 153
<211> LENGTH: 12
<212> TYPE: PRT
<213> ORGANISM: Artificial Sequence
<220> FEATURE:
<223> OTHER INFORMATION: Description of Artificial Sequence: Synthetic peptide

<400> SEQUENCE: 153

Pro Asn Trp Gly Arg Gly Thr Pro Ser Ser Tyr Ile
1 5 10

<210> SEQ ID NO 154
<211> LENGTH: 12
<212> TYPE: PRT
<213> ORGANISM: Artificial Sequence
<220> FEATURE:
<223> OTHER INFORMATION: Description of Artificial Sequence: Synthetic peptide

<400> SEQUENCE: 154

Asn Trp Gly Arg Gly Thr Pro Ser Ser Tyr Ile Asp
1 5 10

<210> SEQ ID NO 155
<211> LENGTH: 12
<212> TYPE: PRT
<213> ORGANISM: Artificial Sequence
<220> FEATURE:
<223> OTHER INFORMATION: Description of Artificial Sequence: Synthetic peptide

<400> SEQUENCE: 155

Trp Gly Arg Gly Thr Pro Ser Ser Tyr Ile Asp Asn
1 5 10

<210> SEQ ID NO 156
<211> LENGTH: 12
<212> TYPE: PRT
<213> ORGANISM: Artificial Sequence
<220> FEATURE:
<223> OTHER INFORMATION: Description of Artificial Sequence: Synthetic peptide

<400> SEQUENCE: 156

Gly Arg Gly Thr Pro Ser Ser Tyr Ile Asp Asn Leu
1 5 10

<210> SEQ ID NO 157
<211> LENGTH: 12
<212> TYPE: PRT

```
<213> ORGANISM: Artificial Sequence
<220> FEATURE:
<223> OTHER INFORMATION: Description of Artificial Sequence: Synthetic
      peptide

<400> SEQUENCE: 157

Arg Gly Thr Pro Ser Ser Tyr Ile Asp Asn Leu Thr
1               5                   10


<210> SEQ ID NO 158
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 158

Gly Thr Pro Ser Ser Tyr Ile Asp Asn Leu Thr Phe
1               5                   10


<210> SEQ ID NO 159
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 159

Thr Pro Ser Ser Tyr Ile Asp Asn Leu Thr Phe Pro
1               5                   10


<210> SEQ ID NO 160
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 160

Ile Asp Phe Asp Tyr Thr Pro Asn Trp Gly Arg Gly Thr
1               5                   10


<210> SEQ ID NO 161
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 161

Asp Phe Asp Tyr Thr Pro Asn Trp Gly Arg Gly Thr Pro
1               5                   10


<210> SEQ ID NO 162
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 162

Phe Asp Tyr Thr Pro Asn Trp Gly Arg Gly Thr Pro Ser
1               5                   10
```

<210> SEQ ID NO 163
<211> LENGTH: 13
<212> TYPE: PRT
<213> ORGANISM: Artificial Sequence
<220> FEATURE:
<223> OTHER INFORMATION: Description of Artificial Sequence: Synthetic peptide

<400> SEQUENCE: 163

Asp Tyr Thr Pro Asn Trp Gly Arg Gly Thr Pro Ser Ser
1 5 10

<210> SEQ ID NO 164
<211> LENGTH: 13
<212> TYPE: PRT
<213> ORGANISM: Artificial Sequence
<220> FEATURE:
<223> OTHER INFORMATION: Description of Artificial Sequence: Synthetic peptide

<400> SEQUENCE: 164

Tyr Thr Pro Asn Trp Gly Arg Gly Thr Pro Ser Ser Tyr
1 5 10

<210> SEQ ID NO 165
<211> LENGTH: 13
<212> TYPE: PRT
<213> ORGANISM: Artificial Sequence
<220> FEATURE:
<223> OTHER INFORMATION: Description of Artificial Sequence: Synthetic peptide

<400> SEQUENCE: 165

Thr Pro Asn Trp Gly Arg Gly Thr Pro Ser Ser Tyr Ile
1 5 10

<210> SEQ ID NO 166
<211> LENGTH: 13
<212> TYPE: PRT
<213> ORGANISM: Artificial Sequence
<220> FEATURE:
<223> OTHER INFORMATION: Description of Artificial Sequence: Synthetic peptide

<400> SEQUENCE: 166

Pro Asn Trp Gly Arg Gly Thr Pro Ser Ser Tyr Ile Asp
1 5 10

<210> SEQ ID NO 167
<211> LENGTH: 13
<212> TYPE: PRT
<213> ORGANISM: Artificial Sequence
<220> FEATURE:
<223> OTHER INFORMATION: Description of Artificial Sequence: Synthetic peptide

<400> SEQUENCE: 167

Asn Trp Gly Arg Gly Thr Pro Ser Ser Tyr Ile Asp Asn
1 5 10

<210> SEQ ID NO 168
<211> LENGTH: 13
<212> TYPE: PRT
<213> ORGANISM: Artificial Sequence
<220> FEATURE:
<223> OTHER INFORMATION: Description of Artificial Sequence: Synthetic peptide

<400> SEQUENCE: 168

Trp Gly Arg Gly Thr Pro Ser Ser Tyr Ile Asp Asn Leu
1 5 10

<210> SEQ ID NO 169
<211> LENGTH: 13
<212> TYPE: PRT
<213> ORGANISM: Artificial Sequence
<220> FEATURE:
<223> OTHER INFORMATION: Description of Artificial Sequence: Synthetic peptide

<400> SEQUENCE: 169

Gly Arg Gly Thr Pro Ser Ser Tyr Ile Asp Asn Leu Thr
1 5 10

<210> SEQ ID NO 170
<211> LENGTH: 13
<212> TYPE: PRT
<213> ORGANISM: Artificial Sequence
<220> FEATURE:
<223> OTHER INFORMATION: Description of Artificial Sequence: Synthetic peptide

<400> SEQUENCE: 170

Arg Gly Thr Pro Ser Ser Tyr Ile Asp Asn Leu Thr Phe
1 5 10

<210> SEQ ID NO 171
<211> LENGTH: 13
<212> TYPE: PRT
<213> ORGANISM: Artificial Sequence
<220> FEATURE:
<223> OTHER INFORMATION: Description of Artificial Sequence: Synthetic peptide

<400> SEQUENCE: 171

Gly Thr Pro Ser Ser Tyr Ile Asp Asn Leu Thr Phe Pro
1 5 10

<210> SEQ ID NO 172
<211> LENGTH: 13
<212> TYPE: PRT
<213> ORGANISM: Artificial Sequence
<220> FEATURE:
<223> OTHER INFORMATION: Description of Artificial Sequence: Synthetic peptide

<400> SEQUENCE: 172

Thr Pro Ser Ser Tyr Ile Asp Asn Leu Thr Phe Pro Lys
1 5 10

<210> SEQ ID NO 173
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 173

Lys Ile Asp Phe Asp Tyr Thr Pro Asn Trp Gly Arg Gly Thr
1 5 10

<210> SEQ ID NO 174
<211> LENGTH: 14
<212> TYPE: PRT
<213> ORGANISM: Artificial Sequence
<220> FEATURE:

<223> OTHER INFORMATION: Description of Artificial Sequence: Synthetic
      peptide

<400> SEQUENCE: 174

Ile Asp Phe Asp Tyr Thr Pro Asn Trp Gly Arg Gly Thr Pro
1               5                   10

<210> SEQ ID NO 175
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 175

Asp Phe Asp Tyr Thr Pro Asn Trp Gly Arg Gly Thr Pro Ser
1               5                   10

<210> SEQ ID NO 176
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 176

Phe Asp Tyr Thr Pro Asn Trp Gly Arg Gly Thr Pro Ser Ser
1               5                   10

<210> SEQ ID NO 177
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 177

Asp Tyr Thr Pro Asn Trp Gly Arg Gly Thr Pro Ser Ser Tyr
1               5                   10

<210> SEQ ID NO 178
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 178

Tyr Thr Pro Asn Trp Gly Arg Gly Thr Pro Ser Ser Tyr Ile
1               5                   10

<210> SEQ ID NO 179
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 179

Thr Pro Asn Trp Gly Arg Gly Thr Pro Ser Ser Tyr Ile Asp
1               5                   10

<210> SEQ ID NO 180

<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 180

Pro Asn Trp Gly Arg Gly Thr Pro Ser Ser Tyr Ile Asp Asn
1 5 10

<210> SEQ ID NO 181
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 181

Asn Trp Gly Arg Gly Thr Pro Ser Ser Tyr Ile Asp Asn Leu
1 5 10

<210> SEQ ID NO 182
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 182

Trp Gly Arg Gly Thr Pro Ser Ser Tyr Ile Asp Asn Leu Thr
1 5 10

<210> SEQ ID NO 183
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 183

Gly Arg Gly Thr Pro Ser Ser Tyr Ile Asp Asn Leu Thr Phe
1 5 10

<210> SEQ ID NO 184
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 184

Arg Gly Thr Pro Ser Ser Tyr Ile Asp Asn Leu Thr Phe Pro
1 5 10

<210> SEQ ID NO 185
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 185

Gly Thr Pro Ser Ser Tyr Ile Asp Asn Leu Thr Phe Pro Lys 1 5 10

<210> SEQ ID NO 186
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 186

Thr Pro Ser Ser Tyr Ile Asp Asn Leu Thr Phe Pro Lys Val
1 5 10

<210> SEQ ID NO 187
<211> LENGTH: 15
<212> TYPE: PRT
<213> ORGANISM: Artificial Sequence
<220> FEATURE:
<223> OTHER INFORMATION: Description of Artificial Sequence: Synthetic peptide

<400> SEQUENCE: 187

Lys Lys Ile Asp Phe Asp Tyr Thr Pro Asn Trp Gly Arg Gly Thr
1 5 10 15

<210> SEQ ID NO 188
<211> LENGTH: 15
<212> TYPE: PRT
<213> ORGANISM: Artificial Sequence
<220> FEATURE:
<223> OTHER INFORMATION: Description of Artificial Sequence: Synthetic peptide

<400> SEQUENCE: 188

Lys Ile Asp Phe Asp Tyr Thr Pro Asn Trp Gly Arg Gly Thr Pro
1 5 10 15

<210> SEQ ID NO 189
<211> LENGTH: 15
<212> TYPE: PRT
<213> ORGANISM: Artificial Sequence
<220> FEATURE:
<223> OTHER INFORMATION: Description of Artificial Sequence: Synthetic peptide

<400> SEQUENCE: 189

Ile Asp Phe Asp Tyr Thr Pro Asn Trp Gly Arg Gly Thr Pro Ser
1 5 10 15

<210> SEQ ID NO 190
<211> LENGTH: 15
<212> TYPE: PRT
<213> ORGANISM: Artificial Sequence
<220> FEATURE:
<223> OTHER INFORMATION: Description of Artificial Sequence: Synthetic peptide

<400> SEQUENCE: 190

Asp Phe Asp Tyr Thr Pro Asn Trp Gly Arg Gly Thr Pro Ser Ser
1 5 10 15

<210> SEQ ID NO 191
<211> LENGTH: 15
<212> TYPE: PRT
<213> ORGANISM: Artificial Sequence
<220> FEATURE:
<223> OTHER INFORMATION: Description of Artificial Sequence: Synthetic peptide

<400> SEQUENCE: 191

Phe Asp Tyr Thr Pro Asn Trp Gly Arg Gly Thr Pro Ser Ser Tyr
1 5 10 15

<210> SEQ ID NO 192
<211> LENGTH: 15
<212> TYPE: PRT
<213> ORGANISM: Artificial Sequence
<220> FEATURE:
<223> OTHER INFORMATION: Description of Artificial Sequence: Synthetic peptide

<400> SEQUENCE: 192

Asp Tyr Thr Pro Asn Trp Gly Arg Gly Thr Pro Ser Ser Tyr Ile
1 5 10 15

<210> SEQ ID NO 193
<211> LENGTH: 15
<212> TYPE: PRT
<213> ORGANISM: Artificial Sequence
<220> FEATURE:
<223> OTHER INFORMATION: Description of Artificial Sequence: Synthetic peptide

<400> SEQUENCE: 193

Tyr Thr Pro Asn Trp Gly Arg Gly Thr Pro Ser Ser Tyr Ile Asp
1 5 10 15

<210> SEQ ID NO 194
<211> LENGTH: 15
<212> TYPE: PRT
<213> ORGANISM: Artificial Sequence
<220> FEATURE:
<223> OTHER INFORMATION: Description of Artificial Sequence: Synthetic peptide

<400> SEQUENCE: 194

Thr Pro Asn Trp Gly Arg Gly Thr Pro Ser Ser Tyr Ile Asp Asn
1 5 10 15

<210> SEQ ID NO 195
<211> LENGTH: 15
<212> TYPE: PRT
<213> ORGANISM: Artificial Sequence
<220> FEATURE:
<223> OTHER INFORMATION: Description of Artificial Sequence: Synthetic peptide

<400> SEQUENCE: 195

Pro Asn Trp Gly Arg Gly Thr Pro Ser Ser Tyr Ile Asp Asn Leu
1 5 10 15

<210> SEQ ID NO 196
<211> LENGTH: 15
<212> TYPE: PRT
<213> ORGANISM: Artificial Sequence
<220> FEATURE:
<223> OTHER INFORMATION: Description of Artificial Sequence: Synthetic peptide

<400> SEQUENCE: 196

Asn Trp Gly Arg Gly Thr Pro Ser Ser Tyr Ile Asp Asn Leu Thr
1 5 10 15

<210> SEQ ID NO 197
<211> LENGTH: 15
<212> TYPE: PRT

<213> ORGANISM: Artificial Sequence
<220> FEATURE:
<223> OTHER INFORMATION: Description of Artificial Sequence: Synthetic
peptide

<400> SEQUENCE: 197

Trp Gly Arg Gly Thr Pro Ser Ser Tyr Ile Asp Asn Leu Thr Phe
1 5 10 15

<210> SEQ ID NO 198
<211> LENGTH: 15
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 198

Gly Arg Gly Thr Pro Ser Ser Tyr Ile Asp Asn Leu Thr Phe Pro
1 5 10 15

<210> SEQ ID NO 199
<211> LENGTH: 15
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 199

Arg Gly Thr Pro Ser Ser Tyr Ile Asp Asn Leu Thr Phe Pro Lys
1 5 10 15

<210> SEQ ID NO 200
<211> LENGTH: 15
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 200

Gly Thr Pro Ser Ser Tyr Ile Asp Asn Leu Thr Phe Pro Lys Val
1 5 10 15

<210> SEQ ID NO 201
<211> LENGTH: 15
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 201

Thr Pro Ser Ser Tyr Ile Asp Asn Leu Thr Phe Pro Lys Val Leu
1 5 10 15

<210> SEQ ID NO 202
<211> LENGTH: 16
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 202

Val Lys Lys Ile Asp Phe Asp Tyr Thr Pro Asn Trp Gly Arg Gly Thr
1 5 10 15

<210> SEQ ID NO 203
<211> LENGTH: 16
<212> TYPE: PRT
<213> ORGANISM: Artificial Sequence
<220> FEATURE:
<223> OTHER INFORMATION: Description of Artificial Sequence: Synthetic peptide

<400> SEQUENCE: 203

Lys Lys Ile Asp Phe Asp Tyr Thr Pro Asn Trp Gly Arg Gly Thr Pro
1 5 10 15

<210> SEQ ID NO 204
<211> LENGTH: 16
<212> TYPE: PRT
<213> ORGANISM: Artificial Sequence
<220> FEATURE:
<223> OTHER INFORMATION: Description of Artificial Sequence: Synthetic peptide

<400> SEQUENCE: 204

Lys Ile Asp Phe Asp Tyr Thr Pro Asn Trp Gly Arg Gly Thr Pro Ser
1 5 10 15

<210> SEQ ID NO 205
<211> LENGTH: 16
<212> TYPE: PRT
<213> ORGANISM: Artificial Sequence
<220> FEATURE:
<223> OTHER INFORMATION: Description of Artificial Sequence: Synthetic peptide

<400> SEQUENCE: 205

Ile Asp Phe Asp Tyr Thr Pro Asn Trp Gly Arg Gly Thr Pro Ser Ser
1 5 10 15

<210> SEQ ID NO 206
<211> LENGTH: 16
<212> TYPE: PRT
<213> ORGANISM: Artificial Sequence
<220> FEATURE:
<223> OTHER INFORMATION: Description of Artificial Sequence: Synthetic peptide

<400> SEQUENCE: 206

Asp Phe Asp Tyr Thr Pro Asn Trp Gly Arg Gly Thr Pro Ser Ser Tyr
1 5 10 15

<210> SEQ ID NO 207
<211> LENGTH: 16
<212> TYPE: PRT
<213> ORGANISM: Artificial Sequence
<220> FEATURE:
<223> OTHER INFORMATION: Description of Artificial Sequence: Synthetic peptide

<400> SEQUENCE: 207

Phe Asp Tyr Thr Pro Asn Trp Gly Arg Gly Thr Pro Ser Ser Tyr Ile
1 5 10 15

<210> SEQ ID NO 208
<211> LENGTH: 16
<212> TYPE: PRT
<213> ORGANISM: Artificial Sequence
<220> FEATURE:
<223> OTHER INFORMATION: Description of Artificial Sequence: Synthetic peptide

<400> SEQUENCE: 208

Asp Tyr Thr Pro Asn Trp Gly Arg Gly Thr Pro Ser Ser Tyr Ile Asp
1 5 10 15

<210> SEQ ID NO 209
<211> LENGTH: 16
<212> TYPE: PRT
<213> ORGANISM: Artificial Sequence
<220> FEATURE:
<223> OTHER INFORMATION: Description of Artificial Sequence: Synthetic peptide

<400> SEQUENCE: 209

Tyr Thr Pro Asn Trp Gly Arg Gly Thr Pro Ser Ser Tyr Ile Asp Asn
1 5 10 15

<210> SEQ ID NO 210
<211> LENGTH: 16
<212> TYPE: PRT
<213> ORGANISM: Artificial Sequence
<220> FEATURE:
<223> OTHER INFORMATION: Description of Artificial Sequence: Synthetic peptide

<400> SEQUENCE: 210

Thr Pro Asn Trp Gly Arg Gly Thr Pro Ser Ser Tyr Ile Asp Asn Leu
1 5 10 15

<210> SEQ ID NO 211
<211> LENGTH: 16
<212> TYPE: PRT
<213> ORGANISM: Artificial Sequence
<220> FEATURE:
<223> OTHER INFORMATION: Description of Artificial Sequence: Synthetic peptide

<400> SEQUENCE: 211

Pro Asn Trp Gly Arg Gly Thr Pro Ser Ser Tyr Ile Asp Asn Leu Thr
1 5 10 15

<210> SEQ ID NO 212
<211> LENGTH: 16
<212> TYPE: PRT
<213> ORGANISM: Artificial Sequence
<220> FEATURE:
<223> OTHER INFORMATION: Description of Artificial Sequence: Synthetic peptide

<400> SEQUENCE: 212

Asn Trp Gly Arg Gly Thr Pro Ser Ser Tyr Ile Asp Asn Leu Thr Phe
1 5 10 15

<210> SEQ ID NO 213
<211> LENGTH: 16
<212> TYPE: PRT
<213> ORGANISM: Artificial Sequence
<220> FEATURE:
<223> OTHER INFORMATION: Description of Artificial Sequence: Synthetic peptide

<400> SEQUENCE: 213

Trp Gly Arg Gly Thr Pro Ser Ser Tyr Ile Asp Asn Leu Thr Phe Pro
1 5 10 15

<210> SEQ ID NO 214
<211> LENGTH: 16
<212> TYPE: PRT
<213> ORGANISM: Artificial Sequence
<220> FEATURE:

<223> OTHER INFORMATION: Description of Artificial Sequence: Synthetic
peptide

<400> SEQUENCE: 214

Gly Arg Gly Thr Pro Ser Ser Tyr Ile Asp Asn Leu Thr Phe Pro Lys
1 5 10 15

<210> SEQ ID NO 215
<211> LENGTH: 16
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 215

Arg Gly Thr Pro Ser Ser Tyr Ile Asp Asn Leu Thr Phe Pro Lys Val
1 5 10 15

<210> SEQ ID NO 216
<211> LENGTH: 16
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 216

Gly Thr Pro Ser Ser Tyr Ile Asp Asn Leu Thr Phe Pro Lys Val Leu
1 5 10 15

<210> SEQ ID NO 217
<211> LENGTH: 16
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 217

Thr Pro Ser Ser Tyr Ile Asp Asn Leu Thr Phe Pro Lys Val Leu Thr
1 5 10 15

<210> SEQ ID NO 218
<211> LENGTH: 17
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 218

Leu Val Lys Lys Ile Asp Phe Asp Tyr Thr Pro Asn Trp Gly Arg Gly
1 5 10 15

Thr

<210> SEQ ID NO 219
<211> LENGTH: 17
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 219

Val Lys Lys Ile Asp Phe Asp Tyr Thr Pro Asn Trp Gly Arg Gly Thr
1 5 10 15

Pro

<210> SEQ ID NO 220
<211> LENGTH: 17
<212> TYPE: PRT
<213> ORGANISM: Artificial Sequence
<220> FEATURE:
<223> OTHER INFORMATION: Description of Artificial Sequence: Synthetic peptide

<400> SEQUENCE: 220

Lys Lys Ile Asp Phe Asp Tyr Thr Pro Asn Trp Gly Arg Gly Thr Pro
1 5 10 15

Ser

<210> SEQ ID NO 221
<211> LENGTH: 17
<212> TYPE: PRT
<213> ORGANISM: Artificial Sequence
<220> FEATURE:
<223> OTHER INFORMATION: Description of Artificial Sequence: Synthetic peptide

<400> SEQUENCE: 221

Lys Ile Asp Phe Asp Tyr Thr Pro Asn Trp Gly Arg Gly Thr Pro Ser
1 5 10 15

Ser

<210> SEQ ID NO 222
<211> LENGTH: 17
<212> TYPE: PRT
<213> ORGANISM: Artificial Sequence
<220> FEATURE:
<223> OTHER INFORMATION: Description of Artificial Sequence: Synthetic peptide

<400> SEQUENCE: 222

Ile Asp Phe Asp Tyr Thr Pro Asn Trp Gly Arg Gly Thr Pro Ser Ser
1 5 10 15

Tyr

<210> SEQ ID NO 223
<211> LENGTH: 17
<212> TYPE: PRT
<213> ORGANISM: Artificial Sequence
<220> FEATURE:
<223> OTHER INFORMATION: Description of Artificial Sequence: Synthetic peptide

<400> SEQUENCE: 223

Asp Phe Asp Tyr Thr Pro Asn Trp Gly Arg Gly Thr Pro Ser Ser Tyr
1 5 10 15

Ile

<210> SEQ ID NO 224
<211> LENGTH: 17
<212> TYPE: PRT
<213> ORGANISM: Artificial Sequence
<220> FEATURE:
<223> OTHER INFORMATION: Description of Artificial Sequence: Synthetic peptide

<400> SEQUENCE: 224

Phe Asp Tyr Thr Pro Asn Trp Gly Arg Gly Thr Pro Ser Ser Tyr Ile
1 5 10 15

Asp

<210> SEQ ID NO 225
<211> LENGTH: 17
<212> TYPE: PRT
<213> ORGANISM: Artificial Sequence
<220> FEATURE:
<223> OTHER INFORMATION: Description of Artificial Sequence: Synthetic peptide

<400> SEQUENCE: 225

Asp Tyr Thr Pro Asn Trp Gly Arg Gly Thr Pro Ser Ser Tyr Ile Asp
1 5 10 15

Asn

<210> SEQ ID NO 226
<211> LENGTH: 17
<212> TYPE: PRT
<213> ORGANISM: Artificial Sequence
<220> FEATURE:
<223> OTHER INFORMATION: Description of Artificial Sequence: Synthetic peptide

<400> SEQUENCE: 226

Tyr Thr Pro Asn Trp Gly Arg Gly Thr Pro Ser Ser Tyr Ile Asp Asn
1 5 10 15

Leu

<210> SEQ ID NO 227
<211> LENGTH: 17
<212> TYPE: PRT
<213> ORGANISM: Artificial Sequence
<220> FEATURE:
<223> OTHER INFORMATION: Description of Artificial Sequence: Synthetic peptide

<400> SEQUENCE: 227

Thr Pro Asn Trp Gly Arg Gly Thr Pro Ser Ser Tyr Ile Asp Asn Leu
1 5 10 15

Thr

<210> SEQ ID NO 228
<211> LENGTH: 17
<212> TYPE: PRT
<213> ORGANISM: Artificial Sequence
<220> FEATURE:
<223> OTHER INFORMATION: Description of Artificial Sequence: Synthetic peptide

<400> SEQUENCE: 228

Pro Asn Trp Gly Arg Gly Thr Pro Ser Ser Tyr Ile Asp Asn Leu Thr
1 5 10 15

Phe

<210> SEQ ID NO 229
<211> LENGTH: 17
<212> TYPE: PRT
<213> ORGANISM: Artificial Sequence
<220> FEATURE:
<223> OTHER INFORMATION: Description of Artificial Sequence: Synthetic peptide

<400> SEQUENCE: 229

Asn Trp Gly Arg Gly Thr Pro Ser Ser Tyr Ile Asp Asn Leu Thr Phe
1 5 10 15

Pro

<210> SEQ ID NO 230
<211> LENGTH: 17
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 230

Trp Gly Arg Gly Thr Pro Ser Ser Tyr Ile Asp Asn Leu Thr Phe Pro
1 5 10 15

Lys

<210> SEQ ID NO 231
<211> LENGTH: 17
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 231

Gly Arg Gly Thr Pro Ser Ser Tyr Ile Asp Asn Leu Thr Phe Pro Lys
1 5 10 15

Val

<210> SEQ ID NO 232
<211> LENGTH: 17
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 232

Arg Gly Thr Pro Ser Ser Tyr Ile Asp Asn Leu Thr Phe Pro Lys Val
1 5 10 15

Leu

<210> SEQ ID NO 233
<211> LENGTH: 17
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 233

Gly Thr Pro Ser Ser Tyr Ile Asp Asn Leu Thr Phe Pro Lys Val Leu
1 5 10 15

Thr

<210> SEQ ID NO 234
<211> LENGTH: 17
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 234

Thr Pro Ser Ser Tyr Ile Asp Asn Leu Thr Phe Pro Lys Val Leu Thr
1 5 10 15

Asp

<210> SEQ ID NO 235
<211> LENGTH: 18
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 235

Tyr Leu Val Lys Lys Ile Asp Phe Asp Tyr Thr Pro Asn Trp Gly Arg
1 5 10 15

Gly Thr

<210> SEQ ID NO 236
<211> LENGTH: 18
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 236

Leu Val Lys Lys Ile Asp Phe Asp Tyr Thr Pro Asn Trp Gly Arg Gly
1 5 10 15

Thr Pro

<210> SEQ ID NO 237
<211> LENGTH: 18
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 237

Val Lys Lys Ile Asp Phe Asp Tyr Thr Pro Asn Trp Gly Arg Gly Thr
1 5 10 15

Pro Ser

<210> SEQ ID NO 238
<211> LENGTH: 18
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 238

Lys Lys Ile Asp Phe Asp Tyr Thr Pro Asn Trp Gly Arg Gly Thr Pro
1 5 10 15

Ser Ser

<210> SEQ ID NO 239
<211> LENGTH: 18
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 239

Lys Ile Asp Phe Asp Tyr Thr Pro Asn Trp Gly Arg Gly Thr Pro Ser
1 5 10 15

Ser Tyr

<210> SEQ ID NO 240
<211> LENGTH: 18
<212> TYPE: PRT
<213> ORGANISM: Artificial Sequence
<220> FEATURE:
<223> OTHER INFORMATION: Description of Artificial Sequence: Synthetic peptide

<400> SEQUENCE: 240

Ile Asp Phe Asp Tyr Thr Pro Asn Trp Gly Arg Gly Thr Pro Ser Ser
1 5 10 15

Tyr Ile

<210> SEQ ID NO 241
<211> LENGTH: 18
<212> TYPE: PRT
<213> ORGANISM: Artificial Sequence
<220> FEATURE:
<223> OTHER INFORMATION: Description of Artificial Sequence: Synthetic peptide

<400> SEQUENCE: 241

Asp Phe Asp Tyr Thr Pro Asn Trp Gly Arg Gly Thr Pro Ser Ser Tyr
1 5 10 15

Ile Asp

<210> SEQ ID NO 242
<211> LENGTH: 18
<212> TYPE: PRT
<213> ORGANISM: Artificial Sequence
<220> FEATURE:
<223> OTHER INFORMATION: Description of Artificial Sequence: Synthetic peptide

<400> SEQUENCE: 242

Phe Asp Tyr Thr Pro Asn Trp Gly Arg Gly Thr Pro Ser Ser Tyr Ile
1 5 10 15

Asp Asn

<210> SEQ ID NO 243
<211> LENGTH: 18
<212> TYPE: PRT
<213> ORGANISM: Artificial Sequence
<220> FEATURE:
<223> OTHER INFORMATION: Description of Artificial Sequence: Synthetic peptide

<400> SEQUENCE: 243

Asp Tyr Thr Pro Asn Trp Gly Arg Gly Thr Pro Ser Ser Tyr Ile Asp
1 5 10 15

Asn Leu

<210> SEQ ID NO 244
<211> LENGTH: 18
<212> TYPE: PRT
<213> ORGANISM: Artificial Sequence
<220> FEATURE:
<223> OTHER INFORMATION: Description of Artificial Sequence: Synthetic peptide

<400> SEQUENCE: 244

Tyr Thr Pro Asn Trp Gly Arg Gly Thr Pro Ser Ser Tyr Ile Asp Asn
1 5 10 15

Leu Thr

<210> SEQ ID NO 245
<211> LENGTH: 18
<212> TYPE: PRT
<213> ORGANISM: Artificial Sequence
<220> FEATURE:
<223> OTHER INFORMATION: Description of Artificial Sequence: Synthetic peptide

<400> SEQUENCE: 245

Thr Pro Asn Trp Gly Arg Gly Thr Pro Ser Ser Tyr Ile Asp Asn Leu
1 5 10 15

Thr Phe

<210> SEQ ID NO 246
<211> LENGTH: 18
<212> TYPE: PRT
<213> ORGANISM: Artificial Sequence
<220> FEATURE:
<223> OTHER INFORMATION: Description of Artificial Sequence: Synthetic peptide

<400> SEQUENCE: 246

Pro Asn Trp Gly Arg Gly Thr Pro Ser Ser Tyr Ile Asp Asn Leu Thr
1 5 10 15

Phe Pro

<210> SEQ ID NO 247
<211> LENGTH: 18
<212> TYPE: PRT
<213> ORGANISM: Artificial Sequence
<220> FEATURE:
<223> OTHER INFORMATION: Description of Artificial Sequence: Synthetic peptide

<400> SEQUENCE: 247

Asn Trp Gly Arg Gly Thr Pro Ser Ser Tyr Ile Asp Asn Leu Thr Phe
1 5 10 15

Pro Lys

<210> SEQ ID NO 248
<211> LENGTH: 18
<212> TYPE: PRT
<213> ORGANISM: Artificial Sequence
<220> FEATURE:
<223> OTHER INFORMATION: Description of Artificial Sequence: Synthetic peptide

<400> SEQUENCE: 248

Trp Gly Arg Gly Thr Pro Ser Ser Tyr Ile Asp Asn Leu Thr Phe Pro
1 5 10 15

Lys Val

<210> SEQ ID NO 249
<211> LENGTH: 18
<212> TYPE: PRT
<213> ORGANISM: Artificial Sequence
<220> FEATURE:
<223> OTHER INFORMATION: Description of Artificial Sequence: Synthetic peptide

<400> SEQUENCE: 249

Gly Arg Gly Thr Pro Ser Ser Tyr Ile Asp Asn Leu Thr Phe Pro Lys
1 5 10 15

Val Leu

<210> SEQ ID NO 250
<211> LENGTH: 18
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 250

Arg Gly Thr Pro Ser Ser Tyr Ile Asp Asn Leu Thr Phe Pro Lys Val
1 5 10 15

Leu Thr

<210> SEQ ID NO 251
<211> LENGTH: 18
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 251

Gly Thr Pro Ser Ser Tyr Ile Asp Asn Leu Thr Phe Pro Lys Val Leu
1 5 10 15

Thr Asp

<210> SEQ ID NO 252
<211> LENGTH: 18
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 252

Thr Pro Ser Ser Tyr Ile Asp Asn Leu Thr Phe Pro Lys Val Leu Thr
1 5 10 15

Asp Lys

<210> SEQ ID NO 253
<211> LENGTH: 19
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 253

Ala Tyr Leu Val Lys Lys Ile Asp Phe Asp Tyr Thr Pro Asn Trp Gly
1 5 10 15

Arg Gly Thr

<210> SEQ ID NO 254
<211> LENGTH: 19
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 254

Tyr Leu Val Lys Lys Ile Asp Phe Asp Tyr Thr Pro Asn Trp Gly Arg
1 5 10 15

Gly Thr Pro

<210> SEQ ID NO 255
<211> LENGTH: 19
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 255

Leu Val Lys Lys Ile Asp Phe Asp Tyr Thr Pro Asn Trp Gly Arg Gly
1 5 10 15

Thr Pro Ser

<210> SEQ ID NO 256
<211> LENGTH: 19
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 256

Val Lys Lys Ile Asp Phe Asp Tyr Thr Pro Asn Trp Gly Arg Gly Thr
1 5 10 15

Pro Ser Ser

<210> SEQ ID NO 257
<211> LENGTH: 19
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 257

Lys Lys Ile Asp Phe Asp Tyr Thr Pro Asn Trp Gly Arg Gly Thr Pro
1 5 10 15

Ser Ser Tyr

<210> SEQ ID NO 258
<211> LENGTH: 19
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 258

Lys Ile Asp Phe Asp Tyr Thr Pro Asn Trp Gly Arg Gly Thr Pro Ser
1 5 10 15

Ser Tyr Ile

<210> SEQ ID NO 259
<211> LENGTH: 19
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 259

Ile Asp Phe Asp Tyr Thr Pro Asn Trp Gly Arg Gly Thr Pro Ser Ser
1 5 10 15

Tyr Ile Asp

<210> SEQ ID NO 260
<211> LENGTH: 19
<212> TYPE: PRT
<213> ORGANISM: Artificial Sequence
<220> FEATURE:
<223> OTHER INFORMATION: Description of Artificial Sequence: Synthetic peptide

<400> SEQUENCE: 260

Asp Phe Asp Tyr Thr Pro Asn Trp Gly Arg Gly Thr Pro Ser Ser Tyr
1               5                   10                  15

Ile Asp Asn

<210> SEQ ID NO 261
<211> LENGTH: 19
<212> TYPE: PRT
<213> ORGANISM: Artificial Sequence
<220> FEATURE:
<223> OTHER INFORMATION: Description of Artificial Sequence: Synthetic peptide

<400> SEQUENCE: 261

Phe Asp Tyr Thr Pro Asn Trp Gly Arg Gly Thr Pro Ser Ser Tyr Ile
1               5                   10                  15

Asp Asn Leu

<210> SEQ ID NO 262
<211> LENGTH: 19
<212> TYPE: PRT
<213> ORGANISM: Artificial Sequence
<220> FEATURE:
<223> OTHER INFORMATION: Description of Artificial Sequence: Synthetic peptide

<400> SEQUENCE: 262

Asp Tyr Thr Pro Asn Trp Gly Arg Gly Thr Pro Ser Ser Tyr Ile Asp
1               5                   10                  15

Asn Leu Thr

<210> SEQ ID NO 263
<211> LENGTH: 19
<212> TYPE: PRT
<213> ORGANISM: Artificial Sequence
<220> FEATURE:
<223> OTHER INFORMATION: Description of Artificial Sequence: Synthetic peptide

<400> SEQUENCE: 263

Tyr Thr Pro Asn Trp Gly Arg Gly Thr Pro Ser Ser Tyr Ile Asp Asn
1               5                   10                  15

Leu Thr Phe

<210> SEQ ID NO 264
<211> LENGTH: 19
<212> TYPE: PRT
<213> ORGANISM: Artificial Sequence
<220> FEATURE:
<223> OTHER INFORMATION: Description of Artificial Sequence: Synthetic peptide

<400> SEQUENCE: 264

Thr Pro Asn Trp Gly Arg Gly Thr Pro Ser Ser Tyr Ile Asp Asn Leu
1               5                   10                  15

Thr Phe Pro

<210> SEQ ID NO 265
<211> LENGTH: 19
<212> TYPE: PRT
<213> ORGANISM: Artificial Sequence
<220> FEATURE:
<223> OTHER INFORMATION: Description of Artificial Sequence: Synthetic peptide

<400> SEQUENCE: 265

Pro Asn Trp Gly Arg Gly Thr Pro Ser Ser Tyr Ile Asp Asn Leu Thr
1 5 10 15

Phe Pro Lys

<210> SEQ ID NO 266
<211> LENGTH: 19
<212> TYPE: PRT
<213> ORGANISM: Artificial Sequence
<220> FEATURE:
<223> OTHER INFORMATION: Description of Artificial Sequence: Synthetic peptide

<400> SEQUENCE: 266

Asn Trp Gly Arg Gly Thr Pro Ser Ser Tyr Ile Asp Asn Leu Thr Phe
1 5 10 15

Pro Lys Val

<210> SEQ ID NO 267
<211> LENGTH: 19
<212> TYPE: PRT
<213> ORGANISM: Artificial Sequence
<220> FEATURE:
<223> OTHER INFORMATION: Description of Artificial Sequence: Synthetic peptide

<400> SEQUENCE: 267

Trp Gly Arg Gly Thr Pro Ser Ser Tyr Ile Asp Asn Leu Thr Phe Pro
1 5 10 15

Lys Val Leu

<210> SEQ ID NO 268
<211> LENGTH: 19
<212> TYPE: PRT
<213> ORGANISM: Artificial Sequence
<220> FEATURE:
<223> OTHER INFORMATION: Description of Artificial Sequence: Synthetic peptide

<400> SEQUENCE: 268

Gly Arg Gly Thr Pro Ser Ser Tyr Ile Asp Asn Leu Thr Phe Pro Lys
1 5 10 15

Val Leu Thr

<210> SEQ ID NO 269
<211> LENGTH: 19
<212> TYPE: PRT
<213> ORGANISM: Artificial Sequence
<220> FEATURE:
<223> OTHER INFORMATION: Description of Artificial Sequence: Synthetic peptide

<400> SEQUENCE: 269

Arg Gly Thr Pro Ser Ser Tyr Ile Asp Asn Leu Thr Phe Pro Lys Val
1 5 10 15

Leu Thr Asp

<210> SEQ ID NO 270
<211> LENGTH: 19
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 270

Gly Thr Pro Ser Ser Tyr Ile Asp Asn Leu Thr Phe Pro Lys Val Leu
1               5                   10                  15

Thr Asp Lys

<210> SEQ ID NO 271
<211> LENGTH: 19
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 271

Thr Pro Ser Ser Tyr Ile Asp Asn Leu Thr Phe Pro Lys Val Leu Thr
1               5                   10                  15

Asp Lys Lys

<210> SEQ ID NO 272
<211> LENGTH: 20
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 272

Leu Ala Tyr Leu Val Lys Lys Ile Asp Phe Asp Tyr Thr Pro Asn Trp
1               5                   10                  15

Gly Arg Gly Thr
            20

<210> SEQ ID NO 273
<211> LENGTH: 20
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 273

Ala Tyr Leu Val Lys Lys Ile Asp Phe Asp Tyr Thr Pro Asn Trp Gly
1               5                   10                  15

Arg Gly Thr Pro
            20

<210> SEQ ID NO 274
<211> LENGTH: 20
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 274

Tyr Leu Val Lys Lys Ile Asp Phe Asp Tyr Thr Pro Asn Trp Gly Arg

```
1               5                   10                  15

Gly Thr Pro Ser
            20


<210> SEQ ID NO 275
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 275

Leu Val Lys Lys Ile Asp Phe Asp Tyr Thr Pro Asn Trp Gly Arg Gly
1               5                   10                  15

Thr Pro Ser Ser
            20


<210> SEQ ID NO 276
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 276

Val Lys Lys Ile Asp Phe Asp Tyr Thr Pro Asn Trp Gly Arg Gly Thr
1               5                   10                  15

Pro Ser Ser Tyr
            20


<210> SEQ ID NO 277
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 277

Lys Lys Ile Asp Phe Asp Tyr Thr Pro Asn Trp Gly Arg Gly Thr Pro
1               5                   10                  15

Ser Ser Tyr Ile
            20


<210> SEQ ID NO 278
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 278

Lys Ile Asp Phe Asp Tyr Thr Pro Asn Trp Gly Arg Gly Thr Pro Ser
1               5                   10                  15

Ser Tyr Ile Asp
            20


<210> SEQ ID NO 279
<211> LENGTH: 20
<212> TYPE: PRT
<213> ORGANISM: Artificial Sequence
<220> FEATURE:
<223> OTHER INFORMATION: Description of Artificial Sequence: Synthetic
```

peptide

<400> SEQUENCE: 279

Ile Asp Phe Asp Tyr Thr Pro Asn Trp Gly Arg Gly Thr Pro Ser Ser
1 5 10 15

Tyr Ile Asp Asn
20

<210> SEQ ID NO 280
<211> LENGTH: 20
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 280

Asp Phe Asp Tyr Thr Pro Asn Trp Gly Arg Gly Thr Pro Ser Ser Tyr
1 5 10 15

Ile Asp Asn Leu
20

<210> SEQ ID NO 281
<211> LENGTH: 20
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 281

Phe Asp Tyr Thr Pro Asn Trp Gly Arg Gly Thr Pro Ser Ser Tyr Ile
1 5 10 15

Asp Asn Leu Thr
20

<210> SEQ ID NO 282
<211> LENGTH: 20
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 282

Asp Tyr Thr Pro Asn Trp Gly Arg Gly Thr Pro Ser Ser Tyr Ile Asp
1 5 10 15

Asn Leu Thr Phe
20

<210> SEQ ID NO 283
<211> LENGTH: 20
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 283

Tyr Thr Pro Asn Trp Gly Arg Gly Thr Pro Ser Ser Tyr Ile Asp Asn
1 5 10 15

Leu Thr Phe Pro
20

<210> SEQ ID NO 284

<211> LENGTH: 20
<212> TYPE: PRT
<213> ORGANISM: Artificial Sequence
<220> FEATURE:
<223> OTHER INFORMATION: Description of Artificial Sequence: Synthetic peptide

<400> SEQUENCE: 284

Thr Pro Asn Trp Gly Arg Gly Thr Pro Ser Ser Tyr Ile Asp Asn Leu
1 5 10 15

Thr Phe Pro Lys
20

<210> SEQ ID NO 285
<211> LENGTH: 20
<212> TYPE: PRT
<213> ORGANISM: Artificial Sequence
<220> FEATURE:
<223> OTHER INFORMATION: Description of Artificial Sequence: Synthetic peptide

<400> SEQUENCE: 285

Pro Asn Trp Gly Arg Gly Thr Pro Ser Ser Tyr Ile Asp Asn Leu Thr
1 5 10 15

Phe Pro Lys Val
20

<210> SEQ ID NO 286
<211> LENGTH: 20
<212> TYPE: PRT
<213> ORGANISM: Artificial Sequence
<220> FEATURE:
<223> OTHER INFORMATION: Description of Artificial Sequence: Synthetic peptide

<400> SEQUENCE: 286

Asn Trp Gly Arg Gly Thr Pro Ser Ser Tyr Ile Asp Asn Leu Thr Phe
1 5 10 15

Pro Lys Val Leu
20

<210> SEQ ID NO 287
<211> LENGTH: 20
<212> TYPE: PRT
<213> ORGANISM: Artificial Sequence
<220> FEATURE:
<223> OTHER INFORMATION: Description of Artificial Sequence: Synthetic peptide

<400> SEQUENCE: 287

Trp Gly Arg Gly Thr Pro Ser Ser Tyr Ile Asp Asn Leu Thr Phe Pro
1 5 10 15

Lys Val Leu Thr
20

<210> SEQ ID NO 288
<211> LENGTH: 20
<212> TYPE: PRT
<213> ORGANISM: Artificial Sequence
<220> FEATURE:
<223> OTHER INFORMATION: Description of Artificial Sequence: Synthetic peptide

<400> SEQUENCE: 288

Gly Arg Gly Thr Pro Ser Ser Tyr Ile Asp Asn Leu Thr Phe Pro Lys
1 5 10 15

-continued

```
Val Leu Thr Asp
            20


<210> SEQ ID NO 289
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 289

Arg Gly Thr Pro Ser Ser Tyr Ile Asp Asn Leu Thr Phe Pro Lys Val
1               5                   10                  15

Leu Thr Asp Lys
            20


<210> SEQ ID NO 290
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 290

Gly Thr Pro Ser Ser Tyr Ile Asp Asn Leu Thr Phe Pro Lys Val Leu
1               5                   10                  15

Thr Asp Lys Lys
            20


<210> SEQ ID NO 291
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 291

Thr Pro Ser Ser Tyr Ile Asp Asn Leu Thr Phe Pro Lys Val Leu Thr
1               5                   10                  15

Asp Lys Lys Tyr
            20


<210> SEQ ID NO 292
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 292

Gln Leu Ala Tyr Leu Val Lys Lys Ile Asp Phe Asp Tyr Thr Pro Asn
1               5                   10                  15

Trp Gly Arg Gly Thr
            20


<210> SEQ ID NO 293
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 293

Leu Ala Tyr Leu Val Lys Lys Ile Asp Phe Asp Tyr Thr Pro Asn Trp
1 5 10 15

Gly Arg Gly Thr Pro
20

<210> SEQ ID NO 294
<211> LENGTH: 21
<212> TYPE: PRT
<213> ORGANISM: Artificial Sequence
<220> FEATURE:
<223> OTHER INFORMATION: Description of Artificial Sequence: Synthetic peptide

<400> SEQUENCE: 294

Ala Tyr Leu Val Lys Lys Ile Asp Phe Asp Tyr Thr Pro Asn Trp Gly
1 5 10 15

Arg Gly Thr Pro Ser
20

<210> SEQ ID NO 295
<211> LENGTH: 21
<212> TYPE: PRT
<213> ORGANISM: Artificial Sequence
<220> FEATURE:
<223> OTHER INFORMATION: Description of Artificial Sequence: Synthetic peptide

<400> SEQUENCE: 295

Tyr Leu Val Lys Lys Ile Asp Phe Asp Tyr Thr Pro Asn Trp Gly Arg
1 5 10 15

Gly Thr Pro Ser Ser
20

<210> SEQ ID NO 296
<211> LENGTH: 21
<212> TYPE: PRT
<213> ORGANISM: Artificial Sequence
<220> FEATURE:
<223> OTHER INFORMATION: Description of Artificial Sequence: Synthetic peptide

<400> SEQUENCE: 296

Leu Val Lys Lys Ile Asp Phe Asp Tyr Thr Pro Asn Trp Gly Arg Gly
1 5 10 15

Thr Pro Ser Ser Tyr
20

<210> SEQ ID NO 297
<211> LENGTH: 21
<212> TYPE: PRT
<213> ORGANISM: Artificial Sequence
<220> FEATURE:
<223> OTHER INFORMATION: Description of Artificial Sequence: Synthetic peptide

<400> SEQUENCE: 297

Val Lys Lys Ile Asp Phe Asp Tyr Thr Pro Asn Trp Gly Arg Gly Thr
1 5 10 15

Pro Ser Ser Tyr Ile
20

<210> SEQ ID NO 298
<211> LENGTH: 21
<212> TYPE: PRT

<213> ORGANISM: Artificial Sequence
<220> FEATURE:
<223> OTHER INFORMATION: Description of Artificial Sequence: Synthetic
peptide

<400> SEQUENCE: 298

Lys Lys Ile Asp Phe Asp Tyr Thr Pro Asn Trp Gly Arg Gly Thr Pro
1 5 10 15

Ser Ser Tyr Ile Asp
20

<210> SEQ ID NO 299
<211> LENGTH: 21
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 299

Lys Ile Asp Phe Asp Tyr Thr Pro Asn Trp Gly Arg Gly Thr Pro Ser
1 5 10 15

Ser Tyr Ile Asp Asn
20

<210> SEQ ID NO 300
<211> LENGTH: 21
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 300

Ile Asp Phe Asp Tyr Thr Pro Asn Trp Gly Arg Gly Thr Pro Ser Ser
1 5 10 15

Tyr Ile Asp Asn Leu
20

<210> SEQ ID NO 301
<211> LENGTH: 21
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 301

Asp Phe Asp Tyr Thr Pro Asn Trp Gly Arg Gly Thr Pro Ser Ser Tyr
1 5 10 15

Ile Asp Asn Leu Thr
20

<210> SEQ ID NO 302
<211> LENGTH: 21
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 302

Phe Asp Tyr Thr Pro Asn Trp Gly Arg Gly Thr Pro Ser Ser Tyr Ile
1 5 10 15

Asp Asn Leu Thr Phe
20

<210> SEQ ID NO 303
<211> LENGTH: 21
<212> TYPE: PRT
<213> ORGANISM: Artificial Sequence
<220> FEATURE:
<223> OTHER INFORMATION: Description of Artificial Sequence: Synthetic peptide

<400> SEQUENCE: 303

```
Asp Tyr Thr Pro Asn Trp Gly Arg Gly Thr Pro Ser Ser Tyr Ile Asp
1               5                   10                  15

Asn Leu Thr Phe Pro
            20
```

<210> SEQ ID NO 304
<211> LENGTH: 21
<212> TYPE: PRT
<213> ORGANISM: Artificial Sequence
<220> FEATURE:
<223> OTHER INFORMATION: Description of Artificial Sequence: Synthetic peptide

<400> SEQUENCE: 304

```
Tyr Thr Pro Asn Trp Gly Arg Gly Thr Pro Ser Ser Tyr Ile Asp Asn
1               5                   10                  15

Leu Thr Phe Pro Lys
            20
```

<210> SEQ ID NO 305
<211> LENGTH: 21
<212> TYPE: PRT
<213> ORGANISM: Artificial Sequence
<220> FEATURE:
<223> OTHER INFORMATION: Description of Artificial Sequence: Synthetic peptide

<400> SEQUENCE: 305

```
Thr Pro Asn Trp Gly Arg Gly Thr Pro Ser Ser Tyr Ile Asp Asn Leu
1               5                   10                  15

Thr Phe Pro Lys Val
            20
```

<210> SEQ ID NO 306
<211> LENGTH: 21
<212> TYPE: PRT
<213> ORGANISM: Artificial Sequence
<220> FEATURE:
<223> OTHER INFORMATION: Description of Artificial Sequence: Synthetic peptide

<400> SEQUENCE: 306

```
Pro Asn Trp Gly Arg Gly Thr Pro Ser Ser Tyr Ile Asp Asn Leu Thr
1               5                   10                  15

Phe Pro Lys Val Leu
            20
```

<210> SEQ ID NO 307
<211> LENGTH: 21
<212> TYPE: PRT
<213> ORGANISM: Artificial Sequence
<220> FEATURE:
<223> OTHER INFORMATION: Description of Artificial Sequence: Synthetic peptide

<400> SEQUENCE: 307

Asn Trp Gly Arg Gly Thr Pro Ser Ser Tyr Ile Asp Asn Leu Thr Phe
1 5 10 15

Pro Lys Val Leu Thr
20

<210> SEQ ID NO 308
<211> LENGTH: 21
<212> TYPE: PRT
<213> ORGANISM: Artificial Sequence
<220> FEATURE:
<223> OTHER INFORMATION: Description of Artificial Sequence: Synthetic peptide

<400> SEQUENCE: 308

Trp Gly Arg Gly Thr Pro Ser Ser Tyr Ile Asp Asn Leu Thr Phe Pro
1 5 10 15

Lys Val Leu Thr Asp
20

<210> SEQ ID NO 309
<211> LENGTH: 21
<212> TYPE: PRT
<213> ORGANISM: Artificial Sequence
<220> FEATURE:
<223> OTHER INFORMATION: Description of Artificial Sequence: Synthetic peptide

<400> SEQUENCE: 309

Gly Arg Gly Thr Pro Ser Ser Tyr Ile Asp Asn Leu Thr Phe Pro Lys
1 5 10 15

Val Leu Thr Asp Lys
20

<210> SEQ ID NO 310
<211> LENGTH: 21
<212> TYPE: PRT
<213> ORGANISM: Artificial Sequence
<220> FEATURE:
<223> OTHER INFORMATION: Description of Artificial Sequence: Synthetic peptide

<400> SEQUENCE: 310

Arg Gly Thr Pro Ser Ser Tyr Ile Asp Asn Leu Thr Phe Pro Lys Val
1 5 10 15

Leu Thr Asp Lys Lys
20

<210> SEQ ID NO 311
<211> LENGTH: 21
<212> TYPE: PRT
<213> ORGANISM: Artificial Sequence
<220> FEATURE:
<223> OTHER INFORMATION: Description of Artificial Sequence: Synthetic peptide

<400> SEQUENCE: 311

Gly Thr Pro Ser Ser Tyr Ile Asp Asn Leu Thr Phe Pro Lys Val Leu
1 5 10 15

Thr Asp Lys Lys Tyr
20

<210> SEQ ID NO 312
<211> LENGTH: 21
<212> TYPE: PRT
<213> ORGANISM: Artificial Sequence
<220> FEATURE:

<223> OTHER INFORMATION: Description of Artificial Sequence: Synthetic
peptide

<400> SEQUENCE: 312

Thr Pro Ser Ser Tyr Ile Asp Asn Leu Thr Phe Pro Lys Val Leu Thr
1 5 10 15

Asp Lys Lys Tyr Ser
20

<210> SEQ ID NO 313
<211> LENGTH: 22
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 313

Phe Gln Leu Ala Tyr Leu Val Lys Lys Ile Asp Phe Asp Tyr Thr Pro
1 5 10 15

Asn Trp Gly Arg Gly Thr
20

<210> SEQ ID NO 314
<211> LENGTH: 22
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 314

Gln Leu Ala Tyr Leu Val Lys Lys Ile Asp Phe Asp Tyr Thr Pro Asn
1 5 10 15

Trp Gly Arg Gly Thr Pro
20

<210> SEQ ID NO 315
<211> LENGTH: 22
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 315

Leu Ala Tyr Leu Val Lys Lys Ile Asp Phe Asp Tyr Thr Pro Asn Trp
1 5 10 15

Gly Arg Gly Thr Pro Ser
20

<210> SEQ ID NO 316
<211> LENGTH: 22
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 316

Ala Tyr Leu Val Lys Lys Ile Asp Phe Asp Tyr Thr Pro Asn Trp Gly
1 5 10 15

Arg Gly Thr Pro Ser Ser
20

<210> SEQ ID NO 317
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 317

Tyr Leu Val Lys Lys Ile Asp Phe Asp Tyr Thr Pro Asn Trp Gly Arg
1               5                   10                  15

Gly Thr Pro Ser Ser Tyr
            20

<210> SEQ ID NO 318
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 318

Leu Val Lys Lys Ile Asp Phe Asp Tyr Thr Pro Asn Trp Gly Arg Gly
1               5                   10                  15

Thr Pro Ser Ser Tyr Ile
            20

<210> SEQ ID NO 319
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 319

Val Lys Lys Ile Asp Phe Asp Tyr Thr Pro Asn Trp Gly Arg Gly Thr
1               5                   10                  15

Pro Ser Ser Tyr Ile Asp
            20

<210> SEQ ID NO 320
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 320

Lys Lys Ile Asp Phe Asp Tyr Thr Pro Asn Trp Gly Arg Gly Thr Pro
1               5                   10                  15

Ser Ser Tyr Ile Asp Asn
            20

<210> SEQ ID NO 321
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 321

Lys Ile Asp Phe Asp Tyr Thr Pro Asn Trp Gly Arg Gly Thr Pro Ser
1               5                   10                  15

Ser Tyr Ile Asp Asn Leu
20

<210> SEQ ID NO 322
<211> LENGTH: 22
<212> TYPE: PRT
<213> ORGANISM: Artificial Sequence
<220> FEATURE:
<223> OTHER INFORMATION: Description of Artificial Sequence: Synthetic peptide

<400> SEQUENCE: 322

Ile Asp Phe Asp Tyr Thr Pro Asn Trp Gly Arg Gly Thr Pro Ser Ser
1 5 10 15

Tyr Ile Asp Asn Leu Thr
20

<210> SEQ ID NO 323
<211> LENGTH: 22
<212> TYPE: PRT
<213> ORGANISM: Artificial Sequence
<220> FEATURE:
<223> OTHER INFORMATION: Description of Artificial Sequence: Synthetic peptide

<400> SEQUENCE: 323

Asp Phe Asp Tyr Thr Pro Asn Trp Gly Arg Gly Thr Pro Ser Ser Tyr
1 5 10 15

Ile Asp Asn Leu Thr Phe
20

<210> SEQ ID NO 324
<211> LENGTH: 22
<212> TYPE: PRT
<213> ORGANISM: Artificial Sequence
<220> FEATURE:
<223> OTHER INFORMATION: Description of Artificial Sequence: Synthetic peptide

<400> SEQUENCE: 324

Phe Asp Tyr Thr Pro Asn Trp Gly Arg Gly Thr Pro Ser Ser Tyr Ile
1 5 10 15

Asp Asn Leu Thr Phe Pro
20

<210> SEQ ID NO 325
<211> LENGTH: 22
<212> TYPE: PRT
<213> ORGANISM: Artificial Sequence
<220> FEATURE:
<223> OTHER INFORMATION: Description of Artificial Sequence: Synthetic peptide

<400> SEQUENCE: 325

Asp Tyr Thr Pro Asn Trp Gly Arg Gly Thr Pro Ser Ser Tyr Ile Asp
1 5 10 15

Asn Leu Thr Phe Pro Lys
20

<210> SEQ ID NO 326
<211> LENGTH: 22
<212> TYPE: PRT
<213> ORGANISM: Artificial Sequence
<220> FEATURE:
<223> OTHER INFORMATION: Description of Artificial Sequence: Synthetic peptide

<400> SEQUENCE: 326

Tyr Thr Pro Asn Trp Gly Arg Gly Thr Pro Ser Ser Tyr Ile Asp Asn
1 5 10 15

Leu Thr Phe Pro Lys Val
20

<210> SEQ ID NO 327
<211> LENGTH: 22
<212> TYPE: PRT
<213> ORGANISM: Artificial Sequence
<220> FEATURE:
<223> OTHER INFORMATION: Description of Artificial Sequence: Synthetic peptide

<400> SEQUENCE: 327

Thr Pro Asn Trp Gly Arg Gly Thr Pro Ser Ser Tyr Ile Asp Asn Leu
1 5 10 15

Thr Phe Pro Lys Val Leu
20

<210> SEQ ID NO 328
<211> LENGTH: 22
<212> TYPE: PRT
<213> ORGANISM: Artificial Sequence
<220> FEATURE:
<223> OTHER INFORMATION: Description of Artificial Sequence: Synthetic peptide

<400> SEQUENCE: 328

Pro Asn Trp Gly Arg Gly Thr Pro Ser Ser Tyr Ile Asp Asn Leu Thr
1 5 10 15

Phe Pro Lys Val Leu Thr
20

<210> SEQ ID NO 329
<211> LENGTH: 22
<212> TYPE: PRT
<213> ORGANISM: Artificial Sequence
<220> FEATURE:
<223> OTHER INFORMATION: Description of Artificial Sequence: Synthetic peptide

<400> SEQUENCE: 329

Asn Trp Gly Arg Gly Thr Pro Ser Ser Tyr Ile Asp Asn Leu Thr Phe
1 5 10 15

Pro Lys Val Leu Thr Asp
20

<210> SEQ ID NO 330
<211> LENGTH: 22
<212> TYPE: PRT
<213> ORGANISM: Artificial Sequence
<220> FEATURE:
<223> OTHER INFORMATION: Description of Artificial Sequence: Synthetic peptide

<400> SEQUENCE: 330

Trp Gly Arg Gly Thr Pro Ser Ser Tyr Ile Asp Asn Leu Thr Phe Pro
1 5 10 15

Lys Val Leu Thr Asp Lys
20

<210> SEQ ID NO 331
<211> LENGTH: 22

<212> TYPE: PRT
<213> ORGANISM: Artificial Sequence
<220> FEATURE:
<223> OTHER INFORMATION: Description of Artificial Sequence: Synthetic
peptide

<400> SEQUENCE: 331

Gly Arg Gly Thr Pro Ser Ser Tyr Ile Asp Asn Leu Thr Phe Pro Lys
1 5 10 15

Val Leu Thr Asp Lys Lys
20

<210> SEQ ID NO 332
<211> LENGTH: 22
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 332

Arg Gly Thr Pro Ser Ser Tyr Ile Asp Asn Leu Thr Phe Pro Lys Val
1 5 10 15

Leu Thr Asp Lys Lys Tyr
20

<210> SEQ ID NO 333
<211> LENGTH: 22
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 333

Gly Thr Pro Ser Ser Tyr Ile Asp Asn Leu Thr Phe Pro Lys Val Leu
1 5 10 15

Thr Asp Lys Lys Tyr Ser
20

<210> SEQ ID NO 334
<211> LENGTH: 22
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 334

Thr Pro Ser Ser Tyr Ile Asp Asn Leu Thr Phe Pro Lys Val Leu Thr
1 5 10 15

Asp Lys Lys Tyr Ser Tyr
20

<210> SEQ ID NO 335
<211> LENGTH: 23
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 335

Thr Phe Gln Leu Ala Tyr Leu Val Lys Lys Ile Asp Phe Asp Tyr Thr
1 5 10 15

Pro Asn Trp Gly Arg Gly Thr

20

<210> SEQ ID NO 336
<211> LENGTH: 23
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 336

Phe Gln Leu Ala Tyr Leu Val Lys Lys Ile Asp Phe Asp Tyr Thr Pro
1 5 10 15

Asn Trp Gly Arg Gly Thr Pro
20

<210> SEQ ID NO 337
<211> LENGTH: 23
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 337

Gln Leu Ala Tyr Leu Val Lys Lys Ile Asp Phe Asp Tyr Thr Pro Asn
1 5 10 15

Trp Gly Arg Gly Thr Pro Ser
20

<210> SEQ ID NO 338
<211> LENGTH: 23
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 338

Leu Ala Tyr Leu Val Lys Lys Ile Asp Phe Asp Tyr Thr Pro Asn Trp
1 5 10 15

Gly Arg Gly Thr Pro Ser Ser
20

<210> SEQ ID NO 339
<211> LENGTH: 23
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 339

Ala Tyr Leu Val Lys Lys Ile Asp Phe Asp Tyr Thr Pro Asn Trp Gly
1 5 10 15

Arg Gly Thr Pro Ser Ser Tyr
20

<210> SEQ ID NO 340
<211> LENGTH: 23
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 340

Tyr Leu Val Lys Lys Ile Asp Phe Asp Tyr Thr Pro Asn Trp Gly Arg
1 5 10 15

Gly Thr Pro Ser Ser Tyr Ile
20

<210> SEQ ID NO 341
<211> LENGTH: 23
<212> TYPE: PRT
<213> ORGANISM: Artificial Sequence
<220> FEATURE:
<223> OTHER INFORMATION: Description of Artificial Sequence: Synthetic peptide

<400> SEQUENCE: 341

Leu Val Lys Lys Ile Asp Phe Asp Tyr Thr Pro Asn Trp Gly Arg Gly
1 5 10 15

Thr Pro Ser Ser Tyr Ile Asp
20

<210> SEQ ID NO 342
<211> LENGTH: 23
<212> TYPE: PRT
<213> ORGANISM: Artificial Sequence
<220> FEATURE:
<223> OTHER INFORMATION: Description of Artificial Sequence: Synthetic peptide

<400> SEQUENCE: 342

Val Lys Lys Ile Asp Phe Asp Tyr Thr Pro Asn Trp Gly Arg Gly Thr
1 5 10 15

Pro Ser Ser Tyr Ile Asp Asn
20

<210> SEQ ID NO 343
<211> LENGTH: 23
<212> TYPE: PRT
<213> ORGANISM: Artificial Sequence
<220> FEATURE:
<223> OTHER INFORMATION: Description of Artificial Sequence: Synthetic peptide

<400> SEQUENCE: 343

Lys Lys Ile Asp Phe Asp Tyr Thr Pro Asn Trp Gly Arg Gly Thr Pro
1 5 10 15

Ser Ser Tyr Ile Asp Asn Leu
20

<210> SEQ ID NO 344
<211> LENGTH: 23
<212> TYPE: PRT
<213> ORGANISM: Artificial Sequence
<220> FEATURE:
<223> OTHER INFORMATION: Description of Artificial Sequence: Synthetic peptide

<400> SEQUENCE: 344

Lys Ile Asp Phe Asp Tyr Thr Pro Asn Trp Gly Arg Gly Thr Pro Ser
1 5 10 15

Ser Tyr Ile Asp Asn Leu Thr
20

<210> SEQ ID NO 345
<211> LENGTH: 23
<212> TYPE: PRT
<213> ORGANISM: Artificial Sequence
<220> FEATURE:
<223> OTHER INFORMATION: Description of Artificial Sequence: Synthetic peptide

<400> SEQUENCE: 345

Ile Asp Phe Asp Tyr Thr Pro Asn Trp Gly Arg Gly Thr Pro Ser Ser
1 5 10 15

Tyr Ile Asp Asn Leu Thr Phe
20

<210> SEQ ID NO 346
<211> LENGTH: 23
<212> TYPE: PRT
<213> ORGANISM: Artificial Sequence
<220> FEATURE:
<223> OTHER INFORMATION: Description of Artificial Sequence: Synthetic peptide

<400> SEQUENCE: 346

Asp Phe Asp Tyr Thr Pro Asn Trp Gly Arg Gly Thr Pro Ser Ser Tyr
1 5 10 15

Ile Asp Asn Leu Thr Phe Pro
20

<210> SEQ ID NO 347
<211> LENGTH: 23
<212> TYPE: PRT
<213> ORGANISM: Artificial Sequence
<220> FEATURE:
<223> OTHER INFORMATION: Description of Artificial Sequence: Synthetic peptide

<400> SEQUENCE: 347

Phe Asp Tyr Thr Pro Asn Trp Gly Arg Gly Thr Pro Ser Ser Tyr Ile
1 5 10 15

Asp Asn Leu Thr Phe Pro Lys
20

<210> SEQ ID NO 348
<211> LENGTH: 23
<212> TYPE: PRT
<213> ORGANISM: Artificial Sequence
<220> FEATURE:
<223> OTHER INFORMATION: Description of Artificial Sequence: Synthetic peptide

<400> SEQUENCE: 348

Asp Tyr Thr Pro Asn Trp Gly Arg Gly Thr Pro Ser Ser Tyr Ile Asp
1 5 10 15

Asn Leu Thr Phe Pro Lys Val
20

<210> SEQ ID NO 349
<211> LENGTH: 23
<212> TYPE: PRT
<213> ORGANISM: Artificial Sequence
<220> FEATURE:
<223> OTHER INFORMATION: Description of Artificial Sequence: Synthetic peptide

<400> SEQUENCE: 349

Tyr Thr Pro Asn Trp Gly Arg Gly Thr Pro Ser Ser Tyr Ile Asp Asn
1 5 10 15

Leu Thr Phe Pro Lys Val Leu
20

```
<210> SEQ ID NO 350
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 350

Thr Pro Asn Trp Gly Arg Gly Thr Pro Ser Ser Tyr Ile Asp Asn Leu
1               5                   10                  15

Thr Phe Pro Lys Val Leu Thr
            20


<210> SEQ ID NO 351
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 351

Pro Asn Trp Gly Arg Gly Thr Pro Ser Ser Tyr Ile Asp Asn Leu Thr
1               5                   10                  15

Phe Pro Lys Val Leu Thr Asp
            20


<210> SEQ ID NO 352
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 352

Asn Trp Gly Arg Gly Thr Pro Ser Ser Tyr Ile Asp Asn Leu Thr Phe
1               5                   10                  15

Pro Lys Val Leu Thr Asp Lys
            20


<210> SEQ ID NO 353
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 353

Trp Gly Arg Gly Thr Pro Ser Ser Tyr Ile Asp Asn Leu Thr Phe Pro
1               5                   10                  15

Lys Val Leu Thr Asp Lys Lys
            20


<210> SEQ ID NO 354
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 354

Gly Arg Gly Thr Pro Ser Ser Tyr Ile Asp Asn Leu Thr Phe Pro Lys
```

```
1               5                   10                  15

Val Leu Thr Asp Lys Lys Tyr
            20


<210> SEQ ID NO 355
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 355

Arg Gly Thr Pro Ser Ser Tyr Ile Asp Asn Leu Thr Phe Pro Lys Val
1               5                   10                  15

Leu Thr Asp Lys Lys Tyr Ser
            20


<210> SEQ ID NO 356
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 356

Gly Thr Pro Ser Ser Tyr Ile Asp Asn Leu Thr Phe Pro Lys Val Leu
1               5                   10                  15

Thr Asp Lys Lys Tyr Ser Tyr
            20


<210> SEQ ID NO 357
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 357

Thr Pro Ser Ser Tyr Ile Asp Asn Leu Thr Phe Pro Lys Val Leu Thr
1               5                   10                  15

Asp Lys Lys Tyr Ser Tyr Arg
            20


<210> SEQ ID NO 358
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 358

Leu Thr Phe Gln Leu Ala Tyr Leu Val Lys Lys Ile Asp Phe Asp Tyr
1               5                   10                  15

Thr Pro Asn Trp Gly Arg Gly Thr
            20


<210> SEQ ID NO 359
<211> LENGTH: 24
<212> TYPE: PRT
<213> ORGANISM: Artificial Sequence
<220> FEATURE:
<223> OTHER INFORMATION: Description of Artificial Sequence: Synthetic
```

peptide

<400> SEQUENCE: 359

Thr Phe Gln Leu Ala Tyr Leu Val Lys Lys Ile Asp Phe Asp Tyr Thr
1 5 10 15

Pro Asn Trp Gly Arg Gly Thr Pro
20

<210> SEQ ID NO 360
<211> LENGTH: 24
<212> TYPE: PRT
<213> ORGANISM: Artificial Sequence
<220> FEATURE:
<223> OTHER INFORMATION: Description of Artificial Sequence: Synthetic peptide

<400> SEQUENCE: 360

Phe Gln Leu Ala Tyr Leu Val Lys Lys Ile Asp Phe Asp Tyr Thr Pro
1 5 10 15

Asn Trp Gly Arg Gly Thr Pro Ser
20

<210> SEQ ID NO 361
<211> LENGTH: 24
<212> TYPE: PRT
<213> ORGANISM: Artificial Sequence
<220> FEATURE:
<223> OTHER INFORMATION: Description of Artificial Sequence: Synthetic peptide

<400> SEQUENCE: 361

Gln Leu Ala Tyr Leu Val Lys Lys Ile Asp Phe Asp Tyr Thr Pro Asn
1 5 10 15

Trp Gly Arg Gly Thr Pro Ser Ser
20

<210> SEQ ID NO 362
<211> LENGTH: 24
<212> TYPE: PRT
<213> ORGANISM: Artificial Sequence
<220> FEATURE:
<223> OTHER INFORMATION: Description of Artificial Sequence: Synthetic peptide

<400> SEQUENCE: 362

Leu Ala Tyr Leu Val Lys Lys Ile Asp Phe Asp Tyr Thr Pro Asn Trp
1 5 10 15

Gly Arg Gly Thr Pro Ser Ser Tyr
20

<210> SEQ ID NO 363
<211> LENGTH: 24
<212> TYPE: PRT
<213> ORGANISM: Artificial Sequence
<220> FEATURE:
<223> OTHER INFORMATION: Description of Artificial Sequence: Synthetic peptide

<400> SEQUENCE: 363

Ala Tyr Leu Val Lys Lys Ile Asp Phe Asp Tyr Thr Pro Asn Trp Gly
1 5 10 15

Arg Gly Thr Pro Ser Ser Tyr Ile
20

<210> SEQ ID NO 364

<211> LENGTH: 24
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 364

Tyr Leu Val Lys Lys Ile Asp Phe Asp Tyr Thr Pro Asn Trp Gly Arg
1 5 10 15

Gly Thr Pro Ser Ser Tyr Ile Asp
20

<210> SEQ ID NO 365
<211> LENGTH: 24
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 365

Leu Val Lys Lys Ile Asp Phe Asp Tyr Thr Pro Asn Trp Gly Arg Gly
1 5 10 15

Thr Pro Ser Ser Tyr Ile Asp Asn
20

<210> SEQ ID NO 366
<211> LENGTH: 24
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 366

Val Lys Lys Ile Asp Phe Asp Tyr Thr Pro Asn Trp Gly Arg Gly Thr
1 5 10 15

Pro Ser Ser Tyr Ile Asp Asn Leu
20

<210> SEQ ID NO 367
<211> LENGTH: 24
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 367

Lys Lys Ile Asp Phe Asp Tyr Thr Pro Asn Trp Gly Arg Gly Thr Pro
1 5 10 15

Ser Ser Tyr Ile Asp Asn Leu Thr
20

<210> SEQ ID NO 368
<211> LENGTH: 24
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 368

Lys Ile Asp Phe Asp Tyr Thr Pro Asn Trp Gly Arg Gly Thr Pro Ser
1 5 10 15

```
Ser Tyr Ile Asp Asn Leu Thr Phe
            20


<210> SEQ ID NO 369
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 369

Ile Asp Phe Asp Tyr Thr Pro Asn Trp Gly Arg Gly Thr Pro Ser Ser
1               5                   10                  15

Tyr Ile Asp Asn Leu Thr Phe Pro
            20


<210> SEQ ID NO 370
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 370

Asp Phe Asp Tyr Thr Pro Asn Trp Gly Arg Gly Thr Pro Ser Ser Tyr
1               5                   10                  15

Ile Asp Asn Leu Thr Phe Pro Lys
            20


<210> SEQ ID NO 371
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 371

Phe Asp Tyr Thr Pro Asn Trp Gly Arg Gly Thr Pro Ser Ser Tyr Ile
1               5                   10                  15

Asp Asn Leu Thr Phe Pro Lys Val
            20


<210> SEQ ID NO 372
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 372

Asp Tyr Thr Pro Asn Trp Gly Arg Gly Thr Pro Ser Ser Tyr Ile Asp
1               5                   10                  15

Asn Leu Thr Phe Pro Lys Val Leu
            20


<210> SEQ ID NO 373
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 373

Tyr Thr Pro Asn Trp Gly Arg Gly Thr Pro Ser Ser Tyr Ile Asp Asn
1 5 10 15

Leu Thr Phe Pro Lys Val Leu Thr
20

<210> SEQ ID NO 374
<211> LENGTH: 24
<212> TYPE: PRT
<213> ORGANISM: Artificial Sequence
<220> FEATURE:
<223> OTHER INFORMATION: Description of Artificial Sequence: Synthetic peptide

<400> SEQUENCE: 374

Thr Pro Asn Trp Gly Arg Gly Thr Pro Ser Ser Tyr Ile Asp Asn Leu
1 5 10 15

Thr Phe Pro Lys Val Leu Thr Asp
20

<210> SEQ ID NO 375
<211> LENGTH: 24
<212> TYPE: PRT
<213> ORGANISM: Artificial Sequence
<220> FEATURE:
<223> OTHER INFORMATION: Description of Artificial Sequence: Synthetic peptide

<400> SEQUENCE: 375

Pro Asn Trp Gly Arg Gly Thr Pro Ser Ser Tyr Ile Asp Asn Leu Thr
1 5 10 15

Phe Pro Lys Val Leu Thr Asp Lys
20

<210> SEQ ID NO 376
<211> LENGTH: 24
<212> TYPE: PRT
<213> ORGANISM: Artificial Sequence
<220> FEATURE:
<223> OTHER INFORMATION: Description of Artificial Sequence: Synthetic peptide

<400> SEQUENCE: 376

Asn Trp Gly Arg Gly Thr Pro Ser Ser Tyr Ile Asp Asn Leu Thr Phe
1 5 10 15

Pro Lys Val Leu Thr Asp Lys Lys
20

<210> SEQ ID NO 377
<211> LENGTH: 24
<212> TYPE: PRT
<213> ORGANISM: Artificial Sequence
<220> FEATURE:
<223> OTHER INFORMATION: Description of Artificial Sequence: Synthetic peptide

<400> SEQUENCE: 377

Trp Gly Arg Gly Thr Pro Ser Ser Tyr Ile Asp Asn Leu Thr Phe Pro
1 5 10 15

Lys Val Leu Thr Asp Lys Lys Tyr
20

<210> SEQ ID NO 378
<211> LENGTH: 24
<212> TYPE: PRT

<213> ORGANISM: Artificial Sequence
<220> FEATURE:
<223> OTHER INFORMATION: Description of Artificial Sequence: Synthetic
peptide

<400> SEQUENCE: 378

Gly Arg Gly Thr Pro Ser Ser Tyr Ile Asp Asn Leu Thr Phe Pro Lys
1 5 10 15

Val Leu Thr Asp Lys Lys Tyr Ser
20

<210> SEQ ID NO 379
<211> LENGTH: 24
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 379

Arg Gly Thr Pro Ser Ser Tyr Ile Asp Asn Leu Thr Phe Pro Lys Val
1 5 10 15

Leu Thr Asp Lys Lys Tyr Ser Tyr
20

<210> SEQ ID NO 380
<211> LENGTH: 24
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 380

Gly Thr Pro Ser Ser Tyr Ile Asp Asn Leu Thr Phe Pro Lys Val Leu
1 5 10 15

Thr Asp Lys Lys Tyr Ser Tyr Arg
20

<210> SEQ ID NO 381
<211> LENGTH: 24
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 381

Thr Pro Ser Ser Tyr Ile Asp Asn Leu Thr Phe Pro Lys Val Leu Thr
1 5 10 15

Asp Lys Lys Tyr Ser Tyr Arg Val
20

<210> SEQ ID NO 382
<211> LENGTH: 25
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 382

Ser Leu Thr Phe Gln Leu Ala Tyr Leu Val Lys Lys Ile Asp Phe Asp
1 5 10 15

Tyr Thr Pro Asn Trp Gly Arg Gly Thr
20 25

<210> SEQ ID NO 383
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 383

```
Leu Thr Phe Gln Leu Ala Tyr Leu Val Lys Lys Ile Asp Phe Asp Tyr
1               5                   10                  15

Thr Pro Asn Trp Gly Arg Gly Thr Pro
            20                  25
```

<210> SEQ ID NO 384
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 384

```
Thr Phe Gln Leu Ala Tyr Leu Val Lys Lys Ile Asp Phe Asp Tyr Thr
1               5                   10                  15

Pro Asn Trp Gly Arg Gly Thr Pro Ser
            20                  25
```

<210> SEQ ID NO 385
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 385

```
Phe Gln Leu Ala Tyr Leu Val Lys Lys Ile Asp Phe Asp Tyr Thr Pro
1               5                   10                  15

Asn Trp Gly Arg Gly Thr Pro Ser Ser
            20                  25
```

<210> SEQ ID NO 386
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 386

```
Gln Leu Ala Tyr Leu Val Lys Lys Ile Asp Phe Asp Tyr Thr Pro Asn
1               5                   10                  15

Trp Gly Arg Gly Thr Pro Ser Ser Tyr
            20                  25
```

<210> SEQ ID NO 387
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 387

```
Leu Ala Tyr Leu Val Lys Lys Ile Asp Phe Asp Tyr Thr Pro Asn Trp
1               5                   10                  15

Gly Arg Gly Thr Pro Ser Ser Tyr Ile
            20                  25


<210> SEQ ID NO 388
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 388

Ala Tyr Leu Val Lys Lys Ile Asp Phe Asp Tyr Thr Pro Asn Trp Gly
1               5                   10                  15

Arg Gly Thr Pro Ser Ser Tyr Ile Asp
            20                  25


<210> SEQ ID NO 389
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 389

Tyr Leu Val Lys Lys Ile Asp Phe Asp Tyr Thr Pro Asn Trp Gly Arg
1               5                   10                  15

Gly Thr Pro Ser Ser Tyr Ile Asp Asn
            20                  25


<210> SEQ ID NO 390
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 390

Leu Val Lys Lys Ile Asp Phe Asp Tyr Thr Pro Asn Trp Gly Arg Gly
1               5                   10                  15

Thr Pro Ser Ser Tyr Ile Asp Asn Leu
            20                  25


<210> SEQ ID NO 391
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 391

Val Lys Lys Ile Asp Phe Asp Tyr Thr Pro Asn Trp Gly Arg Gly Thr
1               5                   10                  15

Pro Ser Ser Tyr Ile Asp Asn Leu Thr
            20                  25


<210> SEQ ID NO 392
<211> LENGTH: 25
<212> TYPE: PRT
<213> ORGANISM: Artificial Sequence
<220> FEATURE:
```

<223> OTHER INFORMATION: Description of Artificial Sequence: Synthetic
      peptide

<400> SEQUENCE: 392

Lys Lys Ile Asp Phe Asp Tyr Thr Pro Asn Trp Gly Arg Gly Thr Pro
1               5                   10                  15

Ser Ser Tyr Ile Asp Asn Leu Thr Phe
            20                  25

<210> SEQ ID NO 393
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 393

Lys Ile Asp Phe Asp Tyr Thr Pro Asn Trp Gly Arg Gly Thr Pro Ser
1               5                   10                  15

Ser Tyr Ile Asp Asn Leu Thr Phe Pro
            20                  25

<210> SEQ ID NO 394
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 394

Ile Asp Phe Asp Tyr Thr Pro Asn Trp Gly Arg Gly Thr Pro Ser Ser
1               5                   10                  15

Tyr Ile Asp Asn Leu Thr Phe Pro Lys
            20                  25

<210> SEQ ID NO 395
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 395

Asp Phe Asp Tyr Thr Pro Asn Trp Gly Arg Gly Thr Pro Ser Ser Tyr
1               5                   10                  15

Ile Asp Asn Leu Thr Phe Pro Lys Val
            20                  25

<210> SEQ ID NO 396
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 396

Phe Asp Tyr Thr Pro Asn Trp Gly Arg Gly Thr Pro Ser Ser Tyr Ile
1               5                   10                  15

Asp Asn Leu Thr Phe Pro Lys Val Leu
            20                  25

```
<210> SEQ ID NO 397
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 397

Asp Tyr Thr Pro Asn Trp Gly Arg Gly Thr Pro Ser Ser Tyr Ile Asp
1               5                   10                  15

Asn Leu Thr Phe Pro Lys Val Leu Thr
            20                  25


<210> SEQ ID NO 398
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 398

Tyr Thr Pro Asn Trp Gly Arg Gly Thr Pro Ser Ser Tyr Ile Asp Asn
1               5                   10                  15

Leu Thr Phe Pro Lys Val Leu Thr Asp
            20                  25


<210> SEQ ID NO 399
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 399

Thr Pro Asn Trp Gly Arg Gly Thr Pro Ser Ser Tyr Ile Asp Asn Leu
1               5                   10                  15

Thr Phe Pro Lys Val Leu Thr Asp Lys
            20                  25


<210> SEQ ID NO 400
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 400

Pro Asn Trp Gly Arg Gly Thr Pro Ser Ser Tyr Ile Asp Asn Leu Thr
1               5                   10                  15

Phe Pro Lys Val Leu Thr Asp Lys Lys
            20                  25


<210> SEQ ID NO 401
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 401

Asn Trp Gly Arg Gly Thr Pro Ser Ser Tyr Ile Asp Asn Leu Thr Phe
1               5                   10                  15
```

Pro Lys Val Leu Thr Asp Lys Lys Tyr
20 25

<210> SEQ ID NO 402
<211> LENGTH: 25
<212> TYPE: PRT
<213> ORGANISM: Artificial Sequence
<220> FEATURE:
<223> OTHER INFORMATION: Description of Artificial Sequence: Synthetic peptide

<400> SEQUENCE: 402

Trp Gly Arg Gly Thr Pro Ser Ser Tyr Ile Asp Asn Leu Thr Phe Pro
1 5 10 15

Lys Val Leu Thr Asp Lys Lys Tyr Ser
20 25

<210> SEQ ID NO 403
<211> LENGTH: 25
<212> TYPE: PRT
<213> ORGANISM: Artificial Sequence
<220> FEATURE:
<223> OTHER INFORMATION: Description of Artificial Sequence: Synthetic peptide

<400> SEQUENCE: 403

Gly Arg Gly Thr Pro Ser Ser Tyr Ile Asp Asn Leu Thr Phe Pro Lys
1 5 10 15

Val Leu Thr Asp Lys Lys Tyr Ser Tyr
20 25

<210> SEQ ID NO 404
<211> LENGTH: 25
<212> TYPE: PRT
<213> ORGANISM: Artificial Sequence
<220> FEATURE:
<223> OTHER INFORMATION: Description of Artificial Sequence: Synthetic peptide

<400> SEQUENCE: 404

Arg Gly Thr Pro Ser Ser Tyr Ile Asp Asn Leu Thr Phe Pro Lys Val
1 5 10 15

Leu Thr Asp Lys Lys Tyr Ser Tyr Arg
20 25

<210> SEQ ID NO 405
<211> LENGTH: 25
<212> TYPE: PRT
<213> ORGANISM: Artificial Sequence
<220> FEATURE:
<223> OTHER INFORMATION: Description of Artificial Sequence: Synthetic peptide

<400> SEQUENCE: 405

Gly Thr Pro Ser Ser Tyr Ile Asp Asn Leu Thr Phe Pro Lys Val Leu
1 5 10 15

Thr Asp Lys Lys Tyr Ser Tyr Arg Val
20 25

<210> SEQ ID NO 406
<211> LENGTH: 25
<212> TYPE: PRT
<213> ORGANISM: Artificial Sequence
<220> FEATURE:
<223> OTHER INFORMATION: Description of Artificial Sequence: Synthetic peptide

<400> SEQUENCE: 406

Thr Pro Ser Ser Tyr Ile Asp Asn Leu Thr Phe Pro Lys Val Leu Thr
1 5 10 15

Asp Lys Lys Tyr Ser Tyr Arg Val Val
20 25

<210> SEQ ID NO 407
<211> LENGTH: 26
<212> TYPE: PRT
<213> ORGANISM: Artificial Sequence
<220> FEATURE:
<223> OTHER INFORMATION: Description of Artificial Sequence: Synthetic peptide

<400> SEQUENCE: 407

Thr Ser Leu Thr Phe Gln Leu Ala Tyr Leu Val Lys Lys Ile Asp Phe
1 5 10 15

Asp Tyr Thr Pro Asn Trp Gly Arg Gly Thr
20 25

<210> SEQ ID NO 408
<211> LENGTH: 26
<212> TYPE: PRT
<213> ORGANISM: Artificial Sequence
<220> FEATURE:
<223> OTHER INFORMATION: Description of Artificial Sequence: Synthetic peptide

<400> SEQUENCE: 408

Ser Leu Thr Phe Gln Leu Ala Tyr Leu Val Lys Lys Ile Asp Phe Asp
1 5 10 15

Tyr Thr Pro Asn Trp Gly Arg Gly Thr Pro
20 25

<210> SEQ ID NO 409
<211> LENGTH: 26
<212> TYPE: PRT
<213> ORGANISM: Artificial Sequence
<220> FEATURE:
<223> OTHER INFORMATION: Description of Artificial Sequence: Synthetic peptide

<400> SEQUENCE: 409

Leu Thr Phe Gln Leu Ala Tyr Leu Val Lys Lys Ile Asp Phe Asp Tyr
1 5 10 15

Thr Pro Asn Trp Gly Arg Gly Thr Pro Ser
20 25

<210> SEQ ID NO 410
<211> LENGTH: 26
<212> TYPE: PRT
<213> ORGANISM: Artificial Sequence
<220> FEATURE:
<223> OTHER INFORMATION: Description of Artificial Sequence: Synthetic peptide

<400> SEQUENCE: 410

Thr Phe Gln Leu Ala Tyr Leu Val Lys Lys Ile Asp Phe Asp Tyr Thr
1 5 10 15

Pro Asn Trp Gly Arg Gly Thr Pro Ser Ser
20 25

<210> SEQ ID NO 411
<211> LENGTH: 26

<212> TYPE: PRT
<213> ORGANISM: Artificial Sequence
<220> FEATURE:
<223> OTHER INFORMATION: Description of Artificial Sequence: Synthetic
peptide

<400> SEQUENCE: 411

Phe Gln Leu Ala Tyr Leu Val Lys Lys Ile Asp Phe Asp Tyr Thr Pro
1               5                   10                  15

Asn Trp Gly Arg Gly Thr Pro Ser Ser Tyr
            20                  25

<210> SEQ ID NO 412
<211> LENGTH: 26
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 412

Gln Leu Ala Tyr Leu Val Lys Lys Ile Asp Phe Asp Tyr Thr Pro Asn
1               5                   10                  15

Trp Gly Arg Gly Thr Pro Ser Ser Tyr Ile
            20                  25

<210> SEQ ID NO 413
<211> LENGTH: 26
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 413

Leu Ala Tyr Leu Val Lys Lys Ile Asp Phe Asp Tyr Thr Pro Asn Trp
1               5                   10                  15

Gly Arg Gly Thr Pro Ser Ser Tyr Ile Asp
            20                  25

<210> SEQ ID NO 414
<211> LENGTH: 26
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 414

Ala Tyr Leu Val Lys Lys Ile Asp Phe Asp Tyr Thr Pro Asn Trp Gly
1               5                   10                  15

Arg Gly Thr Pro Ser Ser Tyr Ile Asp Asn
            20                  25

<210> SEQ ID NO 415
<211> LENGTH: 26
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 415

Tyr Leu Val Lys Lys Ile Asp Phe Asp Tyr Thr Pro Asn Trp Gly Arg
1               5                   10                  15

Gly Thr Pro Ser Ser Tyr Ile Asp Asn Leu 20 25

<210> SEQ ID NO 416
<211> LENGTH: 26
<212> TYPE: PRT
<213> ORGANISM: Artificial Sequence
<220> FEATURE:
<223> OTHER INFORMATION: Description of Artificial Sequence: Synthetic peptide

<400> SEQUENCE: 416

Leu Val Lys Lys Ile Asp Phe Asp Tyr Thr Pro Asn Trp Gly Arg Gly
1 5 10 15

Thr Pro Ser Ser Tyr Ile Asp Asn Leu Thr
20 25

<210> SEQ ID NO 417
<211> LENGTH: 26
<212> TYPE: PRT
<213> ORGANISM: Artificial Sequence
<220> FEATURE:
<223> OTHER INFORMATION: Description of Artificial Sequence: Synthetic peptide

<400> SEQUENCE: 417

Val Lys Lys Ile Asp Phe Asp Tyr Thr Pro Asn Trp Gly Arg Gly Thr
1 5 10 15

Pro Ser Ser Tyr Ile Asp Asn Leu Thr Phe
20 25

<210> SEQ ID NO 418
<211> LENGTH: 26
<212> TYPE: PRT
<213> ORGANISM: Artificial Sequence
<220> FEATURE:
<223> OTHER INFORMATION: Description of Artificial Sequence: Synthetic peptide

<400> SEQUENCE: 418

Lys Lys Ile Asp Phe Asp Tyr Thr Pro Asn Trp Gly Arg Gly Thr Pro
1 5 10 15

Ser Ser Tyr Ile Asp Asn Leu Thr Phe Pro
20 25

<210> SEQ ID NO 419
<211> LENGTH: 26
<212> TYPE: PRT
<213> ORGANISM: Artificial Sequence
<220> FEATURE:
<223> OTHER INFORMATION: Description of Artificial Sequence: Synthetic peptide

<400> SEQUENCE: 419

Lys Ile Asp Phe Asp Tyr Thr Pro Asn Trp Gly Arg Gly Thr Pro Ser
1 5 10 15

Ser Tyr Ile Asp Asn Leu Thr Phe Pro Lys
20 25

<210> SEQ ID NO 420
<211> LENGTH: 26
<212> TYPE: PRT
<213> ORGANISM: Artificial Sequence
<220> FEATURE:
<223> OTHER INFORMATION: Description of Artificial Sequence: Synthetic peptide

<400> SEQUENCE: 420

Ile Asp Phe Asp Tyr Thr Pro Asn Trp Gly Arg Gly Thr Pro Ser Ser
1 5 10 15

Tyr Ile Asp Asn Leu Thr Phe Pro Lys Val
20 25

<210> SEQ ID NO 421
<211> LENGTH: 26
<212> TYPE: PRT
<213> ORGANISM: Artificial Sequence
<220> FEATURE:
<223> OTHER INFORMATION: Description of Artificial Sequence: Synthetic peptide

<400> SEQUENCE: 421

Asp Phe Asp Tyr Thr Pro Asn Trp Gly Arg Gly Thr Pro Ser Ser Tyr
1 5 10 15

Ile Asp Asn Leu Thr Phe Pro Lys Val Leu
20 25

<210> SEQ ID NO 422
<211> LENGTH: 26
<212> TYPE: PRT
<213> ORGANISM: Artificial Sequence
<220> FEATURE:
<223> OTHER INFORMATION: Description of Artificial Sequence: Synthetic peptide

<400> SEQUENCE: 422

Phe Asp Tyr Thr Pro Asn Trp Gly Arg Gly Thr Pro Ser Ser Tyr Ile
1 5 10 15

Asp Asn Leu Thr Phe Pro Lys Val Leu Thr
20 25

<210> SEQ ID NO 423
<211> LENGTH: 26
<212> TYPE: PRT
<213> ORGANISM: Artificial Sequence
<220> FEATURE:
<223> OTHER INFORMATION: Description of Artificial Sequence: Synthetic peptide

<400> SEQUENCE: 423

Asp Tyr Thr Pro Asn Trp Gly Arg Gly Thr Pro Ser Ser Tyr Ile Asp
1 5 10 15

Asn Leu Thr Phe Pro Lys Val Leu Thr Asp
20 25

<210> SEQ ID NO 424
<211> LENGTH: 26
<212> TYPE: PRT
<213> ORGANISM: Artificial Sequence
<220> FEATURE:
<223> OTHER INFORMATION: Description of Artificial Sequence: Synthetic peptide

<400> SEQUENCE: 424

Tyr Thr Pro Asn Trp Gly Arg Gly Thr Pro Ser Ser Tyr Ile Asp Asn
1 5 10 15

Leu Thr Phe Pro Lys Val Leu Thr Asp Lys
20 25

<210> SEQ ID NO 425
<211> LENGTH: 26
<212> TYPE: PRT
<213> ORGANISM: Artificial Sequence
<220> FEATURE:
<223> OTHER INFORMATION: Description of Artificial Sequence: Synthetic peptide

<400> SEQUENCE: 425

```
Thr Pro Asn Trp Gly Arg Gly Thr Pro Ser Ser Tyr Ile Asp Asn Leu
1               5                   10                  15

Thr Phe Pro Lys Val Leu Thr Asp Lys Lys
            20                  25
```

<210> SEQ ID NO 426
<211> LENGTH: 26
<212> TYPE: PRT
<213> ORGANISM: Artificial Sequence
<220> FEATURE:
<223> OTHER INFORMATION: Description of Artificial Sequence: Synthetic peptide

<400> SEQUENCE: 426

```
Pro Asn Trp Gly Arg Gly Thr Pro Ser Ser Tyr Ile Asp Asn Leu Thr
1               5                   10                  15

Phe Pro Lys Val Leu Thr Asp Lys Lys Tyr
            20                  25
```

<210> SEQ ID NO 427
<211> LENGTH: 26
<212> TYPE: PRT
<213> ORGANISM: Artificial Sequence
<220> FEATURE:
<223> OTHER INFORMATION: Description of Artificial Sequence: Synthetic peptide

<400> SEQUENCE: 427

```
Asn Trp Gly Arg Gly Thr Pro Ser Ser Tyr Ile Asp Asn Leu Thr Phe
1               5                   10                  15

Pro Lys Val Leu Thr Asp Lys Lys Tyr Ser
            20                  25
```

<210> SEQ ID NO 428
<211> LENGTH: 26
<212> TYPE: PRT
<213> ORGANISM: Artificial Sequence
<220> FEATURE:
<223> OTHER INFORMATION: Description of Artificial Sequence: Synthetic peptide

<400> SEQUENCE: 428

```
Trp Gly Arg Gly Thr Pro Ser Ser Tyr Ile Asp Asn Leu Thr Phe Pro
1               5                   10                  15

Lys Val Leu Thr Asp Lys Lys Tyr Ser Tyr
            20                  25
```

<210> SEQ ID NO 429
<211> LENGTH: 26
<212> TYPE: PRT
<213> ORGANISM: Artificial Sequence
<220> FEATURE:
<223> OTHER INFORMATION: Description of Artificial Sequence: Synthetic peptide

<400> SEQUENCE: 429

```
Gly Arg Gly Thr Pro Ser Ser Tyr Ile Asp Asn Leu Thr Phe Pro Lys
1               5                   10                  15

Val Leu Thr Asp Lys Lys Tyr Ser Tyr Arg
            20                  25
```

<210> SEQ ID NO 430
<211> LENGTH: 26
<212> TYPE: PRT
<213> ORGANISM: Artificial Sequence
<220> FEATURE:
<223> OTHER INFORMATION: Description of Artificial Sequence: Synthetic peptide

<400> SEQUENCE: 430

```
Arg Gly Thr Pro Ser Ser Tyr Ile Asp Asn Leu Thr Phe Pro Lys Val
1               5                   10                  15

Leu Thr Asp Lys Lys Tyr Ser Tyr Arg Val
            20                  25
```

<210> SEQ ID NO 431
<211> LENGTH: 26
<212> TYPE: PRT
<213> ORGANISM: Artificial Sequence
<220> FEATURE:
<223> OTHER INFORMATION: Description of Artificial Sequence: Synthetic peptide

<400> SEQUENCE: 431

```
Gly Thr Pro Ser Ser Tyr Ile Asp Asn Leu Thr Phe Pro Lys Val Leu
1               5                   10                  15

Thr Asp Lys Lys Tyr Ser Tyr Arg Val Val
            20                  25
```

<210> SEQ ID NO 432
<211> LENGTH: 26
<212> TYPE: PRT
<213> ORGANISM: Artificial Sequence
<220> FEATURE:
<223> OTHER INFORMATION: Description of Artificial Sequence: Synthetic peptide

<400> SEQUENCE: 432

```
Thr Pro Ser Ser Tyr Ile Asp Asn Leu Thr Phe Pro Lys Val Leu Thr
1               5                   10                  15

Asp Lys Lys Tyr Ser Tyr Arg Val Val Val
            20                  25
```

<210> SEQ ID NO 433
<211> LENGTH: 27
<212> TYPE: PRT
<213> ORGANISM: Artificial Sequence
<220> FEATURE:
<223> OTHER INFORMATION: Description of Artificial Sequence: Synthetic peptide

<400> SEQUENCE: 433

```
Ala Thr Ser Leu Thr Phe Gln Leu Ala Tyr Leu Val Lys Lys Ile Asp
1               5                   10                  15

Phe Asp Tyr Thr Pro Asn Trp Gly Arg Gly Thr
            20                  25
```

<210> SEQ ID NO 434
<211> LENGTH: 27
<212> TYPE: PRT
<213> ORGANISM: Artificial Sequence
<220> FEATURE:
<223> OTHER INFORMATION: Description of Artificial Sequence: Synthetic peptide

<400> SEQUENCE: 434

```
Thr Ser Leu Thr Phe Gln Leu Ala Tyr Leu Val Lys Lys Ile Asp Phe
```

1 5 10 15

Asp Tyr Thr Pro Asn Trp Gly Arg Gly Thr Pro
20 25

<210> SEQ ID NO 435
<211> LENGTH: 27
<212> TYPE: PRT
<213> ORGANISM: Artificial Sequence
<220> FEATURE:
<223> OTHER INFORMATION: Description of Artificial Sequence: Synthetic peptide

<400> SEQUENCE: 435

Ser Leu Thr Phe Gln Leu Ala Tyr Leu Val Lys Lys Ile Asp Phe Asp
1 5 10 15

Tyr Thr Pro Asn Trp Gly Arg Gly Thr Pro Ser
20 25

<210> SEQ ID NO 436
<211> LENGTH: 27
<212> TYPE: PRT
<213> ORGANISM: Artificial Sequence
<220> FEATURE:
<223> OTHER INFORMATION: Description of Artificial Sequence: Synthetic peptide

<400> SEQUENCE: 436

Leu Thr Phe Gln Leu Ala Tyr Leu Val Lys Lys Ile Asp Phe Asp Tyr
1 5 10 15

Thr Pro Asn Trp Gly Arg Gly Thr Pro Ser Ser
20 25

<210> SEQ ID NO 437
<211> LENGTH: 27
<212> TYPE: PRT
<213> ORGANISM: Artificial Sequence
<220> FEATURE:
<223> OTHER INFORMATION: Description of Artificial Sequence: Synthetic peptide

<400> SEQUENCE: 437

Thr Phe Gln Leu Ala Tyr Leu Val Lys Lys Ile Asp Phe Asp Tyr Thr
1 5 10 15

Pro Asn Trp Gly Arg Gly Thr Pro Ser Ser Tyr
20 25

<210> SEQ ID NO 438
<211> LENGTH: 27
<212> TYPE: PRT
<213> ORGANISM: Artificial Sequence
<220> FEATURE:
<223> OTHER INFORMATION: Description of Artificial Sequence: Synthetic peptide

<400> SEQUENCE: 438

Phe Gln Leu Ala Tyr Leu Val Lys Lys Ile Asp Phe Asp Tyr Thr Pro
1 5 10 15

Asn Trp Gly Arg Gly Thr Pro Ser Ser Tyr Ile
20 25

<210> SEQ ID NO 439
<211> LENGTH: 27
<212> TYPE: PRT
<213> ORGANISM: Artificial Sequence
<220> FEATURE:
<223> OTHER INFORMATION: Description of Artificial Sequence: Synthetic peptide

<400> SEQUENCE: 439

Gln Leu Ala Tyr Leu Val Lys Lys Ile Asp Phe Asp Tyr Thr Pro Asn
1 5 10 15

Trp Gly Arg Gly Thr Pro Ser Ser Tyr Ile Asp
20 25

<210> SEQ ID NO 440
<211> LENGTH: 27
<212> TYPE: PRT
<213> ORGANISM: Artificial Sequence
<220> FEATURE:
<223> OTHER INFORMATION: Description of Artificial Sequence: Synthetic peptide

<400> SEQUENCE: 440

Leu Ala Tyr Leu Val Lys Lys Ile Asp Phe Asp Tyr Thr Pro Asn Trp
1 5 10 15

Gly Arg Gly Thr Pro Ser Ser Tyr Ile Asp Asn
20 25

<210> SEQ ID NO 441
<211> LENGTH: 27
<212> TYPE: PRT
<213> ORGANISM: Artificial Sequence
<220> FEATURE:
<223> OTHER INFORMATION: Description of Artificial Sequence: Synthetic peptide

<400> SEQUENCE: 441

Ala Tyr Leu Val Lys Lys Ile Asp Phe Asp Tyr Thr Pro Asn Trp Gly
1 5 10 15

Arg Gly Thr Pro Ser Ser Tyr Ile Asp Asn Leu
20 25

<210> SEQ ID NO 442
<211> LENGTH: 27
<212> TYPE: PRT
<213> ORGANISM: Artificial Sequence
<220> FEATURE:
<223> OTHER INFORMATION: Description of Artificial Sequence: Synthetic peptide

<400> SEQUENCE: 442

Tyr Leu Val Lys Lys Ile Asp Phe Asp Tyr Thr Pro Asn Trp Gly Arg
1 5 10 15

Gly Thr Pro Ser Ser Tyr Ile Asp Asn Leu Thr
20 25

<210> SEQ ID NO 443
<211> LENGTH: 27
<212> TYPE: PRT
<213> ORGANISM: Artificial Sequence
<220> FEATURE:
<223> OTHER INFORMATION: Description of Artificial Sequence: Synthetic peptide

<400> SEQUENCE: 443

Leu Val Lys Lys Ile Asp Phe Asp Tyr Thr Pro Asn Trp Gly Arg Gly
1 5 10 15

Thr Pro Ser Ser Tyr Ile Asp Asn Leu Thr Phe
20 25

<210> SEQ ID NO 444

<211> LENGTH: 27
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 444

Val Lys Lys Ile Asp Phe Asp Tyr Thr Pro Asn Trp Gly Arg Gly Thr
1 5 10 15

Pro Ser Ser Tyr Ile Asp Asn Leu Thr Phe Pro
20 25

<210> SEQ ID NO 445
<211> LENGTH: 27
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 445

Lys Lys Ile Asp Phe Asp Tyr Thr Pro Asn Trp Gly Arg Gly Thr Pro
1 5 10 15

Ser Ser Tyr Ile Asp Asn Leu Thr Phe Pro Lys
20 25

<210> SEQ ID NO 446
<211> LENGTH: 27
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 446

Lys Ile Asp Phe Asp Tyr Thr Pro Asn Trp Gly Arg Gly Thr Pro Ser
1 5 10 15

Ser Tyr Ile Asp Asn Leu Thr Phe Pro Lys Val
20 25

<210> SEQ ID NO 447
<211> LENGTH: 27
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 447

Ile Asp Phe Asp Tyr Thr Pro Asn Trp Gly Arg Gly Thr Pro Ser Ser
1 5 10 15

Tyr Ile Asp Asn Leu Thr Phe Pro Lys Val Leu
20 25

<210> SEQ ID NO 448
<211> LENGTH: 27
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 448

Asp Phe Asp Tyr Thr Pro Asn Trp Gly Arg Gly Thr Pro Ser Ser Tyr
1 5 10 15

Ile Asp Asn Leu Thr Phe Pro Lys Val Leu Thr
20 25

<210> SEQ ID NO 449
<211> LENGTH: 27
<212> TYPE: PRT
<213> ORGANISM: Artificial Sequence
<220> FEATURE:
<223> OTHER INFORMATION: Description of Artificial Sequence: Synthetic peptide

<400> SEQUENCE: 449

Phe Asp Tyr Thr Pro Asn Trp Gly Arg Gly Thr Pro Ser Ser Tyr Ile
1 5 10 15

Asp Asn Leu Thr Phe Pro Lys Val Leu Thr Asp
20 25

<210> SEQ ID NO 450
<211> LENGTH: 27
<212> TYPE: PRT
<213> ORGANISM: Artificial Sequence
<220> FEATURE:
<223> OTHER INFORMATION: Description of Artificial Sequence: Synthetic peptide

<400> SEQUENCE: 450

Asp Tyr Thr Pro Asn Trp Gly Arg Gly Thr Pro Ser Ser Tyr Ile Asp
1 5 10 15

Asn Leu Thr Phe Pro Lys Val Leu Thr Asp Lys
20 25

<210> SEQ ID NO 451
<211> LENGTH: 27
<212> TYPE: PRT
<213> ORGANISM: Artificial Sequence
<220> FEATURE:
<223> OTHER INFORMATION: Description of Artificial Sequence: Synthetic peptide

<400> SEQUENCE: 451

Tyr Thr Pro Asn Trp Gly Arg Gly Thr Pro Ser Ser Tyr Ile Asp Asn
1 5 10 15

Leu Thr Phe Pro Lys Val Leu Thr Asp Lys Lys
20 25

<210> SEQ ID NO 452
<211> LENGTH: 27
<212> TYPE: PRT
<213> ORGANISM: Artificial Sequence
<220> FEATURE:
<223> OTHER INFORMATION: Description of Artificial Sequence: Synthetic peptide

<400> SEQUENCE: 452

Thr Pro Asn Trp Gly Arg Gly Thr Pro Ser Ser Tyr Ile Asp Asn Leu
1 5 10 15

Thr Phe Pro Lys Val Leu Thr Asp Lys Lys Tyr
20 25

<210> SEQ ID NO 453
<211> LENGTH: 27
<212> TYPE: PRT
<213> ORGANISM: Artificial Sequence
<220> FEATURE:
<223> OTHER INFORMATION: Description of Artificial Sequence: Synthetic peptide

<400> SEQUENCE: 453

Pro Asn Trp Gly Arg Gly Thr Pro Ser Ser Tyr Ile Asp Asn Leu Thr
1               5                   10                  15

Phe Pro Lys Val Leu Thr Asp Lys Lys Tyr Ser
            20                  25

<210> SEQ ID NO 454
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 454

Asn Trp Gly Arg Gly Thr Pro Ser Ser Tyr Ile Asp Asn Leu Thr Phe
1               5                   10                  15

Pro Lys Val Leu Thr Asp Lys Lys Tyr Ser Tyr
            20                  25

<210> SEQ ID NO 455
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 455

Trp Gly Arg Gly Thr Pro Ser Ser Tyr Ile Asp Asn Leu Thr Phe Pro
1               5                   10                  15

Lys Val Leu Thr Asp Lys Lys Tyr Ser Tyr Arg
            20                  25

<210> SEQ ID NO 456
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 456

Gly Arg Gly Thr Pro Ser Ser Tyr Ile Asp Asn Leu Thr Phe Pro Lys
1               5                   10                  15

Val Leu Thr Asp Lys Lys Tyr Ser Tyr Arg Val
            20                  25

<210> SEQ ID NO 457
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 457

Arg Gly Thr Pro Ser Ser Tyr Ile Asp Asn Leu Thr Phe Pro Lys Val
1               5                   10                  15

Leu Thr Asp Lys Lys Tyr Ser Tyr Arg Val Val
            20                  25

<210> SEQ ID NO 458
<211> LENGTH: 27
<212> TYPE: PRT

<213> ORGANISM: Artificial Sequence
<220> FEATURE:
<223> OTHER INFORMATION: Description of Artificial Sequence: Synthetic peptide

<400> SEQUENCE: 458

Gly Thr Pro Ser Ser Tyr Ile Asp Asn Leu Thr Phe Pro Lys Val Leu
1 5 10 15

Thr Asp Lys Lys Tyr Ser Tyr Arg Val Val Val
20 25

<210> SEQ ID NO 459
<211> LENGTH: 27
<212> TYPE: PRT
<213> ORGANISM: Artificial Sequence
<220> FEATURE:
<223> OTHER INFORMATION: Description of Artificial Sequence: Synthetic peptide

<400> SEQUENCE: 459

Thr Pro Ser Ser Tyr Ile Asp Asn Leu Thr Phe Pro Lys Val Leu Thr
1 5 10 15

Asp Lys Lys Tyr Ser Tyr Arg Val Val Val Asn
20 25

<210> SEQ ID NO 460
<211> LENGTH: 28
<212> TYPE: PRT
<213> ORGANISM: Artificial Sequence
<220> FEATURE:
<223> OTHER INFORMATION: Description of Artificial Sequence: Synthetic peptide

<400> SEQUENCE: 460

Ser Ala Thr Ser Leu Thr Phe Gln Leu Ala Tyr Leu Val Lys Lys Ile
1 5 10 15

Asp Phe Asp Tyr Thr Pro Asn Trp Gly Arg Gly Thr
20 25

<210> SEQ ID NO 461
<211> LENGTH: 28
<212> TYPE: PRT
<213> ORGANISM: Artificial Sequence
<220> FEATURE:
<223> OTHER INFORMATION: Description of Artificial Sequence: Synthetic peptide

<400> SEQUENCE: 461

Ala Thr Ser Leu Thr Phe Gln Leu Ala Tyr Leu Val Lys Lys Ile Asp
1 5 10 15

Phe Asp Tyr Thr Pro Asn Trp Gly Arg Gly Thr Pro
20 25

<210> SEQ ID NO 462
<211> LENGTH: 28
<212> TYPE: PRT
<213> ORGANISM: Artificial Sequence
<220> FEATURE:
<223> OTHER INFORMATION: Description of Artificial Sequence: Synthetic peptide

<400> SEQUENCE: 462

Thr Ser Leu Thr Phe Gln Leu Ala Tyr Leu Val Lys Lys Ile Asp Phe
1 5 10 15

Asp Tyr Thr Pro Asn Trp Gly Arg Gly Thr Pro Ser
20 25

<210> SEQ ID NO 463
<211> LENGTH: 28
<212> TYPE: PRT
<213> ORGANISM: Artificial Sequence
<220> FEATURE:
<223> OTHER INFORMATION: Description of Artificial Sequence: Synthetic peptide

<400> SEQUENCE: 463

```
Ser Leu Thr Phe Gln Leu Ala Tyr Leu Val Lys Lys Ile Asp Phe Asp
1               5                   10                  15

Tyr Thr Pro Asn Trp Gly Arg Gly Thr Pro Ser Ser
            20                  25
```

<210> SEQ ID NO 464
<211> LENGTH: 28
<212> TYPE: PRT
<213> ORGANISM: Artificial Sequence
<220> FEATURE:
<223> OTHER INFORMATION: Description of Artificial Sequence: Synthetic peptide

<400> SEQUENCE: 464

```
Leu Thr Phe Gln Leu Ala Tyr Leu Val Lys Lys Ile Asp Phe Asp Tyr
1               5                   10                  15

Thr Pro Asn Trp Gly Arg Gly Thr Pro Ser Ser Tyr
            20                  25
```

<210> SEQ ID NO 465
<211> LENGTH: 28
<212> TYPE: PRT
<213> ORGANISM: Artificial Sequence
<220> FEATURE:
<223> OTHER INFORMATION: Description of Artificial Sequence: Synthetic peptide

<400> SEQUENCE: 465

```
Thr Phe Gln Leu Ala Tyr Leu Val Lys Lys Ile Asp Phe Asp Tyr Thr
1               5                   10                  15

Pro Asn Trp Gly Arg Gly Thr Pro Ser Ser Tyr Ile
            20                  25
```

<210> SEQ ID NO 466
<211> LENGTH: 28
<212> TYPE: PRT
<213> ORGANISM: Artificial Sequence
<220> FEATURE:
<223> OTHER INFORMATION: Description of Artificial Sequence: Synthetic peptide

<400> SEQUENCE: 466

```
Phe Gln Leu Ala Tyr Leu Val Lys Lys Ile Asp Phe Asp Tyr Thr Pro
1               5                   10                  15

Asn Trp Gly Arg Gly Thr Pro Ser Ser Tyr Ile Asp
            20                  25
```

<210> SEQ ID NO 467
<211> LENGTH: 28
<212> TYPE: PRT
<213> ORGANISM: Artificial Sequence
<220> FEATURE:
<223> OTHER INFORMATION: Description of Artificial Sequence: Synthetic peptide

<400> SEQUENCE: 467

Gln Leu Ala Tyr Leu Val Lys Lys Ile Asp Phe Asp Tyr Thr Pro Asn
1               5                   10                  15

Trp Gly Arg Gly Thr Pro Ser Ser Tyr Ile Asp Asn
            20                  25

<210> SEQ ID NO 468
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 468

Leu Ala Tyr Leu Val Lys Lys Ile Asp Phe Asp Tyr Thr Pro Asn Trp
1               5                   10                  15

Gly Arg Gly Thr Pro Ser Ser Tyr Ile Asp Asn Leu
            20                  25

<210> SEQ ID NO 469
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 469

Ala Tyr Leu Val Lys Lys Ile Asp Phe Asp Tyr Thr Pro Asn Trp Gly
1               5                   10                  15

Arg Gly Thr Pro Ser Ser Tyr Ile Asp Asn Leu Thr
            20                  25

<210> SEQ ID NO 470
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 470

Tyr Leu Val Lys Lys Ile Asp Phe Asp Tyr Thr Pro Asn Trp Gly Arg
1               5                   10                  15

Gly Thr Pro Ser Ser Tyr Ile Asp Asn Leu Thr Phe
            20                  25

<210> SEQ ID NO 471
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 471

Leu Val Lys Lys Ile Asp Phe Asp Tyr Thr Pro Asn Trp Gly Arg Gly
1               5                   10                  15

Thr Pro Ser Ser Tyr Ile Asp Asn Leu Thr Phe Pro
            20                  25

<210> SEQ ID NO 472
<211> LENGTH: 28
<212> TYPE: PRT
<213> ORGANISM: Artificial Sequence
<220> FEATURE:

<223> OTHER INFORMATION: Description of Artificial Sequence: Synthetic
      peptide

<400> SEQUENCE: 472

Val Lys Lys Ile Asp Phe Asp Tyr Thr Pro Asn Trp Gly Arg Gly Thr
1               5                   10                  15

Pro Ser Ser Tyr Ile Asp Asn Leu Thr Phe Pro Lys
            20                  25

<210> SEQ ID NO 473
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 473

Lys Lys Ile Asp Phe Asp Tyr Thr Pro Asn Trp Gly Arg Gly Thr Pro
1               5                   10                  15

Ser Ser Tyr Ile Asp Asn Leu Thr Phe Pro Lys Val
            20                  25

<210> SEQ ID NO 474
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 474

Lys Ile Asp Phe Asp Tyr Thr Pro Asn Trp Gly Arg Gly Thr Pro Ser
1               5                   10                  15

Ser Tyr Ile Asp Asn Leu Thr Phe Pro Lys Val Leu
            20                  25

<210> SEQ ID NO 475
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 475

Ile Asp Phe Asp Tyr Thr Pro Asn Trp Gly Arg Gly Thr Pro Ser Ser
1               5                   10                  15

Tyr Ile Asp Asn Leu Thr Phe Pro Lys Val Leu Thr
            20                  25

<210> SEQ ID NO 476
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 476

Asp Phe Asp Tyr Thr Pro Asn Trp Gly Arg Gly Thr Pro Ser Ser Tyr
1               5                   10                  15

Ile Asp Asn Leu Thr Phe Pro Lys Val Leu Thr Asp
            20                  25

<210> SEQ ID NO 477
<211> LENGTH: 28
<212> TYPE: PRT
<213> ORGANISM: Artificial Sequence
<220> FEATURE:
<223> OTHER INFORMATION: Description of Artificial Sequence: Synthetic peptide

<400> SEQUENCE: 477

Phe Asp Tyr Thr Pro Asn Trp Gly Arg Gly Thr Pro Ser Ser Tyr Ile
1 5 10 15

Asp Asn Leu Thr Phe Pro Lys Val Leu Thr Asp Lys
20 25

<210> SEQ ID NO 478
<211> LENGTH: 28
<212> TYPE: PRT
<213> ORGANISM: Artificial Sequence
<220> FEATURE:
<223> OTHER INFORMATION: Description of Artificial Sequence: Synthetic peptide

<400> SEQUENCE: 478

Asp Tyr Thr Pro Asn Trp Gly Arg Gly Thr Pro Ser Ser Tyr Ile Asp
1 5 10 15

Asn Leu Thr Phe Pro Lys Val Leu Thr Asp Lys Lys
20 25

<210> SEQ ID NO 479
<211> LENGTH: 28
<212> TYPE: PRT
<213> ORGANISM: Artificial Sequence
<220> FEATURE:
<223> OTHER INFORMATION: Description of Artificial Sequence: Synthetic peptide

<400> SEQUENCE: 479

Tyr Thr Pro Asn Trp Gly Arg Gly Thr Pro Ser Ser Tyr Ile Asp Asn
1 5 10 15

Leu Thr Phe Pro Lys Val Leu Thr Asp Lys Lys Tyr
20 25

<210> SEQ ID NO 480
<211> LENGTH: 28
<212> TYPE: PRT
<213> ORGANISM: Artificial Sequence
<220> FEATURE:
<223> OTHER INFORMATION: Description of Artificial Sequence: Synthetic peptide

<400> SEQUENCE: 480

Thr Pro Asn Trp Gly Arg Gly Thr Pro Ser Ser Tyr Ile Asp Asn Leu
1 5 10 15

Thr Phe Pro Lys Val Leu Thr Asp Lys Lys Tyr Ser
20 25

<210> SEQ ID NO 481
<211> LENGTH: 28
<212> TYPE: PRT
<213> ORGANISM: Artificial Sequence
<220> FEATURE:
<223> OTHER INFORMATION: Description of Artificial Sequence: Synthetic peptide

<400> SEQUENCE: 481

Pro Asn Trp Gly Arg Gly Thr Pro Ser Ser Tyr Ile Asp Asn Leu Thr
1 5 10 15

Phe Pro Lys Val Leu Thr Asp Lys Lys Tyr Ser Tyr
20 25

<210> SEQ ID NO 482
<211> LENGTH: 28
<212> TYPE: PRT
<213> ORGANISM: Artificial Sequence
<220> FEATURE:
<223> OTHER INFORMATION: Description of Artificial Sequence: Synthetic peptide

<400> SEQUENCE: 482

Asn Trp Gly Arg Gly Thr Pro Ser Ser Tyr Ile Asp Asn Leu Thr Phe
1 5 10 15

Pro Lys Val Leu Thr Asp Lys Lys Tyr Ser Tyr Arg
20 25

<210> SEQ ID NO 483
<211> LENGTH: 28
<212> TYPE: PRT
<213> ORGANISM: Artificial Sequence
<220> FEATURE:
<223> OTHER INFORMATION: Description of Artificial Sequence: Synthetic peptide

<400> SEQUENCE: 483

Trp Gly Arg Gly Thr Pro Ser Ser Tyr Ile Asp Asn Leu Thr Phe Pro
1 5 10 15

Lys Val Leu Thr Asp Lys Lys Tyr Ser Tyr Arg Val
20 25

<210> SEQ ID NO 484
<211> LENGTH: 28
<212> TYPE: PRT
<213> ORGANISM: Artificial Sequence
<220> FEATURE:
<223> OTHER INFORMATION: Description of Artificial Sequence: Synthetic peptide

<400> SEQUENCE: 484

Gly Arg Gly Thr Pro Ser Ser Tyr Ile Asp Asn Leu Thr Phe Pro Lys
1 5 10 15

Val Leu Thr Asp Lys Lys Tyr Ser Tyr Arg Val Val
20 25

<210> SEQ ID NO 485
<211> LENGTH: 28
<212> TYPE: PRT
<213> ORGANISM: Artificial Sequence
<220> FEATURE:
<223> OTHER INFORMATION: Description of Artificial Sequence: Synthetic peptide

<400> SEQUENCE: 485

Arg Gly Thr Pro Ser Ser Tyr Ile Asp Asn Leu Thr Phe Pro Lys Val
1 5 10 15

Leu Thr Asp Lys Lys Tyr Ser Tyr Arg Val Val Val
20 25

<210> SEQ ID NO 486
<211> LENGTH: 28
<212> TYPE: PRT
<213> ORGANISM: Artificial Sequence
<220> FEATURE:
<223> OTHER INFORMATION: Description of Artificial Sequence: Synthetic peptide -continued

<400> SEQUENCE: 486

```
Gly Thr Pro Ser Ser Tyr Ile Asp Asn Leu Thr Phe Pro Lys Val Leu
1               5                   10                  15

Thr Asp Lys Lys Tyr Ser Tyr Arg Val Val Val Asn
            20                  25
```

<210> SEQ ID NO 487
<211> LENGTH: 28
<212> TYPE: PRT
<213> ORGANISM: Artificial Sequence
<220> FEATURE:
<223> OTHER INFORMATION: Description of Artificial Sequence: Synthetic peptide

<400> SEQUENCE: 487

```
Thr Pro Ser Ser Tyr Ile Asp Asn Leu Thr Phe Pro Lys Val Leu Thr
1               5                   10                  15

Asp Lys Lys Tyr Ser Tyr Arg Val Val Val Asn Gly
            20                  25
```

<210> SEQ ID NO 488
<211> LENGTH: 6
<212> TYPE: PRT
<213> ORGANISM: Artificial Sequence
<220> FEATURE:
<223> OTHER INFORMATION: Description of Artificial Sequence: Synthetic 6xHis tag

<400> SEQUENCE: 488

```
His His His His His His
1               5
```